(12) United States Patent
Berka et al.

(10) Patent No.: US 7,186,513 B2
(45) Date of Patent: Mar. 6, 2007

(54) METHODS FOR MONITORING MULTIPLE GENE EXPRESSION

(75) Inventors: Randy M. Berka, Davis, CA (US); Michael W. Rey, Davis, CA (US); Jeffrey R. Shuster, Davis, CA (US); Sakari Kauppinen, Smoerum (DK); Ib Groth Clausen, Hillerod (DK); Peter Bjarke Olsen, Copenhagen (DK)

(73) Assignee: Novozymes, Inc., Davis, CA (US)

( * ) Notice: Subject to any disclaimer, the term of this patent is extended or adjusted under 35 U.S.C. 154(b) by 495 days.

(21) Appl. No.: 10/653,047

(22) Filed: Aug. 29, 2003

(65) Prior Publication Data

US 2004/0229367 A1    Nov. 18, 2004

Related U.S. Application Data

(60) Division of application No. 09/533,559, filed on Mar. 22, 2000, now Pat. No. 6,902,887, which is a continuation-in-part of application No. 09/273,623, filed on Mar. 22, 1999, now abandoned.

(51) Int. Cl.
*C12Q 1/68* (2006.01)
*C12N 15/30* (2006.01)

(52) U.S. Cl. ........................................ 435/6; 536/24.32
(58) Field of Classification Search ..................... None
See application file for complete search history.

(56) References Cited

OTHER PUBLICATIONS

Watson et al., 1998, Current Opinion in Biotechnology 9: 609-614.
Chu et al., 1998, Science282: 699-705.
Ruan et al., 1998, The Plant Journal 15: 821-833.
Iyer et al., 1999, Science 283: 83-87.
Hayward et al., 2000, Molecular Microbiology 35: 6-14.

*Primary Examiner*—John S. Brusca
(74) *Attorney, Agent, or Firm*—Robert L. Starnes

(57) ABSTRACT

The present invention relates to methods for monitoring differential expression of a plurality of genes in a first filamentous fungal cell relative to expression of the same genes in one or more second filamentous fungal cells using microarrays containing filamentous fungal expressed sequenced tags. The present invention also relates to filamentous fungal expressed sequenced tags and to computer readable media and substrates containing such expressed sequenced tags for monitoring expression of a plurality of genes in filamentous fungal cells.

9 Claims, No Drawings

US 7,186,513 B2

METHODS FOR MONITORING MULTIPLE GENE EXPRESSION

CROSS-REFERENCE TO RELATED APPLICATION

This application is a divisional of U.S. application Ser. No. 09/533,559 filed Mar. 22, 2000 now U.S. Pat. No. 6,902,887, which is a continuation-in-part of U.S. application Ser. No. 09/273,623 filed Mar. 22, 1999, now abandoned, which applications are fully incorporated herein by reference.

BACKGROUND OF THE INVENTION

1. Field of the Invention

The present invention relates to methods for monitoring expression of a plurality of genes in filamentous fungal cells. The present invention also relates to expressed sequenced tags and to substrates and computer readable media containing such expressed sequenced tags for monitoring expression of a plurality of genes in filamentous fungal cells.

2. Description of the Related Art

Microarray technology is increasingly becoming the method of choice for the quantitative and simultaneous analysis of the expression levels of many thousands of genes. Microarray analyses typically follow the steps of gene selection, microarray synthesis, sample preparation, array hybridization, detection, and data analysis (Watson et al., 1998, *Current Opinion in Biotechnology* 9: 609–614).

PCR-amplified coding sequences of genomic DNA are particularly useful in microarrays for obtaining global expression profiles where the genome of the organism has been fully sequenced.

Chu et al., 1998, *Science* 282: 699–705 disclose the use of microarrays containing PCR-amplified genomic coding sequences for determining the temporal expression of *Saccharomyces cerevisiae* genes during sporulation.

For other organisms whose genomes have not been sequenced, global expression profiles may be obtained with arraying (1) random genomic DNA segments or clones (e.g., from a genomic DNA library); (2) random cDNA clones (e.g., from one or more cDNA libraries) that are uncharacterized at the DNA sequence level; or (3) EST clones that have been sequenced and partially characterized with respect to putative identification and function.

However, there are disadvantages with using random genomic or cDNA clones from organisms whose genomes have not been fully sequenced. These disadvantages include (1) more than one gene may be represented on a single clone; (2) no gene(s) may be encoded on a single clone; (3) extensive characterization and DNA sequencing is required to follow-up array spots that appear interesting; and (4) duplicity, multiplicity, and redunancy add to the follow-up work.

Expressed sequenced tags (ESTs) are partial cDNA sequences of expressed genes. Simply stated, an EST is a segment of a sequence from a cDNA clone that corresponds to the mRNA of a specific gene. The use of sequenced ESTs in microarrays compared to genomic clones or random cDNA clones provides several advantages especially for organisms whose genomes have not been sequenced. First, one spot on an array equals one gene or open reading frame, so redundancy is eliminated. Second, since sequence information is available so that redundancy and follow-up characterization is minimized. Third, EST microarrays can be organized based on function of the gene products to facilitate analysis of the results (e.g., ESTs encoding enzymes from the same metabolic pathway can be arranged or grouped accordingly).

Ruan et al., 1998, *The Plant Journal* 15: 821–833, disclose the use of microarrays containing *Arabidopsis thaliana* EST sequences for determining the temporal expression of *Arabidopsis thaliana* genes in root, leaf, and two stages of floral development.

Iyer et al., 1999, *Science* 283; 83–87, disclose the use of microarrays containing human EST sequences for determining the temporal expression of human fibroblast cells in response to serum.

Hayward et al., 2000, *Molecular Microbiology* 35: 6–14, disclose shotgun DNA microarrays and stage-specific gene expression in *Plasmodium falciparum* malaria.

Filamentous fungi are increasingly being used as host microorganisms for the industrial production of enzymes and other proteins whether endogenous or heterogenous to the microorganisms. There is a need in the art to provide methods for monitoring the global expression of genes from filamentous fungal cells to improve the production potential of these microorganisms.

It is an object of the present invention to provide alternative methods for monitoring expression of a plurality of genes in filamentous fungal cells.

SUMMARY OF THE INVENTION

The present invention relates to methods for monitoring differential expression of a plurality of genes in a first filamentous fungal cell relative to expression of the same genes in one or more second filamentous fungal cells, comprising:

(a) adding a mixture of fluorescence-labeled nucleic acids isolated from the filamentous fungal cells to a substrate containing an array of filamentous fungal ESTs under conditions where the nucleic acids hybridize to complementary sequences of the ESTs in the array, wherein the nucleic acids from the first filamentous fungal cell and the one or more second filamentous fungal cells are labeled with a first fluorescent reporter and one or more different second fluorescent reporters, respectively; and (b) examining the array by fluorescence under fluorescence excitation conditions wherein the relative expression of the genes in the filamentous fungal cells is determined by the observed fluorescence emission color of each spot in the array in which (i) the ESTs in the array that hybridize to the nucleic acids obtained from either the first or the one or more second filamentous fungal cells produce a distinct first fluorescence emission color or one or more second fluorescence emission colors, respectively, and (ii) the ESTs in the array that hybridize to the nucleic acids obtained from both the first and one or more second filamentous fungal cells produce a distinct combined fluorescence emission color. In a preferred embodiment, the filamentous fungal ESTs are selected from the group consisting of SEQ ID NOs. 1–7860, nucleic acid fragments of SEQ ID NOs. 1–7860, and nucleic acid sequences having at least 90%, preferably at least 95%, more preferably at least 99%, and most preferably at least 99.9% homology to the sequences of SEQ ID NOs. 1–7860.

The present invention further relates to isolated ESTs obtained from *Fusarium venenatum* (SEQ ID NOs. 1–3770), *Aspergillus niger* (SEQ ID NOs. 3771–4376), *Aspergillus oryzae* (SEQ ID NOs. 4377–7401), and *Trichoderma reesei* (SEQ ID NOs. 7402–7860).

The present invention also relates to computer readable media and substrates containing an array of such filamentous fungal ESTs for monitoring differential expression of a plurality of genes in a first filamentous fungal cell relative to expression of the same genes in one or more second filamentous fungal cells.

DETAILED DESCRIPTION OF THE INVENTION

The present invention relates to methods for monitoring differential expression of a plurality of genes in a first filamentous fungal cell relative to expression of the same genes in one or more second filamentous fungal cells. The methods comprise (a) adding a mixture of fluorescence-labeled nucleic acids isolated from the two or more filamentous fungal cells with different fluorescent reporters for each cell's nucleic acids to a substrate containing an array of filamentous fungal ESTs under conditions where the nucleic acids hybridize to complementary sequences of the ESTs in the array; and (b) examining the array by fluorescence under fluorescence excitation conditions wherein the relative expression of the genes in the two or more cells is determined by the observed fluorescence emission color of each spot in the array.

The methods of the present invention may be used to monitor global expression of a plurality of genes from a filamentous fungal cell, discover new genes, identify possible functions of unknown open reading frames, and monitor gene copy number variation and stability. For example, the global view of changes in expression of genes may be used to provide a picture of the way in which filamentous fungal cells adapt to changes in culture conditions, environmental stress, or other physiological provocation. Other possibilities for monitoring global expression include spore morphogenesis, recombination, metabolic or catabolic pathway engineering.

The methods of the present invention are particularly advantageous because one spot on an array equals one gene or open reading frame; extensive follow-up characterization is unnecessary since sequence information is available, and EST microarrays can be organized based on function of the gene products.

Expressed Sequenced Tags

The term "expressed sequenced tag" or "EST" is defined herein as a segment of a sequence from a cDNA clone of an expressed filamentous fungal gene. The term "EST" will be understood to also include two or more ESTs assembled into a contig. In the methods of the present invention, the filamentous fungal ESTs described herein preferably represent a plurality of genes present in the two or more filamentous fungal cells to be evaluated.

ESTs are generally generated as follows: Total polyadenylated mRNA is isolated from a filamentous fungal cell and reverse transcribed into total cDNA. The total cDNA is digested with a restriction endonuclease, size-selected by agarose gel electrophoresis, isolated, and ligated into a vector, e.g., pZErO-2.1. The ligation mixture is transformed into competent *E. coli* cells and transformants are selected under selective pressure, e.g., kanamycin selection. The cDNA libraries isolated from the selected transformants are amplified, isolated, and partially sequenced. The partial sequences are then compared to sequences in various publicly available databases for identification.

Any method known in the art may be used for generating ESTs (see, for example, Adams et al., 1991, *Science* 252: 1651–1656; Fields, 1996, *Tibtech* 14: 286–289; Weinstock et al., 1994, *Current Opinion in Biotechnology* 5: 599–603; Matsubara and Okubo, 1993, *Current Opinions in Biotechnology* 4: 672–677; Nelson et al., 1997, *Fungal Genet. Biol.* 21: 348–363; Roe at al., http://www.genome.ou.edu/fungal.html).

In the methods of the present invention, the filamentous fungal ESTs are preferably at least about 50 bp in length, more preferably at least about 100 bp in length, even more preferably at least about 150 bp in length, and most preferably at least about 200 bp in length. Furthermore, the ESTs are preferably directional ESTs. However, nondirectional ESTs may also be used. A "directional EST" is defined as a cDNA cloned in the same orientation relative to the vector cloning sites, e.g., 5'→3' or 3'→5'.

The filamentous fungal ESTs may be obtained from any filamentous fungal cell but preferably from an *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma* cell, and more preferably from an *Aspergillus aculeatus*, *Aspergillus awamori*, *Aspergillus foetidus*, *Aspergillus japonicus*, *Aspergillus nidulans*, *Aspergillus niger*, *Aspergillus oryzae*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Trichoderma koningii*, *Trichoderma longibrachiatum*, *Trichoderma reesei*, or *Trichoderma viride* cell.

In a preferred embodiment, the ESTs are obtained from *Fusarium venenatum*. In a more preferred embodiment, the ESTs are obtained from *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another more preferred embodiment, the *Fusarium venenatum* cell is a morphological mutant of *Fusarium venenatum* A3/5 or *Fusarium venenatum* ATCC 20334, as disclosed in WO 97/26330. In a most preferred embodiment, the *Fusarium venenatum* ESTs are selected from the group consisting of SEQ ID NOs. 1–3770, nucleic acid fragments of SEQ ID NOs. 1–3770, and nucleic acid sequences having at least 90%, preferably at least 95%, more preferably at least 99%, and most preferably at least 99.9% homology to SEQ ID NOs. 1–3770.

In another preferred embodiment, the ESTs are obtained from *Aspergillus niger*. In another more preferred embodiment, the *Aspergillus niger* ESTs are selected from the group consisting of SEQ ID NOs. 3771–4376, nucleic acid fragments of SEQ ID NOs. 3771–4376, and nucleotide sequences having at least 90%, preferably at least 95%, more preferably at least 99%, and most preferably at least 99.9% homology to SEQ ID NOs. 3771–4376.

In another preferred embodiment, the ESTs are obtained from *Aspergillus oryzae*. In another more preferred embodiment, the ESTs are obtained from *Aspergillus oryzae* strain IFO 4177. In another most preferred embodiment, the *Aspergillus oryzae* ESTs are selected from the group consisting of SEQ ID NOs. 4377–7401, nucleic acid fragments of SEQ ID NOs. 4377–7401, and nucleic acid sequences having at least 90%, preferably at least 95%, more preferably at least 99%, and most preferably at least 99.9% homology to the sequences of SEQ ID NOs. 4377–7401.

In another preferred embodiment, the ESTs are obtained from *Trichoderma reesei*. In another more preferred embodiment, the ESTs are obtained from *Trichoderma reesei* strain RutC-30 (Montenecourt and Eveleigh, 1979, *Adv. Chem. Ser.* 181: 289–301). In another most preferred embodiment, the *Trichoderma reesei* ESTs are selected from the group consisting of SEQ ID NOs. 7402–7860, nucleic acid fragments of SEQ ID NOs. 7402–7860, or nucleic acid sequences having at least 95%, preferably at least 99% and most preferably at least 99.9% homology to a sequence of SEQ ID NOs. 7402–7860.

For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Microarrays

The term "an array of ESTs" is defined herein as a linear or two-dimensional array of preferably discrete elements of ESTs, each having a finite area, formed on the surface of a solid support.

The term "microarray" is defined herein as an array of EST elements having a density of discrete EST elements of at least about 100/cm$^2$, and preferably at least about 1000/cm$^2$. The EST elements in a microarray have typical dimensions, e.g., diameters, in the range of between about 10 to about 250 μm, preferably in the range of between about 10 to about 200 μm, more preferably in the range of between about 20 to about 150 μm, even more preferably in the range of between about 20 to about 100 μm, most preferably in the range of between about 20 to about 75 μm, and even most preferably in the range of between about 25 to about 50 μm, and are separated from other EST elements in the microarray by about the same distance.

Methods and instruments for forming microarrays on the surface of a solid support are well known in the art. See, for example, U.S. Pat. Nos. 5,807,522; 5,700,637; and 5,770,151. The instrument may be an automated device such as described in U.S. Pat. No. 5,807,522.

The term "a substrate containing an array of ESTs" is defined herein as a solid support having deposited on the surface of the support one or more of a plurality of ESTs for use in detecting binding of labeled cDNAs to the ESTs.

The substrate may, in one aspect, be a glass support (e.g., glass slide) having a hydrophilic or hydrophobic coating on the surface of the support, and an array of distinct ESTs electrostatically bound non-covalently to the coating, where each distinct EST is disposed at a separate, defined position.

Each microarray in the substrate preferably contains at least 10$^3$ distinct ESTs in a surface area of less than about 1 cm$^2$. Each distinct EST (i) is disposed at a separate, defined position in the array, (ii) has a length of at least 50 bp, and (iii) is present in a defined amount between about 0.1 femtomoles and 100 nanomoles or higher if necessary.

For a hydrophilic coating, the glass slide is coated by placing a film of a polycationic polymer with a uniform thickness on the surface of the slide and drying the film to form a dried coating. The amount of polycationic polymer added should be sufficient to form at least a monolayer of polymers on the glass surface. The polymer film is bound to the surface via electrostatic binding between negative silyl-OH groups on the surface and charged cationic groups in the polymers. Such polycationic polymers include, but are not limited to, polylysine and polyarginine.

Another coating strategy employs reactive aldehydes to couple DNA to the slides (Schena et al., 1996, *Proceedings of the National Academy of Science USA* 93: 10614–10619; Heller at al., 1997, *Proceedings of the National Academy of Science USA* 94: 2150–2155).

Alternatively, the surface may have a relatively hydrophobic character, i.e., one that causes aqueous medium deposited on the surface to bead. A variety of known hydrophobic polymers, such as polystyrene, polypropylene, or polyethylene, have desirable hydrophobic properties, as do glass and a variety of lubricant or other hydrophobic films that may be applied to the support surface. A support surface is "hydrophobic" if an aqueous droplet applied to the surface does not spread out substantially beyond the area size of the applied droplet, wherein the surface acts to prevent spreading of the droplet applied to the surface by hydrophobic interaction with the droplet.

In another aspect, the substrate may be a multi-cell substrate where each cell contains a microarray of ESTs, and preferably an identical microarray, formed on a porous surface. For example, a 96-cell array may typically have array dimensions between about 12 and 244 mm in width and 8 and 400 mm in length, with the cells in the array having width and length dimension of 1/12 and 1/8 the array width and length dimensions, respectively, i.e., between about 1 and 20 in width and 1 and 50 mm in length.

The solid support may include a water-impermeable backing such as a glass slide or rigid polymer sheet, or other non-porous material. Formed on the surface of the backing is a water-permeable film which is formed of porous material. Such porous materials include, but are not limited to, nitrocellulose membrane nylon, polypropylene, and PVDF polymer. The thickness of the film is preferably between about 10 and 1000 μm. The film may be applied to the backing by spraying or coating, or by applying a preformed membrane to the backing.

The film surface may be partitioned into a desirable array of cells by water-impermeable grid lines typically at a distance of about 100 to 2000 μm above the film surface. The grid lines can be formed on the surface of the film by laying down an uncured flowable resin or elastomer solution in an array grid, allowing the material to infiltrate the porous film down to the backing, and then curing the grid lines to form the cell-array substrate.

The barrier material of the grid lines may be a flowable silicone, wax-based material, thermoset material (e.g., epoxy), or any other useful material. The grid lines may be applied to the solid support using a narrow syringe, printing techniques, heat-seal stamping, or any other useful method known in the art.

Each well preferably contains a microarray of distinct ESTs. "Distinct ESTs" as applied to the ESTs forming a microarray is defined herein as an array member which is distinct from other array members on the basis of a different EST sequence, and/or different concentrations of the same or distinct ESTs, and/or different mixtures of distinct ESTs or different-concentrations of ESTs. Thus an array of "distinct ESTs" may be an array containing, as its members, (i) distinct ESTs, which may have a defined amount in each member, (ii) different, graded concentrations of given-sequence ESTs, and/or (iii) different-composition mixtures of two or more distinct ESTs.

However, any type of substrate known in the art may be used in the methods of the present invention.

The delivery of a known amount of a selected EST to a specific position on the support surface is preferably performed with a dispensing device equipped with one or more tips for insuring reproducible deposition and location of the ESTs and for preparing multiple arrays. Any dispensing device known in the art may be used in the methods of the present invention. See, for example, U.S. Pat. No. 5,807,522. The dispensing device preferably contains a plurality of tips.

For liquid-dispensing on a hydrophilic surface, the liquid will have less of a tendency to bead, and the dispensed volume will be more sensitive to the total dwell time of the dispenser tip in the immediate vicinity of the support surface.

For liquid-dispensing on a hydrophobic surface, flow of fluid from the tip onto the support surface will continue from the dispenser onto the support surface until it forms a liquid bead. At a given bead size, i.e., volume, the tendency of liquid to flow onto the surface will be balanced by the hydrophobic surface interaction of the bead with the support surface, which acts to limit the total bead area on the surface, and by the surface tension of the droplet, which tends toward a given bead curvature. At this point, a given bead volume will have formed, and continued contact of the dispenser tip with the bead, as the dispenser tip is being withdrawn, will have little or no effect on bead volume.

The desired deposition volume, i.e., bead volume, formed is preferably in the range 2 pl (picoliters) to 2 nl (nanoliters), although volumes as high as 100 nl or more may be dispensed. It will be appreciated that the selected dispensed volume will depend on (i) the "footprint" of the dispenser tip(s), i.e., the size of the area spanned by the tip(s), (ii) the hydrophobicity of the support surface, and (iii) the time of contact with and rate of withdrawal of the tip(s) from the support surface. In addition, bead size may be reduced by increasing the viscosity of the medium, effectively reducing the flow time of liquid from the dispensing device onto the support surface. The drop size may be further constrained by depositing the drop in a hydrophilic region surrounded by a hydrophobic grid pattern on the support surface.

At a given tip size, bead volume can be reduced in a controlled fashion by increasing surface hydrophobicity, reducing time of contact of the tip with the surface, increasing rate of movement of the tip away from the surface, and/or increasing the viscosity of the medium. Once these parameters are fixed, a selected deposition volume in the desired pl to nl range can be achieved in a repeatable fashion.

After depositing a liquid droplet of an EST sample at one selected location on a support, the tip may be moved to a corresponding position on a second support, the EST sample is deposited at that position, and this process is repeated until the EST sample has been deposited at a selected position on a plurality of supports.

This deposition process may then be repeated with another EST sample at another microarray position on each of the supports.

The diameter of each EST region is preferably between about 20–200 μm. The spacing between each region and its closest (non-diagonal) neighbor, measured from center-to-center, is preferably in the range of about 20–400 μm. Thus, for example, an array having a center-to-center spacing of about 250 μm contains about 40 regions/cm$^2$ or 1,600 regions/cm$^2$. After formation of the array, the support is treated to evaporate the liquid of the droplet forming each region, to leave a desired array of dried, relatively flat EST regions. This drying may be done by heating or under vacuum.

Filamentous Fungal Cells

In the methods of the present invention, the two or more filamentous fungal cells may be any filamentous fungal cell where one of the cells is used as a reference for identifying differences in expression of the same or similar complement of genes in the other cell. In one aspect, the two or more cells are the same cell. For example, they may be compared under different growth conditions, e.g., oxygen limitation, nutrition, and/or physiology. In another aspect, one or more cells are mutants of the reference cell. For example, the mutant(s) may have a different phenotype. In a further aspect, the two or more cells are of different species (e.g., *Aspergillus oryzae* and *Aspergillus sojae*). In another further aspect, the two or more cells are of different genera. In an even further aspect, one or more cells are transformants of the reference cell, wherein the one or more transformants exhibit a different property. For example, the transformants may have an improved phenotype relative to the reference cell and/or one of the other transformants. The term "phenotype" is defined herein as an observable or outward characteristic of a cell determined by its genotype and modulated by its environment. Such improved phenotypes may include, but are not limited to, improved secretion or production of a protein or compound, reduced or no secretion or production of a protein or compound, improved or reduced expression of a gene, desirable morphology, an altered growth rate under desired conditions, relief of over-expression mediated growth inhibition, or tolerance to low oxygen conditions.

The filamentous fungal cells may be any filamentous fungal cells, but preferably *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma* cells, and more preferably *Aspergillus aculeatus*, *Aspergillus awamori*, *Aspergillus foetidus*, *Aspergillus japonicus*, *Aspergillus nidulans*, *Aspergillus niger*, *Aspergillus oryzae*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Trichoderma koningii*, *Trichoderma longibrachiatum*, *Trichoderma reesei*, or *Trichoderma viride* cells.

In a preferred embodiment, the filamentous fungal cells are *Fusarium* or *Aspergillus* cells. In a more preferred embodiment, the *Fusarium* cells are *Fusarium venenatum* cells. In another more preferred embodiment, the *Aspergillus* cells are *Aspergillus niger* cells. In another more preferred embodiment, the *Aspergillus* cells are *Aspergillus oryzae* cells.

In a most preferred embodiment, the *Fusarium venenatum* cells are *Fusarium venenatum* A3/5 cells as described herein. In another most preferred embodiment, the *Fusarium venenatum* cells are morphological mutants of *Fusarium venenatum* A3/5 as described herein. In another most preferred embodiment, the *Aspergillus oryzae* cells are *Aspergillus oryzae* strain IFO 4177 cells.

In the methods of the present invention, the cells are cultivated in a nutrient medium suitable for growth using methods well known in the art for isolation of the nucleic acids to be used as probes. For example, the cells may be cultivated by shake flask cultivation, small-scale or large-scale fermentation (including continuous, batch, fed-batch, or solid state fermentations) in laboratory or industrial fermentors performed in a suitable medium. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

Nucleic Acid Probes

The nucleic acid probes from the two or more filamentous fungal cells may be any nucleic acid including genomic DNA, cDNA, and RNA, and may be isolated using standard methods known in the art. For example, cDNA probes may be obtained from the total polyadenylated mRNA isolated from the cells using standard methods and reverse transcribed into total cDNA.

The populations of isolated nucleic acid probes may be labeled with colorimetric, radioactive, fluorescent reporters, or other reporters using methods known in the art (Chen et al, 1998, *Genomics* 51: 313–324; DeRisi et al., 1997, *Science* 278: 680–686; U.S. Pat. No. 5,770,367).

In a preferred embodiment, the probes are labeled with fluorescent reporters. For example, cDNA probes may be labeled during reverse transcription from the respective mRNA pools by incorporation of fluorophores as dye-labeled nucleotides (DeRisi et al., 1997, supra), e.g., Cy5-labeled deoxyuridine triphosphate, or the isolated cDNAs may be directly labeled with different fluorescent functional groups. Fluorescent-labeled nucleotides include, but are not limited to, fluorescein conjugated nucleotide analogs (green fluorescence), lissamine nucleotide analogs (red fluorescence). Fluorescent functional groups include, but are not limited to, Cy3 (a green fluorescent dye) and Cy5 (red fluorescent dye).

Array Hybridization

The labeled nucleic acids from the two or more filamentous fungal cells are then added to a substrate containing an array of ESTs under conditions where the nucleic acid pools from the two or more filamentous fungal cells hybridize to complementary sequences of the ESTs in the array. For purposes of the present invention, hybridization indicates that the labeled nucleic acids from the two or more cells hybridize to the ESTs under very low to very high stringency conditions.

A small volume of the labeled nucleic acids mixture is loaded onto the substrate. The solution will spread to cover the entire microarray. In the case of a multi-cell substrate, one or more solutions are loaded into each cell which stop at the barrier elements.

For nucleic acid probes of at least about 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For nucleic acid probes of at least about 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For shorter nucleic acid probes which are about 50 nucleotides to about 100 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For shorter nucleic acid probes which are about 50 nucleotides to about 100 nucleotides in length, the carrier material is washed once in 6×SCC plus 0.1% SDS for 15 minutes and twice each for 15 minutes using 6×SSC at 5° C. to 10° C. below the calculated $T_m$.

The choice of hybridization conditions will depend on the degree of homology between the ESTs and the nucleic acids obtained from the two or more filamentous fungal cells. For example, where the cells are the same cell from which the ESTs were obtained, high stringency conditions may be most suitable. Where the cells are from a genus or species different from which the ESTs were obtained, low or medium stringency conditions may be more suitable.

In a preferred embodiment, the hybridization is conducted under low stringency conditions. In a more preferred embodiment, the hybridization is conducted under medium stringency conditions. In a most preferred embodiment, the hybridization is conducted under high stringency conditions.

The entire solid support is then reacted with detection reagents if needed and analyzed using standard calorimetric, radioactive, or fluorescent detection means. All processing and detection steps are performed simultaneously to all of the microarrays on the solid support ensuring uniform assay conditions for all of the microarrays on the solid support.

Detection

The most common detection method is laser-induced fluorescence detection using confocal optics (Cheung et al., 1998, *Nat. Genet.* 18: 225–230). The array is examined under fluorescence excitation conditions such that (i) the ESTs in the array that hybridize to the nucleic acid probes obtained from one of the first cell and one or more second cells produces a distinct first fluorescence emission color or one or second fluorescence emission colors, respectively, and (ii) ESTs in the array that hybridize to substantially equal numbers of nucleic acid probes obtained from the first cell and one of the one or more second cells produce a distinct combined fluorescence emission color, respectively; wherein the relative expression of the genes in the two or more cells can be determined by the observed fluorescence emission color of each spot in the array.

The fluorescence excitation conditions are based on the selection of the fluorescence reporters. For example, Cy3 and Cy5 reporters are detected with solid state lasers operating at 532 nm and 632 nm, respectively.

Other methods of detection may be used as described herein

Data Analysis

The fluorescence data obtained from the scanned image may then be analyzed using any of the commercially available image analysis software. The software preferably identifies array elements, subtracts backgrounds, deconvolutes multi-color images, flags or removes artifacts, verifies that controls have performed properly, and normalizes the signals (Chen et al., 1997, *Journal of Biomedical Optics* 2: 364–374).

Several computational methods have been described for the analysis and interpretation of microarray-based expression profiles including cluster analysis (Eisen et al., 1998, *Proc. Nat. Acad. Sci. USA* 95: 14863–14868), parametric ordering of genes (Spellman et al., 1998, *Mol. Biol. Cell* 9: 3273–3297), and supervised clustering methods based on representative hand-picked or computer-generated expression profiles (Chu et al., 1998. *Science* 282: 699–705).

Computer Readable Media

The filamentous fungal ESTs described herein may be "provided" in a variety of mediums to facilitate their use. The term "provided" refers to a manufacture comprising an array of filamentous fungal ESTs. Such manufactures provide a large portion of the genomes of *Fusarium venenatum, Aspergillus niger, Aspergillus oryzae,* or *Trichoderma reesei* and parts thereof (e.g., an open reading frame (ORF)) in a form which allows one skilled in the art to examine the manufacture using means not directly applicable to examining the genome or a subset thereof as it exists in nature or in purified form.

Thus, the present invention also relates to such a manufacture in the form of a computer readable medium comprising an array of ESTs selected from the group consisting of SEQ ID NOs. 1–7860, nucleic acid fragments of SEQ ID NOs. 1–7860, and nucleic acid sequences having at least 90%, preferably at least 95%, more preferably at least 99%, and most preferably at least 99.9% homology to SEQ ID NOs. 1–7860.

In a preferred embodiment, the computer readable medium comprises an array of *Fusarium venenatum* ESTs selected from the group consisting of SEQ ID NOs. 1–3770, nucleic acid fragments of SEQ ID NOs. 1–3770, and nucleic acid sequences having at least 90%, preferably at least 95%, more preferably at least 99%, and most preferably at least 99.9% homology to SEQ ID NOs. 1–3770. In a more preferred embodiment, the computer readable medium comprises an array of ESTs selected from the group consisting of SEQ ID NOs. 1–3770.

In another preferred embodiment, the computer readable medium comprises an array of *Aspergillus niger* ESTs selected from the group consisting of SEQ ID NOs. 3771–4376, nucleic acid fragments of SEQ ID NOs. 3771–4376, and nucleotide sequences having at least 90%, preferably at least 95%, more preferably at least 99%, and most preferably at least 99.9% homology to SEQ ID NOs. 3771–4376. In another more preferred embodiment, the computer readable medium comprises an array of ESTs selected from the group consisting of SEQ ID NOs. 3771–4376.

In another preferred embodiment, the computer readable medium comprises an array of *Aspergillus oryzae* ESTs selected from the group consisting of SEQ ID NOs. 4377–7401, nucleic acid fragments of SEQ ID NOs. 4377–7401, and nucleic acid sequences having at least 90%, preferably at least 95%, more preferably at least 99%, and most preferably at least 99.9% homology to the sequences of SEQ ID NOs. 4377–7401. In another more preferred embodiment, the computer readable medium comprises an array of ESTs selected from the group consisting of SEQ ID NOs. 4377–7401.

In another preferred embodiment, the computer readable medium comprises an array of *Trichoderma reesei* ESTs selected from the group consisting of SEQ ID NOs. 7402–7860, nucleic acid fragments of SEQ ID NOs. 7402–7860, or nucleic acid sequences having at least 95%, preferably at least 99% and most preferably at least 99.9% homology to a sequence of SEQ ID NOs. 7402–7860. In another more preferred embodiment, the computer readable medium comprises an array of *Trichoderma reesei* ESTs selected from the group consisting of SEQ ID NOs. 7402–7860.

In one application of this embodiment, the ESTs of the present invention can be recorded on computer readable media. The term "computer readable media" is defined herein as any medium which can be read and accessed directly by a computer. Such computer readable media include, but are not limited to, magnetic storage media, e.g., floppy discs, hard disc storage medium, and magnetic tape; optical storage media, e.g., CD-ROM, DVD; electrical storage media, e.g., RAM and ROM; and hybrids of these categories, e.g., magnetic/optical storage media. One skilled in the art can readily appreciate how any of the presently known computer readable media can be used to create a manufacture comprising computer readable medium having recorded thereon a nucleotide sequence of the present invention. Likewise, it will be clear to those of skill how additional computer readable media that may be developed also can be used to create analogous manufactures having recorded thereon a nucleotide sequence of the present invention.

As used herein, "recorded" refers to a process for storing information on computer readable medium. One skilled in the art can readily adopt any of the presently known methods for recording information on computer readable medium to generate manufactures comprising the nucleotide sequence information of the present invention.

A variety of data storage structures are available for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data-processor structuring formats (e.g., text file or database) in order to obtain computer readable medium having recorded thereon the nucleotide sequence information of the present invention.

Various computer software are publicly available that allow a skilled artisan to access sequence information provided in a computer readable medium. Thus, by providing in computer readable form an array of ESTs selected from the group consisting of SEQ ID NOs. 1–7860, nucleic acid fragments of SEQ ID NOs. 1–7860, and nucleic acid sequences having at least 90%, preferably at least 95%, more preferably at least 99%, and most preferably at least 99.9% homology to SEQ ID NOs. 1–7860 enables one skilled in the art to routinely access the provided sequence information for a wide variety of purposes.

Software utilizing the BLAST (Altschul et al., 1990, *Journal of Molecular Biology* 215: 403–410) and BLAZE (Brutlag et al., 1993, *Comp. Chem.* 17: 203–207) search algorithms may be used to identify open reading frames (ORFs) within a genome of interest, which contain homology to ORFs or proteins from both *Fusarium venenatum, Aspergillus niger, Aspergillus oryzae*, or *Trichoderma reesei* and from other organisms. Among the ORFs discussed herein are protein encoding fragments of the *Fusarium venenatum, Aspergillus niger, Aspergillus oryzae*, and *Trichoderma reesei* genome useful in producing commercially important proteins, such as enzymes used in fermentation reactions and in the production of commercially useful metabolites.

The present invention further provides systems, particularly computer-based systems, which contain the sequence information described herein. Such systems are designed to identify, among other things, genes and gene products—many of which could be products themselves or used to genetically modify an industrial expression host through increased or decreased expression of a specific gene sequence(s).

The term "a computer-based system" is defined here the hardware means, software means, and data storage means used to analyze the nucleotide sequence information of the present invention. The minimum hardware means of the computer-based systems of the present invention comprises a central processing unit (CPU), input means, output means, and data storage means. One skilled in the art can readily appreciate that any currently available computer-based system is suitable for use in the present invention.

As stated above, the computer-based systems of the present invention comprise a data storage means having stored therein a nucleotide sequence of the present invention and the necessary hardware means and software means for supporting and implementing a search means.

The term "data storage means" is defined herein as memory which can store nucleotide sequence information of the present invention, or a memory access means which can access manufactures having recorded thereon the nucleotide sequence information of the present invention.

The term "search means" refers is defined herein as one or more programs which are implemented on the computer-based system to compare a target sequence or target structural motif with the sequence information stored within the data storage means. Search means are used to identify fragments or regions of the present genomic sequences which match a particular target sequence or target motif. A variety of known algorithms are disclosed publicly and a variety of commercially available software for conducting search means are and can be used in the computer-based systems of the present invention. Examples of such software includes, but is not limited to, MacPattern (Fuchs, 1991, *Comput. Appl. Biosci*. 7: 105–106), BLASTN and BLASTX (NCBI). One skilled in the art can readily recognize that any one of the available algorithms or implementing software packages for conducting homology searches can be adapted for use in the present computer-based systems.

The term "target sequence" is defined here as any DNA or amino acid sequence of six or more nucleotides or two or more amino acids. One skilled in the art can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

The term "a target structural motif" or "target motif" is defined herein as any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences, substrate and cofactor binding domains, transmembrane domains, and sites for post-translational modifications. Nucleic acid target motifs include, but are not limited to, promoter sequences, hairpin structures and inducible expression elements (protein binding sequences), repeats, palindromes, dyad symmetries, intron-exon boundaries, transcription and translation start and stop sites, and polyadenylation signals.

A variety of structural formats for the input and output means can be used to input and output the information in the computer-based systems of the present invention. A preferred format for an output means ranks fragments of the *Fusarium venenatum, Aspergillus niger, Aspergillus oryzae*, and *Trichoderma reesei* genomic sequences possessing varying degrees of homology to the target sequence or target motif. Such presentation provides one skilled in the art with a ranking of sequences which contain various amounts of the target sequence or target motif and identifies the degree of homology contained in the identified fragment.

A variety of comparing means can be used to compare a target sequence or target motif with the data storage means to identify sequence fragments of the *Fusarium venenatum, Aspergillus niger, Aspergillus oryzae*, and *Trichoderma reesei* genomes. For example, implementing software which utilize the BLAST and BLAZE algorithms, described in Altschul et al., 1990, *Journal of Molecular Biology* 215: 403–410, may be used to identify open reading frames within the *Fusarium venenatum, Aspergillus niger, Aspergillus oryzae*, or *Trichoderma reesei* genome or the genomes of other organisms. A skilled artisan can readily recognize that any one of the publicly available homology search programs can be used as the search means for the computer-based systems of the present invention. Of course, suitable proprietary systems that may be known to those of skill also may be employed in this regard.

Tables 1–4 in the present application provide listings of sequences, which can be products themselves or used to genetically modify an industrial expression host through increased or decreased expression of a specific gene sequence(s). These were generated by applying the above-mentioned computer based systems to the sequences of the invention. Tables 1–4 are generally referred to as lists of annotated EST sequences and furthermore serve an important task in the interpretation of the data generated by the method of the present invention.

Substrates

The present invention also relates to substrates as described herein comprising an array of filamentous fungal ESTs. In a preferred embodiment, the substrate comprises an array of filamentous fungal ESTs selected from the group consisting of SEQ ID NOs. 1–7860, nucleic acid fragments of SEQ ID NOs. 1–7860, and nucleic acid sequences having at least 90%, preferably at least 95%, more preferably at least 99%, and most preferably at least 99.9% homology to SEQ ID NOs. 1–7860. In a more preferred embodiment, the substrate comprises an array of EST sequences selected from the group consisting of SEQ ID NOs. 1–7860.

In a preferred embodiment, the substrate comprises an array of *Fusarium venenatum* ESTs selected from the group consisting of SEQ ID NOs. 1–3770, nucleic acid fragments of SEQ ID NOs. 1–3770, and nucleic acid sequences having at least 90%, preferably at least 95%, more preferably at least 99%, and most preferably at least 99.9% homology to SEQ ID NOs. 1–3770. In a more preferred embodiment, the substrate comprises an array of *Fusarium venenatum* ESTs selected from the group consisting of SEQ ID NOs. 1–3770.

In another preferred embodiment, the substrate comprises an array of *Aspergillus niger* ESTs selected from the group consisting of SEQ ID NOs. 3771–4376, nucleic acid fragments of SEQ ID NOs. 3771–4376, and nucleotide sequences having at least 90%, preferably at least 95%, more preferably at least 99%, and most preferably at least 99.9% homology to SEQ ID NOs. 3771–4376. In another more preferred embodiment, the substrate comprises an array of *Aspergillus niger* ESTs selected from the group consisting of SEQ ID NOs.3771–4376.

In another preferred embodiment, the substrate comprises an array of *Aspergillus oryzae* ESTs selected from the group consisting of SEQ ID NOs. 4377–7401, nucleic acid fragments of SEQ ID NOs. 4377–7401, and nucleic acid sequences having at least 90%, preferably at least 95%, more preferably at least 99%, and most preferably at least 99.9% homology to the sequences of SEQ ID NOs. 4377–7401. In another more preferred embodiment, the substrate comprises an array of *Aspergillus oryzae* ESTs selected from the group consisting of SEQ ID NOs. 4377–7401.

In another preferred embodiment, the substrate comprises an array of *Trichoderma reesei* ESTs selected from the group consisting of SEQ ID NOs. 7402–7860, nucleic acid fragments of SEQ ID NOs. 7402–7860, or nucleic acid sequences having at least 95%, preferably at least 99% and most preferably at least 99.9% homology to a sequence of SEQ ID NOs. 7402–7860. In another more preferred embodiment, the substrate comprises an array of *Trichoderma reesei* ESTs selected from the group consisting of SEQ ID NOs. 7402–7860.

Isolated Nucleic Acids

The present invention also relates to isolated filamentous fungal ESTs.

In a preferred embodiment, the isolated ESTs are *Fusarium venenatum* ESTs selected from the group consisting of SEQ ID NOs. 1–3770, nucleic acid fragments of SEQ ID NOs. 1–3770, and nucleic acid sequences having at least 90%, preferably at least 95%, more preferably at least 99%, and most preferably at least 99.9% homology to SEQ ID NOs. 1–3770. In a more preferred embodiment, the *Fusarium venenatum* ESTs are SEQ ID NOs. 1–3770.

In another preferred embodiment, the isolated ESTs are *Aspergillus niger* ESTs selected from the group consisting of SEQ ID NOs. 3771–4376, nucleic acid fragments of SEQ ID NOs. 3771–4376, and nucleotide sequences having at least 90%, preferably at least 95%, more preferably at least 99%, and most preferably at least 99.9% homology to SEQ ID NOs. 3771–4376. In another more preferred embodiment, the *Aspergillus niger* ESTs are SEQ ID NOs. 3771–4376.

In another preferred embodiment, the isolated ESTs are *Aspergillus oryzae* ESTs selected from the group consisting of SEQ ID NOs. 4377–7401, nucleic acid fragments of SEQ ID NOs. 4377–7401, and nucleic acid sequences having at least 90%, preferably at least 95%, more preferably at least 99%, and most preferably at least 99.9% homology to the sequences of SEQ ID NOs. 4377–7401.

In another preferred embodiment, the isolated ESTs are *Trichoderma reesei* ESTs selected from the group consisting of SEQ ID NOs. 7402–7860, nucleic acid fragments of SEQ ID NOs. 7402–7860, or nucleic acid sequences having at least 95%, preferably at least 99% and most preferably at least 99.9% homology to a sequence of SEQ ID NOs. 7402–7860. In another more preferred embodiment, the *Trichoderma reesei* ESTs are SEQ ID NOs. 7402–7860.

The present invention also relates to isolated nucleic acid sequences comprising any of the filamentous fungal ESTs selected from the group consisting of SEQ ID NOs. 1–7860, nucleic acid fragments of SEQ ID NOs. 1–7860, and nucleic acid sequences having at least 90%, preferably at least 95%, more preferably at least 99%, and most preferably at least 99.9% homology to the sequences of SEQ ID NOs. 1–7860.

The present invention is further described by the following examples which should not be construed as limiting the scope of the invention.

EXAMPLES

Chemicals used as buffers and substrates were commercial products of at least reagent grade.

Example 1

Fermentation and Mycelial Tissue

*Fusarium venenatum* CC1-3, a morphological mutant of *Fusarium* strain ATCC 20334 (Wiebe et al., 1991, *Mycol. Research* 95: 1284–1288), was grown in a two-liter lab-scale fermentor using a fed-batch fermentation scheme with maltose syrup as the carbon source and yeast extract. Ammonium phosphate was provided in the feed. The pH was maintained at 6 to 6.5, and the temperature was kept at 30° C. with positive dissolved oxygen. Mycelial samples were harvested at 2, 4, 6, and 8 days post-inoculum and quick-frozen in liquid nitrogen. The samples were stored at −80° C. until they were disrupted for RNA extraction.

*Aspergillus niger* strain Bo-95 was fermented in a minimal salts, maltodextrin based medium with a subsequent carbon feed of glucose at pH 4.75 and 34° C. Mycelia were harvested and frozen at −80° C. The *Aspergillus niger* mycelial sample was ground to a fine powder in the presence of liquid nitrogen prior to extraction of total cellular RNA.

*Aspergillus oryzae* strain A1560 (IFO 4177) was grown in two 20-liter lab fermentors on a 10-liter scale at 34° C. using yeast extract and dextrose in the batch medium, and maltose syrup, urea, yeast extract, and trace metals in the feed. Fungal mycelia from the first lab fermentor were harvested by filtering through a cellulose filter (pore size 7–11 microns) after 27 hours, 68.5 hours, 118 hours, and 139 hours of growth. The growth conditions for the second fermentor were identical to the first one, except for a slower growth rate during the first 20 hours of fermentation. Fungal mycelia from the second lab fermentor were harvested as above after 68.3 hours of growth. The harvested mycelia were immediately frozen in liquid $N_2$ and stored at −80° C.

The *Aspergillus oryzae* strain A1560 was also grown in four 20-liter lab fermentors on a 10-liter scale at 34° C. using sucrose in the batch medium, and maltose syrup, ammonia, and yeast extract in the feed.

The first of the four fermentations was carried out at pH 4.0.

The second of the four fermentations was carried out at pH 7.0 with a constant low agitation rate (550 rpm) to achieve the rapid development of reductive metabolism.

The third of the four fermentations was carried out at pH 7.0 under phosphate limited growth by lowering the amount of phosphate and yeast extract added to the batch medium.

The fourth of the four fermentations was carried out at pH 7.0 and 39° C. After 75 hours of fermentation the temperature was lowered to 34° C. At 98 hours of fermentation the addition of carbon feed was stopped and the culture was allowed to starve for the last 30 hours of the fermentation.

Fungal mycelial samples from the four lab fermentors above were then collected as described above, immediately frozen in liquid $N_2$, and stored at −80° C.

*Aspergillus oryzae* strain A1560 was also grown on Whatman filters placed on Cove-N agar plates for two days. The mycelia were collected, immediately frozen in liquid $N_2$, and stored at −80° C.

*Aspergillus oryzae* strain A1560 was also grown at 30° C. in 150 ml shake flasks containing RS-2 medium (Kofod et al., 1994, *Journal of Biological Chemistry* 269: 29182–29189) or a defined minimal medium. Fungal mycelia were collected after 5 days of growth in the RS-2 medium and 3 and 4 days of growth in the defined minimal medium, immediately frozen in liquid $N_2$, and stored at −80° C.

*Aspergillus oryzae* strain AL-11 was fermented similarly as described above for *Aspergillus oryzae* strain A1560 in a 20-liter lab fermentor on a 10-liter scale at 34° C. using yeast extract and dextrose in the batch medium, and maltose syrup, urea, yeast extract, and trace metals in the feed with a slow growth rate during the first 20 hours of fermentation. Fungal mycelia were harvested at 74.1 hours as above, immediately frozen in liquid $N_2$ and stored at −80° C.

*Trichoderma reesei* strain RutC-30 (Montenecourt and Eveleigh, 1979, *Adv. Chem. Ser.* 181: 289–301) was cultivated in a pilot scale fermentation tank in growth medium containing a complex carbon source. Fungal mycelium was collected from a one-liter sample, and immediately frozen in liquid $N_2$ and stored at −80° C.

Example 2

*Fusarium venenatum* Directional cDNA Library Construction

Total cellular RNA was extracted from the *Fusarium venenatum* mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 μg of poly(A)+mRNA according to the method of Gubler and Hoffman (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen Corporation, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent *E. coli* TOP 10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) which contained kanamycin at a final concentration of 50 μg/ml.

Two independent directional cDNA libraries were constructed using the plasmid cloning vector pZErO-2.1. Library A was made using mRNA from mycelia harvested at four days, and Library B was constructed with mRNA from the six day time point. One library (prepared from 4 day cells) consisted about $7.5 \times 10^4$ independent clones and a second library B (prepared from 6 day cells) consisted of roughly $1.2 \times 10^5$ clones. Miniprep DNA was isolated from forty colonies in each library and checked for the presence and size of cDNA inserts. In this analysis 39 of 40 colonies (97.5%) from Library A contained inserts with sizes ranging from 600 bp to 2200 bp (avg.=1050 bp). Similarly, 39 of 40 colonies (97.5%) picked from Library B had inserts with sizes ranging from 800 bp to 3600 bp (avg.=1380 bp). Each of these libraries was amplified using standard techniques (Birren, et al., 1998, *Genome Analysis*, Volume 2, *Detecting Genes, A Laboratory Manual*. Cold Spring Harbor Laboratory Press, Cold Spring Harbor, N.Y.), and each amplified library was stored as a DNA pool at 4° C. in 10 mM Tris-HCl, pH 7.6, 1 mM EDTA.

Example 3

*Fusarium venenatum* EST Template Preparation

From each directional cDNA library described in Example 2, transformant colonies were picked directly from the transformation plates into 96-well microtiter dishes which contained 200 μl of 2YT broth (Miller, 1992, supra) with 50 μg/ml kanamycin. The plates were incubated overnight at 37° C. without shaking. After incubation 100 μl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 μg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover. DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8).

Example 4

*Aspergillus niger* Directional cDNA Library Construction

Total cellular RNA was extracted from the *Aspergillus niger* mycelial samples described in Example 1 using a QiaEasy RNA maxi kit (QIAGEN, Valencia, Calif.) with the following modification. The extract was sheared by passage up and down in a 16-guage needle three times before the addition of the 70% ethanol step. PolyA+RNA was isolated using a Qiagen Oligotex kit following the instructions provided by the manufacturer (QIAGEN, Valencia, Calif.).

Double-stranded cDNA was synthesized from 5 μg of *Aspergillus oryzae* A1560 poly(A)$^+$ RNA by the RNasc H method (Gubler and Hoffman 1983, *Gene* 25: 263–269; Sambrook et al., 1989, *Molecular Cloning: A Laboratory Manual*, Cold Spring Harbor Laboratory, Cold Spring Harbor, N.Y.) using a hair-pin modification. The poly(A)$^+$ RNA (5 μg in 5 μl of 0.1% diethylpyrocarbonate-treated water) was heated at 70° C. for 8 minutes in a pre-siliconized, RNase-free Eppendorf tube, quenched on ice, and combined in a final volume of 50 μl with reverse transcriptase buffer (50 mM Tris-Cl pH 8.3, 75 mM KCl, 3 mM MgCl$_2$, 10 mM DTT) containing 1 mM of dATP, dGTP and dTTP, and 0.5 mM of 5-methyl-dCTP (Pharmacia, Uppsala, Sweden), 40 units of human placental ribonuclease inhibitor (Promega, Madison, Wis.), 4.81 μg of oligo(dT)$_{18}$-NotI primer (Pharmacia, Uppsala, Sweden) and 1000 units of SuperScript II RNase H-reverse transcriptase (Life Technologies, Gaithersburg, Md.).

First-strand cDNA was synthesized by incubating the reaction mixture at 45° C. for 1 hour. After synthesis, the mRNA:cDNA hybrid mixture was gel filtrated through a MicroSpin S-400 HR (Pharmacia, Uppsala, Sweden) spin column according to the manufacturer's instructions.

After gel filtration, the hybrids were diluted in 250 μl of second strand buffer (20 mM Tris-Cl pH 7.4, 90 mM KCl, 4.6 mM MgCl$_2$, 10 mM (NH$_4$)$_2$SO$_4$, 0.16 mM βNAD$^+$) containing 200 μM of each dNTP, 60 units of *E. coli* DNA polymerase I (Pharmacia, Uppsala, Sweden), 5.25 units of RNase H (Promega, Madison, Wis.), and 15 units of *E. coli* DNA ligase (Boehringer Mannheim, Indianapolis, Ind.). Second strand cDNA synthesis was performed by incubating the reaction tube at 16° C. for 2 hours, and an additional 15 minutes at 25° C. The reaction was stopped by addition of EDTA to 20 mM final concentration followed by phenol and chloroform extractions.

The double-stranded cDNA was purified using a QiaQuick PCR spin column according to the manufacturer's instructions (QIAGEN, Valencia, Calif.), washed in 70% ethanol, dried (SpeedVac), and resuspended in 30 μl of Mung bean nuclease buffer (30 mM sodium acetate pH 4.6, 300 mM NaCl, 1 mM ZnSO$_4$, 0.35 mM dithiothreitol, 2% glycerol) containing 25 units of Mung bean nuclease (Pharmacia, Uppsala, Sweden). The single-stranded hair-pin DNA was clipped by incubating the reaction at 30° C. for 30 minutes, followed by addition of 70 μl of 10 mM Tris-Cl, pH 7.5, 1 mM EDTA, phenol extraction, and ethanol precipitation with 2 volumes of 96% ethanol and 0.1 volume 3 M sodium acetate pH 5.2 on ice for 30 minutes.

After treatment of the cDNA with mung bean nuclease, the cDNA was cut with the restriction endonuclease NotI. The cDNA was ligated into a pZERo2 vector (Invitrogen, Carlsbad, Calif.) that had been previously cut with restriction endonucleases EcoRV and NotI. The ligation mixture was used to transform by electroporation *E. coli* strain DH10B (Life Technologies, Gaithersburg, Md.) to generate approximately 4.5 million kanamycin resistant transformants. The transformants were plated onto 2YT agar plates containing 50 μg/ml kanamycin. The colonies were harvested and DNA was isolated using Qiagen Maxi kits (QIAGEN, Valencia, Calif.) and the instructions supplied by the manufacturer.

An aliquot of the *Aspergillus niger* DNA preparation was cut with restriction endonuclease NotI and run on an agarose gel. Based upon the migration of standard DNA markers, a band containing DNA from molecular size approximately 3.8 kb to 6.1 kb was excised from the gel and purified with a QiaExII purification kit (QIAGEN, Valencia, Calif.). The cDNA was ligated with T4 DNA polymerase using standard conditions, and used to transform *E. coli* strain DH10B to kanamycin resistance by electroporation to generate colonies for sequence analysis.

Example 5

*Aspergillus niger* EST Template Preparation cDNA was isolated from individual kanamycin resistant colonies using a Qiagen 96-well manifold plasmid preparation system (QIAGEN, Valencia, Calif.) and the instructions supplied by the manufacturer.

Example 6

*Aspergillus oryzae* Directional cDNA Library Construction

Total RNA was prepared from the *Aspergillus oryzae* mycelial samples described in Example 1 by extraction with guanidinium thiocyanate followed by ultracentrifugation through a 5.7 M CsCl cushion (Chirgwin et al., 1979, *Biochemistry* 18: 5294–5299) using the following modifications. The frozen mycelia were ground in liquid N$_2$ to a fine powder with a mortar and a pestle, followed by grinding in a precooled coffee mill, and immediately suspended in 5 volumes of RNA extraction buffer (4 M guanidinium thiocyanate, 0.5% sodium laurylsarcosine, 25 mM sodium citrate pH 7.0, 0.1 M β-mercaptoethanol). The mixture was stirred for 30 minutes at room temperature and centrifuged (20 minutes at 10 000 rpm, Beckman) to pellet the cell debris. The supernatant was collected, carefully layered onto a 5.7 M CsCl cushion (5.7 M CsCl, 10 mM EDTA, pH 7.5, 0.1% DEPC; autoclaved prior to use) using 26.5 ml supematant per 12.0 ml of CsCl cushion, and centrifuged to obtain the total RNA (Beckman, SW 28 rotor, 25 000 rpm, room temperature, 24 hours). After centrifugation the supernatant was carefully removed and the bottom of the tube containing the RNA pellet was cut off and rinsed with 70% ethanol. The total RNA pellet was transferred to an Eppendorf tube, suspended in 500 μl of TE, pH 7.6 (if difficult, heat occasionally for 5 minutes at 65° C.), phenol extracted, and precipitated with ethanol for 12 hours at –20° C. (2.5 volumes of ethanol, 0.1 volume of 3M sodium acetate pH 5.2). The RNA was collected by centrifugation, washed in 70% ethanol, and resuspended in a minimum volume of DEPC. The RNA concentration was determined by measuring OD$_{260/280}$.

The poly(A)$^+$ RNA was isolated by oligo(dT)-cellulose affinity chromatography (Aviv & Leder, 1972, *Proceedings of the National Academy of Sciences USA* 69: 1408–1412). A total of 0.2 g of oligo(dT) cellulose (Boehringer Mannheim, Indianapolis, Ind.) was preswollen in 10 ml of 1× of column loading buffer (20 mM Tris-Cl, pH 7.6, 0.5 M NaCl, 1 mM EDTA, 0.1% SDS), loaded onto a DEPC-treated, plugged plastic column (Poly Prep Chromatography Column, BioRad, Hercules, Calif.), and equilibrated with 20 ml of 1× loading buffer. The total RNA (1–2 mg) was heated at 65° C. for 8 minutes, quenched on ice for 5 minutes, and after addition of 1 volume of 2× column loading buffer to the RNA sample loaded onto the column. The eluate was collected and reloaded 2–3 times by heating the sample as above and quenching on ice prior to each loading. The oligo(dT) column was washed with 10 volumes of 1× loading buffer, then with 3 volumes of medium salt buffer (20 mM Tris-Cl, pH 7.6, 0.1 M NaCl, 1 mM EDTA, 0.1% SDS), followed by elution of the poly(A)$^+$RNA with 3 volumes of elution buffer (10 mM Tris-Cl, pH 7.6, 1 mM EDTA, 0.05% SDS) preheated to 65° C., by collecting 500 µl fractions. The $OD_{260}$ was read for each collected fraction, and the mRNA containing fractions were pooled and ethanol precipitated at −20° C. for 12 hours. The poly(A)$^+$ RNA was collected by centrifugation, resuspended in DEPC-DIW and stored in 5–10 µg aliquots at −80° C.

Double-stranded cDNA was synthesized from 5 µg of *Aspergillus oryzae* A1560 poly(A)$^+$ RNA by the RNase H method (Gubler and Hoffman 1983, supra; Sambrook et al., 1989, supra) using a hair-pin modification. The poly(A)$^+$ RNA (5 µg in 5 µl of DEPC-treated water) was heated at 70° C. for 8 minutes in a pre-siliconized, RNase-free Eppendorf tube, quenched on ice, and combined in a final volume of 50 µl with reverse transcriptase buffer (50 mM Tris-Cl pH 8.3, 75 mM KCl, 3 mM $MgCl_2$, 10 mM DTT) containing 1 mM of dATP, dGTP and dTTP, and 0.5 mM of 5-methyl-dCTP, 40 units of human placental ribonuclease inhibitor, 4.81 µg of oligo(dT)$_{18}$-NotI primer and 1000 units of SuperScript II RNase H-reverse transcriptase.

First-strand cDNA was synthesized by incubating the reaction mixture at 45° C. for 1 hour. After synthesis, the mRNA:cDNA hybrid mixture was gel filtrated through a Pharmacia MicroSpin S-400 HR spin column according to the manufacturer's instructions.

After the gel filtration, the hybrids were diluted in 250 µl of second strand buffer (20 mM Tris-Cl pH 7.4, 90 mM KCl, 4.6 mM $MgCl_2$, 10 mM $(NH_4)_2SO_4$, 0.16 mM $BNAD^+$) containing 200 µM of each dNTP, 60 units of *E. coli* DNA polymerase I (Pharmacia, Uppsala, Sweden), 5.25 units of RNase H, and 15 units of *E. coli* DNA ligase. Second strand cDNA synthesis was performed by incubating the reaction tube at 16° C. for 2 hours, and an additional 15 minutes at 25° C. The reaction was stopped by addition of EDTA to 20 mM final concentration followed by phenol and chloroform extractions.

The double-stranded cDNA was ethanol precipitated at −20° C. for 12 hours by addition of 2 volumes of 96% ethanol and 0.2 volume of 10 M ammonium acetate, recovered by centrifugation, washed in 70% ethanol, dried (SpeedVac), and resuspended in 30 µl of Mung bean nuclease buffer (30 mM sodium acetate pH 4.6, 300 mM NaCl, 1 mM $ZnSO_4$, 0.35 mM dithiothreitol, 2% glycerol) containing 25 units of Mung bean nuclease. The single-stranded hair-pin DNA was clipped by incubating the reaction at 30° C. for 30 minutes, followed by addition of 70 µl of 10 mM Tris-Cl, pH 7.5, 1 mM EDTA, phenol extraction, and ethanol precipitation with 2 volumes of 96% ethanol and 0.1 volume 3 M sodium acetate pH 5.2 on ice for 30 minutes.

The double-stranded cDNAs were recovered by centrifugation (20,000 rpm, 30 minutes), and blunt-ended with T4 DNA polymerase in 30 µl of T4 DNA polymerase buffer (20 mM Tris-acetate, pH 7.9, 10 mM magnesium acetate, 50 mM potassium acetate, 1 mM dithiothreitol) containing 0.5 mM of each dNTP, and 5 units of T4 DNA polymerase by incubating the reaction mixture at +16° C. for 1 hour. The reaction was stopped by addition of EDTA to 20 mM final concentration, followed by phenol and chloroform extractions and ethanol precipitation for 12 h at −20° C. by adding 2 volumes of 96% ethanol and 0.1 volume of 3M sodium acetate pH 5.2.

After the fill-in reaction the cDNAs were recovered by centrifugation as above, washed in 70% ethanol, and the DNA pellet was dried in a SpeedVac. The cDNA pellet was resuspended in 25 µl of ligation buffer (30 mM Tris-Cl, pH 7.8, 10 mM $MgCl_2$, 10 mM dithiothreitol, 0.5 mM ATP) containing 2 µg EcoRI adaptors (0.2 µg/µl, Pharmacia, Uppsala, Sweden) and 20 units of T4 ligase by incubating the reaction mix at 16° C. for 12 hours. The reaction was stopped by heating at 65° C. for 20 minutes, and then placed on ice for 5 minutes. The adapted cDNA was digested with NotI by addition of 20 µl autoclaved water, 5 µl of 10×NotI restriction enzyme buffer and 50 units of NotI, followed by incubation for 3 hours at 37° C. The reaction was stopped by heating the sample at 65° C. for 15 minutes. The cDNAs were size-fractionated by agarose gel electrophoresis on a 0.8% SeaPlaque GTG low melting temperature agarose gel (FMC, Rockland, Me.) in 1×TBE (in autoclaved water) to separate unligated adaptors and small cDNAs. The gel was run for 12 hours at 15 V, and the cDNA was size-selected with a cut-off at 0.7 kb by cutting out the lower part of the agarose gel. Then a 1.5% agarose gel was poured in front of the cDNA-containing gel, and the double-stranded cDNAs were concentrated by running the gel backwards until it appeared as a compressed band on the gel. The cDNA-containing gel piece was cut out from the gel and the cDNA was extracted from the gel using the GFX gel band purification kit (Amersham, Arlington Heights, Ill.) as follows. The trimmed gel slice was weighed in a 2 ml Biopure Eppendorf tube, then 10 ml of Capture Buffer was added for each 10 mg of gel slice, the gel slice was dissolved by incubation at 60° C. for 10 minutes, until the agarose was completely solubilized, the sample at the bottom of the tube by brief centrifugation. The melted sample was transferred to the GFX spin column placed in a collection tube, incubated at 25° C. for 1 minite, and then spun at full speed in a microcentrifuge for 30 seconds. The flow-through was discarded, and the column was washed with 500 µl of wash buffer, followed by centrifugation at full speed for 30 seconds. The collection tube was discarded, and the column was placed in a 1.5 ml Eppendorf tube, followed by elution of the cDNA by addition of 50 µl of TE pH 7.5 to the center of the column, incubation at 25° C. for 1 minute, and finally by centrifugation for 1 minute at maximum speed. The eluted cDNA was stored at −20° C. until library construction.

A plasmid DNA preparation for a EcoRI-NotI insert-containing pYES2.0 cDNA clone, was purified using a QIAGEN Tip-100 according to the manufacturer's instructions (QIAGEN, Valencia, Calif. A total of 10 µg of purified plasmid DNA was digested to completion with NotI and EcoRI in a total volume of 60 µl by addition of 6 µl of 10× NEBuffer for EcoRI (New England Biolabs, Beverly, Mass.), 40 units of NotI, and 20 units of EcoRI followed by incubation for 6 hours at 37° C. The reaction was stopped by heating the sample at 65° C. for 20 minutes. The digested plasmid DNA was extracted once with phenol-chloroform, then with chloroform, followed by ethanol precipitation for 12 hours at −20° C. by adding 2 volumes of 96% ethanol and 0.1 volume of 3 M sodium acetate pH 5.2. The precipitated DNA was resuspended in 25 µl of 1×TE pH 7.5, loaded on a 0.8% SeaKem agarose gel in 1×TBE, and run on the gel for 3 hours at 60 V. The digested vector was cut out from the gel, and the DNA was extracted from the gel using the GFX gel band purification kit (Amersham-Pharmacia Biotech, Uppsala, Sweden) according to the manufacturer's instructions. After measuring the DNA concentration by $OD_{260/280}$, the eluted vector was stored at −20° C. until library construction.

To establish the optimal ligation conditions for the cDNA library, four test ligations were carried out in 10 µl of ligation buffer (30 mM Tris-Cl pH 7.8, 10 mM MgCl$_2$, 10 mM DTT, 0.5 mM ATP) containing 7 µl of double-stranded cDNA, (corresponding to approximately 1/10 of the total volume in the cDNA sample), 2 units of T4 ligase, and 25 ng, 50 ng and 75 ng of EcoRI-NotI cleaved pYES2.0 vector, respectively (Invitrogen). The vector background control ligation reaction contained 75 ng of EcoRI-NotI cleaved pYES.0 vector without cDNA. The ligation reactions were performed by incubation at 16° C. for 12 hours, heated at 65° C. for 20 minutes, and then 10 µl of autoclaved water was added to each tube. One µl of the ligation mixtures was electroporated (200 W, 2.5 kV, 25 mF) to 40 µl electrocompetent E. coli DH10B cells (Life Technologies, Gaithersburg, Md.). After addition of 1 ml SOC to each transformation mix, the cells were grown at 37° C. for 1 hour, 50 µl and 5 µl from each electroporation were plated on LB plates supplemented with ampicillin at 100 µg per ml and grown at 37° C. for 12 hours. Using the optimal conditions, 18 *Aspergillus oryzae* A1560 cDNA libraries containing 1–2.5×10$^7$ independent colony forming units was established in E. coli, with a vector background of ca. 1%. The cDNA library was stored as (1) individual pools (25,000 c.f.u./pool) in 20% glycerol at –80° C.; (2) cell pellets of the same pools at –20° C.; (3) Qiagen purified plasmid DNA from individual pools at –20° C. (Qiagen Tip 100); and (4) directional, double-stranded cDNA at –20° C.

Example 7

*Aspergillus oryzae* EST Template Preparation

From each cDNA library described in Example 6, transformant colonies were picked directly from the transformation plates into 96-well microtiter dishes (QIAGEN, GmbH, Hilden Germany) which contained 200 µl TB broth (Life Technologies, Frederick Md.) with 100 µg ampicillin per ml. The plates were incubated 24 hours with agitation (300 rpm) on a rotary shaker. To prevent spilling and cross-contamination, and to allow sufficient aeration, the plates were covered with a microporous tape sheet AirPore™ (QIAGEN GmbH, Hilden Germany).

cDNA was isolated from each well using the QIAprep 96 Turbo kit (QIAGEN GmbH, Hilden Germany).

Example 8

*Trichoderma reesei* Directional cDNA Library Construction

Total RNA was prepared from the *Trichoderma reesei* mycelial samples described in Example 1 by extraction with guanidinium thiocyanate followed by ultracentrifugation through a 5.7 M CsCl cushion (Chirgwin et al., 1979, *Biochemistry* 18: 5294–5299) as described in Example 6. The total RNA concentration was determined by measuring OD$_{260/280}$.

The poly(A)$^+$ RNA was isolated by oligo(dT)-cellulose affinity chromatography (Aviv & Leder, 1972, *Proceedings of the National Academy of Sciences USA* 69: 1408–1412) as described in example 6. Double-stranded EcoRI-NotI-directional cDNA was synthesized from 5 µg of *Trichoderma reesei* RutC-30 poly(A)$^+$ RNA by the method described in example 6. The cDNAs were size-fractionated by agarose gel electrophoresis on a 0.8% SeaPlaque GTG low melting temperature agarose gel (FMC, Rockland, Me.) in 1×TBE (in autoclaved water) to separate unligated adaptors and small cDNAs. The gel was run for 12 hours at 15 V, and the cDNA was size-selected with a cut-off at 0.7 kb by cutting out the lower part of the agarose gel. The cDNAs were recovered from the agarose gel as described in Example 6, and ligated into EcoRI-NotI cleaved pYES2.0 vector, using the optimal ligation conditions described in Example 6, resulting in a cDNA library comprising ca.1×10$^7$ independent colony forming units was established in E. coli, with a vector background of 1%. The cDNA library was stored as (1) individual pools (25,000 c.f.u./pool) in 20% glycerol at –80° C.; (2) cell pellets of the same pools at –20° C.; (3) Qiagen purified plasmid DNA from individual pools at –20° C. (Qiagen Tip 100); and (4) directional, double-stranded cDNA at –20° C.

Example 9

*Trichoderma reesei* EST Template Preparation cDNA was isolated from individual *Trichoderma reesei* colonies using a Qiagen 96-well manifold plasmid preparation system (QIAGEN, Valencia, Calif.) and the instructions supplied by the manufacturer.

Example 10

DNA Sequencing and Analysis of Nucleotide Sequence Data of the *Fusarium venenatum* EST Library Single-pass DNA sequencing was conducted with a Perkin-Elmer Applied Biosystems Model 377 XL Automatic DNA Sequencer (Perkin-Elmer Applied Biosystems, Inc., Foster City, Calif.) using dye-terminator chemistry (Glesecke et al., 1992, *Journal of Virology Methods* 38: 47–60) and the reverse lac sequencing primer.

Nucleotide sequence data were scrutinized for quality, and samples giving improper spacing or ambiguity levels exceeding 2% were discarded or re-run. Vector sequences were trimmed manually with assistance of FACTURA™ software (Perkin-Elmer Applied Biosystems, Inc., Foster City, Calif.). In addition, sequences were truncated at the end of each sample when the number of ambiguous base calls increased. All sequences were compared to each other to construct overlapping contigs using AutoAssembler™ software (Perkin-Elmer Applied Biosystems, Inc., Foster City, Calif.). The contigs were subsequently used in combination with TIGR Assembler software (Sutton et al., 1995, *Genome Science and Technology* 1: 9019) to determine multiplicity of various cDNA species represented in each library. Lastly, all sequences were translated in three frames and searched against a non-redundant data base (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

The *Fusarium venenatum* EST sequences are designated SEQ ID NOs. 1–3770. An "N" in a nucleic acid sequence means that the nucleotide is an A, C, G, or T.

Example 11

DNA Sequencing and Analysis of Nucleotide Sequence Data of the *Aspergillus niger* EST Library DNA sequencing was performed as described in Example 10. Following DNA sequencing, the generation of individual EST sequence files was performed by removal of flanking vector and polyA sequences, removal of sequences with a high percentage of ambiguous base calls, and removal of all sequences less than 100 processed nucleotides in length. Contiguous EST sequences were identified using the TIGR Assembler software (Sutton et al., 1995, supra).

The *Aspergillus niger* EST sequences are designated SEQ ID NOs. 3771–4376. An "N" in a nucleic acid sequence means that the nucleotide is an A, C, G, or T.

Example 12

DNA Sequencing and Analysis of Nucleotide Sequence Data of the *Aspergillus oryzae* EST Library Single-pass DNA sequencing of the *Aspergillus oryzae* ESTs was conducted with a Perkin-Elmer Applied Biosystems Model 377 XL Automatic DNA Sequencer (Perkin-Elmer Applied Biosystems, Inc., Foster City, Calif.) using dye-terminator chemistry (Giesecke et al, 1992, *Journal of Virology Methods* 38: 47–60) and a pYES specific primer (Invitrogen, Carlsbad, Calif.). Vector sequences were removed with the crossmatch program from the Phred/Phrap package (Ewing and Green, 1998, *Genome Research* 8: 186–194). The sequences were assembled with Phrap also from the Phred/Phrap package. The assembled sequences were searched with fastx3 (Pearson and Lipman, 1988, *Proceedings of the National Academy of Science USA* 85: 2444–2448; Pearson, 1990, *Methods in Enzymology* 183: 63–98) against a customized database consisting of protein sequences from SWISSPROT, SWISSPROTNEW, TREMBL, TREMBLNEW, REMTREMBL, PDB and GeneSeqP. The matrix used was BL50.

The *Aspergillus oryzae* EST sequences are designated SEQ ID NOs. 4377–7401. An "N" in a nucleic acid sequence means that the nucleotide is an A, C, G, or T.

Example 13

DNA Sequencing and Analysis of Nucleotide Sequence Data of the *Trichoderma reesei* EST Library Single-pass DNA sequencing of the *Trichoderma reesei* ESTs was conducted with a Perkin-Elmer Applied Biosystems Model 377 XL Automatic DNA Sequencer (Perkin-Elmer Applied Biosystems, Inc., Foster City, Calif.) using dye-terminator chemistry (Giesecke et al., 1992, *Journal of Virology Methods* 38: 47–60) and a pYES specific primer (Invitrogen, Carlsbad, Calif.). Vector sequence and low quality 3' sequence were removed with the pregap program from the Staden package (MRC, Cambridge, England). The sequences were assembled with Cap2 (Huang, 1996, *Genomics* 33: 21–31). The assembled sequences were searched with fastx3 (see Pearson and Lipman, 1988, *Proceedings of the National Academy of Science USA* 85: 2444–2448; Pearson, 1990, *Methods in Enzymology* 183: 63–98) against a customized database consisting of protein sequences from SWISSPROT, SWISSPROTNEW, TREMBL, TREMBLNEW, REMTREMBL, PDB and GeneSeqP. The matrix used was BL50.

The *Trichodenna reesei* EST sequences are designated SEQ ID NOs. 7402–7860. An "N" in a nucleic acid sequence means that the nucleotide is an A, C, G, or T.

Example 14

Compilation of *Fusarium venenatum*, *Aspergillus niger*, *Aspergillus oryzae*, and *Trichoderma reesei* ESTs Tables 1–4 summarize the open reading frames (ORFs) in the *Fusarium venenatum*, *Aspergillus oryzae*, *Aspergillus oryzae*, and *Trichoderma reesei* EST sequences of the invention.

The EST's were annotated by searching the databases as specified in Example 12. The description field from the database hit was assigned to a given EST if the z-score exceeded 200.

Functional categorization was done by use of the COG database (Tatusov et al. *Science* 1997 Oct 24; 278). This database contains 21 complete genomes: Each gene in the database is placed into one of the following categories: Translation, ribosomal structure and biogenesis; transcription; DNA replication, recombination and repair; cell division and chromosome partitioning; posttranslational modification, protein turnover, chaperones; cell envelope biogenesis, outer membrane; cell motility and secretion; inorganic ion transport and metabolism; signal transduction mechanisms; energy production and conversion; carbohydrate transport and metabolism; amino acid transport and metabolism; nucleotide transport and metabolism; coenzyme metabolism; lipid metabolism; general function prediction only; and function unknown. The EST's were searched against the COG database with fastx3 and a functional category was assigned to a sequence if a match was found with a z-score higher than 400.

The sequences were furthermore categorized into enzyme families. Examples of such classification are CAZy (Coutinho, P. M. & Henrissat, B., 1999, Carbohydrate-active enzymes: an integrated database approach, In *Recent Advances in Carbohydrate Bioengineering*, H. J. Gilbert, G. Davies, B. Henrissat and B. Svensson, eds., The Royal Society of Chemistry, Cambridge, in press) and (Coutinho, P. M. & Henrissat, B. (1999) The modular structure of cellulases and other carbohydrate-active enzymes: an integrated database approach, In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15–23) accessible from: Coutinho, P. M. & Henrissat, B. (1999); Carbohydrate-Active Enzymes server at URL: http://afmb.cnrs-mrs.fr/~pedro/CAZY/db.html. At this site classifications into (a) Glycosidases and Transglycosidases (or Glycoside Hydrolases), (b) Glycosyltransferases, and (c) Polysaccharide Lyases and Carbohydrate Esterases are available.

Similarly, classifications of peptidases are available at the MEROPS database at http://www.bi.bbsrc.ac.uk/Merops/Merops.htm. This classification is essentially as identified by Rawlings and Barrett (Rawlings N. D., Barrett A. J., 1993, Evolutionary families of peptidases. *Biochemical Journal* 290: 205–218; Rawlings N. D., Barrett A. J., 1994, Families of serine peptidases. *Methods of Enzymology* 244: 19–61; Rawlings N. D., Barrett A. J., 1994, Families of cysteine peptidases. *Methods of Enzymology* 244: 461–486; Rawlings N. D., Barrett A. J., 1995, Families of aspartic peptidases and those of unknown catalytic mechanism, *Methods of Enzymology* 248: 105–120; and Rawlings N. D., Barrett A. J., 1995, Evolutionary families of metallopeptidases, *Methods of Enzymology* 248: 183–228.

Other classifications of lipases and oxidoreductase families were constructed in a similar manner, where structurally related enzymes were separated into distinct categories.

The EST sequences of the invention were compared by means of computer algorithms for homologies to the content of individual families. All sequences from a given family were used individually as a query to search a database of EST sequences of the invention using a number of different homology search algorithms like FASTA and BLAST (W. R. Pearson, 1990, Rapid and Sensitive Sequence Comparison with FASTP and FASTA, *Methods in Enzymology* 183: 63–98; and Altschul, Stephen F., Warren Gish, Webb Miller, Eugene W. Myers, and David J. Lipman, 1990, Basic local alignment search tool, *Journal of Molecular Biology* 215: 403–10). A distinct hit to a sequence of a given family predicted the particular EST sequence to encode a protein of that family. Using this method, part of the EST sequences listed in the table were shown to belong to distinct enzyme families.

TABLE 1

*Fusarium venenatum* ESTs

| Sequence Listing | zscore | Annotation | Database | Functional category |
|---|---|---|---|---|
| 1 | 2667.2 | *Talaromyces emersonii* glucoamylase | geneseqp Y23339 | ND |
| 2 | 4203.8 | ELONGATION FACTOR 2 (EF-2). | swissprot P32324 | ND |
| 3 | 3198.0 | ATP SYNTHASE BETA CHAIN, MITOCHONDRIAL PRECURSOR (EC 3.6.1.34). | swissnew P23704 | ND |
| 4 | 1956.9 | AMMONIUM TRANSPORTER MEPA | sptrembl q9y877 | Inorganic ion transport and metabolism |
| 6 | 2960.4 | ELONGATION FACTOR 1-ALPHA (EF-1-ALPHA). | swissprot P34825 | ND |
| 7 | 2917.2 | ABC1 TRANSPORTER. | sptrembl O13407 | ND |
| 8 | 2791.3 | GAMMA-ACTIN. | tremblnew AAF00008 | ND |
| 9 | 2703.6 | TUBULIN BETA CHAIN. | swissprot P53374 | ND |
| 12 | 2561.0 | CITRATE SYNTHASE, MITOCHONDRIAL PRECURSOR (EC 4.1.3.7). | swissprot P34085 | ND |
| 13 | 2554.9 | 60S RIBOSOMAL PROTEIN L3. | tremblnew AAF15600 | ND |
| 14 | 2522.1 | *Microscilla furvescens* catalase-53CA1. | geneseqp W33810 | Inorganic ion transport and metabolism |
| 15 | 2436.2 | *Cladosporium herbarum* allergen Clah53. | geneseqp R71891 | Energy production and conversion |
| 16 | 2350.6 | THIAZOLE BIOSYNTHETIC ENZYME PRECURSOR (STRESS-INDUCIBLE PROTEIN ST135). | swissprot P23618 | ND |
| 17 | 2331.8 | SUBTILISIN-LIKE PROTEASE PR1H. | tremblnew CAB63907 | Posttranslational modification, protein turnover, chaperones |
| 18 | 2293.3 | ALPHA-TUBULIN. | tremblnew CAA74848 | ND |
| 21 | 2165.4 | GUANINE NUCLEOTIDE-BINDING PROTEIN BETA SUBUNIT-LIKE PROTEIN (CROSS-PATHWAY CONTROL WD-REPEAT PROTEIN CPC-2). | swissprot Q01369 | ND |
| 22 | 2148.3 | AMINO-ACID PERMEASE INDA1. | swissprot P34054 | ND |
| 24 | 2125.9 | NMT1 PROTEIN HOMOLOG. | swissprot P42882 | Inorganic ion transport and metabolism |
| 25 | 2090.9 | PUTATIVE MULTICOPPER OXIDASE YFL041W PRECURSOR (EC 1.-.-.-). | swissprot P43561 | ND |
| 26 | 2082.1 | PLASMA MEMBRANE ATPASE (EC 3.6.1.35) (PROTON PUMP). | swissprot Q07421 | Inorganic ion transport and metabolism |
| 27 | 2071.7 | PLASMA MEMBRANE ATPASE (EC 3.6.1.35) (PROTON PUMP). | swissprot Q07421 | ND |

TABLE 1-continued

*Fusarium venenatum* ESTs

| Sequence Listing | zscore | Annotation | Database | Functional category |
|---|---|---|---|---|
| 28 | 2039.0 | ADP, ATP CARRIER PROTEIN (ADP/ATP TRANSLOCASE) (ADENINE NUCLEOTIDE TRANSLOCATOR) (ANT). | swissprot P02723 | ND |
| 29 | 2026.4 | ATP SYNTHASE ALPHA CHAIN, MITOCHONDRIAL PRECURSOR (EC 3.6.1.34). | swissnew P37211 | ND |
| 30 | 2025.5 | HEAT SHOCK 70 KD PROTEIN. | swissprot Q05944 | Posttranslational modification, protein turnover, chaperones |
| 31 | 1960.7 | *T. harzianum* exochitinase. | geneseqp W01639 | ND |
| 32 | 1916.8 | PUTATIVE DIHYDROXY-ACID DEHYDRATASE, MITOCHONDRIAL PRECURSOR (EC 4.2.1.9) (DAD) (2,3-DIHYDROXY ACID HYDROLYASE). | swissprot Q10318 | ND |
| 33 | 1905.0 | CUTINASE TRANSCRIPTION FACTOR 1 ALPHA. | swissprot P52958 | ND |
| 34 | 1903.2 | EUKARYOTIC INITIATION FACTOR 4A-LIKE PROTEIN C1F5.10. | swissprot Q10055 | ND |
| 35 | 1894.8 | NADH DEHYDROGENASE SUBUNIT. | sptrembl Q01388 | ND |
| 36 | 1869.1 | TRANSLATION RELEASE FACTOR ERF3. | sptrembl O42787 | Amino acid transport and metabolism |
| 37 | 1868.4 | GLYCERALDEHYDE 3-PHOSPHATE DEHYDROGENASE (EC 1.2.1.12) (GAPDH). | swissprot P35143 | ND |
| 38 | 1852.7 | VACUOLAR ATP SYNTHASE CATALYTIC SUBUNIT A (EC 3.6.1.34) (V-ATPASE 67 KD SUBUNIT). | swissprot P11592 | ND |
| 39 | 1838.0 | PEROXISOMAL HYDRATASE-DEHYDROGENASE-EPIMERASE (HDE) (MULTIFUNCTIONAL BETA-OXIDATION PROTEIN) (MFP) [INCLUDES: 2-ENOYL-COA HYDRATASE (EC 4.2.1.-); D-3-HYDROXYACYL COA DEHYDROGENASE (EC 1.1.1.-)]. | swissnew Q01373 | ND |
| 42 | 1816.8 | *N. crassa* glucoamylase. | geneseqp R71034 | ND |
| 43 | 1798.7 | XANTHINE DEHYDROGENASE (EC 1.1.1.204) (PURINE HYDROXYLASE I). | swissprot Q12553 | ND |
| 44 | 1769.7 | 78 KD GLUCOSE-REGULATED PROTEIN HOMOLOG PRECURSOR (GRP 78) (IMMUNOGLOBULIN HEAVY CHAIN BINDING PROTEIN HOMOLOG) (BIP). | swissnew P78695 | ND |
| 45 | 1769.5 | RIBONUCLEOSIDE-DIPHOSPHATE REDUCTASE M2 CHAIN (EC 1.17.4.1) (RIBONUCLEOTIDE REDUCTASE). | swissprot P31350 | Nucleotide transport |
| 47 | 1740.5 | 6-PHOSPHOGLUCONATE DEHYDROGENASE, DECARBOXYLATING 1 (EC 1.1.1.44). | swissprot P38720 | ND |
| 48 | 1711.5 | SERINE/THREONINE PROTEIN PHOSPHATASE | swissprot P48580 | ND |

TABLE 1-continued

_Fusarium venenatum_ ESTs

| Sequence Listing | zscore | Annotation | Database | Functional category |
|---|---|---|---|---|
| | | PP2A CATALYTIC SUBUNIT (EC 3.1.3.16). | | |
| 49 | 1701.5 | GEL1 PROTEIN. | sptrembl O74687 | ND |
| 50 | 1691.1 | PUTATIVE LYSYL-TRNA SYNTHETASE. | tremblnew CAB52801 | ND |
| 51 | 1671.7 | SIMILAR TO GLUTAMATE DECARBOXYLASE. | sptrembl Q05567 | ND |
| 52 | 1634.0 | GLYCOGEN SYNTHASE. | sptrembl O93869 | Cell envelope biogenesis, outer membrane |
| 53 | 1630.0 | CHROMOSOME XVI READING FRAME ORF YPL235W. | sptrembl Q12464 | DNA replication, recombination and repair |
| 54 | 1626.3 | TRANSALDOLASE (EC 2.2.1.2). | sptrembl O42700 | Carbohydrate transport and metabolism |
| 56 | 1614.8 | KETOL-ACID REDUCTOISOMERASE PRECURSOR (EC 1.1.1.86) (ACETOHYDROXY-ACID REDUCTOISOMERASE) (ALPHA-KETO-BETA-HYDROXYLACIL REDUCTOISOMERASE). | swissnew P38674 | Amino acid transport and metabolism |
| 57 | 1609.5 | GLUTAMATE SYNTHASE [NADH] PRECURSOR (EC 1.4.1.14) (NADH-GOGAT). | swissnew Q03460 | ND |
| 58 | 1600.3 | DICARBOXYLIC AMINO ACID PERMEASE. | swissprot P53388 | ND |
| 59 | 1599.3 | Yeast ribosomal protein S7. | geneseqp W36115 | ND |
| 60 | 1579.6 | SODIUM TRANSPORT ATPASE FST. | sptrembl Q00877 | ND |
| 61 | 1577.3 | SIMILAR TO ASPARTATE AMINOTRANSFERASE. | sptrembl Q17994 | Amino acid transport and metabolism |
| 63 | 1562.2 | EUKARYOTIC INITIATION FACTOR 4A (EIF-4A). | swissprot P47943 | ND |
| 65 | 1552.1 | SUCCINATE DEHYDROGENASE [UBIQUINONE] IRON-SULFUR PROTEIN, MITOCHONDRIAL PRECURSOR (EC 1.3.5.1) (IP). | swissnew O42772 | ND |
| 67 | 1546.9 | ACTIN-LIKE PROTEIN 3. | swissprot P78712 | Cell division and chromosome partitioning |
| 68 | 1538.6 | HYPOTHETICAL 44.3 KD PROTEIN C27E2.03C IN CHROMOSOME I. | sptrembl O13998 | ND |
| 69 | 1529.6 | BETA-GLUCOSIDASE 1 PRECURSOR (EC 3.2.1.21) (GENTIOBIASE) (CELLOBIASE) (BETA-D-GLUCOSIDE GLUCOHYDROLASE). | swissprot P48825 | ND |
| 70 | 1528.3 | GLUCOSE-6-PHOSPHATE ISOMERASE (GPI) (EC 5.3.1.9) (PHOSPHOGLUCOSE ISOMERASE) (PGI) (PHOSPHOHEXOSE ISOMERASE) (PHI). | swissprot P12709 | Carbohydrate transport and metabolism |
| 71 | 1527.0 | 2-OXOGLUTARATE DEHYDROGENASE E1 COMPONENT, MITOCHONDRIAL PRECURSOR (EC 1.2.4.2) (ALPHA-KETOGLUTARATE DEHYDROGENASE). | swissprot P20967 | ND |
| 72 | 1505.5 | PROTEIN DISULPHIDE ISOMERASE PRECURSOR. | sptrembl O74568 | ND |
| 74 | 1497.5 | NADH-UBIQUINONE OXIDOREDUCTASE 51 KD | swissprot P24917 | Energy production and |

TABLE 1-continued

*Fusarium venenatum* ESTs

| Sequence Listing | zscore | Annotation | Database | Functional category |
|---|---|---|---|---|
| | | SUBUNIT PRECURSOR (EC 1.6.5.3) (EC 1.6.99.3) (COMPLEX I-51 KD) (CI-51 KD). | | conversion |
| 75 | 1483.5 | HYPOTHETICAL 26.6 KD PROTEIN IN THYA-COTC INTERGENIC REGION. | swissprot O31803 | ND |
| 76 | 1466.7 | 60S RIBOSOMAL PROTEIN L2 (YL6) (L5) (RP8). | swissprot P05736 | ND |
| 77 | 1464.3 | BETA ADAPTIN-LIKE PROTEIN. | sptrembl O81742 | ND |
| 78 | 1461.9 | 60S RIBOSOMAL PROTEIN L5. | swissprot O59953 | ND |
| 79 | 1457.7 | GTP-BINDING NUCLEAR PROTEIN GSP2/CNR2. | swissprot P32836 | ND |
| 80 | 1454.0 | 3-KETOACYL-COA THIOLASE, PEROXISOMAL PRECURSOR (EC 2.3.1.16) (BETA-KETOTHIOLASE) (ACETYL-COA ACYLTRANSFERASE) (PEROXISOMAL 3-OXOACYL-COA THIOLASE). | swissprot Q05493 | ND |
| 81 | 1442.5 | ELONGATION FACTOR 3 (FRAGMENT). | sptrembl O94226 | ND |
| 82 | 1435.1 | 60S RIBOSOMAL PROTEIN L1-B (L10A). | swissprot O74836 | ND |
| 83 | 1432.7 | HEAT SHOCK PROTEIN 70. | sptrembl O42808 | ND |
| 84 | 1427.4 | TRANSCRIPTIONAL ACTIVATOR PROTEIN ACU15 | swissprot P87000 | ND |
| 85 | 1423.2 | INORGANIC PYROPHOSPHATASE (EC 3.6.1.1) (PYROPHOSPHATE PHOSPHO-HYDROLASE) (PPASE). | swissprot O13505 | Energy production and conversion |
| 86 | 1419.8 | MITOCHONDRIAL ATP-DEPENDENT PROTEASE PRECURSOR (EC 3.4.21.-). | swissprot P36775 | Posttranslational modification, protein turnover, chaperones |
| 87 | 1408.4 | 60S RIBOSOMAL PROTEIN L10. | tremblnew CAA22664 | ND |
| 88 | 1405.9 | CHITINASE. | sptrembl Q92222 | ND |
| 89 | 1399.7 | HISTIDINE KINASE (FRAGMENT). | tremblnew AAD40816 | Signal transduction mechanisms |
| 90 | 1389.9 | CUTINASE G-BOX BINDING PROTEIN. | sptrembl Q00878 | ND |
| 91 | 1388.1 | FLAVOHEMOGLOBIN. | sptrembl O74183 | ND |
| 92 | 1384.8 | ACTIN-LIKE PROTEIN. | tremblnew CAB52711 | Cell division and chromosome partitioning |
| 93 | 1383.3 | *Trichoderma reesei* ACEI transcriptional activator protein. | geneseqp W58572 | ND |
| 94 | 1375.8 | 40S RIBOSOMAL PROTEIN S3AE (S1). | swissprot P40910 | ND |
| 95 | 1370.2 | GLUCOSAMINE-6-PHOSPHATE ISOMERASE (EC 5.3.1.10) (GLUCOSAMINE-6-PHOSPHATE DEAMINASE) (GNPDA) (GLCN6P DEAMINASE) (OSCILLIN) (KIAA0060). | swissprot P46926 | Carbohydrate transport and metabolism |
| 96 | 1365.9 | 14-3-3. | tremblnew BAA89421 | ND |
| 97 | 1360.4 | C-1-TETRAHYDROFOLATE SYNTHASE. | sptrembl O42992 | ND |
| 98 | 1353.6 | PYRABCN (EC 6.3.5.5). | sptrembl O93937 | Nucleotide transport |
| 99 | 1350.8 | ASPARAGINE SYNTHETASE. | sptrembl O42902 | ND |
| 100 | 1349.2 | UBIQUITIN-PROTEIN LIGASE RSP5 (EC 6.3.2.-). | swissprot P39940 | ND |

TABLE 1-continued

*Fusarium venenatum* ESTs

| Sequence Listing | zscore | Annotation | Database | Functional category |
|---|---|---|---|---|
| 101 | 1346.1 | ELONGATION FACTOR 3 (EF-3). | swissprot P25997 | ND |
| 102 | 1338.9 | ENOLASE (EC 4.2.1.11). | tremblnew BAA23760 | ND |
| 103 | 1334.9 | GTP-BINDING PROTEIN YPT1. | swissprot P33723 | ND |
| 104 | 1331.5 | CONSERVED HYPOTHETICAL PROTEIN. | sptrembl O59761 | Energy production and conversion |
| 105 | 1328.2 | CYCLOPHILIN, MITOCHONDRIAL FORM PRECURSOR (EC 5.2.1.8). | sptrembl Q99009 | ND |
| 107 | 1314.0 | 40S RIBOSOMAL PROTEIN S6. | swissprot P05752 | ND |
| 108 | 1310.8 | 26S PROTEASE REGULATORY SUBUNIT 7 HOMOLOG (CIM5 PROTEIN) (TAT-BINDING HOMOLOG 3). | swissprot P33299 | Posttranslational modification, protein turnover, chaperones |
| 109 | 1309.4 | ACETYL-COA HYDROLASE (EC 3.1.2.1) (ACETYL-COA DEACYLASE) (ACETYL-COA ACYLASE) (ACETATE UTILIZATION PROTEIN). | swissprot P15937 | ND |
| 110 | 1309.1 | 60S ACIDIC RIBOSOMAL PROTEIN P0 (L10E). | swissprot P05317 | ND |
| 111 | 1308.8 | CCAAT-BINDING TRANSCRIPTION FACTOR SUBUNIT AAB-1. | sptrembl O13381 | ND |
| 113 | 1291.3 | ADP-RIBOSYLATION FACTOR. | swissprot P34727 | ND |
| 114 | 1290.9 | MALATE DEHYDROGENASE, MITOCHONDRIAL PRECURSOR (EC 1.1.1.37). | swissprot P17505 | ND |
| 116 | 1289.4 | HOMOCITRATE SYNTHASE (EC 4.1.3.21). | sptrembl O94225 | ND |
| 117 | 1285.6 | FIMBRIN. | sptrembl O93981 | ND |
| 118 | 1284.9 | EUKARYOTIC TRANSLATION INITIATION FACTOR 6 (EIF-6). | swissprot Q12522 | ND |
| 119 | 1283.8 | *Malassezia* fungus MF-5 antigenic protein. | geneseqp W29772 | ND |
| 120 | 1282.5 | HOMEODOMAIN DNA-BINDING TRANSCRIPTION FACTOR. | sptrembl O74252 | ND |
| 121 | 1281.8 | CARNITINE ACETYL TRANSFERASE FACC. | sptrembl O13363 | ND |
| 122 | 1281.4 | UBIQUITIN-CONJUGATING ENZYME E2-16 KD (EC 6.3.2.19) (UBIQUITIN-PROTEIN LIGASE) (UBIQUITIN CARRIER PROTEIN) (COLLETOTRICHUM HARD-SURFACE-INDUCED PROTEIN 1). | sptrembl O74196 | ND |
| 123 | 1278.4 | FLAVOHEMOGLOBIN. | sptrembl O74183 | ND |
| 124 | 1275.7 | MUS38. | sptrembl O74126 | DNA replication, recombination and repair |
| 125 | 1274.0 | An enzyme with sugar transferase activity. | geneseqp W88044 | ND |
| 126 | 1270.2 | TUBULIN ALPHA-A CHAIN. | swissprot P38668 | ND |
| 128 | 1266.0 | 40S RIBOSOMAL PROTEIN S9 (S7). | swissprot P52810 | ND |
| 129 | 1244.7 | RAS-RELATED PROTEIN RAB-11B (ORA3). | swissprot P22129 | ND |
| 130 | 1241.0 | PUTATIVE SODIUM P-TYPE ATPASE (FRAGMENT). | tremblnew CAB65298 | ND |
| 131 | 1237.4 | HYDROXYMETHYLGLUTARYL-COA SYNTHASE (EC 4.1.3.5) (HMG-COA | swissprot P54874 | ND |

TABLE 1-continued

*Fusarium venenatum* ESTs

| Sequence Listing | zscore | Annotation | Database | Functional category |
|---|---|---|---|---|
| | | SYNTHASE) (3-HYDROXY-3-METHYLGLUTARYL COENZYME A SYNTHASE). | | |
| 132 | 1232.2 | VACUOLAR ATP SYNTHASE CATALYTIC SUBUNIT A (EC 3.6.1.34) (V-ATPASE 67 KD SUBUNIT). | swissprot P11592 | Energy production and conversion |
| 133 | 1231.7 | SQUALENE SYNTHASE. | sptrembl Q9Y753 | ND |
| 134 | 1230.8 | ADENOSYLHOMOCYSTEINASE (EC 3.3.1.1) (S-ADENOSYL-L-HOMOCYSTEINE HYDROLASE) (ADOHCYASE). | swissprot P39954 | ND |
| 135 | 1224.8 | PYRUVATE CARBOXYLASE. | sptrembl O93918 | Amino acid transport and metabolism |
| 136 | 1217.4 | AMINONITROPHENYL PROPANEDIOL RESISTANCE PROTEIN. | swissprot P32629 | ND |
| 137 | 1213.0 | HYPOTHETICAL 161.2 KD PROTEIN IN NMD5-HOM6 INTERGENIC REGION. | swissprot P47169 | ND |
| 138 | 1211.4 | DIPHTHINE SYNTHASE (EC 2.1.1.98) (DIPHTAMIDE BIOSYNTHESIS METHYLTRANSFERASE). | swissprot P32469 | Translation, ribosomal structure and biogenesis |
| 139 | 1211.2 | 60S RIBOSOMAL PROTEIN L15. | swissprot O13418 | ND |
| 140 | 1211.1 | ENOLASE (EC 4.2.1.11) (2-PHOSPHOGLYCERATE DEHYDRATASE) (2-PHOSPHO-D-GLYCERATE HYDRO-LYASE) (ALLERGEN CLA H 6) (CLA H VI). | swissprot P42040 | Carbohydrate transport and metabolism |
| 141 | 1210.2 | 26S PROTEASOME REGULATORY COMPLEX SUBUNIT P42D. | tremblnew AAF08391 | Posttranslational modification, protein turnover, chaperones |
| 142 | 1208.8 | NADH-UBIQUINONE OXIDOREDUCTASE 23 KD SUBUNIT PRECURSOR (EC 1.6.5.3) (EC 1.6.99.3) (COMPLEX I-23 KD) (CI-23 KD). | swissprot Q12644 | ND |
| 143 | 1208.5 | HEAT SHOCK PROTEIN 90 HOMOLOG (SUPPRESSOR OF VEGETATIVE INCOMPATIBILITY MOD-E). | swissprot O43109 | Posttranslational modification, protein turnover, chaperones |
| 144 | 1208.2 | ATP-DEPENDENT BILE ACID PERMEASE. | swissprot P32386 | ND |
| 145 | 1206.4 | 14-3-3 PROTEIN HOMOLOG (TH1433). | swissprot Q99002 | ND |
| 146 | 1206.4 | AMINOTRANSFERASE 412 aa, chain A + B + C + D | pdb 1YAA | ND |
| 147 | 1205.0 | 40S RIBOSOMAL PROTEIN S0 (RIBOSOME-ASSOCIATED PROTEIN 1). | swissprot Q01291 | Translation, ribosomal structure and biogenesis |
| 148 | 1200.1 | ARGINASE (EC 3.5.3.1). | swissprot P33280 | ND |
| 149 | 1197.8 | RAS-RELATED C3 BOTULINUM TOXIN SUBSTRATE 1 (P21-RAC1) (RAS-LIKE PROTEIN TC25). | swissprot P15154 | ND |
| 150 | 1196.8 | ATP SYNTHASE ALPHA CHAIN, MITOCHONDRIAL PRECURSOR (EC 3.6.1.34). | swissnew P37211 | Energy production and conversion |
| 151 | 1195.9 | MITOCHONDRIAL PROCESSING PEPTIDASE BETA SUBUNIT PRECURSOR (EC 3.4.24.64) (BETA-MPP) (UBIQUINOL-CYTOCHROME C | swissprot P11913 | ND |

TABLE 1-continued

*Fusarium venenatum* ESTs

| Sequence Listing | zscore | Annotation | Database | Functional category |
|---|---|---|---|---|
| | | REDUCTASE COMPLEX CORE PROTEIN I) (EC 1.10.2.2). | | |
| 152 | 1194.5 | POLYUBIQUITIN. | sptrembl O74274 | ND |
| 153 | 1190.6 | FARNESYL PYROPHOSPHATE SYNTHETASE (FPP SYNTHETASE) (FPS) (FARNESYL DIPHOSPHATE SYNTHETASE) [INCLUDES: DIMETHYLALLYLTRANSFE RASE (EC 2.5.1.1); GERANYLTRANSTRANSFE RASE (EC 2.5.1.10)]. | swissprot Q92235 | Coenzyme metabolism |
| 154 | 1188.3 | ALCOHOL DEHYDROGENASE I (EC 1.1.1.1). | swissprot P41747 | ND |
| 155 | 1185.7 | ISOCITRATE DEHYDROGENASE [NADP], MITOCHONDRIAL PRECURSOR (EC 1.1.1.42) (OXALOSUCCINATE DECARBOXYLASE) (IDH) (NADP+-SPECIFIC ICDH) (IDP). | swissprot P79089 | Energy production and conversion |
| 156 | 1184.8 | GLUCOSE-6-PHOSPHATE 1-DEHYDROGENASE (EC 1.1.1.49) (G6PD). | swissprot P41764 | Carbohydrate transport and metabolism |
| 157 | 1184.7 | *A. nidulans* atrC polypeptide. | geneseqp Y21815 | ND |
| 158 | 1183.3 | CALCINEURIN B SUBUNIT (PROTEIN PHOSPHATASE 2B REGULATORY SUBUNIT) (CALCINEURIN REGULATORY SUBUNIT). | swissprot P87072 | ND |
| 159 | 1175.6 | ALPHA-GLUCOSIDASE (EC 3.2.1.20) (MALTASE). | swissprot Q02751 | Carbohydrate transport and metabolism |
| 160 | 1170.2 | RHO1 PROTEIN. | swissprot Q09914 | ND |
| 161 | 1166.6 | HNRNP ARGININE N-METHYLTRANSFERASE (EC 2.1.1.-) (ODP1 PROTEIN). | swissprot P38074 | ND |
| 162 | 1160.6 | VACUOLAR PROTEASE A PRECURSOR (EC 3.4.23.-). | swissprot Q01294 | ND |
| 163 | 1160.4 | PLASMA MEMBRANE ATPASE (EC 3.6.1.35) (PROTON PUMP). | swissprot P07038 | ND |
| 164 | 1156.7 | ISOCITRATE DEHYDROGENASE [NADP], MITOCHONDRIAL PRECURSOR (EC 1.1.1.42) (OXALOSUCCINATE DECARBOXYLASE) (IDH) (NADP+-SPECIFIC ICDH) (IDP). | swissprot P79089 | Energy production and conversion |
| 165 | 1150.9 | 40S RIBOSOMAL PROTEIN S2 (S4) (YS5) (RP12) (OMNIPOTENT SUPRESSOR PROTEIN SUP44). | swissprot P25443 | ND |
| 166 | 1149.4 | CRO1 PROTEIN. | sptrembl O42829 | ND |
| 167 | 1147.5 | RIBOSOMAL PROTEIN L13A. | tremblnew AAD54383 | ND |
| 168 | 1143.0 | MITOCHONDRIAL PHOSPHATE CARRIER PROTEIN (PHOSPHATE TRANSPORT PROTEIN) (PTP) (MITOCHONDRIAL IMPORT RECEPTOR) (P32). | swissprot P23641 | ND |
| 170 | 1136.4 | LONG-CHAIN-FATTY-ACID--COA LIGASE 2 (EC 6.2.1.3) (LONG-CHAIN ACYL-COA SYNTHETASE 2) (FATTY ACID ACTIVATOR 2). | swissprot P39518 | Lipid metabolism |

TABLE 1-continued

_Fusarium venenatum ESTs_

| Sequence Listing | zscore | Annotation | Database | Functional category |
|---|---|---|---|---|
| 171 | 1136.2 | *B. bassiana* POPS reductase protein. | geneseqp Y33673 | Inorganic ion transport and metabolism |
| 173 | 1135.0 | CPC3 PROTEIN. | sptrembl O74297 | ND |
| 174 | 1131.1 | LINOLEATE DIOL SYNTHASE PRECURSOR. | tremblnew AAD49559 | ND |
| 175 | 1129.3 | HYPOTHETICAL 68.3 KD PROTEIN. | sptrembl Q03195 | ND |
| 176 | 1127.7 | ISOCITRATE LYASE (EC 4.1.3.1) (ISOCITRASE) (ISOCITRATASE) (ICL). | swissprot P28299 | Energy production and conversion |
| 177 | 1125.6 | PUTATIVE CASEIN KINASE II CATALYTIC SUBUNIT. | sptrembl O64816 | Signal transduction mechanisms |
| 178 | 1124.8 | PUTATIVE PHOSPHATIDYLINOSITOL-KINASE (FRAGMENT). | sptrembl Q9Y7K2 | ND |
| 179 | 1119.1 | PHOSPHOGLYCERATE KINASE (EC 2.7.2.3). | swissprot P24590 | ND |
| 180 | 1118.8 | NADH-UBIQUINONE OXIDOREDUCTASE 20.8 KD SUBUNIT (EC 1.6.5.3) (EC 1.6.99.3). | swissprot P21976 | ND |
| 181 | 1117.8 | PROTEIN PHOSPHOTASE 2A 65 KD REGULATORY SUBUBIT (A SUBUNIT). | sptrembl Q10293 | ND |
| 182 | 1117.6 | Peptide transport protein ATPTR2Ap. | geneseqp R84891 | ND |
| 183 | 1115.8 | FREQUENCY CLOCK PROTEIN. | swissnew Q00586 | ND |
| 184 | 1114.9 | 60S RIBOSOMAL PROTEIN L11 (L16) (YL16) (39A) (RP39). | swissprot P06380 | ND |
| 185 | 1109.0 | *S. brevicaulis* beta-fructofuranosidase protein sequence. | geneseqp Y05278 | ND |
| 186 | 1104.2 | UBIQUINOL-CYTOCHROME C REDUCTASE COMPLEX CORE PROTEIN 2 PRECURSOR (EC 1.10.2.2). | swissprot O60044 | ND |
| 187 | 1101.6 | NAD-SPECIFIC GLUTAMATE DEHYDROGENASE (EC 1.4.1.2) (NAD-GDH) (FRAGMENTS). | swissprot P00365 | Amino acid transport and metabolism |
| 188 | 1100.9 | PUTATIVE MITOCHONDRIAL CARRIER PROTEIN YHM1/SHM1. | swissprot P38988 | ND |
| 189 | 1096.7 | CYCLOPHILIN (EC 5.2.1.8). | sptrembl O93826 | ND |
| 190 | 1096.0 | THIOREDOXIN REDUCTASE (EC 1.6.4.5). | swissprot P51978 | ND |
| 191 | 1092.3 | 40S RIBOSOMAL PROTEIN S5 (FRAGMENT). | sptrembl O65731 | ND |
| 192 | 1091.5 | HEAT SHOCK PROTEIN 90 HOMOLOG (SUPPRESSOR OF VEGETATIVE INCOMPATIBILITY MOD-E). | swissprot O43109 | Posttranslational modification, protein turnover, chaperones |
| 193 | 1090.3 | 40S RIBOSOMAL PROTEIN S15 (S12). | swissprot P34737 | Translation, ribosomal structure and biogenesis |
| 194 | 1085.4 | MALATE SYNTHASE, GLYOXYSOMAL (EC 4.1.3.2). | swissnew P28344 | ND |
| 195 | 1085.1 | *N. crassa* mtr gene product. | geneseqp R79909 | ND |
| 196 | 1081.1 | 60S RIBOSOMAL PROTEIN L8 (L7A) (L4). | swissprot O13672 | ND |
| 197 | 1080.8 | MITOGEN-ACTIVATED PROTEIN KINASE KINASE CPK1. | sptrembl O93876 | Signal transduction mechanisms |
| 198 | 1080.3 | CORONIN-LIKE PROTEIN. | swissprot O13923 | ND |

TABLE 1-continued

_Fusarium venenatum_ ESTs

| Sequence Listing | zscore | Annotation | Database | Functional category |
|---|---|---|---|---|
| 199 | 1078.7 | PROBABLE ATP-DEPENDENT RNA HELICASE HAS1. | swissprot Q03532 | DNA replication, recombination and repair |
| 200 | 1078.1 | UBI1. | tremblnew AAF24230 | ND |
| 201 | 1077.3 | 60S RIBOSOMAL PROTEIN L7-C. | swissprot O60143 | ND |
| 202 | 1076.8 | 40S RIBOSOMAL PROTEIN S7. | swissprot O43105 | ND |
| 203 | 1076.3 | CHROMOSOME XII COSMID 9470. | sptrembl Q06287 | ND |
| 204 | 1072.5 | SERINE/THREONINE PROTEIN KINASE FSK (FRAGMENT). | sptrembl Q00875 | Signal transduction mechanisms |
| 205 | 1066.5 | RIBOSOMAL PROTEIN S28. | tremblnew CAB56815 | ND |
| 206 | 1064.5 | STRESS-RESPONSIVE GENE PRODUCT. | tremblnew BAA85305 | ND |
| 208 | 1063.3 | TOM70 GENE. | sptrembl O13499 | ND |
| 209 | 1056.9 | TUBULIN BETA CHAIN. | swissprot O42786 | ND |
| 210 | 1056.2 | NADP-SPECIFIC GLUTAMATE DEHYDROGENASE (EC 1.4.1.4) (NADP-GDH). | swissprot P00369 | ND |
| 211 | 1056.0 | PHOSPHORIBOSYLAMIDOI MIDAZOLE-SUCCINOCARBOXAMIDE SYNTHASE, SAICAR SYNTHETASE. | tremblnew CAB52612 | Nucleotide transport |
| 212 | 1054.7 | ADENYLATE KINASE CYTOSOLIC (EC 2.7.4.3) (ATP-AMP TRANSPHOSPHORYLASE). | swissprot P07170 | Nucleotide transport |
| 213 | 1051.1 | LPG22P. | sptrembl Q02908 | Transcription |
| 214 | 1046.3 | ADENOSINE-5'PHOSPHOSULFATE KINASE (EC 2.7.1.25) (ADENYLYLSULFATE KINASE) (APS KINASE). | sptrembl Q12657 | ND |
| 215 | 1045.7 | HYPOTHETICAL 34.2 KD PROTEIN IN CUS1-RPL20A INTERGENIC REGION. | swissprot Q04013 | ND |
| 216 | 1045.0 | RAS-RELATED PROTEIN RAB6. | tremblnew AAD25535 | ND |
| 217 | 1044.8 | 40S RIBOSOMAL PROTEIN S17 (CRP3). | swissprot P27770 | ND |
| 218 | 1039.9 | CLATHRIN HEAVY CHAIN. | swissprot P22137 | ND |
| 219 | 1039.8 | KINESIN. | sptrembl P78718 | ND |
| 220 | 1038.9 | VACUOLAR ASPARTIC PROTEASE PRECURSOR. | sptrembl O42630 | ND |
| 221 | 1036.7 | TUBULIN ALPHA-A CHAIN. | swissprot P38668 | ND |
| 222 | 1035.8 | PROBABLE GYP7 PROTEIN (FRAGMENT). | swissprot P09379 | ND |
| 223 | 1035.7 | PEROXISOMAL HYDRATASE-DEHYDROGENASE-EPIMERASE (HDE) (MULTIFUNCTIONAL BETA-OXIDATION PROTEIN) (MFP) [INCLUDES: 2-ENOYL-COA HYDRATASE (EC 4.2.1.-); D-3-HYDROXYACYL COA DEHYDROGENASE (EC 1.1.1.-)]. | swissnew Q01373 | ND |
| 224 | 1035.5 | SEPTIN HOMOLOG SPN2. | tremblnew CAB57440 | ND |
| 225 | 1032.1 | MYO-INOSITOL 1-PHOSPHATE SYNTHASE (EC 5.5.1.4). | sptrembl O65196 | Lipid metabolism |
| 226 | 1031.5 | GAMMA-ACTIN. | tremblnew AAF00008 | Cell division and chromosome partitioning |

TABLE 1-continued

*Fusarium venenatum* ESTs

| Sequence Listing | zscore | Annotation | Database | Functional category |
|---|---|---|---|---|
| 227 | 1031.2 | PHOSPHO-2-DEHYDRO-3-DEOXYHEPTONATE ALDOLASE, TYROSINE-INHIBITED (EC 4.1.2.15) (PHOSPHO-2-KETO-3-DEOXYHEPTONATE ALDOLASE) (DAHP SYNTHETASE) (3-DEOXY-D-ARABINO-HEPTULOSONATE 7-PHOSPHATE SYNTHASE). | swissprot P32449 | Amino acid transport and metabolism |
| 228 | 1026.8 | PUTATIVE CALCIUM P-TYPE ATPASE (FRAGMENT). | tremblnew CAB65295 | Inorganic ion transport and metabolism |
| 229 | 1026.3 | 60S RIBOSOMAL PROTEIN L2. | sptrembl O94253 | ND |
| 230 | 1026.2 | CU—ZN SUPEROXIDE DISMUTASE. | sptrembl O94178 | ND |
| 231 | 1024.2 | CARBOXY-CIS,CIS-MUCONATE CYCLASE (EC 5.5.1.5) (3-CARBOXY-CIS,CIS-MUCONATE LACTONIZING ENZYME) (CMLE). | swissprot P38677 | ND |
| 232 | 1020.5 | PRP12P/SAP130. | tremblnew BAA86918 | ND |
| 233 | 1020.1 | 26S PROTEASE REGULATORY SUBUNIT 6B HOMOLOG. | swissprot P78578 | Posttranslational modification, protein turnover, chaperones |
| 234 | 1019.3 | NADH-UBIQUINONE OXIDOREDUCTASE 40 KD SUBUNIT PRECURSOR (EC 1.6:5.3) (EC 1.6.99.3) (COMPLEX I-40 KD) (CI-40 KD). | swissprot P25284 | ND |
| 235 | 1017.4 | GLUCOSE-6-PHOSPHATE 1-DEHYDROGENASE (EC 1.1.1.49) (G6PD). | swissprot P48826 | Carbohydrate transport and metabolism |
| 236 | 1012.5 | HEXOKINASE (EC 2.7.1.1). | sptrembl O93964 | ND |
| 237 | 1008.0 | 60S RIBOSOMAL PROTEIN L12. | swissprot P23358 | ND |
| 238 | 1007.8 | POP3, A WD REPEAT PROTEIN. | tremblnew CAB57925 | ND |
| 239 | 1007.4 | 14-3-3 PROTEIN HOMOLOG (TH1433). | swissprot Q99002 | ND |
| 240 | 1007.4 | TRICHODIENE SYNTHASE (EC 4.1.99.6) (SESQUITERPENE CYCLASE) (TS). | swissprot P27679 | ND |
| 241 | 1004.9 | PUTATIVE PROTEOSOME COMPONENT C6G10.04C (EC 3.4.99.46) (MACROPAIN SUBUNIT C6G10.04C) (PROTEINASE YSCE SUBUNIT C6G10.04C) (MULTICATALYTIC ENDOPEPTIDASE COMPLEX SUBUNIT C6G10.04C). | sptrembl O14250 | ND |
| 242 | 1001.3 | YME1 PROTEIN (EC 3.4.24.-) (TAT-BINDING HOMOLOG 11) (OSD1 PROTEIN). | swissprot P32795 | Posttranslational modification, protein turnover, chaperones |
| 243 | 1000.7 | SERINE/THREONINE PROTEIN KINASE. | sptrembl Q99012 | Signal transduction mechanisms |
| 244 | 996.2 | INTRACELLULAR METALLOPROTEINASE MEPB. | sptrembl P97996 | Amino acid transport and metabolism |
| 245 | 995.1 | NADH-UBIQUINONE OXIDOREDUCTASE 30.4 KD SUBUNIT PRECURSOR (EC 1.6.5.3) (EC 1.6.99.3) | swissprot P23710 | ND |

TABLE 1-continued

*Fusarium venenatum* ESTs

| Sequence Listing | zscore | Annotation | Database | Functional category |
|---|---|---|---|---|
| | | (COMPLEX I-30 KD) (CI-31 KD). | | |
| 246 | 990.8 | GENERAL AMINO-ACID PERMEASE GAP1. | swissprot P19145 | Amino acid transport and metabolism |
| 247 | 986.5 | SULPHUR METABOLITE REPRESSION REGULATION PROTEIN SCONCP. | sptrembl Q92229 | ND |
| 248 | 985.2 | DOLICHOL-PHOSPHATE MANNOSYLTRANSFERASE (EC 2.4.1.83) (DOLICHOL-PHOSPHATE MANNOSE SYNTHASE) (DOLICHYL-PHOSPHATE BETA-D-MANNOSYLTRANSFERASE) | sptrembl O14466 | Cell envelope biogenesis, outer membrane |
| 250 | 983.7 | ARI PROTEIN. | sptrembl Q94981 | ND |
| 253 | 979.4 | 40S RIBOSOMAL PROTEIN S13 (S15). | swissprot P33192 | ND |
| 254 | 979.4 | PROBABLE SUCCINYL-COA LIGASE [GDP-FORMING] ALPHA-CHAIN, MITOCHONDRIAL PRECURSOR (EC 6.2.1.4) (SUCCINYL-COA SYNTHETASE, ALPHA CHAIN) (SCS-ALPHA). | swissprot O13750 | ND |
| 255 | 976.7 | 40S RIBOSOMAL PROTEIN S19 (S16). | swissprot P27073 | ND |
| 256 | 976.2 | 40S RIBOSOMAL PROTEIN S14 (CRP2). | swissprot P19115 | ND |
| 257 | 975.8 | SUPEROXIDE DISMUTASE PRECURSOR (EC 1.15.1.1). | sptrembl Q9Y783 | ND |
| 258 | 974.3 | 40S RIBOSOMAL PROTEIN S8 (S14) (YS9) (RP19). | swissprot P05754 | ND |
| 259 | 972.5 | *Cystathionine gamma* lyase. | geneseqp R66223 | Amino acid transport and metabolism |
| 260 | 966.7 | AMINO-ACID PERMEASE INDA1. | swissprot P34054 | Amino acid transport and metabolism |
| 261 | 965.2 | 78 KD GLUCOSE-REGULATED PROTEIN HOMOLOG PRECURSOR (GRP 78) (IMMUNOGLOBULIN HEAVY CHAIN BINDING PROTEIN HOMOLOG) (BIP). | swissnew P78695 | Posttranslational modification, protein turnover, chaperones |
| 262 | 965.1 | PHOSPHOGLUCOMUTASE. | sptrembl O74374 | ND |
| 263 | 964.1 | CALMODULIN. | sptrembl O93930 | ND |
| 264 | 962.0 | EUKARYOTIC TRANSLATION INITIATION FACTOR 2 ALPHA SUBUNIT (EIF-2-ALPHA). | swissprot P20459 | Translation, ribosomal structure and biogenesis |
| 265 | 961.7 | S-ADENOSYLMETHIONINE SYNTHETASE (EC 2.5.1.6) (METHIONINE ADENOSYLTRANSFERASE) (ADOMET SYNTHETASE). | swissprot P48466 | ND |
| 266 | 960.7 | PROBABLE UTP--GLUCOSE-1-PHOSPHATE URIDYLYLTRANSFERASE. | tremblnew CAA22857 | ND |
| 267 | 959.5 | PRPD PROTEIN. | swissprot P77243 | ND |
| 268 | 957.8 | TRANSMEMBRANE PROTEIN. | tremblnew CAB65007 | ND |
| 269 | 955.2 | HYPOTHETICAL 63.5 KD PROTEIN. | sptrembl O74965 | ND |
| 270 | 954.6 | *Aspergillus niger* trehalose synthase. | geneseqp W49027 | Carbohydrate transport and metabolism |
| 271 | 954.6 | SERINE/THREONINE-PROTEIN KINASE STE20 (EC 2.7.1.-). | swissnew Q03497 | Signal transduction mechanisms |
| 272 | 952.4 | HYPOTHETICAL 55.8 KD PROTEIN. | tremblnew CAB63552 | ND |

TABLE 1-continued

_Fusarium venenatum_ ESTs

| Sequence Listing | zscore | Annotation | Database | Functional category |
|---|---|---|---|---|
| 273 | 949.3 | 40S RIBOSOMAL PROTEIN S11 (S18) (YS12) (RP41). | swissprot P26781 | ND |
| 274 | 949.1 | HYPOTHETICAL 44.3 KD PROTEIN C1F7.07C IN CHROMOSOME I. | swissprot Q09919 | Inorganic ion transport and metabolism |
| 275 | 947.0 | 60S RIBOSOMAL PROTEIN L27A (L29). | swissprot P78987 | Translation, ribosomal structure and biogenesis |
| 276 | 946.1 | OXIDOREDUCTASE (H2O2(A)) 293 aa | pdb 2CYP | ND |
| 277 | 944.5 | HYPOTHETICAL 22.1 KD PROTEIN IN CCP1-MET1 INTERGENIC REGION. | swissprot P36149 | ND |
| 278 | 944.4 | PROTEASOME SUBUNIT YC7-ALPHA. | tremblnew CAA40292 | ND |
| 279 | 943.8 | SERINE/THREONINE PROTEIN KINASE. | sptrembl O42795 | Signal transduction mechanisms |
| 280 | 942.9 | CYTOCHROME C1, HEME PROTEIN PRECURSOR. | swissprot P07142 | ND |
| 281 | 942.6 | Yeast ribosomal protein S7. | geneseqp W36115 | Translation, ribosomal structure and biogenesis |
| 282 | 938.9 | FIMBRIN. | sptrembl O93981 | ND |
| 283 | 934.4 | PUTATIVE CHOLINEPHOSPHATE CYTIDYLYLTRANSFERASE. | tremblnew CAA19310 | ND |
| 284 | 930.5 | 40S RIBOSOMAL PROTEIN S12. | sptrembl O59936 | ND |
| 285 | 929.6 | REHYDRIN-LIKE PROTEIN. | sptrembl O94014 | Posttranslational modification, protein turnover, chaperones |
| 286 | 928.1 | PROTEASOME COMPONENT PRE3 PRECURSOR (EC 3.4:99.46) (MACROPAIN SUBUNIT PRE3) (PROTEINASE YSCE SUBUNIT PRE3) (MULTICATALYTIC ENDOPEPTIDASE COMPLEX SUBUNIT PRE3). | swissnew P38624 | Posttranslational modification, protein turnover, chaperones |
| 287 | 927.7 | CARBOXYPEPTIDASE CPDS PRECURSOR (EC 3.4.16.-). | swissprot P52719 | ND |
| 288 | 927.2 | PROBABLE PHOSPHATIDYLINOSITOL-4-PHOSPHATE 5-KINASE FAB1 (EC 2.7.1.68) (1-PHOSPHATIDYLINOSITOL-4-PHOSPHATE KINASE) (PIP5K) (PTDINS(4)P-5-KINASE) (DIPHOSPHOINOSITIDE KINASE). | swissprot P34756 | ND |
| 289 | 926.2 | 40S RIBOSOMAL PROTEIN S18. | swissprot P35271 | ND |
| 290 | 925.6 | GLUTATHIONE-DEPENDENT FORMALDEHYDE DEHYDROGENASE (EC 1.2.1.1) (FDH) (FALDH). | swissprot Q06099 | ND |
| 291 | 925.2 | PROTEIN PHOSPHATASE 2A DELTA (B") REGULATORY SUBUNIT, DELTA3 ISOFORM (B"). | sptrembl O00494 | ND |
| 292 | 924.5 | MANNOSE-1-PHOSPHATE GUANYLTRANSFERASE (EC 2.7.7.13) (MPG1 TRANSFERASE) (ATP-MANNOSE-1-PHOSPHATE GUANYLYLTRANSFERASE) | sptrembl O74624 | Cell envelope biogenesis, outer membrane |

TABLE 1-continued

*Fusarium venenatum* ESTs

| Sequence Listing | zscore | Annotation | Database | Functional category |
|---|---|---|---|---|
| 293 | 924.2 | HYPOTHETICAL 39.3 KD PROTEIN C31G5.04 IN CHROMOSOME I. | sptrembl O14104 | Amino acid transport and metabolism |
| 294 | 921.8 | 60S RIBOSOMAL PROTEIN L20 (L18A). | swissprot P47913 | ND |
| 295 | 917.7 | BETAINE ALDEHYDE DEHYDROGENASE (EC 1.2.1.8) (BADH). | swissprot P17445 | Energy production and conversion |
| 296 | 917.3 | V-TYPE ATPASE SUBUNIT C'. | sptrembl Q9Y874 | Energy production and conversion |
| 297 | 916.8 | 60S RIBOSOMAL PROTEIN L23 (L17). | swissprot P04451 | ND |
| 298 | 915.2 | Amino acid sequence of a maltogenic alpha amylase. | geneseqp Y30621 | ND |
| 299 | 914.1 | PUTATIVE 20 KDA SUBUNIT OF THE V-ATPASE. | sptrembl P87252 | ND |
| 300 | 914.0 | OUTER MITOCHONDRIAL MEMBRANE PROTEIN PORIN. | swissprot P07144 | ND |
| 301 | 913.0 | UTP-AMMONIA LIGASE. | sptrembl O74638 | Nucleotide transport |
| 302 | 912.2 | CYCLIN-DEPENDENT PROTEIN KINASE. | sptrembl Q9Y8B7 | Signal transduction mechanisms |
| 303 | 910.8 | HYPOTHETICAL 57.0 KD TRP-ASP REPEATS CONTAINING PROTEIN IN CPR4-SSK22 INTERGENIC REGION. | swissprot P25382 | ND |
| 304 | 907.8 | VACUOLAR ATP SYNTHASE 16 KD PROTEOLIPID SUBUNIT (EC 3.6.1.34). | swissprot P31413 | Energy production and conversion |
| 305 | 907.4 | 40S RIBOSOMAL PROTEIN S26E (CRP5) (13.6 KD RIBOSOMAL PROTEIN). | swissprot P21772 | ND |
| 306 | 907.4 | PUTATIVE 30.7 KD METHYLTRANSFERASE IN TSM1-ARE1 INTERGENIC REGION. | swissprot P25627 | ND |
| 307 | 906.5 | PEROXISOMAL HYDRATASE-DEHYDROGENASE-EPIMERASE (HDE) (MULTIFUNCTIONAL BETA-OXIDATION PROTEIN) (MFP) [INCLUDES: 2-ENOYL-COA HYDRATASE (EC 4.2.1.-); D-3-HYDROXYACYL COA DEHYDROGENASE (EC 1.1.1.-)]. | swissnew Q01373 | ND |
| 308 | 905.6 | HISTONE H2A. | swissprot P08844 | ND |
| 309 | 905.0 | PUTATIVE SEC14 CYTOSOLIC FACTOR (PHOSPHATIDYLINOSITOL/ PHOSPHATIDYL-CHOLINE TRANSFER PROTEIN) (PI/PC TP). | swissprot Q10137 | ND |
| 310 | 903.7 | PUTATIVE UBIQUITIN FUSION DEGRADATION PROTEIN (FRAGMENT). | tremblnew CAA22594 | ND |
| 311 | 902.0 | CONSERVED HYPOTHETICAL PROTEIN. | tremblnew CAB54867 | Translation, ribosomal structure and biogenesis |
| 312 | 901.5 | FK506-BINDING PROTEIN PRECURSOR (FKBP-21) (PEPTIDYL-PROLYL CIS-TRANS ISOMERASE) (PPTASE) (EC 5.2.1.8). | swissprot O60046 | Posttranslational modification, protein turnover, chaperones |

TABLE 1-continued

_Fusarium venenatum_ ESTs

| Sequence Listing | zscore | Annotation | Database | Functional category |
|---|---|---|---|---|
| 313 | 901.0 | PUTATIVE COATOMER BETA SUBUNIT (FRAGMENT). | sptrembl O74812 | ND |
| 314 | 900.5 | Human aflatoxin B1 aldehyde reductase. | geneseqp Y24920 | ND |
| 316 | 898.6 | HISTIDYL-TRNA SYNTHETASE. | sptrembl O43011 | Translation, ribosomal structure and biogenesis |
| 317 | 897.7 | CHITIN SYNTHASE 3 (EC 2.4.1.16) (CHITIN-UDP ACETYL-GLUCOSAMINYL TRANSFERASE 3) (CLASS-III CHITIN SYNTHASE 3). | swissprot P29070 | ND |
| 318 | 894.2 | PROBABLE T-COMPLEX PROTEIN 1, BETA SUBUNIT (TCP-1-BETA) (CCT-BETA). | swissprot Q10147 | Posttranslational modification, protein turnover, chaperones |
| 319 | 893.0 | ISOCITRATE LYASE (EC 4.1.3.1) (ISOCITRASE) (ISOCITRATASE) (ICL). | swissprot P28299 | Energy production and conversion |
| 320 | 892.9 | EIF-5A. | sptrembl O94083 | ND |
| 321 | 891.6 | 40S RIBOSOMAL PROTEIN S22 (S15A) (YS24). | swissprot P33953 | ND |
| 322 | 889.1 | CUTINASE TRANSCRIPTION FACTOR 1 BETA. | swissprot P52959 | ND |
| 323 | 886.6 | ORNITHINE CARBAMOYLTRANSFERASE PRECURSOR (EC 2.1.3.3) (OTCASE) (ORNITHINE TRANSCARBAMYLASE). | swissprot P11803 | Amino acid transport and metabolism |
| 324 | 885.1 | PUTATIVE ARP2/3 COMPLEX 41 KD SUBUNIT. | tremblnew CAA70202 | ND |
| 325 | 885.0 | LEUCYL-TRNA SYNTHETASE, CYTOPLASMIC (EC 6.1.1.4) (LEUCINE--TRNA LIGASE) (LEURS). | swissprot P10857 | ND |
| 326 | 883.2 | 3-HYDROXY-3-METHYLGLUTARYL-COENZYME A REDUCTASE (EC 1.1.1.34) (HMG-COA REDUCTASE). | swissnew Q12577 | ND |
| 327 | 882.6 | GLYCOSYLTRANSFERASE 858 aa, chain A + B | pdb 1YGP | Carbohydrate transport and metabolism |
| 328 | 880.5 | MINOR ALLERGEN ALT A 7 (ALT A VII). | swissprot P42058 | ND |
| 329 | 879.0 | CARBON CATABOLITE REPRESSION REGULATOR. | sptrembl O94131 | ND |
| 330 | 876.4 | PDI RELATED PROTEIN A. | sptrembl O93914 | Energy production and conversion |
| 331 | 874.2 | ELONGATION FACTOR TU, MITOCHONDRIAL PRECURSOR. | swissprot P02992 | Amino acid transport and metabolism |
| 332 | 872.7 | RAS-LIKE PROTEIN. | swissprot O42785 | ND |
| 333 | 870.4 | SEVERIN KINASE. | sptrembl O61122 | Signal transduction mechanisms |
| 334 | 869.8 | HYPOTHETICAL 65.3 KD PROTEIN IN MAD1-SCY1 INTERGENIC REGION. | swissprot P53154 | Cell envelope biogenesis, outer membrane |
| 335 | 868.3 | T-COMPLEX PROTEIN 1, DELTA SUBUNIT (TCP-1-DELTA) (CCT-DELTA) (STIMULATOR OF TAR RNA BINDING). | swissprot P50991 | Posttranslational modification, protein turnover, chaperones |
| 336 | 867.2 | HISTONE H3. | swissprot P07041 | ND |
| 337 | 865.7 | UBIQUITIN-CONJUGATING ENZYME E2 (EC 6.3.2.19) | sptrembl O76069 | ND |

TABLE 1-continued

*Fusarium venenatum* ESTs

| Sequence Listing | zscore | Annotation | Database | Functional category |
|---|---|---|---|---|
| | | (UBIQUITIN-PROTEIN LIGASE) (UBIQUITIN CARRIER PROTEIN). | | |
| 338 | 863.9 | 60S RIBOSOMAL PROTEIN L19 (L23) (YL14) (RP33) (RP15L). | swissprot P05735 | Translation, ribosomal structure and biogenesis |
| 339 | 863.3 | MRNA CLEAVAGE FACTOR 125 KDA SUBUNIT. | sptrembl O43809 | ND |
| 340 | 862.1 | PROTEIN PHOSPHATASE-1. | tremblnew AAD47567 | ND |
| 341 | 861.8 | PROHIBITIN (FRAGMENT). | sptrembl O13357 | Posttranslational modification, protein turnover, chaperones |
| 342 | 861.0 | 40S RIBOSOMAL PROTEIN S3. | swissprot O60128 | ND |
| 343 | 860.4 | MDM10 GENE. | sptrembl O13498 | ND |
| 344 | 859.6 | PEPTIDYLPROLYL ISOMERASE (EC 5.2.1.8). | sptrembl O60045 | ND |
| 345 | 858.8 | NUCLEAR MIGRATION PROTEIN NUDF. | swissprot Q00664 | ND |
| 347 | 855.8 | SERINE/THREONINE PROTEIN KINASE SSK22 (EC 2.7.-.-). | swissprot P25390 | Signal transduction mechanisms |
| 348 | 853.1 | PROTEIN PHOSPHATASE SSD1 HOMOLOG. | sptrembl O13327 | ND |
| 349 | 853.0 | *Fusarium* 5-aminolevulinic acid synthase (hemA). | geneseqp Y17297 | Coenzyme metabolism |
| 350 | 852.7 | GTP CYCLOHYDROLASE I (EC 3.5.4.16) (GTP-CH-I). | swissprot P51601 | Coenzyme metabolism |
| 351 | 851.7 | POLYMERASE. | sptrembl Q10295 | ND |
| 352 | 851.5 | PUTATIVE SPLICING FACTOR BBP/SF1. | tremblnew AAF02214 | ND |
| 353 | 850.4 | 60S RIBOSOMAL PROTEIN L18. | swissnew Q10192 | Translation, ribosomal structure and biogenesis |
| 354 | 850.1 | PUTATIVE CHROMATIN BINDING SNW FAMILY NUCLEAR PROTEIN. | tremblnew CAB37421 | ND |
| 355 | 849.8 | 5-METHYLTETRAHYDROPTEROYLTRIGLUTAMATE--HOMOCYSTEI METHYLTRANSFERASE(EC 2.1.1.14). | tremblnew CAB57427 | Amino acid transport and metabolism |
| 356 | 849.4 | CONSERVED HYPOTHETICAL PROTEIN. | sptrembl O74739 | ND |
| 357 | 848.6 | ADENYLOSUCCINATE LYASE (EC 4.3.2.2). | sptrembl O75495 | Nucleotide transport |
| 358 | 846.7 | PROBABLE SUCCINATE DEHYDROGENASE FLAVOPROTEIN SUBUNIT PRECURSOR(EC 1.3.5.1). | tremblnew CAB61213 | Energy production and conversion |
| 359 | 846.5 | ACETYL-CoA-ACETYLTRANSFERASE (EC 2.3.1.9). | sptrembl Q9Y838 | Lipid metabolism |
| 360 | 846.4 | ABC TRANSPORTER CDR4. | swissprot O74676 | ND |
| 361 | 846.4 | ACETYL-COA ACETYLTRANSFERASE IB (EC 2.3.1.9) (PEROXISOMAL ACETOACETYL-COA THIOLASE) (THIOLASE IB). | swissprot Q04677 | ND |
| 362 | 846.0 | REPRESSIBLE ALKALINE PHOSPHATASE PRECURSOR (EC 3.1.3.1). | swissprot P11491 | Inorganic ion transport and metabolism |
| 363 | 845.2 | NUCLEOSIDE DIPHOSPHATE KINASE. | tremblnew BAA83495 | ND |
| 364 | 844.7 | PYRUVATE DEHYDROGENASE E1 COMPONENT BETA SUBUNIT, | swissprot Q09171 | Energy production and conversion |

TABLE 1-continued

*Fusarium venenatum* ESTs

| Sequence Listing | zscore | Annotation | Database | Functional category |
|---|---|---|---|---|
| | | MITOCHONDRIAL PRECURSOR (EC 1.2.4.1) (PDHE1-B). | | |
| 365 | 840.2 | BETA-GLUCOSIDASE PRECURSOR (EC 3.2.1.21) (GENTOBIASE) (CELLOBIASE) (AMYGDALASE). | sptrembl Q12601 | ND |
| 366 | 839.4 | PUTATIVE FAMILY-31 GLUCOSIDASE. | tremblnew CAB65603 | Carbohydrate transport and metabolism |
| 367 | 838.8 | NONSENSE-MEDIATED MRNA DECAY PROTEIN 3. | swissprot P38861 | Transcription |
| 368 | 837.9 | HEAT SHOCK PROTEIN SSC1, MITOCHONDRIAL PRECURSOR (ENDONUCLEASE SCEI 75 KD SUBUNIT). | swissprot P12398 | Posttranslational modification, protein turnover, chaperones |
| 369 | 837.0 | GLUTAMATE SYNTHASE [NADPH] PRECURSOR (EC 1.4.1.13) (NADPH-GOGAT). | swissnew Q12680 | ND |
| 370 | 836.5 | TRANSMEMBRANE TRANSPORTER LIZ1P. | sptrembl O43000 | ND |
| 371 | 836.2 | FRUCTOSE-BISPHOSPHATE ALDOLASE (EC 4.1.2.13). | swissprot P36580 | Carbohydrate transport and metabolism |
| 372 | 835.8 | TRICHODIENE OXYGENASE (EC 1.14.-.-) (CYTOCHROME P450 58). | swissprot Q12612 | ND |
| 373 | 834.7 | HEXOKINASE (EC 2.7.1.1). | sptrembl O93964 | ND |
| 374 | 834.3 | PROBABLE ACETYL-COA HYDROLASE. | tremblnew CAB52573 | Energy production and conversion |
| 375 | 833.0 | HYPOTHETICAL 57.3 KD TRP-ASP REPEATS CONTAINING PROTEIN IN POM152-REC114 INTERGENIC REGION. | swissprot Q04225 | ND |
| 376 | 832.9 | 26S PROTEASE REGULATORY SUBUNIT 7 HOMOLOG. | tremblnew CAA16915 | ND |
| 377 | 831.6 | GUANINE NUCLEOTIDE-BINDING PROTEIN BETA SUBUNIT. | swissprot O14435 | ND |
| 378 | 831.5 | SYMBIOSIS-RELATED PROTEIN. | swissprot P87068 | ND |
| 379 | 831.0 | CHAPERONIN HSP78P. | sptrembl O74402 | Posttranslational modification, protein turnover, chaperones |
| 380 | 830.0 | 60S RIBOSOMAL PROTEIN L9-B (L8) (YL11) (RP25). | swissprot P51401 | ND |
| 381 | 829.2 | CLATHRIN COAT ASSEMBLY PROTEIN. | sptrembl Q9Y7L6 | ND |
| 382 | 828.7 | PROBABLE T-COMPLEX PROTEIN 1, ETA SUBUNIT (TCP-1-ETA) (CCT-ETA). | swissprot P87153 | Posttranslational modification, protein turnover, chaperones |
| 383 | 827.2 | HYPOTHETICAL 49.6 KD PROTEIN IN ELM1-PRI2 INTERGENIC REGION. | swissprot P36091 | ND |
| 384 | 826.9 | CLATHRIN COAT ASSEMBLY PROTEIN AP19 (CLATHRIN COAT ASSOCIATED PROTEIN AP19) (GOLGI ADAPTOR AP-1 19 KD ADAPTIN) (HA1 19 KD SUBUNIT) (CLATHRIN ASSEMBLY PROTEIN COMPLEX 1 SMALL CHAIN). | swissprot P56377 | ND |
| 385 | 826.6 | NUCLEAR MOVEMENT PROTEIN NUDC. | swissprot P17624 | ND |

TABLE 1-continued

*Fusarium venenatum* ESTs

| Sequence Listing | zscore | Annotation | Database | Functional category |
|---|---|---|---|---|
| 386 | 825.8 | SERINE/THREONINE-PROTEIN KINASE NRC-2 (EC 2.7.1.-) (NONREPRESSIBLE CONIDIATION PROTEIN 2). | swissprot O42626 | ND |
| 387 | 824.9 | PUTATIVE HOMOSERINE O-ACETYLTRANSFERASE. | sptrembl O13389 | ND |
| 388 | 824.3 | SERINE PROTEASE PRECURSOR. | sptrembl O74236 | Posttranslational modification, protein turnover, chaperones |
| 389 | 823.9 | EUKARYOTIC TRANSLATION INITIATION FACTOR 2 GAMMA SUBUNIT (EIF-2-GAMMA). | swissprot P32481 | Amino acid transport and metabolism |
| 390 | 823.1 | PSU1. | tremblnew BAA83907 | ND |
| 391 | 822.5 | GLUTAMIC ACID DECARBOXYLASE. | tremblnew BAA88152 | Amino acid transport and metabolism |
| 392 | 820.8 | CHROMOSOME XV READING FRAME ORF YOR091W. | sptrembl Q12000 | ND |
| 393 | 820.2 | HYPOTHETICAL 22.4 KD PROTEIN. | sptrembl O13610 | ND |
| 394 | 819.7 | CYTOCHROME C549. | tremblnew BAA85768 | ND |
| 395 | 818.8 | 40S RIBOSOMAL PROTEIN S16 (RP61R). | swissprot P40213 | ND |
| 397 | 817.5 | CALNEXIN (FRAGMENT). | sptrembl Q41798 | ND |
| 398 | 816.8 | PROBABLE UTP--GLUCOSE-1-PHOSPHATE URIDYLYLTRANSFERASE (EC 2.7.7.9) (UDP-GLUCOSE PYROPHOSPHORYLASE) (UDPGP) (UGPASE) (FRAGMENT). | swissprot P78811 | ND |
| 399 | 814.6 | BRANCHING ENZYME. | sptrembl Q9Y8H3 | Carbohydrate transport and metabolism |
| 400 | 814.1 | HEAT SHOCK PROTEIN SSC1, MITOCHONDRIAL PRECURSOR (ENDONUCLEASE SCEI 75 KD SUBUNIT). | swissprot P12398 | Posttranslational modification, protein turnover, chaperones |
| 401 | 813.9 | BENZOATE 4-MONOOXYGENASE (EC 1.14.13.12) (BENZOATE-PARA-HYDROXYLASE) (CYTOCHROME P450 53). | swissnew P17549 | ND |
| 402 | 811.4 | TRANSKETOLASE (EC 2.2.1.1) (TK). | swissprot Q12630 | Carbohydrate transport and metabolism |
| 403 | 811.2 | PROBABLE SERINE/THREONINE-PROTEIN KINASE C1D4.11C (EC 2.7.1.-). | swissprot Q10156 | ND |
| 404 | 811.0 | HAPC. | sptrembl O59848 | DNA replication, recombination and repair |
| 405 | 810.6 | SULFITE OXIDASE PRECURSOR (EC 1.8.3.1). | swissprot Q07116 | ND |
| 406 | 809.6 | BETA-ADAPTIN (PLASMA MEMBRANE ADAPTOR HA2/AP2 ADAPTIN BETA SUBUNIT) (CLATHRIN ASSEMBLY PROTEIN COMPLEX 2 BETA LARGE CHAIN) (AP105B). | swissprot P21851 | ND |
| 407 | 809.6 | Murine RENT1 protein. | geneseqp W36509 | DNA replication, recombination and repair |

TABLE 1-continued

*Fusarium venenatum* ESTs

| Sequence Listing | zscore | Annotation | Database | Functional category |
|---|---|---|---|---|
| 408 | 809.5 | HYPOTHETICAL 69.9 KD PROTEIN IN MIC1-SRB5 INTERGENIC REGION. | swissprot P53261 | ND |
| 409 | 808.8 | Ester hydrolase protein encoded by rec 511 gene. | geneseqp R44609 | ND |
| 410 | 807.7 | PUTATIVE SACCHAROPINE DEHYDROGENASE. | sptrembl O59711 | Amino acid transport and metabolism |
| 411 | 807.2 | PROTEIN TRANSPORT PROTEIN SEC13. | swissprot P53024 | ND |
| 412 | 807.0 | HISTONE H4. | swissprot P04914 | DNA replication, recombination and repair |
| 413 | 806.7 | RHO3 PROTEIN. | swissprot Q00245 | ND |
| 414 | 805.6 | TRANSLATIONALLY CONTROLLED TUMOR PROTEIN HOMOLOG (TCTP). | swissprot P35691 | ND |
| 415 | 805.5 | PROBABLE ATP-DEPENDENT PERMEASE PRECURSOR. | swissprot P25371 | ND |
| 416 | 805.0 | NATURAL KILLER CELL ENHANCING FACTOR. | sptrembl O93241 | Posttranslational modification, protein turnover, chaperones |
| 417 | 804.9 | HYPOTHETICAL 61.8 KD PROTEIN C12B10.03 IN CHROMOSOME I. | swissprot Q10437 | ND |
| 418 | 803.1 | ALPHA-MANNOSIDASE. | sptrembl O13344 | Carbohydrate transport and metabolism |
| 419 | 800.6 | UBIQUITIN. | sptrembl Q9Y736 | ND |
| 420 | 800.3 | ACETYL-COA ACETYLTRANSFERASE. | tremblnew CAA22123 | Lipid metabolism |
| 421 | 800.1 | VANADATE RESISTANCE PROTEIN GOG5/VRG4/VAN2. | swissprot P40107. | ND |
| 422 | 799.0 | HISTONE H4. | swissprot P04914 | ND |
| 423 | 797.3 | CARNITINE ACETYL TRANSFERASE FACC. | sptrembl O13363 | ND |
| 424 | 795.3 | EBURICOL 14 ALPHA-DEMETHYLASE. | tremblnew AAF18469 | ND |
| 425 | 795.1 | HYPOTHETICAL 45.2 KD GTP-BINDING PROTEIN IN TRX1-ZPR1 INTERGENIC REGION. | swissprot P42942 | ND |
| 426 | 793.9 | 26S PROTEASOME REGULATORY SUBUNIT MTS4 (19S REGULATORY CAP REGION OF 26S PROTEASE SUBUNIT 2). | swissprot P87048 | ND |
| 427 | 792.2 | OLIGOSACCHARYLTRANSFERASE SUBUNIT. | sptrembl Q9Y716 | ND |
| 428 | 792.0 | PROBABLE METHYLMALONATE-SEMIALDEHYDE DEHYDROGENASE [ACYLATING] PRECURSOR (EC 1.2.1.27) (MMSDH). | swissprot P52713 | Energy production and conversion |
| 429 | 791.6 | NAM7 PROTEIN (NONSENSE-MEDIATED MRNA DECAY PROTEIN 1) (UP-FRAMESHIFT SUPPRESSOR 1). | swissprot P30771 | DNA replication, recombination and repair |
| 430 | 791.4 | Murine Int6 protein associated with MMTV integration and tumour growth. | geneseqp W02113 | ND |
| 431 | 789.7 | SULFUR METABOLITE REPRESSION CONTROL PROTEIN. | swissprot Q00659 | ND |
| 432 | 788.3 | RRNA BIOGENESIS PROTEIN RRP5. | swissprot Q05022 | ND |

TABLE 1-continued

*Fusarium venenatum* ESTs

| Sequence Listing | zscore | Annotation | Database | Functional category |
|---|---|---|---|---|
| 433 | 787.5 | PUTATIVE POTASSIUM CHANNEL SUBUNIT. | sptrembl O59826 | Energy production and conversion |
| 434 | 787.2 | 40S RIBOSOMAL PROTEIN S26E (CRP5) (13.6 KD RIBOSOMAL PROTEIN). | swissprot P21772 | ND |
| 435 | 786.8 | ELONGATION FACTOR 1-BETA (EF-1-BETA) (P30). | swissprot P30151 | ND |
| 436 | 786.6 | METHIONYL-TRNA SYNTHETASE-LIKE PROTEIN. | tremblnew CAB36842 | Translation, ribosomal structure and biogenesis |
| 437 | 786.4 | Mutant *Aspergillus oryzae* DEBY1058 rescued locus. | geneseqp W37993 | ND |
| 438 | 781.2 | GLUTAMATE--CYSTEINE LIGASE CATALYTIC SUBUNIT (EC 6.3.2.2) (GAMMA-GLUTAMYLCYSTEINE SYNTHETASE) (GAMMA-ECS) (GCS HEAVY CHAIN). | swissprot P19468 | ND |
| 439 | 781.2 | 60S RIBOSOMAL PROTEIN L17-A (YL17-A). | swissprot P05740 | ND |
| 440 | 780.5 | IMPORTIN ALPHA SUBUNIT (KARYOPHERIN ALPHA SUBUNIT) (SERINE-RICH RNA POLYMERASE I SUPPRESSOR PROTEIN). | swissnew O14063 | ND |
| 441 | 780.4 | UBIQUITIN-CONJUGATING ENZYME E2-28.4 KD (EC 6.3.2.19) (UBIQUITIN-PROTEIN LIGASE) (UBIQUITIN CARRIER PROTEIN). | swissprot P33296 | ND |
| 442 | 780.0 | Corn SUG1 polypeptide. | geneseqp W97652 | Posttranslational modification, protein turnover, chaperones |
| 443 | 777.0 | FIBRILLARIN (NUCLEOLAR PROTEIN 1). | swissprot P15646 | ND |
| 444 | 775.9 | HYPOTHETICAL 33.9 KD PROTEIN. | sptrembl P78995 | Amino acid transport and metabolism |
| 445 | 774.0 | NADPH-DEPENDENT ALDEHYDE REDUCTASE (EC 1.1.1.2) (ALCOHOL DEHYDROGENASE (NADP+)) (ALDEHYDE REDUCTASE (NADPH)). | sptrembl Q12707 | ND |
| 446 | 772.5 | ATP SYNTHASE DELTA CHAIN, MITOCHONDRIAL PRECURSOR (EC 3.6.1.34) (FRAGMENT). | swissnew P56525 | ND |
| 447 | 771.5 | UBIQUITIN-CONJUGATING PROTEIN. | tremblnew AAD55983 | ND |
| 448 | 770.1 | HYPOTHETICAL 23.6 KD PROTEIN C23C11.13C IN CHROMOSOME I. | swissprot O13917 | ND |
| 449 | 769.6 | HYPOTHETICAL 68.5 KD PROTEIN. | sptrembl O60111 | ND |
| 450 | 768.7 | UDP-N-ACETYLGLUCOSAMINE PYROPHOSPHORYLASE (EC 2.7.7.23). | swissprot O74933 | ND |
| 451 | 768.1 | ALUMINIUM RESISTANCE PROTEIN 2. | swissprot P43553 | Inorganic ion transport and metabolism |
| 452 | 765.4 | VACUOLAR AMINOPEPTIDASE I PRECURSOR (EC 3.4.11.22) (POLYPEPTIDASE) (LEUCINE AMINOPEPTIDASE IV) (LAPIV) (AMINOPEPTIDASE | swissprot P14904 | Amino acid transport and metabolism |

TABLE 1-continued

*Fusarium venenatum* ESTs

| Sequence Listing | zscore | Annotation | Database | Functional category |
|---|---|---|---|---|
| | | III) (AMINOPEPTIDASE YSCI). | | |
| 453 | 764.2 | NUCLEOSOME ASSEMBLY PROTEIN. | sptrembl O59797 | ND |
| 454 | 763.6 | HYPOTHETICAL 107.9 KD PROTEIN IN POL4-SRD1 INTERGENIC REGION. | swissprot P25618 | ND |
| 455 | 762.7 | GAL10 BIFUNCTIONAL PROTEIN [INCLUDES: UDP-GLUCOSE 4-EPIMERASE (EC 5.1.3.2) (GALACTOWALDENASE); ALDOSE 1-EPIMERASE (EC 5.1.3.3) (MUTAROTASE)]. | swissprot P40801 | Cell envelope biogenesis, outer membrane |
| 456 | 761.4 | REPLICATION PROTEIN. | swissprot P03858 | ND |
| 457 | 760.5 | UBIQUINOL-CYTOCHROME C REDUCTASE IRON-SULFUR SUBUNIT, MITOCHONDRIAL PRECURSOR (EC 1.10.2.2) (RIESKE IRON-SULFUR PROTEIN) (RISP). | swissprot P07056 | Energy production and conversion |
| 458 | 759.8 | POTENTIAL CAAX PRENYL PROTEASE 1 (EC 3.4.24.-) (PRENYL PROTEIN-SPECIFIC ENDOPROTEASE 1) (PPSEP 1). | swissprot Q10071 | Posttranslational modification, protein turnover, chaperones |
| 459 | 758.2 | PUTATIVE MITOCHONDRIAL PHOSPHATE CARRIER PROTEIN. | tremblnew CAB55764 | ND |
| 460 | 757.5 | 31.1 KD PROTEIN IN DCM-SERU INTERGENIC REGION. | swissprot P31658 | ND |
| 461 | 757.3 | BIFUNCTIONAL PURINE BIOSYNTHETIC PROTEIN ADE1 [INCLUDES: PHOSPHORIBOSYLAMINE--GLYCINE LIGASE (EC 6.3.4.13) (GARS) (GLYCINAMIDE RIBONUCLEOTIDE SYNTHETASE) (PHOSPHORIBOSYLGLYCIN AMIDE SYNTHETASE); PHOSPHORIBOSYLFORMYL GLYCINAMIDINE CYCLO-LIGASE (EC 6.3.3.1) (AIRS) (PHOSPHORIBOSYL-AMINOIMIDAZOLE SYNTHETASE) (AIR SYNTHASE)]. | swissprot Q99148 | Nucleotide transport |
| 462 | 757.2 | PATHOGENICITY PROTEIN. | sptrembl O93846 | ND |
| 463 | 754.9 | PUTATIVE DNA-DIRECTED RNA POLYMERASE III LARGEST SUBUNIT. | sptrembl O94666 | Transcription |
| 464 | 753.8 | SECRETORY PATHWAY GDP DISSOCIATION INHIBITOR. | swissprot P39958 | ND |
| 465 | 752.6 | GUANINE NUCLEOTIDE-BINDING PROTEIN ALPHA SUBUNIT. | swissprot O42784 | ND |
| 466 | 752.2 | HYPOTHETICAL 22.7 KD PROTEIN. | sptrembl O60073 | ND |
| 467 | 749.7 | ALLANTOINASE (EC 3.5.2.5). | swissprot P32375 | Nucleotide transport |
| 468 | 748.8 | TRANSCRIPTION FACTOR TRI6. | tremblnew BAA83724 | ND |
| 469 | 748.3 | Ribosomal protein L41. | geneseqp R77658 | Translation, ribosomal structure and biogenesis |

TABLE 1-continued

*Fusarium venenatum* ESTs

| Sequence Listing | zscore | Annotation | Database | Functional category |
|---|---|---|---|---|
| 470 | 748.0 | RAN/SPI1 BINDING PROTEIN. | sptrembl Q09717 | ND |
| 471 | 746.4 | MITOCHONDRIAL PROCESSING PEPTIDASE ALPHA SUBUNIT PRECURSOR (EC 3.4.24.64) (ALPHA-MPP). | swissprot P23955 | ND |
| 472 | 745.3 | Human mammastatin amino acid sequence. | geneseqp Y23756 | ND |
| 473 | 744.9 | NADH-UBIQUINONE OXIDOREDUCTASE 21.3 KD SUBUNIT (EC 1.6.5.3) (EC 1.6.99.3). | swissprot P19968 | ND |
| 474 | 744.1 | MYO-INOSITOL-1-PHOSPHATE SYNTHASE (EC 5.5.1.4) (IPS). | swissprot P42800 | Lipid metabolism |
| 475 | 743.9 | HYPOTHETICAL 61.3 KD PROTEIN CY369.29. | sptrembl P71838 | ND |
| 476 | 743.6 | 60S RIBOSOMAL PROTEIN L27-A. | tremblnew CAB39364 | ND |
| 477 | 741.1 | EUKARYOTIC TRANSLATION INITIATION FACTOR 2 GAMMA SUBUNIT (EIF-2-GAMMA). | swissprot P32481 | Amino acid transport and metabolism |
| 478 | 741.0 | PROTEASOME COMPONENT PRE4 (EC 3.4.99.46) (MACROPAIN SUBUNIT PRE4) (PROTEINASE YSCE SUBUNIT PRE4) (MULTICATALYTIC ENDOPEPTIDASE COMPLEX SUBUNIT PRE4). | swissprot P30657 | ND |
| 479 | 740.3 | MULTICATALYTIC PROTEINASE 222 aa, chain M + 1 | pdb 1RYP | ND |
| 480 | 739.6 | EPD1 PROTEIN PRECURSOR. | swissprot P56092 | ND |
| 481 | 738.3 | PROBABLE GAMMA-GLUTAMYL PHOSPHATE REDUCTASE. | tremblnew CAB57445 | Amino acid transport and metabolism |
| 482 | 737.8 | CONSERVED HYPOTHETICAL PROTEIN. | tremblnew CAB39853 | ND |
| 483 | 736.5 | PROBABLE ARGININOSUCCINATE LYASE (EC 4.3.2.1) (ARGINOSUCCINASE) (ASAL). | swissprot P50514 | Amino acid transport and metabolism |
| 484 | 735.3 | ANTHRANILATE SYNTHASE COMPONENT II (EC 4.1.3.27) [INCLUDES: GLUTAMINE AMIDOTRANSFERASE; INDOLE-3-GLYCEROL PHOSPHATE SYNTHASE (EC 4.1.1.48) (IGPS); N-(5'-PHOSPHORIBOSYL)ANTHR ANILATE ISOMERASE (EC 5.3.1.24) (PRAI)]. | swissprot P00908 | ND |
| 485 | 734.4 | ACONITATE HYDRATASE, MITOCHONDRIAL PRECURSOR (EC 4.2.1.3) (CITRATE HYDRO-LYASE) (ACONITASE). | swissprot O13966 | Energy production and conversion |
| 486 | 733.9 | PROBABLE SUCCINYL-COA LIGASE [GDP-FORMING] BETA-CHAIN, MITOCHONDRIAL PRECURSOR (EC 6.2.1.4) (SUCCINYL-COA SYNTHETASE, BETA CHAIN) (SCS-BETA). | swissprot P53312 | Energy production and conversion |

TABLE 1-continued

*Fusarium venenatum* ESTs

| Sequence Listing | zscore | Annotation | Database | Functional category |
|---|---|---|---|---|
| 487 | 732.9 | Urate oxidase encoded by A. flavus-derived cDNA clone 9C. | geneseqp R10222 | ND |
| 488 | 732.0 | PUTATIVE PHOPHODIESTERASE-NUCLEOTIDE PYROPHOSPHATASE PRECURSOR. | sptrembl O94323 | ND |
| 489 | 731.2 | CAMP-DEPENDENT PROTEIN KINASE REGULATORY CHAIN. | swissnew O14448 | ND |
| 490 | 730.2 | K06A5.6 PROTEIN. | sptrembl O44549 | Lipid metabolism |
| 491 | 730.0 | 60S RIBOSOMAL PROTEIN L21. | tremblnew CAB44755 | Translation, ribosomal structure and biogenesis |
| 492 | 729.0 | PUTATIVE ALANINE AMINOTRANSFERASE, MITOCHONDRIAL PRECURSOR (EC 2.6.1.2) (GLUTAMIC--PYRUVIC TRANSAMINASE) (GPT) (GLUTAMIC--ALANINE TRANSAMINASE). | swissprot P52893 | ND |
| 493 | 726.0 | PUTATIVE NADH-CYTOCHROME B5 REDUCTASE. | sptrembl O74557 | Coenzyme metabolism |
| 494 | 725.9 | CYTOCHROME C1, HEME PROTEIN PRECURSOR. | swissprot P07142 | ND |
| 495 | 725.2 | HYPOTHETICAL 74.5 KD PROTEIN C4H3.03C IN CHROMOSOME I. | swissprot Q10211 | ND |
| 496 | 724.2 | MITOCHONDRIAL PRECURSOR PROTEINS IMPORT RECEPTOR (72 KD MITOCHONDRIAL OUTER MEMBRANE PROTEIN) (MITOCHONDRIAL IMPORT RECEPTOR FOR THE ADP/ATP CARRIER) (TRANSLOCASE OF OUTER MEMBRANE TOM70). | swissprot P23231 | ND |
| 497 | 724.1 | MITOCHONDRIAL RIBOSOMAL PROTEIN S24. | swissprot P08580 | Translation, ribosomal structure and biogenesis |
| 498 | 722.5 | SPERMIDINE SYNTHASE. | sptrembl Q9Y8H7 | Amino acid transport and metabolism |
| 499 | 721.9 | RNA BINDING PROTEIN. | sptrembl O60059 | ND |
| 500 | 721.0 | RNA BINDING PROTEIN. | sptrembl O59800 | ND |
| 501 | 720.5 | HYPOTHETICAL 60.7 KD PROTEIN C1B1.02C IN CHROMOSOME I. | sptrembl O13863 | ND |
| 502 | 718.8 | P-TYPE ATPASE (FRAGMENT). | tremblnew CAB65297 | Inorganic ion transport and metabolism |
| 503 | 718.3 | MNN9 PROTEIN. | swissprot P39107 | ND |
| 504 | 718.3 | HISTONE H2B. | swissprot P23754 | ND |
| 505 | 717.6 | HYPOTHETICAL 67.8 KD PROTEIN IN IKI1-ERG9 INTERGENIC REGION. | swissprot P38875 | ND |
| 506 | 716.6 | BIFUNCTIONAL PURINE BIOSYNTHESIS PROTEIN ADE17 [INCLUDES: PHOSPHORIBOSYLAMINOI MIDAZOLECARBOXAMIDE FORMYLTRANSFERASE (EC 2.1.2.3) (AICAR TRANSFORMYLASE); IMP CYCLOHYDROLASE (EC | swissprot P38009 | Nucleotide transport |

TABLE 1-continued

Fusarium venenatum ESTs

| Sequence Listing | zscore | Annotation | Database | Functional category |
|---|---|---|---|---|
| | | 3.5.4.10) (INOSINICASE) (IMP SYNTHETASE) (ATIC)]. | | |
| 507 | 716.2 | GABA PERMEASE. | sptrembl Q9Y860 | Amino acid transport and metabolism |
| 508 | 715.8 | PUTATIVE MANNOSE-1-PHOSPHATE GAUNYL TRANSFERASE. | sptrembl O60064 | ND |
| 509 | 715.5 | PUTATIVE CYSTINE-RICH TRANSCRIPTIONAL REGULATOR. | sptrembl O74853 | ND |
| 510 | 713.6 | BETA-GLUCOSIDASE PRECURSOR (EC 3.2.1.21). | tremblnew AAF21242 | ND |
| 511 | 712.6 | CHORISMATE MUTASE (EC 5.4.99.5). | sptrembl Q9Y7B2 | ND |
| 512 | 712.4 | PROBABLE ATP-DEPENDENT TRANSPORTER YOL075C. | swissprot Q08234 | ND |
| 513 | 709.4 | CYCLOPHILIN, MITOCHONDRIAL FORM PRECURSOR (EC 5.2.1.8). | sptrembl Q99009 | Posttranslational modification, protein turnover, chaperones |
| 514 | 709.2 | ER-DERIVED VESICLES PROTEIN ERV14. | swissnew P53173 | ND |
| 515 | 707.3 | PUTATIVE CALCIUM P-TYPE ATPASE (FRAGMENT). | tremblnew CAB65293 | Inorganic ion transport and metabolism |
| 516 | 705.7 | RASP F 9 (FRAGMENT). | sptrembl O42800 | ND |
| 517 | 704.8 | HYPOTHETICAL 20.9 KD PROTEIN. | sptrembl O94286 | ND |
| 518 | 704.7 | COATOMER BETA SUBUNIT (BETA-COAT PROTEIN) (BETA-COP). | swissprot P23514 | ND |
| 519 | 702.9 | MSH3 PROTEIN. | sptrembl O81818 | DNA replication, recombination and repair |
| 520 | 702.1 | POTASSIUM-TRANSPORTING ATPASE ALPHA CHAIN (EC 3.6.1.36) (PROTON PUMP) (GASTRIC H+/K+ ATPASE ALPHA SUBUNIT). | swissprot P19156 | ND |
| 521 | 702.0 | PHOSPHATIDATE CYTIDYLYLTRANSFERASE (EC 2.7.7.41) (CDP-DIGLYCERIDE SYNTHETASE) (CDP-DIGLYCERIDE PYROPHOSPHORYLASE) (CDP-DIACYLGLYCEROL SYNTHASE) (CDS) (CTP:PHOSPHATIDATE CYTIDYLYLTRANSFERASE) (CDP-DAG SYNTHASE). | swissprot P38221 | Lipid metabolism |
| 522 | 701.7 | VIRULENCE PROTEIN CAP20. | sptrembl Q00368 | ND |
| 523 | 700.9 | CHROMOSOME XII READING FRAME ORF YLR009W. | sptrembl Q07915 | Translation, ribosomal structure and biogenesis |
| 525 | 699.5 | PUTATIVE YEAST CELL DIVISION CYCLE CDC50 HOMOLOG. | sptrembl O94568 | ND |
| 526 | 698.2 | ACONITATE HYDRATASE, MITOCHONDRIAL PRECURSOR (EC 4.2.1.3) (CITRATE HYDRO-LYASE) (ACONITASE). | swissprot O13966 | Energy production and conversion |
| 527 | 695.7 | PUTATIVE DELTA-1-PYROLINE-5-CARBOXYLATE DEHYDROGENASE. | sptrembl O74766 | Energy production and conversion |

TABLE 1-continued

*Fusarium venenatum* ESTs

| Sequence Listing | zscore | Annotation | Database | Functional category |
|---|---|---|---|---|
| 528 | 694.5 | GLUTATHIONE PEROXIDASE HYR1 (EC 1.11.1.9). | swissprot P40581 | Posttranslational modification, protein turnover, chaperones |
| 529 | 693.9 | PROBABLE VACUOLAR SORTING PROTEIN C9G1.14C (FRAGMENT). | sptrembl O14309 | ND |
| 530 | 693.0 | UBIQUITIN-CONJUGATING ENZYME E2-24 KD (EC 6.3.2.19) (UBIQUITIN-PROTEIN LIGASE) (UBIQUITIN CARRIER PROTEIN). | swissprot P21734 | ND |
| 531 | 692.8 | CYTOCHROME C OXIDASE POLYPEPTIDE V PRECURSOR (EC 1.9.3.1). | swissprot P06810 | ND |
| 532 | 691.7 | HYPOTHETICAL ZINC-TYPE ALCOHOL DEHYDROGENASE-LIKE PROTEIN IN PRE5-FET4 INTERGENIC REGION. | swissprot Q04894 | ND |
| 533 | 691.5 | SECRETORY PATHWAY GDP DISSOCIATION INHIBITOR. | swissprot P39958 | ND |
| 534 | 690.1 | GLUCAN SYNTHASE. | sptrembl Q9Y8B3 | ND |
| 535 | 689.7 | SUPEROXIDE DISMUTASE PRECURSOR (EC 1.15.1.1). | sptrembl Q9Y783 | ND |
| 536 | 689.2 | DOLICHOL-PHOSPHATE MANNOSYLTRANSFERASE (EC 2.4.1.83) (DOLICHOL-PHOSPHATE MANNOSE SYNTHASE) (DOLICHYL-PHOSPHATE BETA-D-MANNOSYLTRANSFERASE) | sptrembl O14466 | ND |
| 537 | 688.9 | PUTATIVE FUMARASE. | sptrembl O24649 | ND |
| 538 | 688.8 | PROBABLE INOSINE-5'-MONOPHOSPHATE DEHYDROGENASE (EC 1.1.1.205) (IMP DEHYDROGENASE) (IMPDH) (IMPD). | swissprot P50095 | ND |
| 539 | 687.4 | CHROMOSOME XV READING FRAME ORF YOR197W. | sptrembl Q08601 | ND |
| 540 | 686.5 | PUTATIVE PROTEASOME COMPONENT PUP1 PRECURSOR (EC 3.4.99.46) (MACROPAIN SUBUNIT) (MULTICATALYTIC ENDOPEPTIDASE COMPLEX SUBUNIT). | swissprot Q09841 | Posttranslational modification, protein turnover, chaperones |
| 541 | 685.3 | SERYL-TRNA SYNTHETASE (EC 6.1.1.11) (SERINE--TRNA LIGASE) (SERRS). | swissprot Q39230 | Translation, ribosomal structure and biogenesis |
| 542 | 684.0 | HYPOTHETICAL 41.3 KD PROTEIN C26F1.12C IN CHROMOSOME I. | swissprot Q10498 | ND |
| 543 | 683.8 | SEXUAL DIFFERENTIATION PROCESS PROTEIN ISP4. | swissprot P40900 | ND |
| 544 | 682.8 | FATTY ACID OMEGA-HYDROXYLASE (P450FOXY). | sptrembl Q9Y8G7 | ND |
| 545 | 680.9 | METHIONINE AMINOPEPTIDASE. | sptrembl O60085 | Translation, ribosomal structure and biogenesis |
| 546 | 679.8 | UBIQUITIN CONJUGATING ENZYME. | tremblnew CAB38416 | ND |
| 547 | 679.5 | NITRITE REDUCTASE. | sptrembl Q92198 | ND |
| 548 | 679.5 | PUTATIVE GOLGI MEMBRANE PROTEIN-SORTING PROTEIN. | sptrembl O94291 | ND |

TABLE 1-continued

*Fusarium venenatum* ESTs

| Sequence Listing | zscore | Annotation | Database | Functional category |
|---|---|---|---|---|
| 549 | 677.1 | COLONY 1. | sptrembl Q01491 | ND |
| 550 | 671.0 | MALTOSE PERMEASE. | sptrembl Q9Y845 | ND |
| 551 | 668.6 | ANNEXIN XIV. | sptrembl O59907 | ND |
| 552 | 667.7 | SQUALENE MONOOXYGENASE (EC 1.14.99.7) (SQUALENE EPOXIDASE) (SE). | swissprot Q92206 | Coenzyme metabolism |
| 553 | 667.2 | PROBABLE ATP-DEPENDENT RNA HELICASE DBP8. | swissprot P38719 | DNA replication, recombination and repair |
| 554 | 666.7 | HYPOTHETICAL 55.8 KD PROTEIN. | tremblnew CAB63552 | ND |
| 555 | 664.9 | CYTOCHROME P450 MONOOXYGENASE (FRAGMENT). | sptrembl O64410 | ND |
| 556 | 664.4 | ATP SYNTHASE PROTEIN 9, MITOCHONDRIAL PRECURSOR (EC 3.6.1.34) (LIPID-BINDING PROTEIN). | swissprot P00842 | ND |
| 557 | 663.4 | ATP SYNTHASE SUBUNIT 4, MITOCHONDRIAL PRECURSOR (EC 3.6.1.34). | swissprot O13349 | ND |
| 558 | 663.4 | ERGOSTEROL BIOSYNTHESIS PROTEIN (KES1). | sptrembl O74178 | ND |
| 559 | 662.8 | URICASE (EC 1.7.3.3) (URATE OXIDASE). | swissprot Q00511 | ND |
| 560 | 662.4 | GLYCEROL-3-PHOSPHATE DEHYDROGENASE (EC 1.1.1.8). | tremblnew CAB58452 | ND |
| 561 | 661.8 | PUTATIVE GLUTAMYL-TRNA SYNTHETASE, CYTOPLASMIC (EC 6.1.1.17) (GLUTAMATE--TRNA LIGASE) (GLURS). | sptrembl O13775 | Translation, ribosomal structure and biogenesis |
| 562 | 661.5 | PHOSPHORIBOSYLFORMYL GLYCINAMIDINE SYNTHASE (EC 6.3.5.3) (FGAM SYNTHASE) (FORMYLGLYCINAMIDE RIBOTIDE AMIDOTRANSFERASE) (FGARAT). | swissprot P15254 | Nucleotide transport |
| 563 | 661.0 | Mutant *Aspergillus oryzae* DEBY932 rescued locus. | geneseqp W37992 | ND |
| 564 | 660.6 | N-MYRISTOYL TRANSFERASE. | tremblnew BAA87865 | ND |
| 565 | 660.1 | HYPOTHETICAL 79.2 KD PROTEIN. | sptrembl Q04585 | Energy production and conversion |
| 566 | 659.6 | PUTATIVE ALDEHYDE DEHYDROGENASE (NAD+) (EC 1.2.1.3). | sptrembl O74187 | Energy production and conversion |
| 567 | 657.9 | PROTEASOME COMPONENT PRE2 PRECURSOR (EC 3.4.99.46) (MACROPAIN SUBUNIT PRE2) (PROTEINASE YSCE SUBUNIT PRE2) (MULTICATALYTIC ENDOPEPTIDASE COMPLEX SUBUNIT PRE2). | swissprot P30656 | Posttranslational modification, protein turnover, chaperones |
| 568 | 657.8 | BIFUNCTIONAL HISTIDINE BIOSYNTHESIS PROTEIN HIS7 [INCLUDES: HISH-TYPE AMIDOTRANSFERASE (EC 2.4.2.-); HISF-TYPE CYCLASE]. | swissprot P33734 | Amino acid transport and metabolism |
| 569 | 657.3 | CYCLOPHILIN OVCYP-2 (EC 5.2.1.8). | sptrembl Q25633 | Posttranslational modification, protein turnover, chaperones |

TABLE 1-continued

_Fusarium venenatum ESTs_

| Sequence Listing | zscore | Annotation | Database | Functional category |
|---|---|---|---|---|
| 570 | 657.0 | 40S RIBOSOMAL PROTEIN S3AE (S1). | swissprot Q09781 | Translation, ribosomal structure and biogenesis |
| 571 | 657.0 | PUTATIVE RHO GDP-DISSOCIATION INHIBITOR (RHO GDI). | sptrembl O14224 | ND |
| 572 | 656.5 | NHP2/RS6 FAMILY PROTEIN YEL026W HOMOLOG. | swissprot Q21568 | Translation, ribosomal structure and biogenesis |
| 573 | 655.1 | Aminopeptidase. | geneseqp W05589 | ND |
| 574 | 655.1 | YNT20 PROTEIN. | swissprot P54964 | ND |
| 575 | 651.4 | ATP SYNTHASE D CHAIN, MITOCHONDRIAL (EC 3.6.1.34). | swissprot O13350 | ND |
| 576 | 649.3 | HISTONE H2B. | swissprot P23754 | ND |
| 577 | 648.3 | RIBOFLAVIN SYNTHASE ALPHA CHAIN. | sptrembl Q9Y7P0 | Coenzyme metabolism |
| 578 | 648.1 | 60S RIBOSOMAL PROTEIN L6-A (L17) (YL16) (RP18). | swissprot Q02326 | ND |
| 579 | 647.9 | CALNEXIN HOMOLOG PRECURSOR. | swissprot P36581 | ND |
| 580 | 647.0 | HYPOTHETICAL 50.5 KD PROTEIN. | sptrembl Q03940 | DNA replication, recombination and repair |
| 581 | 646.7 | HYDROXYMETHYLGLUTARYL-COA LYASE (EC 4.1.3.4) (HMG-COA LYASE) (HL) (3-HYDROXY-3-METHYLGLUTARATE-COA LYASE). | swissprot P13703 | Amino acid transport and metabolism |
| 582 | 645.8 | FATTY ACID DESATURASE (FRAGMENT). | sptrembl O74645 | ND |
| 583 | 644.7 | HET-C PROTEIN. | tremblnew AAD54275 | ND |
| 584 | 643.9 | SIK1 PROTEIN. | swissprot Q12460 | Translation, ribosomal structure and biogenesis |
| 585 | 642.1 | _B. bassiana_ POPS reductase protein. | geneseqp Y33673 | ND |
| 586 | 639.7 | CARBONIC ANHYDRASE (EC 4.2.1.1). | sptrembl Q43061 | Inorganic ion transport and metabolism |
| 587 | 639.5 | CONSERVED HYPOTHETICAL PROTEIN. | sptrembl Q9Y7K1 | Posttranslational modification, protein turnover, chaperones |
| 588 | 638.9 | 3-ISOPROPYLMALATE DEHYDROGENASE (EC 1.1.1.85) (BETA-IPM DEHYDROGENASE) (IMDH) (3-IPM-DH). | swissprot P34738 | Amino acid transport and metabolism |
| 589 | 638.9 | CELL DIVISION CONTROL PROTEIN NDA4. | swissprot P41389 | ND |
| 590 | 637.4 | HYPOTHETICAL 55.4 KD PROTEIN. | sptrembl Q9Y439 | ND |
| 591 | 633.4 | RIBOSOMAL PROTEIN L37 HOMOLOG. | tremblnew CAB58374 | ND |
| 592 | 633.0 | MITOGEN-ACTIVATED PROTEIN KINASE (EC 2.7.1.-) (MAPK). | sptrembl Q00859 | Signal transduction mechanisms |
| 593 | 631.9 | SLA2P. | sptrembl O94097 | ND |
| 594 | 629.4 | HASNA-1. | sptrembl Q92849 | Inorganic ion transport and metabolism |
| 595 | 627.9 | G2/MITOTIC-SPECIFIC CYCLIN B. | swissprot P30284 | ND |
| 596 | 627.4 | CARBOXYPEPTIDASE S1 (EC 3.4.16.6). | swissprot P34946 | ND |
| 597 | 626.5 | MAL3 PROTEIN. | swissnew Q10113 | ND |

TABLE 1-continued

_Fusarium venenatum ESTs_

| Sequence Listing | zscore | Annotation | Database | Functional category |
|---|---|---|---|---|
| 598 | 626.1 | Oat HaSGT protein fragment. | geneseqp W64390 | ND |
| 599 | 625.2 | HYPOTHETICAL PROTEIN C5D6.13 (FRAGMENT). | sptrembl O14205 | ND |
| 600 | 625.0 | 60S RIBOSOMAL PROTEIN L26. | swissnew P78946 | ND |
| 601 | 623.8 | HYPOTHETICAL 43.9 KD PROTEIN IN MSYB-HTRB INTERGENIC REGION (ORF1). | swissprot P25744 | ND |
| 602 | 623.1 | URIDYLATE KINASE (EC 2.7.4.-) (UK) (URIDINE MONOPHOSPHATE KINASE) (UMP KINASE). | swissprot P15700 | Nucleotide transport |
| 603 | 620.9 | HYPOTHETICAL 29.4 KD PROTEIN C4D7.06C IN CHROMOSOME I. | sptrembl O14172 | ND |
| 604 | 620.7 | EPITHELIAL BASOLATELAR CHLORIDE CONDUCTANCE REGULATOR. | sptrembl Q28689 | ND |
| 605 | 619.2 | ALCOHOL DEHYDROGENASE I (EC 1.1.1.1). | swissprot P41747 | ND |
| 606 | 618.9 | N-MYRISTOYL TRANSFERASE. | tremblnew BAA87865 | ND |
| 607 | 618.8 | S. cerevisiae uronate dehydrogenase. | geneseqp W29217 | ND |
| 608 | 617.4 | SEXUAL DIFFERENTIATION PROCESS PROTEIN ISP4. | swissprot P40900 | ND |
| 609 | 616.1 | GALACTOKINASE (EC 2.7.1.6). | swissnew P04385 | Carbohydrate transport and metabolism |
| 610 | 614.9 | 8 KDA CYTOPLASMIC DYNEIN LIGHT CHAIN. | sptrembl O94111 | ND |
| 611 | 614.6 | FATTY ALDEHYDE DEHYDROGENASE (EC 1.2.1.3) (ALDEHYDE DEHYDROGENASE, MICROSOMAL) (ALDH CLASS 3). | swissprot P47740 | Energy production and conversion |
| 612 | 614.4 | HYPOTHETICAL 79.2 KD PROTEIN. | sptrembl Q04585 | Energy production and conversion |
| 613 | 614.3 | CHROMOSOME IV READING FRAME ORF YDL166C. | sptrembl Q12055 | Nucleotide transport |
| 614 | 612.6 | PHOSPHATIDYLSERINE DECARBOXYLASE PROENZYME 1 PRECURSOR (EC 4.1.1.65). | sptrembl O14333 | Lipid metabolism |
| 615 | 612.5 | RIBOSOMAL PROTEIN CRP7. | sptrembl O93798 | ND |
| 616 | 612.4 | SERINE-TYPE CARBOXYPEPTIDASE F PRECURSOR (EC 3.4.16.-) (PROTEINASE F) (CPD-II). | swissprot P52718 | ND |
| 617 | 610.3 | PHOSPHOENOLPYRUVATE CARBOXYKINASE [ATP] (EC 4.1.1.49). | swissprot O13434 | Energy production and conversion |
| 618 | 609.4 | ACYL CARRIER PROTEIN, MITOCHONDRIAL PRECURSOR (ACP) (NADH-UBIQUINONE OXIDOREDUCTASE 9.6 KD SUBUNIT) (EC 1.6.5.3) (EC 1.6.99.3). | swissprot P11943 | ND |
| 619 | 608.2 | GLUCOSE-6-PHOSPHATE ISOMERASE, CYTOSOLIC (EC 5.3.1.9) (GPI) (PHOSPHOGLUCOSE | sptrembl O94371 | Carbohydrate transport and metabolism |

TABLE 1-continued

*Fusarium venenatum* ESTs

| Sequence Listing | zscore | Annotation | Database | Functional category |
|---|---|---|---|---|
| | | ISOMERASE) (PGI) (PHOSPHOHEXOSE ISOMERASE) (PHI). | | |
| 620 | 607.9 | ISOCITRATE LYASE (EC 4.1.3.1) (ISOCITRASE) (ISOCITRATASE) (ICL). | swissprot P28299 | Energy production and conversion |
| 621 | 607.8 | TYROSYL-TRNA SYNTHETASE, MITOCHONDRIAL PRECURSOR (EC 6.1.1.1) (TYROSINE--TRNA LIGASE) (TYRRS). | swissprot P28669 | ND |
| 622 | 605.7 | HYPOTHETICAL 55.8 KD PROTEIN. | tremblnew CAB63552 | ND |
| 623 | 605.6 | HYPOTHETICAL 24.5 KD PROTEIN. | tremblnew CAB52035 | ND |
| 624 | 605.2 | 60S RIBOSOMAL PROTEIN L32-A. | swissprot P79015 | Translation, ribosomal structure and biogenesis |
| 625 | 604.7 | PROBABLE RIBOSE-PHOSPHATE PYROPHOSPHOKINASE 5 (EC 2.7.6.1) (PHOSPHORIBOSYL PYROPHOSPHATE SYNTHETASE 5). | swissprot Q12265 | Nucleotide transport |
| 626 | 604.2 | HYPOTHETICAL 55.5 KD PROTEIN C17A2.05 IN CHROMOSOME I. | sptrembl O13755 | Energy production and conversion |
| 627 | 603.9 | HOMOLOGUES TO NITRILE HYDRATASE REGION 3'-HYPOTHETICAL PROTEIN P47K OF P. CHLORORAPHIS. | sptrembl P94400 | ND |
| 628 | 603.8 | *Cercospora nicotianae* cercosporin resistance sor1 gene product. | geneseqp W71467 | Nucleotide transport |
| 629 | 603.7 | PUTATIVE HYDROXYACYLGLUTATHIONE HYDROLASE. | tremblnew CAB57337 | ND |
| 630 | 602.9 | NADH-UBIQUINONE OXIDOREDUCTASE 21 KD SUBUNIT (EC 1.6.5.3) (EC 1.6.99.3) (COMPLEX I-21 KD) (CI-21 KD). | swissprot Q02854 | ND |
| 631 | 602.6 | OPSIN-1. | tremblnew AAD45253 | ND |
| 632 | 602.0 | PUTATIVE MITOCHONDRIAL PROTEIN IMPORT PROTEIN - DNAJ PROTEIN. | sptrembl O74752 | Posttranslational modification, protein turnover, chaperones |
| 633 | 601.4 | SEPTIN B. | sptrembl P78620 | ND |
| 634 | 601.4 | ORNITHINE DECARBOXYLASE (EC 4.1.1.17) (ODC). | swissprot P27121 | ND |
| 635 | 601.1 | FADE13. | sptrembl O86319 | Lipid metabolism |
| 636 | 598.6 | PUTATIVE GTP CYCLOHYDROLASE. | tremblnew CAB65619 | ND |
| 637 | 597.2 | PROBABLE ATP-DEPENDENT PERMEASE C3F10.11C. | swissprot Q10185 | ND |
| 638 | 596.5 | YEAST REDUCED VIABILITY UPON STARVATION PROTEIN 161 HOMOLOG, IMPLICATED IN CELL GROWTH AND CYTOSKELETAL ORGANISATION. | tremblnew CAA22181 | ND |
| 639 | 595.3 | PROTEIN KINASE DSK1 (EC 2.7.1.-) (DIS1-SUPPRESSING PROTEIN KINASE). | swissprot P36616 | ND |

TABLE 1-continued

_Fusarium venenatum ESTs_

| Sequence Listing | zscore | Annotation | Database | Functional category |
|---|---|---|---|---|
| 640 | 595.2 | HYPOTHETICAL 46.5 KD PROTEIN C12B10.04 IN CHROMOSOME I. | swissprot Q10438 | ND |
| 641 | 595.1 | PUTATIVE HELICASE C6F12.16 IN CHROMOSOME I. | swissprot O14232 | DNA replication, recombination and repair |
| 642 | 594.9 | HYPOTHETICAL 48.3 KD PROTEIN IN MOB1-SGA1 INTERGENIC REGION. | swissprot P40487 | Translation, ribosomal structure and biogenesis |
| 643 | 593.8 | _S. cerevisiae_ type 2 methionine aminopeptidase (MetAP2). | geneseqp W94766 | Translation, ribosomal structure and biogenesis |
| 644 | 593.1 | HYPOTHETICAL 68.3 KD PROTEIN. | sptrembl Q03195 | ND |
| 645 | 593.0 | RAS-2 PROTEIN. | swissnew Q01387 | ND |
| 646 | 591.1 | DIHYDROLIPOAMIDE SUCCINYLTRANSFERASE. | tremblnew AAD47296 | ND |
| 647 | 590.3 | HYPOTHETICAL 68.1 KD PROTEIN. | tremblnew CAB63538 | Nucleotide transport |
| 648 | 590.2 | PUTATIVE TYPE III ALCOHOL DEHYDROGENASE. | sptrembl Q94532 | ND |
| 649 | 590.0 | NUCLEAR TRANSPORT FACTOR 2 (NTF-2). | swissprot P87102 | ND |
| 650 | 589.8 | _Aspergillus niger_ adhA gene. | geneseqp P70497 | ND |
| 651 | 588.9 | NADH-UBIQUINONE OXIDOREDUCTASE 12 KD SUBUNIT PRECURSOR (EC 1.6.5.3) (EC 1.6.99.3) (COMPLEX I-12 KD) (CI-12 KD). | swissprot Q03015 | ND |
| 652 | 588.0 | ALTERNATIVE OXIDASE. | sptrembl O93788 | ND |
| 653 | 587.6 | HYPOTHETICAL 31.1 KD PROTEIN IN SIP18-SPT21 INTERGENIC REGION. | swissprot Q03219 | ND |
| 654 | 587.0 | PISATIN DEMETHYLASE (EC 1.14.-.-) (CYTOCHROME P450 57A1). | swissprot Q12645 | ND |
| 655 | 586.5 | FISSION YEAST. | sptrembl P78771 | ND |
| 656 | 584.1 | ADENYLOSUCCINATE LYASE (EC 4.3.2.2) (ADENYLOSUCCINASE) (ASL). | swissprot Q05911 | Nucleotide transport |
| 657 | 583.8 | PROTEIN TRANSLATION FACTOR SUI1. | swissprot P32911 | ND |
| 658 | 582.3 | HEAT SHOCK PROTEIN 90 HOMOLOG (SUPPRESSOR OF VEGETATIVE INCOMPATIBILITY MOD-E). | swissprot O43109 | ND |
| 659 | 582.3 | CELL DIVISION CONTROL PROTEIN 54. | swissprot P30665 | DNA replication, recombination and repair |
| 660 | 582.2 | HYPOTHETICAL 36.8 KD PROTEIN C9E9.11 IN CHROMOSOME I. | sptrembl O14295 | ND |
| 661 | 581.2 | BIFUNCTIONAL HISTIDINE BIOSYNTHESIS PROTEIN HIS7 [INCLUDES: HISH-TYPE AMIDOTRANSFERASE (EC 2.4.2.-); HISF-TYPE CYCLASE]. | swissprot P33734 | Amino acid transport and metabolism |
| 662 | 581.1 | RIBOSOMAL PROTEIN CRP7. | sptrembl O93798 | ND |
| 663 | 580.4 | HSP78P. | sptrembl Q12137 | Posttranslational modification, protein turnover, chaperones |
| 664 | 579.8 | BASIC AMINO-ACID PERMEASE. | swissprot P38971 | Amino acid transport and metabolism |

TABLE 1-continued

*Fusarium venenatum* ESTs

| Sequence Listing | zscore | Annotation | Database | Functional category |
|---|---|---|---|---|
| 665 | 576.9 | EXTRACELLULAR PUTATIVE DNASE. | tremblnew AAD53090 | ND |
| 666 | 576.2 | TFIID SUBUNIT TAF72P. | sptrembl O13282 | ND |
| 667 | 576.1 | HISTIDYL-TRNA SYNTHETASE (EC 6.1.1.21) (HISTIDINE--TRNA LIGASE) (HISRS). | swissprot P43823 | ND |
| 668 | 575.2 | 40S RIBOSOMAL PROTEIN S27. | swissprot O74330 | ND |
| 669 | 574.9 | MALTOSE PERMEASE MAL3T (MALTOSE TRANSPORT PROTEIN MAL3T). | swissprot P38156 | ND |
| 670 | 574.3 | HYPOTHETICAL 49.9 KD PROTEIN. | sptrembl Q03441 | ND |
| 671 | 573.6 | 60S RIBOSOMAL PROTEIN L37-A (L35) (YP55). | swissprot P49166 | ND |
| 672 | 573.4 | 60S RIBOSOMAL PROTEIN L31 (L34) (YL28). | swissprot P04649 | ND |
| 673 | 572.7 | NUCLEAR PROTEIN SNF4 (REGULATORY PROTEIN CAT3). | swissprot P12904 | ND |
| 674 | 572.2 | OLIGOMYCIN SENSITIVITY CONFERRING PROTEIN. | sptrembl O74190 | Energy production and conversion |
| 675 | 571.4 | 40S RIBOSOMAL PROTEIN S8 (S14) (YS9) (RP19). | swissprot P05754 | Translation, ribosomal structure and biogenesis |
| 676 | 571.1 | 60S RIBOSOMAL PROTEIN L13. | sptrembl Q9Z313 | ND |
| 677 | 570.6 | GAR1 PROTEIN. | swissnew P28007 | ND |
| 678 | 570.6 | GEPHYRIN (PUTATIVE GLYCINE RECEPTOR-TUBULIN LINKER PROTEIN). | swissprot Q03555 | ND |
| 679 | 570.4 | ZINC FINGER PROTEIN SFP1. | swissprot P32432 | ND |
| 680 | 570.3 | RECESSIVE SUPPRESSOR OF SECRETORY DEFECT. | swissprot P32368 | ND |
| 681 | 569.9 | THIAMINE-4 (FRAGMENT). | sptrembl P79048 | ND |
| 682 | 569.2 | PROBABLE SYNAPTOBREVIN HOMOLOG C6G9.11. | swissprot Q92356 | ND |
| 683 | 569.2 | PYRROLINE-5-CARBOXYLATE REDUCTASE (EC 1.5.1.2) (P5CR) (P5C REDUCTASE). | swissprot P22008 | Amino acid transport and metabolism |
| 684 | 569.2 | Human secreted protein encoded by gene 35 clone HTXCS21. | geneseqp W78160 | Posttranslational modification, protein turnover, chaperones |
| 685 | 568.5 | HYPOTHETICAL 15.4 KD PROTEIN IN HAS1-JNM1 INTERGENIC REGION. | swissprot Q03554 | ND |
| 686 | 568.4 | COPROPORPHYRINOGEN III OXIDASE (EC 1.3.3.3) (COPROPORPHYRINOGENASE) (COPROGEN OXIDASE) (COX). | swissprot P11353 | Coenzyme metabolism |
| 687 | 568.3 | GTP-BINDING PROTEIN YPT51/VPS21. | swissprot P36017 | ND |
| 688 | 567.8 | HYPOTHETICAL 56.5 KD PROTEIN IN HXT8 5'REGION AND IN PAU6 5'REGION. | swissprot P39941 | Carbohydrate transport and metabolism |
| 689 | 567.2 | OLIGOMYCIN RESISTANCE ATP-DEPENDENT PERMEASE YOR1. | swissprot P53049 | ND |
| 690 | 567.0 | ACTIN INTERACTING PROTEIN 2. | swissprot P46681 | Energy production and conversion |
| 691 | 563.9 | 60S RIBOSOMAL PROTEIN L43 (L37A) (YL35). | swissprot P49631 | ND |

TABLE 1-continued

_Fusarium venenatum ESTs_

| Sequence Listing | zscore | Annotation | Database | Functional category |
|---|---|---|---|---|
| 692 | 563.6 | HYPOTHETICAL 49.1 KD PROTEIN. | sptrembl O60140 | ND |
| 693 | 563.6 | PEROXISOMAL MEMBRANE PROTEIN PAS20 (PEROXIN-13). | swissprot P80667 | ND |
| 694 | 561.6 | PHOSPHATIDYLGLYCEROL/ PHOSPHATIDYLINOSITOL TRANSFER PROTEIN. | sptrembl O94183 | ND |
| 695 | 561.4 | HYPOTHETICAL 40.7 KD PROTEIN IN PYK1-SNC1 INTERGENIC REGION. | swissprot P39729 | ND |
| 696 | 559.0 | PUTATIVE MITOCHONDRIAL PROTEIN IMPORT PROTEIN - DNAJ PROTEIN. | sptrembl O74752 | Posttranslational modification, protein turnover, chaperones |
| 697 | 558.2 | PEPTIDYL-PROLYL CIS-TRANS ISOMERASE, FK506-BINDING PROTEIN. | tremblnew CAB46710 | ND |
| 698 | 557.9 | PUTATIVE CYSTATHIONINE GAMMA-SYNTHASE (EC 4.2.99.9) (O-SUCCINYLHOMOSERINE (THIOL)-LYASE). | swissprot P47164 | Amino acid transport and metabolism |
| 699 | 557.5 | GLUCOKINASE (EC 2.7.1.2) (GLUCOSE KINASE) (GLK). | swissprot Q92407 | ND |
| 700 | 556.7 | PUTATIVE SEPTIN. | tremblnew CAB61437 | ND |
| 701 | 556.6 | UDP-GLUCOSE 6-DEHYDROGENASE (EC 1.1.1.22) (UDP-GLC DEHYDROGENASE) (UDP-GLCDH) (UDPGDH) (SUGARLESS PROTEIN). | swissprot O02373 | ND |
| 702 | 556.2 | 60S RIBOSOMAL PROTEIN L14-A. | swissprot P36105 | ND |
| 703 | 554.4 | HYPOTHETICAL 25.2 KD PROTEIN. | sptrembl Q9Y7K7 | ND |
| 704 | 553.9 | NADPH-DEPENDENT BETA-KETOACYL REDUCTASE. | tremblnew AAD53514 | ND |
| 705 | 553.3 | HYPOTHETICAL 16.1 KD PROTEIN. | sptrembl O74847 | ND |
| 706 | 553.1 | PROTEASOME COMPONENT PUP2 (EC 3.4.99.46) (MACROPAIN SUBUNIT PUP2) (PROTEINASE YSCE SUBUNIT PUP2) (MULTICATALYTIC ENDOPEPTIDASE COMPLEX SUBUNIT PUP2). | swissprot P32379 | ND |
| 707 | 551.8 | _A. niger_ Bo-1 carboxypeptidase Y. | geneseqp R96737 | ND |
| 708 | 551.5 | SIMILAR TO JUN ACTIVATION DOMAIN BINDING PROTEIN. | sptrembl O23130 | ND |
| 709 | 550.8 | HYPOTHETICAL 47.4 KD PROTEIN IN SHP1-SEC17 INTERGENIC REGION. | sptrembl O13630 | ND |
| 710 | 550.5 | DNA-DIRECTED RNA POLYMERASE III LARGEST SUBUNIT (EC 2.7.7.6) (C160). | swissprot P04051 | Transcription |
| 711 | 549.5 | GENE REGULATION 124 aa, chain A + B + C | pdb 1QD9 | Translation, ribosomal structure and biogenesis |
| 712 | 549.2 | GUANINE NUCLEOTIDE-BINDING PROTEIN BETA SUBUNIT. | swissprot O14435 | ND |
| 713 | 548.6 | TRANSMEMBRANE PROTEIN. | tremblnew CAB65007 | ND |
| 714 | 548.6 | _Aspergillus nidulans_ essential protein AN17. | geneseqp Y06418 | ND |

TABLE 1-continued

Fusarium venenatum ESTs

| Sequence Listing | zscore | Annotation | Database | Funct

TABLE 1-continued

Fusarium venenatum ESTs

| Sequence Listing | zscore | Annotation | Database | Functional category |
|---|---|---|---|---|
| | | 2.5.1.3)(TMP PYROPHOSPHORYLASE) (TMP-PPASE); HYDROXYETHYLTHIAZOLE KINASE (EC 2.7.1.50) (4-METHYL-5-BETA-HYDROXYETHYLTHIAZOLE KINASE) (THZ KINASE) (TH KINASE)]. | | |
| 738 | 532.7 | PUTATIVE MITOCHONDRIAL CARRIER YOR222W. | swissnew Q99297 | ND |
| 739 | 530.9 | TRANSPORTIN. | sptrembl O76331 | ND |
| 740 | 530.6 | GLYCOGEN PHOSPHORYLASE (EC 2.4.1.1). | swissprot P06738 | Carbohydrate transport and metabolism |
| 741 | 530.2 | PUTATIVE ADENOSINE KINASE. | tremblnew CAA19345 | Carbohydrate transport and metabolism |
| 742 | 530.2 | HYPOTHETICAL 18.8 KD PROTEIN. | sptrembl O43073 | ND |
| 743 | 529.7 | DDR48 STRESS PROTEIN (DNA DAMAGE-RESPONSIVE PROTEIN 48) (DDRP 48) (YP 75) (FLOCCULENT SPECIFIC PROTEIN). | swissprot P18899 | ND |
| 744 | 529.6 | 40S RIBOSOMAL PROTEIN S24 (RP50). | swissprot P26782 | ND |
| 745 | 529.5 | JAB1 PROTEIN. | sptrembl O81388 | ND |
| 746 | 529.4 | HYPOTHETICAL 43.7 KD PROTEIN C24B11.08C IN CHROMOSOME I. | swissprot Q09895 | ND |
| 747 | 529.3 | PROTEIN KINASE SKP1P. | sptrembl O94456 | ND |
| 748 | 529.1 | ORM1 PROTEIN. | swissprot P53224 | ND |
| 749 | 529.0 | NAALADASE II PROTEIN. | sptrembl Q9Y3Q0 | ND |
| 750 | 528.9 | PROTEIN PHOSPHOTASE 2A 65 KD REGULATORY SUBUNIT. | tremblnew CAB55176 | ND |
| 751 | 528.3 | NADH-UBIQUINONE OXIDOREDUCTASE 10.5 KD SUBUNIT (EC 1.6.5.3) (EC 1.6.99.3) (COMPLEX I) (CI). | swissprot Q07842 | ND |
| 752 | 527.4 | PUTATIVE MITOCHONDRIAL CARRIER PROTEIN C12B10.09. | swissprot Q10442 | ND |
| 753 | 527.3 | CLATHRIN HEAVY CHAIN. | swissprot P22137 | ND |
| 754 | 527.2 | YNL123W HOMOLOG (FRAGMENT). | sptrembl O42705 | Posttranslational modification, protein turnover, chaperones |
| 755 | 526.6 | CYCLOPROPANE-FATTY-ACYL-PHOSPHOLIPID SYNTHASE. | sptrembl O67624 | ND |
| 756 | 526.1 | HYPOTHETICAL 107.7 KD PROTEIN IN TSP3-IPP2 INTERGENIC REGION. | swissprot Q03516 | ND |
| 757 | 526.0 | PI021 PROTEIN. | sptrembl O13612 | ND |
| 758 | 525.1 | SRP1 PROTEIN. | swissprot Q10193 | ND |
| 759 | 524.4 | SMALL NUCLEAR RIBONUCLEOPROTEIN SM D3 (SNRNP CORE PROTEIN D3) (SM-D3). | swissprot P43331 | Transcription |
| 760 | 524.3 | K09H11.1 PROTEIN. | sptrembl O01590 | ND |
| 761 | 524.1 | COENZYME A SYNTHETASE. | sptrembl O74976 | ND |
| 762 | 524.0 | HYPOTHETICAL 47.0 KD PROTEIN C23H3.03C IN CHROMOSOME I. | sptrembl O42857 | ND |
| 763 | 523.8 | TRIOSEPHOSPHATE ISOMERASE (EC 5.3.1.1) (TIM). | swissprot P04828 | ND |

TABLE 1-continued

*Fusarium venenatum* ESTs

| Sequence Listing | zscore | Annotation | Database | Functional category |
|---|---|---|---|---|
| 764 | 523.6 | HYPOTHETICAL 56.8 KD PROTEIN IN SCJ1-GUA1 INTERGENIC REGION PRECURSOR. | swissprot Q03655 | ND |
| 765 | 522.9 | CGI-110 PROTEIN. | sptrembl Q9Y3B4 | ND |
| 766 | 522.4 | NEUTRAL TREHALASE (EC 3.2.1.28) (ALPHA,ALPHA-TREHALASE) (ALPHA,ALPHA-TREHALOSE GLUCOHYDROLASE). | swissprot O42622 | ND |
| 767 | 521.8 | GTPASE. | sptrembl P87027 | ND |
| 768 | 520.3 | HYPOTHETICAL 12.5 KD PROTEIN. | sptrembl O74948 | ND |
| 769 | 519.1 | Extended human secreted protein sequence, SEQ ID NO. 218. | geneseqp Y35969 | ND |
| 770 | 518.6 | URIC ACID-XANTHINE PERMEASE (UAPA TRANSPORTER). | swissprot Q07307 | ND |
| 771 | 517.3 | DIHYDROLIPOAMIDE ACETYLTRANSFERASE COMPONENT OF PYRUVATE DEHYDROGENASE COMPLEX, MITOCHONDRIAL PRECURSOR (EC 2.3.1.12) (E2) (PDC-E2) (MRP3). | swissprot P20285 | ND |
| 772 | 517.0 | ATP CITRATE LYASE. | sptrembl O93988 | ND |
| 773 | 515.8 | PUTATIVE ZINC-CONTAINING DEHYDROGENASE. | tremblnew CAB53146 | ND |
| 774 | 515.3 | HYPOTHETICAL 25.7 KD PROTEIN IN MSH1-EPT1 INTERGENIC REGION. | swissprot P38829 | ND |
| 775 | 514.4 | PROBABLE CLATHRIN HEAVY CHAIN. | swissprot Q10161 | ND |
| 776 | 513.1 | HYPOTHETICAL 143.7 KD PROTEIN C11D3.15 IN CHROMOSOME I. | swissprot Q10094 | Amino acid transport and metabolism |
| 777 | 513.0 | TRANSCRIPTION FACTOR BTF3 HOMOLOG. | swissprot Q92371 | ND |
| 778 | 511.6 | CROSS-PATHWAY CONTROL PROTEIN 1. | swissprot P11115 | ND |
| 779 | 511.2 | HYPOTHETICAL 37.4 KD PROTEIN. | sptrembl O74907 | ND |
| 780 | 511.0 | ACONITASE. | sptrembl O74699 | Energy production and conversion |
| 781 | 510.5 | Yeast NPC1 protein orthologue. | geneseqp W88447 | ND |
| 782 | 510.4 | HYPOTHETICAL 119.1 KD PROTEIN YPL009C. | sptrembl Q12532 | Cell envelope biogenesis, outer membrane |
| 783 | 509.3 | HYPOTHETICAL 30.9 KD PROTEIN. | sptrembl O53327 | ND |
| 784 | 509.2 | HYPOTHETICAL 33.3 KD PROTEIN. | sptrembl O43060 | ND |
| 785 | 508.7 | 30 KD HEAT SHOCK PROTEIN. | swissprot P19752 | ND |
| 786 | 508.5 | *Schizosaccharomyces pombe* HRR25-like Hhp1+ protein. | geneseqp R76616 | ND |
| 787 | 508.4 | HYPOTHETICAL PROTEIN C22G7.01C IN CHROMOSOME I (FRAGMENT). | swissnew Q09795 | ND |
| 788 | 506.9 | CHROMOSOME XV READING FRAME ORF YOL060C. | sptrembl Q12296 | ND |
| 789 | 506.6 | WD REPEAT-CONTAINING PROTEIN. | sptrembl O94289 | ND |
| 790 | 506.0 | 60S RIBOSOMAL PROTEIN L34-B. | swissprot P40525 | ND |

TABLE 1-continued

_Fusarium venenatum ESTs_

| Sequence Listing | zscore | Annotation | Database | Functional category |
|---|---|---|---|---|
| 791 | 504.2 | PHOSPHORIBOSYLGLYCIN AMIDE FORMYLTRANSFERASE (FRAGMENT). | sptrembl Q9Y7S7 | ND |
| 792 | 504.0 | PUTATIVE AROMATIC AMINO ACID AMINOTRANSFERASE C56E4.03 (EC 2.6.1.-). | sptrembl O14192 | Amino acid transport and metabolism |
| 793 | 503.3 | CALCIUM/CALMODULIN-DEPENDENT PROTEIN KINASE (EC 2.7.1.123). | swissprot O14408 | ND |
| 794 | 502.1 | CYTOCHROME C OXIDASE POLYPEPTIDE IV PRECURSOR (EC 1.9.3.1). | swissprot P04037 | ND |
| 795 | 501.8 | ALCOHOL DEHYDROGENASE I (EC 1.1.1.1). | swissprot P41747 | ND |
| 797 | 501.4 | PHOSPHOGLYCERATE KINASE (EC 2.7.2.3). | swissprot P24590 | ND |
| 798 | 500.6 | 2-HYDROXYACID DEHYDROGENASE HOMOLOG (EC 1.1.1.-). | swissprot P30799 | ND |
| 799 | 500.3 | PROTEASOME COMPONENT PUP3 (EC 3.4.99.46) (MACROPAIN SUBUNIT PUP3) (MULTICATALYTIC ENDOPEPTIDASE COMPLEX SUBUNIT PUP3). | swissprot P25451 | Posttranslational modification, protein turnover, chaperones |
| 800 | 500.2 | PLASMID RECOMBINATION ENZYME (MOBILIZATION PROTEIN). | swissprot P03857 | ND |
| 801 | 499.4 | UV EXCISION REPAIR PROTEIN RAD23 HOMOLOG. | sptrembl O74803 | ND |
| 802 | 499.0 | CHROMOSOME XVI READING FRAME ORF YPL226W (CHROMOSOME XVI LEFT ARM (EU) DNA SEGMENT). | sptrembl Q08972 | ND |
| 803 | 498.3 | RAN GTPASE ACTIVATING PROTEIN 1 (RNA1 PROTEIN). | swissprot P41391 | ND |
| 804 | 497.6 | 60S RIBOSOMAL PROTEIN L36. | sptrembl O94658 | ND |
| 805 | 497.3 | HYPOTHETICAL 46.4 KD PROTEIN C3A12.11C IN CHROMOSOME I. | swissprot P87126 | ND |
| 806 | 496.8 | PUTATIVE SEPTIN. | tremblnew CAB61437 | ND |
| 807 | 496.7 | PROBABLE INVOLVEMENT IN ERGOSTEROL BIOSYNTHESIS. | sptrembl O94512 | ND |
| 808 | 496.1 | CYTOPLASMIC AMINOPEPTIDASE P. | sptrembl O54975 | Amino acid transport and metabolism |
| 809 | 495.5 | NADH-UBIQUINONE OXIDOREDUCTASE 21 KD SUBUNIT PRECURSOR (EC 1.6.5.3) (EC 1.6.99.3) (COMPLEX I-21 KD) (CI-21 KD). | swissprot P25711 | ND |
| 810 | 494.5 | HYPOTHETICAL 31.5 KD PROTEIN C4F10.03C IN CHROMOSOME I. | sptrembl O36015 | Cell division and chromosome partitioning |
| 811 | 493.5 | PISATIN DEMETHYLASE (EC 1.14.-.-) (CYTOCHROME P450 57A2). | swissprot P38364 | ND |
| 812 | 492.6 | NITRATE REDUCTASE. | sptrembl Q92237 | ND |
| 813 | 492.1 | LSM5 PROTEIN. | sptrembl Q9Y4Y9 | ND |

TABLE 1-continued

*Fusarium venenatum* ESTs

| Sequence Listing | zscore | Annotation | Database | Functional category |
|---|---|---|---|---|
| 814 | 491.4 | CHROMOSOME IV READING FRAME ORF YDL019C. | sptrembl Q12451 | ND |
| 815 | 491.2 | 10 KD HEAT SHOCK PROTEIN, MITOCHONDRIAL (HSP10) (10 KD CHAPERONIN). | swissprot O59804 | ND |
| 816 | 490.3 | HYPOTHETICAL ZINC-TYPE ALCOHOL DEHYDROGENASE-LIKE PROTEIN IN GDH3-CNE1 INTERGENIC REGION. | swissprot P39714 | ND |
| 817 | 489.9 | 3-HYDROXYACYL-COA DEHYDROGENASE TYPE II (EC 1.1.1.35). | swissprot O02691 | ND |
| 818 | 489.6 | HYPOTHETICAL 30.7 KD PROTEIN IN RVS161-ADP1 INTERGENIC REGION. | swissprot P25613 | ND |
| 819 | 489.4 | ENOYL REDUCTASE. | sptrembl Q9Y7D0 | ND |
| 820 | 489.1 | SHY1 PROTEIN. | swissprot P53266 | ND |
| 821 | 489.1 | RIBONUCLEOPROTEIN RBM8. | sptrembl Q9Y5S9 | ND |
| 822 | 489.1 | CYTOCHROME C OXIDASE POLYPEPTIDE VIB (EC 1.9.3.1) (AED). | swissprot Q01519 | ND |
| 823 | 488.8 | THIOSULFATE SULFURTRANSFERASE. | sptrembl Q9ZPK0 | Inorganic ion transport and metabolism |
| 824 | 488.1 | CONSERVED PROTEIN. | sptrembl O26459 | Amino acid transport and metabolism |
| 825 | 488.1 | PUTATIVE STERIGMATOCYSTIN BIOSYNTHESIS PROTEIN STCT. | swissprot Q00717 | ND |
| 826 | 487.9 | NONHISTONE CHROMOSOMAL PROTEIN 6B. | swissprot P11633 | ND |
| 827 | 487.7 | NUCLEOSOME ASSEMBLY PROTEIN. | sptrembl O59797 | ND |
| 828 | 487.2 | HYPOTHETICAL 55.5 KD PROTEIN C17A2.05 IN CHROMOSOME I. | sptrembl O13755 | ND |
| 829 | 487.2 | HYPOTHETICAL 96.1 KD PROTEIN. | sptrembl Q9Y7N9 | ND |
| 830 | 486.7 | CONSERVED PROTEIN. | sptrembl O26459 | ND |
| 831 | 486.0 | PROBABLE NEGATIVE REGULATOR OF TRANSCRIPTION SUBUNIT C4G3.15C. | sptrembl P87240 | ND |
| 832 | 483.3 | D9461.13P. | sptrembl Q04053 | ND |
| 833 | 483.2 | SALA. | tremblnew AAF04312 | ND |
| 834 | 483.2 | PROBABLE SODIUM CHANNEL PROTEIN C6F6.01. | sptrembl O14234 | ND |
| 835 | 482.6 | RNA-BINDING POST-TRANSCRIPTIONAL REGULATOR CSX1. | swissprot O13759 | ND |
| 836 | 482.2 | HYPOTHETICAL OXIDOREDUCTASE IN RPB5-CDC28 INTERGENIC REGION (EC 1.-.-.-). | swissprot P38286 | ND |
| 837 | 481.4 | HYPOTHETICAL 13.5 KD PROTEIN C24B11.09 IN CHROMOSOME I. | swissprot Q09896 | ND |
| 838 | 481.4 | RHO2 PROTEIN. | swissprot Q10133 | ND |
| 839 | 480.7 | PUTATIVE ALCOHOL DEHYDROGENASE. | sptrembl O80944 | ND |
| 840 | 480.4 | GLYCERALDEHYDE 3-PHOSPHATE DEHYDROGENASE (EC 1.2.1.12) (GAPDH). | swissprot P32637 | Carbohydrate transport and metabolism |

TABLE 1-continued

*Fusarium venenatum* ESTs

| Sequence Listing | zscore | Annotation | Database | Functional category |
|---|---|---|---|---|
| 841 | 480.0 | TROPOMYOSIN. | swissprot Q02088 | ND |
| 842 | 479.3 | 60S RIBOSOMAL PROTEIN L22. | tremblnew CAB11194 | ND |
| 843 | 478.6 | NONHISTONE CHROMOSOMAL PROTEIN 6B. | swissprot P11633 | ND |
| 844 | 478.6 | HYPOTHETICAL 52.2 KD PROTEIN. | sptrembl Q12116 | ND |
| 845 | 478.2 | DOLICHYL-PHOSPHATE-MANNOSE--PROTEIN MANNOSYLTRANSFERASE 2 (EC 2.4.1.109). | swissprot P31382 | Posttranslational modification, protein turnover, chaperones |
| 846 | 477.8 | MAJOR ALLERGEN ASP F 2 PRECURSOR (ASP F II). | swissnew P79017 | ND |
| 847 | 477.7 | CYTOCHROME C OXIDASE POLYPEPTIDE VI PRECURSOR (EC 1.9.3.1). | swissprot P00427 | ND |
| 848 | 476.8 | PUTATIVE TRANSPORT PROTEIN. | tremblnew CAB52881 | ND |
| 849 | 476.7 | UBIQUITIN-CONJUGATING ENZYME E2-24 KD (EC 6.3.2.19) (UBIQUITIN-PROTEIN LIGASE) (UBIQUITIN CARRIER PROTEIN). | swissprot P28263 | ND |
| 850 | 476.3 | HYPOTHETICAL 11.8 KD PROTEIN C1B3.02C IN CHROMOSOME I. | swissprot O13868 | ND |
| 851 | 475.7 | PROBABLE NICOTINATE PHOSPHORIBOSYLTRANSFERASE (EC 2.4.2.11) (NAPRTASE). | swissnew P39683 | Coenzyme metabolism |
| 852 | 474.6 | CYTOCHROME B2 PRECURSOR (EC 1.1.2.3). | sptrembl Q9Y857 | Energy production and conversion |
| 853 | 474.2 | CDC42. | sptrembl O94103 | ND |
| 854 | 471.5 | PUTATIVE 125.2 KD MEMBRANE GLYCOPROTEIN IN BIO3-HXT17 INTERGENIC REGION. | swissprot P53751 | ND |
| 855 | 470.3 | VACUOLAR PROTEIN SORTING-ASSOCIATED PROTEIN VPS13. | swissprot Q07878 | ND |
| 856 | 470.1 | HYPOTHETICAL PROTEIN (FRAGMENT). | tremblnew BAA87315 | ND |
| 857 | 469.2 | HYPOTHETICAL 61.3 KD PROTEIN CY369.29. | sptrembl P71838 | ND |
| 858 | 468.8 | TRYPTOPHAN SYNTHASE (EC 4.2.1.20). | swissnew P13228 | ND |
| 859 | 468.4 | HYPOTHETICAL 23.6 KD PROTEIN. | sptrembl O14451 | ND |
| 860 | 467.6 | BCDNA.GH07774. | sptrembl Q9Y127 | ND |
| 861 | 467.4 | PROBABLE ATP-DEPENDENT PERMEASE PRECURSOR. | swissprot P25371 | ND |
| 862 | 467.4 | DNA-DIRECTED RNA POLYMERASES I, II, AND III 8.3 KD POLYPEPTIDE (EC 2.7.7.6) (ABC10-BETA) (ABC8). | swissprot P22139 | Transcription |
| 863 | 467.0 | METHIONYL-TRNA SYNTHETASE. | sptrembl O13634 | ND |
| 864 | 466.6 | DOLICHYL-PHOSPHATE-MANNOSE--PROTEIN MANNOSYLTRANSFERASE 2 (EC 2.4.1.109). | swissprot P31382 | Posttranslational modification, protein turnover, chaperones |
| 865 | 466.6 | CUTINASE G-BOX BINDING PROTEIN. | sptrembl Q00878 | ND |
| 866 | 466.6 | PUTATIVE VANADATE RESISTANCE PROTEIN. | tremblnew CAB59698 | ND |
| 867 | 466.3 | HIGH AFFINITY METHIONINE PERMEASE. | swissprot P50276 | ND |

TABLE 1-continued

*Fusarium venenatum* ESTs

| Sequence Listing | zscore | Annotation | Database | Functional category |
|---|---|---|---|---|
| 868 | 465.9 | PUTATIVE SMALL NUCLEAR RIBONUCLEOPROTEIN E. | tremblnew CAB59808 | Transcription |
| 869 | 465.2 | HYPOTHETICAL 35.0 KD PROTEIN IN BGL2-ZUO1 INTERGENIC REGION. | swissprot P53337 | ND |
| 870 | 465.1 | HYPOTHETICAL 79.9 KD PROTEIN C3D6.04C IN CHROMOSOME II. | sptrembl P87169 | ND |
| 871 | 464.6 | BROADLY SELECTIVE SODIUM/NUCLEOSIDE TRANSPORTER HFCNT. | tremblnew AAD52151 | ND |
| 872 | 464.3 | PUTATIVE SYNTAXIN. | tremblnew CAB58411 | ND |
| 873 | 463.9 | HYPOTHETICAL 41.8 KD PROTEIN. | sptrembl O59715 | ND |
| 874 | 462.7 | WD-REPEAT PROTEIN POP2 (PROTEOLYSIS FACTOR SUD1). | swissprot O14170 | ND |
| 875 | 461.4 | LONG-CHAIN-FATTY-ACID--COA LIGASE 1 (EC 6.2.1.3) (LONG-CHAIN ACYL-COA SYNTHETASE 1) (FATTY ACID ACTIVATOR 1). | swissprot P30624 | Lipid metabolism |
| 876 | 460.7 | BING4. | sptrembl Q9Z0H1 | ND |
| 877 | 460.6 | 40S RIBOSOMAL PROTEIN S28 (S33). | swissprot Q10421 | Translation, ribosomal structure and biogenesis |
| 878 | 460.4 | HISTONE H1. | tremblnew AAF16011 | ND |
| 879 | 459.4 | P21 PROTEIN. | sptrembl Q11118 | ND |
| 880 | 458.9 | INORGANIC PHOSPHATE TRANSPORTER PHO88. | swissprot P38264 | ND |
| 881 | 457.7 | EUKARYOTIC TRANSLATION INITIATION FACTOR 4E (EIF-4E) (EIF4E) (MRNA CAP-BINDING PROTEIN) (EIF-4F 25 KD SUBUNIT). | swissprot P78954 | ND |
| 882 | 457.7 | 49 KDA ZINC FINGER PROTEIN. | sptrembl Q9Z326 | ND |
| 883 | 457.4 | PROTEIN KINASE C-LIKE (EC 2.7.1.-). | swissprot Q99014 | ND |
| 884 | 457.2 | MBF1 PROTEIN (ORF YOR298C-A). | sptrembl O14467 | ND |
| 885 | 457.0 | Exon trap L48741. | geneseqp W46753 | Carbohydrate transport and metabolism |
| 886 | 456.9 | CHROMOSOME IV READING FRAME ORF YDL072C. | sptrembl Q07451 | ND |
| 887 | 456.7 | *Phaffia* derived glyceraldehyde-3-phosphate dehydrogenase PRcDNA64. | geneseqp W22489 | Translation, ribosomal structure and biogenesis |
| 888 | 456.7 | 60S RIBOSOMAL PROTEIN L35. | swissprot P42766 | ND |
| 889 | 456.2 | TRANSCRIPTION INITIATION FACTOR IIE, BETA SUBUNIT (TFIIE-BETA) (TRANSCRIPTION FACTOR A SMALL SUBUNIT) (FACTOR A 43 KD SUBUNIT). | swissprot P36145 | ND |
| 890 | 456.0 | ALPHA-SOLUBLE NSF ATTACHMENT PROTEIN (SNAP-ALPHA). | swissnew P54920 | ND |
| 891 | 455.9 | SMALL ZINC FINGER PROTEIN TIM8. | sptrembl Q9Y8C0 | ND |
| 892 | 455.1 | 26S PROTEASE REGULATORY SUBUNIT 4 | swissprot P36612 | Posttranslational modification, |

TABLE 1-continued

*Fusarium venenatum* ESTs

| Sequence Listing | zscore | Annotation | Database | Functional category |
|---|---|---|---|---|
| | | HOMOLOG (MTS2 PROTEIN). | | protein turnover, chaperones |
| 893 | 455.1 | TOXIN PUMP. | sptrembl Q00357 | ND |
| 894 | 454.8 | DEHYDROGENASE. | sptrembl O34788 | ND |
| 895 | 454.7 | UVSB PI-3 KINASE. | tremblnew AAD54313 | ND |
| 896 | 453.2 | PROBABLE T-COMPLEX PROTEIN 1, THETA SUBUNIT. | sptrembl O74816 | Posttranslational modification, protein turnover, chaperones |
| 897 | 453.2 | UBIQUITIN-CONJUGATING ENZYME E2-21 KD (EC 6.3.2.19) (UBIQUITIN-PROTEIN LIGASE) (UBIQUITIN CARRIER PROTEIN) (PEROXIN-4). | swissprot P29340 | ND |
| 898 | 453.0 | DNA-DIRECTED RNA POLYMERASE SUBUNIT. | sptrembl O74825 | ND |
| 899 | 452.3 | TAMEGOLOH. | sptrembl O42346 | ND |
| 900 | 451.4 | HYPOTHETICAL 55.8 KD PROTEIN. | tremblnew CAB63552 | ND |
| 901 | 450.7 | HYPOTHETICAL 38.5 KD PROTEIN. | sptrembl O74959 | ND |
| 902 | 450.6 | PUTATIVE ENOLASE-PHOSPHATASE. | tremblnew CAB55632 | ND |
| 903 | 449.4 | *Mortierella alpina* cytochrome b5. | geneseqp W22848 | ND |
| 904 | 448.6 | CARBOXYVINYL-CARBOXYPHOSPHONATE PHOSPHORYLMUTASE (EC 2.7.8.23) (CARBOXYPHOSPHONOENOLPYRUVATE PHOSPHONOMUTASE) (CPEP PHOSPHONOMUTASE). | swissprot P11435 | ND |
| 905 | 448.2 | Ester hydrolase protein encoded by rec 780-m165r210 gene. | geneseqp R44613 | ND |
| 906 | 447.3 | S-ADENOSYLMETHIONINE DECARBOXYLASE (EC 4.1.1.50) (FRAGMENT). | sptrembl Q9Y8A3 | ND |
| 908 | 446.4 | RASP F 9 (FRAGMENT). | sptrembl O42800 | ND |
| 909 | 446.1 | CHROMOSOME XVI READING FRAME ORF YPL199C. | sptrembl Q08954 | ND |
| 910 | 446.1 | VACUOLAR PROTEIN SORTING-ASSOCIATED PROTEIN VPS35. | swissprot P34110 | ND |
| 911 | 445.9 | PROFILIN. | tremblnew CAB38578 | ND |
| 912 | 445.0 | HET-C PROTEIN. | tremblnew AAD54275 | ND |
| 913 | 444.8 | HYPOTHETICAL 28.0 KD PROTEIN C13C5.04 IN CHROMOSOME I. | swissprot Q09686 | ND |
| 914 | 444.6 | ATP SYNTHASE F CHAIN, MITOCHONDRIAL PRECURSOR (EC 3.6.1.34). | swissprot Q06405 | ND |
| 915 | 444.3 | IONA (SODIUM/POTASSIUM-TRANSPORTING ATPASE) (FRAGMENT). | sptrembl Q95024 | ND |
| 916 | 444.2 | CHITIN SYNTHASE 4 (EC 2.4.1.16) (CHITIN-UDP ACETYL-GLUCOSAMINYL TRANSFERASE 4) (CLASS-IV CHITIN SYNTHASE 4). | swissprot Q01285 | ND |
| 917 | 443.4 | SPP30. | sptrembl Q9XFA1 | ND |
| 918 | 442.9 | UBE-1A. | tremblnew BAA82656 | ND |
| 919 | 442.1 | SIMILAR TO DABA DECARBOXYLASE. | sptrembl Q9Z3R1 | ND |

TABLE 1-continued

_Fusarium venenatum ESTs_

| Sequence Listing | zscore | Annotation | Database | Functional category |
|---|---|---|---|---|
| 920 | 441.9 | VIP1 PROTEIN (P53 ANTIGEN HOMOLOG). | sptrembl P87216 | ND |
| 921 | 441.5 | HYPOTHETICAL PROTEIN (FRAGMENT). | tremblnew BAA87313 | ND |
| 922 | 441.1 | GENERAL AMINO ACID PERMEASE AGP2. | swissprot P38090 | Amino acid transport and metabolism |
| 923 | 441.0 | PUTATIVE N-ACETYLGLUCOSAMINE-6-PHOSPHATE DEACETYLASE (EC 3.5.1.25) (GLCNAC 6-P DEACETYLASE). | swissprot P34480 | ND |
| 924 | 440.0 | PUTATIVE TYPE III ALCOHOL DEHYDROGENASE. | sptrembl Q94532 | ND |
| 925 | 439.3 | HYPOTHETICAL 33.6 KD PROTEIN. | sptrembl O53363 | ND |
| 926 | 439.3 | Yeast MEC3 protein sequence. | geneseqp W73895 | Cell motility and secretion |
| 927 | 438.1 | HYPOTHETICAL 76.3 KD ZINC FINGER PROTEIN IN KTR5-UME3 INTERGENIC REGION. | swissprot P53968 | ND |
| 928 | 438.1 | AMINO ACID PERMEASE. | sptrembl P87251 | ND |
| 929 | 437.9 | STR1 (suppressor of telomeric repression-1) protein. | geneseqp R95601 | ND |
| 930 | 436.9 | PUTATIVE CELL WALL PROTEIN. | sptrembl O74708 | ND |
| 931 | 435.9 | TRANSCRIPTION INITIATION FACTOR TFIID 55 KD SUBUNIT (TAFII-55). | sptrembl O13701 | ND |
| 932 | 435.8 | HYPOTHETICAL 38.3 KD PROTEIN IN CWLA-CISA INTERGENIC REGION. | swissprot P45946 | ND |
| 933 | 435.7 | O-METHYLTRANSFERASE. | sptrembl O67476 | ND |
| 934 | 435.5 | ARG-6 PROTEIN PRECURSOR [CONTAINS: N-ACETYL-GAMMA-GLUTAMYL-PHOSPHATE REDUCTASE (EC 1.2.1.38) (N-ACETYL-GLUTAMATE SEMIALDEHYDE DEHYDROGENASE) (NAGSA DEHYDROGENASE); ACETYLGLUTAMATE KINASE (EC 2.7.2.8) (NAG KINASE) (AGK) (N-ACETYL-L-GLUTAMATE 5-PHOSPHOTRANSFERASE)]. | swissnew P54898 | ND |
| 935 | 435.5 | IMPORTIN ALPHA SUBUNIT. | sptrembl O94374 | ND |
| 936 | 435.3 | HYPOTHETICAL 46.5 KD PROTEIN. | sptrembl O07730 | ND |
| 937 | 435.2 | UBIQUITIN-CONJUGATING ENZYME E2-16 KD. | tremblnew CAB54826 | ND |
| 938 | 434.3 | HYPOTHETICAL 34.8 KD PROTEIN C4H3.04C IN CHROMOSOME I. | swissprot Q10212 | ND |
| 939 | 433.8 | F26A3.2 PROTEIN. | sptrembl Q93594 | Transcription |
| 940 | 432.9 | DYNAMIN-RELATED PROTEIN. | sptrembl P87320 | ND |
| 941 | 432.8 | HYPOTHETICAL 42.7 KD PROTEIN (FRAGMENT). | tremblnew CAB61449 | ND |
| 942 | 431.3 | CHROMOSOME XV READING FRAME ORF YOL119C. | sptrembl Q08268 | ND |
| 943 | 429.4 | Aminopeptidase. | geneseqp W05589 | ND |
| 944 | 429.4 | Phosphoglycerate kinase. | geneseqp R22095 | ND |
| 945 | 428.9 | ADENYLYL CYCLASE. | tremblnew AAD50121 | ND |

TABLE 1-continued

*Fusarium venenatum* ESTs

| Sequence Listing | zscore | Annotation | Database | Functional category |
|---|---|---|---|---|
| 946 | 426.5 | UBIQUITIN CARBOXYL-TERMINAL HYDROLASE (EC 3.1.2.15). | tremblnew AAF01440 | ND |
| 947 | 426.3 | HYPOTHETICAL 46.7 KD PROTEIN C19G10.05 IN CHROMOSOME I. | swissprot Q10335 | ND |
| 948 | 426.3 | RIBOSOMAL PROTEIN S30. | sptrembl O14314 | ND |
| 949 | 426.2 | GLUCAN 1,3-BETA-GLUCOSIDASE PRECURSOR (EC 3.2.1.58) (EXO-1,3-BETA-GLUCANASE) (GP29). | swissprot P15703 | ND |
| 950 | 424.9 | RIBULOSE-PHOSPHATE 3-EPIMERASE (EC 5.1.3.1) (PENTOSE-5-PHOSPHATE 3-EPIMERASE) (PPE) (RPE). | swissnew P46969 | Carbohydrate transport and metabolism |
| 951 | 423.9 | CHROMOSOME XV READING FRAME ORF YOR161C. | sptrembl Q12412 | ND |
| 952 | 422.7 | PYRUVATE DEHYDROGENASE E1 COMPONENT BETA SUBUNIT, MITOCHONDRIAL PRECURSOR (EC 1.2.4.1) (PDHE1-B). | swissprot Q09171 | ND |
| 953 | 422.5 | SPLICING FACTOR U2AF 59 KD SUBUNIT. | tremblnew CAB46760 | ND |
| 954 | 421.2 | ASPARTATE AMINOTRANSFERASE, MITOCHONDRIAL PRECURSOR (EC 2.6.1.1) (TRANSAMINASE A) (GLUTAMATE OXALOACETATE TRANSAMINASE-2). | swissprot P05202 | ND |
| 955 | 420.9 | ESTERASE HDE. | sptrembl Q9XDR4 | Lipid metabolism |
| 956 | 420.8 | ACETYL-COENZYME A SYNTHETASE (EC 6.2.1.1) (ACETATE--COA LIGASE) (ACYL-ACTIVATING ENZYME). | swissprot P16928 | ND |
| 957 | 420.1 | 6-PHOSPHOGLUCONATE DEHYDROGENASE, DECARBOXYLATING. | tremblnew CAA22536 | Carbohydrate transport and metabolism |
| 958 | 419.9 | 60S RIBOSOMAL PROTEIN L29 (YL43). | swissprot P05747 | ND |
| 959 | 418.4 | PUTATIVE NUCLEOPORIN. | tremblnew CAB63497 | ND |
| 960 | 417.7 | 60S RIBOSOMAL PROTEIN L39 (YL36). | swissprot P05767 | Translation, ribosomal structure and biogenesis |
| 961 | 417.0 | PUTATIVE CELL WALL PROTEIN. | sptrembl O74708 | ND |
| 962 | 416.6 | THIAMINE BIOSYNTHETIC BIFUNCTIONAL ENZYME [INCLUDES: THIAMINE-PHOSPHATE PYROPHOSPHORYLASE (EC 2.5.1.3) (TMP PYROPHOSPHORYLASE) (TMP-PPASE); HYDROXYETHYLTHIAZOLE KINASE (EC 2.7.1.50) (4-METHYL-5-BETA-HYDROXYETHYLTHIAZOLE KINASE) (THZ KINASE) (TH KINASE)]. | swissprot P41835 | ND |
| 963 | 415.6 | NUCLEASE. | sptrembl O60168 | ND |
| 964 | 415.3 | HYPOTHETICAL 41.9 KD PROTEIN IN HAC1-CAK1 INTERGENIC REGION. | swissprot P43567 | Amino acid transport and metabolism |

TABLE 1-continued

*Fusarium venenatum* ESTs

| Sequence Listing | zscore | Annotation | Database | Functional category |
|---|---|---|---|---|
| 965 | 415.0 | HYPOTHETICAL 42.5 KD PROTEIN. | sptrembl O53311 | ND |
| 966 | 414.8 | CELLULAR NUCLEIC ACID BINDING PROTEIN HOMOLOG. | swissprot P36627 | ND |
| 967 | 414.2 | PROBABLE ALPHA-GLUCOSIDASE YIL172C/YJL221C (EC 3.2.1.20) (MALTASE). | swissprot P40439 | Carbohydrate transport and metabolism |
| 968 | 413.0 | PROTEIN KINASE (FRAGMENT). | sptrembl Q41384 | ND |
| 969 | 413.0 | TRNA SPLICING PROTEIN SPL1. | swissprot P87185 | Amino acid transport and metabolism |
| 970 | 412.7 | CPC3 PROTEIN. | sptrembl O74297 | ND |
| 971 | 412.6 | ADRENOLEUKODYSTROPHY PROTEIN (ALDP). | swissprot P33897 | ND |
| 972 | 412.5 | CYTOCHROME B2 PRECURSOR (EC 1.1.2.3) (L-LACTATE DEHYDROGENASE (CYTOCHROME)) (L-LACTATE FERRICYTOCHROME C OXIDOREDUCTASE) (L-LCR). | swissprot P00175 | ND |
| 973 | 412.4 | GLYCINE-RICH RNA-BINDING PROTEIN (FRAGMENT). | sptrembl Q39105 | ND |
| 974 | 410.8 | HYPOTHETICAL 8.9 KD PROTEIN. | tremblnew CAB52163 | ND |
| 975 | 410.4 | HYPOTHETICAL 60.1 KD PROTEIN C23C11.06C IN CHROMOSOME I. | swissprot O13912 | ND |
| 976 | 410.2 | OXIDOREDUCTASE, SHORT CHAIN DEHYDROGENASE/REDUCTASE FAMILY. | sptrembl Q9WYD3 | ND |
| 977 | 409.5 | F-ACTIN CAPPING PROTEIN ALPHA-2 SUBUNIT (CAPZ 36/32) (BETA-ACTININ SUBUNIT I). | swissprot P28497 | ND |
| 978 | 409.0 | RNA BINDING PROTEIN - PUTATIVE PRE MRNA SPLICING FACTOR. | sptrembl O74919 | ND |
| 979 | 408.7 | PUTATIVE DNA-3-METHYLADENINE GLYCOSIDASE (EC 3.2.2.20). | tremblnew CAB42917 | ND |
| 980 | 408.1 | ALP11 PROTEIN. | swissprot Q10235 | ND |
| 981 | 407.9 | SMALL ZINC FINGER-LIKE PROTEIN. | sptrembl Q9Y8A7 | ND |
| 982 | 407.8 | PHOSPHATIDYLINOSITOL 4-KINASE STT4 (EC 2.7.1.67) (PI4-KINASE) (PTDINS-4-KINASE). | swissprot P37297 | ND |
| 983 | 406.3 | F-ACTIN CAPPING PROTEIN BETA SUBUNIT (CAPZ). | swissprot P47756 | ND |
| 984 | 406.1 | MITOCHONDRIAL RESPIRATORY CHAIN COMPLEXES ASSEMBLY PROTEIN AFG3 (EC 3.4.24.-) (TAT-BINDING HOMOLOG 10). | swissprot P39925 | Posttranslational modification, protein turnover, chaperones |
| 985 | 405.7 | HYPOTHETICAL OXIDOREDUCTASE C23D3.11 IN CHROMOSOME 1 (EC 1.-.-.-). | swissnew Q09851 | ND |
| 986 | 405.3 | SCD2 PROTEIN. | swissprot P40996 | ND |
| 987 | 405.2 | HYPOTHETICAL PROTEIN (FRAGMENT). | sptrembl Q48361 | ND |
| 988 | 404.8 | FOLYLPOLYGLUTAMATE SYNTHETASE. | sptrembl Q9Y893 | Coenzyme metabolism |

TABLE 1-continued

*Fusarium venenatum* ESTs

| Sequence Listing | zscore | Annotation | Database | Functional category |
|---|---|---|---|---|
| 989 | 404.4 | CLOCK-CONTROLLED GENE-6 PROTEIN. | sptrembl O74694 | ND |
| 990 | 404.3 | 36.7 KD PROTEIN IN CBR5-NOT3 INTERGENIC REGION. | swissprot P40531 | ND |
| 991 | 404.1 | OLIGO-1,6-GLUCOSIDASE (EC 3.2.1.10)(SUCRASE-ISOMALTASE) (LIMIT DEXTRINASE) (ISOMALTASE) (DEXTRIN 6-ALPHA-D-GLUCANOHYDROLASE). | swissprot P29094 | ND |
| 992 | 404.0 | DNA-DIRECTED RNA POLYMERASE II14.2 KD POLYPEPTIDE (EC 2.7.7.6) (B12.6). | swissprot P27999 | ND |
| 993 | 403.4 | *C. albicans* antigenic protein 4. | geneseqp Y06928 | ND |
| 994 | 401.8 | MULTIDRUG RESISTANCE-ASSOCIATED PROTEIN 3. | swissprot O88563 | ND |
| 995 | 401.8 | COP9 COMPLEX SUBUNIT 4. | sptrembl Q9Y677 | ND |
| 996 | 401.1 | PEROXISOMAL MEMBRANE PROTEIN PER10 (PEROXIN-14). | swissprot P78723 | ND |
| 997 | 400.6 | QUINONE OXIDOREDUCTASE (EC 1.6.5.5) (NADPH:QUINONE REDUCTASE). | swissprot P43903 | ND |
| 998 | 400.3 | HYPOTHETICAL 23.4 KD PROTEIN. | sptrembl Q03201 | Translation, ribosomal structure and biogenesis |
| 999 | 399.5 | 40S RIBOSOMAL PROTEIN S25 PRECURSOR (S31) (YS23) (RP45). | swissprot P07282 | ND |
| 1000 | 399.0 | HYPOTHETICAL 49.4 KD PROTEIN. | sptrembl P71984 | Energy production and conversion |
| 1001 | 398.7 | 40S RIBOSOMAL PROTEIN S29-B (S36) (YS29). | swissprot P41058 | Translation, ribosomal structure and biogenesis |
| 1002 | 398.4 | PUTATIVE MITOCHONDRIAL CARRIER YEL006W. | swissprot P39953 | ND |
| 1003 | 398.1 | PUTATIVE ATP-DEPENDENT RNA HELICASE C17G6.14C. | sptrembl O13792 | ND |
| 1004 | 397.7 | ABC TRANSPORTER PROTEIN ATRC. | sptrembl Q9Y748 | ND |
| 1005 | 395.7 | VACUOLAR PROTEIN SORTING-ASSOCIATED PROTEIN VPS5. | swissprot Q92331 | ND |
| 1006 | 395.6 | CHORISMATE SYNTHASE (EC 4.6.1.4) (5-ENOLPYRUVYLSHIKIMATE-3-PHOSPHATE PHOSPHOLYASE). | swissprot Q12640 | ND |
| 1007 | 395.1 | PUTATIVE METAL TRANSPORTER. | sptrembl O94639 | ND |
| 1008 | 393.8 | PUTATIVE MICROSOMAL DIPEPTIDASE PRECURSOR (EC 3.4.13.19) (MDP). | sptrembl O14124 | ND |
| 1009 | 393.0 | INTRACELLULAR METALLOPROTEINASE MEPB. | sptrembl P97996 | ND |
| 1010 | 392.8 | HYPOTHETICAL 52.4 KD PROTEIN IN ATP1-ROX3 INTERGENIC REGION PRECURSOR. | swissprot P38169 | Coenzyme metabolism |
| 1011 | 392.7 | CODED FOR BY *C. ELEGANS* CDNA YK20F6.3. | sptrembl Q18599 | ND |
| 1012 | 391.5 | SEPTIN HOMOLOG SPN2. | tremblnew CAB57440 | ND |

TABLE 1-continued

*Fusarium venenatum* ESTs

| Sequence Listing | zscore | Annotation | Database | Functional category |
|---|---|---|---|---|
| 1013 | 391.4 | TREHALASE PRECURSOR (EC 3.2.1.28) (ALPHA,ALPHA-TREHALASE) (ALPHA,ALPHA-TREHALOSE GLUCOHYDROLASE). | swissprot P32359 | ND |
| 1014 | 391.1 | PUTATIVE PROTEIN TRANSPORT PROTEIN SEC61 GAMMA SUBUNIT. | swissprot Q09827 | ND |
| 1015 | 390.2 | H(+)/MONOSACCHARIDE COTRANSPORTER. | sptrembl O13411 | ND |
| 1016 | 390.2 | HYPOTHETICAL 14.5 KD PROTEIN C6F12.04 IN CHROMOSOME I. | sptrembl O14223 | ND |
| 1017 | 390.1 | PUTATIVE SNRNP SM-LIKE PROTEIN. | sptrembl Q9Y7M4 | ND |
| 1018 | 387.3 | CHITINASE. | tremblnew BAA88380 | ND |
| 1019 | 387.3 | NONHISTONE CHROMOSOMAL PROTEIN 6B. | swissprot P11633 | ND |
| 1020 | 387.2 | Y48B6A.11 PROTEIN. | tremblnew CAB54451 | ND |
| 1021 | 386.7 | CHROMOSOME XV READING FRAME ORF YOR286W. | sptrembl Q08742 | ND |
| 1022 | 386.0 | PROBABLE TRANSPORTER FEN2. | swissprot P25621 | ND |
| 1023 | 385.5 | 3-KETOACYL-COA THIOLASE B, PEROXISOMAL PRECURSOR (EC 2.3.1.16) (BETA-KETOTHIOLASE B) (ACETYL-COA ACYLTRANSFERASE B) (PEROXISOMAL 3-OXOACYL-COA THIOLASE B) (THIOLASE IB). | swissnew P33291 | ND |
| 1024 | 385.4 | NON-FUNCTIONAL FOLATE BINDING PROTEIN. | sptrembl O14597 | ND |
| 1025 | 385.2 | CONSERVED HYPOTHETICAL PROTEIN. | sptrembl O74741 | ND |
| 1026 | 384.4 | 60S RIBOSOMAL PROTEIN L28. | tremblnew CAA22600 | ND |
| 1027 | 384.2 | HYPOTHETICAL 54.7 KD PROTEIN. | sptrembl Q9Y827 | ND |
| 1028 | 384.2 | PUTATIVE MITOCHONDRIAL CARRIER C8C9.12C. | sptrembl O14281 | ND |
| 1029 | 384.0 | CARNITINE RACEMASE HOMOLOG. | sptrembl O23300 | ND |
| 1030 | 383.9 | STAM-LIKE PROTEIN, VHS DOMAIN CONTAINING, PUTATIVE SIGNAL TRANSDUCING ADAPTOR. | sptrembl O74749 | ND |
| 1031 | 383.5 | INACTIVE ISOCITRATE LYASE (EC 4.1.3.1) (ISOCITRASE) (ISOCITRATASE) (ICL). | swissprot Q12031 | ND |
| 1032 | 383.5 | HYPOTHETICAL 21.4 KD PROTEIN C19A8.14 IN CHROMOSOME I. | sptrembl O13830 | ND |
| 1033 | 383.0 | MANNOSE-6-PHOSPHATE ISOMERASE (EC 5.3.1.8) (PHOSPHOMANNOSE ISOMERASE) (PMI) (PHOSPHOHEXOMUTASE). | swissprot P29951 | ND |
| 1034 | 382.9 | HYPOTHETICAL 36.9 KD PROTEIN C21E11.07 IN CHROMOSOME I. | swissprot Q09929 | ND |
| 1035 | 381.6 | SERYL-TRNA SYNTHETASE, | swissprot O14018 | ND |

TABLE 1-continued

*Fusarium venenatum* ESTs

| Sequence Listing | zscore | Annotation | Database | Functional category |
|---|---|---|---|---|
| | | CYTOPLASMIC (EC 6.1.1.11) (SERINE--TRNA LIGASE) (SERRS). | | |
| 1036 | 381.3 | YMC1P. | sptrembl Q12002 | ND |
| 1037 | 381.0 | PXP-18. | tremblnew BAA85152 | ND |
| 1038 | 380.7 | PUTATIVE MAJOR FACILITATOR FAMILY MULTI-DRUG RESISTANCE PROTEIN. | sptrembl O94343 | ND |
| 1039 | 380.6 | SIMILAR TO ACYL-COA THIOESTERASE. NCBI GI: 1213545. | sptrembl Q19781 | ND |
| 1040 | 380.5 | CGI-83 PROTEIN. | sptrembl Q9Y392 | ND |
| 1041 | 380.4 | SIMILARITY TO *S. CEREVISIAE* HYPOTHETICAL PROTEIN L8083.10. | sptrembl Q05515 | ND |
| 1042 | 379.7 | DTDP-4-KETO-6-DEOXY-D-GLUCOSE 4-REDUCTASE. | tremblnew CAB56837 | ND |
| 1043 | 379.5 | URACIL PHOSPHORIBOSYLTRANSFERASE (EC 2.4.2.9) (UMP PYROPHOSPHORYLASE) (UPRTASE). | swissnew P18562 | ND |
| 1044 | 377.9 | WCOR719. | sptrembl Q43655 | ND |
| 1045 | 377.6 | HYPOTHETICAL 117.2 KD PROTEIN IN EXO70-ARP4 INTERGENIC REGION. | swissprot P47029 | ND |
| 1046 | 377.1 | F54C4.2 PROTEIN. | tremblnew AAC68775 | ND |
| 1047 | 376.6 | XAA-PRO DIPEPTIDASE (EC 3.4.13.9) (X-PRO DIPEPTIDASE) (PROLINE DIPEPTIDASE) (PROLIDASE) (IMIDODIPEPTIDASE) PEPTIDASE 4). | swissprot Q11136 | ND |
| 1048 | 375.4 | 60S RIBOSOMAL PROTEIN L6, MITOCHONDRIAL PRECURSOR (YML6). | swissprot P32904 | ND |
| 1049 | 375.3 | GLUCOSE TRANSPORTER TYPE 3, BRAIN. | swissprot P11169 | ND |
| 1050 | 375.0 | Human Ras protein RAPR-1. | geneseqp Y29666 | ND |
| 1051 | 374.8 | UBIQUINOL-CYTOCHROME C REDUCTASE COMPLEX 14 KD PROTEIN (EC 1.10.2.2) (COMPLEX III SUBUNIT VII). | swissprot P49345 | ND |
| 1052 | 374.7 | ATGRP2 (GLYCINE-RICH RNA-BINDING PROTEIN). | sptrembl Q41988 | ND |
| 1053 | 374.4 | Fragment of human secreted protein encoded by gene 3. | geneseqp W78239 | ND |
| 1054 | 374.3 | HYPOTHETICAL 25.7 KD PROTEIN. | sptrembl Q9Y7M6 | ND |
| 1055 | 374.1 | SIMILAR TO RAT SYNAPTIC GLYCOPROTEIN SC2. | sptrembl O94511 | ND |
| 1056 | 373.8 | UVSB PI-3 KINASE. | tremblnew AAD54313 | ND |
| 1057 | 373.8 | CHROMOSOME XV READING FRAME ORF YOR052C. | sptrembl Q08422 | ND |
| 1058 | 373.3 | TRANSLATIONAL ACTIVATOR GCN1. | swissprot P33892 | ND |
| 1059 | 373.1 | HYPOTHETICAL 43.9 KD PROTEIN. | tremblnew CAB62419 | ND |
| 1060 | 372.9 | HYPOTHETICAL 34.0 KD PROTEIN IN CTF13-YPK2 INTERGENIC REGION. | swissprot Q03161 | ND |
| 1061 | 372.7 | MITOCHONDRIAL PROCESSING PEPTIDASE BETA SUBUNIT | swissprot P11913 | ND |

TABLE 1-continued

*Fusarium venenatum* ESTs

| Sequence Listing | zscore | Annotation | Database | Functional category |
|---|---|---|---|---|
| | | PRECURSOR (EC 3.4.24.64) (BETA-MPP) (UBIQUINOL-CYTOCHROME C REDUCTASE COMPLEX CORE PROTEIN I) (EC 1.10.2.2). | | |
| 1062 | 372.3 | PUTATIVE SUGAR TRANSPORTER. | sptrembl O48537 | ND |
| 1063 | 371.2 | SHORT-CHAIN ALCOHOL DEHYDROGENASE-LIKE PROTEIN. | tremblnew CAB63154 | ND |
| 1064 | 371.2 | Protein encoded by open reading frame 3 (ORF-3, dszC) of dsz cluster. | geneseqp W97051 | ND |
| 1065 | 369.4 | CHROMOSOME XV READING FRAME ORF YOL092W. | sptrembl Q12010 | ND |
| 1066 | 369.3 | DNASE1 PROTEIN. | tremblnew CAB63906 | ND |
| 1067 | 369.1 | PUTATIVE STEROID BINDING PROTEIN. | tremblnew AAD23019 | ND |
| 1068 | 368.8 | Human dUTPase (mitochondrial form). | geneseqp W30281 | ND |
| 1069 | 368.5 | CHIP6. | sptrembl O93841 | ND |
| 1070 | 368.4 | CHROMOSOME XV READING FRAME ORF YOR021C. | sptrembl Q12314 | ND |
| 1071 | 368.3 | HYPOTHETICAL 29.3 KD PROTEIN C31G5.18C IN CHROMOSOME I. | sptrembl O14113 | ND |
| 1072 | 368.3 | HYPOTHETICAL 90.1 KD PROTEIN C23H4.15 IN CHROMOSOME I. | sptrembl O13956 | ND |
| 1073 | 367.9 | CYTOCHROME C HEME LYASE (EC 4.4.1.17) (CCHL) (HOLOCYTOCHROME-C SYNTHASE). | swissnew P14187 | ND |
| 1074 | 367.8 | PROBABLE DOLICHYL-PHOSPHATE-MANNOSE--PROTEIN MANNOSYLTRANSFERASE C16C6.09 (EC 2.4.1.109). | swissprot O42933 | ND |
| 1075 | 367.8 | HYPOTHETICAL 187.1 KD PROTEIN IN OGG1-CNA2 INTERGENIC REGION. | swissnew Q04958 | ND |
| 1076 | 367.7 | HYPOTHETICAL 38.5 KD PROTEIN. | sptrembl O74959 | ND |
| 1077 | 367.6 | PROBABLE GLUCAN 1,3-BETA-GLUCOSIDASE PRECURSOR (EC 3.2.1.58) (EXO-1,3-BETA-GLUCANASE). | swissprot Q10444 | ND |
| 1078 | 367.5 | ANTHRANILATE PHOSPHORIBOSYLTRANSFERASE (EC 2.4.2.18). | swissnew O60122 | ND |
| 1079 | 367.2 | HYPOTHETICAL 10.4 KD PROTEIN. | sptrembl O43002 | ND |
| 1080 | 367.2 | HYPOTHETICAL 27.0 KD PROTEIN C12B10.13 IN CHROMOSOME I. | swissprot Q10446 | ND |
| 1081 | 366.7 | HYPOTHETICAL 33.9 KD PROTEIN C14C4.12C IN CHROMOSOME I. | swissprot O13719 | ND |
| 1082 | 366.3 | PDI RELATED PROTEIN A. | sptrembl O93914 | ND |
| 1083 | 366.3 | DOLICHYL-DIPHOSPHOOLIGOSACCHARIDE--PROTEIN (OLIGOSACCHARYLTRANSFERASE). | sptrembl O59866 | ND |
| 1084 | 366.2 | HYPOTHETICAL 24.8 KD PROTEIN. | tremblnew CAB54811 | ND |
| 1085 | 366.2 | PHGA PROTEIN. | sptrembl O96904 | ND |
| 1086 | 366.0 | HYPOTHETICAL 69.0 KD | swissprot P38887 | Nucleotide |

TABLE 1-continued

*Fusarium venenatum* ESTs

| Sequence Listing | zscore | Annotation | Database | Functional category |
|---|---|---|---|---|
| | | PROTEIN IN PPX1-RPS4B INTERGENIC REGION. | | transport |
| 1087 | 365.8 | RIBOSOMAL PROTEIN S5 (FRAGMENT). | tremblnew BAA25815 | ND |
| 1088 | 365.7 | HYPOTHETICAL 31.6 KD PROTEIN. | sptrembl O94465 | ND |
| 1089 | 365.7 | HYDROXYPROLINE-RICH GLYCOPROTEIN DZ-HRGP PRECURSOR. | tremblnew CAB62280 | ND |
| 1090 | 365.7 | HYPOTHETICAL 27.7 KD PROTEIN IN CPT1-SPC98 INTERGENIC REGION. | swissprot P53915 | ND |
| 1091 | 365.5 | CURVED DNA-BINDING PROTEIN (42 KD PROTEIN). | swissprot Q09184 | ND |
| 1092 | 364.6 | ACETATE KINASE (EC 2.7.2.1) (ACETOKINASE). | swissnew Q59331 | ND |
| 1093 | 363.9 | NADH-UBIQUINONE OXIDOREDUCTASE 29.9 KD SUBUNIT PRECURSOR (EC 1.6.5.3) (EC 1.6.99.3) (COMPLEX I-29.9 KD) (CI-29.9 KD). | swissprot P24919 | ND |
| 1094 | 363.8 | MUCIN 2 PRECURSOR (INTESTINAL MUCIN 2). | swissprot Q02817 | ND |
| 1096 | 363.4 | T22K18.2 PROTEIN. | tremblnew AAF04409 | ND |
| 1097 | 363.4 | FRUCTOSYL AMINE:OXYGEN OXIDOREDUCTASE. | sptrembl O42629 | ND |
| 1098 | 363.1 | HYPOTHETICAL 55.5 KD PROTEIN. | sptrembl O82645 | ND |
| 1099 | 361.7 | UBIQUITIN-CONJUGATING ENZYME E2-18 KD (EC 6.3.2.19) (UBIQUITIN-PROTEIN LIGASE HUS5) (UBIQUITIN CARRIER PROTEIN HUS5). | swissprot P40984 | ND |
| 1100 | 360.9 | SERINE/THREONINE-PROTEIN KINASE IRE1 PRECURSOR (EC 2.7.1.-). | swissprot P32361 | ND |
| 1101 | 360.5 | HYPOTHETICAL 61.8 KD PEPTIDASE IN MPR1-GCN20 INTERGENIC REGION (EC 3.4.-.-). | swissprot P43590 | ND |
| 1102 | 360.2 | MANNOSE-1-PHOSPHATE GUANYLTRANSFERASE (EC 2.7.7.13) (MPG1 TRANSFERASE) (ATP-MANNOSE-1-PHOSPHATE GUANYLYLTRANSFERASE) | sptrembl O74624 | ND |
| 1103 | 359.6 | ERP6 PROTEIN PRECURSOR. | swissprot P53198 | ND |
| 1104 | 359.2 | HYPOTHETICAL 26.7 KD PROTEIN C3G9.15C IN CHROMOSOME I. | sptrembl O42877 | ND |
| 1105 | 358.7 | PUTATIVE GTP CYCLOHYDROLASE. | tremblnew CAB65619 | ND |
| 1106 | 358.3 | HYPOTHETICAL 77.8 KD PROTEIN. | sptrembl O74828 | ND |
| 1107 | 358.1 | CALCIUM/PROTON EXCHANGER. | sptrembl O59940 | ND |
| 1108 | 358.0 | GLUCOSIDASE 558 aa | pdb 1UOK | ND |
| 1109 | 357.9 | JM5 PROTEIN. | sptrembl Q9Y484 | ND |
| 1110 | 357.7 | CKS1 protein. | geneseqp W01557 | ND |
| 1111 | 357.7 | MDM10 GENE. | sptrembl O13498 | ND |
| 1112 | 356.7 | NADPH QUINONE OXIDOREDUCTASE, PUTATIVE. | tremblnew AAF12387 | ND |
| 1113 | 356.4 | PUTATIVE SPINDLE POLE BODY ASSOCIATED PROTEIN. | sptrembl Q9Y705 | ND |

TABLE 1-continued

Fusarium venenatum ESTs

| Sequence Listing | zscore | Annotation | Database | Functional category |
|---|---|---|---|---|
| 1114 | 355.8 | CHROMOSOME XV READING FRAME ORF YOR306C. | sptrembl Q08777 | ND |
| 1115 | 354.7 | PUTATIVE PROTEASE. | sptrembl Q9X7U3 | ND |
| 1116 | 354.7 | HYPOTHETICAL PROTEIN. | sptrembl Q12486 | ND |
| 1117 | 354.6 | PUTATIVE SIGNAL TRANSDUCTION PROTEIN. | sptrembl O94321 | ND |
| 1118 | 354.3 | 60S RIBOSOMAL PROTEIN L16, MITOCHONDRIAL PRECURSOR (YML47). | swissprot P38064 | ND |
| 1119 | 354.1 | ELONGATION FACTOR G 1, MITOCHONDRIAL PRECURSOR (MEF-G-1). | swissprot P25039 | ND |
| 1120 | 353.7 | HYPOTHETICAL 183.1 KD HELICASE C3G6.12 IN CHROMOSOME I. | sptrembl O14148 | ND |
| 1121 | 353.1 | FOLYLPOLYGLUTAMATE SYNTHETASE (EC 6.3.2.17). | sptrembl O13492 | ND |
| 1122 | 352.4 | DLTE PROTEIN. | swissprot P39577 | ND |
| 1123 | 351.8 | PSI-7 PROTEIN. | sptrembl O13444 | ND |
| 1124 | 351.7 | W02A2.5 PROTEIN. | sptrembl Q9XUB4 | ND |
| 1125 | 351.6 | HYPOTHETICAL ZINC-TYPE ALCOHOL DEHYDROGENASE-LIKE PROTEIN IN GDH3-CNE1 INTERGENIC REGION. | swissprot P39714 | ND |
| 1126 | 351.3 | CELL DIFFERENTIATION PROTEIN RCD1. | sptrembl Q92368 | ND |
| 1127 | 351.1 | CONSERVED HYPOTHETICAL NIFU-LIKE PROTEIN. | tremblnew CAB52604 | ND |
| 1128 | 351.1 | TRANSLATION INITIATION FACTOR EIF-2B ALPHA SUBUNIT. | tremblnew CAB57849 | ND |
| 1129 | 351.0 | 26S PROTEASE REGULATORY SUBUNIT 6A (TAT-BINDING PROTEIN HOMOLOG 1) (TBP-1). | swissprot P33297 | ND |
| 1130 | 350.5 | PUTATIVE 26S PROTEASOME SUBUNIT. | tremblnew CAB63792 | ND |
| 1131 | 350.4 | HYPOTHETICAL 26.5 KD PROTEIN C24B11.05 IN CHROMOSOME I. | swissprot Q09893 | ND |
| 1132 | 350.3 | HYPOTHETICAL 83.0 KD PROTEIN IN ATP1-ROX3 INTERGENIC REGION. | swissprot P38170 | ND |
| 1133 | 349.8 | PUTATIVE 60S ACIDIC RIBOSOMAL PROTEIN. | tremblnew CAB59805 | ND |
| 1134 | 349.8 | DJ747H23.3 (N-ACETYLGLUCOSAMINE-PHOSPHATE MUTASE) (FRAGMENT). | tremblnew CAB52346 | ND |
| 1135 | 349.7 | ACETOACETYL-COA SYNTHETASE (EC 6.2.1.16). | sptrembl Q9Z3R3 | ND |
| 1136 | 349.2 | 60S RIBOSOMAL PROTEIN L38. | tremblnew CAB54810 | ND |
| 1137 | 347.8 | HYPOTHETICAL 82.9 KD PROTEIN. | sptrembl O42958 | ND |
| 1138 | 347.8 | HYPOTHETICAL 30.9 KD PROTEIN. | sptrembl O95564 | ND |
| 1139 | 347.7 | HYPOTHETICAL 51.9 KD PROTEIN IN PYC1-UBC2 INTERGENIC REGION. | swissprot P53170 | ND |
| 1140 | 347.0 | Human actVA-ORF4-like protein sequence. | geneseqp Y14147 | ND |
| 1141 | 346.9 | PUTATIVE POLY(A)-BINDING PROTEIN FABM. | sptrembl Q92227 | ND |
| 1142 | 346.2 | DJ1014D13.1 (PROTEINS HSPC021 AND HSPC025 (SIMILAR TO C. ELEGANS | tremblnew CAB62978 | ND |

TABLE 1-continued

Fusarium venenatum ESTs

| Sequence Listing | zscore | Annotation | Database | Functional category |
|---|---|---|---|---|
| | | FAT-3 ALCOHOL DEHYDROGENASE)) (FRAGMENT). | | |
| 1143 | 346.0 | CULLIN HOMOLOG 3 (CUL-3). | swissprot Q09760 | ND |
| 1144 | 345.0 | SPHINGOMYELIN PHOSPHODIESTERASE (EC 3.1.4.12) (ACID SPHINGOMYELINASE) (NEUTRAL SPHINGOMYELINASE). | sptrembl Q16841 | ND |
| 1145 | 344.3 | ENOYL-COA HYDRATASE, MITOCHONDRIAL PRECURSOR (EC 4.2.1.17) (SHORT CHAIN ENOYL-COA HYDRATASE) (SCEH) (ENOYL-COA HYDRATASE 1). | swissprot P14604 | ND |
| 1146 | 343.8 | ESTS AU078175(C51476). | tremblnew BAA85408 | ND |
| 1147 | 342.8 | MYO-INOSITOL-1-PHOSPHATE SYNTHASE (EC 5.5.1.4) (IPS). | swissprot P42801 | ND |
| 1148 | 342.8 | 3-OXOACYL-[ACYL-CARRIER PROTEIN] REDUCTASE. | sptrembl O53665 | ND |
| 1149 | 342.7 | HYPOTHETICAL 62.7 KD PROTEIN C29A3.06 IN CHROMOSOME II. | sptrembl P78750 | ND |
| 1150 | 341.9 | MUCIN 2 PRECURSOR (INTESTINAL MUCIN 2). | swissprot Q02817 | ND |
| 1151 | 341.7 | HYPOTHETICAL 27.7 KD PROTEIN IN PRP19-HSP104 INTERGENIC REGION. | swissprot Q07821 | ND |
| 1152 | 341.6 | PUTATIVE TRANSPORTER PROTEIN. | tremblnew CAB61275 | ND |
| 1153 | 340.9 | NADH-CYTOCHROME B5 REDUCTASE PRECURSOR (EC 1.6.2.2) (P34/P32). | swissprot P36060 | ND |
| 1154 | 340.3 | PUTATIVE OXIDOREDUCTASE. | tremblnew CAB53292 | ND |
| 1155 | 339.8 | AMINOPEPTIDASE C (EC 3.4.22.-). | swissprot Q48543 | ND |
| 1156 | 339.5 | PUTATIVE PRE-MRNA SPLICING FACTOR C22A12.09C. | sptrembl O13900 | ND |
| 1157 | 339.0 | COPPER AMINE OXIDASE 1 (EC 1.4.3.6). | swissprot Q12556 | ND |
| 1158 | 338.9 | S-ADENOSYLMETHIONINE SYNTHETASE (EC 2.5.1.6) (METHIONINE ADENOSYLTRANSFERASE) (ADOMET SYNTHETASE). | swissprot P48466 | ND |
| 1159 | 338.3 | CONSERVED PROTEIN. | sptrembl O26459 | ND |
| 1160 | 338.1 | PUTATIVE METALLOPEPTIDASE. | sptrembl O59824 | ND |
| 1161 | 337.4 | SIMILAR TO YEAST VACUOLAR SORTING PROTEIN VPS29/PEP11. | tremblnew CAB52425 | ND |
| 1162 | 337.4 | PMT3P. | sptrembl O74186 | ND |
| 1163 | 336.8 | 3-KETOACYL-COA THIOLASE B, PEROXISOMAL PRECURSOR (EC 2.3.1.16) (BETA-KETOTHIOLASE B) (ACETYL-COA ACYLTRANSFERASE B) (PEROXISOMAL 3-OXOACYL-COA THIOLASE B). | swissnew P07871 | ND |
| 1164 | 335.8 | PEROXISOMAL MEMBRANE PROTEIN PEX16 (PEROXIN-16). | swissprot P78980 | ND |

TABLE 1-continued

Fusarium venenatum ESTs

| Sequence Listing | zscore | Annotation | Database | Functional category |
|---|---|---|---|---|
| 1165 | 335.8 | CYTOCHROME B5 CONTAINING FUSION PROTEIN. | sptrembl Q43469 | ND |
| 1166 | 335.1 | 2-NITROPROPANE DIOXYGENASE (NCD2). | sptrembl O28109 | ND |
| 1167 | 334.6 | HYPOTHETICAL 25.4 KD PROTEIN IN GUT1-RIM1 INTERGENIC REGION. | swissprot P38736 | ND |
| 1168 | 334.3 | G/T MISMATCH-SPECIFIC THYMINE DNA GLYCOSYLASE (EC 3.2.2.-) (C-JUN LEUCINE ZIPPER INTERACTIVE PROTEIN JZA-3). | swissprot P56581 | ND |
| 1169 | 334.2 | PROBABLE ELECTRON TRANSFER FLAVOPROTEIN ALPHA-SUBUNIT PRECURSOR (ALPHA-ETF). | swissprot P78790 | ND |
| 1170 | 333.9 | PROBABLE GLUTAMINYL-TRNA SYNTHETASE. | sptrembl Q9Y7Y8 | ND |
| 1171 | 333.2 | CYTOCHROME P450 MONOOXYGENASE (FRAGMENT). | sptrembl O64410 | ND |
| 1172 | 332.2 | PEROXISOMAL MEMBRANE PROTEIN. | sptrembl Q9Y8B8 | ND |
| 1173 | 330.7 | SHORT-CHAIN ALCOHOL DEHYDROGENASE. | tremblnew AAB51228 | ND |
| 1174 | 330.6 | CRB3 PROTEIN. | swissprot Q10272 | ND |
| 1175 | 330.6 | HYPOTHETICAL 126.1 KD PROTEIN. | sptrembl O94676 | ND |
| 1176 | 330.2 | AUTOPHAGOCYTOSIS PROTEIN AUT1. | swissprot P40344 | ND |
| 1177 | 329.6 | TTP1 PROTEIN. | swissprot P38069 | ND |
| 1178 | 329.6 | HYPOTHETICAL 51.4 KD PROTEIN C13G1.09 IN CHROMOSOME II. | swissprot O60071 | ND |
| 1179 | 329.5 | SERYL-TRNA SYNTHETASE, CYTOPLASMIC (EC 6.1.1.11) (SERINE--TRNA LIGASE) (SERRS). | swissprot P07284 | ND |
| 1180 | 328.9 | HYPOTHETICAL 13.0 KS PROTEIN. | sptrembl P79082 | ND |
| 1181 | 328.6 | ATP11 PROTEIN PRECURSOR. | swissprot P32453 | ND |
| 1182 | 328.3 | GNS1/SUR4 FAMILY PROTEIN. | tremblnew CAB61470 | ND |
| 1183 | 327.6 | GRG-1 PROTEIN. | sptrembl Q9Y836 | ND |
| 1184 | 326.3 | HYPOTHETICAL PROTEIN C26F1.01 IN CHROMOSOME I (FRAGMENT). | swissprot Q10491 | ND |
| 1185 | 326.2 | HEMOLYSIN. | sptrembl Q17063 | ND |
| 1186 | 325.6 | PROBABLE ATP-DEPENDENT PERMEASE YHL035C. | swissprot P38735 | ND |
| 1187 | 325.1 | CONSERVED HYPOTHETICAL PROTEIN. | tremblnew CAB54870 | ND |
| 1188 | 324.9 | HYPOTHETICAL 15.9 KD PROTEIN. | tremblnew CAB52421 | ND |
| 1189 | 324.7 | HYPOTHETICAL 15.4 KD PROTEIN C10F6.16 IN CHROMOSOME I. | sptrembl P79058 | ND |
| 1190 | 324.6 | HYPOTHETICAL 31.0 KD PROTEIN IN GAP1-NAP1 INTERGENIC REGION. | swissprot P36136 | ND |
| 1191 | 324.5 | PROBABLE CYTOCHROME C OXIDASE POLYPEPTIDE VIA PRECURSOR (EC 1.9.3.1). | swissprot O74471 | ND |
| 1192 | 323.4 | ANUCLEATE PRIMARY STERIGMATA PROTEIN. | swissprot Q00083 | ND |
| 1193 | 322.9 | LECTIN (FRAGMENT). | tremblnew AAD27887 | ND |

TABLE 1-continued

*Fusarium venenatum* ESTs

| Sequence Listing | zscore | Annotation | Database | Functional category |
|---|---|---|---|---|
| 1194 | 322.5 | PROTEIN SERINE/THREONINE PHOSPHATASE ALPHA. | sptrembl O96914 | ND |
| 1195 | 321.7 | SLA2P. | sptrembl O94097 | ND |
| 1196 | 321.7 | HYPOTHETICAL 42.4 KD PROTEIN IN CDC12-ORC6 INTERGENIC REGION. | swissprot P38716 | ND |
| 1197 | 321.5 | MUCIN 2 PRECURSOR (INTESTINAL MUCIN 2). | swissprot Q02817 | ND |
| 1198 | 320.5 | PUTATIVE CHOLINE KINASE (EC 2.7.1.32). | swissprot Q10276 | ND |
| 1199 | 320.5 | GLUCOAMYLASE PRECURSOR (EC 3.2.1.3) (GLUCAN 1,4-ALPHA-GLUCOSIDASE) (1,4-ALPHA-D-GLUCAN GLUCOHYDROLASE). | swissprot P36914 | ND |
| 1200 | 319.7 | 60S RIBOSOMAL PROTEIN L27A (L29). | swissprot P78987 | ND |
| 1201 | 319.7 | F26H9.6 PROTEIN. | sptrembl P91857 | ND |
| 1202 | 319.2 | PROBABLE METABOLITE TRANSPORT PROTEIN. | sptrembl O94342 | ND |
| 1203 | 319.0 | HYPOTHETICAL 33.9 KD ESTERASE IN SMC3-MRPL8 INTERGENIC REGION (EC 3.1.1.1). | swissprot P40363 | ND |
| 1204 | 318.8 | RIBOSOMAL PROTEIN S28. | tremblnew CAB56815 | ND |
| 1205 | 317.8 | CELL CYCLE INHIBITOR NIF1. | sptrembl P87159 | ND |
| 1206 | 317.8 | GLUCOSE OXIDASE (EC 1.1.3.4). | tremblnew BAA86908 | ND |
| 1208 | 317.1 | SIMILAR TO SDH4P. | sptrembl Q06236 | ND |
| 1209 | 316.7 | PHOSPHATE/PHOSPHOENOLPYRUVATE TRANSLOCATOR PRECURSOR. | sptrembl P93390 | ND |
| 1210 | 316.4 | SERINE THREONINE PROTEIN KINASE. | sptrembl Q9Y7V4 | ND |
| 1211 | 315.4 | HYPOTHETICAL 29.0 KD PROTEIN. | sptrembl Q9Y7C9 | ND |
| 1212 | 314.6 | Human prostate/colon tumour suppressor protein form 2. | geneseqp R85334 | ND |
| 1213 | 313.8 | 50S RIBOSOMAL PROTEIN L1. | swissprot P36248 | ND |
| 1214 | 313.8 | HYPOTHETICAL 15.4 KD PROTEIN C16C10.11 IN CHROMOSOME III. | swissprot Q09254 | ND |
| 1215 | 313.3 | HYPOTHETICAL 20.5 KD PROTEIN IN ESR1-IRA1 INTERGENIC REGION. | swissprot P38276 | ND |
| 1216 | 313.1 | CHROMOSOME XII READING FRAME ORF YLL032C. | sptrembl Q07834 | ND |
| 1217 | 312.9 | ADENYLYL CYCLASE-ASSOCIATED PROTEIN (CAP). | swissprot P36621 | ND |
| 1218 | 312.6 | FREQUENCY CLOCK PROTEIN. | swissnew Q00586 | ND |
| 1219 | 312.4 | HIGH AFFINITY METHIONINE PERMEASE. | swissprot P50276 | ND |
| 1220 | 312.2 | PUTATIVE SHORT-CHAIN DEHYDROGENASE. | sptrembl Q9Y7P2 | ND |
| 1221 | 312.0 | ARYL-ALCOHOL OXIDASE PRECURSOR (EC 1.1.3.7). | sptrembl O94219 | ND |
| 1222 | 311.6 | RIBOSE-PHOSPHATE PYROPHOSPHOKINASE (EC 2.7.6.1) (PHOSPHORIBOSYL PYROPHOSPHATE SYNTHETASE). | swissprot P41831 | ND |
| 1223 | 311.5 | PROBABLE URACIL PHOSPHORIBOSYLTRANSFERASE. | tremblnew CAB65617 | ND |
| 1224 | 310.7 | CGI-82 PROTEIN. | sptrembl Q9Y391 | ND |

TABLE 1-continued

*Fusarium venenatum* ESTs

| Sequence Listing | zscore | Annotation | Database | Functional category |
|---|---|---|---|---|
| 1225 | 310.5 | HYPOTHETICAL UBIQUINOL-CYTOCHROME C REDUCTASE COMPONENT. | sptrembl O42932 | ND |
| 1226 | 310.3 | HYPOTHETICAL 28.1 KD PROTEIN. | sptrembl O13850 | ND |
| 1227 | 310.3 | PROTEASOME SUBUNIT P55. | sptrembl O00232 | ND |
| 1228 | 310.0 | NADH DEHYDROGENASE SUBUNIT. | sptrembl Q01388 | ND |
| 1229 | 310.0 | CHITINASE PRECURSOR. | sptrembl Q42421 | ND |
| 1230 | 309.6 | CHROMOSOME XII READING FRAME ORF YLL058W. | sptrembl Q12198 | ND |
| 1231 | 309.3 | T02D1.5 PROTEIN. | sptrembl O45730 | ND |
| 1232 | 308.2 | HYPOTHETICAL 34.1 KD PROTEIN. | tremblnew CAB43297 | ND |
| 1233 | 308.2 | L-FUCOSE PERMEASE. | swissprot P44776 | ND |
| 1234 | 307.9 | PHO85P, LPH16P. | sptrembl Q02979 | ND |
| 1235 | 307.6 | LYSOPHOSPHOLIPASE HOMOLOG. | sptrembl O18501 | ND |
| 1236 | 307.0 | UBIQUINOL-CYTOCHROME C REDUCTASE COMPLEX UBIQUINONE-BINDING PROTEIN QP-C (EC 1.10.2.2) (UBIQUINOL-CYTOCHROME C REDUCTASE COMPLEX 11 KD PROTEIN) (COMPLEX III SUBUNIT VIII). | swissprot P48503 | ND |
| 1237 | 307.0 | HYPOTHETICAL 16.9 KD PROTEIN IN ALD6-PDR12 INTERGENIC REGION. | swissprot Q02784 | ND |
| 1238 | 306.9 | HYPOTHETICAL 102.7 KD PROTEIN IN PRP16-SRP40 INTERGENIC REGION. | swissprot P36165 | ND |
| 1239 | 306.8 | ADENYLOSUCCINATE SYNTHETASE, MUSCLE ISOZYME (EC 6.3.4.4) (IMP--ASPARTATE LIGASE). | swissprot P28650 | ND |
| 1240 | 306.4 | ADENYLATE KINASE 2 (EC 2.7.4.3) (ATP-AMP TRANSPHOSPHORYLASE). | swissprot P26364 | ND |
| 1241 | 305.7 | RNA BINDING PROTEIN - PUTATIVE PRE MRNA SPLICING FACTOR. | sptrembl O74919 | ND |
| 1242 | 305.7 | PUTATIVE PHOSPHOMEVALONATE KINASE. | tremblnew CAB52264 | ND |
| 1243 | 305.6 | HYPOTHETICAL 24.1 KD PROTEIN. | sptrembl O94389 | ND |
| 1244 | 305.6 | ARG-6 PROTEIN PRECURSOR [CONTAINS: N-ACETYL-GAMMA-GLUTAMYL-PHOSPHATE REDUCTASE (EC 1.2.1.38) (N-ACETYL-GLUTAMATE SEMIALDEHYDE DEHYDROGENASE) (NAGSA DEHYDROGENASE); ACETYLGLUTAMATE KINASE (EC 2.7.2.8) (NAG KINASE) (AGK) (N-ACETYL-L-GLUTAMATE 5-PHOSPHOTRANSFERASE)]. | swissnew P54898 | ND |
| 1245 | 305.5 | *Chlamydia pneumoniae* transmembrane protein sequence. | geneseqp Y34630 | Posttranslational modification, protein turnover, chaperones |
| 1246 | 305.2 | PUTATIVE RNA MATURATION PROTEIN. | sptrembl O94689 | ND |

TABLE 1-continued

*Fusarium venenatum* ESTs

| Sequence Listing | zscore | Annotation | Database | Functional category |
|---|---|---|---|---|
| 1247 | 305.2 | CYTOSKELETAL P17 PROTEIN (COACTOSIN) (CYCLIC AMP-REGULATED PROTEIN P16). | swissprot P34121 | ND |
| 1248 | 304.7 | UDP-GLUCURONOSYLTRANS-FERASE 2C1 MICROSOMAL (EC 2.4.1.17) (UDPGT) (FRAGMENT). | swissprot P36514 | ND |
| 1249 | 304.5 | C-RECEPTOR. | sptrembl Q9Y5Y0 | ND |
| 1250 | 304.4 | THIOREDOXIN-LIKE PROTEIN. | tremblnew CAB54816 | ND |
| 1251 | 303.8 | HYDROXYPROLINE-RICH GLYCOPROTEIN DZ-HRGP PRECURSOR. | tremblnew CAB62280 | ND |
| 1252 | 303.6 | PUTATIVE POLYA-BINDING PROTEIN. | sptrembl O94430 | ND |
| 1253 | 303.2 | MITOCHONDRIAL FAD CARRIER PROTEIN FLX1. | sptrembl O13660 | ND |
| 1254 | 303.1 | AMINOPEPTIDASE-LIKE PROTEIN. | tremblnew CAB36783 | ND |
| 1255 | 302.8 | HYDROXYPROLINE-RICH GLYCOPROTEIN. | sptrembl Q41814 | ND |
| 1256 | 302.6 | SIMILAR TO MITOCHONDRIAL ADP/ATP CARRIER PROTEIN. | sptrembl Q06497 | ND |
| 1257 | 301.9 | POSSIBLE COPPER TRANSPORT PROTEIN CTR2 (COPPER TRANSPORTER 2). | swissprot P38865 | ND |
| 1258 | 301.8 | HYPOTHETICAL 38.6 KD PROTEIN. | sptrembl O86705 | ND |
| 1259 | 301.4 | PJCHI-2. | sptrembl P91773 | ND |
| 1260 | 300.6 | F14F9.5 PROTEIN. | tremblnew AAC69210 | ND |
| 1261 | 300.1 | HYPOTHETICAL 20.5 KD PROTEIN C31F10.12 IN CHROMOSOME II. | sptrembl P87313 | ND |
| 1262 | 299.9 | *N. crassa* mtr gene product. | geneseqp R79909 | ND |
| 1263 | 299.5 | PUTATIVE DNA POLYMERASE EPSILON, SUBUNIT B. | sptrembl O94263 | ND |
| 1264 | 299.0 | Human actVA-ORF4-like protein sequence. | geneseqp Y14147 | ND |
| 1265 | 298.8 | HYPOTHETICAL ZINC-TYPE ALCOHOL DEHYDROGENASE-LIKE PROTEIN IN GDH3-CNE1 INTERGENIC REGION. | swissprot P39713 | ND |
| 1266 | 298.4 | CHROMOSOME XII COSMID 8167. | sptrembl Q05791 | ND |
| 1267 | 298.2 | H04M03.4 PROTEIN. | tremblnew AAD12787 | ND |
| 1268 | 297.5 | D8035.11P. | sptrembl Q03322 | ND |
| 1269 | 297.2 | HYPOTHETICAL 65.3 KD PROTEIN K12H4.7 IN CHROMOSOME III. | swissprot P34528 | ND |
| 1270 | 297.1 | Protein of the specification. | geneseqp W62553 | ND |
| 1271 | 296.4 | PET191 PROTEIN PRECURSOR. | swissprot Q02772 | ND |
| 1272 | 296.4 | HYPOTHETICAL 22.7 KD PROTEIN. | sptrembl O60073 | ND |
| 1273 | 296.2 | CAMP-DEPENDENT PROTEIN KINASE CATALYTIC SUBUNIT. | sptrembl Q9Y777 | ND |
| 1274 | 296.2 | PUTATIVE ELONGATION FACTOR 3. | sptrembl O94489 | ND |
| 1275 | 296.0 | HYPOTHETICAL 140.6 KD PROTEIN C19A8.02 IN CHROMOSOME I. | sptrembl O13818 | ND |

TABLE 1-continued

*Fusarium venenatum* ESTs

| Sequence Listing | zscore | Annotation | Database | Functional category |
|---|---|---|---|---|
| 1276 | 295.3 | HYPOTHETICAL 30.8 KD PROTEIN IN DUP2-TIF4632 INTERGENIC REGION. | swissprot P53177 | ND |
| 1277 | 295.3 | CHROMOSOME XV READING FRAME ORF YOR301W. | sptrembl Q08760 | ND |
| 1278 | 294.6 | PUTATIVE TRANSLOCATION PROTEIN C2F3.02. | sptrembl O14085 | ND |
| 1279 | 294.1 | BETA-MANNANASE. | tremblnew CAB56855 | ND |
| 1280 | 293.5 | HYPOTHETICAL 16.8 KD PROTEIN IN SMY2-RPS6B INTERGENIC REGION. | swissprot P38293 | ND |
| 1281 | 293.2 | PROBABLE UDP-N-ACETYLGLUCOSAMINE PYROPHOSPHORYLASE (EC 2.7.7.23). | swissprot O64765 | ND |
| 1282 | 293.1 | IKI3 PROTEIN. | swissprot Q06706 | ND |
| 1283 | 292.8 | METHYLMALONYL-COA DECARBOXYLASE GAMMA CHAIN. | tremblnew CAB49799 | ND |
| 1284 | 292.8 | UV-INDUCED PROTEIN UVI31. | swissprot Q12238 | ND |
| 1285 | 292.7 | HYPOTHETICAL 50.6 KD PROTEIN C1D7.03 IN CHROMOSOME II. | sptrembl O14336 | ND |
| 1286 | 292.5 | THIOREDOXIN PEROXIDASE PMP20. | tremblnew AAF04855 | ND |
| 1287 | 291.5 | ARG-6 PROTEIN PRECURSOR [CONTAINS: N-ACETYL-GAMMA-GLUTAMYL-PHOSPHATE REDUCTASE (EC 1.2.1.38) (N-ACETYL-GLUTAMATE SEMIALDEHYDE DEHYDROGENASE) (NAGSA DEHYDROGENASE); ACETYLGLUTAMATE KINASE (EC 2.7.2.8) (NAG KINASE) (AGK) (N-ACETYL-L-GLUTAMATE 5-PHOSPHOTRANSFERASE)]. | swissnew P54898 | ND |
| 1288 | 291.5 | HYPOTHETICAL 50.8 KD PROTEIN IN MIR1-STE18 INTERGENIC REGION. | swissprot P47125 | ND |
| 1289 | 291.4 | U1 SMALL NUCLEAR RIBONUCLEOPROTEIN C (U1-C). | swissprot P09234 | ND |
| 1290 | 291.2 | HYPOTHETICAL 43.5 KD PROTEIN IN RPB9-ALG2 INTERGENIC REGION. | swissprot P53164 | ND |
| 1291 | 290.9 | Kidney injury associated molecule HW034 protein #2. | geneseqp W86311 | ND |
| 1292 | 290.9 | HYDROLASE 210 aa, chain C | pdb 1CMX | ND |
| 1293 | 290.4 | PUTATIVE SHORT CHAIN DEHYDROGENASE. | sptrembl Q9X858 | ND |
| 1294 | 290.2 | KIAA0872 PROTEIN. | sptrembl O94949 | ND |
| 1295 | 289.7 | CHROMOSOME XV READING FRAME ORF YOR367W. | sptrembl Q08873 | ND |
| 1296 | 289.4 | HYPOTHETICAL 78.3 KD PROTEIN IN RIP1-GEA2 INTERGENIC REGION. | swissprot P39992 | ND |
| 1297 | 289.1 | RAB GERANYLGERANYL TRANSFERASE ESCORT PROTEIN (REP). | sptrembl O93831 | ND |
| 1298 | 289.0 | HYPOTHETICAL 37.4 KD PROTEIN. | sptrembl Q03976 | ND |
| 1299 | 288.7 | STREPTOMYCIN BIOSYNTHESIS PROTEIN STRI-RELATED PROTEIN. | tremblnew AAF10934 | ND |

TABLE 1-continued

*Fusarium venenatum* ESTs

| Sequence Listing | zscore | Annotation | Database | Functional category |
|---|---|---|---|---|
| 1300 | 288.7 | HYPOTHETICAL 24.7 KD PROTEIN. | sptrembl O43039 | ND |
| 1301 | 288.5 | SEDOHEPTULOSE-1,7-BISPHOSPHATASE, CHLOROPLAST PRECURSOR (EC 3.1.3.37) (SEDOHEPTULOSE-BISPHOSPHATASE) (SBPASE) (SED(1,7)P2ASE). | swissprot O20252 | ND |
| 1302 | 288.1 | CONSERVED HYPOTHETICAL PROTEIN. | sptrembl Q9WZQ7 | ND |
| 1303 | 287.1 | CYTOCHROME B5 (FRAGMENT). | sptrembl O24651 | ND |
| 1304 | 286.7 | SUR2 PROTEIN (SYRINGOMYCIN RESPONSE PROTEIN 2). | swissprot P38992 | ND |
| 1305 | 286.0 | PUTATIVE TARTRATE TRANSPORTER. | swissprot P70786 | ND |
| 1306 | 285.5 | ER LUMEN PROTEIN RETAINING RECEPTOR (HDEL RECEPTOR). | swissprot P18414 | ND |
| 1307 | 285.1 | SORBITOL DEHYDROGENASE (EC 1.1.1.14) (L-IDITOL 2-DEHYDROGENASE). | swissprot Q06004 | ND |
| 1308 | 285.0 | DNA BINDING PROTEIN NSDD. | sptrembl Q92226 | ND |
| 1309 | 284.4 | KIAA1273 PROTEIN (FRAGMENT). | tremblnew BAA86587 | ND |
| 1310 | 284.3 | QUINATE PERMEASE (QUINATE TRANSPORTER). | swissprot P11636 | ND |
| 1311 | 284.3 | IMPORTIN BETA SUBUNIT. | sptrembl O74476 | ND |
| 1312 | 284.1 | PROBABLE TRANSPORTER SEO1. | swissprot P39709 | ND |
| 1313 | 283.6 | VACUOLAR ATP SYNTHASE 98 KD SUBUNIT (EC 3.6.1.34) (VACUOLAR ATPASE 98 KD SUBUNIT). | swissprot Q01290 | ND |
| 1314 | 283.5 | 40S RIBOSOMAL PROTEIN S26E (CRP5) (13.6 KD RIBOSOMAL PROTEIN). | swissprot P21772 | ND |
| 1315 | 283.4 | GLUTAMINE REPEAT PROTEIN 1. | sptrembl Q61118 | ND |
| 1316 | 283.3 | MUCIN 2 PRECURSOR (INTESTINAL MUCIN 2). | swissprot Q02817 | ND |
| 1317 | 283.2 | VACUOLAR PROTEIN SORTING-LIKE PROTEIN. | tremblnew CAB41098 | ND |
| 1318 | 283.1 | HYPOTHETICAL 31.6 KD PROTEIN. | sptrembl Q9Y7Z5 | ND |
| 1319 | 282.8 | PUTATIVE CARBOXYPEPTIDASE S PRECURSOR (EC 3.4.17.4) (YSCS) (GLY-X CARBOXYPEPTIDASE). | sptrembl O13968 | ND |
| 1320 | 282.2 | PUTATIVE ALDOSE 1-EPIMERASE. | tremblnew CAB62725 | ND |
| 1321 | 282.2 | GLYCYL TRNA SYNTHETASE (FRAGMENT). | tremblnew AAC71652 | ND |
| 1322 | 281.7 | TRANSCRIPTIONAL ACTIVATOR. | sptrembl O42804 | ND |
| 1323 | 281.6 | Omega-cyclohexane fatty acid biosynthesis enzyme #1 ORF6. | geneseqp W71638 | ND |
| 1324 | 281.0 | TOXD PROTEIN. | swissprot P54006 | ND |
| 1325 | 280.9 | ADRENAL GLAND PROTEIN AD-002. | tremblnew AAF14858 | ND |
| 1326 | 280.7 | TRNA-SPLICING ENDONUCLEASE SUBUNIT SEN2 (EC 3.1.27.9) (TRNA-INTRON ENDONUCLEASE). | swissprot P16658 | ND |
| 1327 | 280.6 | TRK-1 PROTEIN. | sptrembl O74723 | ND |
| 1328 | 280.4 | HYPOTHETICAL 89.6 KD PROTEIN C3H8.11 IN CHROMOSOME I. | swissnew Q10146 | ND |

TABLE 1-continued

*Fusarium venenatum* ESTs

| Sequence Listing | zscore | Annotation | Database | Functional category |
|---|---|---|---|---|
| 1329 | 280.4 | CHROMOSOME XII COSMID 9672. | sptrembl Q06541 | ND |
| 1330 | 280.4 | HYPOTHETICAL 22.3 KD PROTEIN. | sptrembl O67071 | ND |
| 1331 | 280.4 | HYPOTHETICAL 86.4 KD PROTEIN IN PHO5-VPS15 INTERGENIC REGION. | swissprot P38254 | ND |
| 1332 | 280.4 | FISSION YEAST (FRAGMENT). | sptrembl P78758 | ND |
| 1333 | 279.9 | INOSITOL POLYPHOSPHATE-5-PHOSPHATASE, 75 KDA (INOSITOL POLYPHOSPHATE 5-PHOSPHATASE II). | sptrembl O54996 | ND |
| 1334 | 279.5 | NADH-UBIQUINONE OXIDOREDUCTASE 17.8 KD SUBUNIT PRECURSOR (EC 1.6.5.3) (EC 1.6.99.3) (COMPLEX I-17.8 KD) (CI-17.8 KD). | swissprot P42116 | ND |
| 1335 | 278.8 | PUTATIVE TRANSCRIPTION FACTOR, CCR4-ASSOCIATED FACTOR HOMOLOG. | sptrembl O74856 | ND |
| 1336 | 278.3 | NODULIN PRECURSOR. | sptrembl Q41402 | ND |
| 1337 | 278.2 | CCAAT-BINDING TRANSCRIPTION FACTOR SUBUNIT AAB-1. | sptrembl O13381 | ND |
| 1338 | 278.2 | HYPOTHETICAL 31.4 KD PROTEIN. | sptrembl Q9X7W7 | ND |
| 1339 | 278.1 | HYDROXYQUINOL 1,2-DIOXYGENASE. | sptrembl Q9ZAM3 | ND |
| 1340 | 277.7 | HYPOTHETICAL 61.9 KD PROTEIN. | tremblnew CAB58161 | ND |
| 1341 | 277.7 | HYPOTHETICAL 39.4 KD PROTEIN IN MET1-SIS2 INTERGENIC REGION. | swissprot P36151 | ND |
| 1342 | 277.0 | CELL DIVISION PROTEIN KINASE 7 (EC 2.7.1.-) (CDK-ACTIVATING KINASE) (CAK) (MO15 HOMOLOG). | swissprot P54685 | ND |
| 1343 | 276.5 | CURVED DNA-BINDING PROTEIN (42 KD PROTEIN). | swissprot Q09184 | ND |
| 1344 | 276.2 | COSMID T20B6. | sptrembl O02049 | ND |
| 1345 | 275.7 | 26S PROTEASOME REGULATORY SUBUNIT NIN1 (NUCLEAR INTEGRITY PROTEIN 1). | swissprot P32496 | ND |
| 1346 | 275.5 | HYPOTHETICAL 12.6 KD PROTEIN C1D7.01 IN CHROMOSOME II. | swissprot O14334 | ND |
| 1347 | 275.4 | MAF1 PROTEIN. | swissprot P41910 | ND |
| 1348 | 274.8 | SNM 1-2 TS (FRAGMENT). | sptrembl Q07072 | ND |
| 1349 | 274.5 | NADH-UBIQUINONE OXIDOREDUCTASE 9.5 KD SUBUNIT (EC 1.6.5.3) (EC 1.6.99.3) (COMPLEX I-9.5 KD) (CI-9.5) (UBIQUINONE-BINDING PROTEIN). | swissprot P42117 | ND |
| 1350 | 274.1 | HYPOTHETICAL 16.2 KD PROTEIN C3D6.08C IN CHROMOSOME II. | swissprot P87173 | ND |
| 1351 | 274.1 | PUTATIVE CHOLINE KINASE. | sptrembl O81024 | ND |
| 1352 | 273.5 | CHITINASE PRECURSOR. | sptrembl Q42421 | ND |
| 1353 | 273.4 | PENTALENENE SYNTHASE (EC 4.6.1.5). | swissprot Q55012 | ND |
| 1354 | 273.0 | GLUTAMINYL-PEPTIDE CYCLOTRANSFERASE PRECURSOR (EC 2.3.2.5) (QC) (GLUTAMINYL-TRNA CYCLOTRANSFERASE) (GLUTAMINYL CYCLASE). | swissprot Q28120 | ND |

TABLE 1-continued

*Fusarium venenatum* ESTs

| Sequence Listing | zscore | Annotation | Database | Functional category |
|---|---|---|---|---|
| 1355 | 272.4 | STRONG SIMILARITY TO HUMAN LEUKOTRIENE A-4 HYDROLASE. | sptrembl O94544 | ND |
| 1356 | 272.1 | KIAA0150 PROTEIN (FRAGMENT). | sptrembl Q14163 | ND |
| 1357 | 271.6 | SQUALENE EPOXIDASE (EC 1.14.99.7). | tremblnew AAD10823 | ND |
| 1358 | 271.1 | HYPOTHETICAL 44.9 KD PROTEIN IN URA10-NRC1 INTERGENIC REGION. | swissprot Q03529 | ND |
| 1359 | 270.1 | 30 KD HEAT SHOCK PROTEIN. | swissprot P19752 | ND |
| 1360 | 270.0 | GLYCEROL KINASE (ATP:GLYCEROL 3-PHOSPHOTRANSFERASE) (EC 2.7.1.30). | tremblnew CAB58269 | ND |
| 1361 | 270.0 | HYPOTHETICAL 31.3 KD HOMEOBOX PROTEIN IN PRP20-VPS45 INTERGENIC REGION. | swissprot P53147 | ND |
| 1362 | 270.0 | 5',5'''-P-1,P-4-TETRAPHOSPHATE PHOSPHORYLASE II (EC 2.7.7.53) (DIADENOSINE 5',5'''-P1,P4-TETRAPHOSPHATE PHOSPHORYLASE) (AP-4-A PHOSPHORYLASE) (AP,A PHOSPHORYLASE) (ATP ADENYLYLTRANSFERASE). | swissprot P49348 | ND |
| 1363 | 269.7 | PEROXISOMAL RECEPTOR FOR PTS2-CONTAINING PROTEINS PEX7P. | sptrembl O59894 | ND |
| 1364 | 269.6 | HYPOTHETICAL 27.1 KD PROTEIN C26H5.13C IN CHROMOSOME I. | sptrembl O13994 | ND |
| 1365 | 269.4 | ISOLEUCYL-TRNA SYNTHETASE, CYTOPLASMIC (EC 6.1.1.5) (ISOLEUCINE--TRNA LIGASE) (ILERS). | swissprot P09436 | ND |
| 1366 | 269.3 | Intact natural cutinase of *Fusarium solani pisi*. | geneseqp R06610 | ND |
| 1367 | 268.8 | OXIDOREDUCTASE, ALDO/KETO REDUCTASE FAMILY. | sptrembl Q9X0A1 | ND |
| 1368 | 268.8 | TRANSCRIPTION INITIATION FACTOR TFIID (TATA-BOX FACTOR) (TATA SEQUENCE-BINDING PROTEIN) (TBP). | swissprot Q12731 | ND |
| 1369 | 268.7 | PUTATIVE TRANSCRIPTION FACTOR OF THE GCS1-GLO3-SPS18 FAMILY. | sptrembl O74345 | ND |
| 1370 | 268.6 | HYPOTHETICAL 18.5 KD PROTEIN B0024.12 IN CHROMOSOME V. | sptrembl Q17427 | ND |
| 1371 | 268.3 | 2-OXOGLUTARATE DEHYDROGENASE E1 COMPONENT, MITOCHONDRIAL PRECURSOR (EC 1.2.4.2) (ALPHA-KETOGLUTARATE DEHYDROGENASE). | swissprot P20967 | ND |
| 1372 | 268.1 | HYPOTHETICAL 51.0 KD PROTEIN IN YIP3-TFC5 INTERGENIC REGION. | swissprot P53960 | ND |
| 1373 | 268.1 | OLIGOSACCHARYLTRANSFERASE. | sptrembl O43244 | ND |
| 1374 | 267.2 | SYMBIOSIS-RELATED PROTEIN. | swissprot P87068 | ND |
| 1375 | 266.3 | HYPOTHETICAL 130.1 KD PROTEIN YPR021C. | sptrembl Q12139 | ND |

TABLE 1-continued

*Fusarium venenatum* ESTs

| Sequence Listing | zscore | Annotation | Database | Functional category |
|---|---|---|---|---|
| 1376 | 266.1 | 2-PYRONE-4,6-DICARBOXYLIC ACID HYDROLASE. | sptrembl O87170 | ND |
| 1377 | 265.8 | HYPOTHETICAL 94.9 KD PROTEIN IN MRPL8-NUP82 INTERGENIC REGION. | swissprot P40367 | ND |
| 1378 | 264.9 | HYPOTHETICAL 34.9 KD PROTEIN IN SMI1-PHO81 INTERGENIC REGION. | swissprot P50085 | ND |
| 1379 | 264.5 | PROTEOPHOSPHOGLYCAN (FRAGMENT). | sptrembl Q9Y075 | ND |
| 1380 | 264.5 | HYPOTHETICAL FUNGAL ZN(2)-CYS(6) ZINC-FINGER PROTEIN. | tremblnew CAB57441 | ND |
| 1381 | 264.5 | HOMOSERINE DEHYDROGENASE (EC 1.1.1.3) (HDH). | swissnew P31116 | ND |
| 1382 | 264.4 | CHITIN BIOSYNTHESIS PROTEIN CHS5. | swissprot O74161 | ND |
| 1383 | 264.3 | SCN1 PROTEIN. | swissprot P41890 | ND |
| 1384 | 263.4 | PUTATIVE PRE-MRNA SPLICING FACTOR. | sptrembl Q9ZT71 | ND |
| 1385 | 263.1 | FUSCA PROTEIN FUS6. | swissprot P45432 | ND |
| 1386 | 263.0 | VERSICOLORIN B SYNTHASE. | sptrembl Q12062 | ND |
| 1387 | 263.0 | PUTATIVE SUGAR TRANSPORTER. | sptrembl Q9XIH7 | ND |
| 1388 | 262.8 | CLOCK-CONTROLLED GENE-6 PROTEIN. | sptrembl O74694 | ND |
| 1389 | 262.5 | PUTATIVE EXOCYST COMPLEX COMPONENT. | sptrembl O74846 | ND |
| 1390 | 262.2 | RIBOKINASE. | tremblnew AAF12258 | ND |
| 1391 | 262.2 | HYPOTHETICAL ZINC METALLOPROTEINASE YIL108W (EC 3.4.24.-). | swissprot P40483 | ND |
| 1392 | 262.0 | PUTATIVE MITOCHONDRIAL CARRIER YMR166C. | swissprot Q03829 | ND |
| 1393 | 261.8 | D8035.13P. | sptrembl Q03327 | ND |
| 1394 | 261.7 | EXTENSIN (FRAGMENT). | sptrembl Q41645 | ND |
| 1395 | 261.6 | PUTATIVE ACETYLTRANSFERASE ATS1. | sptrembl P79081 | ND |
| 1396 | 260.8 | QUINIC ACID UTILIZATION ACTIVATOR. | swissprot P10563 | ND |
| 1397 | 260.2 | Whale mat sample AD3059 esterase es4. | geneseqp W23084 | ND |
| 1398 | 260.2 | TRANSCRIPTION FACTOR ATF21. | sptrembl P78962 | ND |
| 1399 | 260.1 | PUTATIVE ATP SYNTHASE J CHAIN, MITOCHONDRIAL (EC 3.6.1.34). | swissprot O13931 | ND |
| 1400 | 258.5 | MSF1 PROTEIN. | swissprot P35200 | ND |
| 1401 | 258.5 | PUTATIVE PHOSPHOMEVALONATE KINASE. | tremblnew CAB52264 | ND |
| 1402 | 258.4 | CYTOCHROME C OXIDASE COPPER CHAPERONE. | swissprot Q12287 | ND |
| 1403 | 258.3 | CUT8 PROTEIN. | swissprot P38937 | ND |
| 1404 | 257.7 | K09H11.1 PROTEIN. | sptrembl O01590 | ND |
| 1405 | 257.6 | NAD-DEPENDENT 4-HYDROXYBUTYRATE DEHYDROGENASE (EC 1.1.1.61) (4HBD). | sptrembl Q59104 | ND |
| 1406 | 257.4 | DIHYDROLIPOAMIDE SUCCINYLTRANSFERASE. | tremblnew AAD47296 | ND |
| 1407 | 257.3 | HYPOTHETICAL 63.9 KD PROTEIN IN IME2-MEF2 INTERGENIC REGION. | swissprot P42948 | ND |
| 1408 | 257.3 | PROBABLE STERIGMATOCYSTIN BIOSYNTHESIS P450 MONOOXYGENASE STCB | swissprot Q12608 | ND |

TABLE 1-continued

*Fusarium venenatum* ESTs

| Sequence Listing | zscore | Annotation | Database | Functional category |
|---|---|---|---|---|
| | | (EC 1.14.-.-) (CYTOCHROME P450 62). | | |
| 1409 | 257.3 | SCP160 PROTEIN (PROTEIN HX). | swissprot P06105 | ND |
| 1410 | 257.1 | 2,4'-DIHYDROXYACETOPHENONE DIOXYGENASE (EC 1.13.11.41) (FRAGMENT). | tremblnew CAB53781 | ND |
| 1411 | 256.7 | LAMINARINASE. | sptrembl O52754 | ND |
| 1412 | 256.6 | PUTATIVE N-TERMINAL ACETYLTRANSFERASE COMPLEX SUBUNIT, ARD1 FAMILY. | tremblnew CAB52427 | ND |
| 1413 | 256.3 | SERINE/THREONINE-PROTEIN KINASE SAT4 (EC 2.7.1.-). | swissprot P25333 | ND |
| 1414 | 256.1 | YGL010W-LIKE PROTEIN. | sptrembl O65074 | ND |
| 1415 | 255.7 | ANNEXIN VII (SYNEXIN). | swissprot Q92125 | ND |
| 1416 | 255.7 | FUN34 PROTEIN. | swissprot P32907 | ND |
| 1417 | 255.1 | F55A11.3 PROTEIN. | sptrembl Q20798 | ND |
| 1418 | 255.0 | PEROXISOMAL 2,4-DIENOYL COA REDUCTASE PX-2,4-DCR#1. | tremblnew AAF14047 | ND |
| 1419 | 254.9 | PUTATIVE MITOCHONDRIAL CARRIER PROTEIN. | sptrembl O94502 | ND |
| 1420 | 254.5 | ZINC CLUSTER TRANSCRIPTION FACTOR FCR1P. | sptrembl O93870 | ND |
| 1421 | 254.3 | PROBABLE COATOMER GAMMA SUBUNIT (GAMMA-COAT PROTEIN) (GAMMA-COP). | swissprot P87140 | ND |
| 1422 | 254.0 | CONSERVED HYPOTHETICAL PROTEIN. | tremblnew CAB57439 | ND |
| 1423 | 253.6 | XYLITOL DEHYDROGENASE (EC 1.1.1.9). | sptrembl O74230 | ND |
| 1424 | 253.3 | SEC63 PROTEIN. | tremblnew CAB46275 | ND |
| 1425 | 253.2 | HYPOTHETICAL OXIDOREDUCTASE IN MRPL44-MTF1 INTERGENIC REGION (EC 1.-.-.-). | swissprot Q05016 | ND |
| 1426 | 252.9 | PROBABLE LYSYL-TRNA SYNTHETASE (EC 6.1.1.6) (LYSINE--TRNA LIGASE) (LYSRS). | swissprot Q22099 | ND |
| 1427 | 252.8 | *Trichoderma reesei* ACEI transcriptional activator protein. | geneseqp W58572 | ND |
| 1428 | 252.6 | HYPOTHETICAL 13.3 KD PROTEIN C23C4.13 IN CHROMOSOME I. | sptrembl O13932 | ND |
| 1429 | 252.6 | MITOCHONDRIAL BETA SEN-DNA: ND4L GENE 5' END, ARG-TRNA GENE COMPLETE SEQUENCE, CO1 GENE, 3' END (FRAGMENT). | tremblnew AAA32005 | ND |
| 1430 | 252.3 | PUTATIVE 50S RIBOSOMAL PROTEIN L14. | sptrembl O94292 | ND |
| 1431 | 252.2 | PUTATIVE PRT1 PROTEIN. | swissprot P12806 | ND |
| 1432 | 251.7 | PYRUVATE DEHYDROGENASE E1 COMPONENT ALPHA SUBUNIT, MITOCHONDRIAL PRECURSOR (EC 1.2.4.1) (PDHE1-A). | swissprot Q10489 | ND |
| 1433 | 251.2 | Metallothionein protein sequence. | geneseqp W69479 | ND |
| 1434 | 250.4 | ACR-2 PROTEIN. | sptrembl P78704 | ND |

TABLE 1-continued

_Fusarium venenatum_ ESTs

| Sequence Listing | zscore | Annotation | Database | Functional category |
|---|---|---|---|---|
| 1435 | 250.0 | PUTATIVE TRANSCRIPTIONAL REGULATOR. | sptrembl O13337 | ND |
| 1436 | 249.9 | DELTA(24)-STEROL C-METHYLTRANSFERASE (EC 2.1.1.41). | swissprot O74198 | ND |
| 1437 | 249.9 | HALOTOLERANCE PROTEIN. | sptrembl O94505 | ND |
| 1438 | 249.7 | 40S RIBOSOMAL PROTEIN S28, MITOCHONDRIAL PRECURSOR. | swissprot P21771 | ND |
| 1439 | 249.6 | HYPOTHETICAL 51.2 KD PROTEIN (PUTATIVE TRANSCRIPTION FACTOR C31F10.01 IN CHROMOSOME II). | sptrembl P87303 | ND |
| 1440 | 249.4 | HISTONE H3 (FRAGMENT). | sptrembl Q42782 | ND |
| 1441 | 249.3 | DYNEIN LIGHT INTERMEDIATE CHAIN 2, CYTOSOLIC (LIC53/55) (LIC-2). | swissprot Q62698 | ND |
| 1442 | 248.4 | ATP SYNTHASE E CHAIN, MITOCHONDRIAL (EC 3.6.1.34). | swissprot P81449 | ND |
| 1443 | 248.3 | _Cladosporium herbarum_ allergen Clah11. | geneseqp R72669 | ND |
| 1444 | 248.1 | METALLOTHIONEIN-LIKE PROTEIN CAP3. | swissprot Q99334 | ND |
| 1445 | 248.1 | DNA BINDING REGULATORY PROTEIN AMDX. | sptrembl P79045 | ND |
| 1446 | 247.9 | HEPATITIS A VIRUS RECEPTOR. | sptrembl O18984 | ND |
| 1447 | 247.6 | 1-PHOSPHATIDYLINOSITOL-4,5-BISPHOSPHATE PHOSPHODIESTERASE 1 (EC 3.1.4.11) (PLC-1) (PHOSPHOLIPASE C-1). | swissnew P40977 | ND |
| 1448 | 246.6 | CYTOCHROME C OXIDASE COPPER CHAPERONE. | swissprot Q12287 | ND |
| 1449 | 246.5 | _Mycobacterium tuberculosis_ 55 kDa protein. | geneseqp W31855 | ND |
| 1450 | 245.9 | SIMILAR TO AAC-RICH MRNA CLONE AAC11 PROTEIN. | sptrembl Q22204 | ND |
| 1451 | 245.5 | AUTOPHAGY PROTEIN APG6. | swissprot Q02948 | ND |
| 1452 | 245.3 | Maize UDP-glucose dehydrogenase Zmudpgdh2. | geneseqp Y06307 | ND |
| 1453 | 244.0 | HYDROXYPROLINE-RICH GLYCOPROTEIN PRECURSOR. | sptrembl Q41719 | ND |
| 1454 | 243.9 | HYPOTHETICAL 36.4 KD PROTEIN IN SMP1-MBA1 INTERGENIC REGION. | swissprot P38298 | ND |
| 1455 | 243.6 | CLOCK-CONTROLLED GENE-6 PROTEIN. | sptrembl O74694 | ND |
| 1456 | 243.4 | HYDROXYPROLINE-RICH GLYCOPROTEIN DZ-HRGP PRECURSOR. | tremblnew CAB62280 | ND |
| 1457 | 243.4 | AMINOPEPTIDASE II (EC 3.4.11.-) (YSCII). | swissprot P32454 | ND |
| 1458 | 243.1 | F17A22.8 PROTEIN. | sptrembl O82238 | ND |
| 1459 | 243.0 | AUTOIMMUNE REGULATOR. | tremblnew AAD46421 | ND |
| 1460 | 242.9 | HYPOTHETICAL 76.3 KD ZINC FINGER PROTEIN IN KTR5-UME3 INTERGENIC REGION. | swissprot P53968 | ND |
| 1461 | 242.8 | ALCOHOL DEHYDROGENASE. | sptrembl O94564 | ND |
| 1462 | 242.8 | PUTATIVE CYTOCHROME C OXIDASE POLYPEPTIDE. | sptrembl O94705 | ND |

TABLE 1-continued

*Fusarium venenatum* ESTs

| Sequence Listing | zscore | Annotation | Database | Functional category |
|---|---|---|---|---|
| 1463 | 242.8 | PROTEIN KINASE CHK1. | tremblnew CAA22551 | ND |
| 1464 | 242.5 | SIMILAR TO GVPD_HALHA. | sptrembl Q05775 | ND |
| 1465 | 241.9 | HYPOTHETICAL 80.9 KD PROTEIN (FRAGMENT). | tremblnew CAB60246 | ND |
| 1466 | 241.8 | HYPOTHETICAL 53.5 KD PROTEIN C1F5.07C IN CHROMOSOME I. | swissprot Q10062 | ND |
| 1467 | 241.7 | FISSION YEAST (FRAGMENT). | sptrembl P78824 | ND |
| 1468 | 241.6 | OPSIN-1. | tremblnew AAD45253 | ND |
| 1469 | 241.3 | HYPOTHETICAL 43.1 KD PROTEIN C16E9.14C IN CHROMOSOME II. | sptrembl O14329 | ND |
| 1470 | 241.0 | POSITIVE SULPHUR TRANSCRIPTION REGULATOR METR. | sptrembl Q9Y8B4 | ND |
| 1471 | 241.0 | PHOSPHATE-REPRESSIBLE PHOSPHATE PERMEASE. | swissprot P15710 | ND |
| 1472 | 240.9 | HYPOTHETICAL TRANSMEMBRANE PROTEIN. | sptrembl O94060 | ND |
| 1473 | 240.9 | HYPOTHETICAL 11.7 KD PROTEIN C6B12.13 IN CHROMOSOME I. | swissprot O14218 | ND |
| 1474 | 240.7 | HYPOTHETICAL 19.6 KD PROTEIN IN PYK1-SNC1 INTERGENIC REGION. | swissprot P28005 | ND |
| 1475 | 240.7 | HYPOTHETICAL 8.7 KD PROTEIN. | sptrembl Q9ZRV8 | ND |
| 1476 | 240.0 | LETHAL(2)TUMOROUS IMAGINAL DISCS. | sptrembl Q27237 | ND |
| 1477 | 239.7 | HYPOTHETICAL 16.6 KD PROTEIN. | sptrembl O07408 | ND |
| 1478 | 239.7 | Human 5' EST secreted protein SEQ ID NO: 470. | geneseqp Y12157 | ND |
| 1479 | 239.4 | HYDROXYPROLINE-RICH GLYCOPROTEIN PRECURSOR. | sptrembl Q41719 | ND |
| 1480 | 239.3 | MITOCHONDRIAL 60S RIBOSOMAL PROTEIN L25 (YML25). | swissprot P23369 | ND |
| 1481 | 239.0 | HYDROXYPROLINE-RICH GLYCOPROTEIN DZ-HRGP PRECURSOR. | tremblnew CAB62280 | ND |
| 1482 | 239.0 | OXIDOREDUCTASE OF SHORT-CHAIN. | sptrembl Q9X9U8 | ND |
| 1483 | 238.7 | PROH (FRAGMENT). | sptrembl O07508 | ND |
| 1484 | 238.7 | Y25C1A.7B PROTEIN. | tremblnew AAD12839 | ND |
| 1485 | 238.3 | CYTOCHROME C OXIDASE ASSEMBLY PROTEIN COX15. | swissprot P40086 | ND |
| 1486 | 238.1 | DNA REPAIR PROTEIN RHP55 (RAD55 HOMOLOG). | swissnew O14129 | ND |
| 1487 | 238.1 | PEPTIDE SYNTHASE. | sptrembl O69825 | ND |
| 1488 | 238.0 | KIAA1286 PROTEIN (FRAGMENT). | tremblnew BAA86600 | ND |
| 1489 | 237.9 | EXTENSIN (FRAGMENT). | sptrembl O49870 | ND |
| 1490 | 237.7 | GLYCOPROTEIN X PRECURSOR. | swissprot P28968 | ND |
| 1491 | 237.6 | GLUTATHIONE S-TRANSFERASE YA (EC 2.5.1.18) (LIGANDIN) (CHAIN 1) (GST CLASS-ALPHA) (CLONES PGTR112 & PGTB38). | swissprot P04903 | ND |
| 1492 | 236.4 | HYPOTHETICAL 29.0 KD PROTEIN. | sptrembl Q9ZD15 | ND |
| 1493 | 235.9 | 2,3-BISPHOSPHOGLYCERATE-INDEPENDENT | sptrembl Q9X519 | ND |

TABLE 1-continued

*Fusarium venenatum* ESTs

| Sequence Listing | zscore | Annotation | Database | Functional category |
|---|---|---|---|---|
| | | PHOSPHOGLYCERATE MUTASE. | | |
| 1494 | 235.3 | LEU/VAL/ILE AMINO-ACID PERMEASE (BRANCHED-CHAIN AMINO-ACID PERMEASE 2). | swissprot P38084 | ND |
| 1495 | 235.2 | INTEGRAL MEMBRANE PROTEIN. | sptrembl Q9Y785 | ND |
| 1496 | 235.2 | Polylysine peptide NBC32. | geneseqp W65939 | ND |
| 1497 | 235.2 | 40S RIBOSOMAL PROTEIN S20. | swissprot O74893 | ND |
| 1498 | 235.1 | HYPOTHETICAL 45.8 KD PROTEIN C30D10.03C IN CHROMOSOME II. | sptrembl O14349 | ND |
| 1499 | 235.1 | HYPOTHETICAL 29.3 KD PROTEIN. | sptrembl O74943 | ND |
| 1500 | 234.6 | HEROIN ESTERASE. | sptrembl O06441 | ND |
| 1501 | 234.5 | HYPOTHETICAL FUNGAL ZN(2)-CYS(6) ZINC-FINGER PROTEIN. | tremblnew CAB57441 | ND |
| 1502 | 234.5 | PUTATIVE TRANSCRIPTIONAL ACTIVATOR. | sptrembl O59830 | ND |
| 1503 | 234.2 | 3',5'-CYCLIC-NUCLEOTIDE PHOSPHODIESTERASE (EC 3.1.4.17) (PDEASE). | swissprot P32782 | ND |
| 1504 | 234.0 | QUINATE PERMEASE (QUINATE TRANSPORTER). | swissprot P11636 | ND |
| 1505 | 233.9 | INFECTION STRUCTURE SPECIFIC PROTEIN. | sptrembl Q9Y779 | ND |
| 1506 | 233.7 | CHROMOSOME XII COSMID 9638. | sptrembl Q06479 | ND |
| 1507 | 233.0 | QUINIC ACID UTILIZATION ACTIVATOR. | swissprot P10563 | ND |
| 1508 | 233.0 | HYPOTHETICAL 74.0 KD PROTEIN. | sptrembl O65709 | ND |
| 1509 | 232.7 | 26S PROTEASOME REGULATORY SUBUNIT S5A. | sptrembl O81340 | ND |
| 1510 | 232.5 | *Mycobacterium* species protein sequence 50B. | geneseqp Y04998 | ND |
| 1511 | 232.2 | A-AGGLUTININ ATTACHMENT SUBUNIT PRECURSOR. | swissprot P32323 | ND |
| 1512 | 232.1 | CYTOCHROME B2 PRECURSOR (EC 1.1.2.3)(L-LACTATE DEHYDROGENASE (CYTOCHROME))(L-LACTATE FERRICYTOCHROME C OXIDOREDUCTASE) (L-LCR). | swissprot P09437 | ND |
| 1513 | 231.9 | ACR-2 PROTEIN. | sptrembl P78704 | ND |
| 1514 | 231.5 | MSS51 PROTEIN. | swissprot P32335 | ND |
| 1515 | 231.4 | Yeast proteasome YC1 subunit. | geneseqp R22996 | ND |
| 1516 | 231.3 | ISOLEUCYL-TRNA SYNTHETASE. | tremblnew CAB52155 | ND |
| 1517 | 231.1 | CELL WALL-PLASMA MEMBRANE LINKER PROTEIN. | sptrembl Q39353 | ND |
| 1518 | 231.0 | PROLINE-RICH PROTEOGLYCAN PRPG2. | sptrembl Q07611 | ND |
| 1519 | 231.0 | *Fusarium oxysporum* DSM 2672 endoglucanase. | geneseqp R25527 | ND |
| 1520 | 231.0 | SARCOPLASMIC RETICULUM HISTIDINE-RICH CALCIUM-BINDING PROTEIN PRECURSOR (HCP). | swissprot P16230 | ND |
| 1521 | 230.8 | HYPOTHETICAL 28.3 KD PROTEIN (FRAGMENT). | tremblnew CAB55927 | ND |

TABLE 1-continued

*Fusarium venenatum* ESTs

| Sequence Listing | zscore | Annotation | Database | Functional category |
|---|---|---|---|---|
| 1522 | 230.4 | HYPOTHETICAL 80.2 KD PROTEIN. | sptrembl O74423 | ND |
| 1523 | 230.1 | BCDNA.LD28419. | tremblnew AAD55441 | ND |
| 1524 | 229.9 | TRANSLOCATION ELONGATION FACTOR. | sptrembl O74945 | ND |
| 1525 | 229.9 | HYPOTHETICAL 93.5 KD PROTEIN. | sptrembl O59744 | ND |
| 1526 | 229.7 | HYPOTHETICAL 29.3 KD PROTEIN (ORF92). | swissprot O10341 | ND |
| 1527 | 229.7 | RIBOSOMAL PROTEIN L41. | sptrembl Q9Y710 | ND |
| 1528 | 229.7 | HYPOTHETICAL NUCLEAR PROTEIN (FRAGMENT). | tremblnew BAA87112 | ND |
| 1529 | 229.4 | NEUROLYSIN PRECURSOR (EC 3.4.24.16) (NEUROTENSIN ENDOPEPTIDASE) (MITOCHONDRIAL OLIGOPEPTIDASE M) (MICROSOMAL ENDOPEPTIDASE) (MEP) (SOLUBLE ANGIOTENSIN-BINDING PROTEIN) (SABP) (ENDOPEPTIDASE 24.16). | swissnew Q02038 | ND |
| 1530 | 229.3 | TREHALASE PRECURSOR (EC 3.2.1.28) (ALPHA,ALPHA-TREHALASE) (ALPHA,ALPHA-TREHALOSE GLUCOHYDROLASE). | swissprot O43280 | ND |
| 1531 | 229.1 | ASPARTIC PROTEINASE MKC7 PRECURSOR (EC 3.4.23.-). | swissprot P53379 | ND |
| 1532 | 229.1 | PHOSPHOLIPASE A2 ACTIVATING PROTEIN. | sptrembl Q9Y5L1 | ND |
| 1533 | 229.0 | WUGSC:H_GS098E02.1 PROTEIN (FRAGMENT). | tremblnew AAF19251 | ND |
| 1534 | 228.9 | T6C23.12 PROTEIN. | tremblnew AAF22917 | ND |
| 1535 | 228.4 | *Malassezia* fungus MF-7 antigenic protein. | geneseqp W29774 | ND |
| 1536 | 228.3 | MNN4 PROTEIN. | swissprot P36044 | ND |
| 1537 | 227.9 | HYPOTHETICAL TRANSMEMBRANE PROTEIN. | sptrembl O94060 | ND |
| 1538 | 227.7 | SYNTAXIN BINDING PROTEIN 1, SEC1 FAMILY SECRETOR Y PROTEIN. | sptrembl O94590 | ND |
| 1539 | 227.6 | NUCLEAR PORE COMPLEX GLYCOPROTEIN P62. | sptrembl O57397 | ND |
| 1540 | 226.9 | HUMAN 4F5S HOMOLOG. | tremblnew CAB59614 | ND |
| 1541 | 226.5 | CHROMOSOME XVI READING FRAME ORF YPL264C. | sptrembl Q08980 | ND |
| 1542 | 226.4 | PALMITOYL-PROTEIN THIOESTERASE PRECURSOR. | sptrembl O59747 | ND |
| 1543 | 226.0 | PUTATIVE MEMBRANE GLYCOPROTEIN. | sptrembl Q9Y7Y6 | ND |
| 1544 | 225.3 | Human secreted protein encoded by 5' EST SEQ ID NO: 222. | geneseqp Y13208 | ND |
| 1545 | 225.1 | VELVET A. | sptrembl O74625 | ND |
| 1546 | 225.0 | INTEGRAL MEMBRANE PROTEIN. | sptrembl Q9Y785 | ND |
| 1547 | 224.9 | Protease biosynthetic protein. | geneseqp P70581 | ND |
| 1548 | 224.9 | ARGININE METABOLISM REGULATION PROTEIN II. | swissprot P05085 | ND |
| 1549 | 224.6 | BCDNA.GH06451. | tremblnew AAD55420 | ND |
| 1550 | 224.6 | ORF YBR199W (FRAGMENT). | sptrembl P89506 | ND |

TABLE 1-continued

*Fusarium venenatum* ESTs

| Sequence Listing | zscore | Annotation | Database | Functional category |
|---|---|---|---|---|
| 1551 | 224.5 | PUTATIVE MITOCHONDRIAL 40S RIBOSOMAL PROTEIN YMR188C. | swissprot Q03246 | ND |
| 1552 | 223.8 | MANNOSE-SPECIFIC LECTIN PRECURSOR (FRAGMENT). | sptrembl Q38726 | ND |
| 1553 | 223.3 | ORF2 of Enod2b genomic clone. | geneseqp R04119 | ND |
| 1554 | 223.3 | COSMID C27A2. | sptrembl Q18238 | ND |
| 1555 | 223.2 | IKI3 PROTEIN. | swissprot Q06706 | ND |
| 1556 | 223.0 | ALPHA-L-ARABINOFURANOSIDASE. | sptrembl Q9WYB7 | ND |
| 1557 | 222.9 | PUTATIVE ENOYL-COA HYDRATASE. | sptrembl O53211 | ND |
| 1558 | 222.8 | SUGAR TRANSPORTER STL1. | swissprot P39932 | ND |
| 1559 | 222.0 | T4B21.2 PROTEIN. | sptrembl Q9ZS88 | ND |
| 1560 | 221.8 | PUTATIVE PROTEOLIPID PROTEIN C2C4.13. | sptrembl O14046 | ND |
| 1561 | 221.6 | PEROXISOMAL MEMBRANE PROTEIN PMP30B (PMP32) (PEROXIN-11B). | swissprot Q00317 | ND |
| 1562 | 221.1 | HYPOTHETICAL 37.7 KD PROTEIN T09A5.8 IN CHROMOSOME III. | swissprot P45968 | ND |
| 1563 | 221.0 | DJ1042K10.5 (NOVEL PROTEIN) (FRAGMENT). | sptrembl O95516 | ND |
| 1564 | 220.9 | CLATHRIN LIGHT CHAIN. | tremblnew CAB42369 | ND |
| 1565 | 220.8 | EXTENSIN PRECURSOR (CELL WALL HYDROXYPROLINE-RICH GLYCOPROTEIN). | swissprot P13983 | ND |
| 1566 | 220.7 | NPGA PROTEIN. | tremblnew AAF12814 | ND |
| 1567 | 220.5 | MUCIN (FRAGMENT). | sptrembl Q28501 | ND |
| 1568 | 220.5 | PIUS. | tremblnew BAA87611 | ND |
| 1569 | 220.4 | CHROMOSOME XV READING FRAME ORF YOR084W. | sptrembl Q12405 | ND |
| 1570 | 219.9 | CYSTEINE-RICH PROTEIN (FRAGMENT). | sptrembl Q16861 | ND |
| 1571 | 219.6 | HYPOTHETICAL 74.7 KD PROTEIN. | sptrembl O94033 | ND |
| 1572 | 219.4 | HEAT SHOCK PROTEIN 70 HOMOLOG C57A7.12. | sptrembl P87142 | ND |
| 1573 | 219.2 | EMM18.1. | sptrembl Q54703 | ND |
| 1574 | 218.8 | HYPOTHETICAL 26.8 KD PROTEIN IN HYR1 3'REGION. | swissprot P40582 | ND |
| 1575 | 218.0 | HYPOTHETICAL 23.2 KD PROTEIN IN SKM1-TRF4 INTERGENIC REGION. | swissprot Q12322 | ND |
| 1576 | 218.0 | SIMILAR TO ALPHA-SNAP PROTEIN. | sptrembl Q18921 | ND |
| 1577 | 218.0 | CHROMOSOME IV READING FRAME ORF YDL237W. | sptrembl Q07716 | ND |
| 1578 | 217.8 | HYPOTHETICAL PROTEIN (FRAGMENT). | sptrembl Q12742 | ND |
| 1579 | 217.5 | CHROMOSOME XV READING FRAME ORF YOL129W. | sptrembl Q12016 | ND |
| 1580 | 217.4 | POTENTIAL MEMBRANE PROTEIN. | sptrembl O94006 | ND |
| 1581 | 217.3 | CHROMOSOME IV READING FRAME ORF YDL144C. | sptrembl Q07589 | ND |
| 1582 | 217.2 | LIGAND OF NUMB-PROTEIN X (LNXP80). | sptrembl O70263 | ND |
| 1583 | 217.0 | PIG-B. | sptrembl Q92521 | ND |

TABLE 1-continued

*Fusarium venenatum* ESTs

| Sequence Listing | zscore | Annotation | Database | Functional category |
|---|---|---|---|---|
| 1584 | 216.9 | PHOSPHATIDYLSERINE SYNTHASE. | sptrembl Q9ZQW1 | ND |
| 1585 | 216.9 | PUTATIVE CHOLINE KINASE. | sptrembl O81024 | ND |
| 1586 | 216.5 | UV-DAMAGED DNA-BINDING PROTEIN-LIKE. | sptrembl O49552 | ND |
| 1587 | 216.1 | HYDROXYPROLINE-RICH GLYCOPROTEIN DZ-HRGP PRECURSOR. | tremblnew CAB62280 | ND |
| 1588 | 216.0 | CONSERVED HYPOTHETICAL PROTEIN. | sptrembl Q9Y7J3 | ND |
| 1589 | 215.2 | ANTIGEN 2. | sptrembl Q12295 | ND |
| 1590 | 215.0 | PROTEOPHOSPHOGLYCAN PRECURSOR (FRAGMENT). | sptrembl Q9Y076 | ND |
| 1591 | 214.4 | LET-756 PROTEIN. | sptrembl O76831 | ND |
| 1592 | 214.1 | REPRESSIBLE ALKALINE PHOSPHATASE PRECURSOR (EC 3.1.3.1). | swissprot P11491 | ND |
| 1593 | 214.0 | BACITRACIN SYNTHETASE 2 (BA2) (FRAGMENT). | tremblnew BAA36755 | ND |
| 1594 | 213.9 | IMMUNOREACTIVE HEAT SHOCK PROTEIN DNAJ. | sptrembl Q9XCA6 | ND |
| 1595 | 213.9 | HYPOTHETICAL 107.1 KD PROTEIN C24H6.11C IN CHROMOSOME I. | swissprot Q09764 | ND |
| 1596 | 213.7 | HYPOTHETICAL 34.2 KD PROTEIN C31F10.07 IN CHROMOSOME II. | sptrembl P87308 | ND |
| 1597 | 213.4 | HYPOTHETICAL 12.8 KD PROTEIN IN ARO9-SPS100 INTERGENIC REGION PRECURSOR. | swissprot P38841 | ND |
| 1598 | 213.1 | HYPOTHETICAL PROTEIN C3C7.15C IN CHROMOSOME I (FRAGMENT). | sptrembl O14138 | ND |
| 1599 | 213.1 | HARD SURFACE INDUCED PROTEIN 3. | tremblnew AAF00024 | ND |
| 1600 | 213.0 | S18 CHORION PROTEIN. | sptrembl O62009 | ND |
| 1601 | 212.8 | HYPOTHETICAL SH3-CONTAINING PROTEIN. | tremblnew CAB52037 | ND |
| 1602 | 212.4 | ANKYRIN. | sptrembl Q24241 | ND |
| 1603 | 212.0 | PEROXISOMAL MEMBRANE PROTEIN PER9 (PEROXIN-3). | swissprot Q01497 | ND |
| 1604 | 212.0 | HYPOTHETICAL 26.3 KD PROTEIN IN OYE2-GND1 INTERGENIC REGION. | swissprot P38869 | ND |
| 1605 | 211.2 | F24J5.8 PROTEIN. | tremblnew AAD49974 | ND |
| 1606 | 211.1 | HYDROXYPROLINE-RICH GLYCOPROTEIN. | sptrembl Q42366 | ND |
| 1607 | 210.5 | HYPOTHETICAL RHO1 GDP-GTP EXCHANGE PROTEIN. | sptrembl Q9Y7U5 | ND |
| 1608 | 209.8 | PRB1M PROTEIN (FRAGMENT). | sptrembl Q16038 | ND |
| 1609 | 209.6 | CONSERVED HYPOTHETICAL PROTEIN. | sptrembl Q9Y7P1 | ND |
| 1610 | 209.4 | HYPOTHETICAL 30.3 KD PROTEIN. | sptrembl Q9ZC03 | ND |
| 1611 | 209.1 | NONF. | sptrembl Q9XDF2 | ND |
| 1612 | 208.9 | CAP22 PROTEIN. | sptrembl O94177 | ND |
| 1613 | 208.8 | ORIGIN RECOGNITION COMPLEX SUBUNIT 1. | swissprot O74270 | ND |
| 1614 | 208.7 | PUTATIVE SECRETED PROLINE-RICH PROTEIN. | tremblnew CAB63180 | ND |
| 1615 | 208.5 | NON-CLASSICAL EXPORT PROTEIN NCE2. | swissprot Q12207 | ND |
| 1616 | 208.2 | HYPOTHETICAL 36.8 KD PROTEIN. | sptrembl P71847 | ND |
| 1617 | 208.1 | LIGF PROTEIN. | swissprot P30347 | ND |
| 1618 | 208.0 | EUKARYOTIC | swissprot P38431 | ND |

TABLE 1-continued

Fusarium venenatum ESTs

| Sequence Listing | zscore | Annotation | Database | Functional category |
|---|---|---|---|---|
| | | TRANSLATION INITIATION FACTOR 5 (EIF-5). | | |
| 1619 | 207.2 | PUTATIVE FRUCTOSYL AMINO ACID OXIDASE. | tremblnew CAB59618 | ND |
| 1620 | 207.0 | RNA POLYMERASE II SUBUNIT RPB7 (FRAGMENT). | tremblnew CAA20136 | ND |
| 1621 | 206.7 | KYNURENINASE (EC 3.7.1.3) (L-KYNURENINE HYDROLASE). | swissprot Q16719 | ND |
| 1622 | 206.3 | HYPOTHETICAL 25.4 KD PROTEIN IN SAP185-BCK1 INTERGENIC REGION. | swissprot P40858 | ND |
| 1623 | 206.2 | CPC3 PROTEIN. | sptrembl O74297 | ND |
| 1624 | 205.7 | SEVERIN KINASE. | sptrembl O61122 | ND |
| 1625 | 205.7 | HYPOTHETICAL 42.2 KD PROTEIN. | tremblnew CAB62412 | ND |
| 1626 | 205.6 | HYPOTHETICAL PROTEIN HI0828. | swissprot P44887 | ND |
| 1627 | 205.2 | DEVELOPMENTAL REGULATORY PROTEIN. | sptrembl Q00760 | ND |
| 1628 | 205.1 | PUTATIVE GAMMA-BUTYROBETAINE,2-OXOGLUTARATE DIOXYGENASE (EC 1.14.11.1) (GAMMA-BUTYROBETAINE HYDROXYLASE) (GAMMA-BBH). | swissprot Q19000 | ND |
| 1629 | 204.9 | Human epidermoid carcinoma cell line KB clone HP10301 protein. | geneseqp W64553 | ND |
| 1630 | 204.9 | PROTEIN-TYROSINE PHOSPHATASE 99A PRECURSOR (EC 3.1.3.48) (RECEPTOR-LINKED PROTEIN-TYROSINE PHOSPHATASE 99A). | swissprot P35832 | ND |
| 1631 | 204.3 | (VSP-3) PRECURSOR. | sptrembl Q39620 | ND |
| 1632 | 204.3 | HYPOTHETICAL 26.2 KD PROTEIN IN SPC42-PTM1 INTERGENIC REGION. | swissprot P36095 | ND |
| 1633 | 204.3 | PUTATIVE TRANSPORTER C11D3.18C. | swissprot Q10097 | ND |
| 1634 | 204.2 | STERIGMATOCYSTIN BIOSYNTHESIS REGULATORY PROTEIN. | swissprot P52957 | ND |
| 1635 | 204.1 | EXTENSIN PRECURSOR. | sptrembl Q40768 | ND |
| 1636 | 204.0 | HYPOTHETICAL 29.9 KD PROTEIN IN APL6-MES1 INTERGENIC REGION. | swissprot P53323 | ND |
| 1637 | 204.0 | PROLINE RICH PROTEIN PRECURSOR. | sptrembl Q43558 | ND |
| 1638 | 204.0 | 2-OXOGLUTARATE DEHYDROGENASE E1 COMPONENT, MITOCHONDRIAL PRECURSOR (EC 1.2.4.2) (ALPHA-KETOGLUTARATE DEHYDROGENASE). | swissprot P20967 | ND |
| 1639 | 203.4 | An enzyme with sugar transferase activity. | geneseqp W88044 | ND |
| 1640 | 203.4 | AFLR REGULATORY PROTEIN. | sptrembl O94141 | ND |
| 1641 | 202.9 | HYPOTHETICAL 28.8 KD PROTEIN IN PSD1-SKO1 INTERGENIC REGION. | swissprot P53889 | ND |
| 1642 | 202.3 | Mycobacterium species protein sequence 50B. | geneseqp Y04998 | ND |
| 1643 | 202.2 | HYPOTHETICAL 28.2 KD PROTEIN IN GLNQ-ANSR INTERGENIC REGION. | swissprot P54549 | ND |
| 1644 | 202.2 | F56H9.1 PROTEIN. | sptrembl Q20908 | ND |
| 1645 | 202.1 | TRFA. | sptrembl O77033 | ND |

TABLE 1-continued

*Fusarium venenatum* ESTs

| Sequence Listing | zscore | Annotation | Database | Functional category |
|---|---|---|---|---|
| 1646 | 202.1 | HYPOTHETICAL PROTEIN (FRAGMENT). | tremblnew BAA87194 | ND |
| 1647 | 201.9 | Human phosphodiesterase type IV D. | geneseqp R99743 | ND |
| 1648 | 201.0 | Prod. of the AccI fragment of SHR3 gene. | geneseqp R34708 | ND |
| 1649 | 200.7 | HYPOTHETICAL 33.4 KD PROTEIN C3A12.09C IN CHROMOSOME I. | sptrembl P87125 | ND |
| 1650 | 200.6 | UL6 PROTEIN (FRAGMENT). | sptrembl Q65580 | ND |
| 1651 | 200.4 | PUTATIVE 109.8 KD TRANSCRIPTIONAL REGULATORY PROTEIN IN SOK2-FMS1 INTERGENIC REGION. | swissprot P50104 | ND |
| 1652 | 200.4 | HYPOTHETICAL 22.4 KD PROTEIN IN GCN20-CMK1 INTERGENIC REGION PRECURSOR. | swissprot P43595 | ND |
| 1653 | 199.7 | HYDROXYPROLINE-RICH GLYCOPROTEIN DZ-HRGP PRECURSOR. | tremblnew CAB62280 | ND |
| 1654 | 199.6 | EXTENSIN (FRAGMENT). | sptrembl O49870 | ND |
| 1655 | 199.4 | *Mycobacterium* species protein sequence 50B. | geneseqp Y04998 | ND |
| 1656 | 199.1 | CONSERVED HYPOTHETICAL PROTEIN. | tremblnew CAB52741 | ND |
| 1657 | 198.9 | SALIVARY PROLINE-RICH PROTEIN RP4 PRECURSOR. | sptrembl Q04117 | ND |
| 1658 | 198.9 | HYPOTHETICAL 26.5 KD PROTEIN C15A10.05C IN CHROMOSOME I. | swissprot O13725 | ND |
| 1659 | 198.9 | 40S RIBOSOMAL PROTEIN S8 (S14) (YS9) (RP19). | swissprot P05754 | ND |
| 1660 | 198.8 | ZINC FINGER PROTEIN. | sptrembl O59811 | ND |
| 1661 | 198.4 | E2F1-INDUCIBLE PROTEIN (FRAGMENT). | tremblnew AAD53115 | ND |
| 1662 | 198.2 | *Trichoderma reesei* ACEII transcriptional activator protein. | geneseqp W58573 | ND |
| 1663 | 198.1 | HYPOTHETICAL PROTEIN (FRAGMENT). | tremblnew BAA87194 | ND |
| 1664 | 197.9 | Metal-regulated transporter polypeptide ZIP3. | geneseqp W41165 | ND |
| 1665 | 197.8 | HYPOTHETICAL 26.8 KD PROTEIN. | sptrembl O65515 | ND |
| 1666 | 197.6 | F56A11.6 PROTEIN. | sptrembl O44519 | ND |
| 1667 | 197.5 | 5'-AMP-ACTIVATED PROTEIN KINASE. | tremblnew CAA22634 | ND |
| 1668 | 197.5 | GUANINE NUCLEOTIDE-BINDING PROTEIN GAMMA SUBUNIT. | swissprot P18852 | ND |
| 1669 | 197.4 | HYPOTHETICAL 67.0 KD PROTEIN (FRAGMENT). | sptrembl O94367 | ND |
| 1670 | 197.4 | RHODOPSIN (FRAGMENT). | tremblnew AAC27436 | ND |
| 1671 | 197.2 | HYDROXYPROLINE-RICH GLYCOPROTEIN. | sptrembl Q42366 | ND |
| 1672 | 197.1 | OXOGLUTARATE MALATE TRANSLOCATOR. | sptrembl Q43649 | ND |
| 1673 | 196.9 | PISTIL-SPECIFIC EXTENSIN-LIKE PROTEIN (FRAGMENT). | sptrembl Q40552 | ND |
| 1674 | 196.7 | SIMILARITY TO THE CDC2/CDX SUBFAMILY OF SER/THR PROTEIN KINASES. | sptrembl O01775 | ND |
| 1675 | 196.5 | CELL WALL-PLASMA MEMBRANE LINKER PROTEIN. | sptrembl Q39353 | ND |
| 1676 | 195.9 | HYPOTHETICAL 181.5 KD PROTEIN C23D3.13C IN CHROMOSOME I. | swissprot Q09853 | ND |

TABLE 1-continued

*Fusarium venenatum* ESTs

| Sequence Listing | zscore | Annotation | Database | Functional category |
|---|---|---|---|---|
| 1677 | 195.6 | SID478P. | tremblnew BAA84693 | ND |
| 1678 | 195.1 | HYPOTHETICAL 32.9 KD PROTEIN. | sptrembl Q9XA40 | ND |
| 1679 | 194.5 | 3' END (FRAGMENT). | sptrembl Q26893 | ND |
| 1680 | 194.2 | HYDROXYPROLINE-RICH GLYCOPROTEIN DZ-HRGP PRECURSOR. | tremblnew CAB62280 | ND |
| 1681 | 194.2 | SIMILAR TO LONG TANDEM REPEAT REGION OF SIALIDASE. | sptrembl Q23635 | ND |
| 1682 | 194.1 | PHOSPHOLIPID METHYLTRANSFERASE. | sptrembl P87300 | ND |
| 1683 | 194.0 | DNA-DIRECTED RNA POLYMERASE I 13.7 KD POLYPEPTIDE (EC 2.7.7.6) (A12.2). | swissprot P32529 | ND |
| 1684 | 193.8 | Mouse acylcoenzyme A:cholesterol acyltransferase II. | geneseqp W43408 | ND |
| 1685 | 193.4 | Sugar beet chitinase 1. | geneseqp R28150 | ND |
| 1686 | 193.3 | PROLINE-RICH CELL WALL PROTEIN. | sptrembl Q39789 | ND |
| 1687 | 193.2 | SERINE-RICH PROTEIN. | sptrembl O94317 | ND |
| 1688 | 193.0 | *Trichoderma reesei* ACEI transcriptional activator protein. | geneseqp W58572 | ND |
| 1689 | 192.9 | HYPOTHETICAL 96.1 KD PROTEIN IN RIM1-RPS14A INTERGENIC REGION. | swissprot P25623 | ND |
| 1690 | 192.5 | FIBRILLARIN. | swissprot Q22053 | ND |
| 1691 | 192.1 | PUTATIVE COMPONENT OF CCAAT BINDING COMPLEX HAPC. | sptrembl Q00735 | ND |
| 1692 | 192.1 | SALIVARY GLUE PROTEIN SGS-3 PRECURSOR. | swissprot P02840 | ND |
| 1693 | 192.0 | PFC0175W PROTEIN. | sptrembl O97226 | ND |
| 1694 | 191.7 | SERINE-RICH PROTEIN. | sptrembl O94317 | ND |
| 1695 | 191.6 | DNA-DIRECTED RNA POLYMERASE II LARGEST SUBUNIT (EC 2.7.7.6) (FRAGMENT). | swissprot P35084 | ND |
| 1696 | 191.5 | LEE1P. | sptrembl Q06701 | ND |
| 1697 | 191.0 | HYPOTHETICAL NUCLEAR PROTEIN (FRAGMENT). | tremblnew BAA87304 | ND |
| 1698 | 191.0 | VACUOLAR PROTEASE A PRECURSOR (EC 3.4.23.-). | swissprot Q01294 | ND |
| 1699 | 190.9 | PUTATIVE 109.8 KD TRANSCRIPTIONAL REGULATORY PROTEIN IN SOK2-FMS1 INTERGENIC REGION. | swissprot P50104 | ND |
| 1700 | 190.8 | INTEGRAL PEROXISOMAL MEMBRANE PROTEIN. | tremblnew AAF22254 | ND |
| 1701 | 190.4 | ORF 171. | sptrembl Q45944 | ND |
| 1702 | 190.4 | Human regulator of G-protein signalling 1 (RGPS-1). | geneseqp W30560 | ND |
| 1703 | 190.3 | HYPOTHETICAL 63.7 KD PROTEIN C16E9.02C IN CHROMOSOME II. | sptrembl O14319 | ND |
| 1704 | 190.3 | Colon cancer associated antigen precursor sequence. | geneseqp Y07109 | ND |
| 1705 | 190.2 | EXTENSIN (FRAGMENT). | sptrembl Q41645 | ND |
| 1706 | 190.2 | MYELIN GENE EXPRESSION FACTOR 2. | sptrembl Q9Y655 | ND |
| 1707 | 190.2 | HYPOTHETICAL 63.1 KD PROTEIN. | sptrembl O43071 | ND |
| 1708 | 189.6 | ADENOSYLHOMOCYSTEIN ASE (EC 3.3.1.1) (S-ADENOSYL-L-HOMOCYSTEINE HYDROLASE) (ADOHCYASE). | swissprot P10819 | ND |
| 1709 | 189.6 | *Mycobacterium* tuberculosis specific DNA-encoded polypeptide. | geneseqp Y31745 | ND |

TABLE 1-continued

*Fusarium venenatum* ESTs

| Sequence Listing | zscore | Annotation | Database | Functional category |
|---|---|---|---|---|
| 1710 | 189.6 | HYPOTHETICAL 35.4 KD PROTEIN. | sptrembl P93845 | ND |
| 1711 | 189.3 | FLGA insert stabilising polypeptide. | geneseqp W79128 | ND |
| 1712 | 189.3 | 60S RIBOSOMAL PROTEIN L7, MITOCHONDRIAL PRECURSOR (YML7). | swissprot P36519 | ND |
| 1713 | 189.1 | HYPOTHETICAL 33.0 KD PROTEIN IN PROB-PROA INTERGENIC REGION. | swissprot P45637 | ND |
| 1714 | 189.0 | HYPOTHETICAL 33.5 KD PROTEIN IN SEC53-ACT1 INTERGENIC REGION. | swissprot P43558 | ND |
| 1715 | 188.7 | HYPOTHETICAL 70.9 KD PROTEIN IN CBP2 5'REGION. | swissprot P38731 | ND |
| 1716 | 188.6 | TRANSCRIPTION FACTOR DMAX. | sptrembl P91664 | ND |
| 1717 | 188.6 | WAIT-1. | tremblnew AAC68675 | ND |
| 1718 | 188.6 | EXTENSIN-LIKE PROTEIN. | sptrembl O81765 | ND |
| 1719 | 188.3 | PUTATIVE ZINC FINGER PROTEIN. | sptrembl O74256 | ND |
| 1720 | 188.2 | HYPOTHETICAL 18.7 KD PROTEIN IN HMS1-ABF2 INTERGENIC REGION. | swissprot Q04767 | ND |
| 1721 | 187.8 | D-pantolactone hydrolase from *Fusarium oxysporum*. | geneseqp W21857 | ND |
| 1722 | 187.8 | SALIVARY PROLINE-RICH PROTEIN RP4 PRECURSOR. | sptrembl Q04117 | ND |
| 1723 | 187.6 | HYPOTHETICAL 29.7 KD PROTEIN IN RPLI-CPDB INTERGENIC REGION (F286). | swissprot P39315 | ND |
| 1724 | 187.6 | HEPATITIS A VIRUS CELLULAR RECEPTOR 1 LONG FORM (HEPATITIS A VIRUS CELLULAR RECEPTOR 1 SHORT FORM). | sptrembl O46598 | ND |
| 1725 | 187.2 | GLUTAMINE REPEAT PROTEIN 1. | sptrembl Q61118 | ND |
| 1726 | 187.0 | GLUE PROTEIN. | sptrembl Q27423 | ND |
| 1727 | 186.9 | HYPOTHETICAL 11.6 KD PROTEIN. | sptrembl O59764 | ND |
| 1728 | 186.9 | TAMA. | sptrembl Q00741 | ND |
| 1729 | 186.8 | HOL1 PROTEIN. | swissprot P53389 | ND |
| 1730 | 186.3 | PPRB GENE. | sptrembl Q52088 | ND |
| 1731 | 186.2 | YUP8H12R.22 PROTEIN. | sptrembl O64535 | ND |
| 1732 | 186.0 | HYPOTHETICAL 25.9 KD PROTEIN C16A3.04 IN CHROMOSOME II. | sptrembl O42911 | ND |
| 1733 | 185.7 | HAVCR-1 PROTEIN PRECURSOR. | sptrembl Q95144 | ND |
| 1734 | 185.7 | Fragmented human NF-L gene +2 frameshift mutant product. | geneseqp W18658 | ND |
| 1735 | 185.6 | 64AA LONG HYPOTHETICAL PROTEIN. | sptrembl Q9YAL3 | ND |
| 1736 | 185.5 | CUTINASE TRANSCRIPTION FACTOR 1 ALPHA. | swissprot P52958 | ND |
| 1737 | 185.5 | MICROFILARIAL SHEATH PROTEIN SHP3 PRECURSOR. | sptrembl Q17260 | ND |
| 1738 | 185.4 | MEROZOITE SURFACE PROTEIN CMZ-8 (FRAGMENT). | swissprot P09125 | ND |
| 1739 | 185.4 | HYPOTHETICAL 42.9 KD PROTEIN. | sptrembl O74814 | ND |
| 1740 | 185.3 | SUPEROXIDE-GENERATING NADPH OXIDASE FLAVOCYTOCHROME. | sptrembl Q9XYS3 | ND |
| 1741 | 185.2 | NNF1 PROTEIN. | swissprot P47149 | ND |

TABLE 1-continued

*Fusarium venenatum* ESTs

| Sequence Listing | zscore | Annotation | Database | Functional category |
|---|---|---|---|---|
| 1742 | 184.7 | HYPOTHETICAL 57.5 KD PROTEIN IN VMA7-RPS25A INTERGENIC REGION. | swissprot P53214 | ND |
| 1743 | 184.6 | TRANSITIONAL ENDOPLASMIC RETICULUM ATPASE HOMOLOG 2 (P97/CDC48 HOMOLOG 2). | swissnew P54812 | ND |
| 1744 | 184.4 | RNA BINDING PROTEIN (FRAGMENT). | tremblnew BAA83714 | ND |
| 1745 | 184.3 | HYPOTHETICAL PROTEIN MG096. | swissnew P47342 | ND |
| 1746 | 184.3 | Sequence A encoded by a portion of SA307. | geneseqp P60623 | ND |
| 1747 | 184.3 | MUCIN. | sptrembl Q28226 | ND |
| 1748 | 183.9 | MUCIN 2 PRECURSOR (INTESTINAL MUCIN 2). | swissprot Q02817 | ND |
| 1749 | 183.9 | CARBOXYPEPTIDASE S PRECURSOR (EC 3.4.17.4) (YSCS) (GLY-X CARBOXYPEPTIDASE). | swissprot P27614 | ND |
| 1750 | 183.8 | HYPOTHETICAL 55.0 KD PROTEIN. | sptrembl P96824 | ND |
| 1751 | 183.2 | *Aspergillus nidulans* essential protein AN80. | geneseqp Y06416 | ND |
| 1752 | 183.1 | BETA-1,3-GLUCANOSYLTRANSFERASE. | sptrembl O59909 | ND |
| 1753 | 183.1 | RAD1. | tremblnew AAC95465 | ND |
| 1754 | 183.0 | HYPOTHETICAL 28.6 KD PROTEIN. | tremblnew CAB41006 | ND |
| 1755 | 182.9 | BDF1 PROTEIN. | swissprot P35817 | ND |
| 1756 | 182.8 | HYPOTHETICAL 57.2 KD PROTEIN. | sptrembl O68872 | ND |
| 1757 | 182.5 | F14B4.2 PROTEIN. | sptrembl Q19440 | ND |
| 1758 | 182.4 | PUTATIVE CLEAVAGE AND POLYADENYLATION SPECIFICITY FACTOR. | sptrembl O74740 | ND |
| 1759 | 182.3 | EXTENSIN CLASS II PRECURSOR (CELL WALL HYDROXYPROLINE-RICH GLYCOPROTEIN) (HRGP) (TOML-4). | sptrembl Q09084 | ND |
| 1760 | 182.2 | VOLTAGE-DEPENDENT P/Q TYPE CALCIUM CHANNEL ALPHA 1A SUBUNIT (FRAGMENT). | sptrembl O95387 | ND |
| 1761 | 182.1 | HEPATITIS A VIRUS CELLULAR RECEPTOR 1 LONG FORM (HEPATITIS A VIRUS CELLULAR RECEPTOR 1 SHORT FORM). | sptrembl O46598 | ND |
| 1762 | 182.1 | Amino acid sequence of a human secreted protein. | geneseqp Y19477 | ND |
| 1763 | 181.9 | HEPATITIS A VIRUS RECEPTOR. | sptrembl O18984 | ND |
| 1764 | 181.9 | SIMILAR TO *D. MELANOGASTER* BRCORE-Q1-Z1 PROTEIN AND V. VIRUS PROTEIN A55. | sptrembl Q17782 | ND |
| 1765 | 181.8 | LATENT NUCLEAR ANTIGEN. | sptrembl Q9WRM2 | ND |
| 1766 | 181.8 | HOR1-17 C-HORDEIN. | sptrembl Q40053 | ND |
| 1767 | 181.6 | HYPOTHETICAL 112.1 KD PROTEIN. | sptrembl O86637 | ND |
| 1768 | 181.6 | MITOCHONDRIAL TRANSCRIPTION FACTOR 1 PRECURSOR (MTTF1). | swissprot Q00059 | ND |
| 1769 | 181.6 | PUTATIVE ACYL-COA DEHYDROGENASE. | tremblnew CAB46788 | ND |
| 1770 | 181.5 | HYPOTHETICAL 83.7 KD PROTEIN C4F10.07C IN CHROMOSOME I. | sptrembl O36019 | ND |

TABLE 1-continued

Fusarium venenatum ESTs

| Sequence Listing | zscore | Annotation | Database | Functional category |
|---|---|---|---|---|
| 1771 | 181.5 | EXTENSIN-LIKE PROTEIN. | tremblnew AAD55980 | ND |
| 1772 | 181.4 | PROLINE-RICH CELL WALL PROTEIN. | sptrembl Q39763 | ND |
| 1773 | 181.4 | FLGA insert stabilising polypeptide. | geneseqp W79128 | ND |
| 1774 | 181.4 | Hepatitis A virus receptor. | geneseqp R92803 | ND |
| 1775 | 181.2 | CONSERVED HYPOTHETICAL ZINC-FINGER PROTEIN. | sptrembl O94264 | ND |
| 1776 | 181.1 | HYPOTHETICAL 79.1 KD PROTEIN. | sptrembl O60161 | ND |
| 1777 | 181.1 | Rat 25-hydroxyvitamin D3-1-alpha-hydroxylase. | geneseqp W89552 | ND |
| 1778 | 181.0 | Collagen-like polymer. | geneseqp W57645 | ND |
| 1779 | 181.0 | PROBABLE METABOLITE TRANSPORT PROTEIN. | sptrembl O94342 | ND |
| 1780 | 180.8 | PUTATIVE MITOCHONDRIAL 60S RIBOSOMAL PROTEIN L31 PRECURSOR. | tremblnew CAB53083 | ND |
| 1781 | 180.7 | AMINOPEPTIDASE II (EC 3.4.11.-) (YSCII). | swissprot P32454 | ND |
| 1782 | 180.5 | HYPOTHETICAL 61.1 KD PROTEIN (FRAGMENT). | tremblnew CAB63715 | ND |
| 1783 | 180.5 | FLGA insert stabilising polypeptide. | geneseqp W79128 | ND |
| 1784 | 180.4 | HYPOTHETICAL 18.4 KD PROTEIN. | sptrembl Q9Y801 | ND |
| 1785 | 180.1 | A-AGGLUTININ ATTACHMENT SUBUNIT PRECURSOR. | swissprot P32323 | ND |
| 1786 | 180.1 | HYPOTHETICAL 62.9 KD PROTEIN. | sptrembl P74375 | ND |
| 1787 | 179.9 | PUTATIVE ACID PHOSPHATASE. | tremblnew CAB58405 | ND |
| 1788 | 179.4 | CHECKPOINT PROTEIN RAD17. | swissprot P50531 | ND |
| 1789 | 179.3 | Drosophila dCREB1 protein. | geneseqp R91295 | ND |
| 1790 | 178.7 | ABP32. | tremblnew BAA84922 | ND |
| 1791 | 178.5 | Human iduronate 2-sulphatase protein sequence. | geneseqp Y23982 | ND |
| 1792 | 178.5 | QI74 PROTEIN. | sptrembl O74567 | ND |
| 1793 | 178.3 | D9461.15P. | sptrembl Q04066 | ND |
| 1794 | 178.3 | SF16 ISOLOG. | sptrembl O22835 | ND |
| 1795 | 178.0 | SUCAB-LPD OPERON, SUCB AND LPD GENES, COMPLETE CDS, SUCA GENE PARTIAL CDS AND IS-150-LIKE ELEMENT 3' END (FRAGMENT). | sptrembl Q50992 | ND |
| 1796 | 177.6 | PUTATIVE TRANSCRIPTION INITIATION FACTOR IIA LARGE SUBUNIT. | tremblnew CAB57938 | ND |
| 1797 | 177.6 | SPLICING FACTOR, ARGININE/SERINE-RICH 2 (SPLICING FACTOR SC35) (SC-35) (SPLICING COMPONENT, 35 KD) (PR264 PROTEIN). | swissprot P30352 | ND |
| 1798 | 177.5 | DIMETHYLANILINE MONOOXYGENASE-LIKE PROTEIN. | tremblnew CAB43691 | ND |
| 1799 | 177.4 | PROTEOPHOSPHOGLYCAN PRECURSOR (FRAGMENT). | sptrembl Q9Y076 | ND |
| 1800 | 177.2 | SER/ARG-RELATED NUCLEAR MATRIX PROTEIN. | sptrembl O60585 | ND |
| 1801 | 177.2 | PUTATIVE PROLINE-RICH CELL WALL PROTEIN. | sptrembl O82327 | ND |

TABLE 1-continued

*Fusarium venenatum* ESTs

| Sequence Listing | zscore | Annotation | Database | Functional category |
|---|---|---|---|---|
| 1802 | 177.1 | GLYCINE RICH RNA BINDING PROTEIN. | tremblnew CAB56042 | ND |
| 1803 | 177.0 | N AMINO ACID TRANSPORT SYSTEM PROTEIN (METHYLTRYPTOPHAN RESISTANCE PROTEIN). | swissprot P38680 | ND |
| 1804 | 176.9 | (VSP-3) PRECURSOR. | sptrembl Q39620 | ND |
| 1805 | 176.7 | IDI-2 PRECURSOR. | sptrembl O74220 | ND |
| 1806 | 176.6 | HYPOTHETICAL 35.1 KD PROTEIN. | tremblnew CAB38264 | ND |
| 1807 | 176.6 | FERRIC REDUCTASE. | sptrembl Q9Y861 | ND |
| 1808 | 176.5 | ANNEXIN XIV. | sptrembl O59907 | ND |
| 1809 | 176.5 | MUCIN PRECURSOR (FRAGMENT). | sptrembl Q62635 | ND |
| 1810 | 176.4 | SINGLE-STRANDED DNA-BINDING PROTEIN. | sptrembl P77953 | ND |
| 1811 | 176.4 | COSMID C25H3. | sptrembl Q18187 | ND |
| 1812 | 176.3 | PROBABLE EUKARYOTIC TRANSLATION INITIATION FACTOR 5 (EIF-5). | swissprot Q09689 | ND |
| 1813 | 176.2 | MICROTUBULE ASSOCIATED PROTEIN (DJ406A7.2.1) (MICROTUBLE ASSOCIATED PROTEIN E-MAP-115). | sptrembl Q14244 | ND |
| 1814 | 176.2 | (VSP-3) PRECURSOR. | sptrembl Q39620 | ND |
| 1815 | 176.2 | HYPOTHETICAL PROTEIN MJ1055. | swissprot Q58455 | ND |
| 1816 | 176.1 | HYPOTHETICAL 81.2 KD PROTEIN. | sptrembl O81714 | ND |
| 1817 | 175.8 | STRONG SIMILARITY TO HUMAN REV INTERACTING PROTEIN RIP-1. | sptrembl O74777 | ND |
| 1818 | 175.7 | PUTATIVE TRANSCRIPTIONAL REGULATOR. | sptrembl O13337 | ND |
| 1819 | 175.5 | F23N19.12. | tremblnew AAF19547 | ND |
| 1820 | 175.4 | CONSERVED HYPOTHETICAL PROTEIN. | tremblnew CAB53729 | ND |
| 1821 | 175.4 | VITELLOGENIN PRECURSOR. | sptrembl Q9YGK0 | ND |
| 1822 | 175.3 | GP80. | sptrembl P87519 | ND |
| 1823 | 175.3 | YEAST REDUCED VIABILITY UPON STARVATION PROTEIN 161 HOMOLOG, IMPLICATED IN CELL GROWTH AND CYTOSKELETAL ORGANISATION. | tremblnew CAA22181 | ND |
| 1824 | 175.1 | MUTATOR-LIKE TRANSPOSASE. | tremblnew AAD23701 | ND |
| 1825 | 175.0 | MINI-COLLAGEN PRECURSOR (ISOFORM 1). | sptrembl Q00484 | ND |
| 1826 | 174.9 | CYTOSKELETON ASSEMBLY CONTROL PROTEIN SLA2P. | sptrembl O93959 | ND |
| 1827 | 174.8 | SHP1 PROTEIN. | swissprot P34223 | ND |
| 1828 | 174.7 | CYTOCHROME C OXIDASE POLYPEPTIDE IV PRECURSOR (EC 1.9.3.1). | swissprot P04037 | ND |
| 1829 | 174.6 | CUT1 PROTEIN. | swissnew P18296 | ND |
| 1830 | 174.6 | Extracellular domain of prostate specific membrane antigen (PSMA). | geneseqp W47155 | ND |
| 1831 | 174.1 | HYPOTHETICAL PROTEIN (FRAGMENT). | tremblnew CAB61270 | ND |
| 1832 | 173.8 | ARABINOGALACTAN-LIKE PROTEIN. | sptrembl Q41071 | ND |
| 1833 | 173.8 | PROLINE-RICH. | sptrembl Q94273 | ND |
| 1834 | 173.7 | HYDROXYPROLINE-RICH GLYCOPROTEIN. | sptrembl Q42366 | ND |

TABLE 1-continued

*Fusarium venenatum* ESTs

| Sequence Listing | zscore | Annotation | Database | Functional category |
|---|---|---|---|---|
| 1835 | 173.4 | S-PHASE DELAYING PROTEIN 1 (P14 PROTEIN). | sptrembl Q10585 | ND |
| 1836 | 173.4 | SERINE-RICH PROTEIN. | sptrembl O94317 | ND |
| 1837 | 173.2 | RECF (FRAGMENT). | sptrembl O30497 | ND |
| 1838 | 173.2 | BETA-GALACTOSIDASE ALPHA-PEPTIDE (FRAGMENT). | sptrembl Q57170 | ND |
| 1839 | 173.1 | Mouse liver cancer-originated culture cell growth factor. | geneseqp W37482 | ND |
| 1840 | 172.9 | *T. gondii* immunogenic protein. | geneseqp Y29060 | ND |
| 1841 | 172.8 | 156AA LONG HYPOTHETICAL PROTEIN. | sptrembl Q9YAB4 | ND |
| 1842 | 172.7 | AKT2. | sptrembl O93801 | ND |
| 1843 | 172.7 | FLGA insert stabilising polypeptide. | geneseqp W79128 | ND |
| 1844 | 172.6 | CHORD CONTAINING PROTEIN-1. | tremblnew AAF18437 | ND |
| 1845 | 172.4 | UL36. | sptrembl Q65553 | ND |
| 1846 | 172.3 | CELL WALL-PLASMA MEMBRANE LINKER PROTEIN. | sptrembl Q39353 | ND |
| 1847 | 172.2 | SER/ARG-RELATED NUCLEAR MATRIX PROTEIN. | sptrembl O60585 | ND |
| 1848 | 172.2 | F23C8.6 PROTEIN. | tremblnew AAD03134 | ND |
| 1849 | 172.1 | WW DOMAIN BINDING PROTEIN 11. | sptrembl O88539 | ND |
| 1850 | 171.8 | EXTENSIN. | sptrembl Q06802 | ND |
| 1851 | 171.7 | F24O1.18. | sptrembl O48809 | ND |
| 1852 | 171.7 | HYPOTHETICAL 30.6 KD PROTEIN IN SCP160-SMC3 INTERGENIC REGION PRECURSOR. | swissprot P47032 | ND |
| 1853 | 171.4 | GLUTENIN, LOW MOLECULAR WEIGHT SUBUNIT PRECURSOR. | swissprot P10385 | ND |
| 1854 | 171.4 | HYPOTHETICAL 17.5 KD PROTEIN C22H10.02 IN CHROMOSOME I. | swissprot Q10296 | ND |
| 1855 | 171.2 | HYPOTHETICAL 105.9 KD PROTEIN IN RPL15B-GCR3 INTERGENIC REGION. | swissprot P39523 | ND |
| 1856 | 171.2 | POSSIBLE PROTEIN METHYLTRANSFERASE. | sptrembl O27940 | ND |
| 1857 | 171.2 | BIFUNCTIONAL ASPARTOKINASE/HOMO SERINE DEHYDROGENASE I (AKI-HDI) [INCLUDES: ASPARTOKINASE (EC 2.7.2.4); HOMOSERINE DEHYDROGENASE (EC 1.1.1.3)]. | swissnew P27725 | ND |
| 1858 | 171.0 | ZETA-CRYSTALLIN. | sptrembl O97764 | ND |
| 1859 | 170.9 | CCP PROTEIN. | sptrembl Q9WX60 | ND |
| 1860 | 170.9 | 36.1 KD PROTEIN IN BUD2-MIF2 INTERGENIC REGION. | swissprot P33324 | ND |
| 1861 | 170.8 | WP6 PRECURSOR. | sptrembl Q39492 | ND |
| 1862 | 170.7 | HISTIDYL-TRNA SYNTHETASE. | sptrembl O43011 | ND |
| 1863 | 170.6 | CODED FOR BY C. ELEGANS CDNA YK127B8.5. | sptrembl Q20648 | ND |
| 1864 | 170.2 | TRICHODIENE SYNTHASE (EC 4.1.99.6) (SESQUITERPENE CYCLASE) (TS). | swissprot P27679 | ND |
| 1865 | 170.2 | HYPOTHETICAL 46.6 KD PROTEIN. | sptrembl O74477 | ND |
| 1866 | 170.2 | HEPB PROTEIN. | sptrembl O22016 | ND |
| 1867 | 170.2 | CHITINASE. | sptrembl Q92223 | ND |
| 1868 | 170.2 | NADH-UBIQUINONE | swissprot O43676 | ND |

TABLE 1-continued

Fusarium venenatum ESTs

| Sequence Listing | zscore | Annotation | Database | Functional category |
|---|---|---|---|---|
| | | OXIDOREDUCTASE B12 SUBUNIT (EC 1.6.5.3) (EC 1.6.99.3) (COMPLEX I-B12) (CI-B12). | | |
| 1869 | 170.2 | ANTIGEN LPMC-61 (FRAGMENT). | swissprot P15714 | ND |
| 1870 | 170.1 | HYPOTHETICAL 96.0 KD PROTEIN. | sptrembl O74365 | ND |
| 1871 | 170.1 | HYPOTHETICAL 23.4 KD PROTEIN IN CAJ1-HOM3 INTERGENIC REGION. | swissprot P40033 | ND |
| 1872 | 170.0 | ASPARTIC PROTEINASE PRECURSOR (EC 3.4.23.-) (GCSAP). | sptrembl Q00895 | ND |
| 1873 | 169.9 | mSOS1 protein. | geneseqp R84638 | ND |
| 1874 | 169.9 | PROTEOPHOSPHOGLYCAN PRECURSOR (FRAGMENT). | sptrembl Q9Y076 | ND |
| 1875 | 169.9 | HYDROXYPROLINE-RICH GLYCOPROTEIN. | sptrembl Q41814 | ND |
| 1876 | 169.7 | HEPATITIS A VIRUS RECEPTOR. | sptrembl O18984 | ND |
| 1877 | 169.7 | DNA-DIRECTED RNA POLYMERASE II 13.6 KD POLYPEPTIDE (EC 2.7.7.6) (B13.6). | swissprot P38902 | ND |
| 1878 | 169.7 | L4171.3. | sptrembl O15837 | ND |
| 1879 | 169.6 | HYPOTHETICAL 20.3 KD PROTEIN C25H1.03 IN CHROMOSOME I. | sptrembl O13978 | ND |
| 1880 | 169.6 | ARABINOGALACTAN-PROTEIN. | sptrembl Q9ZT15 | ND |
| 1881 | 169.5 | ACROSIN PRECURSOR (EC 3.4.21.10). | swissprot P48038 | ND |
| 1882 | 169.5 | 785AA LONG HYPOTHETICAL HYUA. | sptrembl Q9YCC8 | ND |
| 1883 | 169.3 | COA TRANSFERASE, SUBUNIT B. | tremblnew AAF12248 | ND |
| 1884 | 169.3 | LAMININ ALPHA CHAIN PRECURSOR. | swissprot Q00174 | ND |
| 1885 | 169.2 | SEQ ID NO 383 from WO9922243. | geneseqp Y19665 | ND |
| 1886 | 168.9 | Human heart muscle specific protein. | geneseqp W90172 | ND |
| 1887 | 168.7 | COMES FROM THIS GENE. | sptrembl O23054 | ND |
| 1888 | 168.7 | ACIDIC PROLINE-RICH PROTEIN PRP25 PRECURSOR (FRAGMENT). | swissprot P10164 | ND |
| 1889 | 168.7 | METAL HOMEOSTATIS PROTEIN BSD2. | swissprot P38356 | ND |
| 1890 | 168.7 | HIGH MOLECULAR MASS NUCLEAR ANTIGEN (FRAGMENT). | sptrembl O57580 | ND |
| 1891 | 168.6 | HYPOTHETICAL 26.1 KD PROTEIN C23H3.12C IN CHROMOSOME I. | sptrembl O13942 | ND |
| 1892 | 168.6 | Sugar beet chitinase 1. | geneseqp R28150 | ND |
| 1893 | 168.6 | KEXIN. | sptrembl O94096 | ND |
| 1894 | 168.6 | HYPOTHETICAL PROTEIN (FRAGMENT). | sptrembl Q38962 | ND |
| 1895 | 168.5 | 124AA LONG HYPOTHETICAL PROTEIN. | sptrembl Q9YCC9 | ND |
| 1896 | 168.5 | PUTATIVE ETHANOLAMINEPHOSPHO TRANSFERASE (EC 2.7.8.1) (ETHPT). | sptrembl O13901 | ND |
| 1897 | 168.5 | WP6 PRECURSOR. | sptrembl Q39492 | ND |
| 1898 | 168.4 | HEPATITIS A VIRUS CELLULAR RECEPTOR I LONG FORM (HEPATITIS A VIRUS CELLULAR RECEPTOR I SHORT FORM). | sptrembl O46598 | ND |
| 1899 | 168.1 | PUTATIVE TRANSCRIPTION FACTOR. | tremblnew CAB43914 | ND |

TABLE 1-continued

*Fusarium venenatum* ESTs

| Sequence Listing | zscore | Annotation | Database | Functional category |
|---|---|---|---|---|
| 1900 | 168.0 | BAV3 ORF3 product. | geneseqp R75758 | ND |
| 1901 | 167.8 | HYPOTHETICAL 27.2 KD PROTEIN IN GLS2-RPL26B INTERGENIC REGION. | swissprot P53220 | ND |
| 1902 | 167.8 | SIMILAR TO STF2P. | sptrembl Q06177 | ND |
| 1903 | 167.7 | EMBRYONIC/NEONATAL MYOSIN HEAVY CHAIN (FRAGMENT). | sptrembl Q28700 | ND |
| 1904 | 167.7 | PROTEIN TRANSLATION FACTOR SUI1 HOMOLOG. | swissprot O48650 | ND |
| 1905 | 167.7 | NONF. | sptrembl Q9XDF2 | ND |
| 1906 | 167.6 | MAGNESIUM-CHELATASE 60 KD SUBUNIT (MG-PROTOPORPHYRIN IX CHELATASE) (MG-CHELATASE SUBUNIT D). | swissnew P26175 | ND |
| 1907 | 167.5 | 264AA LONG HYPOTHETICAL PROTEIN. | sptrembl Q9YCX9 | ND |
| 1908 | 167.5 | SERINE/THREONINE PROTEIN KINASE PKAA (EC 2.7.1.-). | swissnew P54739 | ND |
| 1909 | 167.4 | PROTEOPHOSPHOGLYCAN (FRAGMENT). | sptrembl Q9Y075 | ND |
| 1910 | 167.3 | HEPATITIS A VIRUS CELLULAR RECEPTOR 1 LONG FORM (HEPATITIS A VIRUS CELLULAR RECEPTOR 1 SHORT FORM). | sptrembl O46598 | ND |
| 1911 | 167.3 | CDC2-LIKE PROTEIN KINASE (EC 2.7.1.). | sptrembl O76541 | ND |
| 1912 | 167.1 | PUTATIVE SECRETED PROLINE-RICH PROTEIN. | tremblnew CAB63180 | ND |
| 1913 | 167.1 | ARGININE/SERINE-RICH PROTEIN. | tremblnew AAF19004 | ND |
| 1914 | 166.9 | CUTICLE COLLAGEN 40. | swissprot P34804 | ND |
| 1915 | 166.9 | HYPOTHETICAL PROTEIN C30B4.01C IN CHROMOSOME II (FRAGMENT). | sptrembl P87179 | ND |
| 1916 | 166.7 | HISTONE H1. | swissprot P37218 | ND |
| 1917 | 166.6 | NUM1 PROTEIN. | sptrembl Q40363 | ND |
| 1918 | 166.5 | ANTIGEN EM13. | sptrembl Q07840 | ND |
| 1919 | 166.2 | Y18D10A.8 PROTEIN. | sptrembl Q9XW13 | ND |
| 1920 | 166.2 | PARAMECIUM 3′ GENE FRAGMENT FOR G SURFACE ANTIGEN (FRAGMENT). | sptrembl Q94699 | ND |
| 1921 | 166.2 | HYPOTHETICAL 6.1 KD PROTEIN C03B1.10 IN CHROMOSOME X. | swissprot Q11116 | ND |
| 1922 | 166.2 | OVERLAPPING PROTEIN. | sptrembl O91259 | ND |
| 1923 | 166.2 | PUTATIVE SMALL BASIC PROTEIN. | sptrembl O55724 | ND |
| 1924 | 166.1 | T01B7.8 PROTEIN. | sptrembl Q22048 | ND |
| 1925 | 166.1 | 50S RIBOSOMAL PROTEIN L34. | sptrembl O21276 | ND |
| 1926 | 166.0 | MUCIN (FRAGMENT). | sptrembl Q28501 | ND |
| 1927 | 166.0 | 34 KD ANTIGENIC PROTEIN. | swissprot Q04959 | ND |
| 1928 | 165.9 | AQUAPORIN-3. | sptrembl Q9YH65 | ND |
| 1929 | 165.7 | CGI-41 PROTEIN. | sptrembl Q9Y358 | ND |
| 1930 | 165.6 | HIGH MOBILITY GROUP-LIKE NUCLEAR PROTEIN 2. | swissprot P32495 | ND |
| 1931 | 165.6 | PGRS-FAMILY PROTEIN. | sptrembl O53395 | ND |
| 1932 | 165.5 | PUTATIVE ZINC METALLOPEPTIDASE (FRAGMENT). | tremblnew CAB54809 | ND |
| 1933 | 165.5 | Human VEGF-C truncated fragment 4. | geneseqp W86225 | ND |

TABLE 1-continued

*Fusarium venenatum* ESTs

| Sequence Listing | zscore | Annotation | Database | Functional category |
|---|---|---|---|---|
| 1934 | 165.5 | SALIVARY GLUE PROTEIN SGS-3 PRECURSOR. | swissprot P13728 | ND |
| 1935 | 165.4 | U2 SMALL NUCLEAR RIBONUCLEOPROTEIN AUXILIARY FACTOR 35 KD SUBUNIT RELATED-PROTEIN 1. | swissprot Q15695 | ND |
| 1936 | 165.4 | N2,N2-DIMETHYLGUANOSINE TRNA METHYLTRANSFERASE. | tremblnew CAA20101 | ND |
| 1937 | 165.2 | 180AA LONG HYPOTHETICAL PROTEIN. | sptrembl Q9YBV8 | ND |
| 1938 | 165.2 | ADK1. | sptrembl Q9ZWB3 | ND |
| 1939 | 165.1 | D2089.1 PROTEIN. | sptrembl O01159 | ND |
| 1940 | 165.0 | Y44E3A.5 PROTEIN. | tremblnew AAC78231 | ND |
| 1941 | 165.0 | C15A11.1 PROTEIN. | sptrembl Q93208 | ND |
| 1942 | 164.9 | EXTENSIN-LIKE PROTEIN. | tremblnew CAB40769 | ND |
| 1943 | 164.8 | RETINA-DERIVED POU-DOMAIN FACTOR-1 (FRAGMENT). | tremblnew AAC83404 | ND |
| 1944 | 164.8 | 203AA LONG HYPOTHETICAL PROTEIN. | sptrembl Q9YAY3 | ND |
| 1945 | 164.7 | HEPATITIS A VIRUS CELLULAR RECEPTOR 1 LONG FORM (HEPATITIS A VIRUS CELLULAR RECEPTOR 1 SHORT FORM). | sptrembl O46598 | ND |
| 1946 | 164.7 | HYPOTHETICAL 79.1 KD PROTEIN. | sptrembl O60161 | ND |
| 1947 | 164.7 | UNKNOWN PROTEIN. | sptrembl O04210 | ND |
| 1948 | 164.6 | INTESTINAL MUCIN (FRAGMENT). | sptrembl Q14883 | ND |
| 1949 | 164.6 | PROTEOPHOSPHOGLYCAN (FRAGMENT). | sptrembl Q9Y075 | ND |
| 1950 | 164.3 | DBP-5 NUCLEAR PROTEIN. | sptrembl Q14120 | ND |
| 1951 | 164.3 | HYPOTHETICAL 45.9 KD PROTEIN RV2067C. | swissnew Q10678 | ND |
| 1952 | 164.2 | ALPHA/BETA-GLIADIN CLONE PW1215 PRECURSOR (PROLAMIN). | swissprot P04726 | ND |
| 1953 | 164.2 | NONSTRUCTURAL PROTEIN 1 (FRAGMENT). | sptrembl O10460 | ND |
| 1954 | 164.2 | VICILIN-LIKE PROTEIN PRECURSOR (FRAGMENT). | tremblnew AAF18269 | ND |
| 1955 | 164.1 | MITOCHONDRIAL PROTEIN CYT-4. | swissprot P47950 | ND |
| 1956 | 164.1 | 134AA LONG HYPOTHETICAL PROTEIN. | sptrembl Q9Y9Q5 | ND |
| 1957 | 164.1 | SIMILARITY TO *DROSOPHILA HOMEOTIC* GENE REGULATOR BRM. | sptrembl P91094 | ND |
| 1958 | 164.0 | PROBABLE TRANSLATION INITIATION FACTOR EIF-2B DELTA SUBUNIT (EIF-2B GDP-GTP EXCHANGE FACTOR). | swissprot Q09924 | ND |
| 1959 | 163.9 | S2 RIBOSOMAL PROTEIN. | sptrembl O84687 | ND |
| 1960 | 163.9 | COSMID C34D4. | sptrembl Q18444 | ND |
| 1961 | 163.8 | HEPATITIS A VIRUS RECEPTOR. | sptrembl O18984 | ND |
| 1962 | 163.8 | PREDICTED INTEGRAL MEMBRANE PROTEIN. | sptrembl O96177 | ND |
| 1963 | 163.8 | Human bcl2 proto-oncogene wild type protein fragment 1. | geneseqp Y21104 | ND |
| 1964 | 163.7 | ATP SYNTHASE GAMMA CHAIN, MITOCHONDRIAL PRECURSOR (EC 3.6.1.34). | swissnew P49377 | ND |
| 1965 | 163.7 | T1J1.6 PROTEIN. | sptrembl Q9ZPH2 | ND |

TABLE 1-continued

Fusarium venenatum ESTs

| Sequence Listing | zscore | Annotation | Database | Functional category |
|---|---|---|---|---|
| 1966 | 163.6 | PUTATIVE EXTENSIN. | sptrembl Q9ZNU3 | ND |
| 1967 | 163.6 | F25C8.4 PROTEIN. | sptrembl Q9XV68 | ND |
| 1968 | 163.5 | PUTATIVE TRANSCRIPTIONAL REGULATOR, ZINC-FINGER, BINUCLEAR CLUSTERDOMAIN. | tremblnew CAA92308 | ND |
| 1969 | 163.3 | HYPOTHETICAL 29.3 KD PROTEIN (ORF92). | swissprot O10341 | ND |
| 1970 | 163.3 | LUN (LUN PROTEIN). | sptrembl O54743 | ND |
| 1971 | 163.1 | DOLICHYL-DIPHOSPHOOLIGOSACCHA-RIDE--PROTEIN GLYCOSYLTRANSFERASE ALPHA SUBUNIT PRECURSOR (EC 2.4.1.119) (OLIGOSACCHARYL TRANSFERASE ALPHA SUBUNIT) (OLIGOSACCHARYL TRANSFERASE 64 KD SUBUNIT). | swissprot P41543 | ND |
| 1972 | 163.0 | Human alpha-l (XVIII) chain NCl domain variant HU18(NC1-493). | geneseqp W92294 | ND |
| 1973 | 162.9 | CHROMOSOME XII READING FRAME ORF YLR0O2C. | sptrembl Q07896 | ND |
| 1974 | 162.8 | DRPLA. | sptrembl O35126 | ND |
| 1975 | 162.8 | COLLAGEN ALPHA 1 (VIII) CHAIN PRECURSOR. | swissprot Q00780 | ND |
| 1976 | 162.7 | DIACYLGLYCEROL CHOLINEPHOSPHOTRANSFERASE (EC 2.7.8.2) (SN-1,2-DIACYLGLYCEROL CHOLINEPHOSPHOTRANSFERASE) (CHOPT). | swissprot P17898 | ND |
| 1977 | 162.7 | Maize cinnamyl alcohol dehydrogenase. | geneseqp Y05667 | ND |
| 1978 | 162.7 | SALIVARY GLUE PROTEIN SGS-3 PRECURSOR. | swissprot P13729 | ND |
| 1979 | 162.6 | FROM BASES 1830199 TO 1840304 (SECTION 160 OF 400) OF THE COMPLETE GENOME (SECTION 160 OF 400). | sptrembl P77788 | ND |
| 1980 | 162.5 | SKIN SECRETORY PROTEIN XP2 PRECURSOR (APEG PROTEIN). | swissnew P17437 | ND |
| 1981 | 162.5 | PRION PROTEIN PRECURSOR (FRAGMENT). | tremblnew AAD47045 | ND |
| 1982 | 162.5 | HYPOTHETICAL 27.4 KD PROTEIN IN HIT1-CDC8 INTERGENIC REGION. | swissprot P47115 | ND |
| 1983 | 162.5 | HYPOTHETICAL 53.7 KD PROTEIN IN SGA1-KTR7 INTERGENIC REGION. | swissprot P40501 | ND |
| 1984 | 162.4 | SIB 124 intestinal mucin. | geneseqp R12601 | ND |
| 1985 | 162.4 | ALPHA-GLIADIN STORAGE PROTEIN. | sptrembl Q41529 | ND |
| 1986 | 162.4 | GASTRIC MUCIN (FRAGMENT). | sptrembl Q29071 | ND |
| 1987 | 162.3 | BRANCHED-CHAIN AMINO ACID AMINOTRANSFERASE, MITOCHONDRIAL PRECURSOR (EC 2.6.1.42) (BCAT(M)). | swissprot O15382 | ND |
| 1988 | 162.2 | PENICILLIN-BINDING PROTEIN 1. | tremblnew AAF10059 | ND |
| 1989 | 162.1 | N-WASP. | sptrembl O00401 | ND |

TABLE 1-continued

*Fusarium venenatum* ESTs

| Sequence Listing | zscore | Annotation | Database | Functional category |
|---|---|---|---|---|
| 1990 | 162.1 | REGULATORY PROTEIN E2. | sptrembl O56937 | ND |
| 1991 | 162.0 | HYPOTHETICAL 25.3 KD PROTEIN IN TIM23-ARE2 INTERGENIC REGION. | swissprot P53721 | ND |
| 1992 | 162.0 | Hepatitis B virus E antigen (wild-type). | geneseqp R98878 | ND |
| 1993 | 162.0 | MYOCYTE ENHANCER FACTOR 2A (FRAGMENT). | sptrembl O97865 | ND |
| 1994 | 162.0 | THIOREDOXIN. | swissprot P42115 | ND |
| 1995 | 161.9 | *M. tuberculosis* immunogenic polypeptide TbH-29. | geneseqp W81726 | ND |
| 1996 | 161.8 | PROLINE RICH PROTEIN. | sptrembl O22514 | ND |
| 1997 | 161.5 | VIRION PROTEIN. | sptrembl P89479 | ND |
| 1998 | 161.3 | ORF1 (FRAGMENT). | sptrembl Q9W9H9 | ND |
| 1999 | 161.2 | Artificial recognition sequence 5. | geneseqp W43028 | ND |
| 2000 | 161.2 | LOW MOLECULAR WEIGHT GLUTENIN (FRAGMENT). | sptrembl Q41552 | ND |
| 2001 | 161.2 | HYPOTHETICAL 20.8 KD PROTEIN. | sptrembl O53905 | ND |
| 2002 | 161.1 | ORFAB. | sptrembl Q9X982 | ND |
| 2003 | 161.1 | HEPATITIS A VIRUS CELLULAR RECEPTOR 1 LONG FORM (HEPATITIS A VIRUS CELLULAR RECEPTOR 1 SHORT FORM). | sptrembl O46597 | ND |
| 2004 | 161.0 | LOW MOLECULAR WEIGHT GLUTENIN (FRAGMENT). | sptrembl Q41551 | ND |
| 2005 | 160.9 | Intestinal mucin deduced from clone SMUC 87. | geneseqp R07674 | ND |
| 2006 | 160.9 | HYDROXYPROLINE-RICH GLYCOPROTEIN. | sptrembl Q42366 | ND |
| 2007 | 160.8 | PUTATIVE SPLICING FACTOR, ARGININE/SERINE-RICH 2 (SPLICING FACTOR SC35) (SC-35) (SPLICING COMPONENT, 35 KD). | swissprot Q09511 | ND |
| 2008 | 160.8 | ACETAMIDASE REGULATORY PROTEIN. | swissprot P15699 | ND |
| 2009 | 160.7 | GAGA FACTOR CLASS A-ISOFORM. | sptrembl O76940 | ND |
| 2010 | 160.6 | Enzyme donor polypeptide, ED8. | geneseqp R11772 | ND |
| 2011 | 160.6 | PRP2. | geneseqp R29163 | ND |
| 2012 | 160.4 | PUTATIVE SNRNP PROTEIN. | tremblnew CAB45810 | ND |
| 2013 | 160.4 | PHOSPHATE PERMEASE. | sptrembl O74639 | ND |
| 2014 | 160.4 | ORF68. | tremblnew AAF05182 | ND |
| 2015 | 160.3 | LARGEST SUBUNIT OF THE RNA POLYMERASE II COMPLEX. | sptrembl Q9XZS2 | ND |
| 2016 | 160.3 | TOLA PROTEIN. | sptrembl Q9WWX1 | ND |
| 2017 | 160.3 | HYPOTHETICAL 81.2 KD PROTEIN. | sptrembl O81714 | ND |
| 2018 | 160.3 | ANTER-SPECIFIC PROLINE-RICH PROTEIN APG (PROTEIN CEX) (FRAGMENT). | swissprot P40603 | ND |
| 2019 | 160.2 | F22O2.16. | sptrembl Q9ZWD5 | ND |
| 2020 | 160.2 | DNA-DIRECTED RNA POLYMERASE II LARGEST SUBUNIT (EC 2.7.7.6) (RPB1) (FRAGMENT). | swissprot P11414 | ND |

TABLE 1-continued

*Fusarium venenatum* ESTs

| Sequence Listing | zscore | Annotation | Database | Functional category |
|---|---|---|---|---|
| 2021 | 160.1 | SALIVARY PROTEIN MSG2, ISOFORM ALPHA PRECURSOR. | sptrembl O09133 | ND |
| 2022 | 160.1 | 121AA LONG HYPOTHETICAL PROTEIN. | sptrembl Q9YAL7 | ND |
| 2023 | 160.0 | C49F8.1 PROTEIN. | sptrembl Q18710 | ND |
| 2024 | 160.0 | PUTATIVE TRANSCRIPTION INITIATION FACTOR TFIID SUBUNIT. | tremblnew CAB65604 | ND |
| 2025 | 160.0 | LET-653 MUCIN LIKE PROTEIN. | sptrembl Q27394 | ND |
| 2026 | 159.9 | *Rhodococcus rhodochrous* LMGP-18079 cis-epoxysuccinate hydrolase. | geneseqp Y04477 | ND |
| 2027 | 159.9 | REGULATORY PROTEIN E2. | swissprot P06422 | ND |
| 2028 | 159.8 | GAMMA-GLIADIN (GLIADIN B-III) (FRAGMENT). | swissprot P04730 | ND |
| 2029 | 159.7 | ORF 1. | sptrembl O96853 | ND |
| 2030 | 159.7 | FATTY ACID COA LIGASE. | sptrembl O60135 | ND |
| 2031 | 159.4 | EF-HAND PROTEIN. | sptrembl Q09196 | ND |
| 2032 | 159.4 | PROLINE RICH PROTEIN PRECURSOR. | sptrembl Q43558 | ND |
| 2033 | 159.4 | HYPOTHETICAL 37.4 KD PROTEIN. | sptrembl O25304 | ND |
| 2034 | 159.4 | PUTATIVE PROLINE-RICH CELL WALL PROTEIN. | sptrembl O82327 | ND |
| 2035 | 159.3 | IMMEDIATE-EARLY PROTEIN IE180. | swissprot P33479 | ND |
| 2036 | 159.2 | EARLY NODULIN 20 PRECURSOR (N-20). | swissprot P93329 | ND |
| 2037 | 159.2 | *Candida* CaRho1 protein. | geneseqp W30379 | ND |
| 2038 | 159.1 | SALIVARY GLUE PROTEIN SGS-3 PRECURSOR. | swissprot P02840 | ND |
| 2039 | 159.0 | PUTATIVE PROLINE-RICH CELL WALL PROTEIN. | sptrembl O82327 | ND |
| 2040 | 158.9 | PROLINE RICH PROTEIN. | sptrembl Q91810 | ND |
| 2041 | 158.9 | RETINA-DERIVED POU-DOMAIN FACTOR-1 (FRAGMENT). | tremblnew AAC83404 | ND |
| 2042 | 158.9 | HYPOTHETICAL 9.3 KD PROTEIN. | sptrembl O59754 | ND |
| 2043 | 158.8 | Hepatitis A virus receptor. | geneseqp R92803 | ND |
| 2044 | 158.8 | BETA-LACTAMASE PRECURSOR (EC 3.5.2.6) (CEPHALOSPORINASE). | swissnew O05465 | ND |
| 2045 | 158.7 | FISSION YEAST DNA FOR CHROMOSOME II COSMID 1228 SEQUENCE. | sptrembl P78948 | ND |
| 2046 | 158.6 | SERUM OPACITY FACTOR PRECURSOR (FRAGMENT). | tremblnew AAD31504 | ND |
| 2047 | 158.6 | F17L24.2 PROTEIN. | sptrembl Q9ZQJ6 | ND |
| 2048 | 158.6 | F24J5.15 PROTEIN. | tremblnew AAD49981 | ND |
| 2049 | 158.5 | SMUC-41 intestinal mucin. | geneseqp R12535 | ND |
| 2050 | 158.4 | ULTRA HIGH SULFER KERATIN. | sptrembl O75690 | ND |
| 2051 | 158.3 | MUCIN (FRAGMENT). | sptrembl Q28501 | ND |
| 2052 | 158.3 | HYPOTHETICAL 35.1 KD PROTEIN. | tremblnew CAB38264 | ND |
| 2053 | 158.2 | ORF-1 protein sequence from BamHI fragment of HVT. | geneseqp W03546 | ND |
| 2054 | 158.1 | (VSP-3) PRECURSOR. | sptrembl Q39620 | ND |
| 2055 | 158.1 | PUTATIVE TRNA-SPLICING ENDONUCLEASE SUBUNIT. | sptrembl O74908 | ND |
| 2056 | 158.1 | INNER CENTROMERE PROTEIN INCENP. | sptrembl Q9WU62 | ND |
| 2057 | 158.0 | COLLAGEN TYPE XVIII (FRAGMENT). | tremblnew BAA34201 | ND |

TABLE 1-continued

*Fusarium venenatum* ESTs

| Sequence Listing | zscore | Annotation | Database | Functional category |
|---|---|---|---|---|
| 2058 | 158.0 | HYPOTHETICAL PROTEIN C31G5.01 IN CHROMOSOME I (FRAGMENT). | sptrembl O14102 | ND |
| 2059 | 157.9 | PROFILIN P. | swissprot P18322 | ND |
| 2060 | 157.9 | SIMILAR TO BETA-CHIMAERIN. | sptrembl O01825 | ND |
| 2061 | 157.8 | PUTATIVE TETR TRANSCRIPTIONAL REGULATOR. | tremblnew CAB46789 | ND |
| 2062 | 157.8 | CD27L RECEPTOR PRECURSOR (T-CELL ACTIVATION ANTIGEN CD27). | swissprot P41272 | ND |
| 2063 | 157.7 | EXTENSIN CLASS 1 PROTEIN PRECURSOR (EXTENSIN-LIKE PROTEIN). | sptrembl Q41707 | ND |
| 2064 | 157.6 | GASTRIC MUCIN (FRAGMENT). | sptrembl Q29070 | ND |
| 2065 | 157.6 | F24J5.8 PROTEIN. | tremblnew AAD49974 | ND |
| 2066 | 157.6 | CHIMERIC AFGP/TRYPSINOGEN-LIKE SERINE PROTEASE PRECURSOR (FRAGMENT). | sptrembl Q9W6J8 | ND |
| 2067 | 157.4 | 5'-NUCLEOTIDASE (NT5). | sptrembl O29385 | ND |
| 2068 | 157.4 | SIGNAL RECOGNITION PARTICLE 72 KD PROTEIN HOMOLOG (SRP72). | swissprot O59787 | ND |
| 2069 | 157.4 | HYPOTHETICAL 89.3 KD PROTEIN. | sptrembl O96234 | ND |
| 2070 | 157.3 | MYOSIN I HEAVY CHAIN. | sptrembl Q00647 | ND |
| 2071 | 157.2 | W02A2.5 PROTEIN. | sptrembl Q9XUB4 | ND |
| 2072 | 157.2 | GONADOTROPIN INDUCIBLE TRANSCRIPTION REPRESSOR-1 (FRAGMENT). | tremblnew BAA86987 | ND |
| 2073 | 157.2 | HYPOTHETICAL 17.6 KD PROTEIN IN NPR1-RPS3 INTERGENIC REGION. | swissprot P53880 | ND |
| 2074 | 157.1 | HYPOTHETICAL 33.9 KD ZINC FINGER PROTEIN C14C4.06C IN CHROMOSOME I. | sptrembl O13713 | ND |
| 2075 | 157.1 | GERM CELL SPECIFIC Y-BOX BINDING PROTEIN. | sptrembl Q9Y2T7 | ND |
| 2076 | 157.0 | POLY-UBIQUITIN. | sptrembl O59964 | ND |
| 2077 | 157.0 | MULTIDOMAIN PRESYNAPTIC CYTOMATRIX PROTEIN PICCOLO. | tremblnew AAF07822 | ND |
| 2078 | 157.0 | GASTRIC MUCIN (FRAGMENT). | sptrembl Q29070 | ND |
| 2080 | 156.9 | PROBABLE PROTEIN DISULFIDE ISOMERASE ER-60 PRECURSOR (EC 5.3.4.1) (ERP60) (58 KD MICROSOMAL PROTEIN) (P58) (HIP-70) (Q-2). | swissprot P11598 | ND |
| 2081 | 156.9 | HUMAN DNA SEQUENCE FROM CLONE 1177E19 ON CHROMOSOME 1P36.12-36.31. CONTAINS THE 3' PART OF THE DNA-BINDING ZINC FINGER PROTEIN RIZ GENE, ESTS, AN STS, GSSS AND A CPG ISLAND. | tremblnew CAB37643 | ND |
| 2082 | 156.8 | R02F11.1 PROTEIN. | sptrembl O16364 | ND |
| 2083 | 156.8 | YSY6 PROTEIN. | swissprot P38374 | ND |
| 2084 | 156.7 | PUTATIVE RNA-BINDING PROTEIN. | sptrembl O94260 | ND |

TABLE 1-continued

*Fusarium venenatum* ESTs

| Sequence Listing | zscore | Annotation | Database | Functional category |
|---|---|---|---|---|
| 2085 | 156.7 | EARLY NODULIN 20 PRECURSOR (N-20). | swissprot P93329 | ND |
| 2086 | 156.6 | COAT PROTEIN AV1, AV2, AV3, REPLICATION-ASSOCIATED PROTEIN AC1, AC2, AC3, AC4 AND AC5 GENES, COMPLETE CDS. | sptrembl Q88548 | ND |
| 2087 | 156.6 | 121AA LONG HYPOTHETICAL PROTEIN. | sptrembl Q9YAL7 | ND |
| 2088 | 156.6 | HYDROXYNEUROSPORENE DEHYDROGENASE. | sptrembl Q50893 | ND |
| 2089 | 156.5 | Mouse signal transduction protein GRB-7. | geneseqp R80164 | ND |
| 2090 | 156.5 | ERPROT 213-21. | sptrembl O00302 | ND |
| 2091 | 156.5 | COSMID T09D3. | sptrembl Q23036 | ND |
| 2092 | 156.4 | Human secreted protein #3. | geneseqp Y36131 | ND |
| 2093 | 156.3 | PUTATIVE ZINC FINGER TRANSCRIPTION FACTOR OVO1. | sptrembl Q9WTJ2 | ND |
| 2094 | 156.3 | GTP-BINDING PROTEIN (RAN) (FRAGMENT). | sptrembl O13494 | ND |
| 2095 | 156.3 | GAMETOGENESIS EXPRESSED PROTEIN GEG-154. | swissprot P50636 | ND |
| 2096 | 156.2 | OOCYTE ZINC FINGER PROTEIN XLCOF8.4 (FRAGMENT). | swissprot P18753 | ND |
| 2097 | 156.2 | HYPOTHETICAL 14.1 KD PROTEIN IN CYR1-OST1 INTERGENIC REGION. | swissprot P47081 | ND |
| 2098 | 156.2 | HYPOTHETICAL 118.4 KD PROTEIN IN BAT2-DAL5 INTERGENIC REGION PRECURSOR. | swissprot P47179 | ND |
| 2099 | 156.2 | PR-VBETA1. | sptrembl Q64371 | ND |
| 2100 | 156.1 | HYPOTHETICAL 50.0 KD PROTEIN. | sptrembl Q04934 | ND |
| 2101 | 156.1 | *Mycobacterium* species protein sequence 50B. | geneseqp Y04998 | ND |
| 2102 | 156.1 | COBALAMIN SYNTHESIS PROTEIN. | sptrembl O30787 | ND |
| 2103 | 156.0 | ZINC FINGER PROTEIN. | sptrembl Q24081 | ND |
| 2104 | 156.0 | GLUCOSE-1-PHOSPHATE ADENYLYLTRANSFERASE PRECURSOR (EC 2.7.7.27) (ADP-GLUCOSE SYNTHASE) (ADP-GLUCOSE PYROPHOSPHORYLASE). | sptrembl Q42702 | ND |
| 2105 | 156.0 | CTD-BINDING SR-LIKE PROTEIN RA1. | sptrembl Q63624 | ND |
| 2106 | 156.0 | MUCIN 2 PRECURSOR (INTESTINAL MUCIN 2). | swissprot Q02817 | ND |
| 2107 | 156.0 | HYPOTHETICAL 9.2 KD PROTEIN. | sptrembl O59799 | ND |
| 2108 | 155.9 | YUKL PROTEIN. | sptrembl P71076 | ND |
| 2109 | 155.9 | DRPLA PROTEIN. | sptrembl P70200 | ND |
| 2110 | 155.8 | SIMILAR TO THE MYO-TYPE 'HELIX-LOOP-HELIX' DNA-BINDING DOMAIN SIGNATURE. | sptrembl Q20941 | ND |
| 2111 | 155.8 | CHITINASE PRECURSOR. | sptrembl Q42421 | ND |
| 2112 | 155.8 | WISKOTT-ALDRICH SYNDROME PROTEIN HOMOLOG 1. | sptrembl O36027 | ND |
| 2113 | 155.8 | GLUTENIN, HIGH MOLECULAR WEIGHT SUBUNIT DX5 PRECURSOR. | swissprot P10388 | ND |
| 2114 | 155.7 | F31E9.5 PROTEIN. | sptrembl O45429 | ND |
| 2115 | 155.7 | DRPLA PROTEIN. | sptrembl Q99495 | ND |
| 2116 | 155.6 | ORF YOL105C. | sptrembl Q12215 | ND |
| 2117 | 155.6 | SEA ANEMONE TOXIN 46 aa | pdb 1ATX | ND |

TABLE 1-continued

*Fusarium venenatum* ESTs

| Sequence Listing | zscore | Annotation | Database | Functional category |
|---|---|---|---|---|
| 2118 | 155.6 | HYPOTHETICAL 35.8 KD PROTEIN. | sptrembl O60096 | ND |
| 2119 | 155.6 | PROTEOPHOSPHOGLYCAN PRECURSOR (FRAGMENT). | sptrembl Q9Y076 | ND |
| 2120 | 155.6 | SPERM HISTONE P2 PRECURSOR (PROTAMINE P2). | swissprot P35298 | ND |
| 2121 | 155.4 | GLUE PROTEIN. | sptrembl Q27929 | ND |
| 2122 | 155.4 | 2,3-DIHYDROXYBIPHENYL DIOXYGENASE. | sptrembl Q50914 | ND |
| 2123 | 155.4 | HYPOTHETICAL 63.8 KD PROTEIN IN GUT1-RIM1 INTERGENIC REGION PRECURSOR. | swissprot P38739 | ND |
| 2124 | 155.4 | C11G6.3 PROTEIN. | sptrembl Q17909 | ND |
| 2125 | 155.4 | ZINC FINGER PROTEIN 41 (ZFP-41) (CTFIN92) (FRAGMENT). | swissprot Q02526 | ND |
| 2126 | 155.3 | DNAJ. | sptrembl O18427 | ND |
| 2127 | 155.2 | ESTS AU065732(E51179). | tremblnew BAA85201 | ND |
| 2128 | 155.1 | KIAA0691 PROTEIN. | sptrembl O75175 | ND |
| 2129 | 155.1 | *Mycobacterium* species protein sequence 50B. | geneseqp Y04998 | ND |
| 2130 | 155.1 | GLUCOAMYLASE. | tremblnew AAC49609 | ND |
| 2131 | 155.1 | W02A2.5 PROTEIN. | sptrembl Q9XUB4 | ND |
| 2132 | 155.0 | FOOT PROTEIN 1 PRECURSOR (FRAGMENT). | sptrembl O61476 | ND |
| 2133 | 154.9 | INSULIN-LIKE GROWTH FACTOR PRECURSOR (IGF) (FRAGMENT). | swissprot P22618 | ND |
| 2134 | 154.8 | HYPOTHETICAL 67.5 KD PROTEIN IN DBP6-COQ2 INTERGENIC REGION. | swissprot P53735 | ND |
| 2135 | 154.8 | PUTATIVE MEMBRANE PROTEIN. | tremblnew AAF23068 | ND |
| 2136 | 154.6 | PROBABLE SERINE HYDROXYMETHYLTRANSFERASE, CYTOSOLIC (EC 2.1.2.1) (SERINE METHYLASE) (GLYCINE HYDROXYMETHYLTRANSFERASE) (SHMT). | swissprot Q10104 | ND |
| 2137 | 154.5 | LD-VP80. | sptrembl Q9YMM2 | ND |
| 2138 | 154.5 | C45B11.4 PROTEIN. | sptrembl Q18640 | ND |
| 2139 | 154.5 | NEUROFILAMENT TRIPLET H PROTEIN (200 KD NEUROFILAMENT PROTEIN) (NF-H). | swissprot P19246 | ND |
| 2140 | 154.4 | PUTATIVE TRANSMEMBRANE PROTEIN. | tremblnew CAB59607 | ND |
| 2141 | 154.4 | ORF YOR053W. | sptrembl Q08428 | ND |
| 2142 | 154.2 | *A. oryzae* DEBY10.3 locus protein sequence. | geneseqp Y39872 | ND |
| 2143 | 154.2 | HYPOTHETICAL 57.2 KD PROTEIN. | sptrembl O68872 | ND |
| 2144 | 154.1 | PROBABLE ASPARAGINYL-TRNA SYNTHETASE, CYTOPLASMIC (EC 6.1.1.22) (ASPARAGINE--TRNA LIGASE) (ASNRS). | swissprot Q19722 | ND |
| 2145 | 154.1 | ORF_ID:O224#4. | sptrembl Q9ZBC2 | ND |
| 2146 | 154.1 | F54B11.1 PROTEIN. | sptrembl Q20744 | ND |
| 2147 | 154.1 | Y45F10B.3 PROTEIN. | sptrembl O62468 | ND |
| 2148 | 154.1 | EXTENSIN CLASS II PRECURSOR (CELL WALL HYDROXYPROLINE-RICH | sptrembl Q09084 | ND |

TABLE 1-continued

*Fusarium venenatum* ESTs

| Sequence Listing | zscore | Annotation | Database | Functional category |
|---|---|---|---|---|
| | | GLYCOPROTEIN) (HRGP) (TOML-4). | | |
| 2149 | 154.0 | CHITINASE. | sptrembl Q92223 | ND |
| 2150 | 153.9 | HIV A30S protein sequence #1. | geneseqp W99832 | ND |
| 2151 | 153.9 | T2K10.7 PROTEIN. | sptrembl Q9ZUJ1 | ND |
| 2152 | 153.9 | HYPOTHETICAL 58.7 KD PROTEIN. | sptrembl O94644 | ND |
| 2153 | 153.9 | ORF2 (FRAGMENT). | sptrembl Q9WAZ6 | ND |
| 2154 | 153.8 | HYPOTHETICAL 61.1 KD PROTEIN (FRAGMENT). | tremblnew CAB63715 | ND |
| 2155 | 153.7 | BRAIN-2 GENE. | sptrembl O73628 | ND |
| 2156 | 153.7 | RIBOSOMAL PROTEIN LARGE SUBUNIT 2. | sptrembl O99868 | ND |
| 2157 | 153.6 | DJ1042K10.4 (NOVEL PROTEIN) (FRAGMENT). | sptrembl O95512 | ND |
| 2158 | 153.6 | UNKNOWN PROTEIN. | sptrembl O04210 | ND |
| 2159 | 153.6 | F28C1.1 PROTEIN. | sptrembl Q19854 | ND |
| 2160 | 153.6 | HYPOTHETICAL 25.4 KD PROTEIN C4G9.14 IN CHROMOSOME I. | swissprot Q10244 | ND |
| 2161 | 153.6 | INSULIN-LIKE GROWTH FACTOR IB PRECURSOR (IGF-IB) (SOMATOMEDIN C). | swissprot P05019 | ND |
| 2162 | 153.6 | POLLEN ALLERGEN AMB P 5-A PRECURSOR (AMB P V-A). | swissprot P43174 | ND |
| 2163 | 153.6 | 159AA LONG HYPOTHETICAL PROTEIN. | sptrembl Q9YDR4 | ND |
| 2164 | 153.6 | PHOSPHOLIPASE A2 INHIBITOR I PRECURSOR (PLI-I). | sptrembl O57690 | ND |
| 2165 | 153.5 | COSMID F46H5. | sptrembl P90878 | ND |
| 2166 | 153.5 | STR1 (suppressor of telomeric repression-1) protein. | geneseqp R95601 | ND |
| 2167 | 153.4 | 111AA LONG HYPOTHETICAL PROTEIN. | sptrembl Q9YDA7 | ND |
| 2168 | 153.4 | GATA TRANSCRIPTION FACTOR 3. | sptrembl O49742 | ND |
| 2169 | 153.4 | HYPOTHETICAL 32.8 KD PROTEIN (FRAGMENT). | tremblnew CAB59245 | ND |
| 2170 | 153.4 | GTL2 GENE. | sptrembl O48591 | ND |
| 2171 | 153.3 | COSMID C37C3. | sptrembl Q22919 | ND |
| 2172 | 153.3 | STEERIN-1 PROTEIN (FRAGMENT). | tremblnew CAB66088 | ND |
| 2173 | 153.3 | PROTEIN-TYROSINE PHOSPHATASE, PUTATIVE. | tremblnew AAF11466 | ND |
| 2174 | 153.2 | Amino acid sequence of human desaturase gene contig 2 | geneseqp W95509 | ND |
| 2175 | 153.2 | GLYCOPROTEIN G-2 (FRAGMENT). | tremblnew CAB65677 | ND |
| 2176 | 153.2 | TONB PROTEIN. | tremblnew CAB53383 | ND |
| 2177 | 153.1 | BRAIN-2 GENE. | sptrembl O73628 | ND |
| 2178 | 153.1 | APEX NUCLEASE (FRAGMENT). | sptrembl O97870 | ND |
| 2179 | 153.1 | HYPOTHETICAL 57.2 KD PROTEIN. | sptrembl O68872 | ND |
| 2180 | 153.0 | H28G03.2 PROTEIN. | tremblnew AAC67404 | ND |
| 2181 | 153.0 | UL47 PRODUCT HOMOLOG. | tremblnew BAA82943 | ND |
| 2182 | 152.9 | ACUTE MYELOID LEUKEMIA 2 PROTEIN (ONCOGENE AML-2) (CORE-BINDING FACTOR, ALPHA 3 SUBUNIT) (CBF-ALPHA 3) (POLYOMAVIRUS ENHANCER BINDING PROTEIN 2 ALPHA C1 SUBUNIT) (PEBP2-ALPHA C1). | sptrembl Q13761 | ND |

TABLE 1-continued

*Fusarium venenatum* ESTs

| Sequence Listing | zscore | Annotation | Database | Functional category |
|---|---|---|---|---|
| 2183 | 152.9 | APOPTIN (VP3). | swissprot P54095 | ND |
| 2184 | 152.8 | SERINE-RICH PROTEIN. | sptrembl O94317 | ND |
| 2185 | 152.6 | ENVELOPE PROTEIN (FRAGMENT). | sptrembl Q85475 | ND |
| 2186 | 152.6 | DIACYLGLYCEROL ACYLCOA ACYLTRANSFERASE. | tremblnew AAF19345 | ND |
| 2187 | 152.4 | K06A9.1 PROTEIN. | sptrembl P91365 | ND |
| 2188 | 152.4 | F7F22.14. | tremblnew AAF24528 | ND |
| 2189 | 152.4 | CONSERVED HYPOTHETICAL PROTEIN. | tremblnew AAF09626 | ND |
| 2190 | 152.4 | ARABINOGALACTAN-PROTEIN. | sptrembl Q9ZT15 | ND |
| 2191 | 152.4 | NODULATION PROTEIN L (EC 2.3.1.-). | swissprot P28266 | ND |
| 2192 | 152.4 | TCJ2. | sptrembl Q26952 | ND |
| 2193 | 152.3 | HQP0376 PROTEIN. | tremblnew AAF23355 | ND |
| 2194 | 152.3 | LAMININ ALPHA-2 CHAIN PRECURSOR (LAMININ M CHAIN) (MEROSIN HEAVY CHAIN). | swissprot Q60675 | ND |
| 2195 | 152.3 | GAGA-581 ADF-2 ISOFORM. | sptrembl O18349 | ND |
| 2196 | 152.2 | FLGA insert stabilising polypeptide. | geneseqp W79128 | ND |
| 2197 | 152.2 | Recombinant transcription enhancer factor 1 GL2/3/5. | geneseqp W58603 | ND |
| 2198 | 152.1 | ACROSIN PRECURSOR (EC 3.4.21.10). | swissprot P48038 | ND |
| 2199 | 152.1 | SLIME MOLD (*D. DISCOIDEUM*) TRANSPOSON DIRS-1, COMPLETE, CLONE SB41. | sptrembl O96848 | ND |
| 2200 | 152.0 | TRANSCRIPTION TERMINATION FACTOR 1 (TRANSCRIPTION FACTOR). | sptrembl Q62187 | ND |
| 2201 | 152.0 | AGOUTI SWITCH PROTEIN PRECURSOR (AGOUTI SIGNALING PROTEIN) (FRAGMENT). | swissnew P79407 | ND |
| 2202 | 152.0 | RNA POLYMERASE II SUBUNIT 9. | sptrembl O74635 | ND |
| 2203 | 151.9 | DIVISION ABNORMALLY DELAYED PROTEIN PRECURSOR (DALLY PROTEIN). | swissprot Q24114 | ND |
| 2204 | 151.8 | ANTI-DEATH PROTEIN. | sptrembl O75353 | ND |
| 2205 | 151.7 | HYPOTHETICAL PROTEIN (ORF270/2) (FRAGMENT). | sptrembl Q05897 | ND |
| 2206 | 151.7 | PUTATIVE PHOSPHATE/PHOSPHOENOL-PYRUVATE TRANSLOCATOR PROTEIN. | tremblnew AAD20711 | ND |
| 2207 | 151.7 | COSMID R11G11. | sptrembl O16953 | ND |
| 2208 | 151.7 | W05B2.6 PROTEIN. | sptrembl Q9XVG3 | ND |
| 2209 | 151.6 | F3O9.1 PROTEIN. | tremblnew AAD34676 | ND |
| 2210 | 151.6 | ALTERNATIVE OXIDASE (FRAGMENT). | sptrembl Q26681 | ND |
| 2211 | 151.6 | CYC07 PROTEIN, S-PHASE SPECIFIC (FRAGMENT). | sptrembl Q42008 | ND |
| 2212 | 151.6 | SECRETORY MUCIN MUC6 (FRAGMENT). | sptrembl O15329 | ND |
| 2213 | 151.6 | PROBABLE B-TYPE CYTOCHROME. | swissprot P41955 | ND |
| 2214 | 151.5 | PROTEIN C4. | swissprot P17370 | ND |
| 2215 | 151.5 | PROTOCADHERIN 5 (FRAGMENT). | sptrembl O08964 | ND |
| 2216 | 151.4 | KIAA0442 PROTEIN (FRAGMENT). | sptrembl Q9Y4F2 | ND |

TABLE 1-continued

_Fusarium venenatum ESTs_

| Sequence Listing | zscore | Annotation | Database | Functional category |
|---|---|---|---|---|
| 2217 | 151.4 | F46B3.2 PROTEIN. | sptrembl Q9XV16 | ND |
| 2218 | 151.3 | SMUC-41 intestinal mucin. | geneseqp R12535 | ND |
| 2219 | 151.3 | HYPOTHETICAL 62.3 KD PROTEIN. | tremblnew CAB55180 | ND |
| 2220 | 151.3 | DNA-DIRECTED RNA POLYMERASE II LARGEST SUBUNIT (EC 2.7.7.6) (RPB1) (FRAGMENT). | swissprot P11414 | ND |
| 2221 | 151.3 | HTRA2-BETA (TRANSFORMER-2-BETA ISOFORM 3). | sptrembl Q15815 | ND |
| 2222 | 151.2 | ALLERGEN. | sptrembl O74682 | ND |
| 2223 | 151.2 | ZINC FINGER PROTEIN 37 (ZFP-37) (MALE GERM CELL SPECIFIC ZINC FINGER PROTEIN). | swissprot P17141 | ND |
| 2224 | 151.2 | I71-7 PRECURSOR. | sptrembl Q27320 | ND |
| 2225 | 151.1 | HYPOTHETICAL 33.4 KD PROTEIN IN RPL44B-RPC10 INTERGENIC REGION PRECURSOR. | swissprot P38844 | ND |
| 2226 | 151.1 | TRANSLATIONALLY CONTROLLED TUMOR PROTEIN HOMOLOG (TCTP). | swissprot Q10344 | ND |
| 2227 | 151.1 | F4P06. | sptrembl P79027 | ND |
| 2228 | 151.1 | PRE-S1, PRE-S2 AND S. | sptrembl O39887 | ND |
| 2229 | 151.0 | HYPOTHETICAL 15.5 KD PROTEIN. | sptrembl Q62882 | ND |
| 2230 | 151.0 | EXCRETORY/SECRETORY MUCIN MUC-4. | tremblnew AAD49341 | ND |
| 2231 | 151.0 | PROBABLE ATP-DEPENDENT RNA HELICASE DBP3 (HELICASE CA3). | swissprot P20447 | ND |
| 2232 | 151.0 | HYPOTHETICAL 57.2 KD PROTEIN. | sptrembl O68872 | ND |
| 2233 | 151.0 | F43G6.9 PROTEIN. | sptrembl Q20374 | ND |
| 2234 | 151.0 | GAG-POL POLYPROTEIN. | tremblnew AAF20282 | ND |
| 2235 | 150.9 | HYPOTHETICAL OXIDOREDUCTASE IN FHUD-OPUBD INTERGENIC REGION. | swissprot O32223 | ND |
| 2236 | 150.9 | PAC CLONE DJ1110N13 FROM 7P21-P22, COMPLETE SEQUENCE (FRAGMENT). | sptrembl O43376 | ND |
| 2237 | 150.9 | ALDOSE EPIMERASE FAMILY PROTEIN. | tremblnew AAF10324 | ND |
| 2238 | 150.9 | OSMOTIN-LIKE PROTEIN PRECURSOR. | swissnew Q41350 | ND |
| 2239 | 150.8 | W05G11.6 PROTEIN. | sptrembl O44906 | ND |
| 2240 | 150.8 | MYOSIN I HEAVY CHAIN KINASE (FRAGMENT). | sptrembl Q94488 | ND |
| 2241 | 150.8 | ORF3. | sptrembl Q9YL22 | ND |
| 2242 | 150.8 | PRP4. | geneseqp R29166 | ND |
| 2243 | 150.8 | Yeast ribosomal protein S7. | geneseqp W36115 | ND |
| 2244 | 150.7 | _Porphorymonas gingivalis_ protein PG106. | geneseqp Y34446 | ND |
| 2245 | 150.7 | RRNA ADENINE N-6-METHYLTRANSFERASE (EC 2.1.1.48) (MACROLIDE-LINCOSAMIDE-STREPTOGRAMIN B RESISTANCE PROTEIN) (ERYTHROMYCIN RESISTANCE PROTEIN) (NMT). | swissnew P07287 | ND |
| 2246 | 150.7 | HYPOTHETICAL 10.5 KD PROTEIN C31A2.13C IN CHROMOSOME I. | swissprot Q09730 | ND |

TABLE 1-continued

*Fusarium venenatum* ESTs

| Sequence Listing | zscore | Annotation | Database | Functional category |
|---|---|---|---|---|
| 2247 | 150.7 | Human herpesvirus 8 (HHV-8) macrophage inhibitory protein-1A. | geneseqp W40104 | ND |
| 2248 | 150.7 | SPLICING FACTOR, ARGININE/SERINE-RICH 10 (PUTATIVE MYELIN REGULATORY FACTOR 1) (MRF-1) (FRAGMENT). | swissprot Q60701 | ND |
| 2249 | 150.7 | MEGF6. | sptrembl O88281 | ND |
| 2250 | 150.6 | NLPD PROTEIN. | tremblnew CAA06881 | ND |
| 2251 | 150.6 | MITOCHONDRIAL PHOSPHATE CARRIER PROTEIN (PHOSPHATE TRANSPORT PROTEIN) (PTP) (MITOCHONDRIAL IMPORT RECEPTOR) (P32). | swissprot P23641 | ND |
| 2252 | 150.6 | ARABINOGALACTAN-PROTEIN. | sptrembl Q9ZT16 | ND |
| 2253 | 150.5 | Human secreted protein cb96_10. | geneseqp Y05319 | ND |
| 2254 | 150.5 | COLLAGEN ALPHA 1(VIII) CHAIN PRECURSOR (ENDOTHELIAL COLLAGEN). | swissprot P14282 | ND |
| 2255 | 150.5 | MATING-TYPE PROTEIN BETA 1. | sptrembl Q9Y7A5 | ND |
| 2256 | 150.5 | Peptide encoded by HRGP gene cassette. | geneseqp Y01285 | ND |
| 2257 | 150.5 | DJ347H13.5 (NOVEL PROTEIN SIMILAR TO YEAST DNA-DIRECTED RNA POLYMERASE III 25 KD POLYPEPTIDE). | sptrembl Q9Y535 | ND |
| 2258 | 150.4 | TRANSCRIPTION TERMINATION FACTOR RHO. | swissprot P52154 | ND |
| 2259 | 150.4 | PUTATIVE ZINC METALLOPROTEASE. | sptrembl O68338 | ND |
| 2260 | 150.4 | SPERM-SPECIFIC PROTEIN PHI-1. | swissprot Q04621 | ND |
| 2261 | 150.4 | C26C6.1 PROTEIN. | sptrembl Q18210 | ND |
| 2262 | 150.2 | Human tastin. | geneseqp R94900 | ND |
| 2263 | 150.2 | ARABINOGALACTAN-PROTEIN PRECURSOR. | sptrembl Q40786 | ND |
| 2264 | 150.2 | A201A-RESISTANCE ATP-BINDING PROTEIN (ARD1). | sptrembl Q53912 | ND |
| 2265 | 150.2 | Human secreted protein encoded by gene No. 31. | geneseqp Y27730 | ND |
| 2266 | 150.1 | CHROMOSOME IV READING FRAME ORF YDL074C. | sptrembl Q07457 | ND |
| 2267 | 150.1 | SERINE-THREONINE PROTEIN KINASE (FRAGMENT). | sptrembl P78975 | ND |
| 2268 | 150.1 | EBNA-2 NUCLEAR PROTEIN. | sptrembl Q07701 | ND |
| 2269 | 150.1 | 1-PHOSPHATIDYLINOSITOL-4,5-BISPHOSPHATE PHOSPHODIESTERASE 1 (EC 3.1.4.11). | tremblnew CAB52721 | ND |
| 2270 | 150.1 | SUPEROXIDE DISMUTASE (EC 1.15.1.1) (FRAGMENT). | sptrembl Q59593 | ND |
| 2271 | 150.1 | BILE ACID-COENZYME A LIGASE (EC 6.-.-.-). | swissprot P19409 | ND |
| 2272 | 150.0 | SPLICING FACTOR SRP55-1 (FRAGMENT). | sptrembl Q9XSS6 | ND |
| 2273 | 149.9 | C06A1.6 PROTEIN. | sptrembl Q9XVX3 | ND |
| 2274 | 149.9 | PROLINE-RICH PROTEIN PRECURSOR. | sptrembl Q41122 | ND |
| 2275 | 149.9 | NEUROGENIC LOCUS NOTCH HOMOLOG | swissprot P31695 | ND |

TABLE 1-continued

Fusarium venenatum ESTs

| Sequence Listing | zscore | Annotation | Database | Functional category |
|---|---|---|---|---|
| | | PROTEIN 4 PRECURSOR (TRANSFORMING PROTEIN INT-3). | | |
| 2276 | 149.9 | EXPANSIN 18 (FRAGMENT). | tremblnew CAB65694 | ND |
| 2277 | 149.9 | HYPOTHETICAL 31.2 KD PROTEIN RV0891C. | swissnew Q10551 | ND |
| 2278 | 149.9 | SUPPRESSOR PROTEIN SRP40. | swissprot P32583 | ND |
| 2279 | 149.8 | SPERM PROTEIN. | sptrembl Q24404 | ND |
| 2280 | 149.8 | HEPATITIS A VIRUS CELLULAR RECEPTOR 1 LONG FORM (HEPATITIS A VIRUS CELLULAR RECEPTOR 1 SHORT FORM). | sptrembl O46598 | ND |
| 2281 | 149.8 | CODED FOR BY C. ELEGANS CDNA YK117B5.5. | sptrembl O01489 | ND |
| 2282 | 149.8 | HYPOTHETICAL 41.0 KD PROTEIN. | sptrembl O64895 | ND |
| 2283 | 149.7 | SALIVARY GLUE PROTEIN SGS-3 PRECURSOR. | swissprot P13730 | ND |
| 2284 | 149.7 | GTG START CODON. | sptrembl Q45316 | ND |
| 2285 | 149.6 | SIM1 PROTEIN. | swissprot P40472 | ND |
| 2286 | 149.6 | HYPOTHETICAL 15.1 KD PROTEIN (FRAGMENT). | sptrembl P96909 | ND |
| 2287 | 149.6 | HYPOTHETICAL 32.8 KD PROTEIN. | tremblnew AAF10253 | ND |
| 2288 | 149.5 | LOW-SPECIFICITY D-THREONINE ALDOLASE. | tremblnew BAA86032 | ND |
| 2289 | 149.5 | TROPOMYOSIN 1 (ISOFORM 34). | sptrembl Q24425 | ND |
| 2290 | 149.5 | C HORDEIN PRECURSOR. | sptrembl Q40055 | ND |
| 2291 | 149.4 | LATENCY-ASSOCIATED TRANSCRIPT MRNA. | sptrembl Q69079 | ND |
| 2292 | 149.4 | U14 PROTEIN. | sptrembl Q9WT50 | ND |
| 2293 | 149.4 | Mycobacterium species protein sequence 8A. | geneseqp Y04786 | ND |
| 2294 | 149.4 | HYPOTHETICAL 59.4 KD PROTEIN. | sptrembl P74381 | ND |
| 2295 | 149.3 | C03H5.1 PROTEIN. | sptrembl O16660 | ND |
| 2296 | 149.3 | Tissue cement protein fragment encoded by clone 24. | geneseqp Y13498 | ND |
| 2297 | 149.3 | C. parvum p23 protein fragment. | geneseqp W54052 | ND |
| 2298 | 149.2 | Human galectin amino acid sequence. | geneseqp W61955 | ND |
| 2299 | 149.2 | MYBS PROTEIN. | sptrembl O15816 | ND |
| 2300 | 149.2 | TRANSCRIPTION FACTOR SOX-9. | swissprot P48434 | ND |
| 2301 | 149.1 | Mycobacterium species protein sequence 21B'. | geneseqp Y04881 | ND |
| 2302 | 149.1 | A serine/threonine protein kinase. | geneseqp W67639 | ND |
| 2303 | 149.1 | Mycobacterium species protein sequence 50B. | geneseqp Y04998 | ND |
| 2304 | 149.1 | T01D3.6B PROTEIN. | sptrembl O02364 | ND |
| 2305 | 149.0 | PHEROPHORIN III (FRAGMENT). | sptrembl P93694 | ND |
| 2306 | 149.0 | Human secreted protein encoded by gene 89 clone HLHFP03. | geneseqp Y02738 | ND |
| 2307 | 149.0 | HYPOTHETICAL 42.0 KD PROTEIN. | sptrembl O28535 | ND |
| 2308 | 149.0 | HYPOTHETICAL 20.4 KD PROTEIN (FRAGMENT). | sptrembl Q9Y4N2 | ND |
| 2309 | 148.8 | SIMILAR TO PART OF DISEASE RESISTANCE PROTEIN. | tremblnew AAD55639 | ND |
| 2310 | 148.8 | PROLINE-RICH. | sptrembl Q94273 | ND |
| 2311 | 148.8 | KTI12 PROTEIN. | swissprot P34253 | ND |
| 2312 | 148.8 | FERRIC REDUCTASE | sptrembl O94727 | ND |

TABLE 1-continued

Fusarium venenatum ESTs

| Sequence Listing | zscore | Annotation | Database | Functional category |
|---|---|---|---|---|
| | | TRANSMEMBRANE COMPONENT. | | |
| 2313 | 148.8 | AMINOPEPTIDASE 313 aa, chain A + B | pdb 1AZW | ND |
| 2314 | 148.7 | DNA-DIRECTED RNA POLYMERASE II LARGEST SUBUNIT (EC 2.7.7.6). | swissprot P16356 | ND |
| 2315 | 148.7 | KIAA0561 PROTEIN (FRAGMENT). | tremblnew AAD22670 | ND |
| 2316 | 148.7 | DNA-DIRECTED RNA POLYMERASE II LARGE (205 KD) SUBUNIT (EC 2.7.7.6) (FRAGMENT). | sptrembl Q99367 | ND |
| 2317 | 148.7 | PUTATIVE EXTENSIN. | sptrembl Q9ZNU3 | ND |
| 2318 | 148.6 | SWI/SNF RELATED, MATRIX ASSOCIATED, ACTIN DEPENDENT REGULATOR OF CHROMATIN, SUBFAMILY A, MEMBER 4 (BRG1) (FRAGMENT). | sptrembl O35845 | ND |
| 2319 | 148.6 | HIGH MOLECULAR MASS NUCLEAR ANTIGEN (FRAGMENT). | sptrembl O57580 | ND |
| 2320 | 148.6 | PUTATIVE SEC24-LIKE COPII PROTEIN. | tremblnew AAF20236 | ND |
| 2321 | 148.6 | SIMILAR TO EPOXIDE HYDROLASES. | tremblnew BAA84627 | ND |
| 2322 | 148.5 | HYPOTHETICAL 23.8 KD PROTEIN (FRAGMENT). | sptrembl Q9XSR6 | ND |
| 2323 | 148.5 | GLUCOAMYLASE. | tremblnew AAC49609 | ND |
| 2324 | 148.5 | HYPOTHETICAL 27.2 KD PROTEIN. | sptrembl O50997 | ND |
| 2325 | 148.5 | FLBD. | tremblnew AAF01466 | ND |
| 2326 | 148.5 | CUTICLE COLLAGEN 34. | swissprot P34687 | ND |
| 2327 | 148.5 | HYPOTHETICAL 60.7 KD PROTEIN C26A3.15C IN CHROMOSOME I. | swissprot Q10168 | ND |
| 2328 | 148.4 | SPERM PROTAMINE P1. | swissprot P42131 | ND |
| 2329 | 148.4 | T. gondii immunogenic protein. | geneseqp Y29061 | ND |
| 2330 | 148.4 | Human CTR. | geneseqp R37424 | ND |
| 2331 | 148.4 | CYCLIC AMP PHOSPHODIESTERASE. | tremblnew AAC00042 | ND |
| 2332 | 148.4 | Human secreted protein encoded by gene No. 47. | geneseqp Y27757 | ND |
| 2333 | 148.3 | HumB3V1 humanised variable light chain. | geneseqp R95212 | ND |
| 2335 | 148.2 | C04G2.8 PROTEIN. | sptrembl Q17626 | ND |
| 2336 | 148.2 | KIAA0755 PROTEIN. | sptrembl O94855 | ND |
| 2337 | 148.2 | MATING-TYPE PROTEIN A-ALPHA Y3. | swissprot P37934 | ND |
| 2338 | 148.1 | A human tumour necrosis factor-R2-like proteins (TR2P)-2. | geneseqp Y28450 | ND |
| 2339 | 148.1 | T21B6.3 PROTEIN. | sptrembl Q22631 | ND |
| 2340 | 148.1 | HYPOTHETICAL 62.8 KD PROTEIN. | sptrembl O23187 | ND |
| 2341 | 148.1 | CATHEPSIN L PRECURSOR (EC 3.4.22.15) (MAJOR EXCRETED PROTEIN) (MEP) (CYCLIC PROTEIN-2) (CP-2). | swissprot P07154 | ND |
| 2342 | 148.1 | FAMILY 19 CHITINASE (PRYA1 ORF) PRECURSOR. | sptrembl Q9WXI9 | ND |
| 2343 | 148.0 | DNA HELICASE/PRIMASE COMPLEX ASSOCIATED PROTEIN. | swissprot P10192 | ND |
| 2344 | 148.0 | NO COUNTERPART IN HSV-1 OR VZV. | sptrembl O39244 | ND |
| 2345 | 148.0 | DIHYDRODIOL DEHYDROGENASE. | sptrembl Q51748 | ND |

TABLE 1-continued

*Fusarium venenatum* ESTs

| Sequence Listing | zscore | Annotation | Database | Functional category |
|---|---|---|---|---|
| 2346 | 148.0 | EXTENSIN CLASS II PRECURSOR (CELL WALL HYDROXYPROLINE-RICH GLYCOPROTEIN) (HRGP) (TOML-4). | sptrembl Q09084 | ND |
| 2347 | 148.0 | Human secreted protein encoded by gene 64 clone HMWEX24. | geneseqp W74793 | ND |
| 2348 | 148.0 | T13F2.6 PROTEIN. | sptrembl Q94049 | ND |
| 2349 | 148.0 | ENVELOPE GLYCOPROTEIN (FRAGMENT). | sptrembl O39337 | ND |
| 2350 | 147.9 | COAT PROTEIN. | sptrembl Q65970 | ND |
| 2351 | 147.8 | SOX100B PROTEIN. | tremblnew CAB63903 | ND |
| 2352 | 147.8 | NOLC PROTEIN. | swissprot P26508 | ND |
| 2353 | 147.8 | HYPOTHETICAL 47.8 KD PROTEIN. | sptrembl O60158 | ND |
| 2354 | 147.7 | MEROZOITE SURFACE PROTEIN-1 (FRAGMENT). | sptrembl O00879 | ND |
| 2355 | 147.7 | BASEMENT MEMBRANE PROTEOGLYCAN PRECURSOR (PERLECAN HOMOLOG). | swissprot Q06561 | ND |
| 2356 | 147.7 | PHYTOCHROME (FRAGMENT). | sptrembl P93057 | ND |
| 2357 | 147.7 | MELANOCYTE PROTEIN 17 PRECURSOR (FRAGMENT). | sptrembl O97884 | ND |
| 2358 | 147.7 | ANTHER-SPECIFIC PROTEIN SF18 PRECURSOR (FRAGMENT). | swissprot P22357 | ND |
| 2359 | 147.6 | F17C11.1 PROTEIN. | sptrembl Q19521 | ND |
| 2360 | 147.6 | C4SR PROTEIN. | sptrembl Q91708 | ND |
| 2361 | 147.5 | HYPOTHETICAL 112.1 KD PROTEIN C06G4.1 IN CHROMOSOME III. | swissprot P34307 | ND |
| 2362 | 147.5 | RECA PROTEIN (FRAGMENT). | tremblnew AAF25430 | ND |
| 2363 | 147.5 | CODED FOR BY *C. ELEGANS* CDNA YK37G1.5. | sptrembl Q20649 | ND |
| 2364 | 147.5 | MUCIN (FRAGMENT). | sptrembl Q14879 | ND |
| 2365 | 147.3 | REPA1 PROTEIN. | tremblnew CAB56190 | ND |
| 2366 | 147.3 | F32D1.3 PROTEIN. | sptrembl O16296 | ND |
| 2367 | 147.3 | ZINC-PROTEASE TRANSPORTER. | sptrembl O67995 | ND |
| 2368 | 147.3 | *Chlamydia pneumoniae* protein not found in *C. trachomatis*. | geneseqp Y35721 | ND |
| 2369 | 147.2 | HUNCHBACK PROTEIN (HB). | sptrembl O62537 | ND |
| 2370 | 147.2 | EXTENSIN. | sptrembl Q9ZWT0 | ND |
| 2371 | 147.2 | CODED FOR BY *C. ELEGANS* CDNA YK150F2.5. | sptrembl O01681 | ND |
| 2372 | 147.2 | SIMILARITY TO SCAMP37. | sptrembl Q9ZTX0 | ND |
| 2373 | 147.2 | A-lineage conotoxin SmIII prepropeptide. | geneseqp W12767 | ND |
| 2374 | 147.2 | ROX1 REPRESSOR (HYPOXIC FUNCTION REPRESSOR) (HEME-DEPENDENT REPRESSION FACTOR). | swissprot P25042 | ND |
| 2375 | 147.2 | ALPHA-AMYLASE INHIBITOR BMAI-1 PRECURSOR (ALLERGEN HOR V 1) (ALPHA-AMYLASE FLOUR INHIBITOR) (FRAGMENT). | swissprot P16968 | ND |
| 2376 | 147.1 | EXTENSIN CLASS I PROTEIN PRECURSOR (EXTENSIN-LIKE PROTEIN). | sptrembl Q41707 | ND |
| 2377 | 147.1 | PARVALBUMIN ALPHA (PA 4.97). | swissprot P18087 | ND |

TABLE 1-continued

Fusarium venenatum ESTs

| Sequence Listing | zscore | Annotation | Database | Functional category |
|---|---|---|---|---|
| 2378 | 147.1 | P20-gammaZ zein protein sequence. | geneseqp W22526 | ND |
| 2379 | 147.1 | HYPOTHETICAL 30.2 KD PROTEIN. | sptrembl P71863 | ND |
| 2380 | 147.1 | F36F2.2 PROTEIN. | sptrembl O62233 | ND |
| 2381 | 147.0 | PROLINE RICH PROTEIN PRECURSOR. | sptrembl Q43558 | ND |
| 2382 | 147.0 | ORF 50. | sptrembl Q66652 | ND |
| 2383 | 147.0 | HYPOTHETICAL 14.6 KD PROTEIN. | sptrembl O67892 | ND |
| 2384 | 147.0 | POLYPROTEIN (FRAGMENT). | sptrembl Q9YK32 | ND |
| 2385 | 147.0 | RNA POLYMERASE (FRAGMENT). | sptrembl O37355 | ND |
| 2386 | 146.9 | MYOSIN REGULATORY LIGHT CHAIN INTERACTING PROTEIN MIR. | tremblnew AAF18974 | ND |
| 2387 | 146.9 | Human h1CED-6 proline/serine rich region. | geneseqp Y27251 | ND |
| 2388 | 146.9 | MEGF6 (FRAGMENT). | sptrembl O75095 | ND |
| 2389 | 146.9 | ESRS4. | sptrembl Q9Y1B1 | ND |
| 2390 | 146.8 | HYPOTHETICAL PROTEIN E-115. | swissprot P03290 | ND |
| 2391 | 146.8 | ETS-RELATED PROTEIN ERM (ETS TRANSLOCATION VARIANT 5). | swissprot P41161 | ND |
| 2392 | 146.7 | PROBABLE IMIDAZOLEGLYCEROL-PHOSPHATE DEHYDRATASE (EC 4.2.1.19) (IGPD). | swissprot Q58109 | ND |
| 2393 | 146.7 | Streptococcus pneumoniae PspA central region. | geneseqp W14579 | ND |
| 2394 | 146.7 | PUTATIVE ZINC FINGER PROTEIN. | sptrembl O74256 | ND |
| 2395 | 146.7 | PROLINE-RICH PROTEOGLYCAN PRPG2. | sptrembl Q07611 | ND |
| 2396 | 146.7 | HORMONE/GROWTH FACTOR 290 aa, chain B + E | pdb 1QCT | ND |
| 2397 | 146.6 | ORF IIL. | sptrembl Q65223 | ND |
| 2398 | 146.6 | LL5 MRNA. | sptrembl Q63312 | ND |
| 2399 | 146.6 | HYPOTHETICAL PROTEIN (FRAGMENT). | tremblnew BAA87194 | ND |
| 2400 | 146.5 | F55C9.9 PROTEIN. | sptrembl Q9XUZ2 | ND |
| 2401 | 146.5 | RAS-LIKE GTP-BINDING PROTEIN RYL2. | swissprot P41925 | ND |
| 2402 | 146.4 | HYPOTHETICAL 40.1 KD PROTEIN. | sptrembl O06798 | ND |
| 2403 | 146.4 | EIB PROTEIN, LARGE T-ANTIGEN. | swissprot P04491 | ND |
| 2404 | 146.4 | PUTATIVE ABC TRANSPORTER. | tremblnew CAB58409 | ND |
| 2405 | 146.4 | DUAL-SPECIFICITY TYROSINE-(Y)-PHOSPHORYLATION REGULATED KINASE (EC 2.7.1.-) (PROTEIN KINASE MINIBRAIN HOMOLOG) (MP86). | swissprot Q61214 | ND |
| 2406 | 146.4 | CYTOCHROME C OXIDASE POLYPEPTIDE II (EC 1.9.3.1). | sptrembl O47580 | ND |
| 2407 | 146.4 | EXTENSIN PRECURSOR (CELL WALL HYDROXYPROLINE-RICH GLYCOPROTEIN) (HRGP) (PTEL 15). | sptrembl Q06446 | ND |
| 2408 | 146.3 | F38C2.6 PROTEIN. | sptrembl O45492 | ND |
| 2409 | 146.3 | GLYCOSYLTRANSFERASE-LIKE PROTEIN. | tremblnew CAB42905 | ND |

TABLE 1-continued

Fusarium venenatum ESTs

| Sequence Listing | zscore | Annotation | Database | Functional category |
|---|---|---|---|---|
| 2410 | 146.3 | TONB PROTEIN. | tremblnew CAB64965 | ND |
| 2411 | 146.3 | *Drosophila trithorax* zinc finger domain 1266–1483. | geneseqp R38471 | ND |
| 2412 | 146.3 | VESICLE-ASSOCIATED PROTEIN (VAP-1) (FRAGMENT). | swissprot Q06155 | ND |
| 2413 | 146.3 | Human mDia Rho targeting protein. | geneseqp W76734 | ND |
| 2414 | 146.2 | ATP SYNTHASE A CHAIN (EC 3.6.1.34). | sptrembl Q95782 | ND |
| 2415 | 146.2 | F35G12.10 PROTEIN. | sptrembl Q20053 | ND |
| 2416 | 146.2 | CTG3A (FRAGMENT). | sptrembl Q9Y417 | ND |
| 2417 | 146.2 | ROD SHAPE-DETERMINING PROTEIN MREC (MREC). | sptrembl Q9ZCH5 | ND |
| 2418 | 146.2 | KRAB-ZINC FINGER PROTEIN KZF-1. | sptrembl P70590 | ND |
| 2419 | 146.2 | SEIZURE-RELATED GENE PRODUCT 6 TYPE 3 PRECURSOR. | sptrembl Q62224 | ND |
| 2420 | 146.2 | HYPOTHETICAL 172.2 KD PROTEIN. | tremblnew CAB41133 | ND |
| 2421 | 146.1 | EF-G. | tremblnew BAA88140 | ND |
| 2422 | 146.1 | *Actinomadura flexuosa* xylanase. | geneseqp R94881 | ND |
| 2423 | 146.1 | AMYLOID BETA (A4) PRECURSOR PROTEIN-BINDING, FAMILY B, MEMBER 1 (FE65) (FRAGMENT). | sptrembl O08642 | ND |
| 2424 | 146.0 | HUNCHBACK PROTEIN (HB) (FRAGMENTS). | sptrembl O46256 | ND |
| 2425 | 146.0 | HYPOTHETICAL 11.1 KD PROTEIN (ORF 1). | swissprot P11907 | ND |
| 2426 | 146.0 | WW DOMAIN BINDING PROTEIN 5 (FRAGMENT). | sptrembl O08549 | ND |
| 2427 | 146.0 | NADH DEHYDROGENASE SUBUNIT 4 (FRAGMENT). | sptrembl Q96091 | ND |
| 2428 | 146.0 | DBL ALPHA PROTEIN (FRAGMENT). | sptrembl Q9XZA9 | ND |
| 2429 | 146.0 | PUTATIVE KUP ZINC-FINGER {N-TERMINAL, CLONE EST07388}. | tremblnew G407623 | ND |
| 2430 | 145.9 | Canine hookworm Neutrophil Inhibitory Factor isoform 1P. | geneseqp R52986 | ND |
| 2431 | 145.9 | PUTATIVE EXTENSIN. | sptrembl Q9ZNU3 | ND |
| 2432 | 145.9 | NIF-SPECIFIC REGULATORY PROTEIN. | swissprot P09133 | ND |
| 2433 | 145.9 | Amino acid sequence of a virulence factor encoded by ORF25510. | geneseqp Y29194 | ND |
| 2434 | 145.8 | MITOCHONDRIAL CAPSULE SELENOPROTEIN. | sptrembl O70613 | ND |
| 2435 | 145.8 | MUCIN-LIKE PROTEIN. | sptrembl O61035 | ND |
| 2436 | 145.8 | TRANSCRIPTION FACTOR MTF-1. | sptrembl Q9YGM3 | ND |
| 2437 | 145.8 | W02B12.2 PROTEIN. | sptrembl Q23120 | ND |
| 2438 | 145.8 | ACIDIC PROLINE-RICH PROTEIN PRP33 PRECURSOR. | swissprot P04474 | ND |
| 2439 | 145.7 | KINESIN-LIKE DNA BINDING PROTEIN. | sptrembl O94814 | ND |
| 2440 | 145.7 | TRBH PROTEIN. | swissprot P19381 | ND |
| 2441 | 145.7 | *Mycobacterium tuberculosis* antigen TbH-29. | geneseqp W64359 | ND |
| 2442 | 145.6 | HYPOTHETICAL 13.0 KD PROTEIN IN GIT1-PAU3 INTERGENIC REGION. | swissprot P25609 | ND |
| 2443 | 145.6 | METALLOTHIONEIN-III (MT-III) (GROWTH | swissprot P37361 | ND |

TABLE 1-continued

Fusarium venenatum ESTs

| Sequence Listing | zscore | Annotation | Database | Functional category |
|---|---|---|---|---|
| | | INHIBITORY FACTOR) (GIF). | | |
| 2444 | 145.6 | HISTONE H3. | swissprot P07041 | ND |
| 2445 | 145.6 | Amino acid sequence of a virulence factor encoded by ORF6325. | geneseqp Y29127 | ND |
| 2446 | 145.5 | NADH DEHYDROGENASE SUBUNIT 4 (FRAGMENT). | tremblnew AAC98214 | ND |
| 2447 | 145.5 | ORF C1. | sptrembl Q67591 | ND |
| 2448 | 145.5 | HYPOTHETICAL 13.2 KD PROTEIN IN RPS4A-BAT2 INTERGENIC REGION. | swissprot P47174 | ND |
| 2449 | 145.5 | 152AA LONG HYPOTHETICAL PROTEIN. | sptrembl Q9YG78 | ND |
| 2450 | 145.5 | LATE EXPRESSION FACTOR 6. | sptrembl Q9YMT6 | ND |
| 2451 | 145.5 | SPLICING FACTOR SRP54. | sptrembl O61646 | ND |
| 2452 | 145.5 | Human neurofilament-M mutant protein fragment 89. | geneseqp Y20807 | ND |
| 2453 | 145.4 | F24J5.8 PROTEIN. | tremblnew AAD49974 | ND |
| 2454 | 145.3 | DNA POLYMERASE (FRAGMENT). | sptrembl Q9YRJ7 | ND |
| 2455 | 145.3 | SERRATEB. | sptrembl Q9YHU2 | ND |
| 2456 | 145.3 | SPROUTY 2. | tremblnew AAD56005 | ND |
| 2457 | 145.2 | Fragment of human secreted protein encoded by gene 54. | geneseqp Y36675 | ND |
| 2458 | 145.2 | 133AA LONG HYPOTHETICAL PROTEIN. | sptrembl Q9YDU6 | ND |
| 2459 | 145.2 | KIAA1103 PROTEIN (FRAGMENT). | tremblnew BAA83055 | ND |
| 2460 | 145.2 | K07E8.11 PROTEIN. | sptrembl O16693 | ND |
| 2461 | 145.2 | HEMOGLOBIN ALPHA-B CHAIN. | swissprot P51465 | ND |
| 2462 | 145.1 | HYDROXYPROLINE-RICH GLYCOPROTEIN. | sptrembl Q40692 | ND |
| 2463 | 145.1 | NAD(P)H-DEPENDENT XYLOSE REDUCTASE (EC 1.1.1.-) (XR). | swissprot P78736 | ND |
| 2464 | 145.1 | ASPARTATE TRANSAMINASE. | sptrembl P72859 | ND |
| 2465 | 145.1 | GLYCOPROTEIN G-2 (FRAGMENT). | tremblnew CAB65677 | ND |
| 2466 | 145.1 | Glucose repressor CRE1 of *T. reesei*. | geneseqp W13846 | ND |
| 2467 | 145.0 | HOMEOBOX PROTEIN ALX3 (FRAGMENT). | sptrembl O95075 | ND |
| 2468 | 145.0 | HIV-1 ISOLATE 93BR020 FROM BRAZIL COMPLETE GENOME. | sptrembl O70890 | ND |
| 2469 | 145.0 | WASP INTERACTING PROTEIN. | sptrembl O43516 | ND |
| 2470 | 145.0 | BASIC DOMAIN LEUCINE ZIPPER TRANSCRIPTION FACTOR. | sptrembl Q9W6B1 | ND |
| 2471 | 144.9 | VASOPRESSIN REGULATED WATER CHANNEL. | sptrembl Q9Y169 | ND |
| 2472 | 144.9 | PRP8 PROTEIN HOMOLOGUE. | sptrembl O15881 | ND |
| 2473 | 144.9 | GLUE PROTEIN. | sptrembl Q27423 | ND |
| 2474 | 144.9 | MITOCHONDIA ASSOCIATED CYSTEINE-RICH PROTEIN SMCP. | sptrembl Q64298 | ND |
| 2475 | 144.9 | TREACLE PROTEIN (TREACHER COLLINS SYNDROME PROTEIN). | swissprot Q13428 | ND |
| 2476 | 144.8 | MIE2. | sptrembl Q98683 | ND |
| 2477 | 144.8 | LATE 100 KD PROTEIN. | swissprot P11824 | ND |
| 2478 | 144.7 | HYPOTHETICAL 6.3 KD PROTEIN T23F2.5 IN CHROMOSOME X. | swissprot Q22702 | ND |

TABLE 1-continued

*Fusarium venenatum* ESTs

| Sequence Listing | zscore | Annotation | Database | Functional category |
|---|---|---|---|---|
| 2479 | 144.7 | HEPATITIS A VIRUS RECEPTOR. | sptrembl O18984 | ND |
| 2480 | 144.7 | Peptide encoded by HRGP gene cassette incorporating a GAGP construct. | geneseqp Y01282 | ND |
| 2481 | 144.7 | HYPOTHETICAL PROTEIN (FRAGMENT). | sptrembl P72068 | ND |
| 2482 | 144.7 | NCK-ASSOCIATED PROTEIN NAP5 (FRAGMENT). | sptrembl O14513 | ND |
| 2483 | 144.7 | AMPHIOXUS OTX TRANSCRIPTION FACTOR. | sptrembl O45024 | ND |
| 2484 | 144.7 | *A. oryzae* DEBY 10.3 locus protein sequence. | geneseqp Y39872 | ND |
| 2485 | 144.6 | Cyn dI derived from clone 22 (C22). | geneseqp R37919 | ND |
| 2486 | 144.6 | HYPOTHETICAL 14.8 KD PROTEIN. | sptrembl O43034 | ND |
| 2487 | 144.6 | TRISTETRAPROLINE (TTP) (TIS11A) (TIS11) (ZFP-36) (GROWTH FACTOR-INDUCIBLE NUCLEAR PROTEIN NUP475) (TPA INDUCED SEQUENCE 11). | swissprot P22893 | ND |
| 2488 | 144.6 | MACROSIALIN PRECURSOR (CD68). | swissprot P31996 | ND |
| 2489 | 144.5 | SERINE PROTEASE INHIBITOR-3. | sptrembl O77418 | ND |
| 2490 | 144.5 | SPERM PROTAMINE P1. | swissprot P35311 | ND |
| 2491 | 144.5 | HYPOTHETICAL 63.2 KD PROTEIN. | sptrembl O59725 | ND |
| 2492 | 144.5 | ANGIOGENIN (EC 3.1.27.-). | swissprot P31347 | ND |
| 2493 | 144.5 | L549.6. | sptrembl O60967 | ND |
| 2494 | 144.5 | Fibrinogenolytic protein #4 from snake venom. | geneseqp R20557 | ND |
| 2495 | 144.5 | Sequence of spermatozoal antigen peptide. | geneseqp P40632 | ND |
| 2496 | 144.5 | CYSTEINE-RICH PROTEIN (FRAGMENT). | sptrembl Q16861 | ND |
| 2497 | 144.5 | *Streptococcus pneumoniae* PspA central region. | geneseqp W14576 | ND |
| 2498 | 144.5 | CARBAMOYL-PHOSPHATE SYNTHETASE SUBUNIT A. | sptrembl O30576 | ND |
| 2499 | 144.4 | Acylcoenzyme A:cholesterol acyltransferase partial sequence. | geneseqp W43413 | ND |
| 2500 | 144.4 | CAMP-SPECIFIC PHOSPHODIESTERASE. | sptrembl O35470 | ND |
| 2501 | 144.4 | HYPOTHETICAL 21.7 KD PROTEIN. | sptrembl O67497 | ND |
| 2502 | 144.4 | RNA BINDING PROTEIN (FRAGMENT). | tremblnew BAA83714 | ND |
| 2503 | 144.4 | HYPOTHETICAL 26.2 KD PROTEIN. | sptrembl O30169 | ND |
| 2504 | 144.4 | SPDA PROTEIN. | sptrembl Q07193 | ND |
| 2505 | 144.3 | HIGH CYSTEINE KERATIN-ASSOCIATED PROTEIN 12.1. | sptrembl Q9Z287 | ND |
| 2506 | 144.3 | KIAA0775 PROTEIN. | sptrembl O94873 | ND |
| 2507 | 144.3 | MITOCHONDRIAL CAPSULE SELENOPROTEIN. | sptrembl O70613 | ND |
| 2508 | 144.3 | FORKHEAD-RELATED TRANSCRIPTION FACTOR 3 (FREAC-3). | swissnew Q12948 | ND |
| 2509 | 144.3 | HYPOTHETICAL 43.6 KD PROTEIN. | sptrembl Q03935 | ND |
| 2510 | 144.3 | PUTATIVE INTEGRASE. | tremblnew CAB65361 | ND |
| 2511 | 144.2 | NEUTROPHIL PROTEIN (FRAGMENT). | sptrembl Q99331 | ND |
| 2512 | 144.2 | CHORIOGENIN H PRECURSOR. | sptrembl P79817 | ND |
| 2513 | 144.2 | SEGMENTATION GENE. | tremblnew AAD19794 | ND |
| 2514 | 144.2 | DNA BINDING PROTEIN (FRAGMENT). | sptrembl Q40726 | ND |

TABLE 1-continued

*Fusarium venenatum* ESTs

| Sequence Listing | zscore | Annotation | Database | Functional category |
|---|---|---|---|---|
| 2515 | 144.2 | KV3.1 POTASSIUM CHANNEL. | tremblnew AAD52813 | ND |
| 2516 | 144.1 | HYPOTHETICAL 53.5 KD PROTEIN IN GCD14-POS18 INTERGENIC REGION. | swissprot P47018 | ND |
| 2517 | 144.1 | CYTOCHROME P450 17 (EC 1.14.99.9) (CYPXVII) (P450-C17) (STEROID 17-ALPHA-HYDROXYLASE/17,20 LYASE). | swissprot O57525 | ND |
| 2518 | 144.1 | TRANSCRIPTION FACTOR (FRAGMENT). | tremblnew AAD27591 | ND |
| 2519 | 144.1 | MUCIN MUC5B (FRAGMENT). | sptrembl Q99552 | ND |
| 2520 | 144.1 | Hepatocyte nuclear factor 4 alpha polypeptide (exon 8 product). | geneseqp W71571 | ND |
| 2521 | 144.1 | LATENCY ASSOCIATED TRANSCRIPT. | sptrembl Q9YPF7 | ND |
| 2522 | 144.0 | PUTATIVE HYDROLASE. | tremblnew CAB59667 | ND |
| 2523 | 144.0 | PISTIL-SPECIFIC EXTENSIN-LIKE PROTEIN (FRAGMENT). | sptrembl Q40552 | ND |
| 2524 | 144.0 | SMALL PROLINE-RICH PROTEIN WITH PAIRED REPEAT. | sptrembl Q28593 | ND |
| 2525 | 143.9 | W02G9.5 PROTEIN. | sptrembl O61903 | ND |
| 2526 | 143.9 | Mammalian ion channel proline rich motif containing peptide #19. | geneseqp Y41625 | ND |
| 2527 | 143.9 | F24J5.8 PROTEIN. | tremblnew AAD49974 | ND |
| 2528 | 143.9 | CHROMOSOME XII READING FRAME ORF YLR020C. | sptrembl Q07950 | ND |
| 2529 | 143.9 | BETA(1,4)-GLUCAN GLUCANOHYDROLASE PRECURSOR. | sptrembl O31030 | ND |
| 2530 | 143.9 | INSA. | tremblnew AAD45539 | ND |
| 2531 | 143.9 | NICE-1 PROTEIN. | tremblnew CAB65093 | ND |
| 2532 | 143.8 | Human lysosomal membrane sialoglycoprotein lamp-1 | geneseqp R69554 | ND |
| 2533 | 143.8 | *T. gondii* immunogenic protein. | geneseqp Y29081 | ND |
| 2534 | 143.8 | 50 KD PROLINE RICH PROTEIN. | sptrembl Q9ZBP2 | ND |
| 2535 | 143.8 | MITOGEN-ACTIVATED PROTEIN KINASE HOMOLOG NTF6 (EC 2.7.1.-) (P43). | swissprot Q40531 | ND |
| 2536 | 143.7 | Intestinal mucin deduced from clone SMUC 40. | geneseqp R07670 | ND |
| 2537 | 143.7 | PUTATIVE DEUBIQUITINATING ENZYME UBPY. | sptrembl Q9WVP5 | ND |
| 2538 | 143.7 | CALDENDRIN. | sptrembl O88751 | ND |
| 2539 | 143.7 | MULTIDRUG-EFFLUX TRANSPORTER, PUTATIVE. | tremblnew AAF12676 | ND |
| 2540 | 143.7 | F13F21.7 PROTEIN. | sptrembl Q9XIB6 | ND |
| 2541 | 143.7 | METALLOPROTEINASE PRECURSOR. | tremblnew AAF01041 | ND |
| 2542 | 143.7 | HYPOTHETICAL 21.5 KD PROTEIN (FRAGMENT). | sptrembl Q9Y4U5 | ND |
| 2543 | 143.7 | M150R. | tremblnew AAF15037 | ND |
| 2544 | 143.6 | DY3.5 PROTEIN. | sptrembl O45322 | ND |
| 2545 | 143.6 | MACROPHOMATE SYNTHASE. | tremblnew BAA89352 | ND |
| 2546 | 143.6 | Human glial fibrillary acidic protein GFAP mutant fragment 13. | geneseqp Y21004 | ND |
| 2547 | 143.6 | PLENTY-OF-PROLINES-101. | sptrembl O70495 | ND |

TABLE 1-continued

Fusarium venenatum ESTs

| Sequence Listing | zscore | Annotation | Database | Functional category |
|---|---|---|---|---|
| 2548 | 143.6 | KERATIN, HIGH-SULFUR MATRIX PROTEIN, IIIA3. | swissprot P02441 | ND |
| 2549 | 143.6 | Rodent DCMP1 C-lectin family gene protein sequence. | geneseqp W88128 | ND |
| 2550 | 143.5 | ATPASE SUBUNIT 6. | tremblnew AAF17127 | ND |
| 2551 | 143.5 | Peptide derived from the beta subunit of hCG. | geneseqp W42217 | ND |
| 2552 | 143.5 | NEUROFILAMENT TRIPLET L PROTEIN (NF-L). | swissprot Q02916 | ND |
| 2553 | 143.5 | L2602.6. | sptrembl O60961 | ND |
| 2554 | 143.5 | Y69E1A.2 PROTEIN. | sptrembl Q9XW38 | ND |
| 2555 | 143.5 | VERY HYPOTHETICAL PROTEIN. | tremblnew CAB52568 | ND |
| 2556 | 143.4 | Amino acid sequence of a mouse sperm protein designated sp56. | geneseqp W39924 | ND |
| 2557 | 143.4 | HOMOLOG OF HUMAN MLLT2 UNIDENTIFIED GENE (MAF4) (FRAGMENT). | sptrembl O35233 | ND |
| 2558 | 143.4 | HYPOTHETICAL 90.6 KD PROTEIN C09D8.2 IN CHROMOSOME II. | sptrembl Q09434 | ND |
| 2559 | 143.3 | HYPOTHETICAL 57.2 KD PROTEIN. | sptrembl O68872 | ND |
| 2560 | 143.3 | W CHROMOSOME-SPECIFIC XHOI FAMILY REPEAT (FRAGMENT). | sptrembl Q90983 | ND |
| 2561 | 143.3 | PROTO-ONCOGENE FRAT1 (FREQUENTLY REARRANGED IN ADVANCED T-CELL LYMPHOMAS). | swissnew Q92837 | ND |
| 2562 | 143.3 | NHP2/RS6 FAMILY PROTEIN YEL026W. | swissprot P39990 | ND |
| 2563 | 143.2 | Peptide encoded by HRGP gene cassette incorporating a SP construct. | geneseap Y01284 | ND |
| 2564 | 143.2 | ATP SYNTHASE ALPHA CHAIN, MITOCHONDRIAL PRECURSOR (EC 3.6.1.34). | swissnew P37211 | ND |
| 2565 | 143.2 | REPETITIVE SEQUENCE ELEMENT MGP-R5 (FRAGMENT). | sptrembl Q49395 | ND |
| 2566 | 143.2 | PUTATIVE TRANSCRIPTION FACTOR MYB94. | tremblnew CAB61986 | ND |
| 2567 | 143.2 | HYPOTHETICAL 59.4 KD PROTEIN. | sptrembl Q89392 | ND |
| 2568 | 143.2 | VW02B12L.3 PROTEIN. | sptrembl Q9XXA2 | ND |
| 2569 | 143.1 | EG:BACR42I17.8 PROTEIN. | tremblnew CAB65885 | ND |
| 2570 | 143.1 | C30E1.7 PROTEIN. | sptrembl O17330 | ND |
| 2571 | 143.1 | F26D10.11 PROTEIN. | sptrembl Q9XVU1 | ND |
| 2572 | 143.1 | PROLINE-RICH PROTEIN MP-2 PRECURSOR. | swissprot P05142 | ND |
| 2573 | 143.0 | NEUROGENIC DIFFERENTIATION FACTOR 1 (BETA-CELL E-BOX TRANS-ACTIVATOR 2) (BETA2). | swissprot Q60430 | ND |
| 2574 | 143.0 | TOPOISOMERASE I. | sptrembl O24307 | ND |
| 2575 | 143.0 | COSMID F25B4. | sptrembl Q22965 | ND |
| 2576 | 143.0 | ENTERIC BETA-DEFENSIN PRECURSOR. | swissprot O02775 | ND |
| 2577 | 143.0 | ATROPHIN-RELATED PROTEIN ARP. | sptrembl Q9Y2W4 | ND |
| 2578 | 143.0 | Delta-endotoxin MIVDL. | geneseqp R88002 | ND |
| 2579 | 143.0 | A-AGGLUTININ ATTACHMENT SUBUNIT PRECURSOR. | swissprot P32323 | ND |

TABLE 1-continued

*Fusarium venenatum* ESTs

| Sequence Listing | zscore | Annotation | Database | Functional category |
|---|---|---|---|---|
| 2580 | 143.0 | AT2G21830 PROTEIN. | tremblnew AAD20402 | ND |
| 2581 | 143.0 | *Chlamydia pneumoniae* lipoprotein sequence. | geneseqp Y35857 | ND |
| 2582 | 142.9 | REGULATORY PROTEIN P4G. | tremblnew CAB55346 | ND |
| 2583 | 142.9 | HYPOTHETICAL NUCLEAR PROTEIN (FRAGMENT). | tremblnew BAA87215 | ND |
| 2584 | 142.9 | ESTROGEN RECEPTOR BETA (FRAGMENT). | sptrembl Q95171 | ND |
| 2585 | 142.9 | HYPOTHETICAL 35.0 KD PROTEIN IN ARP5-OMP2 INTERGENIC REGION. | swissprot P53947 | ND |
| 2586 | 142.8 | Human glial fibrillary acidic protein GFAP wild type fragment 12. | geneseqp Y20986 | ND |
| 2587 | 142.8 | HYPOTHETICAL 13.4 KD PROTEIN. | sptrembl Q84187 | ND |
| 2588 | 142.8 | CODING REGION FOR PUTATIVE POLYPEPTIDE 2. | sptrembl Q64922 | ND |
| 2589 | 142.8 | Distal-less homeobox gene 3delta (DLX3delta) protein. | geneseqp Y39227 | ND |
| 2590 | 142.8 | SERINE/THREONINE KINASE PAK HOMOLOG DPAK. | sptrembl Q24190 | ND |
| 2591 | 142.8 | PROTEOPHOSPHOGLYCAN (FRAGMENT). | sptrembl Q9Y075 | ND |
| 2592 | 142.7 | Cotton fibrous tissue specific protein KC03. | geneseqp W15761 | ND |
| 2593 | 142.7 | SOLUBLE DEATH RECEPTOR 3 BETA. | sptrembl O14866 | ND |
| 2594 | 142.7 | DNA, TRANSPOSABLE ELEMENT IS31831. | sptrembl Q45144 | ND |
| 2595 | 142.7 | KIAA1239 PROTEIN (FRAGMENT). | tremblnew BAA86553 | ND |
| 2596 | 142.7 | SIMILAR TO TYROSINE AMINOTRANSFERASE. | sptrembl Q9ZC65 | ND |
| 2597 | 142.7 | DEFENSIN GENE PRECURSOR. | sptrembl O65740 | ND |
| 2598 | 142.7 | Human VRF-2 truncated fragment 4. | geneseqp W86217 | ND |
| 2599 | 142.7 | NESTIN. | swissprot P48681 | ND |
| 2600 | 142.7 | RAG1 PROTEIN (FRAGMENT). | tremblnew AAD54537 | ND |
| 2601 | 142.7 | VASOPRESSIN V2 RECEPTOR. | sptrembl O77808 | ND |
| 2602 | 142.7 | DISULFIDE OXIDOREDUCTASE 188 aa, chain A + B | pdb 1FVJ | ND |
| 2603 | 142.6 | HISTIDINE-RICH. | sptrembl Q20689 | ND |
| 2604 | 142.6 | HYPOTHETICAL 31.8 KD PROTEIN. | tremblnew AAD49200 | ND |
| 2605 | 142.6 | DNA-DIRECTED DNA POLYMERASE (EC 2.7.7.7) (DNA NUCLEOTIDYLTRANSFERASE (DNA-DIRECTED)) (FRAGMENT). | sptrembl Q95037 | ND |
| 2606 | 142.6 | F36A2.7 PROTEIN. | sptrembl P90860 | ND |
| 2607 | 142.5 | Mouse Desert hedgehog protein Dhh. | geneseqp Y05511 | ND |
| 2608 | 142.5 | HOMEOBOX PROTEIN HOX-B4 (HOXB-4). | swissnew O13074 | ND |
| 2609 | 142.5 | *Mycobacterium* species protein sequence 15F. | geneseqp Y04837 | ND |
| 2610 | 142.5 | SINGLE-STRAND SELECTIVE MONOFUNCTIONAL URACIL DNA GLYCOSYLASE. | sptrembl O95862 | ND |
| 2611 | 142.4 | 102AA LONG HYPOTHETICAL PROTEIN. | sptrembl Q9YB00 | ND |
| 2612 | 142.4 | 104AA LONG HYPOTHETICAL PROTEIN. | sptrembl Q9YB81 | ND |

TABLE 1-continued

*Fusarium venenatum* ESTs

| Sequence Listing | zscore | Annotation | Database | Functional category |
|---|---|---|---|---|
| 2613 | 142.4 | 152AA LONG HYPOTHETICAL PROTEIN. | sptrembl Q9YEE0 | ND |
| 2614 | 142.3 | LIM HOMEOBOX PROTEIN. | sptrembl P92031 | ND |
| 2615 | 142.3 | *Mycobacterium* species protein sequence 50B. | geneseqp Y04998 | ND |
| 2616 | 142.3 | NODULIN 23 PRECURSOR (N-23). | swissprot P04144 | ND |
| 2617 | 142.3 | A588R PROTEIN. | sptrembl O41070 | ND |
| 2618 | 142.3 | ZK1067.2 PROTEIN. | sptrembl Q23388 | ND |
| 2619 | 142.3 | PROLINE-AND GLUTAMINE-RICH PROTEIN. | tremblnew AAF07181 | ND |
| 2620 | 142.2 | CHLOROPLAST IMPORT-ASSOCIATED CHANNEL HOMOLOG. | tremblnew CAB51191 | ND |
| 2621 | 142.2 | WISKOTT-ALDRICH SYNDROME PROTEIN HOMOLOG 1. | sptrembl O36027 | ND |
| 2622 | 142.2 | PHOSPHOSERINE PHOSPHATASE (EC 3.1.3.3) (PSP) (O-PHOSPHOSERINE PHOSPHOHYDROLASE) (PSP). | swissnew P42941 | ND |
| 2623 | 142.2 | METHYL-CPG BINDING PROTEIN 2 (FRAGMENT). | tremblnew AAF21637 | ND |
| 2624 | 142.2 | FROM BASES 1663181 TO 1676139 (SECTION 145 OF 400) OF THE COMPLETE GENOME (SECTION 145 OF 400). | sptrembl P76176 | ND |
| 2625 | 142.2 | OUTER CAPSID PROTEIN VP2 (FRAGMENT). | sptrembl Q9WHT4 | ND |
| 2626 | 142.1 | 252AA LONG HYPOTHETICAL PROTEIN. | sptrembl Q9YBR3 | ND |
| 2627 | 142.1 | FIBRINOGEN-BINDING PROTEIN PRECURSOR. | sptrembl O70022 | ND |
| 2628 | 142.1 | HYPOTHETICAL 49.9 KD PROTEIN. | tremblnew CAB41154 | ND |
| 2629 | 142.1 | NULLO (FRAGMENT). | sptrembl O02574 | ND |
| 2630 | 142.0 | PUTATIVE OXIDOREDUCTASE. | sptrembl Q9Z4W3 | ND |
| 2631 | 142.0 | AMELOGENIN. | tremblnew BAA84220 | ND |
| 2632 | 142.0 | PHOSPHATIDYLINOSITOL 3-KINASE 2 (EC 2.7.1.137) (P13-KINASE) (PTDINS-3-KINASE) (P13K). | swissprot P54674 | ND |
| 2633 | 142.0 | Sequence encoded by plasmid pUC18RRstop in *E. coli*. | geneseqp P94507 | ND |
| 2634 | 142.0 | THIOREDOXIN M-TYPE, CHLOROPLAST PRECURSOR (TRX-M). | swissprot P07591 | ND |
| 2635 | 142.0 | PUTATIVE SENSORY HISTIDINE KINASE. | sptrembl O86808 | ND |
| 2636 | 141.9 | METHYL-CPG BINDING PROTEIN. | sptrembl O15248 | ND |
| 2637 | 141.9 | SPERM PROTAMINE P1. | swissprot O18748 | ND |
| 2638 | 141.9 | 4Heptad-F zipper protein. | geneseqp W00956 | ND |
| 2639 | 141.9 | 113AA LONG HYPOTHETICAL PROTEIN. | sptrembl O58987 | ND |
| 2640 | 141.8 | SEQ ID NO 474 from WO9922243. | geneseqp Y19756 | ND |
| 2641 | 141.8 | HYPOTHETICAL 10.3 KD PROTEIN. | sptrembl O32903 | ND |
| 2642 | 141.8 | HYPOTHETICAL 19.8 KD PROTEIN. | sptrembl Q52968 | ND |
| 2643 | 141.8 | PSEUDOURIDYLATE SYNTHASE 1 (EC 4.2.1.70) (PSEUDOURIDINE SYNTHASE 1). | swissprot Q12211 | ND |
| 2644 | 141.7 | (SCSV1). | sptrembl Q87008 | ND |
| 2645 | 141.7 | Human receptor interacting protein. | geneseqp W04628 | ND |

TABLE 1-continued

*Fusarium venenatum* ESTs

| Sequence Listing | zscore | Annotation | Database | Functional category |
|---|---|---|---|---|
| 2646 | 141.7 | SPROUTY 2. | sptrembl O43597 | ND |
| 2647 | 141.6 | VARIABLE SURFACE ANTIGEN V-1, HEMADSORPTION NEGATIVE (VSAHA-) (FRAGMENT). | sptrembl Q50323 | ND |
| 2648 | 141.6 | BCL-X (FRAGMENT). | tremblnew AAC72232 | ND |
| 2649 | 141.6 | Fragment of human secreted protein encoded by gene 10. | geneseqp Y36432 | ND |
| 2650 | 141.6 | SRC protein tyrosine kinase derived peptide #4. | geneseqp R93347 | ND |
| 2651 | 141.6 | COAGULATION FACTOR XII PRECURSOR (EC 3.4.21.38) (HAGEMAN FACTOR) (HAF). | swissprot P00748 | ND |
| 2652 | 141.5 | P53. | tremblnew AAF03996 | ND |
| 2653 | 141.5 | SIMILAR TO TREHALASE PRECURSOR NCBI GI: 1086612. | sptrembl Q22195 | ND |
| 2654 | 141.5 | 151AA LONG HYPOTHETICAL PROTEIN. | sptrembl Q9YEG3 | ND |
| 2655 | 141.4 | HYPOTHETICAL 49.7 KD PROTEIN. | sptrembl P72863 | ND |
| 2656 | 141.4 | CYCLIN-E BINDING PROTEIN 1. | tremblnew BAA88519 | ND |
| 2657 | 141.4 | BLACKJACK. | sptrembl Q26471 | ND |
| 2658 | 141.4 | HPV16 E6/E7 proteins. | geneseqp R63865 | ND |
| 2659 | 141.4 | HYPOTHETICAL 69.8 KD PROTEIN. | tremblnew CAB52444 | ND |
| 2660 | 141.3 | CHORDIN. | sptrembl Q9Z0E2 | ND |
| 2661 | 141.3 | F53B6.2 PROTEIN. | sptrembl P90884 | ND |
| 2662 | 141.3 | ENVELOPE GLYCOPROTEIN (FRAGMENT). | sptrembl O91928 | ND |
| 2663 | 141.3 | TRANSCRIPTION FACTOR BTD (BUTTONHEAD). | swissprot Q24266 | ND |
| 2664 | 141.3 | NATURAL KILLER-ASSOCIATED TRANSCRIPT 2A PROTEIN. | sptrembl Q92803 | ND |
| 2665 | 141.3 | HOMEOBOX PROTEIN. | sptrembl Q9YGT0 | ND |
| 2666 | 141.3 | Sequence A encoded by a portion of SA307. | geneseqp P60623 | ND |
| 2667 | 141.3 | SIMILAR TO *C. ELEGANS* PROTEIN D1044.3. | sptrembl Q20462 | ND |
| 2668 | 141.2 | MOVEMENT PROTEIN. | sptrembl Q9YJR6 | ND |
| 2669 | 141.2 | HEPATITIS A VIRUS CELLULAR RECEPTOR 1 LONG FORM (HEPATITIS A VIRUS CELLULAR RECEPTOR 1 SHORT FORM). | sptrembl O46598 | ND |
| 2670 | 141.2 | HYPOTHETICAL 69.2 KD PROTEIN IN HSP30-PMP1 INTERGENIC REGION. | swissprot P25351 | ND |
| 2671 | 141.2 | GENOME, PARTIAL SEQUENCE. | sptrembl Q98440 | ND |
| 2672 | 141.2 | RIBOSOME-INACTIVATING PROTEIN LUFFIN-B (RRNA N-GLYCOSIDASE) (EC 3.2.2.22). | swissprot P22851 | ND |
| 2673 | 141.1 | AGP6 PROTEIN. | sptrembl Q9XFR4 | ND |
| 2674 | 141.1 | INSULIN-LIKE PEPTIDE INSL5. | sptrembl Q9WUG6 | ND |
| 2675 | 141.1 | T09F5.2 PROTEIN. | sptrembl O62373 | ND |
| 2676 | 141.0 | EXTENSIN PRECURSOR (PROLINE-RICH GLYCOPROTEIN). | swissprot P24152 | ND |
| 2677 | 141.0 | ANTI-DEATH PROTEIN. | sptrembl O75353 | ND |
| 2678 | 141.0 | MITC. | sptrembl Q9WVY1 | ND |

TABLE 1-continued

*Fusarium venenatum* ESTs

| Sequence Listing | zscore | Annotation | Database | Functional category |
|---|---|---|---|---|
| 2679 | 141.0 | 109AA LONG HYPOTHETICAL PROTEIN. | sptrembl Q9Y9G9 | ND |
| 2680 | 141.0 | RECOMBINATION-ACTIVATING PROTEIN 1. | sptrembl Q9W699 | ND |
| 2681 | 141.0 | ANTIVIRAL PROTEIN SK12. | swissprot P35207 | ND |
| 2682 | 141.0 | NUCLEAR POLYADENYLATED RNA-BINDING PROTEIN NAB2. | swissprot P32505 | ND |
| 2683 | 141.0 | HEMAGGLUTININ (FRAGMENT). | tremblnew AAD51242 | ND |
| 2684 | 140.9 | FOOT PROTEIN 1 PRECURSOR (FRAGMENT). | sptrembl O61477 | ND |
| 2685 | 140.9 | YCZB PROTEIN. | sptrembl O31467 | ND |
| 2686 | 140.9 | SARCOPHAGA PRO-CATHEPSIN B PRECURSOR. | sptrembl Q26655 | ND |
| 2687 | 140.9 | F6E13.10 PROTEIN. | sptrembl O80567 | ND |
| 2688 | 140.9 | T01C3.1 PROTEIN. | sptrembl Q22059 | ND |
| 2689 | 140.8 | ERPROT 213-21. | sptrembl O00302 | ND |
| 2690 | 140.8 | BAV3 ORF5 product. | geneseqp R75760 | ND |
| 2691 | 140.8 | PUTATIVE RAS-RELATED PROTEIN F43D9.2. | swissprot Q20365 | ND |
| 2692 | 140.8 | SP85 (FRAGMENT). | sptrembl O61134 | ND |
| 2693 | 140.7 | *Macadamia integrifolia* antimicrobial protein. | geneseqp W62829 | ND |
| 2694 | 140.7 | ANTIGENIC PROTEIN PFEMP2 (FRAGMENT). | sptrembl Q06165 | ND |
| 2695 | 140.7 | N-MYC PROTO-ONCOGENE PROTEIN. | swissprot P26014 | ND |
| 2696 | 140.7 | Human secreted protein #80. | geneseqp Y36208 | ND |
| 2697 | 140.7 | HYPOTHETICAL 46.3 KD PROTEIN. | sptrembl Q9X039 | ND |
| 2698 | 140.6 | HYPOTHETICAL 32.1 KD PROTEIN. | sptrembl O79459 | ND |
| 2699 | 140.5 | F3I6.13 PROTEIN. | sptrembl O48687 | ND |
| 2700 | 140.5 | KAPPA CASEIN PRECURSOR. | sptrembl Q9XSD6 | ND |
| 2701 | 140.5 | WINGLESS (FRAGMENT). | sptrembl O46291 | ND |
| 2702 | 140.5 | MEROZOITE SURFACE PROTEIN-1 (FRAGMENT). | sptrembl O00877 | ND |
| 2703 | 140.5 | KIAA1290 PROTEIN (FRAGMENT). | tremblnew BAA86604 | ND |
| 2704 | 140.5 | MAJOR CENTROMERE AUTOANTIGEN B (CENTROMERE PROTEIN B) (CENP-B). | swissprot P48988 | ND |
| 2705 | 140.5 | TONB PROTEIN. | swissprot Q05613 | ND |
| 2706 | 140.5 | GLUE PROTEIN. | sptrembl Q27423 | ND |
| 2707 | 140.4 | HYPOTHETICAL 14.6 KD PROTEIN. | tremblnew CAB57548 | ND |
| 2708 | 140.4 | PROTAMINE P1. | sptrembl O18749 | ND |
| 2709 | 140.4 | HYPOTHETICAL 18.3 KD PROTEIN. | tremblnew AAF09839 | ND |
| 2710 | 140.4 | TRANSPOSON TOL2. | sptrembl Q98969 | ND |
| 2711 | 140.4 | VPR PROTEIN. | tremblnew AAF07319 | ND |
| 2712 | 140.4 | Intestinal mucin deduced from clone SMUC 41. | geneseqp R07671 | ND |
| 2713 | 140.4 | Murine BMP-15 related protein PC-3. | geneseqp W11260 | ND |
| 2714 | 140.3 | BZIP TRANSCRIPTION FACTOR. | sptrembl Q24525 | ND |
| 2715 | 140.3 | D1086.6 PROTEIN. | sptrembl O17729 | ND |
| 2716 | 140.3 | HYPOTHETICAL 30.3 KD PROTEIN. | sptrembl O85856 | ND |
| 2717 | 140.3 | FIMP. | sptrembl Q46525 | ND |
| 2718 | 140.3 | HMG-Y RELATED PROTEIN B (SB16B PROTEIN) (FRAGMENT). | swissprot Q10370 | ND |
| 2719 | 140.3 | NEUTROPHIL PROTEIN (FRAGMENT). | sptrembl Q99331 | ND |
| 2720 | 140.3 | PUTATIVE GLYOXYLATE PATHWAY REGULATOR C5D6.09C. | sptrembl O14201 | ND |

TABLE 1-continued

Fusarium venenatum ESTs

| Sequence Listing | zscore | Annotation | Database | Functional category |
|---|---|---|---|---|
| 2721 | 140.3 | HYPOTHETICAL 19.1 KD PROTEIN IN PDI1-GLK1 INTERGENIC REGION. | swissprot P25571 | ND |
| 2722 | 140.2 | HOMEOBOX PROTEIN (FRAGMENT). | sptrembl O97671 | ND |
| 2723 | 140.2 | TATA BINDING PROTEIN (FRAGMENT). | tremblnew BAA21084 | ND |
| 2724 | 140.2 | NUCLEAR SEGREGATION PROTEIN BFR1. | swissprot P38934 | ND |
| 2725 | 140.2 | SYNAPSIN IB. | sptrembl O88935 | ND |
| 2726 | 140.2 | PISTIL-SPECIFIC EXTENSIN-LIKE PROTEIN (FRAGMENT). | sptrembl Q40550 | ND |
| 2727 | 140.2 | HYPOTHETICAL PROTEIN IN FTR 5'REGION (ORFU) (FRAGMENT). | swissprot P56510 | ND |
| 2728 | 140.2 | PUTATIVE TRANSCRIPTIONAL REGULATORY PROTEIN. | tremblnew CAB53122 | ND |
| 2729 | 140.2 | Bioadhesive precursor protein from cDNA 52. | geneseqp P82971 | ND |
| 2730 | 140.2 | W09G12.6 PROTEIN. | sptrembl O45197 | ND |
| 2731 | 140.2 | SIMILAR TO HERV-H PROTEASE AND HERV-E INTEGRASE. | sptrembl Q68997 | ND |
| 2732 | 140.1 | MEDEA. | sptrembl O65312 | ND |
| 2733 | 140.1 | CYTOCHROME B (FRAGMENT). | tremblnew AAD47483 | ND |
| 2734 | 140.1 | F32D1.9 PROTEIN. | sptrembl O16293 | ND |
| 2735 | 140.1 | PEARLI 1-LIKE PROTEIN. | tremblnew CAB41719 | ND |
| 2736 | 140.1 | ANION EXCHANGE PROTEIN 3 (NEURONAL BAND 3-LIKE PROTEIN) (ANION EXCHANGER 3 BRAIN ISOFORM). | swissnew O18917 | ND |
| 2737 | 140.1 | HYPOTHETICAL 55.0 KD PROTEIN. | sptrembl O94256 | ND |
| 2738 | 140.1 | Aspergillus niger beta-fructofuranosidase. | geneseqp W23298 | ND |
| 2739 | 140.1 | FIBRIL PROTEIN. | sptrembl O66099 | ND |
| 2740 | 140.0 | NS3F4 (FRAGMENT). | sptrembl Q86914 | ND |
| 2741 | 140.0 | HOMEOBOX PROTEIN NK-1 (S59/2). | swissprot P22807 | ND |
| 2742 | 140.0 | HYPOTHETICAL 47.8 KD PROTEIN IN HSP26-TIF32 INTERGENIC REGION. | swissprot P38244 | ND |
| 2743 | 139.9 | ARGINYL-TRNA SYNTHETASE (EC 6.1.1.19) (ARGININE--TRNA LIGASE) (ARGRS). | swissprot O83803 | ND |
| 2744 | 139.9 | T01B7.8 PROTEIN. | sptrembl Q22048 | ND |
| 2745 | 139.9 | HOMEOBOX PROTEIN HOX-A3 (HOX-1E). | swissprot O43365 | ND |
| 2746 | 139.8 | METABOTROPIC GLUTAMATE RECEPTOR (FRAGMENT). | tremblnew AAD47893 | ND |
| 2747 | 139.8 | ECDYSONE-INDUCIBLE PROTEIN E75. | swissnew Q08893 | ND |
| 2748 | 139.8 | HYPOTHETICAL 21.2 KD PROTEIN IN TOR2-MNN4 INTERGENIC REGION. | swissprot P36042 | ND |
| 2749 | 139.8 | F40F12.5A PROTEIN. | tremblnew CAB54246 | ND |
| 2750 | 139.7 | PREDICTED SECRETED PROTEIN (THROMBOSPONDIN DOMAIN). | sptrembl O96207 | ND |
| 2751 | 139.7 | UL7 PROTEIN. | sptrembl Q9YVB6 | ND |
| 2752 | 139.7 | Amino acid sequence of a virulence factor encoded by ORF29729. | geneseqp Y29213 | ND |

TABLE 1-continued

*Fusarium venenatum* ESTs

| Sequence Listing | zscore | Annotation | Database | Functional category |
|---|---|---|---|---|
| 2753 | 139.7 | UNKNOWN PROTEIN (FRAGMENT). | sptrembl Q29175 | ND |
| 2754 | 139.7 | SPERM HISTONE P2 PRECURSOR (PROTAMINE MP2). | swissprot P07978 | ND |
| 2755 | 139.7 | PLATELET GLYCOPROTEIN V (FRAGMENT). | tremblnew AAF08787 | ND |
| 2756 | 139.7 | ATP OPERON (FRAGMENT). | sptrembl Q53031 | ND |
| 2757 | 139.7 | PEPTIDE CHAIN RELEASE FACTOR HOMOLOG (RF-H). | swissprot P28369 | ND |
| 2758 | 139.7 | PROBABLE TRANSLATION INITIATION FACTOR IF-2. | swissprot Q10251 | ND |
| 2759 | 139.6 | CLASS IV ZYGOTE SPECIFIC CELL WALL HYDROXYPROLINE-RICH GLYCOPROTEIN (FRAGMENT). | sptrembl Q41178 | ND |
| 2760 | 139.6 | NHOA. | sptrembl P96848 | ND |
| 2761 | 139.6 | HYPOTHETICAL 30.8 KD PROTEIN. | tremblnew AAF09969 | ND |
| 2762 | 139.6 | GAG. | sptrembl Q9Y1H4 | ND |
| 2763 | 139.6 | PI021 PROTEIN. | sptrembl O13612 | ND |
| 2764 | 139.6 | 122AA LONG HYPOTHETICAL PROTEIN. | sptrembl Q9YBE6 | ND |
| 2765 | 139.6 | T13D8.9 PROTEIN. | sptrembl O80743 | ND |
| 2766 | 139.6 | MEMBRANE PROTEIN MOSC. | swissprot Q07609 | ND |
| 2767 | 139.5 | SIMILARITY TO TYPE 1 INOSITOL 1. | sptrembl O04649 | ND |
| 2768 | 139.5 | COSMID ZK813. | sptrembl Q23606 | ND |
| 2769 | 139.5 | Fragmented human NF-L gene +2 frameshift mutant product. | geneseqp W18658 | ND |
| 2770 | 139.5 | DNA-DIRECTED RNA POLYMERASE SUBUNIT B' (EC 2.7.7.6). | swissprot P41557 | ND |
| 2771 | 139.5 | *S. lividans* protease P5-6. | geneseqp R80506 | ND |
| 2772 | 139.5 | IGG FC BINDING PROTEIN (FRAGMENT). | sptrembl O95784 | ND |
| 2773 | 139.4 | EXTENSIN = NODULE-SPECIFIC PROLINE-RICH PROTEIN {CLONE VFNDS-E}. | tremblnew G425682 | ND |
| 2774 | 139.4 | C01B7.3 PROTEIN. | sptrembl Q17546 | ND |
| 2775 | 139.4 | PRECOAT PROTEIN. | sptrembl Q9WPG4 | ND |
| 2776 | 139.3 | DELTA-AMINOLEVULINIC ACID DEHYDRATASE (EC 4.2.1.24) (PORPHOBILINOGEN SYNTHASE) (ALADH). | swissnew P05373 | ND |
| 2777 | 139.3 | Mammalian ion channel proline rich motif containing peptide #19. | geneseqp Y41625 | ND |
| 2778 | 139.3 | CYSTEINE PROTEASE. | tremblnew CAB59816 | ND |
| 2779 | 139.3 | UL26 protease deletion mutant DD, amino acids 219–635 deleted. | geneseqp R28645 | ND |
| 2780 | 139.3 | Chlamydial major outer membrane protein (MOMP) H fragment. | geneseqp W95280 | ND |
| 2781 | 139.3 | L4830.11 PROTEIN. | sptrembl O97215 | ND |
| 2782 | 139.3 | CAGO. | sptrembl P94828 | ND |
| 2783 | 139.3 | LECTIN = CHITIN-BINDING PROTEIN. | tremblnew G688080 | ND |
| 2784 | 139.2 | PUTATIVE PHOSPHATE/PHOSPHOENOL-PYRUVATE TRANSLOCATOR. | tremblnew AAD55791 | ND |
| 2785 | 139.2 | PUTATIVE GLYCOPROTEIN. | sptrembl O36424 | ND |

TABLE 1-continued

_Fusarium venenatum_ ESTs

| Sequence Listing | zscore | Annotation | Database | Functional category |
|---|---|---|---|---|
| 2786 | 139.2 | Carbonic anhydrase as deduced from DNA carried on pCCA20. | geneseqp P81228 | ND |
| 2787 | 139.2 | Plasmid pASK75 open reading frame (c) translation. | geneseqp R88636 | ND |
| 2788 | 139.2 | HYPOTHETICAL 16.6 KD PROTEIN. | sptrembl O67910 | ND |
| 2789 | 139.2 | RABPHILIN-3A RELATED PROTEIN. | sptrembl O54880 | ND |
| 2790 | 139.2 | HYPOTHETICAL 48.0 KD PROTEIN. | sptrembl Q50175 | ND |
| 2791 | 139.2 | HYPOTHETICAL 7.2 KD PROTEIN. | sptrembl Q9X477 | ND |
| 2792 | 139.2 | PUTATIVE U4/U6 SMALL NUCLEAR RIBONUCLEOPROTEIN. | tremblnew AAD25639 | ND |
| 2793 | 139.2 | DEF chimeric molecule hA110-120/I-E-d-beta/FC-gamma-2a protein. | geneseqp W99773 | ND |
| 2794 | 139.2 | SPERM PROTAMINE P1. | swissprot O18747 | ND |
| 2795 | 139.1 | ATPASE SUBUNIT 6 (FRAGMENT). | tremblnew AAD34165 | ND |
| 2796 | 139.1 | Human HUPF-I mutant protein fragment 33. | geneseqp Y21385 | ND |
| 2797 | 139.1 | PROLINE-RICH PROTEIN. | sptrembl O94274 | ND |
| 2798 | 139.1 | HYPOTHETICAL 42.7 KD PROTEIN. | tremblnew CAB58294 | ND |
| 2799 | 139.0 | F11A6.2 PROTEIN. | sptrembl O62149 | ND |
| 2800 | 139.0 | HYPOTHETICAL 47.8 KD PROTEIN YOR009W. | sptrembl Q12218 | ND |
| 2801 | 139.0 | HYPOTHETICAL 18.8 KD PROTEIN (ORF4). | swissprot P15605 | ND |
| 2802 | 139.0 | 105AA LONG HYPOTHETICAL PROTEIN. | sptrembl Q9YCK7 | ND |
| 2803 | 139.0 | PUTATIVE REGULATORY PROTEIN FMDB. | swissprot Q50229 | ND |
| 2804 | 139.0 | HOXB-3 PRODUCT. | tremblnew G913072 | ND |
| 2805 | 139.0 | EXTENSIN PRECURSOR (CELL WALL HYDROXYPROLINE-RICH GLYCOPROTEIN). | swissprot P13983 | ND |
| 2806 | 139.0 | DETHIOBIOTIN SYNTHETASE (EC 6.3.3.3) (DETHIOBIOTIN SYNTHASE) (DTB SYNTHETASE) (DTBS). | swissprot P45486 | ND |
| 2807 | 139.0 | PUTATIVE 2,3-BISPHOSPHOGLYCERATE-INDEPENDENT PHOSPHOGLYCERATE MUTASE (EC 5.4.2.1) (PHOSPHOGLYCEROMUTASE) (BPG-INDEPENDENT PGAM). | swissprot Q06464 | ND |
| 2808 | 138.9 | SPID PRECURSOR (FRAGMENT). | sptrembl Q23804 | ND |
| 2809 | 138.9 | SIMILAR TO HUMAN MRNA FOR ALPHA 1. | sptrembl Q9XJ18 | ND |
| 2810 | 138.9 | OPA REPEAT (FRAGMENT). | sptrembl Q62006 | ND |
| 2811 | 138.9 | NADH DEHYDROGENASE SUBUNIT 3. | tremblnew BAA84934 | ND |
| 2812 | 138.9 | PMS2 RELATED PROTEIN HPMSR6. | sptrembl Q13670 | ND |
| 2813 | 138.9 | Human 5' EST secreted protein SEQ ID NO:250. | geneseqp Y11598 | ND |
| 2814 | 138.9 | N-ACETYLGLUCOSAMINE-1-PHOSPHATE URIDYLTRANSFERASE (GLMU) (FRAGMENT). | sptrembl O50225 | ND |
| 2815 | 138.8 | COAT PROTEIN. | sptrembl Q84827 | ND |
| 2816 | 138.8 | PDHB. | sptrembl O06160 | ND |
| 2817 | 138.8 | NON-STRUCTURAL 5A PROTEIN (FRAGMENT). | sptrembl Q68657 | ND |

TABLE 1-continued

*Fusarium venenatum* ESTs

| Sequence Listing | zscore | Annotation | Database | Functional category |
|---|---|---|---|---|
| 2818 | 138.8 | VEGF/CPG2 fusion protein CPV165H6. | geneseqp W38237 | ND |
| 2819 | 138.8 | F38B7.1 PROTEIN. | sptrembl Q20155 | ND |
| 2820 | 138.8 | Human breast tumour-associated protein 30. | geneseqp Y48569 | ND |
| 2821 | 138.8 | LIM PROTEIN PIN-2. | swissprot Q19157 | ND |
| 2822 | 138.8 | AT2G28660 PROTEIN. | tremblnew AAD24369 | ND |
| 2823 | 138.8 | CYSTEINE-RICH OUTER MEMBRANE PROTEIN 3 PRECURSOR. | swissprot P27606 | ND |
| 2824 | 138.8 | TRANSITION PROTEIN 2. | sptrembl O77645 | ND |
| 2825 | 138.8 | K08F4.2 PROTEIN. | sptrembl Q21351 | ND |
| 2826 | 138.7 | 138AA LONG HYPOTHETICAL PROTEIN. | sptrembl Q9YF84 | ND |
| 2827 | 138.7 | SPERMATID-SPECIFIC PROTEIN S1. | swissprot P13275 | ND |
| 2828 | 138.7 | MHC CELL SURFACE GLYCOPROTEIN (FRAGMENT). | sptrembl Q31250 | ND |
| 2829 | 138.7 | HYPOTHETICAL 14.6 KD PROTEIN. | sptrembl Q54774 | ND |
| 2830 | 138.7 | U1-SNRNP BINDING PROTEIN HOMOLOG. | sptrembl Q16560 | ND |
| 2831 | 138.7 | HYPOTHETICAL 29.1 KD PROTEIN. | sptrembl Q50506 | ND |
| 2832 | 138.6 | TAT PROTEIN. | sptrembl O93199 | ND |
| 2833 | 138.6 | Human acid sphingomyelinase mutant fsP330. | geneseqp W35283 | ND |
| 2834 | 138.6 | K03D3.4 PROTEIN. | sptrembl O45642 | ND |
| 2835 | 138.6 | GEP PROTEIN. | tremblnew BAA85464 | ND |
| 2836 | 138.6 | HYPOTHETICAL 6.6 KD PROTEIN. | sptrembl P74795 | ND |
| 2837 | 138.5 | ALTERNATIVE OXIDASE. | sptrembl O48519 | ND |
| 2838 | 138.5 | K01A2.2 PROTEIN. | tremblnew AAC69504 | ND |
| 2839 | 138.5 | HOMOLOGUE OF RETROVIRAL PSEUDOPROTEASE. | sptrembl Q85302 | ND |
| 2840 | 138.5 | ORF YOR053W. | sptrembl Q08428 | ND |
| 2841 | 138.5 | CYTOCHROME BC SUBUNIT IV PETD. | sptrembl Q9ZGF9 | ND |
| 2842 | 138.5 | GERANYLGERANYL PYROPHOSPHATE SYNTHASE-RELATED PROTEIN PRECURSOR. | sptrembl Q39108 | ND |
| 2843 | 138.5 | SEED STORAGE PROTEIN 31 aa, chain A | pdb 1PNB | ND |
| 2844 | 138.4 | Immunodominant fragment of flagellar pocket antigen of *T. brucei*. | geneseqp R85174 | ND |
| 2845 | 138.4 | RIBONUCLEOSIDE-DIPHOSPHATE REDUCTASE SMALL CHAIN (EC 1.17.4.1) (RIBONUCLEOTIDE REDUCTASE M2 SUBUNIT). | swissprot O46310 | ND |
| 2846 | 138.4 | ALGINATE LYASE PRECURSOR (EC 4.2.2.3) (POLY(BETA-D-MANNURONATE) LYASE) (POLY(MANA) ALGINATE LYASE). | swissprot Q59478 | ND |
| 2847 | 138.4 | Protein encoded by ORF A of the EcoRI-EcoRI fragment of ILTV. | geneseqp W71199 | ND |
| 2848 | 138.4 | HYPOTHETICAL BHLF1 PROTEIN. | swissprot P03181 | ND |
| 2849 | 138.4 | 140-KD SECRETORY PROTEIN (SP140) (FRAGMENT). | sptrembl Q23802 | ND |
| 2850 | 138.4 | Human 5' EST secreted protein SEQ ID No: 502. | geneseqp Y11902 | ND |

TABLE 1-continued

*Fusarium venenatum* ESTs

| Sequence Listing | zscore | Annotation | Database | Functional category |
|---|---|---|---|---|
| 2851 | 138.3 | TOPOISOMERASE. | sptrembl Q9Z5W4 | ND |
| 2852 | 138.3 | KERATIN, ULTRA HIGH-SULFUR MATRIX PROTEIN (UHS KERATIN). | swissprot P26372 | ND |
| 2853 | 138.3 | GLUE PROTEIN. | sptrembl Q27423 | ND |
| 2854 | 138.3 | T11J7.8 PROTEIN. | sptrembl O49334 | ND |
| 2855 | 138.3 | HYPOTHETICAL 31.4 KD PROTEIN B0285.2 IN CHROMOSOME III. | swissprot P46552 | ND |
| 2856 | 138.3 | MEMBRANE ASSOCIATED PROTEIN. | sptrembl O89260 | ND |
| 2857 | 138.3 | PUTATIVE ALCOHOL DEHYDROGENASE. | tremblnew AAF04851 | ND |
| 2858 | 138.3 | KILLER CELL LECTIN-LIKE RECEPTOR 7 (T-CELL SURFACE GLYCOPROTEIN LY-49G) (LY49-G ANTIGEN). | swissnew Q60654 | ND |
| 2859 | 138.3 | RNA-BINDING PROTEIN 5 (FRAGMENT). | sptrembl Q26275 | ND |
| 2860 | 138.3 | *B. burgdorferi* antigenic protein, t940.aa. | geneseqp Y19811 | ND |
| 2861 | 138.2 | Peptide resembling an SH3 domain binding peptide SEQ ID NO:366. | geneseqp W38969 | ND |
| 2862 | 138.2 | ALPHA/BETA-GLIADIN CLONE PW8142 PRECURSOR (PROLAMIN). | swissprot P04727 | ND |
| 2863 | 138.2 | MITOTIC MAD2 PROTEIN. | swissprot P40958 | ND |
| 2864 | 138.2 | KIAA0339. | sptrembl O15047 | ND |
| 2865 | 138.2 | CAPSID PROTEIN (CP). | sptrembl Q9WIJ8 | ND |
| 2866 | 138.2 | MYB-LIKE DNA-BINDING DOMAIN PROTEIN. | sptrembl O49019 | ND |
| 2867 | 138.2 | HYPOTHETICAL 71.1 KD PROTEIN. | sptrembl O65642 | ND |
| 2868 | 138.2 | RNPH PROTEIN (FRAGMENT). | tremblnew CAB60663 | ND |
| 2869 | 138.1 | 284R. | sptrembl O71105 | ND |
| 2870 | 138.1 | F14F9.2 PROTEIN. | sptrembl O17062 | ND |
| 2871 | 138.1 | D4B DOPAMINE RECEPTOR. | sptrembl O42322 | ND |
| 2872 | 138.1 | T31E10.8 PROTEIN. | sptrembl O64689 | ND |
| 2873 | 138.1 | GC-B. | geneseqp R38863 | ND |
| 2874 | 138.1 | WW DOMAIN BINDING PROTEIN 11. | sptrembl O88539 | ND |
| 2875 | 138.1 | Intestinal mucin deduced from clone SMUC 41. | geneseqp R07671 | ND |
| 2876 | 138.0 | PUTATIVE KINESIN MOTOR PROTEIN (FRAGMENT). | tremblnew BAA87207 | ND |
| 2877 | 138.0 | HYPOTHETICAL 26.5 KD PROTEIN. | sptrembl O49443 | ND |
| 2878 | 138.0 | RORGAMMA T. | tremblnew AAD46913 | ND |
| 2879 | 138.0 | PROBABLE THIOREDOXIN. | swissprot Q09433 | ND |
| 2880 | 138.0 | HYPOTHETICAL 43.0 KD PROTEIN. | tremblnew CAB57416 | ND |
| 2881 | 138.0 | Human neurofilament-H mutant protein fragment 2. | geneseqp Y20843 | ND |
| 2882 | 138.0 | TACHYLECTIN-3 PRECURSOR. | sptrembl O97404 | ND |
| 2883 | 138.0 | UBIQUITIN-CONJUGATING ENZYME E2 (EC 6.3.2.19) (UBIQUITIN-PROTEIN LIGASE) (UBIQUITIN CARRIER PROTEIN). | sptrembl Q9Y2D3 | ND |
| 2884 | 138.0 | LUTROPIN BETA CHAIN (LUTEINIZING HORMONE) (LSH-B) (LH-B). | swissprot P25330 | ND |
| 2885 | 137.9 | SERINE 1 ULTRA HIGH SULFUR PROTEIN. | sptrembl Q64507 | ND |
| 2886 | 137.9 | GLYCOPROTEIN B (FRAGMENT). | tremblnew AAD46114 | ND |

TABLE 1-continued

*Fusarium venenatum* ESTs

| Sequence Listing | zscore | Annotation | Database | Functional category |
|---|---|---|---|---|
| 2887 | 137.9 | ISLET-BRAIN 1. | tremblnew AAD20443 | ND |
| 2888 | 137.9 | ORNITHINE DECARBOXYLASE ANTIZYME 2 (ODC-AZ 2) (AZ2). | swissnew O95190 | ND |
| 2889 | 137.9 | HOMEOBOX PROTEIN HOX-D3. | swissprot O93353 | ND |
| 2890 | 137.9 | ORF2 5' OF EPOR. | sptrembl Q64239 | ND |
| 2891 | 137.9 | AKIN GAMMA. | tremblnew CAB64718 | ND |
| 2892 | 137.9 | Human secreted protein encoded by gene No. 80. | geneseqp Y27646 | ND |
| 2893 | 137.8 | CHITINASE II PRECURSOR (EC 3.2.1.14). | sptrembl Q59145 | ND |
| 2894 | 137.8 | 117AA LONG HYPOTHETICAL PROTEIN. | sptrembl Q9YD41 | ND |
| 2895 | 137.8 | T27A16.25 PROTEIN. | sptrembl O82390 | ND |
| 2896 | 137.8 | LIM HOMEODOMAIN TRANSCRIPTION FACTOR. | sptrembl O96686 | ND |
| 2897 | 137.8 | BINDIN PRECURSOR (FRAGMENT). | tremblnew AAF07137 | ND |
| 2898 | 137.8 | Putative calcium channel encoded by clone SCCL-B. | geneseqp R34550 | ND |
| 2899 | 137.8 | HEMOMUCIN. | sptrembl Q24160 | ND |
| 2900 | 137.8 | 73AA LONG HYPOTHETICAL 30S RIBOSOMAL PROTEIN S27. | sptrembl Q9YF01 | ND |
| 2901 | 137.8 | HYPOTHETICAL 16.4 KD PROTEIN (FRAGMENT). | sptrembl O18970 | ND |
| 2902 | 137.7 | FEMALE-SPECIFIC TRANSFORMER PROTEIN. | swissprot Q23949 | ND |
| 2903 | 137.7 | ZINC FINGER PROTEIN 80 (ZNFPT17). | swissprot P51504 | ND |
| 2904 | 137.7 | CYSTEINE-RICH PROTEIN (FRAGMENT). | sptrembl Q16861 | ND |
| 2905 | 137.7 | EGF motif containing protein. | geneseqp Y18109 | ND |
| 2906 | 137.7 | TRANSCRIPTION FACTOR ATF-A AND ATF-A-DELTA. | swissnew P17544 | ND |
| 2907 | 137.7 | HYPOTHETICAL 26.6 KD PROTEIN C17A2.10C IN CHROMOSOME I. | sptrembl O13760 | ND |
| 2908 | 137.7 | Human DIP protein C-terminal sequence. | geneseqp Y18027 | ND |
| 2909 | 137.7 | ENDOCHITINASE ISOLOG. | sptrembl O24654 | ND |
| 2910 | 137.6 | GLUE PROTEIN. | sptrembl Q27423 | ND |
| 2911 | 137.6 | ACETYLCHOLINE RECEPTOR PROTEIN, ALPHA-1A CHAIN PRECURSOR. | swissprot P22456 | ND |
| 2912 | 137.6 | POTENTIAL PROTEASOME ACTIVATOR HPA28 SUBUNIT BETA (FRAGMENT). | sptrembl Q95292 | ND |
| 2913 | 137.6 | Human CD2:IgG2a constant region fusion protein. | geneseqp W35861 | ND |
| 2914 | 137.5 | HYPOTHETICAL LYSINE-RICH PROTEIN. | tremblnew CAB52566 | ND |
| 2915 | 137.5 | NUCLEAR TRANSITION PROTEIN 2 (TP-2). | swissprot Q05952 | ND |
| 2916 | 137.5 | PUTATIVE RHO/RAC GUANINE NUCLEOTIDE EXCHANGE FACTOR (RHO/RAC GEF) (FACIOGENITAL DYSPLASIA PROTEIN). | swissprot P98174 | ND |
| 2917 | 137.5 | NADH DEHYDROGENASE SUBUNIT F (FRAGMENT). | tremblnew AAF08186 | ND |
| 2918 | 137.5 | BRANCHED-CHAIN AMINO ACID ABC TRANSPORTER, PERMEASE PROTEIN (BRAE-4). | sptrembl O28878 | ND |
| 2919 | 137.5 | 118AA LONG HYPOTHETICAL PROTEIN. | sptrembl Q9Y951 | ND |

TABLE 1-continued

*Fusarium venenatum* ESTs

| Sequence Listing | zscore | Annotation | Database | Functional category |
|---|---|---|---|---|
| 2920 | 137.4 | PUTATIVE CHITIN SYNTHASE (EC 2.4.1.16). | sptrembl Q9Y7H9 | ND |
| 2921 | 137.4 | ARABINOGALACTAN-PROTEIN. | sptrembl Q9ZT16 | ND |
| 2922 | 137.4 | HYPOTHETICAL 32.5 KD PROTEIN F52C9.6 IN CHROMOSOME III. | swissprot Q10126 | ND |
| 2923 | 137.3 | PUTATIVE TRANSMEMBRANE EFFLUX PROTEIN (FRAGMENT). | tremblnew CAB60461 | ND |
| 2924 | 137.3 | Gp IIb/IIIa receptor ligand used in scintigraphic imaging of thrombi. | geneseqp R69293 | ND |
| 2925 | 137.3 | HYPOTHETICAL 41.0 KD PROTEIN C1F8.06 IN CHROMOSOME I. | swissprot Q92344 | ND |
| 2926 | 137.3 | VITAMIN D RECEPTOR-INTERACTING PROTEIN. | sptrembl Q9Y652 | ND |
| 2927 | 137.3 | CONSERVED HYPOTHETICAL PROTEIN. | tremblnew AAF10237 | ND |
| 2928 | 137.3 | CYTOCHROME B. | swissprot Q37713 | ND |
| 2929 | 137.2 | *Mycobacterium tuberculosis* specific DNA-encoded polypeptide. | geneseqp Y31745 | ND |
| 2930 | 137.2 | GCD14 PROTEIN. | swissprot P46959 | ND |
| 2931 | 137.2 | UBIQUITIN ACTIVATING ENZYME. | sptrembl O82692 | ND |
| 2932 | 137.2 | PROTEASE VII PRECURSOR (EC 3.4.21.87) (OMPTIN) (OUTER MEMBRANE PROTEIN 3B) (PROTEASE A). | swissprot P09169 | ND |
| 2933 | 137.2 | ENVELOPE GLYCOPROTEIN (FRAGMENT). | sptrembl Q70525 | ND |
| 2934 | 137.1 | EBA-175 (FRAGMENT). | tremblnew AAB52719 | ND |
| 2935 | 137.1 | FLOCCULIN (FRAGMENT). | sptrembl P87107 | ND |
| 2936 | 137.1 | CYTIDINE DEAMINASE 8. | sptrembl Q9XHQ8 | ND |
| 2937 | 137.1 | N-terminal fragment of secretory leukocyte protease inhibitor. | geneseqp R84055 | ND |
| 2938 | 137.1 | PUTATIVE RING ZINC FINGER PROTEIN. | tremblnew AAD24830 | ND |
| 2939 | 137.1 | AMELOGENIN, CLASS I PRECURSOR. | swissprot P02817 | ND |

TABLE 2

*Aspergillus niger* ESTs

| Sequence Listing | zscore | Annotation | Database | Functional Category |
|---|---|---|---|---|
| 3771 | 4033.3 | GLUCOAMYLASE G1 AND G2 PRECURSOR (EC 3.2.1.3) (GLUCAN 1,4-ALPHA-GLUCOSIDASE) (1,4-ALPHA-D-GLUCAN GLUCOHYDROLASE). | swissprot P04064 | ND |
| 3772 | 1863.3 | Glycosyltransferase. | geneseqp R42995 | ND |
| 3773 | 1724.7 | Porphobilinogen synthase. | geneseqp W41499 | Coenzyme metabolism |
| 3774 | 1648.5 | *Aspergillus awamori* glucoamylase mutant N20C, A27C, S30P, G137A. | geneseqp W55977 | ND |
| 3775 | 1543.7 | ALPHA-AMYLASE A PRECURSOR (EC 3.2.1.1) (TAKA-AMYLASE A) (TAA) | swissprot P10529 | ND |

TABLE 2-continued

*Aspergillus niger* ESTs

| Sequence Listing | zscore | Annotation | Database | Functional Category |
|---|---|---|---|---|
| 3776 | 1534.2 | (1,4-ALPHA-D-GLUCAN GLUCANOHYDROLASE). ACID ALPHA-AMYLASE (EC 3.2.1.1) (1,4-ALPHA-D-GLUCAN GLUCANOHYDROLASE). | swissprot P56271 | ND |
| 3777 | 1364.8 | PUTATIVE THIAZOLE SYNTHASE. | tremblnew AAF25444 | ND |
| 3778 | 1339.2 | *A. oryzae* DEBY932 locus protein sequence. | geneseqp Y39873 | Carbohydrate transport and metabolism |
| 3779 | 1321.0 | CYTOCHROME C OXIDASE SUBUNIT V. | sptrembl O93980 | ND |
| 3780 | 1285.2 | ADP-RIBOSYLATION FACTOR. | swissprot P34727 | ND |
| 3781 | 1250.9 | POLYUBIQUITIN. | sptrembl O74274 | ND |
| 3782 | 1220.9 | C-4 METHYL STEROL OXIDASE (EC 1.-.-.-). | swissprot O59933 | ND |
| 3783 | 1218.0 | *Sphingomonas capsulata* aminopeptidase I. | geneseqp W89587 | ND |
| 3784 | 1203.0 | *Aspergillus awamori* glucoamylase mutant N20C, A27C. | geneseqp W55976 | ND |
| 3785 | 1195.2 | *Aspergillus niger* glucoamylase enzyme. | geneseqp Y23338 | ND |
| 3786 | 1156.2 | Plasmid pASK75 open reading frame (b) translation. | geneseqp R88635 | ND |
| 3787 | 1150.6 | 60S RIBOSOMAL PROTEIN L7-C. | swissprot O60143 | Translation, ribosomal structure and biogenesis |
| 3788 | 1150.4 | 60S RIBOSOMAL PROTEIN L10. | tremblnew CAA22664 | Translation, ribosomal structure and biogenesis |
| 3789 | 1149.4 | Truncated *A. niger* glucoamylase G1 protein sequence. | geneseqp Y18090 | ND |
| 3790 | 1145.5 | An enzyme with sugar transferase activity. | geneseqp W88044 | ND |
| 3791 | 1144.1 | ACID-STABLE ALPHA-AMYLASE. | sptrembl O13296 | ND |
| 3792 | 1140.9 | PUTATIVE THIAZOLE SYNTHASE. | tremblnew AAF25444 | ND |
| 3793 | 1138.7 | RIBOSOMAL PROTEIN S28. | tremblnew CAB56815 | Translation, ribosomal structure and biogenesis |
| 3794 | 1135.4 | 40S RIBOSOMAL PROTEIN S5 (S2) (YS8) (RP14). | swissprot P26783 | Translation, ribosomal structure and biogenesis |
| 3795 | 1133.4 | UBI1. | tremblnew AAF24230 | ND |
| 3796 | 1122.5 | ALPHA-AMYLASE A PRECURSOR (EC 3.2.1.1) (1,4-ALPHA-D-GLUCAN GLUCANOHYDROLASE A). | swissprot Q02905 | ND |
| 3797 | 1108.7 | SERYL-TRNA SYNTHETASE, CYTOPLASMIC (EC 6.1.1.11) (SERINE--TRNA LIGASE) (SERRS). | swissprot O14018 | Translation, ribosomal structure and biogenesis |
| 3798 | 1106.3 | GLYCERALDEHYDE 3-PHOSPHATE DEHYDROGENASE (EC 1.2.1.12) (GAPDH). | swissprot Q12552 | Carbohydrate transport and metabolism |
| 3799 | 1072.2 | *Aspergillus awamori* glucoamylase mutant N20C, A27C. | geneseqp W55976 | ND |
| 3800 | 1060.9 | *Aspergillus awamori* glucoamylase mutant N20C, A27C. | geneseqp W55976 | ND |

TABLE 2-continued

*Aspergillus niger* ESTs

| Sequence Listing | zscore | Annotation | Database | Functional Category |
|---|---|---|---|---|
| 3801 | 1053.5 | RASP F 9 (FRAGMENT). | sptrembl O42800 | Carbohydrate transport and metabolism |
| 3802 | 1036.4 | FRUCTOSE-BISPHOSPHATE ALDOLASE (EC 4.1.2.13). | swissprot P53444 | Carbohydrate transport and metabolism |
| 3803 | 1034.1 | TRANSPOSASE. | sptrembl O00050 | ND |
| 3804 | 1026.3 | 40S RIBOSOMAL PROTEIN S15 (S12). | swissprot P34737 | Translation, ribosomal structure and biogenesis |
| 3805 | 1022.0 | 60S RIBOSOMAL PROTEIN L2 (YL6) (L5) (RP8). | swissprot P05736 | Translation, ribosomal structure and biogenesis |
| 3806 | 1014.6 | ADENOSINE-5'PHOSPHOSULFATE KINASE (EC 2.7.1.25) (ADENYLYLSULFATE KINASE) (APS KINASE). | sptrembl Q12657 | Inorganic ion transport and metabolism |
| 3807 | 1009.1 | CYCLOPHILIN-LIKE PEPTIDYL PROLYL CIS-TRANS ISOMERASE (EC 5.2.1.8). | sptrembl O94184 | Posttranslational modification, protein turnover, chaperones |
| 3808 | 1001.9 | HISTONE H2A. | sptrembl O13413 | ND |
| 3809 | 993.9 | ARP2/3 COMPLEX 20 KD SUBUNIT (P20-ARC). | swissprot O15509 | ND |
| 3810 | 964.0 | UBIQUITIN. | sptrembl Q9Y736 | ND |
| 3811 | 963.2 | 60S RIBOSOMAL PROTEIN L8 (L7A) (L4). | swissprot O13672 | Translation, ribosomal structure and biogenesis |
| 3812 | 955.7 | UBIQUINOL-CYTOCHROME C REDUCTASE IRON-SULFUR SUBUNIT, MITOCHONDRIAL PRECURSOR (EC 1.10.2.2) (RIESKE IRON-SULFUR PROTEIN) (RISP). | swissprot P07056 | Energy production and conversion |
| 3813 | 952.3 | ENOLASE (EC 4.2.1.11) (2-PHOSPHOGLYCERATE DEHYDRATASE) (2-PHOSPHO-D-GLYCERATE HYDRO-LYASE). | swissprot Q12560 | Carbohydrate transport and metabolism |
| 3814 | 950.5 | RIBOSOMAL PROTEIN L13A. | tremblnew AAD54383 | Translation, ribosomal structure and biogenesis |
| 3815 | 935.8 | *Aspergillus awamori* glucoamylase mutant N20C, A27C. | geneseqp W55976 | ND |
| 3816 | 933.7 | PROTEIN DISULFIDE ISOMERASE PRECURSOR (PDI) (EC 5.3.4.1). | swissnew Q12730 | ND |
| 3817 | 930.5 | 60S RIBOSOMAL PROTEIN L23. | swissprot Q07760 | Translation, ribosomal structure and biogenesis |
| 3818 | 928.4 | *Aspergillus awamori* glucoamylase mutant N20C, A27C, S411A. | geneseqp W55980 | ND |
| 3819 | 926.5 | ATP SYNTHASE BETA CHAIN, MITOCHONDRIAL PRECURSOR (EC 3.6.1.34). | swissnew P23704 | Energy production and conversion |
| 3820 | 912.5 | 40S RIBOSOMAL PROTEIN S4 (S7) (YS6) (RP5). | swissprot P05753 | Translation, ribosomal structure and biogenesis |
| 3821 | 909.6 | HYPOTHETICAL 32.5 KD PROTEIN YLR351C. | swissprot P49954 | ND |

TABLE 2-continued

_Aspergillus niger ESTs_

| Sequence Listing | zscore | Annotation | Database | Functional Category |
|---|---|---|---|---|
| 3822 | 907.3 | 60S ACIDIC RIBOSOMAL PROTEIN P0 (L10E). | swissprot P05317 | Translation, ribosomal structure and biogenesis |
| 3823 | 897.7 | 40S RIBOSOMAL PROTEIN S17 (CRP3). | swissprot P27770 | Translation, ribosomal structure and biogenesis |
| 3824 | 897.5 | _Aspergillus awamori_ glucoamylase mutant S411A. | geneseqp W55979 | ND |
| 3825 | 884.9 | 5-METHYLTETRAHYDROPTEROYLTRIGLUTAMATE--HOMOCYSTEI METHYLTRANSFERASE (EC 2.1.1.14). | tremblnew CAB57427 | Amino acid transport and metabolism |
| 3826 | 880.2 | _Aspergillus awamori_ glucoamylase mutant N20C, A27C. | geneseqp W55976 | ND |
| 3827 | 879.3 | _Aspergillus awamori_ glucoamylase mutant N20C, A27C, S30P, G137A. | geneseqp W55977 | ND |
| 3828 | 877.7 | 60S RIBOSOMAL PROTEIN L20 (L18A). | swissprot P47913 | ND |
| 3829 | 869.3 | MONOUBIQUITIN/CARBOXY EXTENSION PROTEIN FUSION. | sptrembl O74216 | ND |
| 3830 | 868.8 | GLYCERALDEHYDE 3-PHOSPHATE DEHYDROGENASE (EC 1.2.1.12) (GAPDH). | swissprot Q12552 | Carbohydrate transport and metabolism |
| 3831 | 867.9 | UBIQUITIN FUSION PROTEIN. | sptrembl Q9Y854 | ND |
| 3832 | 865.9 | Yeast ribosomal protein S7. | geneseqp W36115 | Translation, ribosomal structure and biogenesis |
| 3833 | 862.0 | FATTY ACID SYNTHASE, BETA SUBUNIT. | sptrembl P78616 | Lipid metabolism |
| 3834 | 859.7 | CYTOCHROME C. | swissprot P56205 | ND |
| 3835 | 856.3 | ADP,ATP CARRIER PROTEIN (ADP/ATP TRANSLOCASE) (ADENINE NUCLEOTIDE TRANSLOCATOR) (ANT). | swissprot P02723 | ND |
| 3836 | 856.3 | 60S RIBOSOMAL PROTEIN L27A (L29). | swissprot P78987 | Translation, ribosomal structure and biogenesis |
| 3837 | 855.9 | ALPHA-AMYLASE (EC 3.2.1.1). | tremblnew AAF14264 | ND |
| 3838 | 851.3 | PROBABLE PEROXISOMAL MEMBRANE PROTEIN PMP20 (ALLERGEN ASP F 3). | swissprot O43099 | ND |
| 3839 | 850.9 | NON-FUNCTIONAL FOLATE BINDING PROTEIN. | sptrembl O14597 | ND |
| 3840 | 837.5 | ASPARAGINYL-TRNA SYNTHETASE, CYTOPLASMIC (EC 6.1.1.22) (ASPARAGINE--TRNA LIGASE) (ASNRS). | swissprot P38707 | Translation, ribosomal structure and biogenesis |
| 3841 | 835.4 | ATP SYNTHASE DELTA CHAIN, MITOCHONDRIAL PRECURSOR (EC 3.6.1.34) (FRAGMENT). | swissnew P56525 | Energy production and conversion |
| 3842 | 821.8 | HISTONE H3. | swissprot P23753 | DNA replication, recombination and repair |
| 3843 | 821.7 | 60S RIBOSOMAL PROTEIN L18. | swissnew Q10192 | Translation, ribosomal structure and biogenesis |

TABLE 2-continued

_Aspergillus niger ESTs_

| Sequence Listing | zscore | Annotation | Database | Functional Category |
|---|---|---|---|---|
| 3844 | 817.6 | *Aspergillus awamori* glucoamylase mutant N20C, A27C, S30P, G137A. | geneseqp W55977 | ND |
| 3845 | 803.2 | Ribosomal protein L41. | geneseqp R77658 | Translation, ribosomal structure and biogenesis |
| 3846 | 797.5 | 60S RIBOSOMAL PROTEIN L9-B (L8) (YL11) (RP25). | swissprot P51401 | Translation, ribosomal structure and biogenesis |
| 3847 | 797.2 | NMT1 PROTEIN HOMOLOG. | swissprot P42882 | Inorganic ion transport and metabolism |
| 3848 | 797.1 | Truncated *A. niger* glucoamylase G1 protein sequence. | geneseqp Y18090 | ND |
| 3849 | 791.7 | GLUCOAMYLASE. | sptrembl Q02296 | ND |
| 3850 | 788.8 | 40S RIBOSOMAL PROTEIN S22 (S15A) (YS24). | swissprot P33953 | Translation, ribosomal structure and biogenesis |
| 3851 | 769.6 | VACUOLAR ATP SYNTHASE SUBUNIT B (EC 3.6.1.34) (V-ATPASE 57 KD SUBUNIT). | swissprot P11593 | Energy production and conversion |
| 3852 | 760.4 | NUCLEOSIDE DIPHOSPHATE KINASE. | tremblnew BAA83495 | Nucleotide transport |
| 3853 | 759.6 | MALATE DEHYDROGENASE, MITOCHONDRIAL PRECURSOR (EC 1.1.1.37). | swissprot P17505 | Energy production and conversion |
| 3854 | 759.5 | 40S RIBOSOMAL PROTEIN S2 (S4) (YS5) (RP12) (OMNIPOTENT SUPRESSOR PROTEIN SUP44). | swissprot P25443 | Translation, ribosomal structure and biogenesis |
| 3855 | 756.4 | SPERMIDINE SYNTHASE. | sptrembl Q9Y8H7 | Amino acid transport and metabolism |
| 3856 | 756.3 | 60S RIBOSOMAL PROTEIN L20 (L18A). | swissprot P47913 | ND |
| 3857 | 755.3 | Truncated *A. niger* glucoamylase G1 protein sequence. | geneseqp Y18090 | ND |
| 3858 | 753.8 | *Candida albicans* fungal antigen - allergen SEQ ID NO:5. | geneseqp W53251 | Energy production and conversion |
| 3859 | 748.8 | PEPTIDYL-PROLYL CIS/TRANS ISOMERASE. | sptrembl O42735 | Posttranslational modification, protein turnover, chaperones |
| 3860 | 733.6 | 60S RIBOSOMAL PROTEIN L17-B (YL17-B). | swissprot P46990 | Translation, ribosomal structure and biogenesis |
| 3861 | 728.8 | PUTATIVE ADENOSINE KINASE. | tremblnew AAF23253 | Carbohydrate transport and metabolism |
| 3862 | 723.7 | HIT FAMILY PROTEIN 1. | swissprot Q04344 | ND |
| 3863 | 723.4 | *Aspergillus awamori* glucoamylase mutant N20C, A27C, S411A. | geneseqp W55980 | ND |
| 3864 | 719.9 | OUTER MITOCHONDRIAL MEMBRANE PROTEIN PORIN. | swissprot P07144 | ND |
| 3865 | 716.9 | 40S RIBOSOMAL PROTEIN S26E (CRP5) (13.6 KD RIBOSOMAL PROTEIN). | swissprot P21772 | ND |
| 3866 | 715.0 | HYPOTHETICAL 27.9 KD PROTEIN C22A12.17C IN CHROMOSOME I. | sptrembl O13908 | ND |
| 3867 | 706.4 | HYDROLASE 108 aa | pdb 1AC0 | ND |
| 3868 | 695.7 | EF-HAND PROTEIN. | tremblnew CAB55175 | ND |

TABLE 2-continued

*Aspergillus niger* ESTs

| Sequence Listing | zscore | Annotation | Database | Functional Category |
|---|---|---|---|---|
| 3869 | 694.9 | POLYSACCHARIDE DEGRADATION 108 aa | pdb 1ACZ | ND |
| 3870 | 690.7 | PUTATIVE ARSENICAL PUMP-DRIVING ATPASE (EC 3.6.1.-) (ARSENITE-TRANSLOCATING ATPASE) (ARSENICAL RESISTANCE ATPASE). | swissnew P30632 | Inorganic ion transport and metabolism |
| 3871 | 690.1 | MULTICATALYTIC PROTEINASE 222 aa, chain M + 1 | pdb 1RYP | Posttranslational modification, protein turnover, chaperones |
| 3872 | 679.0 | DIHYDROLIPOAMIDE ACETYLTRANSFERASE COMPONENT OF PYRUVATE DEHYDROGENASE COMPLEX, MITOCHONDRIAL PRECURSOR (EC 2.3.1.12) (E2) (PDC-E2) (MRP3). | swissprot P20285 | Energy production and conversion |
| 3873 | 672.8 | OLIGO-1,4-1,4-GLUCANTRANSFERASE/ AMYLO-1,6-GLUCOSIDASE. | sptrembl O93808 | Carbohydrate transport and metabolism |
| 3874 | 671.9 | CYCLIN-DEPENDENT KINASES REGULATORY SUBUNIT (CELL DIVISION CONTROL PROTEIN CKS1). | swissprot P20486 | ND |
| 3875 | 665.8 | Sequence encoded by *A. awamori* glucoamylase genomic region. | geneseqp P40212 | ND |
| 3876 | 642.3 | HISTONE H3. | swissprot P23753 | DNA replication, recombination and repair |
| 3877 | 635.2 | CYCLOPHILIN B (EC 5.2.1.8). | sptrembl O94190 | Posttranslational modification, protein turnover, chaperones |
| 3878 | 631.8 | ALPHA-AMYLASE A PRECURSOR (EC 3.2.1.1) (1,4-ALPHA-D-GLUCAN GLUCANOHYDROLASE A). | swissprot Q02905 | ND |
| 3879 | 630.4 | 60S RIBOSOMAL PROTEIN L3. | tremblnew AAF15600 | Translation, ribosomal structure and biogenesis |
| 3880 | 628.4 | NUCLEOSIDE DIPHOSPHATE KINASE. | tremblnew BAA83495 | Nucleotide transport |
| 3881 | 627.1 | D-LACTATE DEHYDROGENASE [CYTOCHROME] PRECURSOR (EC 1.1.2.4) (D-LACTATE FERRICYTOCHROME C OXIDOREDUCTASE) (D-LCR). | swissprot Q12627 | Energy production and conversion |
| 3882 | 626.8 | HYPOTHETICAL 34.3 KD PROTEIN. | sptrembl O43015 | ND |
| 3883 | 626.6 | 40S RIBOSOMAL PROTEIN S22 (S15A) (YS24). | swissprot P33953 | Translation, ribosomal structure and biogenesis |
| 3884 | 625.1 | HYPOTHETICAL 20.9 KD PROTEIN. | sptrembl O94286 | ND |
| 3885 | 620.0 | VACUOLAR ATP SYNTHASE 16 KD PROTEOLIPID SUBUNIT (EC 3.6.1.34). | swissprot Q00607 | Energy production and conversion |
| 3886 | 619.1 | PI023 PROTEIN. | sptrembl O13614 | ND |
| 3887 | 611.8 | RS6/L7A RIBOSOMAL PROTEIN HOMOLOG. | sptrembl O74690 | Translation, ribosomal structure and biogenesis |

TABLE 2-continued

_Aspergillus niger ESTs_

| Sequence Listing | zscore | Annotation | Database | Functional Category |
|---|---|---|---|---|
| 3888 | 611.0 | RIBOSOMAL PROTEIN L32E. | sptrembl O94008 | Translation, ribosomal structure and biogenesis |
| 3889 | 610.2 | SUR2 PROTEIN (SYRINGOMYCIN RESPONSE PROTEIN 2). | swissprot P38992 | ND |
| 3890 | 609.0 | HYPOTHETICAL 15.9 KD PROTEIN C4A8.02C IN CHROMOSOME I. | swissprot O14155 | ND |
| 3891 | 608.4 | PUTATIVE TRANSPORTER YIL166C. | swissprot P40445 | ND |
| 3892 | 605.6 | PUTATIVE CTP SYNTHASE C10F6.03C (EC 6.3.4.2) (UTP--AMMONIA LIGASE C10F6.03C) (CTP SYNTHETASE C10F6.03C). | sptrembl O42644 | Nucleotide transport |
| 3893 | 602.5 | NUCLEAR TRANSPORT FACTOR 2 (NTF-2) (NUCLEAR TRANSPORT FACTOR P10). | swissprot P33331 | ND |
| 3894 | 601.5 | PROTEIN TRANSLATION FACTOR SUI1. | swissprot P32911 | Translation, ribosomal structure and biogenesis |
| 3895 | 599.9 | HYPOTHETICAL 12.5 KD PROTEIN. | sptrembl O74948 | ND |
| 3896 | 598.8 | HYDROLASE 108 aa | pdb 1AC0 | ND |
| 3897 | 594.2 | Beta-1 integrin modulator B171. | geneseqp W19771 | ND |
| 3898 | 591.9 | GLYCERALDEHYDE 3-PHOSPHATE DEHYDROGENASE (EC 1.2.1.12) (GAPDH). | swissprot Q12552 | Carbohydrate transport and metabolism |
| 3899 | 589.2 | 60S RIBOSOMAL PROTEIN L12. | swissprot O75000 | Translation, ribosomal structure and biogenesis |
| 3900 | 588.0 | 60S RIBOSOMAL PROTEIN L30. | tremblnew CAB54828 | Translation, ribosomal structure and biogenesis |
| 3901 | 584.7 | RIBOSOMAL PROTEIN L31. | sptrembl Q9XGL4 | Translation, ribosomal structure and biogenesis |
| 3902 | 579.0 | NADH-UBIQUINONE OXIDOREDUCTASE 12 KD SUBUNIT PRECURSOR (EC 1.6.5.3) (EC 1.6.99.3) (COMPLEX I-12 KD) (CI-12 KD). | swissprot Q03015 | ND |
| 3903 | 574.1 | 60S RIBOSOMAL PROTEIN L43 (L37A) (YL35). | swissprot P49631 | Translation, ribosomal structure and biogenesis |
| 3904 | 570.3 | 60S RIBOSOMAL PROTEIN L35. | swissprot P17078 | Translation, ribosomal structure and biogenesis |
| 3905 | 570.2 | D-LACTATE DEHYDROGENASE [CYTOCHROME] PRECURSOR (EC 1.1.2.4) (D-LACTATE FERRICYTOCHROME C OXIDOREDUCTASE) (D-LCR). | swissprot Q12627 | Energy production and conversion |
| 3906 | 569.3 | 60S RIBOSOMAL PROTEIN L34-B. | swissprot P40525 | Translation, ribosomal structure and biogenesis |
| 3907 | 565.0 | GATA TRANSCRIPTION FACTOR. | sptrembl O59842 | ND |

TABLE 2-continued

_Aspergillus niger ESTs_

| Sequence Listing | zscore | Annotation | Database | Functional Category |
|---|---|---|---|---|
| 3908 | 560.4 | 60S RIBOSOMAL PROTEIN L43 (L37A) (YL35). | swissprot P49631 | Translation, ribosomal structure and biogenesis |
| 3909 | 557.9 | PROBABLE SUCCINYL-COA:3-KETOACID-COENZYME A TRANSFERASE PRECURSOR (EC 2.8.3.5) (3-OXOACID COA-TRANSFERASE). | swissprot Q09450 | Lipid metabolism |
| 3910 | 555.7 | HYPOTHETICAL 31.6 KD PROTEIN. | sptrembl O13844 | ND |
| 3911 | 548.3 | RIBOSOMAL PROTEIN L26 (FRAGMENT). | sptrembl O82579 | Translation, ribosomal structure and biogenesis |
| 3912 | 546.8 | 40S RIBOSOMAL PROTEIN S20. | swissprot O74893 | Translation, ribosomal structure and biogenesis |
| 3913 | 546.1 | IGE-BINDING PROTEIN (FRAGMENT). | sptrembl O74263 | ND |
| 3914 | 543.1 | 40S RIBOSOMAL PROTEIN S27. | swissprot O74330 | Translation, ribosomal structure and biogenesis |
| 3915 | 537.5 | 2-OXOGLUTARATE DEHYDROGENASE E1 COMPONENT, MITOCHONDRIAL PRECURSOR (EC 1.2.4.2) (ALPHA-KETOGLUTARATE DEHYDROGENASE). | swissprot P20967 | Energy production and conversion |
| 3916 | 536.2 | 40S RIBOSOMAL PROTEIN S27. | swissprot O74330 | Translation, ribosomal structure and biogenesis |
| 3917 | 535.7 | HYPOTHETICAL 21.4 KD PROTEIN C19A8.14 IN CHROMOSOME I. | sptrembl O13830 | ND |
| 3918 | 534.3 | 60S ACIDIC RIBOSOMAL PROTEIN P0 (L10E). | swissprot P05317 | Translation, ribosomal structure and biogenesis |
| 3919 | 529.2 | ACYL CARRIER PROTEIN, MITOCHONDRIAL PRECURSOR (ACP) (NADH-UBIQUINONE OXIDOREDUCTASE 9.6 KD SUBUNIT) (EC 1.6.5.3) (EC 1.6.99.3). | swissprot P11943 | ND |
| 3920 | 527.2 | PROBABLE GYP7 PROTEIN (FRAGMENT). | swissprot P09379 | ND |
| 3921 | 523.2 | ATP SYNTHASE GAMMA CHAIN, MITOCHONDRIAL PRECURSOR. | sptrembl O74754 | Energy production and conversion |
| 3922 | 522.6 | S-ADENOSYLMETHIONINE DECARBOXYLASE (EC 4.1.1.50) (FRAGMENT). | sptrembl Q9Y8A3 | ND |
| 3923 | 519.9 | An enzyme with sugar transferase activity. | geneseqp W88044 | ND |
| 3924 | 511.6 | ACETOLACTATE SYNTHASE SMALL SUBUNIT PRECURSOR (EC 4.1.3.18) (AHAS) (ACETOHYDROXY-ACID SYNTHASE SMALL SUBUNIT) (ALS). | swissnew P25605 | Amino acid transport and metabolism |
| 3925 | 511.2 | NADH-UBIQUINONE OXIDOREDUCTASE 21.3 KD SUBUNIT (EC 1.6.5.3) (EC 1.6.99.3). | swissprot P25710 | ND |
| 3926 | 511.0 | THIOREDOXIN. | swissprot P29429 | ND |

TABLE 2-continued

_Aspergillus niger_ ESTs

| Sequence Listing | zscore | Annotation | Database | Functional Category |
|---|---|---|---|---|
| 3927 | 509.0 | Protein encoded by multiple drug resistance gene atrD. | geneseqp Y02630 | ND |
| 3928 | 505.7 | HYDROLASE 108 aa | pdb 1KUM | ND |
| 3929 | 503.5 | HYPOTHETICAL 52.3 KD PROTEIN. | tremblnew CAB58401 | ND |
| 3930 | 502.5 | RIBOSOMAL PROTEIN L26 (FRAGMENT). | sptrembl O82579 | Translation, ribosomal structure and biogenesis |
| 3931 | 499.0 | UBIQUINOL-CYTOCHROME C REDUCTASE COMPLEX SUBUNIT. | sptrembl O74533 | ND |
| 3932 | 498.8 | _A. fumigatus_ allergen rAsp f8 sequence. | geneseqp W61478 | Translation, ribosomal structure and biogenesis |
| 3933 | 490.7 | VACUOLAR ATP SYNTHASE SUBUNIT G (EC 3.6.1.34) (V-ATPASE 13 KD SUBUNIT) (VACUOLAR H(+)-ATPASE SUBUNIT G). | swissprot P78713 | ND |
| 3934 | 488.3 | UBIQUINOL-CYTOCHROME C REDUCTASE COMPLEX SUBUNIT. | sptrembl O74533 | ND |
| 3935 | 488.1 | ACTIN-RELATED PROTEIN. | sptrembl O94805 | Cell division and chromosome partitioning |
| 3936 | 487.5 | VACUOLAR ATP SYNTHASE SUBUNIT G (EC 3.6.1.34) (V-ATPASE 13 KD SUBUNIT) (VACUOLAR H(+)-ATPASE SUBUNIT G). | swissprot P78713 | ND |
| 3937 | 480.0 | HYPOTHETICAL 11.8 KD PROTEIN C1B3.02C IN CHROMOSOME I. | swissprot O13868 | ND |
| 3938 | 479.8 | CYANATE LYASE (EC 4.3.99.1) (CYANATE HYDROLASE) (CYANASE). | swissnew Q59948 | Inorganic ion transport and metabolism |
| 3939 | 479.0 | 40S RIBOSOMAL PROTEIN S21 (S26) (YS25). | swissprot P05760 | ND |
| 3940 | 475.9 | HYPOTHETICAL 11.5 KD PROTEIN IN HTB2-NTH2 INTERGENIC REGION. | swissprot P35195 | ND |
| 3941 | 473.8 | HYPOTHETICAL 23.4 KD PROTEIN. | sptrembl Q03201 | Translation, ribosomal structure and biogenesis |
| 3942 | 466.6 | ACTIN, MUSCLE (LPM) (FRAGMENT). | swissprot Q25381 | Cell division and chromosome partitioning |
| 3943 | 465.8 | _N. crassa_ mtr gene product. | geneseqp R79909 | ND |
| 3944 | 462.4 | PUTATIVE TRANSCRIPTIONAL REGULATOR. | sptrembl O13337 | ND |
| 3945 | 460.7 | _A. oryzae_ DEBY1058 locus protein sequence. | geneseqp Y39874 | ND |
| 3946 | 460.3 | PROBABLE ADENOSINE DEAMINASE (EC 3.5.4.4) (ADENOSINE AMINOHYDROLASE). | swissprot P53909 | Nucleotide transport |
| 3947 | 459.8 | RIBOSOMAL PROTEIN S28. | tremblnew CAB56815 | Translation, ribosomal structure and biogenesis |
| 3948 | 459.5 | PYRUVATE DEHYDROGENASE E1 COMPONENT BETA SUBUNIT, MITOCHONDRIAL PRECURSOR (EC 1.2.4.1) (PDHE1-B). | swissprot P32473 | Energy production and conversion |

TABLE 2-continued

Aspergillus niger ESTs

| Sequence Listing | zscore | Annotation | Database | Functional Category |
|---|---|---|---|---|
| 3949 | 458.2 | HYPOTHETICAL 37.4 KD PROTEIN IN SEC27-RPL1B INTERGENIC REGION. | swissprot P53123 | Cell division and chromosome partitioning |
| 3950 | 457.8 | LIPASE 4 PRECURSOR (EC 3.1.1.3). | swissprot P32948 | ND |
| 3951 | 454.0 | SEC65 PROTEIN. | tremblnew CAB55335 | Cell motility and secretion |
| 3952 | 453.8 | TRP-ASP REPEAT CONTAINING PROTEIN. | sptrembl O74855 | ND |
| 3953 | 451.6 | PUTATIVE GOLGI URIDINE DIPHOSPHATE-N-ACETYLGLUCOSAMINE TRANSPORTER. | sptrembl O74750 | ND |
| 3954 | 449.2 | PROBABLE INOSINE-5'-MONOPHOSPHATE DEHYDROGENASE (EC 1.1.1.205) (IMP DEHYDROGENASE) (IMPDH) (IMPD). | swissprot O00086 | Nucleotide transport |
| 3955 | 448.6 | HYDROLASE 108 aa | pdb 1KUM | ND |
| 3956 | 448.2 | CALMODULIN. | swissprot Q02052 | ND |
| 3957 | 447.3 | CYTOCHROME C OXIDASE POLYPEPTIDE VIB (EC 1.9.3.1) (AED). | swissprot Q01519 | ND |
| 3958 | 444.9 | KIAA0363 (FRAGMENT). | sptrembl O15069 | ND |
| 3959 | 442.8 | HEAT SHOCK PROTEIN 60 PRECURSOR. | tremblnew AAB46362 | ND |
| 3960 | 438.9 | RIBOSOMAL PROTEIN S31 HOMOLOG. | sptrembl O74172 | ND |
| 3961 | 436.1 | RIBOSOMAL PROTEIN L14. | sptrembl O94238 | Translation, ribosomal structure and biogenesis |
| 3962 | 430.8 | ELONGATION FACTOR 1-BETA (EF-1-BETA). | swissprot P32471 | Translation, ribosomal structure and biogenesis |
| 3963 | 428.5 | 40S RIBOSOMAL PROTEIN S29-B (S36) (YS29). | swissprot P41058 | Translation, ribosomal structure and biogenesis |
| 3964 | 427.7 | UBIQUINOL-CYTOCHROME C REDUCTASE COMPLEX UBIQUINONE-BINDING PROTEIN QP-C (EC 1.10.2.2) (UBIQUINOL-CYTOCHROME C REDUCTASE COMPLEX 11 KD PROTEIN) (COMPLEX III SUBUNIT VIII). | swissprot P48503 | ND |
| 3965 | 424.7 | 60S RIBOSOMAL PROTEIN L36-B (L39B) (YL39). | swissprot O14455 | ND |
| 3966 | 422.2 | NADH-UBIQUINONE OXIDOREDUCTASE 9.5 KD SUBUNIT (EC 1.6.5.3) (EC 1.6.99.3) (COMPLEX I-9.5 KD) (CI-9.5) (UBIQUINONE-BINDING PROTEIN). | swissprot P42117 | ND |
| 3967 | 420.2 | 40S RIBOSOMAL PROTEIN S29-B (S36) (YS29). | swissprot P41058 | Translation, ribosomal structure and biogenesis |
| 3968 | 417.1 | Ubiquitin-like domain of the yeast protein SMT3. | geneseqp W87987 | ND |
| 3969 | 416.8 | 40S RIBOSOMAL PROTEIN S30. | swissprot Q12087 | ND |
| 3970 | 416.1 | 60S RIBOSOMAL PROTEIN L39 (YL36). | swissprot P05767 | ND |
| 3971 | 401.3 | ACETOLACTATE SYNTHASE SMALL SUBUNIT PRECURSOR (EC 4.1.3.18) (AHAS) (ACETOHYDROXY-ACID | swissnew P25605 | Amino acid transport and metabolism |

TABLE 2-continued

*Aspergillus niger* ESTs

| Sequence Listing | zscore | Annotation | Database | Functional Category |
|---|---|---|---|---|
| | | SYNTHASE SMALL SUBUNIT) (ALS). | | |
| 3972 | 399.7 | PUTATIVE PROTEIN TRANSPORT PROTEIN SEC61 GAMMA SUBUNIT. | swissprot Q09827 | ND |
| 3973 | 398.0 | *Streptomyces clavuligerus* protein sequence of orfdwn1. | geneseqp W69712 | ND |
| 3974 | 396.5 | 60S RIBOSOMAL PROTEIN L33-A (L37A) (YL37) (RP47). | swissprot P05744 | ND |
| 3975 | 394.8 | MALATE DEHYDROGENASE, MITOCHONDRIAL PRECURSOR. | sptrembl Q9Y7R8 | ND |
| 3976 | 387.9 | PUTATIVE GOLGI URIDINE DIPHOSPHATE-N-ACETYLGLUCOSAMINE TRANSPORTER. | sptrembl O74750 | ND |
| 3977 | 387.0 | HEAT SHOCK PROTEIN HSP1 (65 KD IGE-BINDING PROTEIN) (FRAGMENT). | swissprot P40292 | ND |
| 3978 | 383.8 | ELONGATION FACTOR 1-GAMMA 2 (EF-1-GAMMA 2). | swissprot P36008 | ND |
| 3979 | 377.0 | TYROSYL-TRNA SYNTHETASE, CYTOPLASMIC (EC 6.1.1.1) (TYROSYL--TRNA LIGASE) (TYRRS). | swissprot P36421 | Translation, ribosomal structure and biogenesis |
| 3980 | 371.9 | SERINE PALMITOYLTRANSFERASE 2 (EC 2.3.1.50) (LONG CHAIN BASE BIOSYNTHESIS PROTEIN 2) (SPT 2). | swissprot Q09925 | ND |
| 3981 | 371.6 | CCDB. | tremblnew BAA84907 | ND |
| 3982 | 370.7 | PUTATIVE ATP SYNTHASE F CHAIN, MITOCHONDRIAL PRECURSOR. | sptrembl O94377 | ND |
| 3983 | 369.8 | 60S RIBOSOMAL PROTEIN L6, MITOCHONDRIAL PRECURSOR (YML6). | swissprot P32904 | ND |
| 3984 | 367.9 | *H. pylori* GHPO 1315 protein. | geneseqp W98517 | ND |
| 3985 | 364.8 | *S. pneumoniae* protein SEQ ID NO:465. | geneseqp Y11355 | Translation, ribosomal structure and biogenesis |
| 3986 | 364.3 | 60S RIBOSOMAL PROTEIN L29 (YL43). | swissprot P05747 | ND |
| 3987 | 353.3 | SPORE-WALL FUNGAL HYDROPHOBIN DEWA PRECURSOR. | swissprot P52750 | ND |
| 3988 | 350.3 | PUTATIVE PROGESTERONE-BINDING PROTEIN HOMOLOG. | sptrembl Q9XFM6 | ND |
| 3989 | 345.9 | ATP SYNTHASE DELTA CHAIN FAMILY, OLIGOMYCIN SENSITIVITY CONFERRING PROTEIN. | sptrembl O74479 | ND |
| 3990 | 343.1 | CGI-111 PROTEIN. | sptrembl Q9Y3B5 | ND |
| 3991 | 341.4 | TRANSLATIONALLY CONTROLLED TUMOR PROTEIN HOMOLOG (TCTP). | swissprot P35691 | ND |
| 3992 | 341.2 | PUTATIVE ADENINE PHOSPHORIBOSYLTRANSFERASE. | sptrembl O42842 | ND |
| 3993 | 340.6 | URACIL PHOSPHORIBOSYLTRANSFERASE. | sptrembl P93394 | ND |
| 3994 | 337.0 | HYDROLASE 108 aa | pdb 1KUL | ND |
| 3995 | 335.6 | HYDROLASE 476 aa | pdb 7TAA | ND |
| 3996 | 329.0 | NADH-UBIQUINONE OXIDOREDUCTASE 29.9 KD SUBUNIT PRECURSOR (EC | swissprot P24919 | ND |

TABLE 2-continued

_Aspergillus niger ESTs_

| Sequence Listing | zscore | Annotation | Database | Functional Category |
|---|---|---|---|---|
| | | 1.6.5.3) (EC 1.6.99.3) (COMPLEX I-29.9 KD) (CI-29.9 KD). | | |
| 3997 | 327.7 | AT2G20490 PROTEIN. | tremblnew AAD25649 | ND |
| 3998 | 317.8 | NHP2/RS6 FAMILY PROTEIN YEL026W. | swissprot P39990 | ND |
| 3999 | 317.5 | _Aspergillus niger_ aspartic protease PEPE. | geneseqp R75299 | ND |
| 4000 | 315.1 | HYPOTHETICAL 24.1 KD PROTEIN IN PDR11-FAA3 INTERGENIC REGION. | swissprot P40553 | ND |
| 4001 | 314.9 | NAD(+)-SPECIFIC GLUTAMATE DEHYDROGENASE. | sptrembl Q02222 | ND |
| 4002 | 311.1 | 40S RIBOSOMAL PROTEIN S13. | swissprot P28189 | ND |
| 4003 | 310.7 | ATP CITRATE LYASE. | sptrembl O93988 | ND |
| 4004 | 310.5 | CELL CYCLE PROTEIN KINASE HSK1. | sptrembl O94678 | ND |
| 4005 | 308.3 | REPRESSOR PROTEIN. | sptrembl Q00784 | ND |
| 4006 | 308.3 | CYTOCHROME C OXIDASE POLYPEPTIDE VIA PRECURSOR (EC 1.9.3.1). | swissprot P32799 | ND |
| 4007 | 307.0 | Human epidermoid carcinoma cell line KB clone HP10301 protein. | geneseqp W64553 | ND |
| 4008 | 304.5 | HISTONE H3. | swissprot P23753 | ND |
| 4009 | 299.8 | _Sulfolobus solfataricus_ esterase P1-8LC. | geneseqp W23077 | ND |
| 4010 | 299.5 | DPM2-LIKE PROTEIN. | tremblnew CAB57919 | ND |
| 4011 | 297.1 | HYPOTHETICAL 40.5 KD PROTEIN IN UBP15-GAS1 INTERGENIC REGION PRECURSOR. | swissprot Q04951 | ND |
| 4012 | 294.1 | VIP1 PROTEIN (P53 ANTIGEN HOMOLOG). | sptrembl P87216 | ND |
| 4013 | 293.7 | PUTATIVE RNA-BINDING PROTEIN 3 (RNPL). | swissprot P98179 | ND |
| 4014 | 293.6 | CYTOCHROME C OXIDASE COPPER CHAPERONE. | swissprot Q12287 | ND |
| 4015 | 291.2 | CYSTEINE-RICH PROTEIN (FRAGMENT). | sptrembl Q16861 | ND |
| 4016 | 290.6 | C34B2.10 PROTEIN. | sptrembl O44953 | ND |
| 4017 | 290.6 | CLONING VECTOR PZERO-2T. | sptrembl O53022 | ND |
| 4018 | 290.3 | 40S RIBOSOMAL PROTEIN S19 (S16). | swissprot P27073 | ND |
| 4019 | 288.9 | 13 KDA DIFFERENTIATION-ASSOCIATED PROTEIN. | tremblnew AAF17196 | ND |
| 4020 | 280.8 | HYPOTHETICAL 10.1 KD PROTEIN. | sptrembl O74707 | ND |
| 4021 | 278.1 | UV-DAMAGED DNA-BINDING PROTEIN-LIKE. | sptrembl O49552 | ND |
| 4022 | 275.9 | CHOLINE TRANSPORT PROTEIN. | swissprot P19807 | ND |
| 4023 | 274.0 | QUEUINE TRNA-RIBOSYLTRANSFERASE. | sptrembl O94460 | ND |
| 4024 | 272.4 | NADH-UBIQUINONE OXIDOREDUCTASE 13 KD-A SUBUNIT PRECURSOR (EC 1.6.5.3) (EC 1.6.99.3) (COMPLEX I-13KD-A) (CI-13KD-A). | swissprot P23934 | ND |
| 4025 | 268.2 | INTEGRAL MEMBRANE PROTEIN. | sptrembl Q9Y786 | ND |
| 4026 | 267.1 | PROBABLE EUKARYOTIC TRANSLATION INITIATION FACTOR 5 (EIF-5). | swissprot Q09689 | ND |
| 4027 | 267.0 | HYPOTHETICAL 18.5 KD PROTEIN IN NDC1-TSA1 INTERGENIC REGION. | swissprot Q03713 | ND |

TABLE 2-continued

Aspergillus niger ESTs

| Sequence Listing | zscore | Annotation | Database | Functional Category |
|---|---|---|---|---|
| 4028 | 261.4 | TRANSCRIPTION INITIATION FACTOR TFIID (TATA-BOX FACTOR) (TATA SEQUENCE-BINDING PROTEIN) (TBP). | swissprot Q12731 | ND |
| 4029 | 257.1 | GLYCERALDEHYDE 3-PHOSPHATE DEHYDROGENASE (EC 1.2.1.12) (GAPDH). | swissprot Q12552 | ND |
| 4030 | 255.6 | VIP1 PROTEIN (P53 ANTIGEN HOMOLOG). | sptrembl P87216 | ND |
| 4031 | 255.2 | HISTONE H2B. | sptrembl Q12606 | ND |
| 4032 | 251.3 | CYTOCHROME P450 97B2 (EC 1.14.-.-). | swissprot O48921 | ND |
| 4033 | 251.0 | RIBOSOMAL PROTEIN S5 (FRAGMENT). | tremblnew BAA25815 | ND |
| 4034 | 249.6 | ISOVALERYL DEHYDROGENASE. | tremblnew AAF20182 | ND |
| 4035 | 245.2 | URACIL-DNA GLYCOSYLASE. | tremblnew AAD51974 | ND |
| 4036 | 244.8 | ISOCITRATE DEHYDROGENASE [NADP], MITOCHONDRIAL PRECURSOR (EC 1.1.1.42) (OXALOSUCCINATE DECARBOXYLASE) (IDH) (NADP+-SPECIFIC ICDH) (IDP). | swissprot P79089 | ND |
| 4037 | 243.2 | SPINDLE ASSEMBLY CHECKPOINT PROTEIN SLDA. | sptrembl O59901 | ND |
| 4038 | 243.0 | FISSION YEAST (FRAGMENT). | sptrembl P78767 | ND |
| 4039 | 242.1 | HYPOTHETICAL 29.3 KD PROTEIN (ORF92). | swissprot O10341 | ND |
| 4040 | 241.8 | HEMOLYSIN. | sptrembl Q00050 | ND |
| 4041 | 241.5 | PUTATIVE PROTEIN TRANSPORT PROTEIN SEC61 GAMMA SUBUNIT. | swissprot Q09827 | ND |
| 4042 | 237.4 | ASCORBATE PEROXIDASE. | sptrembl Q39780 | ND |
| 4043 | 235.2 | R07B7.5 PROTEIN. | sptrembl Q21795 | ND |
| 4044 | 233.2 | MITOCHONDRIAL THIOREDOXIN PRECURSOR (MT-TRX). | swissprot Q95108 | ND |
| 4045 | 232.3 | C-1-TETRAHYDROFOLATE SYNTHASE, CYTOPLASMIC (C1-THF SYNTHASE) [INCLUDES: METHYLENETETRAHYDRO FOLATE DEHYDROGENASE (EC 1.5.1.5); METHENYLTETRAHYDROF OLATE CYCLOHYDROLASE (EC 3.5.4.9); FORMYLTETRAHYDROFOL ATE SYNTHETASE (EC 6.3.4.3)]. | swissprot P07245 | ND |
| 4046 | 232.0 | GLUTATHIONE PEROXIDASE (EC 1.11.1.9). | swissnew O59858 | ND |
| 4047 | 228.2 | SIMILAR TO SDH4P. | sptrembl Q06236 | ND |
| 4048 | 226.2 | CHROMOSOME IV READING FRAME ORF YDL193W. | sptrembl Q12063 | ND |
| 4049 | 225.8 | HYPOTHETICAL 8.6 KD PROTEIN. | sptrembl Q03482 | ND |
| 4050 | 225.7 | ATPASE INHIBITOR, MITOCHONDRIAL. | swissprot P09940 | ND |
| 4051 | 223.9 | DPM2 mannosyl transferase. | geneseqp R47201 | ND |
| 4052 | 223.7 | POSSIBLE COPPER TRANSPORT PROTEIN CTR2 (COPPER TRANSPORTER 2). | swissprot P38865 | ND |
| 4053 | 223.6 | ORF2 of Enod2b genomic clone. | geneseqp R04119 | ND |

TABLE 2-continued

_Aspergillus niger ESTs_

| Sequence Listing | zscore | Annotation | Database | Functional Category |
|---|---|---|---|---|
| 4054 | 222.4 | SALIVARY PROLINE-RICH PROTEIN PO (ALLELE K) [CONTAINS: PEPTIDE P-D] (FRAGMENT). | swissprot P10162 | ND |
| 4055 | 221.7 | DNA REPAIR PROTEIN RAD14. | swissprot P28519 | ND |
| 4056 | 221.5 | RIBOSOMAL PROTEIN L41. | tremblnew CAB52162 | ND |
| 4057 | 217.8 | NIFU-LIKE PROTEIN. | sptrembl O49627 | ND |
| 4058 | 217.1 | PUTATIVE TRANSCRIPTIONAL REGULATOR. | sptrembl Q9X7Q2 | ND |
| 4059 | 216.4 | ATP SYNTHASE DELTA CHAIN, MITOCHONDRIAL PRECURSOR (EC 3.6.1.34) (FRAGMENT). | swissnew P56525 | ND |
| 4060 | 214.0 | CELL WALL-PLASMA MEMBRANE LINKER PROTEIN HOMOLOG. | tremblnew AAD11796 | ND |
| 4061 | 212.3 | PROHIBITIN. | sptrembl O04331 | ND |
| 4062 | 210.7 | RIBOSOMAL PROTEIN L33-LIKE PROTEIN. | sptrembl O75394 | ND |
| 4063 | 209.1 | EXTENSIN (FRAGMENT). | sptrembl O49870 | ND |
| 4064 | 207.2 | GLUE PROTEIN. | sptrembl Q27423 | ND |
| 4065 | 206.8 | RIBOSOMAL PROTEIN S31 HOMOLOG. | sptrembl O74172 | ND |
| 4066 | 204.8 | EXTENSIN PRECURSOR (CELL WALL HYDROXYPROLINE-RICH GLYCOPROTEIN). | swissprot P13983 | ND |
| 4067 | 204.5 | GLYCOPROTEIN GP150. | tremblnew AAF19315 | ND |
| 4068 | 204.0 | NON-FUNCTIONAL FOLATE BINDING PROTEIN. | sptrembl O14597 | ND |
| 4069 | 202.5 | GLUE PROTEIN. | sptrembl Q27423 | ND |
| 4070 | 202.3 | HAVCR-1 PROTEIN PRECURSOR. | sptrembl Q95144 | ND |
| 4071 | 201.6 | ACIDIC RIBOSOMAL PROTEIN. | sptrembl O96938 | ND |
| 4072 | 201.6 | PHEROPHORIN-S PRECURSOR. | sptrembl P93797 | ND |
| 4073 | 201.3 | F23N19.12. | tremblnew AAF19547 | ND |
| 4074 | 200.7 | BINDING PROTEIN 113 aa | pdb 1YAT | ND |
| 4075 | 198.7 | HYPOTHETICAL PROTEIN C30B4.01C IN CHROMOSOME II (FRAGMENT). | sptrembl P87179 | ND |
| 4076 | 197.6 | F32D1.2 PROTEIN. | sptrembl O16298 | ND |
| 4077 | 194.3 | EXTENSIN PRECURSOR. | sptrembl Q40768 | ND |
| 4078 | 192.7 | DELTA-6 FATTY ACID DESATURASE. | sptrembl Q9Z122 ND | |
| 4079 | 192.6 | COSMID C37C3. | sptrembl Q22919 | ND |
| 4080 | 192.5 | Sequence A encoded by a portion of SA307. | geneseqp P60623 | ND |
| 4081 | 192.4 | ATP SYNTHASE E CHAIN, MITOCHONDRIAL (EC 3.6.1.34). | swissprot P81449 | ND |
| 4082 | 192.3 | RIBOSOMAL PROTEIN S31 HOMOLOG. | sptrembl O74172 | ND |
| 4083 | 192.2 | SMALL PROLINE-RICH PROTEIN 1A. | tremblnew AAD10126 | ND |
| 4084 | 191.5 | ORF YDL133W. | sptrembl Q12516 | ND |
| 4085 | 188.0 | ENOLASE (EC 4.2.1.11) (2-PHOSPHOGLYCERATE DEHYDRATASE) (2-PHOSPHO-D-GLYCERATE HYDRO-LYASE). | swissprot Q12560 | ND |
| 4086 | 187.8 | 60S RIBOSOMAL PROTEIN L44 (L41). | swissprot P31866 | ND |
| 4087 | 185.6 | TROPOMYOSIN 1. | swissprot P17536 | ND |

TABLE 2-continued

_Aspergillus niger ESTs_

| Sequence Listing | zscore | Annotation | Database | Functional Category |
|---|---|---|---|---|
| 4088 | 185.3 | HYPOTHETICAL 15.4 KD PROTEIN YPR056C. | sptrembl Q12160 | ND |
| 4089 | 184.3 | *M. tuberculosis* recombinant antigen protein TbH-30. | geneseqp Y39014 | ND |
| 4090 | 183.1 | ALPHA-INTERFERON INDUCIBLE PROTEIN (FRAGMENT). | tremblnew AAF23490 | ND |
| 4091 | 182.4 | Mutant *Aspergillus oryzae* DEBY932 rescued locus. | geneseqp W37992 | ND |
| 4092 | 182.2 | CYSTEINE-RICH EXTENSIN-LIKE PROTEIN 2. | sptrembl Q08195 | ND |
| 4093 | 181.9 | HYPOTHETICAL PROLINE-RICH PROTEIN (FRAGMENT). | swissprot P21260 | ND |
| 4094 | 181.8 | UBI1. | tremblnew AAF24230 | ND |
| 4095 | 181.5 | Silk like protein (SLP)C-SLPF. | geneseqp R95140 | ND |
| 4096 | 181.5 | PUTATIVE MITOSIS AND MAINTENANCE OF PLOIDY PROTEIN. | sptrembl O94360 | ND |
| 4097 | 181.4 | NAPRP3. | sptrembl Q41192 | ND |
| 4098 | 181.0 | YSY6 PROTEIN. | swissprot P38374 | ND |
| 4099 | 179.6 | METALLOTHIONEIN-LIKE PROTEIN CAP5. | swissprot Q00369 | ND |
| 4100 | 178.5 | *Streptococcus pneumoniae* PspA central region. | geneseqp W14574 | ND |
| 4101 | 177.8 | GASTRIC MUCIN (FRAGMENT). | sptrembl Q29071 | ND |
| 4102 | 177.6 | PUTATIVE GLYCOSYLTRANSFERASE. | tremblnew CAB60235 | ND |
| 4103 | 177.4 | HYDROXYPROLINE-RICH GLYCOPROTEIN DZ-HRGP PRECURSOR. | tremblnew CAB62280 | ND |
| 4104 | 175.1 | HISTIDINE-RICH GLYCOPROTEIN PRECURSOR. | swissprot P04929 | ND |
| 4105 | 175.0 | YPT1-RELATED PROTEIN 5. | swissprot P36586 | ND |
| 4106 | 175.0 | SULFATED SURFACE GLYCOPROTEIN 185 (SSG 185). | swissprot P21997 | ND |
| 4107 | 174.4 | *T. gondii* immunogenic protein. | geneseqp Y29039 | ND |
| 4108 | 172.3 | HYPOTHETICAL 11.3 KD PROTEIN IN MIR1-STE18 INTERGENIC REGION. | swissprot P47131 | ND |
| 4109 | 171.8 | F56H9.1 PROTEIN. | sptrembl Q20908 | ND |
| 4110 | 171.4 | HEMOLYSIN-LIKE PROTEIN. | sptrembl O32337 | ND |
| 4111 | 171.3 | EXTENSIN PRECURSOR (PROLINE-RICH GLYCOPROTEIN). | swissprot P24152 | ND |
| 4112 | 170.4 | CELL WALL PROTEIN PRECURSOR. | sptrembl Q39005 | ND |
| 4113 | 170.1 | GOLGIN-95. | swissprot Q08379 | ND |
| 4114 | 169.8 | BACTENECIN 7 PRECURSOR (BAC7) (PR-59). | swissprot P19661 | ND |
| 4115 | 169.8 | ANTER-SPECIFIC PROLINE-RICH PROTEIN APG (PROTEIN CEX) (FRAGMENT). | swissprot P40603 | ND |
| 4116 | 169.8 | HYPOTHETICAL 17.1 KD PROTEIN IN PUR5 3'REGION. | swissprot P38898 | ND |
| 4117 | 169.6 | EXTENSIN (PROLINE-RICH GLYCOPROTEIN) (CLONE W6) (FRAGMENT). | sptrembl Q01945 | ND |
| 4118 | 169.5 | F23N19.12. | tremblnew AAF19547 | ND |
| 4119 | 169.2 | MYOCYTE-SPECIFIC ENHANCER FACTOR 2D. | swissnew Q63943 | ND |
| 4120 | 168.8 | FISSION YEAST (FRAGMENT). | sptrembl P78755 | ND |

TABLE 2-continued

_Aspergillus niger_ ESTs

| Sequence Listing | zscore | Annotation | Database | Functional Category |
|---|---|---|---|---|
| 4121 | 168.4 | NUCLEAR PROTEIN (FRAGMENT). | sptrembl Q95294 | ND |
| 4122 | 168.3 | MYOCYTE-SPECIFIC ENHANCER FACTOR 2D. | swissnew Q63943 | ND |
| 4123 | 167.8 | Cyanovirin-N protein sequence. | geneseqp Y39909 | ND |
| 4124 | 166.8 | DVE PROTEIN. | sptrembl O77289 | ND |
| 4125 | 166.2 | KERATIN, ULTRA HIGH-SULFUR MATRIX PROTEIN (UHS KERATIN). | swissprot P26372 | ND |
| 4126 | 165.5 | 50 KD PROLINE RICH PROTEIN. | sptrembl Q9ZBP2 | ND |
| 4127 | 165.1 | PROTEOPHOSPHOGLYCAN (FRAGMENT). | sptrembl Q9Y075 | ND |
| 4128 | 164.8 | EARLY NODULIN 20 PRECURSOR (N-20). | swissprot P93329 | ND |
| 4129 | 164.7 | 60S RIBOSOMAL PROTEIN L23A. | swissprot O22644 | ND |
| 4130 | 163.2 | PUTATIVE MEMBRANE PROTEIN. | tremblnew CAB52863 | ND |
| 4131 | 161.6 | MITOCHONDRIAL CAPSULE SELENOPROTEIN. | sptrembl O70613 | ND |
| 4132 | 161.4 | STRUCTURAL WALL PROTEIN PRECURSOR. | sptrembl Q07373 | ND |
| 4133 | 161.0 | POLYSACCHARIDE DEGRADATION 108 aa | pdb 1ACZ | ND |
| 4134 | 160.0 | EXTENSIN-LIKE PROTEIN. | tremblnew CAB40769 | ND |
| 4135 | 160.0 | HYPOTHETICAL 14.0 KD PROTEIN. | sptrembl O74383 | ND |
| 4136 | 159.9 | C-REL PROTO-ONCOGENE PROTEIN (C-REL PROTEIN). | swissprot P15307 | ND |
| 4137 | 159.5 | THROMBOSPONDIN-RELATED ANONYMOUS PROTEIN (FRAGMENT). | sptrembl Q94727 | ND |
| 4138 | 158.7 | EXTENSIN (FRAGMENT). | sptrembl Q41645 | ND |
| 4139 | 158.5 | F18A11.4 PROTEIN. | sptrembl Q9XTB1 | ND |
| 4140 | 158.5 | INSERTION ELEMENT ISR1 HYPOTHETICAL 30.8 KD PROTEIN A. | swissprot P17986 | ND |
| 4141 | 158.5 | HISTONE H4. | swissprot P09322 | ND |
| 4142 | 158.4 | HYPOTHETICAL PROTEIN H10983. | swissprot P43907 | ND |
| 4143 | 158.1 | NADH DEHYDROGENASE SUBUNIT 4. | sptrembl O63595 | ND |
| 4144 | 157.2 | TONB2. | tremblnew AAF04082 | ND |
| 4145 | 157.1 | O-SIALOGLYCOPROTEIN ENDOPEPTIDASE, PUTATIVE. | tremblnew CAB50493 | ND |
| 4146 | 156.8 | BCD (BICOID) GENE INVOLVED IN ANTERIOR POSITIONAL SPECIFICATION DURING EMBRYOGENESIS (BICOID). | sptrembl Q24615 | ND |
| 4147 | 156.4 | Immunodominant fragment of flagellar pocket antigen of _T. brucei_. | geneseqp R85174 | ND |
| 4148 | 155.5 | ORF YOR309C. | sptrembl Q12444 | ND |
| 4149 | 155.3 | REGULATORY PROTEIN E2. | sptrembl O56955 | ND |
| 4150 | 155.0 | BASSOON. | sptrembl O88737 | ND |
| 4151 | 154.8 | TUMOR NECROSIS FACTOR RECEPTOR TYPE II (FRAGMENT). | sptrembl Q9WUL4 | ND |
| 4152 | 154.6 | G1 PHASE-SPECIFIC GENE {3' REGION (FRAGMENT). | sptrembl Q16164 | ND |
| 4153 | 154.5 | PROTEASE B INHIBITORS 2 AND 1 (PROTEINASE INHIBITOR I(B)2). | swissprot P01095 | ND |
| 4154 | 154.4 | PROLINE-RICH CELL WALL PROTEIN. | sptrembl Q39763 | ND |

TABLE 2-continued

*Aspergillus niger* ESTs

| Sequence Listing | zscore | Annotation | Database | Functional Category |
|---|---|---|---|---|
| 4155 | 153.9 | GASTRIC MUCIN (FRAGMENT). | sptrembl Q29071 | ND |
| 4156 | 153.5 | CBD-cellulase from *Melanocarpus albomyces*. | geneseqp W16545 | ND |
| 4157 | 153.4 | TAT PROTEIN. | tremblnew CAB53046 | ND |
| 4158 | 152.5 | ERYTHROCYTE MEMBRANE PROTEIN 1 (FRAGMENT). | sptrembl O61124 | ND |
| 4159 | 152.5 | 137AA LONG HYPOTHETICAL PROTEIN. | sptrembl Q9YDR3 | ND |
| 4160 | 152.3 | IG ALPHA CHAIN C REGION. | swissprot P01878 | ND |
| 4161 | 152.1 | *Mycobacterium* species protein sequence 50B. | geneseqp Y04998 | ND |
| 4162 | 151.9 | G-protein coupled human thromboxane A2 receptor. | geneseqp W02688 | ND |
| 4163 | 151.8 | HYPOTHETICAL 82.1 KD PROTEIN. | sptrembl O64621 | ND |
| 4164 | 151.7 | HYPOTHETICAL 13.1 KD PROTEIN. | sptrembl Q9XFU9 | ND |
| 4165 | 150.9 | 40S RIBOSOMAL PROTEIN S15A (S24). | swissprot P50891 | ND |
| 4166 | 150.8 | L1332.3A PROTEIN. | tremblnew CAB63874 | ND |
| 4167 | 150.5 | DYNAMIN IIIBB ISOFORM. | tremblnew AAF07848 | ND |
| 4168 | 149.1 | OUTER MEMBRANE PROTEIN. | tremblnew AAF08549 | ND |
| 4169 | 149.0 | ZEIN-BETA PRECURSOR (ZEIN 2) (16 KD) (ZEIN ZC1). | swissprot P08031 | ND |
| 4170 | 149.0 | *Thermus thermophilus* heat resistance MutM protein. | geneseqp Y29572 | ND |
| 4171 | 149.0 | HYPOTHETICAL 24.1 KD PROTEIN IN LEF4-P33 INTERGENIC REGION. | swissprot P41479 | ND |
| 4172 | 148.9 | DNA-BINDING PROTEIN K10. | swissnew P13468 | ND |
| 4173 | 148.5 | METALLOTHIONEIN (FRAGMENT). | sptrembl O76957 | ND |
| 4174 | 148.2 | HYPOTHETICAL 54.7 KD PROTEIN IN COII INTRON 2 REGION. | sptrembl Q02696 | ND |
| 4175 | 148.1 | ASKI TRANSCRIPTION FACTOR (FRAGMENT). | sptrembl Q90230 | ND |
| 4176 | 148.1 | STEROID HORMONE RECEPTOR FAMILY MEMBER NHR-22. | swissprot Q09587 | ND |
| 4177 | 147.7 | HISTIDINE-RICH PROTEIN (FRAGMENT). | sptrembl Q26056 | ND |
| 4178 | 147.7 | CHROMOSOME IV READING FRAME ORF YDL196W. | sptrembl Q12187 | ND |
| 4179 | 147.6 | T06A4.2 PROTEIN. | tremblnew AAC67472 | ND |
| 4180 | 147.6 | CORTICOLIBERIN PRECURSOR (CORTICOTROPIN-RELEASING FACTOR) (CRF). | swissprot P06296 | ND |
| 4181 | 147.5 | HYPOTHETICAL 141.5 KD PROTEIN IN YPT53-RHO2 INTERGENIC REGION. | swissprot P53935 | ND |
| 4182 | 147.4 | LOW MOLECULAR WEIGHT GLUTENIN (FRAGMENT). | sptrembl Q41551 | ND |
| 4183 | 147.4 | INTEGRIN BETA 5 SUBUNIT (FRAGMENT). | sptrembl Q64657 | ND |
| 4184 | 147.0 | ANTIGEN RECEPTOR (FRAGMENT). | sptrembl Q9YHR0 | ND |
| 4185 | 146.8 | *P. furiosus* pyroglutamyl peptidase fragment. | geneseqp R89125 | ND |

TABLE 2-continued

*Aspergillus niger* ESTs

| Sequence Listing | zscore | Annotation | Database | Functional Category |
|---|---|---|---|---|
| 4186 | 146.8 | SFT2 PROTEIN. | swissprot P38166 | ND |
| 4187 | 146.7 | TDP-6-DEOXY-4-KETOHEXOSE 2,3-DEHYDRATASE. | tremblnew AAF18990 | ND |
| 4188 | 146.6 | SALIVARY PROLINE-RICH PROTEIN RP15 PRECURSOR. | sptrembl Q04154 | ND |
| 4189 | 146.1 | SPLICING FACTOR U2AF 38 KD SUBUNIT (U2 AUXILIARY FACTOR 38 KD SUBUNIT) (U2 SNRNP AUXILIARY FACTOR SMALL SUBUNIT). | swissprot Q94535 | ND |
| 4190 | 146.0 | PAX TRANSCRIPTION ACTIVATION DOMAIN INTERACTING PROTEIN PTIP. | sptrembl Q9Z0W6 | ND |
| 4191 | 145.5 | COLLAGEN ALPHA 5(IV) CHAIN (FRAGMENT). | swissprot Q28247 | ND |
| 4192 | 145.0 | 40S RIBOSOMAL PROTEIN S8 (FRAGMENT). | sptrembl O93915 | ND |
| 4193 | 145.0 | CDC37 PROTEIN. | sptrembl O94740 | ND |
| 4194 | 144.8 | HYPOTHETICAL 36.0 KD PROTEIN. | tremblnew CAB62810 | ND |
| 4195 | 144.6 | CELL DIVISION PROTEIN FTSK. | swissprot P46889 | ND |
| 4196 | 144.0 | HYPOTHETICAL 57.5 KD PROTEIN IN VMA7-RPS25A INTERGENIC REGION. | swissprot P53214 | ND |
| 4197 | 143.9 | ZK899.1 PROTEIN. | sptrembl Q23659 | ND |
| 4198 | 143.8 | GTP CYCLOHYDROLASE II (EC 3.5.4.25). | swissnew P44571 | ND |
| 4199 | 143.7 | R09E10.2 PROTEIN (EC 3.1.3.48). | sptrembl Q21877 | ND |
| 4200 | 143.6 | HYPOTHETICAL 33.1 KD PROTEIN. | tremblnew AAF10810 | ND |
| 4201 | 143.4 | W03G1.5 PROTEIN. | tremblnew AAD14753 | ND |
| 4202 | 143.2 | Human thoracic aorta G-protein coupled receptor. | geneseqp W02727 | ND |
| 4203 | 142.9 | T09E11.2 PROTEIN. | sptrembl O02305 | ND |
| 4204 | 142.9 | D2062.3 PROTEIN. | sptrembl O16599 | ND |
| 4205 | 142.4 | ATTACHMENT GLYCOPROTEIN (FRAGMENT). | sptrembl Q9YNF2 | ND |
| 4206 | 142.0 | COSMID C03G6. | sptrembl O01454 | ND |
| 4207 | 142.0 | HYPOTHETICAL 48.4 KD PROTEIN RV2008C. | swissnew Q10849 | ND |
| 4208 | 142.0 | HYPOTHETICAL 31.4 KD PROTEIN. | sptrembl O51346 | ND |
| 4209 | 141.8 | DNA-BINDING RESPONSE REGULATOR. | tremblnew AAF11967 | ND |
| 4210 | 141.8 | ZK1025.5 PROTEIN. | tremblnew CAA18363 | ND |
| 4211 | 141.7 | 686AA LONG HYPOTHETICAL DNA TOPOISOMERASE I. | sptrembl O58356 | ND |
| 4212 | 141.7 | HYPOTHETICAL NUCLEAR PROTEIN (FRAGMENT). | tremblnew BAA87224 | ND |
| 4213 | 141.6 | MYELOBLAST KIAA0244 (FRAGMENT). | sptrembl Q92576 | ND |
| 4214 | 141.5 | 220AA LONG HYPOTHETICAL PROTEIN. | sptrembl Q9YFG0 | ND |
| 4215 | 141.4 | HYPOTHETICAL 34.8 KD PROTEINF YDL037C. | sptrembl Q12140 | ND |
| 4216 | 141.3 | HUNCHBACK PROTEIN (HB) (FRAGMENTS). | sptrembl O46254 | ND |
| 4217 | 141.2 | F57B1.7 PROTEIN. | sptrembl Q20920 | ND |
| 4218 | 141.1 | DOLICHYL-DIPHOSPHOOLIGOSACCHARIDE--PROTEIN GLYCOSYLTRANSFERASE ALPHA SUBUNIT PRECURSOR (EC 2.4.1.119) | swissprot P41543 | ND |

TABLE 2-continued

_Aspergillus niger ESTs_

| Sequence Listing | zscore | Annotation | Database | Functional Category |
|---|---|---|---|---|
| | | (OLIGOSACCHARYL TRANSFERASE ALPHA SUBUNIT) (OLIGOSACCHARYL TRANSFERASE 64 KD SUBUNIT). | | |
| 4219 | 141.0 | *H. influenzae* Hap protein autotransporter membrane integration region. | geneseqp W27705 | ND |
| 4220 | 140.9 | BETA-GLUCOSYL-HMC-ALPHA-GLUCOSYL-TRANSFERASE (EC 2.4.1.-). | swissprot Q06717 | ND |
| 4221 | 140.9 | T-lymphocyte stimulatory protein. | geneseqp R84086 | ND |
| 4222 | 140.9 | DJ465N24.2.1 (PUTATIVE NOVEL PROTEIN) (ISOFORM 1). | sptrembl O95927 | ND |
| 4223 | 140.8 | 120AA LONG HYPOTHETICAL PROTEIN. | sptrembl Q9YF04 | ND |
| 4224 | 140.6 | PROLIN RICH PROTEIN. | sptrembl Q41848 | ND |
| 4225 | 140.2 | ORF 4. | sptrembl O32454 | ND |
| 4226 | 140.1 | Y116A8C.17 PROTEIN. | tremblnew CAB55123 | ND |
| 4227 | 140.0 | LOX18 HOMEODOMAIN PROTEIN (FRAGMENT). | tremblnew AAD54933 | ND |
| 4228 | 139.9 | ORF6 = 14K. | sptrembl Q65006 | ND |
| 4229 | 139.8 | *Mycobacterium* species protein sequence 47B. | geneseqp Y04983 | ND |
| 4230 | 139.8 | GUANYL-SPECIFIC RIBONUCLEASE SA. | tremblnew AAF10029 | ND |
| 4231 | 139.6 | T-lymphocyte stimulatory protein. | geneseqp R84086 | ND |
| 4232 | 139.5 | CODED FOR BY *C. ELEGANS* CDNA YK79A3.5. | sptrembl O02076 | ND |
| 4233 | 139.4 | 152AA LONG HYPOTHETICAL PROTEIN. | sptrembl Q9YE05 | ND |
| 4234 | 139.4 | AMINO-ACID ACETYLTRANSFERASE (EC 2.3.1.1) (N-ACETYLGLUTAMATE SYNTHASE) (AGS). | swissprot P32042 | ND |
| 4235 | 139.2 | 64AA LONG HYPOTHETICAL PROTEIN. | sptrembl Q9YAL3 | ND |
| 4236 | 139.1 | Filistata peptide 10, a Ca-blocking polypeptide from spider venom. | geneseqp R40035 | ND |
| 4237 | 139.1 | AUXIN INDUCED PROLINE RICH PROTEIN. | sptrembl O24072 | ND |
| 4238 | 138.6 | OVARIAN TUMOR LOCUS PROTEIN. | swissprot P10383 | ND |
| 4239 | 138.6 | 5T4 ONCOFETAL ANTIGEN HOMOLOG. | tremblnew AAF21770 | ND |
| 4240 | 138.5 | (MSA-2) (FRAGMENT). | sptrembl Q25947 | ND |
| 4241 | 138.5 | SMALL NUCLEAR RIBONUCLEOPROTEIN B. | tremblnew AAD54488 | ND |
| 4242 | 138.3 | TRANSPOSABLE ELEMENT MU1 SEQUENCE. | sptrembl Q41863 | ND |
| 4243 | 138.3 | PISTIL-SPECIFIC EXTENSIN-LIKE PROTEIN (FRAGMENT). | sptrembl Q40549 | ND |
| 4244 | 138.3 | Extracellular region of metastasis-specific CD44 surface protein | geneseqp R14769 | ND |
| 4245 | 138.1 | PHYTOENE SYNTHASE. | sptrembl O04007 | ND |
| 4246 | 137.8 | B0238.12 PROTEIN. | sptrembl O16488 | ND |
| 4247 | 137.7 | NADH DEHYDROGENASE, SUBUNIT 9 (EC 1.6.5.3). | sptrembl O21271 | ND |
| 4248 | 137.7 | F10G19.2 PROTEIN. | sptrembl O23120 | ND |
| 4249 | 137.2 | PAIRED-BOX TRANSCRIPTION FACTOR PROTEIN (FRAGMENT). | sptrembl O13081 | ND |
| 4250 | 137.2 | Human adult retina secreted protein bk112_15. | geneseqp W95345 | ND |

TABLE 3

_Aspergillus oryzae_ ESTs

| Sequence Listing | zscore | Annotation | Database | Functional Category |
|---|---|---|---|---|
| 4376 | 999.7 | PUTATIVE GLUCOSYLTRANSFERASE C17C9.07 (EC 2.4.1.-). | swissprot Q10479 | ND |
| 4377 | 997.5 | HEAT SHOCK PROTEIN HSP88. | sptrembl O74225 | Posttranslational modification, protein turnover, chaperones |
| 4378 | 996.4 | 40S RIBOSOMAL PROTEIN S8. | swissprot O14049 | Translation, ribosomal structure and biogenesis |
| 4379 | 995.7 | SERINE/THREONINE-PROTEIN KINASE IRE1 PRECURSOR (EC 2.7.1.-). | swissprot P32361 | Signal transduction mechanisms |
| 4380 | 993.4 | DIMETHYL-ALLYL-TRYPTPHAN-SYNTHASE. | sptrembl O94204 | ND |
| 4381 | 992.6 | PROTEIN TRANSPORT PROTEIN SEC61 ALPHA SUBUNIT. | swissprot P78979 | Cell motility and secretion |
| 4382 | 992.1 | PROTEASOME COMPONENT PRE6 (EC 3.4.99.46) (MACROPAIN SUBUNIT PRE6) (PROTEINASE YSCE SUBUNIT PRE6) (MULTICATALYTIC ENDOPEPTIDASE COMPLEX SUBUNIT PRE6). | swissprot P40303 | Posttranslational modification, protein turnover, chaperones |
| 4383 | 990.1 | MITOCHONDRIAL PHOSPHATE CARRIER PROTEIN (PHOSPHATE TRANSPORT PROTEIN) (PTP) (MITOCHONDRIAL IMPORT RECEPTOR) (P32). | swissprot P23641 | ND |
| 4384 | 989.3 | SLA2P. | sptrembl O94097 | ND |
| 4385 | 988.3 | ADP-RIBOSYLATION FACTOR-LIKE PROTEIN 1. | swissprot P38116 | ND |
| 4386 | 987.3 | PUTATIVE FIZZY-RELATED PROTEIN. | sptrembl O82740 | ND |
| 4387 | 985.5 | 2-OXOGLUTARATE DEHYDROGENASE E1 COMPONENT, MITOCHONDRIAL PRECURSOR (EC 1.2.4.2) (ALPHA-KETOGLUTARATE DEHYDROGENASE). | swissprot P20967 | Energy production and conversion |
| 4388 | 985.2 | VACUOLAR ATP SYNTHASE 16 KD PROTEOLIPID SUBUNIT (EC 3.6.1.34). | swissprot P31413 | Energy production and conversion |
| 4389 | 985.1 | WD REPEAT PROTEIN, HUMAN U5 SNRNP-SPECIFIC-LIKE. | sptrembl O94620 | ND |
| 4390 | 984.0 | HISTONE H2B. | swissprot P23754 | ND |
| 4391 | 983.8 | DOLICHYL-PHOSPHATE-MANNOSE--PROTEIN MANNOSYLTRANSFERASE 4 (EC 2.4.1.109). | swissprot P46971 | Posttranslational modification, protein turnover, chaperones |
| 4392 | 983.3 | PUTATIVE CA-CALMODULIN-DEPENDENT SERINE-THREONINE-PROTEIN KINASE. | sptrembl O94547 | Signal transduction mechanisms |
| 4393 | 983.0 | HYPOTHETICAL 102.5 KD PROTEIN IN KRE1-HXT14 INTERGENIC REGION. | swissprot P42839 | Inorganic ion transport and metabolism |
| 4394 | 981.2 | RHO1 PROTEIN. | swissprot Q09914 | ND |
| 4395 | 980.2 | _Aspergillus nidulans_ essential protein AN80. | geneseqp Y06416 | ND |
| 4396 | 978.2 | NADPH CYTOCHROME P450 OXIDOREDUCTASE. | sptrembl Q00141 | Inorganic ion transport and metabolism |
| 4397 | 977.8 | RASP F 4 (FRAGMENT). | sptrembl O60024 | ND |
| 4398 | 977.4 | SYMBIOSIS-RELATED PROTEIN. | swissprot P87068 | ND |

TABLE 3-continued

Aspergillus oryzae ESTs

| Sequence Listing | zscore | Annotation | Database | Functional Category |
|---|---|---|---|---|
| 4399 | 976.6 | 40S RIBOSOMAL PROTEIN S19 (S16). | swissprot P27073 | Translation, ribosomal structure and biogenesis |
| 4400 | 976.1 | GABA-SPECIFIC PERMEASE (GABA-SPECIFIC TRANSPORT PROTEIN). | swissprot P32837 | Amino acid transport and metabolism |
| 4401 | 972.7 | A. oryzae P4-8.1 locus protein sequence. | geneseqp Y39875 | Posttranslational modification, protein turnover, chaperones |
| 4402 | 972.7 | ATP CITRATE LYASE. | sptrembl O93988 | ND |
| 4403 | 970.8 | Protein kinase (Hhp1+). | geneseqp R56520 | Signal transduction mechanisms |
| 4404 | 967.7 | NUCLEOLAR PROTEIN INVOLVED IN PRE-RRNA PROCESSING. | sptrembl O94514 | Translation, ribosomal structure and biogenesis |
| 4405 | 964.2 | 3-KETOACYL-COA THIOLASE, PEROXISOMAL PRECURSOR (EC 2.3.1.16) (BETA-KETOTHIOLASE) (ACETYL-COA ACYLTRANSFERASE) (PEROXISOMAL 3-OXOACYL-COA THIOLASE). | swissprot Q05493 | Lipid metabolism |
| 4406 | 963.8 | 40S RIBOSOMAL PROTEIN S14 (CRP2). | swissprot P19115 | Translation, ribosomal structure and biogenesis |
| 4407 | 963.8 | DNA POLYMERASE ALPHA CATALYTIC SUBUNIT (EC 2.7.7.7) (DNA POLYMERASE I). | swissprot P28040 | DNA replication, recombination and repair |
| 4408 | 963.4 | DOLICHOL-PHOSPHATE MANNOSYLTRANSFERASE (EC 2.4.1.83) (DOLICHOL-PHOSPHATE MANNOSE SYNTHASE) (DOLICHYL-PHOSPHATE BETA-D-MANNOSYLTRANSFERASE) | sptrembl O14466 | Cell envelope biogenesis, outer membrane |
| 4409 | 962.9 | PROBABLE MANNOSYL-OLIGOSACCHARIDE GLUCOSIDASE (EC 3.2.1.106) (PROCESSING A-GLUCOSIDASE I). | swissprot O14255 | ND |
| 4410 | 962.1 | HYPOTHETICAL 41.0 KD PROTEIN IN YIP1-CBP4 INTERGENIC REGION. | swissprot P53295 | ND |
| 4411 | 961.1 | PUTATIVE ASPARTATE AMINOTRANSFERASE, CYTOPLASMIC (EC 2.6.1.1) (TRANSAMINASE A). | sptrembl O42652 | Amino acid transport and metabolism |
| 4412 | 961.0 | 40S RIBOSOMAL PROTEIN S2. | swissprot O74892 | Translation, ribosomal structure and biogenesis |
| 4413 | 960.7 | 40S RIBOSOMAL PROTEIN S17 (CRP3). | swissprot P27770 | Translation, ribosomal structure and biogenesis |
| 4414 | 960.5 | CHROMOSOME XV READING FRAME ORF YOR197W. | sptrembl Q08601 | ND |
| 4415 | 960.4 | 2-ISOPROPYLMALATE SYNTHASE. | sptrembl O59736 | Amino acid transport and metabolism |
| 4416 | 960.2 | TRYPTOPHANYL-TRNA SYNTHETASE, CYTOPLASMIC (EC 6.1.1.2) | swissprot Q12109 | Translation, ribosomal structure and |

TABLE 3-continued

Aspergillus oryzae ESTs

| Sequence Listing | zscore | Annotation | Database | Functional Category |
|---|---|---|---|---|
| | | (TRYPTOPHAN--TRNA LIGASE) (TRPRS). | | biogenesis |
| 4417 | 960.0 | PHOSPHORYLASE 263 aa | pdb 3PNP | Nucleotide transport |
| 4418 | 959.5 | ISOCITRATE DEHYDROGENASE [NADP], MITOCHONDRIAL PRECURSOR (EC 1.1.1.42) (OXALOSUCCINATE DECARBOXYLASE) (IDH) (NADP+-SPECIFIC ICDH) (IDP). | swissprot P79089 | Energy production and conversion |
| 4419 | 958.6 | RAN/SPI1 BINDING PROTEIN. | sptrembl Q09717 | ND |
| 4420 | 958.2 | SYNAPTOBREVIN. | sptrembl O13312 | ND |
| 4421 | 957.3 | MULTICATALYTIC PROTEINASE 222 aa, chain M + 1 | pdb 1RYP | Posttranslational modification, protein turnover, chaperones |
| 4422 | 956.8 | HYPOTHETICAL 53.0 KD PROTEIN C22E12.17C IN CHROMOSOME I. | swissprot Q10367 | ND |
| 4423 | 956.1 | PUTATIVE ABC TRANSPORTER. | sptrembl Q9Y840 | ND |
| 4424 | 953.0 | TRANSLATION RELEASE FACTOR ERF3. | sptrembl O42787 | Amino acid transport and metabolism |
| 4425 | 951.3 | CELL DIVISION CONTROL PROTEIN 48. | swissprot P25694 | Posttranslational modification, protein turnover, chaperones |
| 4426 | 950.0 | HYPOTHETICAL 73.1 KD PROTEIN (FRAGMENT). | sptrembl O14164 | ND |
| 4427 | 948.6 | PYRUVATE DEHYDROGENASE E1 COMPONENT ALPHA SUBUNIT, MITOCHONDRIAL PRECURSOR (EC 1.2.4.1) (PDHE1-A). | swissprot Q10489 | Energy production and conversion |
| 4428 | 948.1 | DOLICHYL-PHOSPHATE-MANNOSE--PROTEIN MANNOSYLTRANSFERASE 2 (EC 2.4.1.109). | swissprot P31382 | Posttranslational modification, protein turnover, chaperones |
| 4429 | 947.3 | PUTATIVE PROHIBITIN ANTIPROLIFERATIVE PROTEIN. | sptrembl O94550 | Posttranslational modification, protein turnover, chaperones |
| 4430 | 947.2 | PUTATIVE MITOCHONDRIAL CARRIER YOR222W. | swissnew Q99297 | ND |
| 4431 | 947.0 | CYTOCHROME C PEROXIDASE PRECURSOR (EC 1.11.1.5)(CCP). | swissprot P00431 | Inorganic ion transport and metabolism |
| 4432 | 945.8 | ATP SYNTHASE BETA CHAIN, MITOCHONDRIAL PRECURSOR (EC 3.6.1.34). | swissnew P23704 | Energy production and conversion |
| 4433 | 942.1 | TYROSYL-TRNA SYNTHETASE, CYTOPLASMIC (EC 6.1.1.1) (TYROSYL--TRNA LIGASE) (TYRRS). | swissprot P36421 | Translation, ribosomal structure and biogenesis |
| 4434 | 941.2 | UBIQUINOL-CYTOCHROME C REDUCTASE COMPLEX CORE PROTEIN 2 PRECURSOR (EC 1.10.2.2). | swissprot O60044 | ND |
| 4435 | 937.8 | ASPARTATE AMINOTRANSFERASE, MITOCHONDRIAL PRECURSOR (EC 2.6.1.1) (TRANSAMINASE A) (GLUTAMATE | swissprot P12344 | Amino acid transport and metabolism |

TABLE 3-continued

*Aspergillus oryzae* ESTs

| Sequence Listing | zscore | Annotation | Database | Functional Category |
|---|---|---|---|---|
| | | OXALOACETATE TRANSAMINASE-2). | | |
| 4436 | 936.9 | *Zea mays* eIF-4E protein #4. | geneseqp Y29948 | ND |
| 4437 | 936.5 | CELL PATTERN FORMATION-ASSOCIATED PROTEIN. | swissprot P36011 | ND |
| 4438 | 934.7 | GLYCOLIPID ANCHORED SURFACE PROTEIN PRECURSOR (GLYCOPROTEIN GP115). | swissprot P22146 | ND |
| 4439 | 934.3 | HYPOTHETICAL 79.2 KD PROTEIN. | sptrembl Q04585 | Energy production and conversion |
| 4440 | 934.2 | DTDP-GLUCOSE 4-6-DEHYDRATASES-LIKE PROTEIN. | tremblnew CAB62035 | Carbohydrate transport and metabolism |
| 4441 | 933.8 | 40S RIBOSOMAL PROTEIN S11 (S18) (YS12) (RP41). | swissprot P26781 | Translation, ribosomal structure and biogenesis |
| 4442 | 933.2 | GLYCOGEN SYNTHASE. | sptrembl O93869 | Cell envelope biogenesis, outer membrane |
| 4443 | 933.2 | 60S RIBOSOMAL PROTEIN L19. | sptrembl O42699 | Translation, ribosomal structure and biogenesis |
| 4444 | 931.5 | MEMBRANE TRANSPORTER. | sptrembl O59700 | ND |
| 4445 | 931.0 | 40S RIBOSOMAL PROTEIN S15 (S12). | swissprot P34737 | Translation, ribosomal structure and biogenesis |
| 4446 | 930.5 | HYPOTHETICAL 63.9 KD PROTEIN C22A12.08C IN CHROMOSOME I. | sptrembl O13899 | ND |
| 4447 | 928.0 | RIBONUCLEOSIDE-DIPHOSPHATE REDUCTASE SMALL CHAIN 1 (EC 1.17.4.1) (RIBONUCLEOTIDE REDUCTASE). | swissprot P09938 | Nucleotide transport |
| 4448 | 927.0 | POLY(A)+ RNA TRANSPORT PROTEIN PTR3P. | sptrembl O94609 | Coenzyme metabolism |
| 4449 | 926.3 | MAGO NASHI PROTEIN HOMOLOG. | swissprot O65806 | ND |
| 4450 | 925.4 | 01232. | sptrembl Q05663 | ND |
| 4451 | 925.2 | HYPOTHETICAL 32.2 KD PROTEIN IN ARE2-SWP73 INTERGENIC REGION. | swissprot P53722 | ND |
| 4452 | 921.7 | NUCLEAR PROTEIN. | tremblnew CAB41231 | ND |
| 4453 | 921.0 | GLUTAMATE DEHYDROGENASE (EC 1.4.1.4). | tremblnew AAF00006 | Amino acid transport and metabolism |
| 4454 | 920.5 | CHROMOSOME XV READING FRAME ORF YOR090C. | sptrembl Q12511 | Signal transduction mechanisms |
| 4455 | 920.3 | *Cladosporium herbarum* allergen Clah53. | geneseqp R71891 | Energy production and conversion |
| 4456 | 919.5 | PUTATIVE ACONITASE IN PRP21-UBP12 INTERGENIC REGION (EC 4.2.1.3). | swissprot P39533 | Energy production and conversion |
| 4457 | 918.8 | SPLICEOSOME ASSOCIATED PROTEIN 49 (SAP 49) (SF3B53). | swissprot Q15427 | ND |
| 4458 | 918.7 | Yeast proteasome YC1 subunit. | geneseqp R22996 | Posttranslational modification, protein turnover, chaperones |
| 4460 | 916.8 | HYPOTHETICAL 15.5 KD PROTEIN IN MFAL2-MAD1 INTERGENIC REGION. | swissprot P53152 | ND |

TABLE 3-continued

_Aspergillus oryzae ESTs_

| Sequence Listing | zscore | Annotation | Database | Functional Category |
|---|---|---|---|---|
| 4461 | 913.8 | FRUCTOSE-1,6-BISPHOSPHATASE (EC 3.1.3.11) (D-FRUCTOSE-1,6-BISPHOSPHATE 1-PHOSPHOHYDROLASE) (FBPASE). | swissprot P09201 | Carbohydrate transport and metabolism |
| 4462 | 911.4 | HYPOTHETICAL 46.6 KD PROTEIN IN DAL80-GAP1 INTERGENIC REGION. | swissnew P36132 | Posttranslational modification, protein turnover, chaperones |
| 4463 | 909.6 | RAN GTPASE ACTIVATING PROTEIN 1 (RNA1 PROTEIN). | swissprot P41391 | ND |
| 4464 | 909.4 | SCO1 PROTEIN PRECURSOR. | swissprot P23833 | ND |
| 4465 | 907.9 | PHOSPHOPROTEIN PHOSPHATASE A. | sptrembl Q23922 | ND |
| 4466 | 906.4 | RIBOSOMAL PROTEIN SUBUNIT S18. | sptrembl O94754 | Translation, ribosomal structure and biogenesis |
| 4467 | 906.3 | O-METHYLTRANSFERASE | tremblnew BAA86103 | ND |
| 4468 | 906.1 | RIBONUCLEASE T2 PRECURSOR (EC 3.1.27.1) (RNASE T2). | swissprot P10281 | ND |
| 4469 | 903.9 | NADH-UBIQUINONE OXIDOREDUCTASE 20.8 KD SUBUNIT (EC 1.6.5.3) (EC 1.6.99.3). | swissprot P21976 | ND |
| 4470 | 903.9 | PUTATIVE GTP CYCLOHYDROLASE. | tremblnew CAB65619 | ND |
| 4471 | 903.8 | PYRUVATE KINASE (EC 2.7.1.40) (PK). | swissprot Q12669 | Carbohydrate transport and metabolism |
| 4472 | 903.7 | PROBABLE MITOCHONDRIAL IMPORT INNER MEMBRANE TRANSLOCASE SUBUNIT TIM44 PRECURSOR. | swissprot O60084 | ND |
| 4473 | 901.7 | 60S RIBOSOMAL PROTEIN L23 (L17). | swissprot P04451 | Translation, ribosomal structure and biogenesis |
| 4474 | 901.6 | 3-METHYLCROTONYL-COA CARBOXYLASE PRECURSOR (EC 6.4.1.4). | sptrembl Q42523 | ND |
| 4475 | 901.5 | HYPOTHETICAL 50.3 KD PROTEIN. | tremblnew CAB52038 | ND |
| 4476 | 900.4 | 14-3-3. | tremblnew BAA89421 | ND |
| 4477 | 900.0 | HOMEODOMAIN DNA-BINDING TRANSCRIPTION FACTOR. | sptrembl O74252 | ND |
| 4478 | 899.9 | SERINE/THREONINE PROTEIN PHOSPHATASE PP2A CATALYTIC SUBUNIT (EC 3.1.3.16). | swissprot P48580 | Signal transduction mechanisms |
| 4479 | 899.8 | ACTIN INTERACTING PROTEIN 2. | swissprot P46681 | Energy production and conversion |
| 4480 | 899.4 | ACTIVATOR OF HSP70 AND HSP90 CHAPERONES. | tremblnew CAB39910 | ND |
| 4481 | 899.2 | HYPOTHETICAL 22.1 KD PROTEIN IN CCP1-MET1 INTERGENIC REGION. | swissprot P36149 | ND |
| 4482 | 897.8 | INITIATION FACTOR 5A-1 (EIF-5A) (EIF-4D) (HYPUSINE CONTAINING PROTEIN HP1). | swissprot P19211 | Translation, ribosomal structure and biogenesis |
| 4483 | 897.5 | HISTONE H3. | swissprot P23753 | DNA replication, recombination and repair |

TABLE 3-continued

_Aspergillus oryzae ESTs_

| Sequence Listing | zscore | Annotation | Database | Functional Category |
|---|---|---|---|---|
| 4484 | 894.8 | PUTATIVE ATP-DEPENDENT RNA HELICASE C17G6.14C. | sptrembl O13792 | DNA replication, recombination and repair |
| 4485 | 893.9 | SIRTUIN TYPE 3. | sptrembl Q9Y6E8 | Coenzyme metabolism |
| 4486 | 892.1 | PH RESPONSIVE PROTEIN 1 PRECURSOR (PH-REGULATED PROTEIN 1). | swissprot P43076 | ND |
| 4487 | 890.0 | TRANSKETOLASE 2 (EC 2.2.1.1) (TK 2). | swissprot P33315 | Carbohydrate transport and metabolism |
| 4488 | 888.2 | CDC37 PROTEIN. | sptrembl O94740 | ND |
| 4489 | 887.1 | SQUALENE MONOOXYGENASE (EC 1.14.99.7) (SQUALENE EPOXIDASE) (SE). | swissprot Q92206 | Coenzyme metabolism |
| 4490 | 886.7 | T02D1.5 PROTEIN. | sptrembl O45730 | Lipid metabolism |
| 4491 | 885.9 | Translational initiation factor 1A (EIF1AX) gene product. | geneseqp W81509 | Translation, ribosomal structure and biogenesis |
| 4492 | 882.7 | HYPOTHETICAL 52.9 KD PROTEIN IN SAP155-YMR31 INTERGENIC REGION. | swissprot P43616 | Amino acid transport and metabolism |
| 4493 | 882.0 | FISSION YEAST. | sptrembl P78887 | Coenzyme metabolism |
| 4494 | 880.6 | UBIQUITIN. | sptrembl O13697 | ND |
| 4495 | 879.0 | PROTEIN KINASE DSK1 (EC 2.7.1.-) (DIS1-SUPPRESSING PROTEIN KINASE). | swissprot P36616 | Signal transduction mechanisms |
| 4496 | 878.1 | CGI-35 PROTEIN. | sptrembl Q9Y324 | ND |
| 4497 | 877.5 | 60S RIBOSOMAL PROTEIN L20 (L18A). | swissprot P47913 | ND |
| 4498 | 875.7 | PDI RELATED PROTEIN A. | sptrembl O93914 | ND |
| 4499 | 875.0 | SUCCINATE SEMIALDEHYDE DEHYDROGENASE (EC 1.2.1.24) (NAD(+)-DEPENDENT SUCCINIC SEMIALDEHYDE DEHYDROGENASE) (FRAGMENT). | swissprot P51649 | Energy production and conversion |
| 4500 | 874.4 | Glyceraldehyde-3-phosphate dehydrogenase. | geneseqp R22097 | Carbohydrate transport and metabolism |
| 4501 | 873.6 | 40S RIBOSOMAL PROTEIN S26E (CRP5) (13.6 KD RIBOSOMAL PROTEIN). | swissprot P21772 | ND |
| 4502 | 871.4 | HYPOTHETICAL 41.9 KD PROTEIN IN HAC1-CAK1 INTERGENIC REGION. | swissprot P43567 | Amino acid transport and metabolism |
| 4503 | 870.9 | HYPOTHETICAL 33.9 KD PROTEIN. | sptrembl P78995 | Amino acid transport and metabolism |
| 4505 | 868.2 | HYPOTHETICAL 22.7 KD PROTEIN. | sptrembl O60073 | ND |
| 4506 | 867.9 | PROBABLE 3-HYDROXYBUTYRYL-COA DEHYDROGENASE (EC 1.1.1.157) (BETA-HYDROXYBUTYRYL-COA DEHYDROGENASE) (BHBD). | swissprot P45856 | Lipid metabolism |
| 4507 | 866.9 | HYPOTHETICAL 103.2 KD PROTEIN C24B11.10C IN CHROMOSOME I. | swissprot Q09897 | ND |
| 4508 | 865.9 | ENDO ALPHA-1,4 POLYGALACTOSAMINIDASE PRECURSOR PRECURSOR. | sptrembl Q52423 | ND |
| 4509 | 865.9 | BETA-1,3-GLUCANOSYLTRANSFERASE. | sptrembl O59909 | ND |

TABLE 3-continued

*Aspergillus oryzae* ESTs

| Sequence Listing | zscore | Annotation | Database | Functional Category |
|---|---|---|---|---|
| 4510 | 865.1 | 60S RIBOSOMAL PROTEIN L27A (L29). | swissprot P78987 | Translation, ribosomal structure and biogenesis |
| 4511 | 864.4 | HYPOTHETICAL 98.1 KD PROTEIN. | tremblnew CAB58402 | ND |
| 4512 | 862.7 | PORPHOBILINOGEN DEAMINASE. | sptrembl O94048 | Coenzyme metabolism |
| 4513 | 862.4 | RIBOSOMAL PROTEIN S16 HOMOLOG (FRAGMENT). | tremblnew BAA33368 | Translation, ribosomal structure and biogenesis |
| 4514 | 862.3 | PROTEIN PHOSPHATASE 2C HOMOLOG 2 (EC 3.1.3.16) (PP2C-2). | swissprot Q09172 | Signal transduction mechanisms |
| 4516 | 861.6 | HYPOTHETICAL 32.8 KD PROTEIN IN BIO3-HXT17 INTERGENIC REGION. | swissprot P53750 | ND |
| 4517 | 861.4 | RER1 PROTEIN. | swissnew O15258 | ND |
| 4518 | 861.1 | SERYL-TRNA SYNTHETASE, CYTOPLASMIC (EC 6.1.1.11) (SERINE--TRNA LIGASE) (SERRS). | swissprot P07284 | Translation, ribosomal structure and biogenesis |
| 4519 | 859.4 | ALANYL-TRNA SYNTHETASE, CYTOPLASMIC (EC 6.1.1.7) (ALANINE--TRNA LIGASE) (ALARS). | swissprot P40825 | Translation, ribosomal structure and biogenesis |
| 4520 | 859.4 | PROBABLE STERIGMATOCYSTIN BIOSYNTHESIS P450 MONOOXYGENASE STCS (EC 1.14.-.-) (CYTOCHROME P450 59). | swissprot Q00714 | ND |
| 4521 | 859.0 | DOLICHYL-PHOSPHATE-MANNOSE--PROTEIN MANNOSYLTRANSFERASE 4 (EC 2.4.1.109). | swissprot P46971 | Posttranslational modification, protein turnover, chaperones |
| 4522 | 858.4 | CYCLOHEXANONE MONOOXYGENASE (EC 1.14.13.22). | swissprot P12015 | Inorganic ion transport and metabolism |
| 4524 | 854.6 | PUTATIVE CALCIUM P-TYPE ATPASE (FRAGMENT). | tremblnew CAB65293 | ND |
| 4525 | 854.5 | ORM1 PROTEIN. | swissprot P53224 | ND |
| 4526 | 852.2 | RAS PROTEIN. | sptrembl P87018 | ND |
| 4527 | 851.5 | PUTATIVE SECRETORY PATHWAY GDP DISSOCIATION INHIBITOR. | swissprot Q10305 | ND |
| 4528 | 850.4 | GLUCOAMYLASE PRECURSOR (EC 3.2.1.3) (GLUCAN 1,4-ALPHA-GLUCOSIDASE) (1,4-ALPHA-D-GLUCAN GLUCOHYDROLASE). | swissprot P36914 | ND |
| 4529 | 849.8 | GATA FACTOR SREP. | swissprot Q92259 | ND |
| 4530 | 848.8 | FRUCTOSE-BISPHOSPHATE ALDOLASE (EC 4.1.2.13). | swissprot P14540 | Carbohydrate transport and metabolism |
| 4531 | 848.8 | PUTATIVE TRANSCRIPTIONAL REGULATOR. | sptrembl O13337 | ND |
| 4532 | 848.3 | CYTOPLASMIC RIBOSOMAL PROTEIN S13. | tremblnew BAA88058 | Translation, ribosomal structure and biogenesis |
| 4533 | 848.0 | PROBABLE PROTEIN KINASE. | tremblnew BAA21391 | Signal transduction mechanisms |
| 4534 | 847.4 | HYPOTHETICAL 34.2 KD PROTEIN IN CUS1-RPL20A INTERGENIC REGION. | swissprot Q04013 | ND |

TABLE 3-continued

_Aspergillus oryzae ESTs_

| Sequence Listing | zscore | Annotation | Database | Functional Category |
|---|---|---|---|---|
| 4535 | 847.0 | Yeast RNA-binding protein ZPR1. | geneseqp W38455 | ND |
| 4536 | 845.2 | HYPOTHETICAL 72.8 KD PROTEIN C4G3.09C IN CHROMOSOME III. | sptrembl P87234 | ND |
| 4537 | 844.6 | VACUOLAR ATP SYNTHASE SUBUNIT E (EC 3.6.1.34) (V-ATPASE E SUBUNIT) (V-ATPASE 26 KD SUBUNIT). | swissprot Q01278 | Energy production and conversion |
| 4538 | 844.5 | HYPOTHETICAL 42.4 KD PROTEIN IN CDC12-ORC6 INTERGENIC REGION. | swissprot P38716 | Amino acid transport and metabolism |
| 4539 | 843.7 | NADH-UBIQUINONE OXIDOREDUCTASE 21.3 KD SUBUNIT (EC 1.6.5.3) (EC 1.6.99.3). | swissprot P19968 | ND |
| 4540 | 842.3 | 40S RIBOSOMAL PROTEIN S12. | sptrembl O59936 | ND |
| 4541 | 841.2 | HYPOTHETICAL GTP-BINDING PROTEIN IN SEH1-PRP20 INTERGENIC REGION. | swissprot P53145 | ND |
| 4542 | 840.9 | PROBABLE PEROXISOMAL MEMBRANE PROTEIN PMP20 (ALLERGEN ASP F 3). | swissprot O43099 | ND |
| 4543 | 839.2 | CONSERVED HYPOTHETICAL PROTEIN. | tremblnew CAB52883 | Nucleotide transport |
| 4544 | 839.1 | BIFUNCTIONAL HISTIDINE BIOSYNTHESIS PROTEIN HIS7 [INCLUDES: HISH-TYPE AMIDOTRANSFERASE (EC 2.4.2.-); HISF-TYPE CYCLASE]. | swissprot P33734 | ND |
| 4545 | 839.1 | HYPOTHETICAL 61.8 KD PROTEIN C12B10.03 IN CHROMOSOME I. | swissprot Q10437 | ND |
| 4546 | 837.9 | 40S RIBOSOMAL PROTEIN S22 (S15A) (YS24). | swissprot P33953 | Translation, ribosomal structure and biogenesis |
| 4547 | 837.6 | CHITIN SYNTHASE REGULATORY FACTOR. | sptrembl P87065 | ND |
| 4548 | 835.4 | ACID TREHALASE PRECURSOR (EC 3.2.1.28) (ALPHA,ALPHA-TREHALASE) (ALPHA,ALPHA-TREHALOSE GLUCOHYDROLASE). | swissprot P78617 | ND |
| 4549 | 835.2 | NADH-UBIQUINONE OXIDOREDUCTASE 21 KD SUBUNIT PRECURSOR (EC 1.6.5.3) (EC 1.6.99.3) (COMPLEX I-21 KD) (CI-2IKD). | swissprot P25711 | ND |
| 4550 | 832.7 | PYRUVATE DEHYDROGENASE E1 COMPONENT BETA SUBUNIT, MITOCHONDRIAL PRECURSOR (EC 1.2.4.1) (PDHE1-B). | swissprot Q09171 | Energy production and conversion |
| 4551 | 831.6 | CYTOCHROME C. | swissprot P56205 | ND |
| 4552 | 827.9 | HISTIDINOL-PHOSPHATE AMINOTRANSFERASE (EC 2.6.1.9) (IMIDAZOLE ACETOL-PHOSPHATE TRANSAMINASE). | swissprot P36605 | Amino acid transport and metabolism |
| 4553 | 827.9 | 8 KDA CYTOPLASMIC DYNEIN LIGHT CHAIN. | sptrembl O94111 | ND |

TABLE 3-continued

*Aspergillus oryzae* ESTs

| Sequence Listing | zscore | Annotation | Database | Functional Category |
|---|---|---|---|---|
| 4554 | 827.8 | Protein involved in cephalosporin C biosynthesis. | geneseqp W14439 | ND |
| 4555 | 826.4 | HYPOTHETICAL 74.0 KD PROTEIN IN CAJ1-HOM3 INTERGENIC REGION. | swissprot P40032 | ND |
| 4556 | 825.6 | HYPOTHETICAL 61.8 KD PEPTIDASE IN MPR1-GCN20 INTERGENIC REGION (EC 3.4.-.-). | swissprot P43590 | Amino acid transport and metabolism |
| 4557 | 824.1 | 6-PHOSPHOFRUCTOKINASE (EC 2.7.1.11) (PHOSPHOFRUCTOKINASE) (PHOSPHOHEXOKINASE). | swissprot P78985 | ND |
| 4558 | 824.0 | BROADLY SELECTIVE SODIUM/NUCLEOSIDE TRANSPORTER HFCNT. | tremblnew AAD52151 | Nucleotide transport |
| 4559 | 823.5 | PUTATIVE ZINC-CONTAINING DEHYDROGENASE. | tremblnew CAB53146 | ND |
| 4560 | 822.3 | GAL10 BIFUNCTIONAL PROTEIN [INCLUDES: UDP-GLUCOSE 4-EPIMERASE (EC 5.1.3.2) (GALACTOWALDENASE), ALDOSE 1-EPIMERASE (EC 5.1.3.3) (MUTAROTASE)]. | swissprot P40801 | Cell envelope biogenesis, outer membrane |
| 4561 | 822.2 | DPM2 mannosyl transferase. | geneseqp R47201 | Posttranslational modification, protein turnover, chaperones |
| 4562 | 821.6 | DYNAMIN-RELATED PROTEIN DNM1. | swissprot P54861 | ND |
| 4563 | 819.3 | SUPEROXIDE DISMUTASE [MN] PRECURSOR (EC 1.15.1.1) (FRAGMENT). | swissprot Q92450 | Inorganic ion transport and metabolism |
| 4564 | 816.0 | *Aspergillus niger* tpiA gene. | geneseqp P70498 | Carbohydrate transport and metabolism |
| 4565 | 816.0 | ENOYL-COA HYDRATASE. | sptrembl O53418 | Lipid metabolism |
| 4566 | 815.9 | PUTATIVE MITOCHONDRIAL IMPORT INNER MEMBRANE TRANSLOCASE SUBUNIT. | tremblnew CAB53081 | ND |
| 4567 | 814.2 | SUCCINYL-COA:3-KETOACID-COENZYME A TRANSFERASE PRECURSOR (EC 2.8.3.5) (SUCCINYL COA:3-OXOACID COA-TRANSFERASE) (OXCT). | swissprot P55809 | Lipid metabolism |
| 4569 | 813.2 | GENERAL AMINO ACID PERMEASE AGP2. | swissprot P38090 | Amino acid transport and metabolism |
| 4570 | 813.0 | YMC1P. | sptrembl Q12002 | ND |
| 4571 | 812.7 | HISTONE H4.1. | swissprot P23750 | DNA replication, recombination and repair |
| 4572 | 812.6 | 60S RIBOSOMAL PROTEIN L9-B (L8) (YL11) (RP25). | swissprot P51401 | Translation, ribosomal structure and biogenesis |
| 4573 | 812.5 | PROBABLE CALCIUM-TRANSPORTING ATPASE 6 (EC 3.6.1.38). | swissprot P39986 | Inorganic ion transport and metabolism |
| 4574 | 811.1 | ALPHA-ADAPTIN HOMOLOG. | swissprot P91926 | ND |
| 4575 | 810.8 | PUTATIVE SMALL NUCLEAR RIBONUCLEOPROTEIN C19A8.13. | sptrembl O13829 | Transcription |
| 4576 | 810.0 | NUCLEOSIDE DIPHOSPHATE KINASE. | tremblnew BAA83495 | Nucleotide transport |

TABLE 3-continued

_Aspergillus oryzae ESTs_

| Sequence Listing | zscore | Annotation | Database | Functional Category |
|---|---|---|---|---|
| 4577 | 809.0 | ERV25 PROTEIN PRECURSOR. | swissprot P54837 | ND |
| 4578 | 808.6 | ATP SYNTHASE ALPHA CHAIN, MITOCHONDRIAL PRECURSOR (EC 3.6.1.34). | swissnew P37211 | Energy production and conversion |
| 4579 | 808.0 | ELONGATION FACTOR 1-BETA HOMOLOG. | tremblnew AAC13264 | Translation, ribosomal structure and biogenesis |
| 4580 | 807.8 | HYPOTHETICAL 49.1 KD PROTEIN C11D3.06 IN CHROMOSOME I. | swissprot Q10085 | ND |
| 4581 | 807.7 | PUTATIVE DELTA-1-PYROLINE-5-CARBOXYLATE DEHYDROGENASE. | sptrembl O74766 | Energy production and conversion |
| 4582 | 807.7 | MITOCHONDRIAL PHOSPHATE CARRIER PROTEIN (PHOSPHATE TRANSPORT PROTEIN) (PTP) (MITOCHONDRIAL IMPORT RECEPTOR) (P32). | swissprot P23641 | ND |
| 4583 | 807.5 | HISTONE H2A VARIANT. | swissprot P48003 | ND |
| 4584 | 806.5 | PUTATIVE HUMAN SPLICEOSOME ASSOCIATED PROTEIN 145 (SAP 145) HOMOLOGUE. | tremblnew CAB52720 | ND |
| 4585 | 806.2 | PUTATIVE CELL DIVISION PROTEIN KINASE C2F3.15 (EC 2.7.1.-). | sptrembl O14098 | Signal transduction mechanisms |
| 4586 | 805.4 | An enzyme with sugar transferase activity. | geneseqp W88044 | ND |
| 4587 | 803.7 | PUTATIVE ESTERASE. | tremblnew CAB63539 | Lipid metabolism |
| 4588 | 803.3 | MEMBRANE ATPASE. | sptrembl O74431 | Inorganic ion transport and metabolism |
| 4589 | 802.1 | COPROPORPHYRINOGEN III OXIDASE PRECURSOR (EC 1.3.3.3) (COPROPORPHYRINOGENASE) (COPROGEN OXIDASE). | swissprot P35055 | Coenzyme metabolism |
| 4590 | 802.1 | MRNA CLEAVAGE FACTOR I25 KDA SUBUNIT. | sptrembl O43809 | ND |
| 4591 | 801.2 | RETINOBLASTOMA BINDING PROTEIN. | tremblnew AAC36349 | ND |
| 4592 | 800.4 | 3-OXOACYL-[ACYL-CARRIER-PROTEIN]-SYNTHASE. | sptrembl O13355 | Lipid metabolism |
| 4593 | 800.4 | TRICHOTHECENE 3-O-ACETYLTRANSFERASE. | sptrembl O74644 | ND |
| 4594 | 798.1 | HYPOTHETICAL 26.3 KD PROTEIN IN OYE2-GND1 INTERGENIC REGION. | swissprot P38869 | ND |
| 4595 | 797.2 | FISSION YEAST (FRAGMENT). | sptrembl P78824 | Carbohydrate transport and metabolism |
| 4596 | 797.1 | HYPOTHETICAL 54.2 KD PROTEIN IN ERP5-ORC6 INTERGENIC REGION. | swissprot P38821 | Amino acid transport and metabolism |
| 4597 | 796.8 | REPRESSOR PROTEIN. | sptrembl Q00784 | ND |
| 4598 | 796.4 | PUTATIVE ABC TRANSPORTER. | sptrembl Q9Y840 | ND |
| 4599 | 796.0 | MALTOSE PERMEASE. | sptrembl Q9Y845 | ND |
| 4600 | 795.1 | PUTATIVE ALANINE AMINOTRANSFERASE, MITOCHONDRIAL PRECURSOR (EC 2.6.1.2) (GLUTAMIC--PYRUVIC TRANSAMINASE) (GPT) (GLUTAMIC--ALANINE TRANSAMINASE). | swissprot P52893 | Amino acid transport and metabolism |

TABLE 3-continued

_Aspergillus oryzae ESTs_

| Sequence Listing | zscore | Annotation | Database | Functional Category |
|---|---|---|---|---|
| 4601 | 793.9 | PUTATIVE BETA-MANNOSYLTRANSFERASE. | tremblnew CAB16885 | Cell envelope biogenesis, outer membrane |
| 4602 | 793.7 | Product of the ADE1 gene from _Candida utilis_. | geneseqp R22438 | Nucleotide transport |
| 4603 | 793.4 | ATP SYNTHASE DELTA CHAIN, MITOCHONDRIAL PRECURSOR (EC 3.6.1.34) (FRAGMENT). | swissnew P56525 | Energy production and conversion |
| 4604 | 792.8 | PSU1. | tremblnew BAA83907 | ND |
| 4605 | 791.6 | BETA-N-ACETYLGLUCOSAMINIDASE PRECURSOR (EC 3.2.1.30). | sptrembl O82840 | Carbohydrate transport and metabolism |
| 4606 | 789.3 | WD-40 domain-contg. IEF SSP 9306 protein. | geneseqp R85866 | ND |
| 4607 | 789.2 | LINOLEATE DIOL SYNTHASE PRECURSOR. | tremblnew AAD49559 | ND |
| 4608 | 788.8 | ALCOHOL DEHYDROGENASE. | tremblnew CAA21782 | ND |
| 4609 | 788.5 | METAL RESISTANCE PROTEIN YCF1 (YEAST CADMIUM FACTOR 1). | swissprot P39109 | ND |
| 4610 | 787.7 | RS6/L7A RIBOSOMAL PROTEIN HOMOLOG. | tremblnew CAB63790 | Translation, ribosomal structure and biogenesis |
| 4611 | 785.6 | PUTATIVE 20 KDA SUBUNIT OF THE V-ATPASE. | sptrembl P87252 | ND |
| 4612 | 785.3 | ACYL-COA DEHYDROGENASE, SHORT/BRANCHED CHAIN SPECIFIC PRECURSOR (EC 1.3.99.-) (SBCAD) (2-METHYL BRANCHED CHAIN ACYL-COA DEHYDROGENASE) (2-MEBCAD). | swissprot P45954 | Lipid metabolism |
| 4613 | 783.6 | ADRENOLEUKODYSTROPHY PROTEIN (ALDP). | swissprot P33897 | Lipid metabolism |
| 4614 | 782.2 | 4-AMINOBUTYRATE AMINOTRANSFERASE (EC 2.6.1.19) (GAMMA-AMINO-N-BUTYRATE TRANSAMINASE) (GABA TRANSAMINASE) (GABA AMINOTRANSFERASE). | swissprot P14010 | Amino acid transport and metabolism |
| 4615 | 777.3 | HISTONE H4.2. | swissprot P23751 | DNA replication, recombination and repair |
| 4616 | 776.8 | CONSERVED HYPOTHETICAL PROTEIN. | tremblnew CAB39853 | ND |
| 4617 | 775.9 | BLI-3 PROTEIN. | swissprot Q01358 | ND |
| 4618 | 775.0 | N-ACETYLGLUCOSAMINE-PHOSPHATE MUTASE. | tremblnew AAD55097 | Carbohydrate transport and metabolism |
| 4619 | 771.8 | OPSIN-1. | tremblnew AAD45253 | ND |
| 4620 | 768.2 | PUTATIVE ADENOSINE KINASE. | tremblnew CAA19345 | Carbohydrate transport and metabolism |
| 4621 | 768.1 | METHIONINE AMINOPEPTIDASE. | sptrembl O60085 | Translation, ribosomal structure and biogenesis |
| 4622 | 768.1 | IMPORTIN BETA SUBUNIT. | sptrembl O74476 | ND |
| 4623 | 767.9 | PROBABLE ELECTRON TRANSFER FLAVOPROTEIN ALPHA-SUBUNIT PRECURSOR (ALPHA-ETF). | swissprot P78790 | Energy production and conversion |
| 4624 | 767.4 | CHROMOSOME XV READING FRAME ORF YOR091W. | sptrembl Q12000 | ND |

TABLE 3-continued

_Aspergillus oryzae ESTs_

| Sequence Listing | zscore | Annotation | Database | Functional Category |
|---|---|---|---|---|
| 4625 | 766.0 | 60S RIBOSOMAL PROTEIN L17-B (YL17-B). | swissprot P46990 | Translation, ribosomal structure and biogenesis |
| 4626 | 763.9 | PUTATIVE NADH-DEPENDENT FLAVIN OXIDOREDUCTASE. | sptrembl O94467 | Energy production and conversion |
| 4627 | 763.6 | GTPASE ACTIVATING PROTEIN HOMOLOG. | sptrembl O13384 | ND |
| 4628 | 762.9 | HYPOTHETICAL 55.8 KD PROTEIN. | tremblnew CAB63552 | ND |
| 4629 | 762.6 | SID478P. | tremblnew BAA84693 | ND |
| 4630 | 762.0 | Multiple drug resistance Afu-MDR1 protein. | geneseqp W01022 | ND |
| 4631 | 761.4 | SIMILAR TO ASPARTATE AMINOTRANSFERASE. | sptrembl Q17994 | Amino acid transport and metabolism |
| 4632 | 760.1 | ACTIVATOR I41 KD SUBUNIT (REPLICATION FACTOR C 41 KD SUBUNIT). | swissprot P40348 | DNA replication, recombination and repair |
| 4633 | 759.8 | ENDOGLUCANASE I (EC 3.2.1.4) (ENDO-1,4-BETA-GLUCANASE) (CARBOXYMETHYL-CELLULASE I) (CMCASE I). | swissprot P23044 | ND |
| 4634 | 759.2 | PUTATIVE THIAZOLE SYNTHASE. | tremblnew AAF25444 | ND |
| 4635 | 758.9 | SIGNAL SEQUENCE RECEPTOR ALPHA SUBUNIT. | sptrembl Q9Y7B0 | Cell motility and secretion |
| 4636 | 757.7 | HYPOTHETICAL 55.5 KD PROTEIN C17A2.05 IN CHROMOSOME I. | sptrembl O13755 | Energy production and conversion |
| 4637 | 757.6 | NONALLELIC VEGETATIVE INCOMPATIBILITY PROTEIN HET-C. | sptrembl Q01571 | ND |
| 4638 | 757.5 | _A. oryzae_ ATCC20386 carboxypeptidase I protein. | geneseqp W56099 | ND |
| 4639 | 756.3 | NI-BINDING UREASE ACCESSORY PROTEIN UREG. | sptrembl Q9XGS2 | ND |
| 4640 | 755.1 | HYPOTHETICAL 92.5 KD PROTEIN C25H2.03 IN CHROMOSOME II. | sptrembl P87145 | ND |
| 4641 | 754.8 | HYPOTHETICAL 45.2 KD PROTEIN C19A8.06 IN CHROMOSOME I. | sptrembl O13822 | ND |
| 4642 | 754.7 | PUTATIVE PROLYL AMINOPEPTIDASE. | tremblnew CAB66205 | ND |
| 4643 | 754.2 | PUTATIVE PERMEASE C29B12.14C. | sptrembl O14035 | Coenzyme metabolism |
| 4644 | 751.9 | PROBABLE HISTIDINOL-PHOSPHATASE (EC 3.1.3.15). | swissnew O14059 | ND |
| 4645 | 749.9 | POTENTIAL PROTEASOME COMPONENT C5 (EC 3.4.99.46) (MULTICATALYTIC ENDOPEPTIDASE COMPLEX SUBUNIT C5). | swissprot P23724 | Posttranslational modification, protein turnover, chaperones |
| 4646 | 747.1 | ATP SYNTHASE D CHAIN, MITOCHONDRIAL (EC 3.6.1.34). | swissprot O13350 | ND |
| 4647 | 747.0 | 4-DIHYDROMETHYL-TRISPORATE DEHYDROGENASE. | sptrembl Q01213 | ND |
| 4648 | 746.8 | IMPORTIN BETA-1 SUBUNIT (KARYOPHERIN BETA-1 SUBUNIT) (IMPORTIN 95). | swissprot O13864 | ND |

TABLE 3-continued

*Aspergillus oryzae* ESTs

| Sequence Listing | zscore | Annotation | Database | Functional Category |
|---|---|---|---|---|
| 4649 | 744.5 | PUTATIVE GOLGI MEMBRANE PROTEIN-SORTING PROTEIN. | sptrembl O94291 | ND |
| 4650 | 744.5 | NAD(+)-ISOCITRATE DEHYDROGENASE SUBUNIT I PRECURSOR. | sptrembl O13302 | Amino acid transport and metabolism |
| 4651 | 743.9 | DNA LIGASE (EC 6.5.1.1) (POLYDEOXYRIBONUCLEO TIDE SYNTHASE [ATP]). | swissprot P12000 | DNA replication, recombination and repair |
| 4652 | 743.7 | PROBABLE ATP-DEPENDENT TRANSPORTER YOL075C. | swissprot Q08234 | ND |
| 4653 | 743.1 | PUTATIVE METHYLTRANSFERASE NCL1 (EC 2.1.1.-). | swissnew P38205 | Translation, ribosomal structure and biogenesis |
| 4654 | 742.7 | 20 KD NUCLEAR CAP BINDING PROTEIN (NCBP) (CBP20) (FRAGMENT). | swissprot P52299 | Transcription |
| 4655 | 741.3 | MULTICATALYTIC PROTEINASE 222 aa, chain M + 1 | pdb 1RYP | Posttranslational modification, protein turnover, chaperones |
| 4656 | 740.4 | 60S RIBOSOMAL PROTEIN L21. | tremblnew CAB44755 | Translation, ribosomal structure and biogenesis |
| 4657 | 739.5 | PUTATIVE THIAMINE BIOSYNTHESIS PROTEIN. | sptrembl O94266 | ND |
| 4658 | 739.2 | PROBABLE GLUCOSE TRANSPORTER RCO-3. | swissprot Q92253 | ND |
| 4660 | 738.9 | YIP3 PROTEIN. | swissprot P53633 | ND |
| 4661 | 737.7 | SERINE PALMITOYLTRANSFERASE 2 (EC 2.3.1.50) (LONG CHAIN BASE BIOSYNTHESIS PROTEIN 2) (SPT 2). | swissprot Q09925 | Coenzyme metabolism |
| 4662 | 737.6 | RASP F 9 (FRAGMENT). | sptrembl O42800 | Carbohydrate transport and metabolism |
| 4663 | 737.2 | UBIQUITIN CARBOXYL-TERMINAL HYDROLASE (HOMOLOGY TO UBIQUITIN CARBOXYL-TERMINAL HYDROLASE). | sptrembl Q11119 | ND |
| 4664 | 737.1 | EUKARYOTIC TRANSLATION INITIATION FACTOR 2 ALPHA SUBUNIT (EIF-2-ALPHA). | swissprot P56286 | Translation, ribosomal structure and biogenesis |
| 4665 | 736.7 | PUTATIVE GLYCOSYL TRANSFERASE. | sptrembl O74878 | Cell envelope biogenesis, outer membrane |
| 4666 | 735.3 | GLUCOSE-6-PHOSPHATE ISOMERASE, CYTOSOLIC (EC 5.3.1.9) (GPI) (PHOSPHOGLUCOSE ISOMERASE) (PGI) (PHOSPHOHEXOSE ISOMERASE) (PHI). | sptrembl O94371 | Carbohydrate transport and metabolism |
| 4667 | 733.7 | PUTATIVE ALPHA-GLUCAN SYNTHASE. | sptrembl O94638 | ND |
| 4668 | 732.9 | PROBABLE LACTOYLGLUTATHIONE LYASE (EC 4.4.1.5) (METHYLGLYOXALASE) (ALDOKETOMUTASE) (GLYOXALASE I) (GLX I) (KETONE-ALDEHYDE MUTASE) (S-D-LACTOYLGLUTATHIONE METHYLGLYOXAL LYASE). | swissprot Q09751 | Amino acid transport and metabolism |
| 4669 | 732.1 | GMP SYNTHASE [GLUTAMINE- | swissprot P38625 | Nucleotide transport |

TABLE 3-continued

*Aspergillus oryzae* ESTs

| Sequence Listing | zscore | Annotation | Database | Functional Category |
|---|---|---|---|---|
| | | HYDROLYZING] (EC 6.3.5.2) (GLUTAMINE AMIDOTRANSFERASE) (GMP SYNTHETASE). | | |
| 4670 | 731.7 | SIMILAR TO CALCIUM-BINDING EF-HAND PROTEIN. | sptrembl O22788 | ND |
| 4671 | 731.6 | CHROMOSOME XII COSMID 9470. | sptrembl Q06287 | ND |
| 4672 | 731.3 | PROBABLE ZINC METALLOPEPTIDASE C17A5.04C PRECURSOR (EC 3.4.24.-). | swissprot O13766 | ND |
| 4673 | 730.7 | HYPOTHETICAL 54.2 KD TRP-ASP REPEATS CONTAINING PROTEIN C29A4.08C IN CHROMOSOME I. | swissprot O14011 | ND |
| 4674 | 729.8 | PUTATIVE TRIGLYCERIDE LIPASE-CHOLESTEROL ESTERASE (EC 3.1.1.-). | sptrembl P78898 | ND |
| 4675 | 729.1 | PHOSPHOLIPASE D PRECURSOR (EC 3.1.4.4) (CHOLINE PHOSPHATASE). | swissprot Q59332 | ND |
| 4676 | 727.5 | HYPOTHETICAL 32.5 KD PROTEIN YLR351C. | swissprot P49954 | ND |
| 4677 | 724.6 | 60S RIBOSOMAL PROTEIN L27-A. | swissprot O14388 | ND |
| 4678 | 723.9 | PHOSPHOENOLPYRUVATE CARBOXYKINASE [ATP] (EC 4.1.1.49). | swissprot O13434 | Energy production and conversion |
| 4679 | 723.8 | AMINOPEPTIDASE Y PRECURSOR (EC 3.4.11.-). | swissprot P37302 | ND |
| 4680 | 723.7 | ATP SYNTHASE SUBUNIT 4, MITOCHONDRIAL PRECURSOR (EC 3.6.1.34). | swissprot O13349 | ND |
| 4681 | 723.7 | GUANOSINE-DIPHOSPHATASE (EC 3.6.1.42) (GDPASE). | swissprot P32621 | ND |
| 4682 | 723.5 | PUTATIVE POLY(A)-BINDING PROTEIN FABM. | sptrembl Q92227 | Transcription |
| 4683 | 722.7 | MSF1 PROTEIN. | swissprot P35200 | ND |
| 4684 | 722.3 | FLAVOHEMOGLOBIN. | sptrembl O74183 | Energy production and conversion |
| 4685 | 720.6 | PUTATIVE RIBOSE 5-PHOSPHATE ISOMERASE. | tremblnew CAB61273 | Carbohydrate transport and metabolism |
| 4686 | 720.5 | HYPOTHETICAL 20.9 KD PROTEIN. | sptrembl O94286 | ND |
| 4687 | 720.4 | PUTATIVE HYDROXYMETHYLGLUTA RYL-COA LYASE PRECURSOR. | sptrembl O81027 | Amino acid transport and metabolism |
| 4688 | 720.0 | 60S RIBOSOMAL PROTEIN L23A (L25). | swissprot P51997 | Translation, ribosomal structure and biogenesis |
| 4689 | 720.0 | PHOSPHOGLUCOMUTASE 2 (EC 5.4.2.2) (GLUCOSE PHOSPHOMUTASE 2) (PGM 2). | swissprot P37012 | Carbohydrate transport and metabolism |
| 4690 | 717.6 | *Aspergillus nidulans* essential protein AN17. | geneseqp Y06418 | ND |
| 4691 | 713.2 | SMALL ZINC FINGER-LIKE PROTEIN. | sptrembl Q9Y8A7 | ND |
| 4692 | 712.9 | PROHIBITIN (FRAGMENT). | sptrembl O13357 | Posttranslational modification, protein turnover, chaperones |
| 4693 | 712.8 | MULTIDRUG RESISTANCE PROTEIN 1. | sptrembl O43121 | ND |

TABLE 3-continued

_Aspergillus oryzae ESTs_

| Sequence Listing | zscore | Annotation | Database | Functional Category |
|---|---|---|---|---|
| 4694 | 712.1 | SIMILAR TO YEAST VACUOLAR SORTING PROTEIN VPS29/PEP11. | tremblnew CAB52425 | ND |
| 4695 | 711.6 | PROBABLE GLUTAMYL-TRNA(GLN) AMIDOTRANSFERASE SUBUNIT A, MITOCHONDRIAL PRECURSOR (GLU-ADT SUBUNIT A). | swissnew Q03557 | Translation, ribosomal structure and biogenesis |
| 4696 | 711.3 | HYPOTHETICAL 48.3 KD PROTEIN IN HSP26-TIF32 INTERGENIC REGION. | swissprot P38248 | ND |
| 4697 | 710.3 | AGSPL1 PROTEIN. | sptrembl O60028 | Amino acid transport and metabolism |
| 4698 | 707.9 | PUTATIVE PROLINE-TRNA SYNTHETASE. | sptrembl O74765 | Translation, ribosomal structure and biogenesis |
| 4699 | 707.7 | 60S RIBOSOMAL PROTEIN L9, MITOCHONDRIAL PRECURSOR (YML9). | swissprot P31334 | Translation, ribosomal structure and biogenesis |
| 4700 | 707.0 | Dihydroxyacetone-3-phosphate protein. | geneseqp Y23747 | ND |
| 4701 | 706.5 | 60S RIBOSOMAL PROTEIN L13. | swissprot O74175 | ND |
| 4702 | 706.1 | PUTATIVE GLUCANASE PRECURSOR. | tremblnew CAB57923 | ND |
| 4703 | 705.7 | An enzyme with sugar transferase activity. | geneseqp W88044 | ND |
| 4704 | 705.0 | PUTATIVE PROLYL-TRNA SYNTHETASE YHR020W (EC 6.1.1.15) (PROLINE--TRNA LIGASE) (PRORS). | swissprot P38708 | Translation, ribosomal structure and biogenesis |
| 4705 | 704.5 | HYPOTHETICAL 18.8 KD PROTEIN. | sptrembl O43073 | ND |
| 4706 | 704.4 | MITOCHONDRIAL LON PROTEASE HOMOLOG 1 PRECURSOR (EC 3.4.21.-). | swissprot P93647 | Posttranslational modification, protein turnover, chaperones |
| 4707 | 703.9 | GAR1 PROTEIN. | swissnew P28007 | ND |
| 4708 | 702.3 | HYPOTHETICAL 51.9 KD PROTEIN IN PFK27-RPL25 INTERGENIC REGION PRECURSOR. | swissprot Q08271 | ND |
| 4709 | 700.1 | HYPOTHETICAL 80.9 KD PROTEIN (FRAGMENT). | tremblnew CAB60246 | ND |
| 4710 | 699.6 | HYPOTHETICAL 56.4 KD PROTEIN IN RPL30-CWH41 INTERGENIC REGION PRECURSOR. | swissprot P53189 | ND |
| 4711 | 698.7 | HOMOSERINE DEHYDROGENASE (EC 1.1.1.3) (HDH). | swissnew P31116 | Amino acid transport and metabolism |
| 4712 | 698.6 | NUCLEAR TRANSPORT FACTOR 2 (NTF-2) (NUCLEAR TRANSPORT FACTOR P10). | swissprot P33331 | ND |
| 4713 | 698.5 | PHENYLALANINE AMMONIUM LYASE. | sptrembl O93967 | ND |
| 4714 | 698.3 | VEGETABLE INCOMPATIBILITY PROTEIN HET-E-1. | swissprot Q00808 | ND |
| 4715 | 697.6 | HYPOTHETICAL 130.6 KD PROTEIN C9G1.10C IN CHROMOSOME I. | sptrembl O14306 | ND |
| 4716 | 695.3 | HYPOTHETICAL 57.6 KD PROTEIN. | sptrembl Q9Y7D4 | ND |
| 4717 | 694.5 | ADENYLOSUCCINATE SYNTHETASE (EC 6.3.4.4). | tremblnew CAB59683 | Nucleotide transport |
| 4718 | 694.4 | T-COMPLEX PROTEIN 1, ALPHA SUBUNIT | sptrembl O94501 | Posttranslational modification, |

TABLE 3-continued

_Aspergillus oryzae ESTs_

| Sequence Listing | zscore | Annotation | Database | Functional Category |
|---|---|---|---|---|
| | | HOMOLOG, CHAPERONIN FAMILY. | | protein turnover, chaperones |
| 4719 | 693.3 | HYPOTHETICAL 34.2 KD PROTEIN IN CUS1-RPL20A INTERGENIC REGION. | swissprot Q04013 | ND |
| 4720 | 693.3 | HYPOTHETICAL 29.4 KD PROTEIN IN STE6-LOS1 INTERGENIC REGION. | swissprot P36039 | ND |
| 4721 | 692.4 | HYPOTHETICAL 24.1 KD PROTEIN C17A5.08 IN CHROMOSOME I PRECURSOR. | swissprot O13770 | ND |
| 4722 | 691.9 | PROBABLE MALATE OXIDOREDUCTASE [NAD] (EC 1.1.1.38) (MALIC ENZYME). | swissprot P26616 | ND |
| 4723 | 691.6 | PROBABLE ZINC METALLOPEPTIDASE C17A5.04C PRECURSOR (EC 3.4.24.-). | swissprot O13766 | ND |
| 4724 | 690.4 | ADENOSYLHOMOCYSTEINASE (EC 3.3.1.1) (S-ADENOSYL-L-HOMOCYSTEINE HYDROLASE) (ADOHCYASE). | swissprot P39954 | Coenzyme metabolism |
| 4725 | 690.4 | EXO-1,3-BETA-GLUCANASE/1,3-BETA-D-GLUCAN GLUCANOHYDROLASE (EC 3.2.1.58) (GLUCAN 1,3-BETA-GLUCOSIDASE) (EXO-1,3-BETA-GLUCOSIDASE). | sptrembl Q12626 | ND |
| 4726 | 689.7 | EUKARYOTIC INITIATION FACTOR 4A (EIF-4A). | swissprot P47943 | DNA replication, recombination and repair |
| 4727 | 689.6 | PURU PROTEIN. | sptrembl Q9X7F7 | Nucleotide transport |
| 4728 | 689.4 | ALFA-L-RHAMNOSIDASE (EC 3.2.1.40). | tremblnew CAB53341 | ND |
| 4729 | 688.1 | FATTY ACID DESATURASE (FRAGMENT). | sptrembl O74645 | ND |
| 4730 | 687.9 | HYPOTHETICAL 34.1 KD PROTEIN C11D3.03C IN CHROMOSOME I. | swissprot Q10082 | ND |
| 4731 | 687.6 | DOLICHYL-PHOSPHATE-MANNOSE--PROTEIN MANNOSYLTRANSFERASE 1 (EC 2.4.1.109). | swissprot O74189 | Posttranslational modification, protein turnover, chaperones |
| 4732 | 687.3 | HEAT SHOCK PROTEIN 70 (FRAGMENT). | sptrembl Q92260 | Posttranslational modification, protein turnover, chaperones |
| 4733 | 686.7 | EF-HAND PROTEIN. | tremblnew CAB55175 | ND |
| 4734 | 686.6 | PEPTIDE SYNTHETASE. | sptrembl Q01135 | ND |
| 4735 | 684.8 | HYPOTHETICAL 285.2 KD PROTEIN. | sptrembl O60055 | ND |
| 4736 | 684.7 | 25 KDA PROTEIN ELICITOR. | tremblnew AAD53944 | ND |
| 4737 | 684.5 | GENRAL ALPHA-GLUCOSIDE PERMEASE. | swissprot P53048 | ND |
| 4738 | 684.3 | GLUTATHIONE S-TRANSFERASE. | sptrembl O59827 | Posttranslational modification, protein turnover, chaperones |
| 4739 | 684.1 | HYPOTHETICAL 49.5 KD PROTEIN. | tremblnew CAB41125 | Posttranslational modification, protein turnover, chaperones |

TABLE 3-continued

*Aspergillus oryzae* ESTs

| Sequence Listing | zscore | Annotation | Database | Functional Category |
|---|---|---|---|---|
| 4740 | 683.8 | SERINE-TYPE CARBOXYPEPTIDASE F PRECURSOR (EC 3.4.16.-) (PROTEINASE F) (CPD-II). | swissprot P52718 | ND |
| 4741 | 682.2 | ZK669.4 PROTEIN. | sptrembl Q23571 | Energy production and conversion |
| 4742 | 681.5 | NIF-U LIKE PROTEIN. | tremblnew CAB61462 | Energy production and conversion |
| 4743 | 681.3 | RODLET PROTEIN PRECURSOR. | swissprot P28346 | ND |
| 4744 | 681.0 | HYPOTHETICAL 39.9 KD PROTEIN. | sptrembl O74507 | ND |
| 4745 | 680.8 | HYPOTHETICAL 97.1 KD PROTEIN C32A11.02C IN CHROMOSOME I. | swissprot Q10327 | ND |
| 4746 | 680.5 | PUTATIVE RHO GDP-DISSOCIATION INHIBITOR (RHO GDI). | sptrembl O14224 | ND |
| 4747 | 679.6 | HYPOTHETICAL 17.3 KD PROTEIN. | sptrembl Q9X7U1 | ND |
| 4748 | 679.1 | UBIQUITIN-LIKE PROTEIN DSK2. | swissprot P48510 | ND |
| 4749 | 679.0 | LPG20P. | sptrembl Q02895 | Energy production and conversion |
| 4750 | 678.7 | HYDROXYLASE. | sptrembl O94115 | ND |
| 4751 | 678.7 | ACTIN. | swissprot O13419 | Cell division and chromosome partitioning |
| 4752 | 678.6 | 20 KD NUCLEAR CAP BINDING PROTEIN (NCBP) (CBP20) (FRAGMENT). | swissprot P52299 | Transcription |
| 4754 | 677.4 | PROBABLE ATP-DEPENDENT TRANSPORTER C29A3.09C. | sptrembl O59672 | ND |
| 4755 | 677.1 | HELICASE. | sptrembl Q92770 | ND |
| 4756 | 676.6 | HEAT SHOCK PROTEIN 70 HOMOLOG YHR064C. | swissprot P38788 | Posttranslational modification, protein turnover, chaperones |
| 4757 | 675.7 | SPLICESOME-ASSOCIATED PROTEIN. | sptrembl O59706 | ND |
| 4758 | 675.0 | F27D4.5 PROTEIN. | sptrembl Q93619 | Energy production and conversion |
| 4759 | 674.2 | CHROMOSOME XII READING FRAME ORF YLR009W. | sptrembl Q07915 | Translation, ribosomal structure and biogenesis |
| 4760 | 674.2 | BRANCHED-CHAIN AMINO ACID AMINOTRANSFERASE, CYTOSOLIC (EC 2.6.1.42) (BCAT) (TWT2 PROTEIN). | swissprot P47176 | Coenzyme metabolism |
| 4761 | 673.0 | 60S RIBOSOMAL PROTEIN L6-B (L17) (YL16) (RP18). | swissprot P05739 | ND |
| 4762 | 671.0 | PROBABLE SUCCINYL-COA LIGASE [GDP-FORMING] ALPHA-CHAIN, MITOCHONDRIAL PRECURSOR (EC 6.2.1.4) (SUCCINYL-COA SYNTHETASE, ALPHA CHAIN) (SCS-ALPHA). | swissprot O13750 | Energy production and conversion |
| 4763 | 670.8 | TRYPTOPHANYL-TRNA SYNTHETASE, CYTOPLASMIC (EC 6.1.1.2) (TRYPTOPHAN--TRNA LIGASE) (TRPRS). | swissprot Q12109 | Translation, ribosomal structure and biogenesis |
| 4764 | 670.4 | 26S PROTEASOME REGULATORY SUBUNIT SUN1. | swissprot P38886 | ND |

TABLE 3-continued

*Aspergillus oryzae* ESTs

| Sequence Listing | zscore | Annotation | Database | Functional Category |
|---|---|---|---|---|
| 4765 | 670.4 | HYPOTHETICAL 49.1 KD PROTEIN. | sptrembl O42964 | ND |
| 4766 | 669.8 | SPLICING FACTOR U2AF 50 KD SUBUNIT (U2 AUXILIARY FACTOR 50 KD SUBUNIT) (U2 SNRNP AUXILIARY FACTOR LARGE SUBUNIT). | swissprot Q24562 | ND |
| 4767 | 669.6 | HEXOSE TRANSPORTER. | sptrembl O13311 | ND |
| 4768 | 669.3 | UTR2 PROTEIN (UNKNOWN TRANSCRIPT 2 PROTEIN). | swissprot P32623 | Carbohydrate transport and metabolism |
| 4769 | 669.1 | PROBABLE KYNURENINASE (EC 3.7.1.3) (L-KYNURENINE HYDROLASE). | swissprot Q05979 | Amino acid transport and metabolism |
| 4770 | 668.9 | GLUTATHIONE REDUCTASE (GR). | sptrembl Q9WXD5 | Energy production and conversion |
| 4771 | 668.1 | PATHOGENICITY PROTEIN. | sptrembl O93846 | ND |
| 4772 | 667.8 | ELECTRON TRANSPORT 312 aa, chain A | pdb 1EFV | Energy production and conversion |
| 4773 | 667.6 | YEAST PROTEASOME COMPONENT PRE4 HOMOLOG. | tremblnew CAB54818 | Posttranslational modification, protein turnover, chaperones |
| 4774 | 667.4 | SEXUAL DEVELOPMENT REGULATOR 1. | tremblnew CAB52588 | ND |
| 4775 | 667.1 | SMALL ZINC FINGER-LIKE PROTEIN. | sptrembl Q9Y8A8 | ND |
| 4776 | 665.5 | HYPOTHETICAL 64.0 KD PROTEIN C20G4.05C IN CHROMOSOME I. | swissprot O13890 | ND |
| 4777 | 664.4 | PUTATIVE COATOMER BETA SUBUNIT. | tremblnew CAB46767 | ND |
| 4778 | 664.2 | RNA BINDING PROTEIN. | sptrembl O74978 | Transcription |
| 4779 | 663.5 | MOLYBDOPTERIN SYNTHASE LARGE SUBUNIT CNXH. | sptrembl Q9Y8C1 | ND |
| 4780 | 661.9 | MOLLUSK-DERIVED GROWTH FACTOR. | sptrembl O96697 | ND |
| 4781 | 661.2 | HEXOKINASE (EC 2.7.1.1). | sptrembl O93964 | ND |
| 4782 | 659.4 | OXIDOREDUCTASE OF SHORT-CHAIN. | sptrembl Q9X9S4 | ND |
| 4783 | 657.9 | PROTEIN KINASE. | sptrembl O59790 | ND |
| 4784 | 657.5 | PUTATIVE 26S PROTEASOME SUBUNIT. | tremblnew CAB63792 | ND |
| 4785 | 656.7 | ZINC-FINGER PROTEIN ZPR1. | swissprot O13724 | ND |
| 4786 | 656.6 | HYPOTHETICAL 14.4 KD PROTEIN IN RNR1-ALD3 INTERGENIC REGION. | swissprot P40046 | ND |
| 4787 | 656.2 | MAL3 PROTEIN. | swissnew Q10113 | ND |
| 4788 | 655.9 | HYPOTHETICAL AMINOTRANSFERASE C6B12.04C (EC 2.6.1.-). | swissprot O14209 | Amino acid transport and metabolism |
| 4789 | 654.8 | PUTATIVE CINNAMOYL-COA REDUCTASE. | tremblnew CAB58730 | Carbohydrate transport and metabolism |
| 4790 | 651.0 | SEC13-RELATED PROTEIN. | swissprot P55735 | ND |
| 4791 | 650.8 | HYPOTHETICAL 42.3 KD PROTEIN IN YTA2-DIT1 INTERGENIC REGION. | swissprot Q04179 | Nucleotide transport |
| 4792 | 649.9 | 60S RIBOSOMAL PROTEIN L32-A. | swissprot P79015 | Translation, ribosomal structure and biogenesis |
| 4793 | 648.8 | AVERANTIN OXIDOREDUCTASE (EC 1.14.-.-) (CYTOCHROME P450 60A1). | swissprot Q12732 | ND |

TABLE 3-continued

_Aspergillus oryzae ESTs_

| Sequence Listing | zscore | Annotation | Database | Functional Category |
|---|---|---|---|---|
| 4794 | 648.1 | ZINC FINGER PROTEIN SFP1. | swissprot P32432 | ND |
| 4795 | 647.4 | FISSION YEAST (FRAGMENT). | sptrembl P78810 | ND |
| 4796 | 647.2 | IGE-BINDING PROTEIN (FRAGMENT). | sptrembl O74263 | ND |
| 4797 | 646.9 | GLYCINE DEHYDROGENASE [DECARBOXYLATING], MITOCHONDRIAL PRECURSOR (EC 1.4.4.2) (GLYCINE DECARBOXYLASE) (GLYCINE CLEAVAGE SYSTEM P-PROTEIN). | swissprot P49095 | Amino acid transport and metabolism |
| 4798 | 644.7 | 6-PHOSPHOGLUCONATE DEHYDROGENASE (EC 1.1.1.44). | sptrembl O60037 | Carbohydrate transport and metabolism |
| 4799 | 644.3 | 60S RIBOSOMAL PROTEIN L5. | swissprot O59953 | Translation, ribosomal structure and biogenesis |
| 4800 | 643.1 | ACYL-COA DEHYDROGENASE, PUTATIVE. | tremblnew AAF12182 | Lipid metabolism |
| 4801 | 642.9 | PROBABLE GAMMA-GLUTAMYL PHOSPHATE REDUCTASE. | tremblnew CAB57445 | Amino acid transport and metabolism |
| 4802 | 642.5 | ALK2. | sptrembl O74128 | ND |
| 4803 | 642.2 | HYPOTHETICAL 52.2 KD PROTEIN. | sptrembl Q12116 | ND |
| 4804 | 639.5 | ISOTRICHODERMIN C-15 HYDROXYLASE (EC 1.14.-.-) (CYTOCHROME P450 65A1). | swissprot O13317 | ND |
| 4805 | 638.6 | FK506-BINDING PROTEIN PRECURSOR (FKBP-21) (PEPTIDYL-PROLYL CIS-TRANS ISOMERASE) (PPIASE) (EC 5.2.1.8). | swissprot O60046 | Posttranslational modification, protein turnover, chaperones |
| 4806 | 638.4 | ATP PHOSPHORIBOSYLTRANSFERASE (EC 2.4.2.17). | swissprot P40373 | Amino acid transport and metabolism |
| 4807 | 638.2 | 40S RIBOSOMAL PROTEIN S24 (RP50). | swissprot P26782 | Translation, ribosomal structure and biogenesis |
| 4808 | 638.0 | NAD(P) TRANSHYDROGENASE (EC 1.6.1.1) (PYRIDINE NUCLEOTIDE TRANSHYDROGENASE) (NICOTINAMIDE NUCLEOTIDE TRANSHYDROGENASE). | sptrembl Q18031 | Energy production and conversion |
| 4809 | 637.5 | PROBABLE ELECTRON TRANSFER FLAVOPROTEIN-UBIQUINONE OXIDOREDUCTASE PRECURSOR (EC 1.5.5.1) (ETF-QO) (ETF-UBIQUINONE OXIDOREDUCTASE) (ETF DEHYDROGENASE) (ELECTRON-TRANSFERRING-FLAVOPROTEIN DEHYDROGENASE). | swissprot P87111 | Energy production and conversion |
| 4810 | 636.9 | CAMP-DEPENDENT PROTEIN KINASE REGULATORY CHAIN. | swissnew O59922 | ND |
| 4811 | 636.3 | ATP SYNTHASE BETA CHAIN, MITOCHONDRIAL PRECURSOR (EC 3.6.1.34). | swissnew P23704 | Energy production and conversion |

TABLE 3-continued

_Aspergillus oryzae ESTs_

| Sequence Listing | zscore | Annotation | Database | Functional Category |
|---|---|---|---|---|
| 4812 | 635.4 | 60S RIBOSOMAL PROTEIN L17-B (YL17-B). | swissprot P46990 | Translation, ribosomal structure and biogenesis |
| 4813 | 635.3 | PROBABLE MEMBRANE PROTEIN YOL130W. | sptrembl O13657 | Inorganic ion transport and metabolism |
| 4814 | 634.9 | MITOCHONDRIAL IMPORT RECEPTOR SUBUNIT TOM20 (MITOCHONDRIAL 20 KD OUTER MEMBRANE PROTEIN) (MOM19 PROTEIN) (TRANSLOCASE OF OUTER MEMBRANE 20 KD SUBUNIT). | swissprot P35848 | ND |
| 4815 | 634.2 | NADH DEHYDROGENASE SUBUNIT. | sptrembl Q01388 | ND |
| 4816 | 634.2 | 60S RIBOSOMAL PROTEIN L33-B (L37B) (YL37) (RP47). | swissprot P41056 | ND |
| 4817 | 634.1 | GLUTATHIONE S-TRANSFERASE. | sptrembl O59827 | Posttranslational modification, protein turnover, chaperones |
| 4818 | 633.8 | CALCIUM-TRANSPORTING ATPASE 3 (EC 3.6.1.38). | swissprot P22189 | Inorganic ion transport and metabolism |
| 4819 | 633.4 | HYPOTHETICAL 33.0 KD PROTEIN C25H2.06C IN CHROMOSOME II. | sptrembl P87148 | ND |
| 4820 | 632.5 | PEROXISOMAL MEMBRANE PROTEIN PMP47A. | swissprot P21245 | ND |
| 4821 | 632.2 | HYPOTHETICAL 41.7 KD PROTEIN C3C7.07C IN CHROMOSOME I. | sptrembl O14133 | ND |
| 4822 | 632.1 | PUTATIVE CINNAMOYL-COA REDUCTASE. | tremblnew CAB58730 | Carbohydrate transport and metabolism |
| 4823 | 629.5 | 6,7-DIMETHYL-8-RIBITYLLUMAZINE SYNTHASE. | tremblnew AAD55372 | ND |
| 4824 | 629.5 | OXIDOREDUCTASE, SHORT CHAIN DEHYDROGENASE/REDUCTASE FAMILY. | sptrembl Q9WYD3 | ND |
| 4825 | 629.3 | PUTATIVE OXIDOREDUCTASE C2F3.05C (EC 1.-.-.-). | sptrembl O14088 | ND |
| 4826 | 628.7 | MITOCHONDRIAL PHOSPHATE CARRIER PROTEIN (PHOSPHATE TRANSPORT PROTEIN) (PTP) (MITOCHONDRIAL IMPORT RECEPTOR) (P32). | swissprot P23641 | ND |
| 4827 | 628.0 | Yeast immunophilin FKBP46. | geneseqp W68011 | Posttranslational modification, protein turnover, chaperones |
| 4828 | 627.9 | VACUOLAR PROTEIN SORTING-ASSOCIATED PROTEIN VPS28. | swissprot Q02767 | ND |
| 4829 | 627.8 | Human cytidine deaminase. | geneseqp W13658 | Nucleotide transport |
| 4830 | 626.3 | SMALL NUCLEAR RIBONUCLEOPROTEIN SM D3 (SNRNP CORE PROTEIN D3) (SM-D3). | swissprot P43331 | Transcription |
| 4831 | 623.8 | MITOCHONDRIAL RESPIRATORY FUNCTION PROTEIN HOMOLOG. | swissprot Q10488 | ND |
| 4832 | 623.6 | MALTOSE PERMEASE. | sptrembl Q9Y845 | ND |
| 4833 | 623.0 | CONSERVED HYPOTHETICAL PROTEIN. | sptrembl O74797 | ND |

TABLE 3-continued

_Aspergillus oryzae ESTs_

| Sequence Listing | zscore | Annotation | Database | Functional Category |
|---|---|---|---|---|
| 4834 | 621.6 | GABA PERMEASE. | sptrembl Q9Y860 | Amino acid transport and metabolism |
| 4835 | 621.2 | GTP CYCLOHYDROLASE II (EC 3.5.4.25). | swissprot P50139 | Coenzyme metabolism |
| 4836 | 621.1 | NADH-UBIQUINONE OXIDOREDUCTASE 14.8 KD SUBUNIT (EC 1.6.5.3) (EC 1.6.99.3) (COMPLEX I-14.8 KD) (CI-14.8 KD). | swissprot P42114 | ND |
| 4837 | 620.7 | ASPARTIC PROTEINASE II-1. | tremblnew G1246046 | ND |
| 4838 | 620.2 | AMINO ACID PERMEASE. | sptrembl O59813 | ND |
| 4839 | 620.0 | TRANSLATIONALLY CONTROLLED TUMOR PROTEIN HOMOLOG (TCTP). | swissprot P35691 | ND |
| 4840 | 619.9 | SERINE/THREONINE-PROTEIN KINASE KSP1 (EC 2.7.1.-). | swissnew P38691 | Signal transduction mechanisms |
| 4841 | 619.6 | HEAT SHOCK PROTEIN STI1. | swissprot P15705 | ND |
| 4842 | 619.5 | PROTEIN TRANSLATION FACTOR SUI1. | swissprot P32911 | Translation, ribosomal structure and biogenesis |
| 4843 | 618.4 | ASH1. | sptrembl Q24189 | ND |
| 4844 | 618.2 | PROBABLE ATP-DEPENDENT PERMEASE PRECURSOR. | swissprot P25371 | ND |
| 4845 | 617.9 | PEPTIDYL-PROLYL CIS-TRANSISOMERASE, FK506-BINDING PROTEIN. | tremblnew CAB46710 | Posttranslational modification, protein turnover, chaperones |
| 4846 | 617.4 | UBIQUINONE BIOSYNTHESIS METHYLTRANSFERASE COQ5(EC 2.1.1.-). | swissprot P49017 | Coenzyme metabolism |
| 4847 | 615.9 | RAS-2 PROTEIN. | swissnew Q01387 | ND |
| 4848 | 615.8 | O-METHYLSTERIGMATOCYSTIN OXIDOREDUCTASE (EC 1.14.1.-) (OMST OXIDOREDUCTASE) (CYTOCHROME P450 64). | swissprot O13345 | ND |
| 4849 | 615.4 | HYPOTHETICAL 27.1 KD PROTEIN IN ACS1-GCV3 INTERGENIC REGION. | swissprot P39721 | ND |
| 4850 | 615.4 | HYPOTHETICAL 23.6 KD PROTEIN. | sptrembl O14451 | ND |
| 4851 | 614.2 | c424 gene product. | geneseqp R43654 | ND |
| 4852 | 613.9 | 60S RIBOSOMAL PROTEIN L37. | swissprot O44125 | Translation, ribosomal structure and biogenesis |
| 4853 | 613.6 | HYPOTHETICAL 39.6 KD PROTEIN IN MTD1-NUP133 INTERGENIC REGION. | swissprot P36160 | ND |
| 4854 | 612.4 | ORF YPL252C. | sptrembl Q12184 | Energy production and conversion |
| 4855 | 612.1 | PECTATE LYASE D. | sptrembl Q00845 | ND |
| 4856 | 611.9 | HYPOTHETICAL 44.2 KD PROTEIN. | tremblnew CAB65618 | ND |
| 4857 | 611.7 | ATP SYNTHASE ALPHA CHAIN, MITOCHONDRIAL PRECURSOR (EC 3.6.1.34). | swissnew P24487 | Energy production and conversion |
| 4858 | 611.4 | TRANSMEMBRANE PROTEIN. | tremblnew CAB65007 | ND |
| 4859 | 611.2 | THYMOCYTE PROTEIN CTHY28 KD. | sptrembl Q90679 | ND |
| 4860 | 609.5 | PUTATIVE TRANSCRIPTIONAL REPRESSOR C30D10.02. | sptrembl O14348 | ND |

TABLE 3-continued

_Aspergillus oryzae ESTs_

| Sequence Listing | zscore | Annotation | Database | Functional Category |
|---|---|---|---|---|
| 4861 | 609.4 | HYPOTHETICAL 38.3 KD PROTEIN IN PRP16-SRP40 INTERGENIC REGION. | swissprot P36164 | ND |
| 4862 | 609.3 | THIOREDOXIN. | swissprot P29429 | Energy production and conversion |
| 4863 | 608.8 | HYPOTHETICAL 31.1 KD PROTEIN IN SIP18-SPT21 INTERGENIC REGION. | swissprot Q03219 | ND |
| 4864 | 608.1 | CYTOCHROME C HEME LYASE (EC 4.1.1.17) (CCHL) (HOLOCYTOCHROME-C SYNTHASE). | swissnew P14187 | ND |
| 4865 | 607.9 | NADH-UBIQUINONE OXIDOREDUCTASE 10.5 KD SUBUNIT (EC 1.6.5.3) (EC 1.6.99.3) (COMPLEX I) (CI). | swissprot Q07842 | ND |
| 4866 | 607.7 | PUTATIVE D-3-PHOSPHOGLYCERATE DEHYDROGENASE YIL074W (EC 1.1.1.95) (PGDH). | swissprot P40510 | ND |
| 4867 | 606.5 | BETA-GLUCOSIDASE 1 PRECURSOR (EC 3.2.1.21) (GENTIOBIASE) (CELLOBIASE) (BETA-D-GLUCOSIDE GLUCOHYDROLASE). | swissprot P48825 | ND |
| 4868 | 606.0 | CALNEXIN HOMOLOG PRECURSOR. | swissprot P36581 | ND |
| 4869 | 605.8 | NUCLEASE. | sptrembl O60168 | ND |
| 4870 | 605.8 | PUTATIVE D-3-PHOSPHOGLYCERATE DEHYDROGENASE YER081W (EC 1.1.1.95) (PGDH). | swissprot P40054 | Amino acid transport and metabolism |
| 4871 | 605.6 | B0250.5 PROTEIN. | sptrembl Q9XT10 | Lipid metabolism |
| 4872 | 605.6 | UNKNOWN PROTEIN. | sptrembl O22730 | ND |
| 4873 | 604.9 | TOXD PROTEIN. | swissprot P54006 | ND |
| 4874 | 604.8 | HYPOTHETICAL 41.5 KD PROTEIN IN GZF3-IME2 INTERGENIC REGION. | swissprot P42946 | ND |
| 4875 | 604.8 | HYPOTHETICAL 81.0 KD PROTEIN C1B3.10C IN CHROMOSOME I PRECURSOR. | sptrembl O13875 | ND |
| 4876 | 602.9 | 60S RIBOSOMAL PROTEIN L26. | swissprot Q39411 | Translation, ribosomal structure and biogenesis |
| 4877 | 602.4 | TOLUENESULFONATE ZINC-INDEPENDENT ALCOHOL DEHYDROGENASE. | sptrembl P94681 | ND |
| 4878 | 602.2 | YPT1-RELATED PROTEIN 2. | swissprot P17609 | ND |
| 4879 | 600.9 | PREDICTED PROTEIN OF UNKNOWN FUNCTION. | sptrembl Q9ZR11 | ND |
| 4880 | 600.6 | DUTP PYROPHOSPHATASE-LIKE PROTEIN (EC 3.6.1.23). | tremblnew CAB51171 | Nucleotide transport |
| 4881 | 600.1 | LANOSTEROL SYNTHASE (EC 5.4.99.7) (OXIDOSQUALENE--LANOSTEROL CYCLASE) (2,3-EPOXYSQUALENE--LANOSTEROL CYCLASE) (OSC). | swissprot Q10231 | Lipid metabolism |
| 4882 | 598.3 | HYPOTHETICAL 38.7 KD PROTEIN. | tremblnew CAB59917 | ND |
| 4883 | 598.0 | HYPOTHETICAL 49.1 KD PROTEIN. | sptrembl O74556 | ND |

TABLE 3-continued

_Aspergillus oryzae ESTs_

| Sequence Listing | zscore | Annotation | Database | Functional Category |
|---|---|---|---|---|
| 4884 | 595.0 | MBF1 PROTEIN (ORF YOR298C-A). | sptrembl O14467 | ND |
| 4885 | 592.6 | 60S RIBOSOMAL PROTEIN L22. | tremblnew CAB11194 | ND |
| 4886 | 592.4 | EIF-5A. | sptrembl O94083 | Translation, ribosomal structure and biogenesis |
| 4887 | 592.4 | HYPOTHETICAL 23.4 KD PROTEIN C3G6.05 IN CHROMOSOME I. | sptrembl O14142 | ND |
| 4888 | 591.4 | RNA POLYMERASE I SECOND-LARGEST SUBUNIT (EC 2.7.7.6). | sptrembl O74633 | Transcription |
| 4889 | 591.4 | PUTATIVE SEPTIN. | tremblnew CAB52419 | ND |
| 4890 | 589.2 | UBIQUITIN-CONJUGATING ENZYME E2-17 KD 4 (EC 6.3.2.19) (UBIQUITIN-PROTEIN LIGASE) (UBIQUITIN CARRIER PROTEIN) (E2(17)KB 4). | swissprot P70711 | ND |
| 4891 | 589.0 | CYTOCHROME B2 PRECURSOR (EC 1.1.2.3) (L-LACTATE DEHYDROGENASE (CYTOCHROME)) (L-LACTATE FERRICYTOCHROME C OXIDOREDUCTASE) (L-LCR). | swissprot P09437 | Energy production and conversion |
| 4892 | 588.8 | HYPOTHETICAL 32.0 KD PROTEIN IN GOG5-NIF3 INTERGENIC REGION. | swissprot P53078 | ND |
| 4893 | 588.6 | HYPOTHETICAL 67.7 KD PROTEIN C23C11.03 IN CHROMOSOME I. | swissprot O13910 | ND |
| 4894 | 588.3 | ENDOSOMAL P24B PROTEIN PRECURSOR (24 KD ENDOMEMBRANE PROTEIN) (BASIC 24 KD LATE ENDOCYTIC INTERMEDIATE COMPONENT). | swissprot P32803 | ND |
| 4895 | 588.2 | UBIQUITIN-CONJUGATING ENZYME E2-17.5 KD (EC 6.3.2.19) (UBIQUITIN-PROTEIN LIGASE) (UBIQUITIN CARRIER PROTEIN). | swissprot P52490 | ND |
| 4896 | 587.7 | HYPOTHETICAL 32 KD PROTEIN. | sptrembl Q01391 | ND |
| 4897 | 587.2 | IMPORTIN BETA-1 SUBUNIT (KARYOPHERIN BETA-1 SUBUNIT) (IMPORTIN 95). | swissprot O13864 | ND |
| 4898 | 586.4 | NUCLEAR PROTEIN SNF4 (REGULATORY PROTEIN CAT3). | swissprot P12904 | ND |
| 4899 | 586.0 | PUTATIVE ATP-DEPENDENT RNA HELICASE. | sptrembl O48534 | ND |
| 4900 | 585.7 | HYPOTHETICAL 49.6 KD PROTEIN IN FBA1-TOA2 INTERGENIC REGION. | swissprot P35728 | ND |
| 4901 | 584.7 | LIGASE 603 aa, chain A | pdb 1BS2 | Translation, ribosomal structure and biogenesis |
| 4902 | 584.4 | SPERMIDINE SYNTHASE. | sptrembl Q9Y8H7 | Amino acid transport and metabolism |
| 4903 | 584.1 | SORBITOL UTILIZATION PROTEIN SOU2. | swissprot P87218 | ND |

TABLE 3-continued

Aspergillus oryzae ESTs

| Sequence Listing | zscore | Annotation | Database | Functional Category |
|---|---|---|---|---|
| 4904 | 582.6 | HYPOTHETICAL 65.8 KD PROTEIN. | sptrembl O74963 | ND |
| 4905 | 582.6 | MINICHROMOSOME MAINTENANCE PROTEIN 3 HOMOLOG. | swissprot P30666 | DNA replication, recombination and repair |
| 4906 | 582.5 | RAT PHOSPHORIBOSYLPHOSPHATE SYNTHETASE (PRPS2). | sptrembl Q63462 | Nucleotide transport |
| 4907 | 580.6 | PUTATIVE ZINC-BINDING DEHYDROGENASE. | sptrembl Q9X9X1 | ND |
| 4908 | 580.5 | HYPOTHETICAL 23.4 KD PROTEIN. | sptrembl Q03201 | Translation, ribosomal structure and biogenesis |
| 4909 | 580.4 | TRANSCRIPTION FACTOR BTF3 (RNA POLYMERASE B TRANSCRIPTION FACTOR 3). | swissprot P20290 | ND |
| 4910 | 580.3 | PROBABLE EUKARYOTIC TRANSLATION INITIATION FACTOR 3 RNA-BINDING SUBUNIT (EIF-3 RNA-BINDING SUBUNIT) (EIF3 P33) (TRANSLATION INITIATION FACTOR EIF3, P33 SUBUNIT). | swissprot P78795 | Transcription |
| 4911 | 579.6 | AMP DEAMINASE (EC 3.5.4.6) (MYOADENYLATE DEAMINASE). | swissprot P15274 | ND |
| 4912 | 579.6 | ACYL CARRIER PROTEIN, MITOCHONDRIAL PRECURSOR (ACP) (NADH-UBIQUINONE OXIDOREDUCTASE 9.6 KD SUBUNIT) (EC 1.6.5.3) (EC 1.6.99.3). | swissprot P11943 | ND |
| 4913 | 579.5 | REPRESSIBLE ALKALINE PHOSPHATASE PRECURSOR (EC 3.1.3.1). | swissprot P11491 | Inorganic ion transport and metabolism |
| 4914 | 579.4 | SIMILARITY NEAR C-TERMINUS TO UNDULIN EXTRACELLULAR MATRIX GLYCOPROTEIN. | sptrembl Q06682 | ND |
| 4915 | 578.5 | AT2G05170 PROTEIN. | tremblnew AAD29055 | ND |
| 4916 | 578.4 | YEAST NRD1-LIKE PROTEIN. | tremblnew CAB60701 | ND |
| 4917 | 577.2 | PUTATIVE SECRETORY PROTEIN. | sptrembl O74903 | ND |
| 4918 | 575.7 | SPORULATION PROTEIN SPS19 (SPORULATION-SPECIFIC PROTEIN SPX19). | swissprot P32573 | ND |
| 4919 | 575.2 | UBIQUITIN FUSION DEGRADATION PROTEIN-2. | sptrembl O60009 | ND |
| 4920 | 573.7 | COPPER RESISTANCE-ASSOCIATED P-TYPE ATPASE. | tremblnew AAF04593 | Inorganic ion transport and metabolism |
| 4921 | 573.6 | A. fumigatus allergen rAsp f8 sequence. | geneseqp W61478 | Translation, ribosomal structure and biogenesis |
| 4922 | 573.6 | ALDEHYDE REDUCTASE II. | tremblnew AAF15999 | ND |
| 4923 | 573.3 | ACETAMIDASE. | sptrembl O59805 | ND |
| 4924 | 573.1 | THIOREDOXIN. | swissprot P34723 | Energy production and conversion |
| 4925 | 571.7 | CYSTATHIONINE BETA-LYASE. | tremblnew AAF20155 | Amino acid transport and metabolism |
| 4926 | 570.9 | PUTATIVE PHENYLALANYL-TRNA SYNTHETASE BETA CHAIN CYTOPLASMIC (EC 6.1.1.20) | sptrembl O42870 | ND |

TABLE 3-continued

_Aspergillus oryzae ESTs_

| Sequence Listing | zscore | Annotation | Database | Functional Category |
|---|---|---|---|---|
| | | (PHENYLALANINE--TRNA LIGASE BETA CHAIN). | | |
| 4927 | 570.8 | NMT1 PROTEIN HOMOLOG. | swissprot P42882 | Inorganic ion transport and metabolism |
| 4928 | 570.1 | ALPHA,ALPHA-TREHALOSE-PHOSPHATE SYNTHASE [UDP-FORMING] 1 (EC 2.4.1.15) (TREHALOSE-6-PHOSPHATE SYNTHASE) (UDP-GLUCOSE-GLUCOSEPHOSPHATE GLUCOSYLTRANSFERASE). | swissprot Q00075 | ND |
| 4929 | 570.1 | 36.7 KD PROTEIN IN CBR5-NOT3 INTERGENIC REGION. | swissprot P40531 | ND |
| 4930 | 569.4 | PROTEIN KINASE INHIBITOR P58. | sptrembl Q13217 | ND |
| 4931 | 569.2 | D-ARABINITOL 2-DEHYDROGENASE [RIBULOSE FORMING] (EC 1.1.1.250) (ARDH). | swissprot P43066 | ND |
| 4932 | 569.0 | P-CUMIC ALDEHYDE DEHYDROGENASE. | sptrembl O33455 | Energy production and conversion |
| 4933 | 568.6 | CGI-110 PROTEIN. | sptrembl Q9Y3B4 | ND |
| 4934 | 567.7 | UBIQUITIN-LIKE PROTEIN. | sptrembl O14399 | ND |
| 4935 | 567.2 | CAMP-INDEPENDENT REGULATORY PROTEIN PAC2. | sptrembl Q10294 | ND |
| 4936 | 566.5 | PHOSPHOSERINE AMINOTRANSFERASE (EC 2.6.1.52) (PSAT). | swissprot P33330 | Coenzyme metabolism |
| 4937 | 566.3 | MEIOTIC RECOMBINATION PROTEIN REC14. | swissprot Q09150 | ND |
| 4938 | 566.3 | C-8 STEROL ISOMERASE (DELTA-8--DELTA-7 STEROL ISOMERASE). | swissprot Q92254 | ND |
| 4939 | 566.2 | HYPOTHETICAL 76.3 KD PROTEIN. | sptrembl Q04562 | ND |
| 4940 | 566.1 | HYPOTHETICAL 28.3 KD PROTEIN IN PPR1-SNF7 INTERGENIC REGION. | swissprot Q07953 | ND |
| 4941 | 565.9 | NADH-CYTOCHROME B5 REDUCTASE PRECURSOR (EC 1.6.2.2) (P34/P32). | swissprot P36060 | Coenzyme metabolism |
| 4942 | 565.8 | THREONYL-TRNA SYNTHETASE, CYTOPLASMIC (EC 6.1.1.3) (THREONINE--TRNA LIGASE) (THRRS). | swissprot P26639 | Translation, ribosomal structure and biogenesis |
| 4943 | 565.6 | TRANSCRIPTION ELONGATION FACTOR S-II (TFIIS). | swissprot P49373 | Transcription |
| 4944 | 565.6 | HOMOGENTISATE 1,2-DIOXYGENASE (EC 1.13.11.5). | sptrembl Q9ZRA2 | ND |
| 4945 | 565.0 | ASPARAGINE-RICH ZINC FINGER PROTEIN AZF1. | swissprot P41696 | ND |
| 4946 | 564.9 | NICOTINATE-NUCLEOTIDE PYROPHOSPHORYLASE [CARBOXYLATING] (EC 2.4.2.19) (QUINOLINATE PHOSPHORIBOSYLTRANSFERASE [DECARBOXYLATING]) (QAPRTASE). | swissprot Q15274 | Coenzyme metabolism |
| 4947 | 561.2 | FUSCA PROTEIN FUS6. | swissprot P45432 | ND |
| 4949 | 559.0 | PHASE SPECIFIC (YPS-3). | sptrembl Q00950 | ND |
| 4950 | 558.6 | FISSION YEAST (FRAGMENT). | sptrembl P78791 | ND |
| 4951 | 558.3 | PUTATIVE HEAVY METAL | sptrembl O74869 | ND |

TABLE 3-continued

*Aspergillus oryzae* ESTs

| Sequence Listing | zscore | Annotation | Database | Functional Category |
|---|---|---|---|---|
| | | TRANSPORT PROTEIN (FRAGMENT). | | |
| 4952 | 557.1 | HYPOTHETICAL 56.6 KD PROTEIN IN URE2-SSU72 INTERGENIC REGION. | swissprot P53867 | ND |
| 4953 | 556.5 | PROBABLE DIMERIC DIHYDRODIOL DEHYDROGENASE. | tremblnew CAB58729 | ND |
| 4954 | 555.8 | GAMMA-BUTYROBETAINE,2-OXOGLUTARATE DIOXYGENASE (EC 1.14.11.1) (GAMMA-BUTYROBETAINE HYDROXYLASE) (GAMMA-BBH). | swissprot O75936 | ND |
| 4955 | 555.8 | AMINOTRANSFERASE. | sptrembl O94562 | Amino acid transport and metabolism |
| 4956 | 555.0 | ANNEXIN XIV. | sptrembl O59907 | ND |
| 4957 | 554.9 | NADPH-DEPENDENT BETA-KETOACYL REDUCTASE. | tremblnew AAD53514 | ND |
| 4958 | 554.3 | HYPOTHETICAL 92.7 KD PROTEIN. | sptrembl O74334 | ND |
| 4960 | 552.3 | HYPOTHETICAL 48.7 KD PROTEIN (FRAGMENT). | tremblnew CAB43225 | ND |
| 4961 | 550.4 | ATP SYNTHASE GAMMA CHAIN, MITOCHONDRIAL PRECURSOR (EC 3.6.1.34). | swissnew P49377 | Energy production and conversion |
| 4962 | 550.3 | ACETYL-COA-ACETYLTRANSFERASE (EC 2.3.1.9). | sptrembl Q9Y838 | ND |
| 4963 | 548.4 | 40S RIBOSOMAL PROTEIN S27. | swissprot O74330 | Translation, ribosomal structure and biogenesis |
| 4964 | 547.6 | ORF YDL147W. | sptrembl Q12250 | ND |
| 4966 | 547.3 | STEROID MONOOXYGENASE. | sptrembl O50641 | Inorganic ion transport and metabolism |
| 4967 | 546.0 | TRANSCRIPTION INITIATION FACTOR TFIIF SMALL SUBUNIT (TRANSCRIPTION FACTOR G 30 KD SUBUNIT) (ANC1 PROTEIN). | swissprot P35189 | ND |
| 4968 | 545.5 | 60S ACIDIC RIBOSOMAL PROTEIN P1 (ALLERGEN CLA H 12) (CLA H XII). | swissprot P50344 | ND |
| 4969 | 545.0 | SIMILAR TO MITOCHONDRIAL ADP/ATP CARRIER PROTEIN. | sptrembl Q06497 | ND |
| 4970 | 544.3 | KIAA0363 (FRAGMENT). | sptrembl O15069 | Transcription |
| 4971 | 544.1 | AMINONITROPHENYL PROPANEDIOL RESISTANCE PROTEIN. | swissprot P32629 | ND |
| 4972 | 543.6 | HYPOTHETICAL 29.7 KD PROTEIN. | sptrembl O74529 | ND |
| 4973 | 543.3 | HYPOTHETICAL 86.4 KD PROTEIN IN PHO5-VPS15 INTERGENIC REGION. | swissprot P38254 | ND |
| 4974 | 543.3 | ORF YOL080C. | sptrembl Q08237 | DNA replication, recombination and repair |
| 4975 | 542.2 | PUTATIVE ZUOTIN-LIKE PROTEIN C30D10.01 (FRAGMENT). | sptrembl O14347 | Posttranslational modification, protein turnover, chaperones |
| 4976 | 541.9 | HYPOTHETICAL PROTEIN AQ 1575. | swissnew O67517 | ND |
| 4977 | 541.6 | H(+)/MONOSACCHARIDE COTRANSPORTER. | sptrembl O13411 | ND |

TABLE 3-continued

_Aspergillus oryzae ESTs_

| Sequence Listing | zscore | Annotation | Database | Functional Category |
|---|---|---|---|---|
| 4978 | 540.8 | 40S RIBOSOMAL PROTEIN S20. | swissprot O74893 | Translation, ribosomal structure and biogenesis |
| 4979 | 539.8 | DICARBOXYLIC AMINO ACID PERMEASE. | swissprot P53388 | Amino acid transport and metabolism |
| 4980 | 539.8 | C. magnoliae carbonyl reductase. | geneseqp W64777 | ND |
| 4981 | 538.8 | PI023 PROTEIN. | sptrembl O13614 | ND |
| 4982 | 538.4 | 3-KETOACYL-COA THIOLASE, PEROXISOMAL PRECURSOR (EC 2.3.1.16) (BETA-KETOTHIOLASE) (ACETYL-COA ACYLTRANSFERASE) (PEROXISOMAL 3-OXOACYL-COA THIOLASE). | swissprot Q05493 | Lipid metabolism |
| 4983 | 538.0 | PROBABLE RIBOSE-PHOSPHATE PYROPHOSPHOKINASE 5 (EC 2.7.6.1) (PHOSPHORIBOSYL PYROPHOSPHATE SYNTHETASE 5). | swissprot Q12265 | Nucleotide transport |
| 4984 | 537.4 | MYB-LIKE DNA BINDING PROTEIN FLBD. | sptrembl Q00658 | ND |
| 4985 | 537.2 | HYPOTHETICAL 50.8 KD PROTEIN IN PAU2-GLY1 INTERGENIC REGION. | swissprot P32614 | ND |
| 4986 | 536.6 | 60S RIBOSOMAL PROTEIN L35. | swissprot P17078 | Translation, ribosomal structure and biogenesis |
| 4987 | 534.5 | HYPOTHETICAL 57.7 KD PROTEIN. | sptrembl O59714 | ND |
| 4988 | 534.5 | CALCIUM/CALMODULIN-DEPENDENT PROTEIN KINASE (EC 2.7.1.123) (CMPK). | swissprot Q00771 | ND |
| 4989 | 533.4 | CYTOCHROME B-245 HEAVY CHAIN (P22 PHAGOCYTE B-CYTOCHROME) (NEUTROPHIL CYTOCHROME B, 91 KD POLYPEPTIDE) (CGD91-PHOX) (GP91-PHOX) (CYTOCHROME B(558) BETA CHAIN) (SUPEROXIDE-GENERATING NADPH OXIDASE HEAVY CHAIN SUBUNIT). | swissprot P04839 | ND |
| 4990 | 532.6 | PROBABLE MEMBRANE TRANSPORTER. | tremblnew CAB65616 | ND |
| 4991 | 531.3 | MYO-INOSITOL TRANSPORTER 1. | swissnew Q10286 | ND |
| 4992 | 531.0 | OPDA-REDUCTASE HOMOLOG. | sptrembl Q9XHD2 | Energy production and conversion |
| 4993 | 529.7 | MORPHINE 6-DEHYDROGENASE (EC 1.1.1.218) (NALOXONE REDUCTASE). | swissprot Q02198 | ND |
| 4994 | 528.7 | DENTIN PHOSPHORYN (FRAGMENT). | sptrembl O95815 | ND |
| 4995 | 527.1 | HYPOTHETICAL 27.5 KD PROTEIN IN SPO1-SIS1 INTERGENIC REGION. | swissprot P53981 | ND |
| 4996 | 527.0 | UDP-GALACTOSE TRANSPORTER (GOLGI UDP-GAL TRANSPORTER). | swissprot P87041 | ND |

TABLE 3-continued

_Aspergillus oryzae ESTs_

| Sequence Listing | zscore | Annotation | Database | Functional Category |
|---|---|---|---|---|
| 4997 | 526.8 | SRP1 PROTEIN. | swissprot Q10193 | ND |
| 4998 | 526.6 | MYOSIN-RELATED PROTEIN HOMOLOG MLPA (FRAGMENT). | tremblnew AAF18567 | ND |
| 4999 | 525.6 | GCY PROTEIN (EC 1.1.1.-). | swissprot P14065 | ND |
| 5000 | 525.5 | PISATIN DEMETHYLASE (EC 1.14.-.-) (CYTOCHROME P450 57A2). | swissprot P38364 | ND |
| 5001 | 525.4 | VIRULENCE PROTEIN CAP20. | sptrembl Q00368 | ND |
| 5002 | 525.3 | ALLYL ALCOHOL DEHYDROGENASE. | tremblnew BAA89423 | ND |
| 5003 | 525.1 | DNA REPLICATION HELICASE DNA2. | swissprot P38859 | DNA replication, recombination and repair |
| 5004 | 524.6 | HYPOTHETICAL TPR DOMAIN-CONTAINING PROTEIN. | sptrembl O94474 | ND |
| 5005 | 523.1 | CLATHRIN-ASSOCIATED ADAPTOR COMPLEX AP-2 MEDIUM CHAIN. | tremblnew AAF14248 | ND |
| 5006 | 522.5 | Protein involved in cephalosporin C biosynthesis. | geneseqp W14440 | ND |
| 5007 | 522.4 | HYPOTHETICAL 40.3 KD PROTEIN. | sptrembl O74384 | ND |
| 5008 | 522.0 | IGE-BINDING PROTEIN (FRAGMENT). | sptrembl O74263 | ND |
| 5009 | 521.5 | DNA-DIRECTED RNA POLYMERASE I AND III 14 KDA POLYPEPTIDE. | swissprot Q09177 | Transcription |
| 5010 | 521.4 | SIMILAR TO PHOSPHATIDIC ACID PHOSPHATASE. | tremblnew CAB52620 | ND |
| 5011 | 521.3 | C5,6 DESATURASE. | sptrembl O93875 | ND |
| 5012 | 520.8 | QUINATE PERMEASE (QUINATE TRANSPORTER). | swissprot P11636 | ND |
| 5013 | 520.6 | DNAJ RELATED PROTEIN. | sptrembl O94657 | Posttranslational modification, protein turnover, chaperones |
| 5014 | 518.6 | BEM46 PROTEIN (FRAGMENT). | swissprot P54069 | ND |
| 5015 | 517.6 | CURVED DNA-BINDING PROTEIN (42 KD PROTEIN). | swissprot Q09184 | ND |
| 5016 | 517.2 | HYPOTHETICAL 42.5 KD PROTEIN IN TSM1-ARE1 INTERGENIC REGION. | swissprot P25625 | ND |
| 5017 | 516.7 | HYPOTHETICAL 13.5 KD PROTEIN C24B11.09 IN CHROMOSOME I. | swissprot Q09896 | ND |
| 5018 | 514.5 | 6-PHOSPHOGLUCONATE DEHYDROGENASE, DECARBOXYLATING (EC 1.1.1.44). | swissprot O13287 | Carbohydrate transport and metabolism |
| 5019 | 514.1 | LYSOPHOSPHOLIPASE. | sptrembl O42881 | ND |
| 5020 | 513.7 | D-AMINOPEPTIDASE (EC 3.4.11.19) (D-STEREOSPECIFIC AMINOPEPTIDASE). | sptrembl Q59632 | ND |
| 5021 | 513.7 | HYPOTHETICAL 17.1 KD PROTEIN IN SIP3-MRPL30 INTERGENIC REGION. | swissprot P53849 | ND |
| 5022 | 513.7 | PUTATIVE CYSTEINE DIOXYGENASE (EC 1.13.11.20) (CDO). | sptrembl Q20893 | ND |
| 5023 | 513.6 | 26S PROTEASOME REGULATORY COMPLEX SUBUNIT P110 (FRAGMENT). | tremblnew AAF08384 | ND |
| 5024 | 513.1 | HYPOTHETICAL 17.7 KD PROTEIN IN RNR3-ARC15 INTERGENIC REGION. | swissprot P40515 | ND |
| 5025 | 512.3 | 1,4-BUTANEDIOL DIACRYLATE ESTERASE. | sptrembl Q9WXD6 | ND |

TABLE 3-continued

_Aspergillus oryzae ESTs_

| Sequence Listing | zscore | Annotation | Database | Functional Category |
|---|---|---|---|---|
| 5026 | 511.7 | TIJ1.6 PROTEIN. | sptrembl Q9ZPH2 | Posttranslational modification, protein turnover, chaperones |
| 5027 | 511.2 | HYPOTHETICAL 40.2 KD PROTEIN IN TAF145-YOR1 INTERGENIC REGION PRECURSOR. | swissprot P53334 | ND |
| 5028 | 511.2 | PUTATIVE SUCCINATE DEHYDROGENASE CYTOCHROME B SUBUNIT PRECURSOR. | sptrembl O74882 | ND |
| 5029 | 510.6 | BLASTICIDIN-S DEAMINASE (EC 3.5.4.23) (FRAGMENT). | sptrembl P78986 | ND |
| 5030 | 509.9 | Peptide transport protein ATPTR2Ap. | geneseqp R84891 | ND |
| 5031 | 509.8 | GLYCINE CLEAVAGE SYSTEM H PROTEIN. | sptrembl Q9WY55 | Amino acid transport and metabolism |
| 5032 | 509.4 | YEL007C-AP. | sptrembl P89886 | ND |
| 5033 | 509.3 | ZINC FINGER PROTEIN. | sptrembl O59811 | ND |
| 5034 | 509.1 | HYPOTHETICAL OXIDOREDUCTASE IN MRPL44-MTF1 INTERGENIC REGION (EC 1.-.-.-). | swissprot Q05016 | ND |
| 5035 | 508.9 | HYPOTHETICAL 54.7 KD PROTEIN. | sptrembl Q9Y827 | ND |
| 5036 | 508.0 | UBIQUITIN CARBOXYL-TERMINAL HYDROLASE ISOZYME L3 (EC 3.1.2.15) (UCH-L3) (UBIQUITIN THIOLESTERASE L3). | swissprot P15374 | ND |
| 5037 | 506.3 | HYPOTHETICAL 31.8 KD PROTEIN. | tremblnew CAB52731 | ND |
| 5038 | 506.3 | _S. lipmanii_ epimerase. | geneseqp R14187 | ND |
| 5039 | 506.3 | HYPOTHETICAL 34.0 KD PROTEIN IN CTF13-YPK2 INTERGENIC REGION. | swissprot Q03161 | Carbohydrate transport and metabolism |
| 5040 | 506.2 | Cytosolic glycerol-3-phosphate dehydrogenase encoded by GPD2. | geneseqp Y26167 | Energy production and conversion |
| 5041 | 506.0 | RIBOSOMAL PROTEIN L31. | sptrembl Q9XGL4 | Translation, ribosomal structure and biogenesis |
| 5042 | 505.9 | HIGH-AFFINITY GLUCOSE TRANSPORTER. | swissprot O74713 | ND |
| 5043 | 505.4 | COATOMER ZETA SUBUNIT. | sptrembl O74891 | ND |
| 5044 | 505.3 | CARBOXYPEPTIDASE S1 (EC 3.4.16.6). | swissprot P34946 | ND |
| 5045 | 504.9 | QUINATE PERMEASE (QUINATE TRANSPORTER). | swissprot P15325 | ND |
| 5046 | 504.0 | CYTOCHROME P450 51 (EC 1.14.14.1) (CYPL1) (P450-L1A1) (STEROL 14-ALPHA DEMETHYLASE) (EBURICOL 14-ALPHA-DEMETHYLASE) (P450-14DM). | swissprot Q12664 | ND |
| 5047 | 502.3 | Ester hydrolase protein encoded by rec 511 gene. | geneseqp R44609 | ND |
| 5048 | 501.8 | _C. magnoliae_ carbonyl reductase. | geneseqp W64777 | ND |
| 5049 | 501.4 | HYPOTHETICAL 72.2 KD PROTEIN C12C2.05C IN CHROMOSOME II. | swissprot Q09746 | ND |
| 5050 | 501.0 | LOW-AFFINITY FE(II) TRANSPORT PROTEIN. | swissprot P40988 | ND |
| 5051 | 498.7 | CHROMOSOME XV READING FRAME ORF YOR197W. | sptrembl Q08601 | ND |

TABLE 3-continued

_Aspergillus oryzae ESTs_

| Sequence Listing | zscore | Annotation | Database | Functional Category |
|---|---|---|---|---|
| 5052 | 498.5 | HYPOTHETICAL 53.5 KD PROTEIN C1F5.07C IN CHROMOSOME I. | swissprot Q10062 | ND |
| 5053 | 497.6 | SIMILAR TO ACETYL-COENZYME A SYNTHETASE. NCBI GI: 1118129. | sptrembl Q21166 | ND |
| 5054 | 497.3 | SULFUR METABOLITE REPRESSION CONTROL PROTEIN. | swissprot Q00659 | ND |
| 5055 | 497.1 | PUTATIVE MAJOR FACILITATOR FAMILY MULTI-DRUG RESISTANCE PROTEIN. | sptrembl O94343 | ND |
| 5056 | 496.7 | HYPOTHETICAL 24.1 KD PROTEIN. | sptrembl O94389 | ND |
| 5057 | 496.7 | GLUTATHIONE SYNTHETASE LARGE CHAIN (EC 6.3.2.3) (GLUTATHIONE SYNTHASE LARGE CHAIN) (GSH SYNTHETASE LARGE CHAIN) (GSH-S) (PHYTOCHELATIN SYNTHETASE). | swissprot P35669 | ND |
| 5058 | 496.0 | CYTOCHROME C OXIDASE POLYPEPTIDE IV PRECURSOR (EC 1.9.3.1). | swissprot P04037 | ND |
| 5060 | 494.8 | ALPHA-AMYLASE (EC 3.2.1.1). | tremblnew AAF14264 | ND |
| 5061 | 494.6 | PUTATIVE TRANSPORT PROTEIN. | tremblnew CAB52881 | ND |
| 5062 | 494.5 | HYPOTHETICAL TRP-ASP REPEATS CONTAINING PROTEIN C29E6.01 IN CHROMOSOME I (FRAGMENT). | swissprot Q09855 | ND |
| 5063 | 494.4 | HYPOTHETICAL 46.5 KD PROTEIN. | sptrembl O07730 | ND |
| 5064 | 494.1 | UBIQUINOL-CYTOCHROME C REDUCTASE COMPLEX SUBUNIT. | sptrembl O74533 | ND |
| 5065 | 493.9 | PUTATIVE OXIDOREDUCTASE BLI-4 PRECURSOR (EC 1.-.-.-). | swissprot Q92247 | ND |
| 5066 | 493.1 | HYPOTHETICAL 44.2 KD PROTEIN IN RME1-TFC4 INTERGENIC REGION. | swissprot P53230 | ND |
| 5067 | 492.8 | NONHISTONE PROTEIN 6. | tremblnew AAF06350 | ND |
| 5068 | 492.0 | ALDEHYDE DEHYDROGENASE. | sptrembl Q55811 | Energy production and conversion |
| 5069 | 4911.3 | TYROSINASE (EC 1.14.18.1) (MONOPHENOL MONOOXYGENASE). | swissprot Q00234 | ND |
| 5070 | 491.9 | HYPOTHETICAL 50.3 KD PROTEIN IN TFA1-PAN3 INTERGENIC REGION. | swissprot P36101 | Coenzyme metabolism |
| 5071 | 491.7 | PROBABLE SERINE HYDROXYMETHYLTRANSFERASE, CYTOSOLIC (EC 2.1.2.1) (SERINE METHYLASE) (GLYCINE HYDROXYMETHYLTRANSFERASE) (SHMT). | swissprot Q10104 | Amino acid transport and metabolism |
| 5072 | 491.3 | URACIL PHOSPHORIBOSYLTRANSFERASE (EC 2.4.2.9) (UMP PYROPHOSPHORYLASE) (UPRTASE). | swissnew P18562 | Nucleotide transport |

TABLE 3-continued

_Aspergillus oryzae ESTs_

| Sequence Listing | zscore | Annotation | Database | Functional Category |
|---|---|---|---|---|
| 5073 | 491.0 | CONSERVED PHOSDUCIN-LIKE HYPOTHETICAL PROTEIN. | sptrembl Q9Y7L1 | ND |
| 5074 | 490.8 | HYPOTHETICAL 25.9 KD PROTEIN C6C3.07 IN CHROMOSOME I. | swissprot Q10311 | ND |
| 5075 | 490.6 | ATP SYNTHASE DELTA CHAIN FAMILY, OLIGOMYCIN SENSITIVITY CONFERRING PROTEIN. | sptrembl O74479 | Energy production and conversion |
| 5076 | 489.8 | 60S RIBOSOMAL PROTEIN L10, MITOCHONDRIAL PRECURSOR (YML10). | swissprot P36520 | Translation, ribosomal structure and biogenesis |
| 5077 | 488.8 | MSF TRANSPORTER. | tremblnew CAA20760 | ND |
| 5078 | 486.8 | 40S RIBOSOMAL PROTEIN S8. | swissprot O14049 | Translation, ribosomal structure and biogenesis |
| 5079 | 486.2 | 40S RIBOSOMAL PROTEIN S28 (S33). | swissprot Q10421 | Translation, ribosomal structure and biogenesis |
| 5080 | 485.2 | 49 KDA ZINC FINGER PROTEIN. | sptrembl Q9Z326 | ND |
| 5081 | 485.0 | MYOSIN I HEAVY CHAIN. | sptrembl Q00647 | ND |
| 5082 | 484.5 | PUTATIVE DEHYDROGENASE. | tremblnew CAB61800 | ND |
| 5083 | 484.4 | SIGNAL RECOGNITION PARTICLE 19 KD PROTEIN HOMOLOG. | swissprot P41922 | Cell motility and secretion |
| 5084 | 484.2 | SIMILAR TO BOVINE PERIPHERAL-TYPE BENZODIAZEPINE RECEPTOR. | sptrembl O94327 | ND |
| 5085 | 483.7 | GLUTATHIONE-DEPENDENT FORMALDEHYDE DEHYDROGENASE (EC 1.2.1.1) (FDH) (FALDH). | swissprot P47734 | ND |
| 5086 | 483.5 | KIAA1259 PROTEIN (FRAGMENT). | tremblnew BAA86573 | DNA replication, recombination and repair |
| 5087 | 482.1 | HYPOTHETICAL 42.5 KD PROTEIN. | sptrembl O74737 | ND |
| 5088 | 482.1 | PUTATIVE FAD SYNTHETASE. | sptrembl O74841 | ND |
| 5089 | 482.0 | MUTANT VEA1 PROTEIN. | tremblnew AAD44048 | ND |
| 5090 | 481.8 | P21 PROTEIN. | sptrembl Q11118 | ND |
| 5091 | 481.8 | 278AA LONG HYPOTHETICAL ERYTHROCYTE BAND 7 INTEGRAL MEMBRANE PROTEIN. | sptrembl Q9Y9Y6 | Posttranslational modification, protein turnover, chaperones |
| 5092 | 481.7 | DNA-DIRECTED RNA POLYMERASES I, II, AND III 8.3 KD POLYPEPTIDE (EC 2.7.7.6) (ABC10-BETA). | swissprot O13877 | Transcription |
| 5093 | 480.8 | HYPOTHETICAL 45.1 KD PROTEIN C6B12.08 IN CHROMOSOME I. | sptrembl O14213 | ND |
| 5094 | 480.3 | TRNA ISOPENTENYLTRANSFERASE (EC 2.5.1.8) (ISOPENTENYL-DIPHOSPHATE: TRNA ISOPENTENYLTRANSFERASE) (IPP TRANSFERASE) (IPPT). | swissprot P07884 | Translation, ribosomal structure and biogenesis |
| 5095 | 479.9 | HEXOSE TRANSPORTER. | sptrembl O13311 | ND |
| 5096 | 479.6 | HYPOTHETICAL 18.5 KD PROTEIN. | tremblnew CAB61465 | ND |

TABLE 3-continued

_Aspergillus oryzae ESTs_

| Sequence Listing | zscore | Annotation | Database | Functional Category |
|---|---|---|---|---|
| 5097 | 478.9 | SIMILAR TO POLYADENYLATE-BINDING PROTEIN. | sptrembl Q06106 | Transcription |
| 5098 | 478.7 | PUTATIVE CA-CALMODULIN-DEPENDENT SERINE-THREONINE-PROTEIN KINASE. | sptrembl O94547 | ND |
| 5099 | 477.9 | MICROSOMAL DIPEPTIDASE PRECURSOR (EC 3.4.13.19) (MDP) (DEHYDROPEPTIDASE-I) (RENAL DIPEPTIDASE) (RDP). | swissprot P31430 | ND |
| 5100 | 477.0 | URACIL PHOSPHORIBOSYLTRANSFERASE (EC 2.4.2.9) (UMP PYROPHOSPHORYLASE) (UPRTASE). | swissnew P93394 | ND |
| 5101 | 476.1 | 10 KD HEAT SHOCK PROTEIN, MITOCHONDRIAL (HSP10) (10 KD CHAPERONIN). | swissprot O59804 | Posttranslational modification, protein turnover, chaperones |
| 5102 | 475.4 | SUR1 PROTEIN. | swissprot P33300 | ND |
| 5103 | 474.9 | CHROMOSOME IV READING FRAME ORF YDL128W. | sptrembl Q99385 | Inorganic ion transport and metabolism |
| 5104 | 474.5 | NA,K-ATPASE ALPHA-2-SUBUNIT (FRAGMENT). | sptrembl Q9Z1G6 | ND |
| 5105 | 473.9 | 40S RIBOSOMAL PROTEIN S8. | swissprot O14049 | Translation, ribosomal structure and biogenesis |
| 5106 | 473.1 | PUTATIVE NADH-DEPENDENT FLAVIN OXIDOREDUCTASE. | sptrembl O94467 | Energy production and conversion |
| 5107 | 473.1 | 60S RIBOSOMAL PROTEIN L14-A. | swissprot P36105 | Translation, ribosomal structure and biogenesis |
| 5108 | 472.4 | ACTIN-BINDING PROTEIN 134 aa, chain A | pdb 1QPV | ND |
| 5109 | 472.3 | CHOLINE TRANSPORT PROTEIN. | swissprot P19807 | Amino acid transport and metabolism |
| 5110 | 470.8 | HYPOTHETICAL 137.8 KD PROTEIN C2F12.05C IN CHROMOSOME II. | sptrembl O14340 | ND |
| 5111 | 470.8 | HYPOTHETICAL 98.4 KD PROTEIN C24H6.13 IN CHROMOSOME I. | swissprot Q09766 | ND |
| 5112 | 470.4 | CYTOCHROME P450. | sptrembl O13490 | ND |
| 5113 | 470.3 | IGE-BINDING PROTEIN (FRAGMENT). | sptrembl O60025 | ND |
| 5114 | 470.3 | L-SERINE DEHYDRATASE (EC 4.2.1.13) (L-SERINE DEAMINASE). | swissprot P17324 | Amino acid transport and metabolism |
| 5115 | 470.2 | PUTATIVE SNRNP SPLICING FACTOR. | sptrembl O74499 | ND |
| 5116 | 469.8 | NADH-UBIQUINONE OXIDOREDUCTASE 9.5 KD SUBUNIT (EC 1.6.5.3) (EC 1.6.99.3) (COMPLEX I-9.5 KD) (CI-9.5) (UBIQUINONE-BINDING PROTEIN). | swissprot P42117 | ND |
| 5117 | 469.2 | HYPOTHETICAL 37.2 KD PROTEIN YOR007C. | sptrembl Q12118 | ND |
| 5118 | 468.6 | HT-1080 PROTEIN. | sptrembl O75794 | ND |
| 5119 | 468.5 | 3-PHYTASE B PRECURSOR (EC 3.1.3.8) (MYO-INOSITOL-HEXAPHOSPHATE 3-PHOSPHOHYDROLASE B) (3 PHYTASE B) (MYO-INOSITOL | swissprot P34754 | ND |

TABLE 3-continued

_Aspergillus oryzae ESTs_

| Sequence Listing | zscore | Annotation | Database | Functional Category |
|---|---|---|---|---|
| 5120 | 467.2 | HEXAKISPHOSPHATE PHOSPHOHYDROLASE B). GLYCINE-RICH RNA-BINDING PROTEIN (FRAGMENT). | sptrembl Q39105 | ND |
| 5121 | 466.7 | HYPOTHETICAL 24.5 KD PROTEIN IN PTA-FOLX INTERGENIC REGION. | swissprot P77526 | Posttranslational modification, protein turnover, chaperones |
| 5122 | 466.2 | TRANSFERASE 196 aa | pdb 1UKZ | Nucleotide transport |
| 5123 | 465.8 | HYPOTHETICAL 48.7 KD PROTEIN. | sptrembl O74498 | ND |
| 5124 | 465.4 | U6 SNRNA-ASSOCIATED SM-LIKE PROTEIN LSM6. | tremblnew AAD56230 | ND |
| 5125 | 465.4 | PUTATIVE DEHYDROGENASE. | sptrembl O88068 | ND |
| 5126 | 464.8 | 3-OXOACYL-[ACYL-CARRIER-PROTEIN]-SYNTHASE. | sptrembl O94297 | Lipid metabolism |
| 5127 | 464.4 | PROFILIN. | swissprot P39825 | ND |
| 5128 | 463.7 | HYPOTHETICAL 43.0 KD PROTEIN C8A4.09C IN CHROMOSOME I. | swissprot Q09885 | ND |
| 5129 | 462.9 | PUTATIVE G-PROTEIN. | sptrembl O08582 | ND |
| 5130 | 462.4 | PUTATIVE SECRETED LIPASE. | tremblnew CAB50950 | ND |
| 5131 | 462.4 | FLAVONOID 3',5'-HYDROXYLASE (EC 1.14.-.-) (F3'5'H) (CYTOCHROME P450 75A4). | swissprot Q96581 | ND |
| 5132 | 462.3 | B SUBUNIT OF PROPIONYL-COA CARBOXYLASE. | sptrembl P94970 | Lipid metabolism |
| 5133 | 462.1 | SUCCINATE-SEMIALDEHYDE DEHYDROGENASE [NADP+] (EC 1.2.1.16) (SSDH). | swissprot P25526 | Energy production and conversion |
| 5134 | 461.6 | EXO-POLYGALACTURONASE. | tremblnew AAF05088 | ND |
| 5135 | 461.3 | QUINATE PERMEASE (QUINATE TRANSPORTER). | swissprot P15325 | ND |
| 5136 | 461.0 | MITOCHONDRIAL RNA SPLICING PROTEIN MSR4. | swissprot P23500 | ND |
| 5137 | 460.8 | 60S RIBOSOMAL PROTEIN L28. | tremblnew CAA22600 | ND |
| 5138 | 460.5 | CONSERVED HYPOTHETICAL PROTEIN. | sptrembl Q9WZQ7 | ND |
| 5139 | 460.4 | CHITIN SYNTHASE 3 (EC 2.4.1.16) (CHITIN-UDP ACETYL-GLUCOSAMINYL TRANSFERASE 3) (CLASS-III CHITIN SYNTHASE 3). | swissprot P30602 | ND |
| 5140 | 459.0 | CHROMOSOME XV READING FRAME ORF YOL092W. | sptrembl Q12010 | ND |
| 5141 | 458.9 | CONSERVED HYPOTHETICAL PROTEIN. | tremblnew CAB52741 | ND |
| 5142 | 458.8 | CALCINEURIN B SUBUNIT (PROTEIN PHOSPHATASE 2B REGULATORY SUBUNIT) (CALCINEURIN REGULATORY SUBUNIT). | swissprot P87072 | ND |
| 5143 | 458.6 | _A. niger_ pyruvate kinase. | geneseqp R13247 | ND |
| 5144 | 458.2 | CHROMOSOME XV READING FRAME ORF YOL119C. | sptrembl Q08268 | ND |
| 5145 | 456.7 | DNA LIGASE I (EC 6.5.1.1) (POLYDEOXYRIBONUCLEO TIDE SYNTHASE [ATP]). | swissprot P37913 | ND |

TABLE 3-continued

*Aspergillus oryzae* ESTs

| Sequence Listing | zscore | Annotation | Database | Functional Category |
|---|---|---|---|---|
| 5146 | 456.1 | TROPOMYOSIN 2. | swissprot P40414 | ND |
| 5147 | 455.8 | 60S RIBOSOMAL PROTEIN L34-B. | swissprot P40525 | Translation, ribosomal structure and biogenesis |
| 5148 | 455.6 | INTEGRAL MEMBRANE PROTEIN. | sptrembl Q9Y784 | ND |
| 5149 | 454.5 | HYPOTHETICAL 22.0 KD PROTEIN IN FOX3-UBP7 INTERGENIC REGION. | swissprot P40452 | ND |
| 5150 | 454.3 | HYPOTHETICAL 86.9 KD PROTEIN (FRAGMENT). | tremblnew CAB55332 | ND |
| 5151 | 454.3 | CHROMOSOME XV READING FRAME ORF YOR049C. | sptrembl Q08417 | ND |
| 5152 | 454.0 | HYPOTHETICAL 41.6 KD PROTEIN. | sptrembl O94305 | ND |
| 5153 | 453.3 | HYPOTHETICAL 27.9 KD PROTEIN C20F10.10 IN CHROMOSOME II. | sptrembl O42979 | ND |
| 5154 | 453.0 | PUTATIVE MEMBRANE TRANSPORT PROTEIN. | sptrembl O74923 | ND |
| 5155 | 452.5 | PIM1 GTPASE PROTEIN. | tremblnew CAB60670 | ND |
| 5156 | 452.2 | SIMILAR TO *S. CEREVISIAE* YHR110P. | sptrembl Q05359 | ND |
| 5157 | 451.4 | Human actVA-ORF4-like protein sequence. | geneseqp Y14147 | ND |
| 5158 | 451.1 | CSK2B. | tremblnew AAF03911 | ND |
| 5159 | 450.8 | 26S PROTEASE REGULATORY SUBUNIT 4 HOMOLOG. | tremblnew CAB58406 | ND |
| 5160 | 450.5 | HYPOTHETICAL 83.7 KD PROTEIN. | sptrembl O13853 | ND |
| 5161 | 450.3 | *Mortierella alpina* cytochrome b5. | geneseqp W22848 | ND |
| 5162 | 450.1 | NUCLEAR DISTRIBUTION PROTEIN NUDE. | sptrembl O74689 | ND |
| 5163 | 449.9 | 60S RIBOSOMAL PROTEIN L2, MITOCHONDRIAL PRECURSOR (YML2) (YMR6). | swissprot P12687 | Translation, ribosomal structure and biogenesis |
| 5164 | 448.7 | HYPOTHETICAL 157.7 KD PROTEIN C2F7.16C IN CHROMOSOME I. | swissprot Q09706 | ND |
| 5165 | 448.1 | NODULIN PRECURSOR. | sptrembl Q41402 | ND |
| 5166 | 447.5 | HYPOTHETICAL 15.3 KD PROTEIN. | tremblnew CAB57336 | Posttranslational modification, protein turnover, chaperones |
| 5167 | 447.1 | PROBABLE ATP-DEPENDENT PERMEASE YHL035C. | swissprot P38735 | ND |
| 5168 | 446.6 | TRANSCRIPTIONAL REPRESSOR TUP1. | sptrembl O76734 | ND |
| 5169 | 446.3 | PUTATIVE TRANSPORTER. | tremblnew CAB63540 | ND |
| 5170 | 445.6 | CUTINASE TRANSCRIPTION FACTOR 1 ALPHA. | swissprot P52958 | ND |
| 5171 | 444.9 | PUTATIVE DEHYDROGENASE. | sptrembl O88068 | ND |
| 5172 | 444.5 | NADH-DEPENDENT FLAVIN OXIDOREDUCTASE, PUTATIVE. | tremblnew AAF11740 | ND |
| 5173 | 444.4 | DIMETHYL-ALLYL-TRYPTPHAN-SYNTHASE. | sptrembl O94204 | ND |
| 5174 | 444.3 | PUTATIVE TRANSPORTER YBL042C. | swissprot P38196 | Coenzyme metabolism |
| 5175 | 444.3 | HYPOTHETICAL 45.0 KD PROTEIN IN PIS1-CLB2 INTERGENIC REGION. | swissprot Q06489 | ND |

TABLE 3-continued

_Aspergillus oryzae_ ESTs

| Sequence Listing | zscore | Annotation | Database | Functional Category |
|---|---|---|---|---|
| 5176 | 442.9 | RASP F 7 (FRAGMENT). | sptrembl O42799 | ND |
| 5177 | 441.8 | HYPOTHETICAL 18.5 KD PROTEIN. | tremblnew CAB11189 | ND |
| 5178 | 441.8 | PUTATIVE CELL WALL PROTEIN. | sptrembl O74708 | ND |
| 5179 | 441.2 | HYPOTHETICAL 55.5 KD PROTEIN C17A2.05 IN CHROMOSOME I. | sptrembl O13755 | Energy production and conversion |
| 5180 | 440.6 | GABA PERMEASE. | sptrembl Q9Y860 | ND |
| 5181 | 440.2 | ALCOHOL DEHYDROGENASE I (EC 1.1.1.1). | swissprot P00330 | ND |
| 5182 | 440.2 | NADH-UBIQUINONE OXIDOREDUCTASE 29.9 KD SUBUNIT PRECURSOR (EC 1.6.5.3) (EC 1.6.99.3) (COMPLEX I-29.9 KD) (CI-29.9 KD). | swissprot P24919 | ND |
| 5183 | 440.2 | HYPOTHETICAL 15.9 KD PROTEIN. | tremblnew CAB52421 | ND |
| 5184 | 440.0 | PUTATIVE SMALL NUCLEAR RIBONUCLEOPROTEIN E. | tremblnew CAB59808 | Transcription |
| 5185 | 439.2 | T7123.15 PROTEIN. | sptrembl O81909 | ND |
| 5186 | 438.8 | NADH:UBIQUINONE OXIDOREDUCTASE (NADH DEHYDROGENASE), 14 KDA (FRAGMENT). | sptrembl Q01407 | ND |
| 5187 | 438.3 | H04M03.4 PROTEIN. | tremblnew AAD12787 | Coenzyme metabolism |
| 5188 | 4363.7 | PYRUVATE DECARBOXYLASE. | sptrembl O94185 | Coenzyme metabolism |
| 5189 | 436.4 | QUEUINE TRNA-RIBOSYLTRANSFERASE (EC 2.4.2.29) (TRNA-GUANINE TRANSGLYCOSYLASE) (GUANINE INSERTION ENZYME). | swissprot P54578 | ND |
| 5190 | 436.2 | DICARBOXYLIC AMINO ACID PERMEASE. | swissprot P53388 | Amino acid transport and metabolism |
| 5191 | 435.9 | PEROXISOMAL TARGETING SIGNAL RECEPTOR (PEROXISOMAL PROTEIN PAY32) (PEROXIN-5) (PTS1 RECEPTOR). | swissprot Q99144 | ND |
| 5192 | 435.7 | NUCLEAR AND CYTOPLASMIC POLYADENYLATED RNA-BINDING PROTEIN PUB1 (ARS CONSENSUS BINDING PROTEIN ACBP-60) (POLY(U)-BINDING PROTEIN) (POLY URIDYLATE-BINDING PROTEIN). | swissprot P32588 | Transcription |
| 5193 | 435.5 | 60S RIBOSOMAL PROTEIN L36-A (L39A) (YL39). | swissprot P05745 | ND |
| 5194 | 434.2 | URACIL PERMEASE. | swissprot Q10279 | ND |
| 5195 | 433.3 | PHOSPHORUS ACQUISITION CONTROLLING PROTEIN. | swissprot P20824 | ND |
| 5196 | 433.0 | HYPOTHETICAL 34.2 KD PROTEIN C31F10.07 IN CHROMOSOME II. | sptrembl P87308 | ND |
| 5197 | 431.3 | NIPSNAP1 PROTEIN (FRAGMENT). | tremblnew CAB56701 | ND |
| 5198 | 431.0 | HYPOTHETICAL 23.0 KD PROTEIN C3F10.12C IN CHROMOSOME I. | swissprot Q10186 | ND |
| 5199 | 430.2 | CARNITINE/ACYL CARNITINE CARRIER. | sptrembl Q9Y7G4 | ND |

TABLE 3-continued

Aspergillus oryzae ESTs

| Sequence Listing | zscore | Annotation | Database | Functional Category |
|---|---|---|---|---|
| 5200 | 429.9 | RNA-BINDING PROTEIN AXRNBP. | sptrembl O93465 | ND |
| 5201 | 429.2 | CONSERVED HYPOTHETICAL PROTEIN. | sptrembl O94380 | ND |
| 5202 | 428.5 | PUTATIVE 60S RIBOSOMAL PROTEIN L7/L12. | tremblnew CAB60683 | Translation, ribosomal structure and biogenesis |
| 5203 | 428.1 | PUTATIVE SNRNP PROTEIN. | tremblnew CAB45810 | ND |
| 5204 | 426.3 | ATP SYNTHASE F CHAIN, MITOCHONDRIAL PRECURSOR (EC 3.6.1.34). | swissprot Q06405 | ND |
| 5205 | 426.1 | Human adult testis secreted protein ck181_7. | geneseqp W81998 | ND |
| 5206 | 425.3 | ORIGIN RECOGNITION COMPLEX SUBUNIT 4-RELATED PROTEIN ORP4P. | sptrembl Q9Y794 | ND |
| 5207 | 424.9 | HYDROPHOBIN PRECURSOR. | sptrembl O13503 | ND |
| 5208 | 424.5 | MLO3 PROTEIN. | swissnew Q09330 | ND |
| 5209 | 424.2 | MITOCHONDRIAL IMPORT RECEPTOR SUBUNIT TOM22 (MITOCHONDRIAL 22 KD OUTER MEMBRANE PROTEIN) (MOM22 PROTEIN) (TRANSLOCASE OF OUTER MEMBRANE 22 KD SUBUNIT). | swissprot Q07335 | ND |
| 5210 | 424.1 | Aminopeptidase. | geneseqp W05589 | ND |
| 5212 | 423.4 | Ubiquitin-like domain of the yeast protein SMT3. | geneseqp W87987 | ND |
| 5213 | 422.4 | PUTATIVE LIPASE. | sptrembl Q9Z360 | ND |
| 5214 | 421.9 | ALP11 PROTEIN. | swissprot Q10235 | ND |
| 5215 | 421.7 | HYPOTHETICAL 17.1 KD PROTEIN IN SAH1-MEI4 INTERGENIC REGION. | swissprot P40030 | ND |
| 5216 | 421.1 | ACTIN-LIKE PROTEIN. | tremblnew CAB65803 | ND |
| 5217 | 420.9 | DEOXYRIBOSE-PHOSPHATE ALDOLASE (EC 4.1.2.4) (PHOSPHODEOXYRIBOALDOLASE) (DEOXYRIBOALDOLASE). | swissprot P44430 | Nucleotide transport |
| 5218 | 420.3 | PUTATIVE FRUCTOSE-1,6-BISPHOSPHATASE (EC 3.1.3.11). | tremblnew CAB64834 | Carbohydrate transport and metabolism |
| 5219 | 420.3 | DNA REPAIR HELICASE RAD3. | swissprot P06839 | DNA replication, recombination and repair |
| 5220 | 420.2 | ARYLSULFATASE (EC 3.1.6.1) (ARYL-SULFATE SULPHOHYDROLASE). | swissprot P51691 | ND |
| 5221 | 420.0 | PHOSPHORIBOSYLFORMYL GLYCINAMIDINE SYNTHASE (EC 6.3.5.3) (FGAM SYNTHASE) (FORMYLGLYCINAMIDE RIBOTIDE AMIDOTRANSFERASE) (FGARAT). | swissprot P38972 | Nucleotide transport |
| 5222 | 419.6 | ATP-DEPENDENT BILE ACID PERMEASE. | swissprot P32386 | ND |
| 5223 | 419.6 | HYPOTHETICAL 61.1 KD PROTEIN C11D3.05 IN CHROMOSOME I. | swissprot Q10084 | ND |
| 5224 | 419.5 | GABA PERMEASE. | sptrembl Q9Y860 | ND |
| 5225 | 417.7 | Human transmembrane protein, HP01737. | geneseqp Y13942 | ND |
| 5226 | 417.6 | MEMBRANE ASSOCIATED PROTEIN SLP-2. | tremblnew AAF09142 | ND |

TABLE 3-continued

_Aspergillus oryzae ESTs_

| Sequence Listing | zscore | Annotation | Database | Functional Category |
|---|---|---|---|---|
| 5227 | 416.9 | SUPL15H. | tremblnew BAA78781 | ND |
| 5228 | 416.7 | PISATIN DEMETHYLASE (EC 1.14.-.-) (CYTOCHROME P450 57A2). | swissprot P38364 | ND |
| 5229 | 416.5 | PUTATIVE PROTEIN FARNESYLTRANSFERASE BETA SUBUNIT (EC 2.5.1.-) (CAAX FARNESYLTRANSFERASE BETA SUBUNIT) (RAS PROTEINS PRENYLTRANSFERASE) (FTASE-BETA). | sptrembl O13782 | ND |
| 5230 | 416.0 | HYPOTHETICAL 15.4 KD PROTEIN C10F6.16 IN CHROMOSOME I. | sptrembl P79058 | ND |
| 5231 | 413.9 | PROBABLE 40S RIBOSOMAL PROTEIN S9, MITOCHONDRIAL PRECURSOR. | swissprot P38120 | Translation, ribosomal structure and biogenesis |
| 5232 | 413.7 | CHROMOSOME IV READING FRAME ORF YDL237W. | sptrembl Q07716 | ND |
| 5233 | 412.4 | PUTATIVE AROMATIC AMINO ACID AMINOTRANSFERASE C56E4.03 (EC 2.6.1.-). | sptrembl O14192 | Amino acid transport and metabolism |
| 5234 | 412.3 | HYPOTHETICAL 143.0 KD PROTEIN C11E3.02C IN CHROMOSOME I. | swissprot O13683 | ND |
| 5235 | 412.3 | PUTATIVE GLYCEROL-3-PHOSPHATE DEHYDROGENASE. | tremblnew AAF02807 | ND |
| 5236 | 411.8 | _P. putida_ R-(–)-mandelate monooxygenase protein. | geneseqp W53916 | ND |
| 5237 | 411.7 | PUTATIVE PHOSPHOADENOSINE PHOSPHOSULFATE REDUCTASE (EC 1.8.99.4) (PAPS REDUCTASE, THIOREDOXIN DEPENDENT) (PADOPS REDUCTASE) (3'-PHOSPHOADENYLYLSULFATE REDUCTASE). | swissprot Q10270 | Coenzyme metabolism |
| 5238 | 411.6 | RP42. | tremblnew AAF04863 | ND |
| 5239 | 411.4 | CYTOCHROME C OXIDASE ASSEMBLY PROTEIN COX15. | swissprot P40086 | Posttranslational modification, protein turnover, chaperones |
| 5240 | 409.9 | N AMINO ACID TRANSPORT SYSTEM PROTEIN (METHYLTRYPTOPHAN RESISTANCE PROTEIN). | swissprot P38680 | ND |
| 5241 | 409.8 | INTEGRAL MEMBRANE PROTEIN. | sptrembl Q9Y786 | ND |
| 5242 | 409.7 | CAT5 PROTEIN (UBIQUINONE BIOSYNTHESIS PROTEIN COQ7). | swissprot P41735 | ND |
| 5243 | 409.4 | PUTATIVE D-AMINO ACID OXIDASE. | sptrembl Q9Y7N4 | ND |
| 5244 | 409.0 | HIGH MOBILITY GROUP-LIKE NUCLEAR PROTEIN 2. | swissprot P32495 | Translation, ribosomal structure and biogenesis |
| 5245 | 408.2 | PYRROLINE-5-CARBOXYLATE REDUCTASE (EC 1.5.1.2) (P5CR) (P5C REDUCTASE). | swissprot P22008 | ND |

TABLE 3-continued

Aspergillus oryzae ESTs

| Sequence Listing | zscore | Annotation | Database | Functional Category |
|---|---|---|---|---|
| 5246 | 408.2 | PXP-18. | tremblnew BAA85152 | ND |
| 5247 | 407.9 | TRNA ISOPENTENYLTRANSFERASE. | tremblnew CAB52278 | ND |
| 5248 | 407.6 | HYPOTHETICAL 56.2 KD PROTEIN IN ERG8-UBP8 INTERGENIC REGION. | swissprot Q04991 | ND |
| 5249 | 406.1 | T1G11.14 PROTEIN. | sptrembl O23024 | ND |
| 5250 | 405.9 | PHOSPHOETHANOLAMINE CYTIDYLYLTRANSFERASE. | sptrembl Q99447 | ND |
| 5251 | 405.0 | C-1-TETRAHYDROFOLATE SYNTHASE, CYTOPLASMIC (C1-THF SYNTHASE) [INCLUDES: METHYLENETETRAHYDROFOLATE DEHYDROGENASE (EC 1.5.1.5); METHENYLTETRAHYDROFOLATE CYCLOHYDROLASE (EC 3.5.4.9); FORMYLTETRAHYDROFOLATE SYNTHETASE (EC 6.3.4.3)]. | swissprot P07245 | Coenzyme metabolism |
| 5252 | 405.0 | PYRROLINE-5-CARBOXYLATE REDUCTASE (EC 1.5.1.2) (P5CR) (P5C REDUCTASE). | swissprot Q12740 | ND |
| 5253 | 404.6 | HYPOTHETICAL 52.3 KD PROTEIN IN MRPL10-ERG24 INTERGENIC REGION PRECURSOR. | swissprot P53832 | ND |
| 5254 | 404.4 | SUGAR TRANSPORTER STL1. | swissprot P39932 | ND |
| 5255 | 404.1 | PUTATIVE RHO GDP-DISSOCIATION INHIBITOR (RHO GDI). | sptrembl O14224 | ND |
| 5256 | 403.0 | PUTATIVE TRANSPORTER. | tremblnew CAB63540 | ND |
| 5257 | 402.7 | DNA-DIRECTED RNA POLYMERASE I 135 KD POLYPEPTIDE (EC 2.7.7.6) (A135) (RNA POLYMERASE I SUBUNIT 2). | swissprot P22138 | Transcription |
| 5258 | 402.1 | RIBOSOMAL PROTEIN S30. | sptrembl O14314 | ND |
| 5259 | 400.7 | HYPOTHETICAL 56.8 KD PROTEIN IN SCJ1-GUA1 INTERGENIC REGION PRECURSOR. | swissprot Q03655 | ND |
| 5260 | 400.0 | SRC HOMOLOGY 3 DOMAIN-CONTAINING PROTEIN HIP-55. | tremblnew AAF13701 | ND |
| 5261 | 397.2 | TRANSMEMBRANE TRANSPORTER LIZ1P. | sptrembl O43000 | ND |
| 5262 | 397.1 | ORNITHINE AMINOTRANSFERASE (EC 2.6.1.13) (ORNITHINE--OXO-ACID AMINOTRANSFERASE). | swissprot Q92413 | ND |
| 5263 | 395.9 | UNC-50 RELATED PROTEIN. | sptrembl O55227 | ND |
| 5264 | 395.8 | UBIQUITIN FUSION DEGRADATION PROTEIN 1 (UB FUSION PROTEIN 1) (POLYMERASE-INTERACTING PROTEIN 3). | swissprot P53044 | ND |
| 5265 | 395.3 | KINESIN-LIKE DNA BINDING PROTEIN. | sptrembl Q14807 | ND |
| 5266 | 395.0 | L-A VIRUS GAG PROTEIN N-ACETYLTRANSFERASE (EC 2.3.1.-). | swissprot Q03503 | ND |
| 5267 | 394.4 | DICARBOXYLIC AMINO ACID PERMEASE. | swissprot P53388 | ND |
| 5268 | 393.9 | KREV-1 PROTEIN. | sptrembl O74112 | ND |

TABLE 3-continued

_Aspergillus oryzae ESTs_

| Sequence Listing | zscore | Annotation | Database | Functional Category |
|---|---|---|---|---|
| 5269 | 393.9 | Wheat glutathione transferase subunit TaGST1. | geneseqp Y05537 | ND |
| 5270 | 393.2 | HYPOTHETICAL 26.6 KD PROTEIN. | sptrembl P75897 | ND |
| 5271 | 393.0 | HYPOTHETICAL 85.7 KD PROTEIN C20G8.02 IN CHROMOSOME I. | sptrembl P87109 | ND |
| 5272 | 392.9 | ALCOHOL OXIDASE (EC 1.1.3.13) (AOX) (METHANOL OXIDASE) (MOX). | swissprot Q00922 | ND |
| 5273 | 392.8 | HYPOTHETICAL 105.9 KD PROTEIN C11E3.11C IN CHROMOSOME I. | sptrembl O13690 | ND |
| 5274 | 391.6 | HYPOTHETICAL 13.0 KS PROTEIN. | sptrembl P79082 | ND |
| 5275 | 391.5 | MANNITOL 2-DEHYDROGENASE (EC 1.1.1.67) (MDH). | sptrembl O08355 | ND |
| 5276 | 391.4 | THIOREDOXIN. | swissprot P29429 | ND |
| 5277 | 391.4 | HYPOTHETICAL 59.0 KD PROTEIN C30D11.14 IN CHROMOSOME I. | swissprot Q09911 | ND |
| 5278 | 390.7 | YEAST REDUCED VIABILITY UPON STARVATION PROTEIN RVS167 HOMOLOG, SH3 DOMAIN CONTAINING. | sptrembl O74352 | ND |
| 5279 | 390.3 | CHOLINE DEHYDROGENASE. | sptrembl Q9X2M2 | ND |
| 5280 | 390.2 | HYPOTHETICAL 39.5 KD PROTEIN IN PDXH-SLYB INTERGENIC REGION. | swissprot P77570 | ND |
| 5281 | 390.2 | R06A4.4B PROTEIN. | sptrembl O62333 | ND |
| 5282 | 389.8 | SIMILAR TO PHOSPHATIDIC ACID PHOSPHATASE. | tremblnew CAB52620 | ND |
| 5283 | 389.7 | HYPOTHETICAL 65.9 KD PROTEIN C31A2.12 IN CHROMOSOME I. | swissprot Q09729 | ND |
| 5284 | 389.6 | CYTOCHROME C OXIDASE POLYPEPTIDE VI PRECURSOR (EC 1.9.3.1). | swissprot P00427 | ND |
| 5285 | 389.3 | PUTATIVE AMINE TRANSPORTER. | sptrembl O74852 | ND |
| 5286 | 389.3 | GTP CYCLOHYDROLASE I (EC 3.5.4.16) (GTP-CH-I). | swissprot P51601 | Coenzyme metabolism |
| 5287 | 388.7 | HYPOTHETICAL 132.6 KD PROTEIN YPL006W. | sptrembl Q12200 | ND |
| 5288 | 388.6 | CHROMOSOME XVI COSMID 9513. | sptrembl Q06839 | ND |
| 5289 | 388.3 | ATP10 PROTEIN. | swissprot P18496 | ND |
| 5290 | 387.8 | CONSERVED HYPOTHETICAL PROTEIN. | sptrembl O94257 | ND |
| 5291 | 387.8 | HYDROXYPROLINE-RICH GLYCOPROTEIN DZ-HRGP PRECURSOR. | tremblnew CAB62280 | ND |
| 5292 | 387.5 | HYPOTHETICAL 44.7 KD PROTEIN. | sptrembl O13885 | ND |
| 5293 | 387.5 | CHOLINE TRANSPORT PROTEIN. | swissprot P19807 | Amino acid transport and metabolism |
| 5294 | 386.7 | RASP F 7 (FRAGMENT). | sptrembl O42799 | ND |
| 5295 | 386.3 | CURVED DNA-BINDING PROTEIN (42 KD PROTEIN). | swissprot Q09184 | ND |
| 5296 | 385.8 | THIOREDOXIN. | swissprot P42115 | ND |
| 5297 | 385.6 | MUCIN 2 PRECURSOR (INTESTINAL MUCIN 2). | swissprot Q02817 | ND |
| 5298 | 385.6 | CYTOCHROME P450-CC24, MITOCHONDRIAL PRECURSOR (EC 1.14.-.-) (P450-CC24) (VITAMIN D(3) 24-HYDROXYLASE) (1,25-DIHYDROXYVITAMIN D(3) | swissprot Q64441 | ND |

TABLE 3-continued

_Aspergillus oryzae ESTs_

| Sequence Listing | zscore | Annotation | Database | Functional Category |
|---|---|---|---|---|
| | | 24-HYDROXYLASE) (24-OHASE). | | |
| 5299 | 385.2 | ORF YPL152W. | sptrembl Q12461 | ND |
| 5300 | 384.6 | CAMP-DEPENDENT PROTEIN KINASE SCH9 (EC 2.7.1.37). | swissprot P11792 | Signal transduction mechanisms |
| 5301 | 384.6 | F7F22.17. | tremblnew AAF24531 | ND |
| 5302 | 384.3 | SUGAR TRANSPORTER, PUTATIVE. | tremblnew AAF12486 | ND |
| 5303 | 384.0 | PROTEIN KINASE SKP1P. | sptrembl O94456 | ND |
| 5304 | 383.6 | HYPOTHETICAL 15.0 KD PROTEIN C23C4.09C IN CHROMOSOME I. | swissnew O13929 | ND |
| 5305 | 382.9 | AMINOMETHYLTRANSFERASE PRECURSOR (EC 2.1.2.10) (GLYCINE CLEAVAGE SYSTEM T PROTEIN). | swissprot P48015 | Amino acid transport and metabolism |
| 5306 | 382.3 | COLLETOTRICHUM GLOEOSPORIOIDES NITROGEN STARVATION-INDUCED GLUTAMINE RICH PROTEIN. | sptrembl O43117 | ND |
| 5307 | 382.2 | PUTATIVE IMPORTIN BETA-4 SUBUNIT (KARYOPHERIN BETA-4 SUBUNIT). | swissprot O60100 | ND |
| 5308 | 381.6 | TRNA LIGASE (EC 6.5.1.3). | swissprot P09880 | ND |
| 5309 | 381.1 | PEROXISOMAL MEMBRANE PROTEIN PAS20 (PEROXIN-13). | swissprot P80667 | ND |
| 5310 | 380.9 | HYPOTHETICAL 39.0 KD PROTEIN. | tremblnew CAA22566 | ND |
| 5312 | 380.4 | CHROMOSOME XV READING FRAME ORF YOL060C. | sptrembl Q12296 | ND |
| 5313 | 380.2 | HYPOTHETICAL 65.5 KD PROTEIN. | sptrembl O74441 | ND |
| 5314 | 379.6 | FADE13. | sptrembl O86319 | Lipid metabolism |
| 5315 | 379.5 | HYPOTHETICAL 74.5 KD PROTEIN C4H3.03C IN CHROMOSOME I. | swissprot Q10211 | ND |
| 5316 | 379.1 | PROBABLE STERIGMATOCYSTIN BIOSYNTHESIS P450 MONOOXYGENASE STCB (EC 1.14.-.-) (CYTOCHROME P450 62). | swissprot Q12608 | ND |
| 5317 | 379.1 | DJ69E11.3 (YEAST YPR037W AND WORM C02C2.6 PREDICTED PROTEINS LIKE). | sptrembl O75663 | ND |
| 5318 | 379.0 | MRNA, PARTIAL CDS, SIMILAR TO HUMAN GA17 PROTEIN (FRAGMENT). | tremblnew BAA31742 | ND |
| 5319 | 378.9 | COATOMER COMPLEX COPI DELTA-COP SUBUNIT (FRAGMENT). | tremblnew AAF14250 | ND |
| 5320 | 378.7 | PYRROLINE-5-CARBOXYLATE REDUCTASE (EC 1.5.1.2) (P5CR) (P5C REDUCTASE). | swissprot P22008 | ND |
| 5321 | 378.1 | HYPOTHETICAL 58.0 KD PROTEIN C1672.03C IN CHROMOSOME III. | swissnew O14057 | ND |
| 5322 | 377.9 | ADENYLOSUCCINATE LYASE (EC 4.3.2.2) (ADENYLOSUCCINASE) (ASL). | swissprot Q05911 | ND |
| 5323 | 377.9 | SYG1 PROTEIN. | swissprot P40528 | ND |
| 5324 | 377.7 | HYPOTHETICAL 31.3 KD PROTEIN. | sptrembl P72926 | ND |

TABLE 3-continued

_Aspergillus oryzae ESTs_

| Sequence Listing | zscore | Annotation | Database | Functional Category |
|---|---|---|---|---|
| 5325 | 377.5 | PEPTIDE TRANSPORTER PTR2 (PEPTIDE PERMEASE PTR2). | swissprot P32901 | ND |
| 5326 | 377.5 | 6-HYDROXY-D-NICOTINE OXIDASE (EC 1.5.3.6) (6-HDNO). | swissprot P08159 | ND |
| 5327 | 375.6 | KIAA0770 PROTEIN (FRAGMENT). | sptrembl O94869 | ND |
| 5328 | 375.5 | CHROMOSOME XII COSMID 8039. | sptrembl Q05924 | ND |
| 5329 | 374.9 | PUTATIVE TRANSCRIPTIONAL REGULATION PROTEIN, TRP-ASP REPEAT CONTAINING. | sptrembl O74863 | ND |
| 5330 | 374.2 | HYPOTHETICAL 10.4 KD PROTEIN. | sptrembl O43002 | ND |
| 5331 | 373.6 | F16M14.11 PROTEIN. | sptrembl O80443 | ND |
| 5332 | 373.2 | Human actVA-ORF4-like protein sequence. | geneseqp Y14147 | ND |
| 5333 | 372.8 | HYPOTHETICAL 83.8 KD PROTEIN. | tremblnew CAB66097 | ND |
| 5334 | 372.5 | HYPOTHETICAL 50.5 KD PROTEIN IN RNA1-RNT1 INTERGENIC REGION. | swissprot Q05031 | ND |
| 5335 | 371.7 | POTASSIUM TRANSPORTER. | sptrembl Q9Y7B9 | ND |
| 5336 | 371.6 | HYPOTHETICAL 63.9 KD PROTEIN C22A12.08C IN CHROMOSOME I. | sptrembl O13899 | ND |
| 5337 | 370.8 | RD PROTEIN. | swissnew P18615 | ND |
| 5338 | 370.6 | PUTATIVE CHORISMATE MUTASE/PREPHENATE DEHYDRATASE PHEA. | tremblnew AAF06690 | ND |
| 5339 | 370.2 | MULTIDRUG RESISTANCE PROTEIN HOMOLOG 50 (P-GLYCOPROTEIN 50). | swissprot Q00449 | ND |
| 5340 | 369.5 | CHOLINE TRANSPORT PROTEIN. | swissprot P19807 | Amino acid transport and metabolism |
| 5341 | 369.0 | _Humicola lanuginosa_ lipase type II variant. | geneseqp R22635 | ND |
| 5342 | 368.8 | RIBOSOMAL PROTEIN S31 HOMOLOG. | sptrembl O74172 | ND |
| 5343 | 368.1 | PUTATIVE ATP-DEPENDENT DNA HELICASE. | sptrembl O94395 | ND |
| 5344 | 367.8 | 30 KD HEAT SHOCK PROTEIN. | swissprot P40920 | ND |
| 5345 | 367.8 | PUTATIVE SYNTAXIN. | tremblnew CAB58411 | ND |
| 5346 | 367.7 | 60S RIBOSOMAL PROTEIN L32 PRECURSOR. | sptrembl O94379 | ND |
| 5347 | 367.7 | DNA POLYMERASE ALPHA SUBUNIT B (P86 SUBUNIT). | swissprot P38121 | ND |
| 5348 | 367.5 | HYPOTHETICAL 61.3 KD PROTEIN IN PMP2-VAC8 INTERGENIC REGION. | swissprot P39998 | ND |
| 5349 | 367.5 | CAMP-REGULATED GUANINE NUCLEOTIDE EXCHANGE FACTOR I. | sptrembl O95634 | ND |
| 5350 | 367.1 | CHROMOSOME XV READING FRAME ORF YOL119C. | sptrembl Q08268 | ND |
| 5351 | 365.9 | HYPOTHETICAL 36.8 KD PROTEIN C26A3.16 IN CHROMOSOME I. | swissprot Q10169 | ND |
| 5352 | 365.1 | C01B4.6 PROTEIN. | tremblnew AAD14698 | ND |
| 5353 | 364.7 | PROBABLE CYTOCHROME C OXIDASE POLYPEPTIDE VIA PRECURSOR (EC 1.9.3.1). | swissprot O74471 | ND |

TABLE 3-continued

_Aspergillus oryzae ESTs_

| Sequence Listing | zscore | Annotation | Database | Functional Category |
|---|---|---|---|---|
| 5354 | 3632.3 | ALPHA-AMYLASE A PRECURSOR (EC 3.2.1.1) (TAKA-AMYLASE A) (TAA) (1,4-ALPHA-D-GLUCAN GLUCANOHYDROLASE). | swissprot P10529 | ND |
| 5355 | 363.7 | _Mus musculus_ Tub Interactor (mTI-3) protein. | geneseqp W59132 | Posttranslational modification, protein turnover, chaperones |
| 5356 | 363.6 | PROBABLE SUCCINYL-COA LIGASE [GDP-FORMING] ALPHA-CHAIN, MITOCHONDRIAL PRECURSOR (EC 6.2.1.4) (SUCCINYL-COA SYNTHETASE, ALPHA CHAIN) (SCS-ALPHA). | swissprot O13750 | ND |
| 5357 | 363.5 | HYPOTHETICAL 55.5 KD PROTEIN C17A2.05 IN CHROMOSOME I. | sptrembl O13755 | ND |
| 5358 | 362.4 | INTEGRAL MEMBRANE PROTEIN. | sptrembl Q9Y786 | ND |
| 5359 | 361.9 | PHO85P,LPH16P. | sptrembl Q02979 | ND |
| 5360 | 361.6 | PUTATIVE MITOCHONDRIAL CARRIER C29A3.11C. | sptrembl O59674 | ND |
| 5361 | 361.6 | RHO3 PROTEIN. | swissprot Q00245 | ND |
| 5362 | 361.2 | FRNE PROTEIN. | tremblnew AAF10238 | ND |
| 5363 | 361.0 | NICOTINATE-NUCLEOTIDE PYROPHOSPHORYLASE [CARBOXYLATING] (EC 2.4.2.19) (QUINOLINATE PHOSPHORIBOSYLTRANSFERASE [DECARBOXYLATING]) (QAPRTASE). | swissprot Q15274 | ND |
| 5364 | 360.9 | U1 SMALL NUCLEAR RIBONUCLEOPROTEIN C (U1-C). | swissprot P09234 | ND |
| 5365 | 360.6 | HYPOTHETICAL 108.5 KD PROTEIN IN UME3-HDA1 INTERGENIC REGION. | swissprot P53971 | ND |
| 5366 | 360.0 | ELONGATION FACTOR 1-GAMMA TYPE 2 (EF-1-GAMMA) (P47). | swissprot Q91375 | ND |
| 5367 | 359.9 | HYPOTHETICAL 130.3 KD PROTEIN. | sptrembl O59742 | ND |
| 5368 | 358.2 | HYPOTHETICAL 24.7 KD PROTEIN C3A12.04C IN CHROMOSOME I. | swissprot P87120 | ND |
| 5369 | 358.0 | PUTATIVE TRANSFERASE. | sptrembl O53185 | ND |
| 5370 | 357.4 | 60S RIBOSOMAL PROTEIN L38. | tremblnew CAB54810 | ND |
| 5371 | 357.1 | Aluminium resistance gene ALR2. | geneseqp W07873 | ND |
| 5372 | 356.5 | ARYL-ALCOHOL OXIDASE PRECURSOR (EC 1.1.3.7). | sptrembl O94219 | ND |
| 5373 | 3551.3 | _Aspergillus oryzae_ protease PepC. | geneseqp W31629 | Posttranslational modification, protein turnover, chaperones |
| 5374 | 355.9 | HYPOTHETICAL 35.9 KD PROTEIN C17G6.02C IN CHROMOSOME I. | sptrembl O13780 | ND |
| 5375 | 354.1 | HYPOTHETICAL 26.3 KD PROTEIN C3G6.03C IN CHROMOSOME I. | sptrembl O14141 | ND |
| 5376 | 353.8 | PAD-1. | sptrembl Q9Y7A8 | ND |
| 5377 | 353.7 | GRA-ORF6 PROTEIN. | tremblnew CAA09651 | ND |
| 5378 | 353.2 | PUTATIVE STERIGMATOCYSTIN | swissprot Q00727 | ND |

TABLE 3-continued

Aspergillus oryzae ESTs

| Sequence Listing | zscore | Annotation | Database | Functional Category |
|---|---|---|---|---|
| | | BIOSYNTHESIS DEHYDROGENASE STCV (EC 1.1.1.-). | | |
| 5379 | 353.0 | HYPOTHETICAL 22.6 KD PROTEIN C3G9.04 IN CHROMOSOME I. | sptrembl O42868 | ND |
| 5380 | 352.9 | D-ARABINONO-1,4-LACTONE OXIDASE (EC 1.1.3.24). | sptrembl O93852 | ND |
| 5381 | 352.8 | HEAT SHOCK PROTEIN 70. | sptrembl O42808 | ND |
| 5382 | 352.0 | PUTATIVE 40S RIBOSOMAL PROTEIN YNR037C. | swissprot P53733 | ND |
| 5383 | 351.2 | TRANSLIN. | swissprot P79769 | ND |
| 5384 | 351.0 | GPI-ANCHOR TRANSAMIDASE (EC 3.-.-.-). | swissprot P49018 | ND |
| 5385 | 350.9 | PUTATIVE ACETYLTRANSFERASE IN HXT11-HXT8 INTERGENIC REGION (EC 2.3.1.-). | swissprot P40892 | ND |
| 5386 | 350.6 | THIOESTERASE II. | sptrembl O15261 | ND |
| 5387 | 350.4 | COLLETOTRICHUM GLOEOSPORIOIDES NITROGEN STARVATION-INDUCED GLUTAMINE RICH PROTEIN. | sptrembl O43117 | ND |
| 5388 | 349.9 | NADH-UBIQUINONE OXIDOREDUCTASE 17.8 KD SUBUNIT PRECURSOR (EC 1.6.5.3) (EC 1.6.99.3) (COMPLEX I-17.8 KD) (CI-17.8 KD). | swissprot P42116 | ND |
| 5389 | 349.7 | HYDROXYPROLINE-RICH GLYCOPROTEIN DZ-HRGP PRECURSOR. | tremblnew CAB62280 | ND |
| 5390 | 348.7 | WD-40 REPEAT PROTEIN. | tremblnew BAA75544 | ND |
| 5391 | 348.6 | CYTOCHROME P450 10 (EC 1.14.-.-) (CYPX). | swissprot P48416 | ND |
| 5392 | 347.2 | HYPOTHETICAL 16.7 KD PROTEIN IN CDC5-MVP1 INTERGENIC REGION. | swissprot Q03667 | ND |
| 5393 | 347.2 | POTASSIUM TRANSPORT PROTEIN, HIGH-AFFINITY. | swissprot P28569 | ND |
| 5394 | 347.2 | SIGNAL RECOGNITION PARTICLE 72 KD PROTEIN HOMOLOG (SRP72). | swissprot P38688 | ND |
| 5395 | 347.0 | HYPOTHETICAL 49.2 KD PROTEIN. | sptrembl O69515 | ND |
| 5396 | 346.4 | FISSION YEAST. | sptrembl P78794 | ND |
| 5397 | 346.3 | HYPOTHETICAL 37.0 KD PROTEIN (FRAGMENT). | sptrembl Q9Y3V5 | ND |
| 5398 | 346.1 | HYPOTHETICAL 33.9 KD PROTEIN CY13D12.11. | sptrembl P72043 | ND |
| 5399 | 345.1 | CHROMOSOME XV READING FRAME ORF YOR052C. | sptrembl Q08422 | ND |
| 5400 | 344.0 | POTENTIAL MEMBRANE PROTEIN. | sptrembl O94006 | ND |
| 5401 | 343.9 | NPGAP. | sptrembl Q9Y7C5 | ND |
| 5402 | 343.8 | HYPOTHETICAL 26.5 KD PROTEIN. | tremblnew AAF18285 | ND |
| 5403 | 343.4 | GABA PERMEASE. | sptrembl Q9Y860 | ND |
| 5404 | 342.8 | SIMILAR TO SDH4P. | sptrembl Q06236 | ND |
| 5405 | 342.7 | MUCIN 2 PRECURSOR (INTESTINAL MUCIN 2). | swissprot Q02817 | ND |
| 5406 | 342.6 | SCD1 PROTEIN. | swissprot P40995 | ND |
| 5407 | 342.5 | HYDROXYPROLINE-RICH GLYCOPROTEIN DZ-HRGP PRECURSOR. | tremblnew CAB62280 | ND |
| 5408 | 341.9 | SRP1 PROTEIN. | swissprot Q10193 | ND |
| 5409 | 341.7 | RNA BINDING PROTEIN (FRAGMENT). | sptrembl O60176 | ND |

TABLE 3-continued

*Aspergillus oryzae* ESTs

| Sequence Listing | zscore | Annotation | Database | Functional Category |
|---|---|---|---|---|
| 5410 | 340.9 | P. membranaefaciens NADH kinase. | geneseqp W22341 | ND |
| 5411 | 340.5 | SSU81 PROTEIN (SHO1 OSMOSENSOR). | swissprot P40073 | ND |
| 5412 | 340.0 | HYPOTHETICAL 76.7 KD PROTEIN. | sptrembl Q12753 | ND |
| 5413 | 338.2 | PUTATIVE PROTEIN TRANSPORT PROTEIN SEC61 GAMMA SUBUNIT. | swissprot Q09827 | ND |
| 5414 | 337.9 | ORF YDL161W. | sptrembl Q12518 | ND |
| 5415 | 336.8 | MITOCHONDRIAL IMPORT INNER MEMBRANE TRANSLOCASE SUBUNIT TIM17 (MITOCHONDRIAL PROTEIN IMPORT PROTEIN 2) (MITOCHONDRIAL INNER MEMBRANE PROTEIN MIM17). | swissprot P39515 | ND |
| 5416 | 335.8 | HYPOTHETICAL 130.3 KD PROTEIN. | sptrembl O59742 | ND |
| 5417 | 335.7 | CYTOCHROME P450 ALKANE HYDROXYLASE. | sptrembl Q9Y758 | ND |
| 5418 | 335.1 | HYPOTHETICAL 34.3 KD PROTEIN. | tremblnew CAB40775 | ND |
| 5419 | 334.9 | PUTATIVE POLYA-BINDING PROTEIN. | sptrembl O94430 | ND |
| 5420 | 334.6 | SERINE/THREONINE-PROTEIN KINASE SSP1 (EC 2.7.1.-). | swissprot P50526 | ND |
| 5421 | 334.4 | NUCLEAR POLYADENYLATED RNA-BINDING PROTEIN NAB2. | swissprot P32505 | ND |
| 5422 | 334.2 | P68 RNA HELICASE. | sptrembl Q9XTP2 | ND |
| 5423 | 334.1 | PUTATIVE EXOCYST COMPLEX COMPONENT. | sptrembl O74846 | ND |
| 5424 | 332.2 | CHROMOSOME XV READING FRAME ORF YOR359W. | sptrembl Q08831 | ND |
| 5425 | 331.9 | PUTATIVE TRANSCRIPTION FACTOR TFIIIB COMPONENT. | sptrembl O94481 | ND |
| 5426 | 331.7 | REGULATORY PROTEIN. | sptrembl Q00170 | ND |
| 5427 | 331.0 | W02A2.5 PROTEIN. | sptrembl Q9XUB4 | ND |
| 5428 | 329.9 | HYPOTHETICAL 46.6 KD PROTEIN. | sptrembl O74477 | ND |
| 5429 | 329.3 | CHOLINE TRANSPORT PROTEIN. | swissprot P19807 | ND |
| 5430 | 329.3 | GLUCOSAMINE-6-PHOSPHATE DEAMINASE. | tremblnew AAD42233 | ND |
| 5431 | 329.1 | Y38C9A.2 PROTEIN. | tremblnew AAD14761 | ND |
| 5432 | 329.1 | CONSERVED HYPOTHETICAL PROTEIN. | tremblnew AAF12184 | ND |
| 5433 | 329.1 | PUTATIVE D-AMINO ACID OXIDASE. | sptrembl Q9Y7N4 | ND |
| 5434 | 329.0 | HYPOTHETICAL 24.4 KD PROTEIN. | sptrembl O86620 | ND |
| 5435 | 328.7 | AMINO-ACID PERMEASE. | tremblnew CAB60020 | ND |
| 5436 | 328.2 | GIBBERELLIN 20-OXIDASE-ARABIDOPSIS THALIANA (EC 1.14.11.). | tremblnew CAB45519 | ND |
| 5437 | 325.2 | OXONONANOATE SYNTHASE. | sptrembl Q9Z6L6 | ND |
| 5438 | 324.8 | 60S RIBOSOMAL PROTEIN. | sptrembl O74884 | ND |
| 5439 | 323.8 | CERCOSPORIN RESISTANCE PROTEIN. | sptrembl Q9Y788 | ND |
| 5440 | 323.5 | PUTATIVE TRP-ASP REPEAT PROTEIN. | tremblnew CAB52280 | ND |
| 5441 | 323.1 | ALLANTOINASE (EC 3.5.2.5). | swissprot P32375 | ND |
| 5442 | 323.0 | QUINATE PERMEASE (QUINATE TRANSPORTER). | swissprot P15325 | ND |

TABLE 3-continued

_Aspergillus oryzae ESTs_

| Sequence Listing | zscore | Annotation | Database | Functional Category |
|---|---|---|---|---|
| 5443 | 321.9 | SHY1 PROTEIN. | swissprot P53266 | ND |
| 5444 | 321.5 | F15K9.5 PROTEIN. | sptrembl Q9ZVT6 | ND |
| 5445 | 320.7 | DNA-DIRECTED RNA POLYMERASE II 19 KD POLYPEPTIDE (EC 2.7.7.6) (B16). | swissprot P34087 | ND |
| 5446 | 319.6 | N-CARBAMYL-L-AMINO ACID AMIDOHYDROLASE (EC 3.5.1.-). | swissprot Q53389 | ND |
| 5447 | 318.9 | SIMILAR TO YEAST SUR1 PROTEIN. | tremblnew CAB55770 | ND |
| 5448 | 318.4 | CHROMOSOME XV READING FRAME ORF YOR267C. | sptrembl Q08732 | ND |
| 5449 | 317.1 | PUTATIVE MAJOR FACILITATOR FAMILY MULTI-DRUG RESISTANCE PROTEIN. | sptrembl O94343 | ND |
| 5450 | 316.7 | F23C8.6 PROTEIN. | tremblnew AAD03134 | ND |
| 5451 | 316.6 | SURFEIT LOCUS PROTEIN 4 HOMOLOG. | swissprot O74559 | ND |
| 5452 | 316.6 | PUTATIVE TRANSLATION INITIATION FACTOR EIF-2B BETA SUBUNIT. | tremblnew CAB52277 | ND |
| 5453 | 315.7 | HYPOTHETICAL 42.6 KD PROTEIN. | tremblnew CAB52800 | ND |
| 5454 | 315.6 | VIP1 PROTEIN (P53 ANTIGEN HOMOLOG). | sptrembl P87216 | ND |
| 5455 | 314.2 | HYPOTHETICAL 35.7 KD PROTEIN (FRAGMENT). | sptrembl Q9Y3V1 | ND |
| 5456 | 314.2 | HIGH AFFINITY COPPER TRANSPORTER. | tremblnew CAB52305 | ND |
| 5457 | 314.1 | Collagen-like polymer. | geneseqp W57645 | ND |
| 5458 | 314.1 | HYPOTHETICAL 16.4 KD PROTEIN. | sptrembl Q9Z4W2 | ND |
| 5459 | 3135.5 | ELONGATION FACTOR 3 (FRAGMENT). | sptrembl O42734 | ND |
| 5460 | 313.2 | PROTEIN TYROSINE KINASE 9 (A6 PROTEIN TYROSINE KINASE HOMOLOG). | sptrembl O09132 | ND |
| 5461 | 311.9 | CELL WALL PROTEIN. | sptrembl Q40336 | ND |
| 5462 | 311.1 | DUAL SPECIFICITY PROTEIN PHOSPHATASE 1 (EC 3.1.3.48) (EC 3.1.3.16) (MAP KINASE PHOSPHATASE-1) (MPK-1) (MAP KINASE PHOSPHATASE-1) (FRAGMENT). | sptrembl O42253 | ND |
| 5464 | 311.0 | WDR1 PROTEIN. | tremblnew AAD05045 | ND |
| 5465 | 310.9 | RIBONUCLEASE H1. | sptrembl O00870 | ND |
| 5466 | 310.8 | FRUCTOSYL AMINE. | sptrembl O43029 | ND |
| 5467 | 310.2 | PROBABLE ATP-DEPENDENT RNA HELICASE P47 HOMOLOG. | swissprot Q07478 | ND |
| 5468 | 309.5 | T25B24.3 PROTEIN. | tremblnew AAD25548 | ND |
| 5469 | 309.2 | NON-CLASSICAL EXPORT PROTEIN NCE2. | swissprot Q12207 | ND |
| 5470 | 308.2 | HYPOTHETICAL 40.5 KD PROTEIN IN UBP15-GAS1 INTERGENIC REGION PRECURSOR. | swissprot Q04951 | ND |
| 5471 | 306.7 | DOPA DECARBOXYLASE ISOFORM 2 (EC 4.1.1.26). | sptrembl O61718 | ND |
| 5472 | 306.6 | SUPPRESSOR PROTEIN MPT4 (STM1 PROTEIN) (GU4 NUCLEIC-BINDING | swissprot P39015 | ND |

TABLE 3-continued

_Aspergillus oryzae ESTs_

| Sequence Listing | zscore | Annotation | Database | Functional Category |
|---|---|---|---|---|
| | | PROTEIN 2) (G4P2 PROTEIN). | | |
| 5473 | 306.5 | TRANSACTIVATING PROTEIN BRIDGE. | sptrembl Q9WTV5 | ND |
| 5474 | 306.4 | Candida albicans KRE9. | geneseqp Y24918 | ND |
| 5475 | 306.3 | GLYCEROL-3-PHOSPHATE DEHYDROGENASE (NAD(P)+). | sptrembl O94310 | ND |
| 5476 | 306.0 | HYPOTHETICAL 76.7 KD PROTEIN IN SPO1-SIS1 INTERGENIC REGION. | swissprot P53983 | ND |
| 5477 | 304.5 | PUTATIVE ACYL-COA DEHYDROGENASE. | tremblnew CAB46788 | ND |
| 5478 | 304.4 | HYPOTHETICAL 63.2 KD PROTEIN. | sptrembl O59725 | ND |
| 5479 | 304.4 | HYPOTHETICAL 26.5 KD PROTEIN. | tremblnew CAB46672 | ND |
| 5480 | 304.2 | Aluminium resistance gene ALR2. | geneseqp W07873 | ND |
| 5481 | 304.0 | HYPOTHETICAL 39.0 KD PROTEIN IN GLNQ-ANSR INTERGENIC REGION. | swissprot P54564 | ND |
| 5482 | 303.9 | MYOSIN-2 ISOFORM. | swissprot P19524 | ND |
| 5483 | 303.8 | GRPE PROTEIN HOMOLOG PRECURSOR. | swissnew O43047 | ND |
| 5484 | 303.7 | ENOYL REDUCTASE. | sptrembl Q9Y7D0 | ND |
| 5485 | 303.5 | FISSION YEAST (FRAGMENT). | sptrembl P78815 | ND |
| 5486 | 303.2 | HEMOLYSIN. | sptrembl Q00050 | ND |
| 5487 | 303.1 | POB1P PROTEIN. | sptrembl O74653 | ND |
| 5488 | 303.1 | HYPOTHETICAL 89.0 KD PROTEIN. | sptrembl O43023 | ND |
| 5489 | 302.5 | PUTATIVE ADAPTOR PROTEIN. | tremblnew CAB59686 | ND |
| 5490 | 302.4 | HYPOTHETICAL 31.5 KD PROTEIN. | sptrembl O14443 | ND |
| 5491 | 302.3 | HYPOTHETICAL 19.4 KD PROTEIN IN TSM1-ARE1 INTERGENIC REGION. | swissprot P25626 | ND |
| 5492 | 301.5 | HYPOTHETICAL C2H2 ZINC FINGER PROTEIN. | sptrembl Q9Y815 | ND |
| 5493 | 301.5 | HYPOTHETICAL 16.1 KD PROTEIN. | sptrembl O74847 | ND |
| 5494 | 300.6 | HYDROXYMETHYLGLUTA RYL-COA SYNTHASE (EC 4.1.3.5) (HMG-COA SYNTHASE) (3-HYDROXY-3-METHYLGLUTARYL COENZYME A SYNTHASE). | swissprot P54874 | ND |
| 5495 | 300.3 | EXTENSIN PRECURSOR (CELL WALL HYDROXYPROLINE-RICH GLYCOPROTEIN). | swissprot P13983 | ND |
| 5496 | 2991.7 | BETA-GLUCOSIDASE 1 PRECURSOR (EC 3.2.1.21) (GENTIOBIASE) (CELLOBIASE) (BETA-D-GLUCOSIDE GLUCOHYDROLASE). | swissprot P48825 | ND |
| 5497 | 299.9 | TRANSMEMBRANE PROTEIN. | tremblnew CAB65007 | ND |
| 5498 | 299.8 | HYPOTHETICAL 26.9 KD PROTEIN IN BTN1-PEP8 INTERGENIC REGION. | swissprot P47044 | ND |
| 5499 | 299.7 | NONF. | sptrembl Q9XDF2 | ND |
| 5500 | 299.7 | PDGF ASSOCIATED PROTEIN. | tremblnew AAF03506 | ND |
| 5501 | 299.7 | HYPOTHETICAL 63.9 KD PROTEIN IN IME2-MEF2 INTERGENIC REGION. | swissprot P42948 | ND |

TABLE 3-continued

Aspergillus oryzae ESTs

| Sequence Listing | zscore | Annotation | Database | Functional Category |
|---|---|---|---|---|
| 5502 | 299.0 | PUTATIVE TRANSCRIPTIONAL REGULATOR. | tremblnew CAB54824 | ND |
| 5503 | 299.0 | PUTATIVE TRANSFERASE (FRAGMENT). | sptrembl Q9X843 | ND |
| 5504 | 298.7 | HYPOTHETICAL 33.9 KD PROTEIN C4C5.03 IN CHROMOSOME I. | swissprot O14166 | ND |
| 5505 | 298.6 | HYPOTHETICAL 157.7 KD PROTEIN C2F7.16C IN CHROMOSOME I. | swissprot Q09706 | ND |
| 5506 | 298.6 | PUTATIVE DEHYDROGENASE. | sptrembl O53547 | ND |
| 5507 | 298.2 | HYPOTHETICAL 48.1 KD PROTEIN IN SEC12-SSK2 INTERGENIC REGION. | swissprot P53729 | ND |
| 5508 | 298.0 | HYPOTHETICAL 90.8 KD PROTEIN IN HUL5-SEC27 INTERGENIC REGION. | swissprot P53121 | ND |
| 5509 | 297.8 | SIS1 PROTEIN. | sptrembl O13303 | ND |
| 5510 | 297.6 | HYPOTHETICAL UBIQUINOL-CYTOCHROME C REDUCTASE COMPONENT. | sptrembl O42932 | ND |
| 5511 | 297.4 | CAFFEINE-INDUCED DEATH PROTEIN 1. | sptrembl O13833 | ND |
| 5512 | 297.1 | CHROMOSOME XV READING FRAME ORF YOL137W. | sptrembl Q08280 | ND |
| 5513 | 296.7 | HYPOTHETICAL 69.9 KD PROTEIN IN MIC1-SRB5 INTERGENIC REGION. | swissprot P53261 | ND |
| 5514 | 296.5 | 4MES. | sptrembl O13320 | ND |
| 5515 | 296.4 | RNA BINDING PROTEIN - PUTATIVE PRE MRNA SPLICING FACTOR. | sptrembl O74919 | ND |
| 5516 | 296.4 | CHROMOSOME XV READING FRAME ORF YOR059C. | sptrembl Q08448 | ND |
| 5517 | 2959.7 | Aspergillus oryzae protease PepE. | geneseqp W31628 | ND |
| 5518 | 2951.7 | ALDEHYDE DEHYDROGENASE (EC 1.2.1.3) (ALDDH). | swissprot P08157 | Energy production and conversion |
| 5519 | 2951.0 | TRANSLATION ELONGATION FACTOR 1 ALPHA. | sptrembl Q9Y713 | Amino acid transport and metabolism |
| 5520 | 295.8 | NUCLEASE. | sptrembl O60168 | ND |
| 5521 | 295.1 | PROTEIN-S ISOPRENYLCYSTEINE O-METHYLTRANSFERASE (EC 2.1.1.100) (ISOPRENYLCYSTEINE CARBOXYLMETHYLTRANSFERASE). | swissprot P32584 | ND |
| 5522 | 2944.2 | HEAT SHOCK PROTEIN HSP1 (65 KD IGE-BINDING PROTEIN) (FRAGMENT). | swissprot P40292 | Posttranslational modification, protein turnover, chaperones |
| 5523 | 294.9 | SCP160 PROTEIN (PROTEIN HX). | swissprot P06105 | ND |
| 5524 | 294.9 | PUTATIVE METHYLTRANSFERASE. | sptrembl O94628 | ND |
| 5525 | 294.8 | Saccharomyces cerevisiae nucleolin like protein, NOL1. | geneseqp W10529 | ND |
| 5526 | 294.7 | HYDROXYPROLINE-RICH GLYCOPROTEIN DZ-HRGP PRECURSOR. | tremblnew CAB62280 | ND |
| 5527 | 294.6 | ISOCITRATE DEHYDROGENASE [NADP], MITOCHONDRIAL PRECURSOR (EC 1.1.1.42) (OXALOSUCCINATE DECARBOXYLASE) (IDH) | swissprot P79089 | ND |

TABLE 3-continued

*Aspergillus oryzae* ESTs

| Sequence Listing | zscore | Annotation | Database | Functional Category |
|---|---|---|---|---|
| | | (NADP+-SPECIFIC ICDH) (IDP). | | |
| 5528 | 294.4 | | sptrembl O23042 | ND |
| 5529 | 294.4 | HYDROXYPROLINE-RICH GLYCOPROTEIN PRECURSOR. | sptrembl Q41719 | ND |
| 5530 | 294.4 | HYPOTHETICAL 24.7 KD PROTEIN C5H10.03 IN CHROMOSOME I. | swissprot Q09676 | ND |
| 5531 | 294.3 | VESICULAR TRANSPORT PROTEIN BOS1. | swissprot P25385 | ND |
| 5532 | 293.5 | HYPOTHETICAL 44.5 KD PROTEIN. | sptrembl O74728 | ND |
| 5533 | 2928.1 | PLASMA MEMBRANE H(+)ATPASE. | sptrembl O93862 | Inorganic ion transport and metabolism |
| 5534 | 292.9 | FATTY ACYL-COA REDUCTASE. | sptrembl P94129 | ND |
| 5535 | 291.8 | HYPOTHETICAL 36.4 KD PROTEIN IN SMP1-MBA1 INTERGENIC REGION. | swissprot P38298 | ND |
| 5536 | 290.9 | 2-OXOGLUTARATE DEHYDROGENASE E1 COMPONENT. | sptrembl O74378 | ND |
| 5537 | 290.7 | NORSOLORINIC ACID REDUCTASE (EC 1.1.1.-). | swissprot Q00049 | ND |
| 5538 | 290.0 | Amino acid sequence of *M. vaccae* antigen GV-33. | geneseqp Y14924 | ND |
| 5539 | 2895.1 | 26S PROTEASE REGULATORY SUBUNIT 6B HOMOLOG. | swissprot P78578 | Posttranslational modification, protein turnover, chaperones |
| 5540 | 289.1 | HYPOTHETICAL 34.8 KD PROTEIN C4H3.04C IN CHROMOSOME I. | swissprot Q10212 | ND |
| 5541 | 2881.2 | *Aspergillus nidulans* palmitate-CoA delta-9 desaturase enzyme. | geneseqp Y28844 | Lipid metabolism |
| 5542 | 288.5 | TIP120. | sptrembl P97536 | ND |
| 5543 | 288.1 | CUT8 PROTEIN. | swissprot P38937 | ND |
| 5544 | 287.8 | HYPOTHETICAL 109.7 KD PROTEIN. | sptrembl Q9Y7Q7 | ND |
| 5545 | 287.7 | Metal-regulated transporter polypeptide ZRT2. | geneseqp W41169 | ND |
| 5546 | 287.6 | HYPOTHETICAL 115.3 KD PROTEIN. | tremblnew CAB63746 | ND |
| 5547 | 287.5 | FLAVIN 651 aa, chain B | pdb 1FOH | ND |
| 5548 | 286.9 | HYPOTHETICAL 63.7 KD PROTEIN C16E9.02C IN CHROMOSOME II. | sptrembl O14319 | ND |
| 5549 | 286.9 | HYDROXYQUINOL 1,2-DIOXYGENASE. | sptrembl Q9ZAM3 | ND |
| 5550 | 286.7 | PHENAZINE BIOSYNTHESIS PROTEIN PHZF. | swissprot Q51792 | ND |
| 5551 | 286.7 | ALCOHOL DEHYDROGENASE. | sptrembl O33308 | ND |
| 5552 | 286.5 | HYPOTHETICAL 25.4 KD PROTEIN C4G9.14 IN CHROMOSOME I. | swissprot Q10244 | ND |
| 5553 | 286.0 | *S. cerevisiae* uronate dehydrogenase. | geneseqp W29217 | ND |
| 5554 | 2857.0 | CYTOCHROME P450 51 (EC 1.14.14.1) (CYPL1) (P450-L1A1) (STEROL 14-ALPHA DEMETHYLASE) (EBURICOL 14-ALPHA-DEMETHYLASE) (P450-14 DM). | swissprot Q12664 | ND |
| 5555 | 285.7 | HIGH-AFFINITY GLUCOSE TRANSPORTER. | swissprot P49374 | ND |
| 5556 | 285.1 | HYPOTHETICAL 191.5 KD PROTEIN IN NSP1-KAR2 INTERGENIC REGION. | swissprot P47054 | ND |

TABLE 3-continued

_Aspergillus oryzae ESTs_

| Sequence Listing | zscore | Annotation | Database | Functional Category |
|---|---|---|---|---|
| 5557 | 284.9 | C-FACTOR (C SIGNAL). | swissprot P21158 | ND |
| 5558 | 284.6 | MITOGEN-ACTIVATED PROTEIN KINASE. | tremblnew AAF12815 | ND |
| 5559 | 284.2 | HYPOTHETICAL 11.4 KD PROTEIN. | sptrembl O74837 | ND |
| 5560 | 283.4 | CIRCUMSPOROZOITE (CS) PROTEIN (FRAGMENT). | sptrembl Q25648 | ND |
| 5561 | 283.1 | HYDROXYPROLINE-RICH GLYCOPROTEIN DZ-HRGP PRECURSOR. | tremblnew CAB62280 | ND |
| 5562 | 2824.0 | HEXOKINASE (EC 2.7.1.1). | sptrembl O93964 | ND |
| 5563 | 282.6 | CHROMOSOME XVI READING FRAME ORF YPL263C. | sptrembl Q08979 | ND |
| 5564 | 282.4 | PTB-ASSOCIATED SPLICING FACTOR (PSF). | swissnew P23246 | ND |
| 5565 | 282.4 | ZINC-FINGER PROTEIN. | sptrembl O60106 | ND |
| 5566 | 282.2 | MAJOR FACILITATOR SUPERFAMILY PROTEIN. | sptrembl O74395 | ND |
| 5567 | 282.0 | HYPOTHETICAL 31.7 KD PROTEIN. | sptrembl O43125 | ND |
| 5568 | 281.6 | EXTENSIN PRECURSOR. | sptrembl Q40768 | ND |
| 5569 | 281.6 | PRPD PROTEIN. | swissprot P74840 | ND |
| 5570 | 281.4 | PROBABLE DOLICHYL-DIPHOSPHOOLIGOSACCHARIDE--PROTEIN GLYCOSYLTRANSFERASE EPSILON SUBUNIT (EC 2.4.1.119) (OLIGOSACCHARYL TRANSFERASE EPSILON SUBUNIT) (OLIGOSACCHARYL TRANSFERASE 16 KD SUBUNIT). | swissprot O14238 | ND |
| 5571 | 281.4 | GTP CYCLOHYDROLASE I (EC 3.5.4.16) (GTP-CH-I). | swissprot P51601 | ND |
| 5572 | 280.8 | HYPOTHETICAL 69.5 KD PROTEIN (FRAGMENT). | tremblnew CAB63721 | ND |
| 5573 | 280.8 | PUTATIVE HYDROLASE. | sptrembl Q9WX01 | ND |
| 5574 | 280.5 | HYPOTHETICAL 41.3 KD PROTEIN. | sptrembl O42896 | ND |
| 5575 | 280.4 | HYPOTHETICAL 91.7 KD PROTEIN. | tremblnew CAB62413 | ND |
| 5576 | 280.3 | POLY(A)-SPECIFIC RIBONUCLEASE. | sptrembl O95453 | ND |
| 5577 | 280.3 | HYPOTHETICAL 31.0 KD PROTEIN IN GAP1-NAP1 INTERGENIC REGION. | swissprot P36136 | ND |
| 5578 | 280.1 | LA PROTEIN HOMOLOG (LA RIBONUCLEOPROTEIN) (LA AUTOANTIGEN HOMOLOG). | swissprot P87058 | ND |
| 5579 | 280.1 | HYPOTHETICAL 105.9 KD PROTEIN IN AAC3-RFC5 INTERGENIC REGION. | sptrembl O13621 | ND |
| 5580 | 280.0 | INTEGRAL MEMBRANE PROTEIN. | sptrembl Q9Y786 | ND |
| 5581 | 279.8 | PROTEOPHOSPHOGLYCAN PRECURSOR (FRAGMENT). | sptrembl Q9Y076 | ND |
| 5582 | 278.7 | SWI6 PROTEIN, REPRESSION OF SILENT MATING TYPE LOCI. | tremblnew CAB57340 | ND |
| 5583 | 278.3 | CONSERVED HYPOTHETICAL PROTEIN. | sptrembl Q9WZQ7 | ND |
| 5584 | 278.1 | Amino acid sequence of a human secreted peptide. | geneseqp Y12916 | ND |
| 5585 | 277.7 | Mutant YLR087c protein from cold sensitive yeast strain. | geneseqp W36093 | ND |
| 5586 | 277.7 | S-ANTIGEN PROTEIN PRECURSOR. | swissprot P09593 | ND |
| 5587 | 277.5 | INTEGRAL MEMBRANE PROTEIN. | sptrembl Q9Y784 | ND |

TABLE 3-continued

Aspergillus oryzae ESTs

| Sequence Listing | zscore | Annotation | Database | Functional Category |
|---|---|---|---|---|
| 5588 | 277.2 | EXTENSIN-LIKE PROTEIN. | tremblnew AAD55980 | ND |
| 5589 | 277.0 | HYPOTHETICAL 90.1 KD PROTEIN C6G10.07 IN CHROMOSOME I. | sptrembl O14253 | ND |
| 5590 | 276.9 | HYPOTHETICAL 100.1 KD PROTEIN. | sptrembl O43024 | ND |
| 5591 | 276.9 | NODULATION PROTEIN G. | swissprot P17611 | ND |
| 5592 | 276.7 | CARBAMOYL-PHOSPHATE SYNTHASE. | sptrembl O94313 | ND |
| 5593 | 276.4 | LUSTRIN A. | sptrembl O44341 | ND |
| 5594 | 275.9 | F56H9.1 PROTEIN. | sptrembl Q20908 | ND |
| 5595 | 275.8 | HYPOTHETICAL 35.9 KD PROTEIN. | sptrembl O74947 | ND |
| 5596 | 275.7 | S-ADENOSYLMETHIONINE SYNTHETASE (EC 2.5.1.6) (METHIONINE ADENOSYLTRANSFERASE) (ADOMET SYNTHETASE). | swissprot P48466 | ND |
| 5597 | 275.3 | PROLINE-RICH PROTEIN MP-2 PRECURSOR. | swissprot P05142 | ND |
| 5598 | 275.2 | PUTATIVE CLEAVAGE AND POLYADENYLATION SPECIFICITY FACTOR. | sptrembl O13794 | ND |
| 5599 | 275.1 | BILE ACID-INDUCIBLE OPERON PROTEIN F (BAIF-3). | sptrembl O28954 | ND |
| 5600 | 274.8 | AUTOPHAGOCYTOSIS PROTEIN AUT1. | swissprot P40344 | ND |
| 5601 | 274.8 | DJ1042K10.5 (NOVEL PROTEIN) (FRAGMENT). | sptrembl O95516 | ND |
| 5602 | 274.8 | HALOACETATE DEHALOGENASE H-2 (EC 3.8.1.3). | swissnew Q01399 | ND |
| 5603 | 274.6 | HYPOTHETICAL 95.2 KD PROTEIN. | sptrembl O43051 | ND |
| 5604 | 274.6 | ACTIVATED PROTEIN KINASE C RECEPTOR HOMOLOG TRACK. | sptrembl O61075 | ND |
| 5605 | 274.4 | HYPOTHETICAL 30.9 KD PROTEIN K07C11.7 IN CHROMOSOME V. | swissprot Q21268 | ND |
| 5606 | 274.0 | 40S RIBOSOMAL PROTEIN S7. | swissprot O43105 | ND |
| 5607 | 2739.8 | GLUCOSAMINE--FRUCTOSE-6-PHOSPHATE AMINOTRANSFERASE [ISOMERIZING] (EC 2.6.1.16) (HEXOSEPHOSPHATE AMINOTRANSFERASE) (D-FRUCTOSE-6-PHOSPHATE AMIDOTRANSFERASE) (GFAT). | swissprot P53704 | Cell envelope biogenesis, outer membrane |
| 5608 | 273.7 | PUTATIVE NUCLEOPORIN, NUCLEAR PORE PROTEIN, RANBP BINDING DOMAIN. | tremblnew CAB52154 | ND |
| 5609 | 272.6 | HYPOTHETICAL 96.1 KD PROTEIN. | sptrembl Q9Y7N9 | ND |
| 5610 | 272.5 | CLATHRIN COAT ASSEMBLY PROTEIN. | sptrembl Q9Y7L6 | ND |
| 5611 | 272.3 | HYPOTHETICAL 42.4 KD PROTEIN. | sptrembl O24844 | ND |
| 5612 | 2718.8 | Aspergillus sp. recombinant protein-disulfide-isomerase. | geneseqp R69506 | Energy production and conversion |
| 5613 | 271.9 | HYPOTHETICAL 14.0 KD PROTEIN IN RPL15B-GCR3 INTERGENIC REGION. | swissprot Q03880 | ND |
| 5614 | 271.8 | HYPOTHETICAL 198.1 KD PROTEIN. | sptrembl O23363 | ND |
| 5615 | 271.5 | CALCIUM/PROTON EXCHANGER. | sptrembl O59940 | ND |

TABLE 3-continued

_Aspergillus oryzae_ ESTs

| Sequence Listing | zscore | Annotation | Database | Functional Category |
|---|---|---|---|---|
| 5616 | 271.5 | PUTATIVE PHOSPHATIDYLSERINE DECARBOXYLASE. | tremblnew CAB39662 | ND |
| 5617 | 271.4 | HYPOTHETICAL 25.3 KD PROTEIN IN TIM23-ARE2 INTERGENIC REGION. | swissprot P53721 | ND |
| 5618 | 271.1 | PUTATIVE ACETYLORNITHINE DEACETYLASE. | sptrembl O74916 | ND |
| 5619 | 271.0 | HYDROXYQUINOL 1,2-DIOXYGENASE. | tremblnew BAA82713 | ND |
| 5620 | 2708.1 | PROBABLE ATP-DEPENDENT TRANSPORTER YER036C. | swissprot P40024 | ND |
| 5621 | 270.3 | SPHERULIN 4 PRECURSOR. | swissprot P11113 | ND |
| 5622 | 2692.9 | ACTIN. | swissprot O13419 | Cell division and chromosome partitioning |
| 5623 | 269.9 | YEST PROTEIN. | sptrembl O31523 | ND |
| 5624 | 269.4 | HYPOTHETICAL 70.6 KD LIPOPROTEIN IN FEUA-SIGW INTERGENIC REGION PRECURSOR (ORF1). | swissprot P40406 | ND |
| 5625 | 269.1 | HYPOTHETICAL 14.1 KD PROTEIN IN NIF3-CLG1 INTERGENIC REGION. | swissprot P53082 | ND |
| 5626 | 268.6 | BCS1 PROTEIN. | swissnew P32839 | ND |
| 5627 | 268.2 | MITOCHONDRIAL 40S RIBOSOMAL PROTEIN MRP17. | swissprot P28778 | ND |
| 5628 | 268.0 | HYPOTHETICAL 56.6 KD PROTEIN IN URE2-SSU72 INTERGENIC REGION. | swissprot P53867 | ND |
| 5629 | 267.8 | 60S RIBOSOMAL PROTEIN L30, MITOCHONDRIAL PRECURSOR (YML30). | swissprot P36528 | ND |
| 5630 | 267.6 | HYPOTHETICAL 23.1 KD PROTEIN. | sptrembl P95145 | ND |
| 5631 | 267.1 | DIHYDROLIPOAMIDE SUCCINYLTRANSFERASE. | tremblnew AAD47296 | ND |
| 5632 | 267.0 | POTENTIAL MEMBRANE PROTEIN. | sptrembl O94006 | ND |
| 5633 | 266.4 | HYPOTHETICAL 137.7 KD PROTEIN IN UGS1-FAB1 INTERGENIC REGION. | swissprot P43597 | ND |
| 5634 | 266.3 | HUNKI MRNA. | sptrembl O60885 | ND |
| 5635 | 266.0 | ASPARTYL-TRNA SYNTHETASE, CYTOPLASMIC (EC 6.1.1.12) (ASPARTATE--TRNA LIGASE) (ASPRS). | swissprot P04802 | ND |
| 5636 | 265.9 | MALIC ACID TRANSPORT PROTEIN (MALATE PERMEASE). | swissprot P50537 | ND |
| 5637 | 265.3 | HYPOTHETICAL 45.1 KD PROTEIN. | sptrembl O30447 | ND |
| 5638 | 265.0 | Neurite extending activity protein. | geneseqp Y17863 | ND |
| 5639 | 2644.2 | PHOSPHOGLYCERATE KINASE (EC 2.7.2.3). | swissprot P41756 | Carbohydrate transport and metabolism |
| 5640 | 2640.0 | NMT1 PROTEIN HOMOLOG. | swissprot P42882 | Inorganic ion transport and metabolism |
| 5641 | 264.6 | SALIVARY PROLINE-RICH PROTEIN II-1 (FRAGMENT). | swissprot P81489 | ND |
| 5642 | 264.5 | ANKYRIN G119. | sptrembl Q13484 | ND |
| 5643 | 264.0 | PHOSPHOSERINE PHOSPHATASE (EC 3.1.3.3) (PSP) (O-PHOSPHOSERINE PHOSPHOHYDROLASE) (PSP). | swissnew P42941 | ND |
| 5644 | 263.8 | CHROMOSOME XVI COSMID 9513. | sptrembl Q06810 | ND |

TABLE 3-continued

_Aspergillus oryzae ESTs_

| Sequence Listing | zscore | Annotation | Database | Functional Category |
|---|---|---|---|---|
| 5645 | 263.7 | SER/THR-RICH PROTEIN T10 IN DGCR REGION. | swissprot P54797 | ND |
| 5646 | 263.3 | EXTENSIN PRECURSOR (CELL WALL HYDROXYPROLINE-RICH GLYCOPROTEIN). | swissprot P13983 | ND |
| 5647 | 263.2 | CHROMOSOME XVI COSMID 9325. | sptrembl Q06214 | ND |
| 5649 | 2627.8 | GLUCOAMYLASE PRECURSOR (EC 3.2.1.3) (GLUCAN 1,4-ALPHA-GLUCOSIDASE) (1,4-ALPHA-D-GLUCAN GLUCOHYDROLASE). | swissprot P36914 | ND |
| 5650 | 262.9 | SNARE PROTEIN YKT6. | sptrembl O15498 | ND |
| 5651 | 262.7 | PUTATIVE PROGESTERONE-BINDING PROTEIN HOMOLOG. | sptrembl Q9XFM5 | ND |
| 5652 | 262.6 | HYPOTHETICAL 39.6 KD PROTEIN. | sptrembl O06179 | ND |
| 5653 | 262.6 | EUKARYOTIC TRANSLATION INITIATION FACTOR 2 BETA SUBUNIT (EIF-2-BETA). | swissprot P09064 | ND |
| 5654 | 262.3 | HYPOTHETICAL 31.3 KD PROTEIN. | sptrembl P72926 | ND |
| 5655 | 262.1 | WUGSC:H_RG054D04.2 PROTEIN (FRAGMENT). | sptrembl O95035 | ND |
| 5656 | 262.1 | ACTIVATOR OF HSP70 AND HSP90 CHAPERONES. | tremblnew CAB39910 | ND |
| 5657 | 261.7 | CONSERVED HYPOTHETICAL PROTEIN. | tremblnew CAB59799 | ND |
| 5658 | 261.7 | CONSERVED HYPOTHETICAL PROTEIN. | sptrembl Q9Y7K8 | ND |
| 5659 | 261.7 | U3 SMALL NUCLEOLAR RIBONUCLEOPROTEIN PROTEIN LCP5. | swissnew P40079 | ND |
| 5660 | 261.5 | EXTENSIN PRECURSOR (CELL WALL HYDROXYPROLINE-RICH GLYCOPROTEIN). | swissprot P13983 | ND |
| 5661 | 261.4 | PROLINE-RICH PROTEIN PRECURSOR. | sptrembl O49201 | ND |
| 5662 | 2603.0 | PUTATIVE THIAZOLE SYNTHASE. | tremblnew AAF25444 | ND |
| 5663 | 260.9 | UBIQUITIN-CONJUGATING ENZYME E2-24 KD (EC 6.3.2.19) (UBIQUITIN-PROTEIN LIGASE) (UBIQUITIN CARRIER PROTEIN). | swissprot P21734 | ND |
| 5664 | 260.9 | HYPOTHETICAL 106.1 KD PROTEIN C4F10.13C IN CHROMOSOME I. | sptrembl O36025 | ND |
| 5665 | 260.8 | WBSCR1 ALTERNATIVE SPLICED PRODUCT. | sptrembl Q9WUK3 | ND |
| 5666 | 260.7 | HYPOTHETICAL 8.2 KD PROTEIN C26A3.14C IN CHROMOSOME I. | swissprot Q10167 | ND |
| 5667 | 260.0 | HYPOTHETICAL 93.5 KD PROTEIN. | sptrembl O59744 | ND |
| 5668 | 259.8 | PHOSPHATIDYLETHANOLAMINE METHYLTRANSFERASE. | sptrembl P87301 | ND |
| 5669 | 259.5 | HYPOTHETICAL 40.7 KD PROTEIN IN DAK1-ORC1 INTERGENIC REGION. | swissprot Q04651 | ND |
| 5670 | 259.2 | HYPOTHETICAL 39.4 KD PROTEIN. | sptrembl Q12449 | ND |
| 5671 | 259.2 | ORF N118 (FRAGMENT). | sptrembl Q92363 | ND |
| 5672 | 259.1 | PUTATIVE RNA BINDING PROTEIN. | tremblnew CAB53728 | ND |
| 5673 | 2583.2 | TUBULIN ALPHA-2 CHAIN. | swissprot P24634 | ND |

TABLE 3-continued

_Aspergillus oryzae_ ESTs

| Sequence Listing | zscore | Annotation | Database | Functional Category |
|---|---|---|---|---|
| 5674 | 258.5 | HYPOTHETICAL 114.3 KD PROTEIN. | sptrembl O74839 | ND |
| 5675 | 258.4 | PROLINE-RICH PROTEIN MP-2 PRECURSOR. | swissprot P05142 | ND |
| 5676 | 257.9 | C-HORDEIN. | sptrembl Q41210 | ND |
| 5677 | 257.9 | PROLINE-RICH SALIVARY PROTEIN (FRAGMENT). | sptrembl Q62106 | ND |
| 5678 | 257.6 | _Malassezia fungus_ MF-7 antigenic protein. | geneseqp W29774 | ND |
| 5679 | 256.9 | HYPOTHETICAL 22.7 KD PROTEIN. | sptrembl O94723 | ND |
| 5680 | 256.8 | PUTATIVE SMC FAMILY PROTEIN. | tremblnew CAB11195 | ND |
| 5681 | 256.7 | PUTATIVE ACETYLORNITHINE DEACETYLASE. | sptrembl O74916 | ND |
| 5682 | 256.4 | WEB1 PROTEIN. | sptrembl O13637 | ND |
| 5683 | 256.3 | INTEGRAL MEMBRANE PROTEIN. | sptrembl Q9Y784 | ND |
| 5684 | 256.3 | C-7 hydroxycephem methyltransferase coupling protein. | geneseqp R92153 | ND |
| 5685 | 256.2 | FLGA insert stabilising polypeptide. | geneseqp W79128 | ND |
| 5686 | 256.0 | HYPOTHETICAL 34.4 KD PROTEIN IN IDS2-MPI2 INTERGENIC REGION. | swissprot P47008 | ND |
| 5687 | 2556.9 | GEL1 PROTEIN. | sptrembl O74687 | ND |
| 5688 | 2554.6 | ALCOHOL DEHYDROGENASE I (EC 1.1.1.1). | swissprot P41747 | ND |
| 5689 | 255.7 | HYPOTHETICAL 9.1 KD PROTEIN. | sptrembl O04820 | ND |
| 5690 | 255.5 | PUTATIVE PROLINE-RICH PROTEIN. | sptrembl Q9ZW08 | ND |
| 5691 | 255.3 | HYPOTHETICAL 14.6 KD PROTEIN. | tremblnew CAB61466 | ND |
| 5692 | 255.1 | HYPOTHETICAL 27.8 KD PROTEIN. | tremblnew CAB66105 | ND |
| 5693 | 254.7 | ANUCLEATE PRIMARY STERIGMATA PROTEIN. | swissprot Q00083 | ND |
| 5694 | 254.0 | SUPEROXIDE DISMUTASE (EC 1.15.1.1). | tremblnew CAB61430 | ND |
| 5695 | 2534.2 | MANNOSE-1-PHOSPHATE GUANYLTRANSFERASE (EC 2.7.7.13) (MPG1 TRANSFERASE) (ATP-MANNOSE-1-PHOSPHATE GUANYLYLTRANSFERASE) | sptrembl O74624 | Cell envelope biogenesis, outer membrane |
| 5696 | 253.8 | PROLINE RICH PROTEIN. | sptrembl O22514 | ND |
| 5697 | 253.5 | PROBABLE ATP-DEPENDENT RNA HELICASE DBP3 (HELICASE CA3). | swissprot P20447 | ND |
| 5698 | 2523.1 | 60S RIBOSOMAL PROTEIN L3. | tremblnew AAF15600 | Translation, ribosomal structure and biogenesis |
| 5699 | 252.6 | HYPOTHETICAL 31.1 KD PROTEIN C1E8.05 IN CHROMOSOME II PRECURSOR. | sptrembl O42970 | ND |
| 5700 | 252.5 | TGF BETA RECEPTOR ASSOCIATED PROTEIN-1. | sptrembl O60466 | ND |
| 5701 | 252.4 | HYDROXYPROLINE-RICH GLYCOPROTEIN. | sptrembl Q41814 | ND |
| 5702 | 252.3 | PUTATIVE INTEGRAL MEMBRANE GTPASE ACTIVATING PROTEIN, RABGAP DOMAIN CONTAININGYEAST MIC1 HOMOLOG. | sptrembl O43048 | ND |

TABLE 3-continued

_Aspergillus oryzae ESTs_

| Sequence Listing | zscore | Annotation | Database | Functional Category |
|---|---|---|---|---|
| 5703 | 251.7 | HYPOTHETICAL 55.1 KD PROTEIN IN FAB1-PES4 INTERGENIC REGION. | swissprot P43601 | ND |
| 5704 | 251.6 | HYPOTHETICAL 8.1 KD PROTEIN C3G6.02 IN CHROMOSOME I. | sptrembl O14140 | ND |
| 5705 | 251.6 | PUTATIVE ZINC FINGER TRANSCRIPTION FACTOR. | tremblnew AAF15889 | ND |
| 5706 | 250.9 | HYPOTHETICAL 21.6 KD PROTEIN C56F8.11 IN CHROMOSOME I. | swissprot Q10259 | ND |
| 5707 | 250.6 | CONSERVED HYPOTHETICAL PROTEIN. | sptrembl Q9WZF4 | ND |
| 5708 | 2495.5 | ELONGATION FACTOR 2 (EF-2). | swissprot P32324 | Translation, ribosomal structure and biogenesis |
| 5709 | 2493.2 | NAD-DEPENDENT FORMATE DEHYDROGENASE (EC 1.2.1.2). | sptrembl Q9Y790 | ND |
| 5710 | 249.9 | PUTATIVE SERINE/THREONINE-PROTEIN KINASE PKWA (EC 2.7.1.-). | swissnew P49695 | ND |
| 5711 | 249.7 | 40S MITOCHONDRIAL RIBOSOMAL PROTEIN. | sptrembl O59772 | ND |
| 5712 | 249.3 | HYPOTHETICAL 49.6 KD PROTEIN IN ELM1-PRI2 INTERGENIC REGION. | swissprot P36091 | ND |
| 5713 | 2489.1 | SERINE HYDROXYMETHYLTRANSFERASE, CYTOSOLIC (EC 2.1.2.1) (SERINE METHYLASE) (GLYCINE HYDROXYMETHYLTRANSFERASE) (SHMT). | swissprot P34898 | Amino acid transport and metabolism |
| 5714 | 248.4 | ZK1307.8 PROTEIN. | sptrembl Q23440 | ND |
| 5715 | 248.3 | 26S PROTEASOME REGULATORY SUBUNIT NIN1 (NUCLEAR INTEGRITY PROTEIN 1). | swissprot P32496 | ND |
| 5716 | 248.1 | EXTENSIN-LIKE PROTEIN. | tremblnew AAD55980 | ND |
| 5717 | 248.0 | PUTATIVE NUCLEOPORIN. | tremblnew CAA91133 | ND |
| 5718 | 2473.9 | CATALASE B (EC 1.11.1.6). | swissprot Q92405 | Inorganic ion transport and metabolism |
| 5719 | 247.8 | HYPOTHETICAL 31.6 KD PROTEIN. | sptrembl Q9Y7Z5 | ND |
| 5720 | 247.6 | CHROMOSOME XV READING FRAME ORF YOR320C. | sptrembl Q12096 | ND |
| 5721 | 247.4 | HYPOTHETICAL 20.9 KD PROTEIN IN ROX1-SPE3 INTERGENIC REGION. | swissprot Q12425 | ND |
| 5722 | 247.3 | COSMID C27A2. | sptrembl Q18238 | ND |
| 5723 | 247.3 | FIL1 PROTEIN PRECURSOR. | swissprot P38771 | ND |
| 5724 | 247.1 | OXIDOREDUCTASE. | sptrembl O53608 | ND |
| 5725 | 246.9 | A-AGGLUTININ ATTACHMENT SUBUNIT PRECURSOR. | swissprot P32323 | ND |
| 5726 | 246.6 | _P. putida_ R-(−)-mandelate monooxygenase protein. | geneseqp W53916 | ND |
| 5727 | 246.2 | 382AA LONG HYPOTHETICAL SARCOSINE OXIDASE. | sptrembl O59089 | ND |
| 5728 | 246.1 | PUTATIVE TRANSPORTER. | tremblnew CAB63540 | ND |
| 5729 | 245.8 | 60S RIBOSOMAL PROTEIN L37, MITOCHONDRIAL PRECURSOR (YML37). | swissprot P36532 | ND |

TABLE 3-continued

*Aspergillus oryzae* ESTs

| Sequence Listing | zscore | Annotation | Database | Functional Category |
|---|---|---|---|---|
| 5730 | 245.7 | PUTATIVE RNA MATURATION PROTEIN. | sptrembl O94689 | ND |
| 5731 | 245.1 | MEIOTIC MRNA STABILITY PROTEIN KINASE UME5 (EC 2.7.1.-). | swissprot P39073 | ND |
| 5732 | 245.1 | EXTENSIN (FRAGMENT). | sptrembl Q41645 | ND |
| 5733 | 244.5 | HYPOTHETICAL 41.8 KD PROTEIN. | sptrembl O65023 | ND |
| 5734 | 244.3 | HYPOTHETICAL 81.2 KD PROTEIN C3D6.13C IN CHROMOSOME II. | swissprot P87178 | ND |
| 5735 | 244.0 | EXTENSIN-LIKE PROTEIN. | tremblnew AAD55980 | ND |
| 5736 | 244.0 | REPETITIVE PROLINE-RICH CELL WALL PROTEIN 1. | sptrembl Q01979 | ND |
| 5737 | 243.8 | PROTEIN-TYROSINE PHOSPHATASE (EC 3.1.3.48). | sptrembl O94526 | ND |
| 5738 | 243.5 | SIMILAR TO HUMAN DIMETHYLANILINE MONOOXYGENASE. | tremblnew BAA88195 | ND |
| 5739 | 2420.7 | CATALASE ISOZYME P. | tremblnew AAF01463 | Inorganic ion transport and metabolism |
| 5740 | 242.8 | HYDROXYPROLINE-RICH GLYCOPROTEIN DZ-HRGP PRECURSOR. | tremblnew CAB62280 | ND |
| 5741 | 242.7 | F19G10.4 PROTEIN. | sptrembl O23122 | ND |
| 5742 | 242.5 | F3L24.19 PROTEIN. | tremblnew AAF14029 | ND |
| 5743 | 242.2 | MYCELIAL SURFACE ANTIGEN PRECURSOR. | sptrembl O74249 | ND |
| 5744 | 242.1 | DNA-DIRECTED RNA POLYMERASE II LARGEST SUBUNIT (EC 2.7.7.6) (RPB1) (FRAGMENT). | swissprot P11414 | ND |
| 5745 | 242.1 | PUTATIVE SECRETED PROTEIN. | sptrembl O69822 | ND |
| 5746 | 241.7 | HYDROXYPROLINE-RICH GLYCOPROTEIN DZ-HRGP PRECURSOR. | tremblnew CAB62280 | ND |
| 5747 | 241.4 | FISSION YEAST. | sptrembl P78821 | ND |
| 5748 | 241.4 | HOMOSERINE DEHYDROGENASE (EC 1.1.1.3) (HDH). | swissnew P31116 | ND |
| 5749 | 241.2 | *Cryptosporidium parvum* GP900 antigen. | geneseqp W48299 | ND |
| 5750 | 241.2 | TOXD PROTEIN. | swissprot P54006 | ND |
| 5751 | 241.2 | MUCIN 2 PRECURSOR (INTESTINAL MUCIN 2). | swissprot Q02817 | ND |
| 5752 | 241.1 | CELL WALL PROTEIN PRECURSOR. | sptrembl Q39005 | ND |
| 5753 | 241.0 | HYPOTHETICAL 52.9 KD SERINE-RICH PROTEIN C11G7.01 IN CHROMOSOME I. | swissprot O13695 | ND |
| 5754 | 240.9 | TRICHODIENE OXYGENASE (EC 1.14.-.-) (CYTOCHROME P450 58). | swissprot Q12612 | ND |
| 5755 | 240.6 | HYPOTHETICAL 27.5 KD PROTEIN. | sptrembl Q03973 | ND |
| 5756 | 240.2 | ZINC CLUSTER TRANSCRIPTION FACTOR FCR1P. | sptrembl O93870 | ND |
| 5757 | 240.0 | PUTATIVE METHYLTRANSFERASE SLL0829 (EC 2.1.1.-). | swissprot Q55423 | ND |
| 5758 | 239.8 | CHOLINE/ETHANOLAMINE KINASE-ALPHA. | tremblnew BAA88154 | ND |
| 5759 | 239.5 | BETA-GALACTOSIDASE ALPHA PEPTIDE (FRAGMENT). | sptrembl Q46478 | ND |

TABLE 3-continued

_Aspergillus oryzae ESTs_

| Sequence Listing | zscore | Annotation | Database | Functional Category |
|---|---|---|---|---|
| 5760 | 239.4 | HYPOTHETICAL HELICASE K12H4.8 IN CHROMOSOME III. | swissprot P34529 | ND |
| 5761 | 239.1 | HYDROXYPROLINE-RICH GLYCOPROTEIN DZ-HRGP PRECURSOR. | tremblnew CAB62280 | ND |
| 5762 | 2384.6 | SPLICEOSOMAL PROTEIN SAP 155 (PUTATIVE NUCLEAR PROTEIN). | sptrembl O75533 | ND |
| 5763 | 237.6 | Human follicle stimulating hormone GPR N-terminal sequence. | geneseqp W03627 | ND |
| 5764 | 237.6 | GLUCOAMYLASE S1/S2 PRECURSOR (EC 3.2.1.3) (GLUCAN 1,4-ALPHA-GLUCOSIDASE) (1,4-ALPHA-D-GLUCAN GLUCOHYDROLASE). | swissprot P08640 | ND |
| 5765 | 237.4 | ANNEXIN VII (SYNEXIN). | swissprot P24639 | ND |
| 5766 | 237.3 | HYDROXYLASE. | sptrembl O94115 | ND |
| 5767 | 236.2 | PTERIN-4-ALPHA-CARBINOLAMINE DEHYDRATASE (EC 4.2.1.96) (PHS) (4-ALPHA-HYDROXY-TETRAHYDROPTERIN DEHYDRATASE) (PHENYLALANINE HYDROXYLASE-STIMULATING PROTEIN) (PCD). | swissprot P43335 | ND |
| 5768 | 2356.2 | TUBULIN BETA-1 CHAIN. | swissprot P10653 | ND |
| 5769 | 2350.7 | ELONGATION FACTOR 2 (FRAGMENT). | tremblnew CAB52147 | Translation, ribosomal structure and biogenesis |
| 5770 | 235.7 | HYDROXYPROLINE-RICH GLYCOPROTEIN DZ-HRGP PRECURSOR. | tremblnew CAB62280 | ND |
| 5771 | 235.0 | HYDROXYPROLINE-RICH GLYCOPROTEIN. | sptrembl Q42366 | ND |
| 5772 | 234.9 | KINESIN-LIKE PROTEIN KIF2 (FRAGMENT). | sptrembl Q9WV63 | ND |
| 5773 | 233.9 | ACYL-COA-BINDING PROTEIN (ACBP) (DIAZEPAM BINDING INHIBITOR) (DBI) (ENDOZEPINE) (EP). | swissprot P07108 | ND |
| 5774 | 233.9 | HISTONE H1. | tremblnew AAF16011 | ND |
| 5775 | 233.6 | ISOFLAVONE REDUCTASE HOMOLOG IRL (EC 1.3.1.-). | swissprot P52580 | ND |
| 5776 | 233.2 | SRC2. | sptrembl O04133 | ND |
| 5777 | 233.2 | HYPOTHETICAL 118.4 KD PROTEIN IN BAT2-DAL5 INTERGENIC REGION PRECURSOR. | swissprot P47179 | ND |
| 5778 | 233.2 | SAFRAMYCIN MX1 SYNTHETASE A. | sptrembl Q50858 | ND |
| 5779 | 233.2 | HYPOTHETICAL PROTEIN. | sptrembl O23692 | ND |
| 5780 | 233.0 | PROLINE RICH PROTEIN PRECURSOR. | sptrembl Q43558 | ND |
| 5781 | 232.6 | HOL1 PROTEIN. | swissprot P53389 | ND |
| 5782 | 232.5 | LONG-CHAIN-FATTY-ACID--COA LIGASE (FADD-5). | sptrembl O29233 | ND |
| 5783 | 232.5 | HYPOTHETICAL 31.6 KD PROTEIN. | sptrembl Q9Y7Z5 | ND |
| 5784 | 232.2 | HYPOTHETICAL 67.0 KD PROTEIN. | sptrembl O60107 | ND |
| 5785 | 232.2 | EXTENSIN CLASS II PRECURSOR (CELL WALL HYDROXYPROLINE-RICH | sptrembl Q09085 | ND |

TABLE 3-continued

_Aspergillus oryzae ESTs_

| Sequence Listing | zscore | Annotation | Database | Functional Category |
|---|---|---|---|---|
| | | GLYCOPROTEIN) (HRGP) (HYP2.13) (FRAGMENT). | | |
| 5786 | 231.8 | A-AGGLUTININ ATTACHMENT SUBUNIT PRECURSOR. | swissprot P32323 | ND |
| 5787 | 231.8 | HYPOTHETICAL 52.3 KD PROTEIN IN FRE2 5'REGION. | swissprot P36032 | ND |
| 5788 | 231.7 | PUTATIVE 101.8 KD TRANSCRIPTIONAL REGULATORY PROTEIN IN LAS1-CCP1 INTERGENIC REGION. | swissprot P36023 | ND |
| 5789 | 231.5 | AUXIN-INDUCED PROTEIN. | sptrembl Q43677 | ND |
| 5790 | 231.5 | HYPOTHETICAL 8.6 KD PROTEIN. | sptrembl Q03482 | ND |
| 5791 | 231.5 | HYPOTHETICAL 64.2 KD PROTEIN. | sptrembl Q9Y8A1 | ND |
| 5792 | 231.3 | PUTATIVE PRE-MRNA SPLICING FACTOR. | sptrembl P78814 | ND |
| 5793 | 231.3 | MINICHROMOSOME MAINTENANCE PROTEIN MCM7P. | sptrembl O75001 | ND |
| 5794 | 231.1 | RNA EXPORT FACTOR GLE1. | swissprot Q12315 | ND |
| 5795 | 230.7 | ATPASE STABILIZING FACTOR 15 KD PROTEIN. | swissprot P16965 | ND |
| 5796 | 230.6 | MUCIN (FRAGMENT). | sptrembl Q28501 | ND |
| 5797 | 230.6 | GIBBERELLIN OXIDASE-LIKE PROTEIN. | tremblnew CAB46041 | ND |
| 5798 | 230.4 | PUTATIVE MULTIPLE DRUG RESISTANCE PROTEIN. | sptrembl Q9Y835 | ND |
| 5799 | 230.3 | MUCIN 2 PRECURSOR (INTESTINAL MUCIN 2). | swissprot Q02817 | ND |
| 5800 | 230.3 | HYDROXYPROLINE-RICH GLYCOPROTEIN DZ-HRGP PRECURSOR. | tremblnew CAB62280 | ND |
| 5801 | 230.0 | Human lung tumour protein SAL-68 predicted amino acid sequence. | geneseqp Y29561 | ND |
| 5802 | 229.7 | MUCIN 2 PRECURSOR (INTESTINAL MUCIN 2). | swissprot Q02817 | ND |
| 5803 | 229.6 | ADENYLYL CYCLASE. | tremblnew AAD50121 | ND |
| 5804 | 229.3 | HYPOTHETICAL 17.7 KD PROTEIN IN AMD1-RAD52 INTERGENIC REGION. | swissprot Q03712 | ND |
| 5805 | 229.0 | UBIQUITIN--PROTEIN LIGASE RSP5 (EC 6.3.2.-). | swissprot P39940 | ND |
| 5806 | 228.9 | HYPOTHETICAL 54.9 KD PROTEIN IN CBR5-NOT3 INTERGENIC REGION. | swissprot P40533 | ND |
| 5807 | 228.8 | RAB11-LIKE (FRAGMENT). | sptrembl Q94149 | ND |
| 5808 | 228.5 | F24J5.4. | tremblnew AAD49970 | ND |
| 5809 | 228.2 | ZINC FINGER PROTEIN 1. | swissprot P28875 | ND |
| 5810 | 228.1 | CYCLIN ANIA-6B (FRAGMENT). | tremblnew AAF23011 | ND |
| 5811 | 227.6 | EXTENSIN (EXT) PRECURSOR. | sptrembl Q40402 | ND |
| 5812 | 227.1 | _D. immitis_ ankyrin pDiAnk303 protein. | geneseqp W76774 | ND |
| 5813 | 2268.2 | ALPHA-GLUCOSIDASE (EC 3.2.1.20) (MALTASE). | swissprot Q02751 | Carbohydrate transport and metabolism |
| 5814 | 2265.0 | CHITINASE. | sptrembl Q92222 | ND |
| 5815 | 226.5 | RIBOSOMAL PROTEIN L41. | sptrembl Q9Y710 | ND |
| 5816 | 226.2 | PUTATIVE MITOCHONDRIAL 40S RIBOSOMAL PROTEIN YNR036C. | swissprot P53732 | ND |

TABLE 3-continued

_Aspergillus oryzae ESTs_

| Sequence Listing | zscore | Annotation | Database | Functional Category |
|---|---|---|---|---|
| 5817 | 226.2 | PROBABLE COATOMER GAMMA SUBUNIT (GAMMA-COAT PROTEIN) (GAMMA-COP). | swissprot P87140 | ND |
| 5818 | 226.1 | TETRATRICOPEPTIDE REPEAT PROTEIN. | sptrembl Q99614 | ND |
| 5819 | 225.8 | MICROFILARIAL SHEATH PROTEIN PRECURSOR. | sptrembl Q17242 | ND |
| 5820 | 224.7 | EXTENSIN PRECURSOR (CELL WALL HYDROXYPROLINE-RICH GLYCOPROTEIN). | swissprot P13983 | ND |
| 5821 | 224.7 | CGI-82 PROTEIN. | sptrembl Q9Y391 | ND |
| 5822 | 224.6 | PROTEOPHOSPHOGLYCAN PRECURSOR (FRAGMENT). | sptrembl Q9Y076 | ND |
| 5823 | 224.0 | YCR028C-A. | sptrembl O11851 | ND |
| 5824 | 224.0 | MEMBRANE GLYCOPROTEIN. | sptrembl O39781 | ND |
| 5825 | 223.9 | PRO-RICH. | sptrembl Q84565 | ND |
| 5826 | 223.9 | PROLINE RICH PROTEIN. | sptrembl O22514 | ND |
| 5827 | 223.7 | KERATIN COMPLEX 2, BASIC, PROTEIN 2 (KERATIN 2 EPIDERMIS). | sptrembl Q61869 | ND |
| 5828 | 223.5 | HYPOTHETICAL 41.5 KD PROTEIN. | tremblnew CAB66198 | ND |
| 5829 | 222.9 | CYTOCHROME P450 4F3 (EC 1.14.13.30) (CYPIVF3) (LEUKOTRIENE-B4 OMEGA-HYDROXYLASE) (LEUKOTRIENE-B4 20-MONOOXYGENASE) (CYTOCHROME P450-LTB-OMEGA). | swissnew Q08477 | ND |
| 5830 | 222.5 | EXTENSIN-LIKE PROTEIN. | tremblnew AAD55980 | ND |
| 5831 | 222.4 | CHROMOSOME XV READING FRAME ORF YOR380W. | sptrembl Q08904 | ND |
| 5832 | 222.3 | KIAA0544 PROTEIN (FRAGMENT). | sptrembl O60291 | ND |
| 5833 | 222.2 | PROTEOPHOSPHOGLYCAN (FRAGMENT). | sptrembl Q9Y075 | ND |
| 5834 | 222.2 | EXTENSIN (FRAGMENT). | sptrembl Q41645 | ND |
| 5835 | 222.2 | HEMOLYSIN. | sptrembl Q00050 | ND |
| 5836 | 221.9 | PROSTACYCLIN SYNTHASE (EC 5.3.99.4) (PROSTAGLANDIN I2 SYNTHASE). | sptrembl Q62969 | ND |
| 5837 | 221.8 | HYPOTHETICAL 22.4 KD PROTEIN. | sptrembl Q9X7Q3 | ND |
| 5838 | 221.5 | Cyanovirin-N. | geneseqp W06811 | ND |
| 5839 | 2207.9 | CATALASE (EC 1.11.1.6). | sptrembl O14436 | Inorganic ion transport and metabolism |
| 5840 | 220.8 | PTB-ASSOCIATED SPLICING FACTOR (PSF). | swissnew P23246 | ND |
| 5841 | 220.3 | PUTATIVE TRANSCRIPTIONAL COACTIVATOR. | sptrembl O94301 | ND |
| 5842 | 220.3 | C11G6.3 PROTEIN. | sptrembl Q17909 | ND |
| 5843 | 220.3 | PUTATIVE CYTOCHROME C OXIDASE POLYPEPTIDE. | sptrembl O94705 | ND |
| 5844 | 220.0 | EXTENSIN PRECURSOR (PROLINE-RICH GLYCOPROTEIN). | swissprot P14918 | ND |
| 5845 | 219.9 | EXTENSIN PRECURSOR (CELL WALL HYDROXYPROLINE-RICH GLYCOPROTEIN). | swissprot P13983 | ND |
| 5846 | 219.6 | EXTENSIN (FRAGMENT). | sptrembl Q41645 | ND |
| 5847 | 219.5 | EXTENSIN (FRAGMENT). | sptrembl Q41645 | ND |
| 5848 | 219.2 | MADS-BOX HOMOLOG UMC1. | sptrembl O42725 | ND |

TABLE 3-continued

*Aspergillus oryzae* ESTs

| Sequence Listing | zscore | Annotation | Database | Functional Category |
|---|---|---|---|---|
| 5849 | 219.2 | Y63D3A.5 PROTEIN. | tremblnew CAB63398 | ND |
| 5850 | 219.1 | SPCB. | tremblnew AAD50452 | ND |
| 5851 | 219.0 | ZINC FINGER PROTEIN. | sptrembl Q00069 | ND |
| 5852 | 2184.1 | Urate oxidase encoded by *A. flavus*-derived cDNA clone 9C. | geneseqp R10222 | ND |
| 5853 | 218.7 | HYPOTHETICAL 49.5 KD PROTEIN IN UBP3-PET122 INTERGENIC REGION. | swissprot P10356 | ND |
| 5854 | 218.7 | PUTATIVE GALACTINOL SYNTHASE (EC 2.4.1.123). | sptrembl Q9XGG4 | ND |
| 5855 | 218.5 | ALCOHOL DEHYDROGENASE II (EC 1.1.1.1) (ADH II). | swissprot P54202 | ND |
| 5856 | 218.5 | PROLINE RICH PROTEIN. | sptrembl O22514 | ND |
| 5857 | 218.2 | DEHYDROGENASE. | sptrembl O34788 | ND |
| 5858 | 217.6 | PROBABLE PROTEIN-TYROSINE PHOSPHATASE CDC14 (EC 3.1.3.48). | swissprot Q00684 | ND |
| 5859 | 217.3 | HYPOTHETICAL 118.4 KD PROTEIN IN BAT2-DAL5 INTERGENIC REGION PRECURSOR. | swissprot P47179 | ND |
| 5860 | 217.1 | HYPOTHETICAL 58.8 KD PROTEIN IN GLK1-SRO9 INTERGENIC REGION. | swissprot P25568 | ND |
| 5861 | 2168.3 | SPINDLE ASSEMBLY CHECKPOINT PROTEIN SLDB. | sptrembl O59902 | ND |
| 5862 | 216.0 | FATTY ACID AMIDE HYDROLASE. | tremblnew BAA86917 | ND |
| 5863 | 2159.5 | POLYUBIQUITIN. | sptrembl O74295 | ND |
| 5864 | 2156.3 | NADH-UBIQUINONE OXIDOREDUCTASE 40 KD SUBUNIT PRECURSOR (EC 1.6.5.3) (EC 1.6.99.3) (COMPLEX I-40 KD) (CI-40 KD). | swissprot P25284 | ND |
| 5865 | 215.9 | MITOCHONDRIAL NUCLEASE (EC 3.1.30.-). | swissprot P08466 | ND |
| 5866 | 215.6 | HYPOTHETICAL 49.5 KD PROTEIN. | tremblnew AAD51406 | ND |
| 5867 | 215.4 | HYPOTHETICAL PROTEIN C30B4.01C IN CHROMOSOME II (FRAGMENT). | sptrembl P87179 | ND |
| 5868 | 2148.5 | ENOLASE (EC 4.2.1.11). | tremblnew BAA23760 | Carbohydrate transport and metabolism |
| 5869 | 214.7 | COLLETOTRICHUM GLOEOSPORIOIDES NITROGEN STARVATION-INDUCED GLUTAMINE RICH PROTEIN. | sptrembl O43117 | ND |
| 5870 | 214.6 | HYPOTHETICAL RYANODINE RECEPTOR DOMAIN CONTAINING PROTEIN. | sptrembl O74497 | ND |
| 5871 | 214.1 | KIAA0122 PROTEIN (FRAGMENT). | sptrembl Q14136 | ND |
| 5872 | 214.1 | NEUROFILAMENT-M SUBUNIT (FRAGMENT). | sptrembl O77788 | ND |
| 5873 | 214.0 | TEMPERATURE-DEPENDENT PROTEIN BYS1. | sptrembl Q00300 | ND |
| 5874 | 214.0 | *D. immitis* ankyrin pDiAnk348 protein. | geneseqp W76775 | ND |
| 5875 | 213.9 | HYPOTHETICAL 61.8 KD PROTEIN IN KGD1-SIM1 INTERGENIC REGION. | swissprot P40475 | ND |
| 5876 | 213.7 | MEMBRANE GLYCOPROTEIN. | sptrembl O39782 | ND |

TABLE 3-continued

*Aspergillus oryzae* ESTs

| Sequence Listing | zscore | Annotation | Database | Functional Category |
|---|---|---|---|---|
| 5877 | 213.4 | HYDROXYPROLINE-RICH GLYCOPROTEIN PRECURSOR. | sptrembl Q41719 | ND |
| 5878 | 212.8 | REGULATORY PROTEIN E2. | swissprot P50766 | ND |
| 5879 | 212.7 | HYPOTHETICAL 10.3 KD PROTEIN. | tremblnew CAB55848 | ND |
| 5880 | 212.4 | EATRO 164 KINETOPLAST (CR4). | sptrembl Q33564 | ND |
| 5881 | 212.4 | PUTATIVE HYDROLASE. | tremblnew CAB61556 | ND |
| 5882 | 212.2 | CHITIN SYNTHASE 1 (EC 2.4.1.16) (CHITIN-UDP ACETYL-GLUCOSAMINYL TRANSFERASE 1) (CLASS-II CHITIN SYNTHASE 1). | swissprot P30600 | ND |
| 5883 | 211.9 | EG:BACR37P7.3 PROTEIN. | tremblnew CAB65851 | ND |
| 5884 | 211.8 | PUTATIVE NICOTINATE PHOSPHORIBOSYLTRANSFERASE. | tremblnew CAB62416 | ND |
| 5885 | 211.3 | ATP-DEPENDENT BILE ACID PERMEASE. | swissprot P32386 | ND |
| 5886 | 211.3 | GLUCOAMYLASE S1/S2 PRECURSOR (EC 3.2.1.3) (GLUCAN 1,4-ALPHA-GLUCOSIDASE) (1,4-ALPHA-D-GLUCAN GLUCOHYDROLASE). | swissprot P08640 | ND |
| 5887 | 211.1 | HYPOTHETICAL 50.9 KD PROTEIN. | sptrembl O94548 | ND |
| 5888 | 211.0 | HYPOTHETICAL 29.3 KD PROTEIN (ORF92). | swissprot O10341 | ND |
| 5890 | 2106.6 | METHYLMALONATE-SEMIALDEHYDE DEHYDROGENASE [ACYLATING] PRECURSOR (EC 1.2.1.27) (MMSDH). | swissprot Q02253 | Energy production and conversion |
| 5891 | 2102.8 | PROBABLE INOSINE-5'-MONOPHOSPHATE DEHYDROGENASE (EC 1.1.1.205) (IMP DEHYDROGENASE) (IMPDH) (IMPD). | sptrembl O14344 | ND |
| 5892 | 210.9 | Truncated sec71p allele protein sequence. | geneseqp Y39942 | ND |
| 5893 | 210.6 | HYPOTHETICAL 56.3 KD PROTEIN IN ARO3-KRS1 INTERGENIC REGION. | swissprot P28817 | ND |
| 5894 | 210.2 | YMFI PROTEIN. | sptrembl O31767 | ND |
| 5895 | 210.0 | HYDROXYPROLINE-RICH GLYCOPROTEIN DZ-HRGP PRECURSOR. | tremblnew CAB62280 | ND |
| 5896 | 210.0 | Cyanovirin-N protein sequence. | geneseqp Y39909 | ND |
| 5897 | 2094.5 | *A. niger* PacC zinc finger DNA binding domain. | geneseqp Y08483 | ND |
| 5898 | 209.5 | PUTATIVE ACETYLORNITHINE DEACETYLASE. | sptrembl O74916 | ND |
| 5899 | 209.4 | CONIDIATION-SPECIFIC PROTEIN 8. | swissprot P10169 | ND |
| 5900 | 209.4 | GASTRIC MUCIN (FRAGMENT). | sptrembl Q29071 | ND |
| 5901 | 209.4 | HYPOTHETICAL 26.9 KD PROTEIN IN YHB1-PFK1 INTERGENIC REGION. | swissprot P50087 | ND |
| 5902 | 209.3 | PUTATIVE PROLINE-RICH CELL WALL PROTEIN. | sptrembl O82327 | ND |
| 5903 | 209.0 | PROBABLE PROTEIN KINASE C20G4.03C (EC 2.7.1.-). | sptrembl O13889 | ND |
| 5904 | 209.0 | MAJOR PRION PROTEIN 1 PRECURSOR (PRP) (MAJOR | swissprot P40242 | ND |

TABLE 3-continued

_Aspergillus oryzae ESTs_

| Sequence Listing | zscore | Annotation | Database | Functional Category |
|---|---|---|---|---|
| | | SCRAPIE-ASSOCIATED FIBRIL PROTEIN 1). | | |
| 5905 | 208.5 | Mutant Aspergillus oryzae DEBY932 rescued locus. | geneseqp W37992 | ND |
| 5906 | 2076.7 | 26S PROTEASE REGULATORY SUBUNIT 7 HOMOLOG. | tremblnew CAA16915 | Posttranslational modification, protein turnover, chaperones |
| 5907 | 2076.6 | NIDULANS, CPA-LIKE (FRAGMENT). | sptrembl O42806 | Nucleotide transport |
| 5908 | 207.6 | CHROMOSOME XVI READING FRAME ORF YPL233W. | sptrembl Q12143 | ND |
| 5909 | 207.4 | HYPOTHETICAL 30.8 KD PROTEIN IN SPR6-RPL23B INTERGENIC REGION. | swissprot P40072 | ND |
| 5910 | 207.3 | EXTENSIN CLASS 1 PROTEIN PRECURSOR (EXTENSIN-LIKE PROTEIN). | sptrembl Q41707 | ND |
| 5911 | 207.2 | CYSTATHIONINE BETA-SYNTHASE (EC 4.2.1.22) (SERINE SULFHYDRASE) (BETA-THIONASE). | swissprot P46794 | ND |
| 5912 | 206.9 | HYPOTHETICAL 24.4 KD PROTEIN. | sptrembl O86620 | ND |
| 5913 | 206.6 | F24J5.8 PROTEIN. | tremblnew AAD49974 | ND |
| 5914 | 206.5 | (VSP-3) PRECURSOR. | sptrembl Q39620 | ND |
| 5915 | 206.3 | Cationic peptide Bac7. | geneseqp W66400 | ND |
| 5916 | 205.7 | HYPOTHETICAL 46.7 KD PROTEIN (FRAGMENT). | sptrembl O42840 | ND |
| 5917 | 205.6 | EXTENSIN (FRAGMENT). | sptrembl Q41645 | ND |
| 5918 | 205.6 | SYNTHASE OF THE TYPE 3 PNEUMOCOCCAL CAPSULAR POLYSACCHARIDE. | sptrembl P72520 | ND |
| 5919 | 205.5 | HYPOTHETICAL 15.6 KD PROTEIN C29B12.13 IN CHROMOSOME I. | sptrembl O14034 | ND |
| 5921 | 2041.4 | DNA-DEPENDENT RNA POLYMERASE II RPB140 (FRAGMENT). | tremblnew AAF19066 | Transcription |
| 5922 | 204.9 | HYPOTHETICAL 47.0 KD PROTEIN C23H3.03C IN CHROMOSOME I. | sptrembl O42857 | ND |
| 5923 | 204.7 | HYDROXYPROLINE-RICH GLYCOPROTEIN DZ-HRGP PRECURSOR. | tremblnew CAB62280 | ND |
| 5924 | 204.7 | INTEGRAL MEMBRANE PROTEIN. | sptrembl Q9Y784 | ND |
| 5925 | 204.6 | TOL. | sptrembl O93882 | ND |
| 5926 | 204.2 | COSMID C33G8. | sptrembl Q18401 | ND |
| 5927 | 204.1 | RHO-LIKE PROTEIN C16A10.04. | sptrembl P87296 | ND |
| 5928 | 203.9 | C35E7.9 PROTEIN. | sptrembl O61765 | ND |
| 5929 | 203.6 | PROBABLE MANNOSYLTRANSFERASE. | sptrembl O94565 | ND |
| 5930 | 203.2 | HYPOTHETICAL 45.7 KD PROTEIN IN RPS3-PSD1 INTERGENIC REGION. | swissprot P53883 | ND |
| 5931 | 203.1 | TRANSCRIPTIONAL FACTOR SWI5. | swissprot P08153 | ND |
| 5932 | 203.1 | PUTATIVE ATP SYNTHASE F CHAIN, MITOCHONDRIAL PRECURSOR. | sptrembl O94377 | ND |
| 5933 | 2025.1 | FIMBRIN (ABP67). | swissprot P32599 | ND |
| 5934 | 202.8 | PROTEOPHOSPHOGLYCAN (FRAGMENT). | sptrembl Q9Y075 | ND |
| 5935 | 202.7 | EXTENSIN PRECURSOR (CELL WALL HYDROXYPROLINE-RICH GLYCOPROTEIN). | swissprot P13983 | ND |

TABLE 3-continued

_Aspergillus oryzae ESTs_

| Sequence Listing | zscore | Annotation | Database | Functional Category |
|---|---|---|---|---|
| 5936 | 202.7 | CLONING VECTOR PZERO-2T. | sptrembl O53022 | ND |
| 5937 | 202.4 | 60S RIBOSOMAL PROTEIN L37A (FRAGMENT). | swissprot O17307 | ND |
| 5938 | 202.2 | NUCLEAR PROTEIN SDK3 (FRAGMENT). | sptrembl O60899 | ND |
| 5939 | 202.2 | C12D12.1 PROTEIN. | sptrembl Q17921 | ND |
| 5940 | 202.1 | RNA BINDING PROTEIN (FRAGMENT). | tremblnew BAA83717 | ND |
| 5941 | 202.0 | CHROMOSOME XV READING FRAME ORF YOR306C. | sptrembl Q08777 | ND |
| 5942 | 201.5 | STEROL-C-METHYLTRANSFERASE. | sptrembl P74388 | ND |
| 5943 | 201.2 | SALIVARY PROLINE-RICH PROTEIN PRECURSOR (CLONES CP3, CP4 AND CP5) [CONTAINS: BASIC PEPTIDE IB-6; PEPTIDE P-H]. | swissprot P04280 | ND |
| 5944 | 201.2 | Banana ripening fruit Gluc. translated polypeptide. | geneseqp Y05839 | ND |
| 5945 | 201.1 | DNA-DIRECTED RNA POLYMERASE II LARGEST SUBUNIT (EC 2.7.7.6) (RPB1) (FRAGMENT). | swissprot P11414 | ND |
| 5946 | 201.0 | GLYCERALDEHYDE-3-PHOSPHATE DEHYDOGENAE (FRAGMENT). | tremblnew CAB63214 | ND |
| 5947 | 200.7 | HYPOTHETICAL 26.5 KD PROTEIN IN FUS2-RNH1 INTERGENIC REGION. | swissprot Q05024 | ND |
| 5948 | 200.7 | K09A9.6 PROTEIN. | sptrembl Q93178 | ND |
| 5949 | 200.6 | NITRATE REDUCTASE (EC 1.6.6.1) (NR). | swissprot P36841 | ND |
| 5950 | 200.6 | HYPOTHETICAL PROTEIN (FRAGMENT). | sptrembl Q12742 | ND |
| 5951 | 200.5 | PROLINE-RICH PROTEIN. | sptrembl Q64306 | ND |
| 5952 | 200.5 | HYPOTHETICAL 57.5 KD PROTEIN IN VMA7-RPS25A INTERGENIC REGION. | swissprot P53214 | ND |
| 5953 | 200.4 | RNA-BINDING PROTEIN FUS/TLS. | swissprot P35637 | ND |
| 5954 | 200.4 | HYPOTHETICAL PROTEIN MJ1187. | swissprot Q58588 | ND |
| 5955 | 200.3 | ADENYLYL CYCLASE. | tremblnew AAD50121 | ND |
| 5956 | 200.1 | HYPOTHETICAL PROTEIN MJ0301. | swissprot Q57749 | ND |
| 5957 | 200.1 | COMPLEX (DNA-BINDING PROTEIN/DNA) 155 aa, chain A | pdb 2GLI | ND |
| 5958 | 1996.1 | CHITIN SYNTHASE D (EC 2.4.1.16) (CHITIN-UDP ACETYL-GLUCOSAMINYL TRANSFERASE) (CLASS-V CHITIN SYNTHASE). | sptrembl O13281 | ND |
| 5959 | 199.8 | HYPOTHETICAL 41.6 KD PROTEIN (FRAGMENT). | sptrembl O94558 | ND |
| 5960 | 199.8 | Plasmid pRZTL1, Tetracycline resistance protein. | geneseqp Y42545 | ND |
| 5961 | 199.7 | HYPOTHETICAL 34.7 KD PROTEIN IN RHO3-HIS5 INTERGENIC REGION. | swissprot P40476 | ND |
| 5962 | 199.5 | WSC4 HOMOLOGUE. | sptrembl Q9Y849 | ND |
| 5963 | 199.5 | NUCLEOLIN (PROTEIN C23). | swissprot P19338 | ND |
| 5964 | 199.5 | RNA BINDING PROTEIN (FRAGMENT). | tremblnew BAA83717 | ND |
| 5965 | 199.1 | SIMILARITY TO COLLAGENS. | sptrembl O02123 | ND |
| 5966 | 199.0 | COS46.3. | sptrembl P91589 | ND |
| 5967 | 199.0 | EXTENSIN (FRAGMENT). | sptrembl Q41645 | ND |

TABLE 3-continued

_Aspergillus oryzae ESTs_

| Sequence Listing | zscore | Annotation | Database | Functional Category |
|---|---|---|---|---|
| 5968 | 199.0 | HYPOTHETICAL PROTEIN (FRAGMENT). | tremblnew BAA87194 | ND |
| 5969 | 1986.0 | ARGINASE (EC 3.5.3.1). | swissprot Q12611 | Amino acid transport and metabolism |
| 5970 | 1985.6 | FATTY ACID SYNTHASE, BETA SUBUNIT. | sptrembl P78616 | ND |
| 5971 | 198.9 | DNA BINDING PROTEIN NSDD. | sptrembl Q92226 | ND |
| 5972 | 198.8 | HYPOTHETICAL 40.3 KD PROTEIN. | sptrembl O69481 | ND |
| 5973 | 198.8 | HYDROXYPROLINE-RICH GLYCOPROTEIN. | sptrembl Q41814 | ND |
| 5974 | 198.5 | CTR9 PROTEIN. | swissprot P89105 | ND |
| 5975 | 198.1 | F32D1.2 PROTEIN. | sptrembl O16298 | ND |
| 5976 | 198.0 | PLENTY-OF-PROLINES-101. | sptrembl O70495 | ND |
| 5977 | 1978.8 | GLUTAMINE SYNTHETASE (EC 6.3.1.2) (GLUTAMATE--AMMONIA LIGASE). | swissprot Q12613 | Amino acid transport and metabolism |
| 5978 | 197.9 | TRANSLATION INITIATION FACTOR IF-3. | swissnew O67653 | ND |
| 5979 | 197.8 | K02F3.4 PROTEIN. | tremblnew AAA50709 | ND |
| 5980 | 197.8 | HYPOTHETICAL 45.6 KD PROTEIN C29A3.03C IN CHROMOSOME II. | sptrembl O59668 | ND |
| 5981 | 1965.3 | MITOCHONDRIAL PROCESSING PEPTIDASE BETA SUBUNIT PRECURSOR (EC 3.4.24.64) (BETA-MPP) (UBIQUINOL-CYTOCHROME C REDUCTASE COMPLEX CORE PROTEIN I) (EC 1.10.2.2). | swissprot P11913 | ND |
| 5982 | 196.8 | HYPOTHETICAL 75.4 KD PROTEIN. | tremblnew AAF04882 | ND |
| 5983 | 196.6 | LONGEVITY-ASSURANCE PROTEIN 1 (LONGEVITY ASSURANCE FACTOR 1). | swissprot P78970 | ND |
| 5984 | 196.4 | YLR391W-AP. | sptrembl O13547 | ND |
| 5985 | 1958.9 | NAD(+)-ISOCITRATE DEHYDROGENASE SUBUNIT I PRECURSOR. | sptrembl O13302 | Amino acid transport and metabolism |
| 5986 | 1958.6 | HEAT SHOCK PROTEIN 70. | sptrembl O93866 | Posttranslational modification, protein turnover, chaperones |
| 5987 | 195.8 | F4P13.11 PROTEIN. | tremblnew AAF01541 | ND |
| 5988 | 195.6 | CHROMOSOME XII COSMID 8003. | sptrembl Q05874 | ND |
| 5989 | 195.6 | U86. | tremblnew AAD49674 | ND |
| 5990 | 195.6 | ZP2 (CLONE C692). | sptrembl Q90354 | ND |
| 5991 | 195.5 | SORTING NEXIN 8. | sptrembl Q9Y5X2 | ND |
| 5992 | 195.5 | HYPOTHETICAL 23.9 KD PROTEIN IN COQ1-FLR1 INTERGENIC REGION. | swissprot P38212 | ND |
| 5993 | 195.2 | MUCIN. | sptrembl Q63549 | ND |
| 5994 | 195.2 | PROTEASE B INHIBITORS 2 AND 1 (PROTEINASE INHIBITOR I(B)2). | swissprot P01095 | ND |
| 5995 | 195.2 | F21E10.7 PROTEIN. | sptrembl O65245 | ND |
| 5996 | 195.2 | NUCLEOLIN (PROTEIN C23). | swissprot P08199 | ND |
| 5997 | 195.0 | C. albicans antigenic protein 3. | geneseqp Y06927 | ND |
| 5998 | 1946.7 | ADP,ATP CARRIER PROTEIN (ADP/ATP TRANSLOCASE) (ADENINE NUCLEOTIDE TRANSLOCATOR) (ANT). | swissprot P02723 | ND |

TABLE 3-continued

_Aspergillus oryzae ESTs_

| Sequence Listing | zscore | Annotation | Database | Functional Category |
|---|---|---|---|---|
| 6000 | 194.8 | HYPOTHETICAL 71.2 KD MEMBRANE PROTEIN C17G6.01 IN CHROMOSOME I. | sptrembl O13779 | ND |
| 6001 | 194.7 | 3-OXOACYL-[ACYL-CARRIER-PROTEIN]-REDUCTASE. | sptrembl O42774 | ND |
| 6002 | 194.7 | SEX DETERMINATION PROTEIN TASSELSEED 2. | swissprot P50160 | ND |
| 6003 | 194.1 | EXTENSIN CLASS II PRECURSOR (CELL WALL HYDROXYPROLINE-RICH GLYCOPROTEIN) (HRGP) (TOML-4). | sptrembl Q09084 | ND |
| 6004 | 194.1 | (VSP-3) PRECURSOR. | sptrembl Q39620 | ND |
| 6005 | 194.0 | NADH OXIDASE. | sptrembl Q9WYL1 | ND |
| 6006 | 1934.3 | HOMOACONITASE PRECURSOR (EC 4.2.1.36) (HOMOACONITATE HYDRATASE). | swissprot Q92412 | Energy production and conversion |
| 6007 | 193.9 | HYPOTHETICAL 25.3 KD PROTEIN C2C4.09 IN CHROMOSOME I. | sptrembl O14042 | ND |
| 6008 | 193.9 | SPORE COAT PROTEIN SP96. | swissprot P14328 | ND |
| 6009 | 193.8 | NADH-UBIQUINONE OXIDOREDUCTASE CHAIN 5 (EC 1.6.5.3). | swissprot P04540 | ND |
| 6010 | 193.8 | H14E04.2A PROTEIN. | tremblnew AAD12809 | ND |
| 6011 | 193.8 | MUCIN-LIKE PROTEIN. | sptrembl O77242 | ND |
| 6012 | 193.8 | WD REPEAT PROTEIN. | tremblnew CAB54817 | ND |
| 6013 | 193.7 | HYPOTHETICAL 46.2 KD PROTEIN. | tremblnew CAB36521 | ND |
| 6014 | 193.7 | WSC4 HOMOLOGUE. | sptrembl Q9Y849 | ND |
| 6015 | 193.6 | LATENT NUCLEAR ANTIGEN. | sptrembl Q9WRM2 | ND |
| 6016 | 193.5 | HYDROXYPROLINE-RICH GLYCOPROTEIN DZ-HRGP PRECURSOR. | tremblnew CAB62280 | ND |
| 6017 | 193.3 | HYPOTHETICAL 43.5 KD PROTEIN IN RPB9-ALG2 INTERGENIC REGION. | swissprot P53164 | ND |
| 6018 | 193.1 | EYELID. | sptrembl O61603 | ND |
| 6019 | 193.0 | HYPOTHETICAL 72.4 KD PROTEIN IN PTP3-ILV1 INTERGENIC REGION. | swissprot P40053 | ND |
| 6020 | 1920.0 | HOMOGENTISATE 1,2-DIOXYGENASE (EC 1.13.11.5) (HOMOGENTISICASE) (HOMOGENTISATE OXYGENASE) (HOMOGENTISIC ACID OXIDASE). | swissprot Q00667 | ND |
| 6021 | 192.9 | HYPOTHETICAL 45.2 KD PROTEIN. | sptrembl Q9YPA9 | ND |
| 6022 | 192.8 | HYPOTHETICAL 64.5 KD PROTEIN IN COX4-GTS1 INTERGENIC REGION. | swissprot P53099 | ND |
| 6023 | 192.5 | HAPB. | sptrembl O59847 | ND |
| 6024 | 192.4 | MPV17 PROTEIN. | swissprot P19258 | ND |
| 6025 | 192.0 | MEROZOITE SURFACE PROTEIN-1 (FRAGMENT). | sptrembl O00879 | ND |
| 6027 | 1910.6 | GLUCOAMYLASE PRECURSOR (EC 3.2.1.3) (GLUCAN 1,4-ALPHA-GLUCOSIDASE) (1,4-ALPHA-D-GLUCAN GLUCOHYDROLASE). | swissprot P36914 | ND |
| 6028 | 191.9 | HYPOTHETICAL 34.8 KD PROTEINF YDL037C. | sptrembl Q12140 | ND |

TABLE 3-continued

*Aspergillus oryzae* ESTs

| Sequence Listing | zscore | Annotation | Database | Functional Category |
|---|---|---|---|---|
| 6029 | 191.9 | HYPOTHETICAL 18.8 KD PROTEIN C25H2.09 IN CHROMOSOME II. | swissprot P87150 | ND |
| 6030 | 191.8 | MUCIN (FRAGMENT). | sptrembl Q14888 | ND |
| 6031 | 191.4 | HYPOTHETICAL CALCIUM-BINDING PROTEIN C18B11.04 IN CHROMOSOME I. | swissprot Q09711 | ND |
| 6032 | 191.2 | PROTEOPHOSPHOGLYCAN PRECURSOR (FRAGMENT). | sptrembl Q9Y076 | ND |
| 6033 | 191.1 | F23N19.12. | tremblnew AAF19547 | ND |
| 6034 | 190.9 | YGHL2 (FRAGMENT). | sptrembl Q91457 | ND |
| 6035 | 190.9 | STB5 PROTEIN. | swissprot P38699 | ND |
| 6036 | 190.8 | INTEGRIN BETA SUBUNIT. | sptrembl O97343 | ND |
| 6037 | 190.8 | HYDROXYPROLINE-RICH GLYCOPROTEIN PRECURSOR. | sptrembl Q41719 | ND |
| 6038 | 190.8 | KEXIN-LIKE SERINE ENDOPROTEASE (FRAGMENT). | tremblnew AAF21601 | ND |
| 6039 | 190.8 | PAROTID 'O' PROTEIN (FRAGMENT). | sptrembl O00600 | ND |
| 6040 | 190.8 | EXTENSIN. | sptrembl Q40503 | ND |
| 6041 | 190.6 | PROLINE-RICH PROTEIN MP-3 (FRAGMENT). | swissprot P05143 | ND |
| 6042 | 190.4 | Pig leukocyte prophenin peptide Proph1. | geneseqp R82569 | ND |
| 6043 | 190.4 | SALIVARY GLUE PROTEIN SGS-3 PRECURSOR. | swissprot P13728 | ND |
| 6044 | 190.3 | PROTEOPHOSPHOGLYCAN (FRAGMENT). | sptrembl Q9Y075 | ND |
| 6045 | 190.3 | (VSP-3) PRECURSOR. | sptrembl Q39620 | ND |
| 6046 | 190.2 | HIGH MOLECULAR WEIGHT BASIC NUCLEAR PROTEIN (FRAGMENT). | sptrembl Q91238 | ND |
| 6047 | 190.1 | ARGININE-RICH 54 KD NUCLEAR PROTEIN. | sptrembl Q05519 | ND |
| 6048 | 1899.3 | PEROXISOMAL HYDRATASE-DEHYDROGENASE-EPIMERASE (HDE) (MULTIFUNCTIONAL BETA-OXIDATION PROTEIN) (MFP) [INCLUDES: 2-ENOYL-COA HYDRATASE (EC 4.2.1.-); D-3-HYDROXYACYL COA DEHYDROGENASE (EC 1.1.1.-)]. | swissnew Q01373 | ND |
| 6049 | 189.9 | SALIVARY PROLINE-RICH PROTEIN PO PRECURSOR (ALLELE S). | swissprot P10163 | ND |
| 6050 | 189.8 | 36.4 KD PROLINE-RICH PROTEIN. | swissprot Q00451 | ND |
| 6051 | 189.7 | RIBOSOMAL PROTEIN L38 (FRAGMENT). | tremblnew BAA25844 | ND |
| 6052 | 189.6 | JASMONATE INDUCIBLE PROTEIN ISOLOG. | sptrembl O04310 | ND |
| 6053 | 189.5 | MUCIN 10, SUBMANDIBULAR GLAND SALIVARY MUCIN PRECURSOR (MUCIN APOPROTEIN). | sptrembl Q61002 | ND |
| 6054 | 189.4 | TRANSLATION INITIATION PROTEIN-BELONGS TO THE SUA5-YRDC-YCIO-YWLC FAMILY. | sptrembl O94530 | ND |
| 6055 | 189.4 | LOW MOLECULAR WEIGHT GLUTENIN (FRAGMENT). | sptrembl Q41551 | ND |
| 6056 | 189.3 | PROLINE-RICH PROTEIN. | sptrembl Q64306 | ND |

TABLE 3-continued

_Aspergillus oryzae ESTs_

| Sequence Listing | zscore | Annotation | Database | Functional Category |
|---|---|---|---|---|
| 6057 | 189.0 | ATRIAL-SPECIFIC MYOSIN HEAVY-CHAIN (FRAGMENT). | sptrembl Q90767 | ND |
| 6058 | 188.7 | HYPOTHETICAL 45.3 KD PROTEIN. | sptrembl O74840 | ND |
| 6059 | 188.5 | PROLINE RICH PROTEIN PRECURSOR. | sptrembl Q43558 | ND |
| 6060 | 188.1 | SERINE/THREONINE PROTEIN KINASE. | tremblnew CAA92266 | ND |
| 6061 | 187.9 | MORPHOGENESIS-RELATED PROTEIN (MULTICOPY SUPPRESSION OF A BUDDING DEFECT 1). | swissprot P21339 | ND |
| 6062 | 187.8 | F58A3.1B PROTEIN. | sptrembl Q93807 | ND |
| 6063 | 187.7 | HYPOTHETICAL BROMODOMAIN CONTAINING PROTEIN. | sptrembl O74350 | ND |
| 6064 | 187.6 | HYPOTHETICAL 36.9 KD PROTEIN C02D5.2 IN CHROMOSOME III. | swissprot P34276 | ND |
| 6065 | 1868.6 | SONA. | sptrembl O74224 | ND |
| 6067 | 1860.7 | GLUTAMIC ACID DECARBOXYLASE. | tremblnew BAA88152 | Amino acid transport and metabolism |
| 6068 | 1860.0 | F57B10.3 PROTEIN. | sptrembl O44742 | Carbohydrate transport and metabolism |
| 6069 | 186.8 | GLUE PROTEIN. | sptrembl Q27423 | ND |
| 6070 | 186.8 | KIAA0595 PROTEIN (FRAGMENT). | sptrembl Q9Y4E0 | ND |
| 6071 | 186.8 | _Cercospora kikuchii_ membrane pump protein. | geneseqp W35808 | ND |
| 6072 | 186.8 | MEMBRANE COMPONENT, CHROMOSOME 17, SURFACE MARKER 2 (OVARIAN CARCINOMA ANTIGEN CA125) (1A1-3B) (KIAA0049). | swissprot Q14596 | ND |
| 6073 | 186.8 | WP6 PRECURSOR. | sptrembl Q39492 | ND |
| 6074 | 186.6 | DNA-DIRECTED RNA POLYMERASE II LARGEST SUBUNIT (EC 2.7.7.6). | swissprot P16356 | ND |
| 6075 | 186.6 | COMES FROM THIS GENE. | sptrembl O23054 | ND |
| 6076 | 186.5 | AT2G11910 PROTEIN. | tremblnew AAD22502 | ND |
| 6077 | 186.1 | ADENOMATOSIS POLYPOSIS COLI (APC) (BALB/C APC). | sptrembl Q61315 | ND |
| 6078 | 186.0 | PROTEOPHOSPHOGLYCAN (FRAGMENT). | sptrembl Q9Y075 | ND |
| 6079 | 1854.7 | TRANSCRIPTION INITIATION FACTOR TFIID (TATA-BOX FACTOR) (TATA SEQUENCE-BINDING PROTEIN) (TBP). | swissprot Q12731 | Transcription |
| 6080 | 185.8 | DJ37E16.2 PROTEIN. | sptrembl Q9Y3L3 | ND |
| 6081 | 185.7 | HYPOTHETICAL 30.6 KD PROTEIN. | sptrembl O94440 | ND |
| 6082 | 185.6 | CAPSULAR ASSOCIATED PROTEIN. | sptrembl Q9Y8B9 | ND |
| 6083 | 185.6 | HAC1 PROTEIN. | swissnew P41546 | ND |
| 6084 | 185.2 | CANDIDAPEPSIN 3 PRECURSOR (EC 3.4.23.24) (ASPARTATE PROTEASE 3) (ACP 3) (SECRETED ASPARTIC PROTEASE 3). | swissprot P43092 | ND |
| 6085 | 185.0 | GLUTATHIONE S-TRANSFERASE 1 (EC 2.5.1.18) (SR8) (GST CLASS-THETA). | swissprot P28342 | ND |
| 6086 | 1841.8 | FATTY ACID SYNTHASE, ALPHA SUBUNIT. | sptrembl P78615 | Lipid metabolism |

TABLE 3-continued

_Aspergillus oryzae ESTs_

| Sequence Listing | zscore | Annotation | Database | Functional Category |
|---|---|---|---|---|
| 6087 | 184.9 | PROTEIN PHOSPHATASE 2C HOMOLOG 3 (EC 3.1.3.16) (PP2C-3). | swissprot Q09173 | ND |
| 6088 | 184.7 | PUTATIVE IMPORTIN ALPHA SUBUNIT (FRAGMENT). | tremblnew BAA87276 | ND |
| 6089 | 184.6 | HYPOTHETICAL 69.2 KD PROTEIN IN HSP30-PMP1 INTERGENIC REGION. | swissprot P25351 | ND |
| 6090 | 184.6 | RNA BINDING PROTEIN (FRAGMENT). | tremblnew BAA83714 | ND |
| 6091 | 184.3 | HYPOTHETICAL PROTEIN IN LEU2 3' REGION (FRAGMENT). | swissprot P34735 | ND |
| 6092 | 184.3 | REGION B OF COSMID SCY07H7. | sptrembl O06266 | ND |
| 6093 | 184.1 | VIRAL PROTEIN TPX. | swissprot P19275 | ND |
| 6094 | 184.1 | SON OF SEVENLESS PROTEIN HOMOLOG 1 (SOS-1) (MSOS-1). | swissprot Q62245 | ND |
| 6095 | 184.0 | PROTEOPHOSPHOGLYCAN (FRAGMENT). | sptrembl Q9Y075 | ND |
| 6096 | 1839.9 | HYPOTHETICAL 44.3 KD PROTEIN C27E2.03C IN CHROMOSOME I. | sptrembl O13998 | ND |
| 6097 | 1832.6 | PUTATIVE DISULFIDE ISOMERASE TIGA PRECURSOR (EC 5.3.4.1). | swissprot Q00216 | ND |
| 6098 | 1830.2 | CYSTEIN RICH PROTEIN. | sptrembl O13319 | ND |
| 6099 | 183.9 | DENTIN PHOSPHOPROTEIN PRECURSOR. | sptrembl P70578 | ND |
| 6100 | 183.9 | EXTENSIN-LIKE PROTEIN. | tremblnew CAB40774 | ND |
| 6101 | 183.9 | HU1-70K SMALL NUCLEAR RNP PROTEIN (RNP12) (FRAGMENT). | sptrembl P78494 | ND |
| 6102 | 183.8 | HYPOTHETICAL 35.1 KD PROTEIN. | tremblnew CAB38264 | ND |
| 6103 | 183.7 | PUTATIVE CARBOXYPEPTIDASE. | sptrembl Q9X7P4 | ND |
| 6104 | 183.7 | HYPOTHETICAL 113.1 KD PROTEIN IN PRE5-FET4 INTERGENIC REGION. | swissprot Q04893 | ND |
| 6105 | 183.7 | _Mycobacterium tuberculosis_ antigen TbH-30. | geneseqp W64360 | ND |
| 6106 | 183.6 | PROTEOPHOSPHOGLYCAN (FRAGMENT). | sptrembl Q9Y075 | ND |
| 6107 | 183.4 | PLENTY-OF-PROLINES-101. | sptrembl O70495 | ND |
| 6108 | 183.4 | NITROGEN METABOLITE REPRESSION REGULATOR NMRA. | sptrembl O59919 | ND |
| 6109 | 183.4 | MEI2 protein kinase PAT1 encoded by AR301. | geneseqp W00160 | ND |
| 6110 | 183.3 | GENOME, PARTIAL SEQUENCE. | sptrembl Q84529 | ND |
| 6111 | 183.2 | LARGE TEGUMENT PROTEIN. | swissprot P03186 | ND |
| 6112 | 182.9 | PREDICTED PROTEIN OF UNKNOWN FUNCTION. | sptrembl O22758 | ND |
| 6113 | 182.6 | HYPOTHETICAL 28.3 KD PROTEIN IN AROD-COMER INTERGENIC REGION. | swissprot P54458 | ND |
| 6114 | 182.6 | SALIVARY PROLINE-RICH PROTEIN RP15 PRECURSOR. | sptrembl Q04154 | ND |
| 6115 | 182.5 | MITOCHONDRIAL OUTER MEMBRANE PROTEIN MMM1. | swissprot P41800 | ND |
| 6116 | 182.3 | EXTENSIN = NODULE-SPECIFIC PROLINE-RICH PROTEIN {CLONE VFNDS-E}. | tremblnew G425682 | ND |

TABLE 3-continued

_Aspergillus oryzae ESTs_

| Sequence Listing | zscore | Annotation | Database | Functional Category |
|---|---|---|---|---|
| 6117 | 182.3 | F24K9.9 PROTEIN. | tremblnew AAF00656 | ND |
| 6118 | 182.1 | DNA-DIRECTED RNA POLYMERASE II LARGE (205 KD) SUBUNIT (EC 2.7.7.6) (FRAGMENT). | sptrembl Q99368 | ND |
| 6119 | 182.0 | AT2G42310 PROTEIN. | tremblnew AAD23714 | ND |
| 6120 | 1812.2 | G PROTEIN ALPHA SUBUNIT HOMOLOG GANAP. | sptrembl Q9Y7E3 | ND |
| 6121 | 1810.8 | MEDUSA. | sptrembl O74251 | ND |
| 6122 | 1810.1 | ISOCITRATE LYASE (EC 4.1.3.1) (ISOCITRASE) (ISOCITRATASE) (ICL). | swissprot P28298 | Energy production and conversion |
| 6123 | 181.8 | PUTATIVE GLUCOSAMINE--FRUCTOSE-6-PHOSPHATE AMINOTRANSFERASE [ISOMERIZING] (EC 2.6.1.16) (HEXOSEPHOSPHATE AMINOTRANSFERASE) (D-FRUCTOSE-6-PHOSPHATE AMIDOTRANSFERASE) (GFAT). | swissprot Q09740 | ND |
| 6124 | 181.8 | HYPOTHETICAL 15.8 KD PROTEIN IN SMI1-PHO81 INTERGENIC REGION. | swissprot P50084 | ND |
| 6125 | 181.7 | NTR. | tremblnew AAF23950 | ND |
| 6126 | 181.6 | HYPOTHETICAL 15.6 KD PROTEIN C29B12.13 IN CHROMOSOME I. | sptrembl O14034 | ND |
| 6127 | 181.6 | QUINATE PERMEASE (QUINATE TRANSPORTER). | swissprot P15325 | ND |
| 6128 | 181.4 | HYPOTHETICAL 15.2 KD PROTEIN. | sptrembl Q9XEF8 | ND |
| 6129 | 181.3 | _M. tuberculosis_ antigen TbH-30 amino acid sequence. | geneseqp Y39157 | ND |
| 6130 | 181.1 | EXTENSIN PRECURSOR (CELL WALL HYDROXYPROLINE-RICH GLYCOPROTEIN). | swissprot P13983 | ND |
| 6131 | 181.1 | PUTATIVE SNRNP PROTEIN. | tremblnew CAB45810 | ND |
| 6132 | 181.0 | CEOA. | sptrembl O06470 | ND |
| 6133 | 1809.7 | GENERAL AMINO-ACID PERMEASE GAP1. | swissprot P19145 | Amino acid transport and metabolism |
| 6134 | 1801.9 | _Aspergillus oryzae_ alpha-glucosidase. | geneseqp W15191 | ND |
| 6135 | 180.9 | C-HORDEIN. | sptrembl Q41210 | ND |
| 6136 | 180.9 | TRFA. | sptrembl O77033 | ND |
| 6137 | 180.9 | HIGH MOLECULAR WEIGHT BASIC NUCLEAR PROTEIN (FRAGMENT). | sptrembl Q91238 | ND |
| 6138 | 180.9 | Human breast tumour-associated protein 62. | geneseqp Y48517 | ND |
| 6139 | 180.6 | SPLICEOSOME ASSOCIATED PROTEIN 49 (SAP 49) (SF3B53). | swissprot Q15427 | ND |
| 6140 | 180.5 | PUTATIVE VICILIN STORAGE PROTEIN (GLOBULIN-LIKE). | sptrembl Q9ZU69 | ND |
| 6141 | 180.5 | Fragment of human secreted protein encoded by gene 79. | geneseqp Y41541 | ND |
| 6142 | 180.4 | PROBABLE MONOOXYGENASE RV0892 (EC 1.14.13.-). | swissnew Q10532 | ND |
| 6143 | 180.2 | HYPOTHETICAL 50.3 KD PROTEIN. | tremblnew CAB55170 | ND |
| 6144 | 180.1 | _Mycobacterium_ species protein sequence 5C'. | geneseqp Y04776 | ND |

TABLE 3-continued

*Aspergillus oryzae* ESTs

| Sequence Listing | zscore | Annotation | Database | Functional Category |
|---|---|---|---|---|
| 6145 | 1791.2 | GLUCOSE-6-PHOSPHATE 1-DEHYDROGENASE (EC 1.1.1.49) (G6PD). | swissprot P48826 | Carbohydrate transport and metabolism |
| 6146 | 1790.6 | PHOSPHOENOLPYRUVATE CARBOXYKINASE [ATP] (EC 4.1.1.49). | swissprot O43112 | Energy production and conversion |
| 6147 | 179.8 | SERINE 2 ULTRA HIGH SULFUR PROTEIN. | sptrembl Q62220 | ND |
| 6148 | 179.4 | CYCLOPHILIN-RELATED PROTEIN. | tremblnew AAA35734 | ND |
| 6149 | 179.3 | PROLINE-RICH PROTEIN. | sptrembl Q64306 | ND |
| 6150 | 178.9 | HYPOTHETICAL PROTEIN C30B4.01C IN CHROMOSOME II (FRAGMENT). | sptrembl P87179 | ND |
| 6151 | 178.5 | PISTIL-SPECIFIC EXTENSIN-LIKE PROTEIN (FRAGMENT). | sptrembl Q40552 | ND |
| 6152 | 178.4 | RNA BINDING PROTEIN (FRAGMENT). | tremblnew BAA83714 | ND |
| 6153 | 178.3 | GLUE PROTEIN. | sptrembl Q27929 | ND |
| 6154 | 178.2 | HYPOTHETICAL 14.0 KD PROTEIN IN RPL15B-GCR3 INTERGENIC REGION. | swissprot Q03880 | ND |
| 6155 | 178.1 | EXTENSIN-LIKE PROTEIN. | tremblnew CAB37452 | ND |
| 6156 | 178.0 | YFKN PROTEIN. | sptrembl O34313 | ND |
| 6157 | 178.0 | GAMMA-BUTYROBETAINE,2-OXOGLUTARATE DIOXYGENASE (EC 1.14.11.1) (GAMMA-BUTYROBETAINE HYDROXYLASE) (GAMMA-BBH). | swissprot P80193 | ND |
| 6158 | 1771.1 | ALTERNATIVE OXIDASE PRECURSOR (EC 1.-.-.-). | swissnew O74180 | ND |
| 6159 | 177.9 | AP-1-LIKE TRANSCRIPTION FACTOR. | tremblnew CAB66170 | ND |
| 6160 | 177.9 | HYPOTHETICAL 118.4 KD PROTEIN IN BAT2-DAL5 INTERGENIC REGION PRECURSOR. | swissprot P47179 | ND |
| 6161 | 177.8 | HYPOTHETICAL STRUCTURAL PROTEIN. | tremblnew CAB53076 | ND |
| 6162 | 177.6 | HYPOTHETICAL 77.4 KD PROTEIN. | sptrembl O65530 | ND |
| 6163 | 177.6 | EXTENSIN (FRAGMENT). | sptrembl Q41645 | ND |
| 6164 | 177.4 | HYPOTHETICAL 14.0 KD PROTEIN. | sptrembl O74383 | ND |
| 6165 | 177.4 | EXTENSIN (FRAGMENT). | sptrembl Q41645 | ND |
| 6166 | 177.2 | FROM BASES 2561111 TO 2573808 (SECTION 222 OF 400) OF THE COMPLETE GENOME (SECTION 222 OF 400). | sptrembl P76555 | ND |
| 6167 | 177.1 | PEARLI 1-LIKE PROTEIN. | tremblnew CAB41720 | ND |
| 6168 | 177.1 | TRANSCRIPTION FACTOR ZFM1. | sptrembl Q15637 | ND |
| 6169 | 177.0 | CORE PROTEIN. | sptrembl Q64897 | ND |
| 6170 | 177.0 | GASTRIC MUCIN (FRAGMENT). | sptrembl Q29070 | ND |
| 6171 | 177.0 | EXTENSIN (FRAGMENT). | sptrembl Q41645 | ND |
| 6172 | 1764.6 | *Aspergillus oryzae* porphobilinogen synthase. | geneseqp W30558 | Coenzyme metabolism |
| 6173 | 1760.0 | CITRATE SYNTHASE, MITOCHONDRIAL PRECURSOR (EC 4.1.3.7). | swissprot P51044 | Energy production and conversion |
| 6174 | 176.8 | Human complement factor CR4 vWF domain sequence. | geneseqp Y21992 | ND |
| 6175 | 176.8 | GASTRIC MUCIN (FRAGMENT). | sptrembl Q29070 | ND |

TABLE 3-continued

_Aspergillus oryzae ESTs_

| Sequence Listing | zscore | Annotation | Database | Functional Category |
|---|---|---|---|---|
| 6176 | 176.7 | C24B5.5 PROTEIN. | tremblnew AAD31546 | ND |
| 6177 | 176.7 | PROTEOPHOSPHOGLYCAN PRECURSOR (FRAGMENT). | sptrembl Q9Y076 | ND |
| 6178 | 176.4 | SPLICING FACTOR, ARGININE/SERINE-RICH 8 (SUPPRESSOR OF WHITE APRICOT PROTEIN HOMOLOG). | swissprot Q12872 | ND |
| 6179 | 176.3 | EXTENSIN. | sptrembl Q39599 | ND |
| 6180 | 176.3 | PROLINE-RICH MUCIN HOMOLOG. | sptrembl Q9XDH2 | ND |
| 6181 | 176.3 | PROTEOPHOSPHOGLYCAN (FRAGMENT). | sptrembl Q9Y075 | ND |
| 6182 | 176.2 | HYPOTHETICAL 41.5 KD PROTEIN. | tremblnew CAB66198 | ND |
| 6183 | 176.2 | AP-1-LIKE TRANSCRIPTION FACTOR. | swissprot P56095 | ND |
| 6184 | 1750.0 | PUTATIVE ATP-CITRATE (PRO-S-)-LYASE (EC 4.1.3.8) (CITRATE CLEAVAGE ENZYME). | sptrembl O13907 | ND |
| 6185 | 175.9 | SF16 ISOLOG. | sptrembl O22835 | ND |
| 6186 | 175.5 | HEPATITIS A VIRUS RECEPTOR. | sptrembl O18984 | ND |
| 6187 | 175.4 | HYPOTHETICAL 52.3 KD PROTEIN IN MRPL10-ERG24 INTERGENIC REGION PRECURSOR. | swissprot P53832 | ND |
| 6188 | 175.3 | F19G14.12 PROTEIN. | sptrembl Q9XIL9 | ND |
| 6189 | 175.3 | HYPOTHETICAL 59.4 KD PROTEIN. | sptrembl Q89392 | ND |
| 6190 | 174.9 | PUTATIVE TRANSCRIPTIONAL ACTIVATOR. | tremblnew CAB59617 | ND |
| 6191 | 174.8 | MRNA EXPRESSED IN CUCUMBER HYPOCOTYLS, COMPLETE CDS. | sptrembl Q9XIV1 | ND |
| 6192 | 174.7 | _Teredinibacter endoglucanase._ | geneseqp W34989 | ND |
| 6193 | 174.7 | PLENTY-OF-PROLINES-101. | sptrembl O70495 | ND |
| 6194 | 174.6 | KIAA0396 (FRAGMENT). | sptrembl O43146 | ND |
| 6195 | 174.6 | HYPOTHETICAL PROLINE-RICH PROTEIN (FRAGMENT). | swissprot P21260 | ND |
| 6196 | 174.6 | P210 PROTEIN (FRAGMENT). | sptrembl Q9XGA4 | ND |
| 6197 | 174.2 | Helix modification recognition protein Hmpl. | geneseqp W19120 | ND |
| 6198 | 174.0 | Human alternatively spliced ETS2 repressor factor (AERF). | geneseqp W07701 | ND |
| 6199 | 1736.2 | ACETAMIDASE REGULATORY PROTEIN. | swissprot Q06157 | ND |
| 6200 | 173.9 | HEPATITIS A VIRUS CELLULAR RECEPTOR 1 LONG FORM (HEPATITIS A VIRUS CELLULAR RECEPTOR 1 SHORT FORM). | sptrembl O46597 | ND |
| 6201 | 173.9 | TYROSINE-PROTEIN KINASE RECEPTOR TIE-1 PRECURSOR (EC 2.7.1.112). | swissprot Q06806 | ND |
| 6202 | 173.9 | EXTENSIN. | sptrembl Q39599 | ND |
| 6203 | 173.9 | PUTATIVE SPINDLE POLE BODY COMPONENT, PUTATIVE GAMMA-TUBULIN INTERACTING PROTEIN, YEAST SCP98 HOMOLOG (FRAGMENT). | sptrembl O94366 | ND |
| 6204 | 173.9 | F35E2.5 PROTEIN. | sptrembl O62223 | ND |
| 6205 | 173.9 | PUTATIVE. | sptrembl Q9ZKY5 | ND |
| 6206 | 173.8 | HYPOTHETICAL 76.9 KD PROTEIN. | sptrembl O43085 | ND |

TABLE 3-continued

*Aspergillus oryzae* ESTs

| Sequence Listing | zscore | Annotation | Database | Functional Category |
|---|---|---|---|---|
| 6207 | 173.8 | PROTEOPHOSPHOGLYCAN (FRAGMENT). | sptrembl Q9Y075 | ND |
| 6208 | 173.8 | FIBROIN-4 (FRAGMENT). | sptrembl Q16988 | ND |
| 6209 | 173.7 | PISTIL-SPECIFIC EXTENSIN-LIKE PROTEIN PRECURSOR (PELP). | swissprot Q03211 | ND |
| 6210 | 173.6 | ANOTHER TRANSCRIPTION UNIT PROTEIN (ATU). | sptrembl Q94546 | ND |
| 6211 | 173.6 | (VSP-3) PRECURSOR. | sptrembl Q39620 | ND |
| 6212 | 173.5 | SER/ARG-RELATED NUCLEAR MATRIX PROTEIN. | sptrembl O60585 | ND |
| 6213 | 173.5 | MUCIN 2 PRECURSOR (INTESTINAL MUCIN 2). | swissprot Q02817 | ND |
| 6214 | 173.4 | WP6 PRECURSOR. | sptrembl Q39492 | ND |
| 6215 | 173.3 | SALIVARY PROLINE-RICH PROTEIN RP4 PRECURSOR. | sptrembl Q04117 | ND |
| 6216 | 173.3 | Fragmented human NF-H gene +2 frameshift mutant product. | geneseqp W18663 | ND |
| 6217 | 173.2 | K09A9.6 PROTEIN. | sptrembl Q93178 | ND |
| 6218 | 173.1 | PENICILLIN-BINDING PROTEIN 1. | tremblnew AAF10059 | ND |
| 6219 | 173.1 | MICROTUBULE-ASSOCIATED PROTEIN 4 (FRAGMENT). | sptrembl Q98906 | ND |
| 6220 | 173.0 | HYPOTHETICAL PROTEIN C30B4.01C IN CHROMOSOME II (FRAGMENT). | sptrembl P87179 | ND |
| 6221 | 173.0 | HYPOTHETICAL 29.3 KD PROTEIN (ORF92). | swissprot O10341 | ND |
| 6222 | 1725.6 | TIP49. | sptrembl O35753 | DNA replication, recombination and repair |
| 6223 | 172.9 | HYPERPOLARIZATION-ACTIVATED CATION CHANNEL, HAC1. | sptrembl O88703 | ND |
| 6224 | 172.8 | F40E10.1 PROTEIN. | sptrembl Q20200 | ND |
| 6225 | 172.8 | TRANSCRIPTION FACTOR RCC/EPB-1. | sptrembl Q91294 | ND |
| 6226 | 172.8 | DNA-DIRECTED RNA POLYMERASE II LARGE (205 KD) SUBUNIT (EC 2.7.7.6) (FRAGMENT). | sptrembl Q99366 | ND |
| 6227 | 172.7 | M01F1.5 PROTEIN. | sptrembl Q21455 | ND |
| 6228 | 172.4 | CUTINASE TRANSCRIPTION FACTOR 1 BETA. | swissprot P52959 | ND |
| 6229 | 172.4 | HYPOTHETICAL PROLINE-RICH PROTEIN (FRAGMENT). | swissprot P21260 | ND |
| 6230 | 172.2 | STE20/PAK KINASE HOMOLOGUE. | sptrembl O00911 | ND |
| 6231 | 172.1 | WP6 PRECURSOR. | sptrembl Q39492 | ND |
| 6232 | 172.0 | HYPOTHETICAL 33.4 KD PROTEIN IN RPL44B-RPC10 INTERGENIC REGION PRECURSOR. | swissprot P38844 | ND |
| 6233 | 172.0 | TRANSCRIPTION FACTOR MBP1 (MBF SUBUNIT P120). | swissprot P39679 | ND |
| 6234 | 1710.3 | ER CHAPERONE BIP. | tremblnew BAA82597 | Posttranslational modification, protein turnover, chaperones |
| 6235 | 171.8 | MEROZOITE SURFACE PROTEIN 2 (FRAGMENT). | sptrembl O15691 | ND |
| 6236 | 171.8 | TRANSCRIPTION FACTOR AP-2 ISOFORM 1 (FRAGMENT). | sptrembl Q60740 | ND |
| 6237 | 171.8 | Y41E3.2 PROTEIN. | sptrembl O62432 | ND |
| 6238 | 171.7 | PEARLI 4 PROTEIN. | tremblnew AAD29820 | ND |

TABLE 3-continued

Aspergillus oryzae ESTs

| Sequence Listing | zscore | Annotation | Database | Functional Category |
|---|---|---|---|---|
| 6239 | 171.3 | CONSERVED HYPOTHETICAL PROTEIN. | tremblnew AAF10001 | ND |
| 6240 | 171.2 | ACETYLXYLAN ESTERASE PRECURSOR (EC 3.1.1.72). | sptrembl Q99034 | ND |
| 6241 | 171.1 | HOMEOBOX PROTEIN. | sptrembl Q98911 | ND |
| 6242 | 171.1 | ATPASE 6. | sptrembl Q33561 | ND |
| 6243 | 1703.0 | ALANYL DIPEPTIDYL PEPTIDASE. | sptrembl Q9Y8E3 | Amino acid transport and metabolism |
| 6244 | 1701.3 | DNA POLYMERASE EPSILON HOMOLOG. | sptrembl O93845 | DNA replication, recombination and repair |
| 6245 | 170.8 | FIBROIN HEAVY CHAIN PRECURSOR (FIB-H) (FRAGMENTS). | swissprot P05790 | ND |
| 6246 | 170.7 | Fragmented human NF-H gene +2 frameshift mutant product. | geneseqp W18663 | ND |
| 6247 | 170.7 | PUTATIVE EXTENSIN. | sptrembl Q9ZNU3 | ND |
| 6248 | 170.6 | HEPATITIS A VIRUS CELLULAR RECEPTOR 1 LONG FORM (HEPATITIS A VIRUS CELLULAR RECEPTOR 1 SHORT FORM). | sptrembl O46598 | ND |
| 6249 | 170.2 | MULTIDRUG RESISTANCE PROTEIN 2 (MULTIDRUG-EFFLUX TRANSPORTER 2). | swissprot P39843 | ND |
| 6250 | 170.1 | ZONA PELLUCIDA PROTEIN (ZP). | sptrembl Q91236 | ND |
| 6251 | 170.1 | RNA BINDING PROTEIN (FRAGMENT). | tremblnew BAA83714 | ND |
| 6252 | 1693.9 | SACCHAROPINE DEHYDROGENASE [NADP+, L-GLUTAMATE FORMING] (EC 1.5.1.10). | swissprot P38999 | Amino acid transport and metabolism |
| 6253 | 1690.9 | NITRITE REDUCTASE [NAD(P)H] (EC 1.6.6.4). | swissprot P22944 | Energy production and conversion |
| 6254 | 169.9 | FLGA insert stabilising polypeptide. | geneseqp W79128 | ND |
| 6255 | 169.6 | PROTEOPHOSPHOGLYCAN (FRAGMENT). | sptrembl Q9Y075 | ND |
| 6256 | 169.6 | SYNAPSIN I (FRAGMENT). | sptrembl O62732 | ND |
| 6257 | 169.6 | A-AGGLUTININ ATTACHMENT SUBUNIT PRECURSOR. | swissprot P32323 | ND |
| 6258 | 169.4 | SUPPRESSOR PROTEIN SRP40. | swissprot P32583 | ND |
| 6259 | 169.3 | KIAA1052 PROTEIN. | tremblnew BAA83004 | ND |
| 6260 | 169.3 | LACTATE DEHYDROGENASE (EC 1.1.1.27). | sptrembl Q43000 | ND |
| 6261 | 169.1 | DNA METHYLASE. | sptrembl O33298 | ND |
| 6262 | 168.8 | HYPOTHETICAL 35.5 KD PROTEIN IN TRANSPOSON TN4556. | swissprot P20186 | ND |
| 6263 | 168.5 | HP8 PEPTIDE. | sptrembl Q92657 | ND |
| 6264 | 168.5 | PROTEOPHOSPHOGLYCAN (FRAGMENT). | sptrembl Q9Y075 | ND |
| 6265 | 168.5 | HOMEOBOX PROTEIN GMIX. | sptrembl O73592 | ND |
| 6266 | 168.2 | GNAS1 PROTEIN (FRAGMENT). | sptrembl O75685 | ND |
| 6267 | 168.1 | PVA1 GENE. | sptrembl Q26195 | ND |
| 6268 | 168.0 | SPERM MITOCHONDRIAL CAPSULE SELENOPROTEIN (MCS). | swissprot P49901 | ND |
| 6269 | 1672.1 | HEXOSE TRANSPORTER. | sptrembl O13311 | ND |
| 6270 | 167.7 | SER/ARG-RELATED NUCLEAR MATRIX PROTEIN. | sptrembl O60585 | ND |

TABLE 3-continued

*Aspergillus oryzae* ESTs

| Sequence Listing | zscore | Annotation | Database | Functional Category |
|---|---|---|---|---|
| 6271 | 167.5 | IRON TRANSPORT MULTICOPPER OXIDASE PRECURSOR (EC 1.-.-.-). | swissprot P38993 | ND |
| 6272 | 167.5 | NUCLEAR PROTEIN. | sptrembl Q24898 | ND |
| 6273 | 167.5 | FERTILIZATION-INDEPENDENT SEED 2 PROTEIN. | sptrembl Q9ZNT9 | ND |
| 6274 | 167.5 | P2567 PROTEIN. | sptrembl Q99373 | ND |
| 6275 | 167.4 | HYPOTHETICAL 29.3 KD PROTEIN. | sptrembl O74943 | ND |
| 6276 | 167.2 | SPLICING COACTIVATOR SUBUNIT SRM300. | tremblnew AAF21439 | ND |
| 6277 | 167.1 | F23M19.11 PROTEIN. | sptrembl Q9XIC7 | ND |
| 6278 | 167.1 | HYPOTHETICAL 26.6 KD PROTEIN C17A2.10C IN CHROMOSOME I. | sptrembl O13760 | ND |
| 6279 | 167.1 | HYPOTHETICAL 133.5 KD PROTEIN F26C11.3 IN CHROMOSOME II. | swissprot Q09550 | ND |
| 6280 | 167.0 | LONG-CHAIN-FATTY-ACID COA LIGASE. | sptrembl O51162 | ND |
| 6281 | 166.9 | ULTRA HIGH SULFER KERATIN. | sptrembl O75690 | ND |
| 6282 | 166.9 | F12K2.3 PROTEIN. | sptrembl Q9XIP3 | ND |
| 6283 | 166.9 | IMMEDIATE-EARLY PROTEIN IE180. | swissprot P33479 | ND |
| 6284 | 166.9 | EXTENSIN-LIKE PROTEIN. | tremblnew CAB40774 | ND |
| 6285 | 166.9 | LOW MOLECULAR WEIGHT GLUTENIN (FRAGMENT). | sptrembl Q41552 | ND |
| 6286 | 166.7 | PROTEOPHOSPHOGLYCAN PRECURSOR (FRAGMENT). | sptrembl Q9Y076 | ND |
| 6287 | 166.7 | TYPE VII COLLAGEN. | sptrembl Q63870 | ND |
| 6288 | 166.5 | ENDO16 PROTEIN (FRAGMENT). | swissprot P13665 | ND |
| 6289 | 166.5 | CYSTEINE-RICH PROTEIN (FRAGMENT). | sptrembl Q16861 | ND |
| 6290 | 166.4 | CELL WALL-PLASMA MEMBRANE LINKER PROTEIN. | sptrembl Q39353 | ND |
| 6291 | 166.4 | RETINA-DERIVED POU-DOMAIN FACTOR-1. | sptrembl P78425 | ND |
| 6292 | 166.4 | HYPOTHETICAL 59.1 KD SERINE-RICH PROTEIN C23C4.10 IN CHROMOSOME I. | sptrembl O13930 | ND |
| 6293 | 166.4 | DENTIN PHOSPHOPROTEIN PRECURSOR. | sptrembl P70578 | ND |
| 6294 | 166.3 | GLUE PROTEIN. | sptrembl Q27423 | ND |
| 6295 | 166.3 | NTR. | tremblnew AAF23950 | ND |
| 6296 | 166.2 | 36.4 KD PROLINE-RICH PROTEIN. | swissprot Q00451 | ND |
| 6297 | 166.2 | F4P13.11 PROTEIN. | tremblnew AAF01541 | ND |
| 6298 | 166.1 | F-BOX PROTEIN FBX11 (FRAGMENT). | tremblnew AAF04520 | ND |
| 6299 | 166.0 | PROTEIN TYROSINE PHOSPHATASE, RECEPTOR TYPE, C PRECURSOR (EC 3.1.3.48) (LYMPHOCYTE COMMON ANTIGEN). | sptrembl Q61812 | ND |
| 6300 | 1653.7 | FUMARYLACETOACETASE (EC 3.7.1.2) (FUMARYLACETOACETATE HYDROLASE) (BETA-DIKETONASE) (FAA) (FAAH) (FAH). | sptrembl Q00770 | ND |
| 6301 | 165.9 | Amino acid sequence of a collagen-like protein. | geneseqp Y23937 | ND |
| 6302 | 165.9 | KIAA0775 PROTEIN. | sptrembl O94873 | ND |

TABLE 3-continued

*Aspergillus oryzae* ESTs

| Sequence Listing | zscore | Annotation | Database | Functional Category |
|---|---|---|---|---|
| 6303 | 165.8 | HYPOTHETICAL 15.4 KD PROTEIN YPR056C. | sptrembl Q12160 | ND |
| 6304 | 165.7 | 2-HYDROXY-6-KETONONA-2,4-DIENOATE HYDROLASE. | sptrembl O05145 | ND |
| 6305 | 165.7 | G-BOX BINDING FACTOR (GBF). | swissprot P36417 | ND |
| 6306 | 165.7 | F4P13.11 PROTEIN. | tremblnew AAF01541 | ND |
| 6307 | 165.6 | POP3. | sptrembl O74184 | ND |
| 6308 | 165.3 | NADH-UBIQUINONE OXIDOREDUCTASE ASHI SUBUNIT PRECURSOR (EC 1.6.5.3) (EC 1.6.99.3) (COMPLEX I-ASHI) (CI-ASHI). | swissprot Q02372 | ND |
| 6309 | 165.3 | PROTEOPHOSPHOGLYCAN (FRAGMENT). | sptrembl Q9Y075 | ND |
| 6310 | 165.3 | HYPOTHETICAL 18.3 KD PROTEIN. | tremblnew CAB65601 | ND |
| 6311 | 165.2 | MATING PROCESS PROTEIN MID2 (SERINE-RICH PROTEIN SMS1) (PROTEIN KINASE A INTERFERENCE PROTEIN). | swissprot P36027 | ND |
| 6312 | 165.2 | ORF OF UNKNOWN FUNCTION. | sptrembl Q09149 | ND |
| 6313 | 165.1 | *Mycobacterium* species protein sequence 50B. | geneseqp Y04998 | ND |
| 6314 | 165.0 | VITELLINE MEMBRANE PROTEIN HOMOLOG. | sptrembl O01362 | ND |
| 6315 | 1649.9 | C-4 METHYL STEROL OXIDASE (EC 1.-.-.-). | swissprot O59933 | ND |
| 6316 | 1644.6 | DIACYLGLYCEROL LIPASE. | sptrembl P78583 | ND |
| 6317 | 164.9 | CELL SURFACE GLYCOPROTEIN 1 PRECURSOR (OUTER LAYER PROTEIN B) (S-LAYER PROTEIN 1). | swissprot Q06852 | ND |
| 6318 | 164.9 | HYPOTHETICAL 97.8 KD PROTEIN. | sptrembl O94685 | ND |
| 6319 | 164.3 | ISOFLAVONE REDUCTASE HOMOLOG (EC 1.3.1.-). | swissprot P52578 | ND |
| 6320 | 164.2 | O-METHYLTRANSFERASE. | sptrembl O07431 | ND |
| 6321 | 164.1 | Y41E3.11 PROTEIN. | tremblnew CAB63361 | ND |
| 6322 | 164.0 | HYPOTHETICAL 39.1 KD PROTEIN. | sptrembl Q9XE89 | ND |
| 6323 | 1639.4 | *Aspergillus oryzae* AreA regulator protein. | geneseqp W31630 | ND |
| 6324 | 1637.8 | Hydroxyphenyl pyruvate dehydrogenase (HPDD) protein. | geneseqp Y15821 | ND |
| 6325 | 1636.3 | SUCCINATE DEHYDROGENASE [UBIQUINONE] IRON-SULFUR PROTEIN, MITOCHONDRIAL PRECURSOR (EC 1.3.5.1) (IP). | swissnew O42772 | Energy production and conversion |
| 6326 | 1633.0 | *A. niger* SFAG 2 carboxypeptidase Y. | geneseqp R96738 | ND |
| 6327 | 163.9 | SIMILARITY TO CHICKEN LIMB DEFORMITY PROTEIN. | sptrembl Q22534 | ND |
| 6328 | 163.9 | HYPOTHETICAL PROTEIN IRL5 (TRL5). | swissprot P16803 | ND |
| 6329 | 163.9 | 5E5 ANTIGEN. | swissprot Q63003 | ND |
| 6330 | 163.8 | VITELLOGENIN (FRAGMENT). | sptrembl Q90237 | ND |
| 6331 | 163.6 | Nucleic acid binding domain from apoB-100. | geneseqp W96830 | ND |

TABLE 3-continued

_Aspergillus oryzae ESTs_

| Sequence Listing | zscore | Annotation | Database | Functional Category |
|---|---|---|---|---|
| 6332 | 163.6 | ANTER-SPECIFIC PROLINE-RICH PROTEIN APG PRECURSOR. | swissprot P40602 | ND |
| 6333 | 163.6 | ARGININE-RICH 54 KD NUCLEAR PROTEIN. | sptrembl Q05519 | ND |
| 6334 | 163.5 | XSMAD4A. | sptrembl Q9W639 | ND |
| 6335 | 163.4 | PRP4 PROTEIN KINASE HOMOLOG (FRAGMENT). | sptrembl O88378 | ND |
| 6336 | 163.2 | SUPPRESSOR PROTEIN SRP40. | swissprot P32583 | ND |
| 6337 | 163.2 | HYPOTHETICAL 77.4 KD PROTEIN. | sptrembl O65530 | ND |
| 6338 | 163.1 | PROLINE-RICH SALIVARY PROTEIN (FRAGMENT). | sptrembl Q62107 | ND |
| 6339 | 1622.8 | GUANINE NUCLEOTIDE-BINDING PROTEIN BETA SUBUNIT-LIKE PROTEIN (CROSS-PATHWAY CONTROL WD-REPEAT PROTEIN CPC-2). | swissprot Q01369 | ND |
| 6340 | 1620.0 | GLUTAMINASE A. | tremblnew BAA86934 | ND |
| 6341 | 162.9 | Peptide fragment of N-type calcium channel. | geneseqp R96419 | ND |
| 6342 | 162.9 | IMMEDIATE-EARLY PROTEIN IE-0. | swissprot O10369 | ND |
| 6343 | 162.8 | SALIVARY GLUE PROTEIN SGS-3 PRECURSOR. | swissprot P13730 | ND |
| 6344 | 162.7 | TOUCAN PROTEIN. | sptrembl O46112 | ND |
| 6345 | 162.7 | COMPLETE GENOME. | tremblnew AAF19337 | ND |
| 6346 | 162.6 | SALIVARY PROLINE-RICH PROTEIN II-1 (FRAGMENT). | swissprot P81489 | ND |
| 6347 | 162.6 | MUCIN (FRAGMENT). | sptrembl Q14888 | ND |
| 6348 | 162.6 | WD REPEAT PROTEIN. | tremblnew CAB52157 | ND |
| 6349 | 162.5 | SIMILAR TO _DROSOPHILA MELANOGASTER_ ANKYRIN. | sptrembl Q84566 | ND |
| 6350 | 162.3 | Notch hN5k full length clone. | geneseqp R28964 | ND |
| 6351 | 162.2 | PROBABLE PROLYL-TRNA SYNTHETASE, CYTOPLASMIC (EC 6.1.1.15) (PROLINE--TRNA LIGASE) (PRORS). | swissprot P39965 | ND |
| 6352 | 162.2 | CODED FOR BY _C. ELEGANS_ CDNA YK91G9.5. | sptrembl Q21721 | ND |
| 6353 | 162.2 | _S. lavendulae_ ORF3 gene product. | geneseqp R72381 | ND |
| 6354 | 162.2 | THIOREDOXIN. | swissnew P50338 | ND |
| 6355 | 162.1 | EXTENSIN PRECURSOR (PROLINE-RICH GLYCOPROTEIN). | swissprot P14918 | ND |
| 6356 | 162.0 | HYPOTHETICAL 48.2 KD PROTEIN. | sptrembl Q04921 | ND |
| 6357 | 1614.5 | EUKARYOTIC INITIATION FACTOR 4A (EIF-4A). | swissprot P47943 | DNA replication, recombination and repair |
| 6358 | 1611.8 | SIGNAL RECOGNITION PARTICLE 54 KD PROTEIN HOMOLOG. | swissprot Q00179 | Cell motility and secretion |
| 6359 | 161.9 | LDLBP. | sptrembl Q9Z160 | ND |
| 6360 | 161.8 | HYPOTHETICAL 36.5 KD PROTEIN. | tremblnew AAD49213 | ND |
| 6361 | 161.8 | DEFECTIVE CHORION-1 PROTEIN PRECURSOR (FRAGMENTS). | sptrembl Q23933 | ND |
| 6362 | 161.7 | TEGUMENT PROTEIN. | sptrembl O09799 | ND |
| 6363 | 161.6 | MUCIN-LIKE PROTEIN. | sptrembl O77242 | ND |
| 6364 | 161.5 | 336AA LONG HYPOTHETICAL DTDP-GLUCOSE 4,6-DEHYDRATASE. | sptrembl O58151 | ND |

TABLE 3-continued

_Aspergillus oryzae ESTs_

| Sequence Listing | zscore | Annotation | Database | Functional Category |
|---|---|---|---|---|
| 6365 | 161.4 | WW DOMAIN BINDING PROTEIN 11. | sptrembl O88539 | ND |
| 6366 | 161.2 | NOC1 PROTEIN. | sptrembl P79065 | ND |
| 6367 | 161.1 | PUTATIVE TRANSCRIPTIONAL REGULATOR. | sptrembl O13337 | ND |
| 6368 | 161.1 | Human N-methyl-D-aspartate receptor subunit encoded by clone NMDA24. | geneseqp W87504 | ND |
| 6369 | 161.0 | THERMAL HYSTERESIS PROTEIN ISOFORM 4–9 PRECURSOR. | tremblnew AAD55256 | ND |
| 6370 | 161.0 | _M. tuberculosis_ immunogenic polypeptide TbH-29. | geneseqp W81726 | ND |
| 6371 | 1608.6 | _Aspergillus niger_ Sulphydryl oxidase (SOX). | geneseqp R43074 | ND |
| 6372 | 1604.5 | ACETYL-COENZYME A SYNTHETASE (EC 6.2.1.1) (ACETATE--COA LIGASE) (ACYL-ACTIVATING ENZYME). | swissprot P16928 | Lipid metabolism |
| 6373 | 1603.1 | 40S RIBOSOMAL PROTEIN S3AE (S1). | swissprot P40910 | Translation, ribosomal structure and biogenesis |
| 6374 | 1602.9 | NADH-UBIQUINONE OXIDOREDUCTASE 30.4 KD SUBUNIT PRECURSOR (EC 1.6.5.3) (EC 1.6.99.3) (COMPLEX I-30 KD) (CI-31 KD). | swissprot P23710 | Energy production and conversion |
| 6375 | 160.8 | ATTACHMENT PROTEIN. | sptrembl Q65306 | ND |
| 6376 | 160.7 | L3162.7. | sptrembl O60978 | ND |
| 6377 | 160.7 | HYPOTHETICAL 49.6 KD PROTEIN C18B11.03C IN CHROMOSOME I. | swissprot Q09710 | ND |
| 6378 | 160.6 | Y53H1A.1 PROTEIN. | tremblnew CAB63392 | ND |
| 6379 | 160.6 | ARGININE/SERINE-RICH PROTEIN. | tremblnew AAF19004 | ND |
| 6380 | 160.6 | CODED FOR BY _C. ELEGANS_ CDNA YK60B10.5. | sptrembl Q94247 | ND |
| 6381 | 160.5 | HYPOTHETICAL 57.2 KD PROTEIN. | sptrembl O68872 | ND |
| 6382 | 160.1 | SERINE/ARGININE-RICH PROTEIN. | tremblnew AAF17288 | ND |
| 6383 | 160.1 | WUGSC:H_NH0353P23.1 PROTEIN (FRAGMENT). | sptrembl O95033 | ND |
| 6384 | 160.0 | LOW MOLECULAR WEIGHT GLUTENIN SUBUNIT PRECURSOR (FRAGMENT). | sptrembl Q9XGE9 | ND |
| 6385 | 160.0 | JAGGED 2 (JAGGED 2 PROTEIN) (FRAGMENT). | sptrembl O70219 | ND |
| 6386 | 159.9 | Peptide encoded by HRGP gene cassette incorporating a GAGP construct. | geneseqp Y01282 | ND |
| 6387 | 159.8 | ADRENAL CREB-RP HOMOLOG. | sptrembl Q99635 | ND |
| 6388 | 159.7 | HYPOTHETICAL 29.0 KD PROTEIN. | sptrembl Q9Y7C9 | ND |
| 6389 | 159.7 | HYDROXYPROLINE-RICH GLYCOPROTEIN. | sptrembl Q40692 | ND |
| 6390 | 159.7 | Mouse Fas-binding protein Daxx. | geneseqp W61532 | ND |
| 6391 | 159.4 | TRANSPOSASE. | sptrembl Q9WXF7 | ND |
| 6392 | 159.4 | KIAA0303 (FRAGMENT). | sptrembl O15021 | ND |
| 6393 | 159.4 | HYPOTHETICAL 31.5 KD PROTEIN. | swissprot P46218 | ND |
| 6394 | 159.4 | COILED-COIL PROTEIN. | sptrembl Q9Y708 | ND |
| 6395 | 159.4 | MUCIN-LIKE PROTEIN. | sptrembl Q9YMX0 | ND |

TABLE 3-continued

*Aspergillus oryzae* ESTs

| Sequence Listing | zscore | Annotation | Database | Functional Category |
|---|---|---|---|---|
| 6396 | 159.3 | TAIL-SPECIFIC THYROID HORMONE UP-REGULATED (GENE 5). | sptrembl Q91638 | ND |
| 6397 | 159.2 | EXTENSIN-LIKE PROTEIN. | tremblnew AAD55980 | ND |
| 6398 | 159.2 | HYPOTHETICAL 96.9 KD PROTEIN. | tremblnew CAA22569 | ND |
| 6399 | 1587.5 | *A. crysogenum* cystathionine beta-synthase. | geneseqp R72589 | Amino acid transport and metabolism |
| 6400 | 1584.8 | PENTAFUNCTIONAL AROM POLYPEPTIDE [INCLUDES: 3-DEHYDROQUINATE SYNTHASE (EC 4.6.1.3); 3-DEHYDROQUINATE DEHYDRATASE (EC 4.2.1.10) (3-DEHYDROQUINASE); SHIKIMATE 5-DEHYDROGENASE (EC 1.1.1.25); SHIKIMATE KINASE (EC 2.7.1.71); EPSP SYNTHASE (EC 2.5.1.19)]. | swissnew P07547 | Amino acid transport and metabolism |
| 6401 | 158.8 | PAP8 PRODUCT (FRAGMENT). | sptrembl Q43586 | ND |
| 6402 | 158.8 | CODED FOR BY *C. ELEGANS* CDNA YK127B8.5. | sptrembl Q20648 | ND |
| 6403 | 158.8 | N-WASP. | sptrembl O00401 | ND |
| 6404 | 158.6 | CTG7A (FRAGMENT). | sptrembl O15413 | ND |
| 6405 | 158.6 | ENDOSPERM TISSUE PRECURSOR. | sptrembl Q41295 | ND |
| 6406 | 158.6 | Fragmented human NF-H gene +2 frameshift mutant product. | geneseqp W18663 | ND |
| 6407 | 158.5 | HYPOTHETICAL 54.4 KD PROTEIN. | tremblnew CAB51187 | ND |
| 6408 | 158.5 | 50 KD PROLINE RICH PROTEIN. | sptrembl Q9ZBP2 | ND |
| 6409 | 158.5 | KIAA0674 PROTEIN (FRAGMENT). | sptrembl Q9Y4D0 | ND |
| 6410 | 158.5 | C46C2.1 PROTEIN. | sptrembl Q18657 | ND |
| 6411 | 158.5 | F13F21.7 PROTEIN. | sptrembl Q9XIB6 | ND |
| 6412 | 158.4 | PROLINE-RICH PROTEIN PRECURSOR. | sptrembl Q41122 | ND |
| 6413 | 158.2 | MOBP. | sptrembl Q13874 | ND |
| 6414 | 158.1 | ATROPHIN-1 (FRAGMENT). | sptrembl O97923 | ND |
| 6415 | 158.1 | PLENTY-OF-PROLINES-101. | sptrembl O70495 | ND |
| 6416 | 158.1 | CNS MYELIN PROTEIN MOBP-169. | tremblnew AAD44968 | ND |
| 6417 | 158.1 | MHC CLASS I CHAIN-RELATED PROTEIN (FRAGMENT). | sptrembl O98020 | ND |
| 6418 | 158.0 | EXTENSIN CLASS II PRECURSOR (CELL WALL HYDROXYPROLINE-RICH GLYCOPROTEIN) (HRGP) (TOML-4). | sptrembl Q09084 | ND |
| 6419 | 1577.4 | ACTIN-RELATED PROTEIN ARPA. | sptrembl Q9Y721 | Cell division and chromosome partitioning |
| 6420 | 1576.4 | 14-3-3 PROTEIN HOMOLOG (TH1433). | swissprot Q99002 | ND |
| 6421 | 1572.6 | INORGANIC PYROPHOSPHATASE (EC 3.6.1.1) (PYROPHOSPHATE PHOSPHO-HYDROLASE) (PPASE). | swissprot O13505 | Energy production and conversion |
| 6422 | 157.9 | Ubiquitin-beta-galactosidase junction. | geneseqp R22231 | ND |
| 6423 | 157.9 | COSMID R153. | sptrembl Q22001 | ND |
| 6424 | 157.9 | PROTEASE (EC 3.4.23.-) (FRAGMENT). | sptrembl Q01875 | ND |
| 6425 | 157.9 | HYPOTHETICAL 32.8 KD PROTEIN (FRAGMENT). | tremblnew CAB55954 | ND |

TABLE 3-continued

Aspergillus oryzae ESTs

| Sequence Listing | zscore | Annotation | Database | Functional Category |
|---|---|---|---|---|
| 6426 | 157.8 | PUTATIVE CYTOCHROME P450. | tremblnew AAF04170 | ND |
| 6427 | 157.8 | HYPOTHETICAL 24.0 KD PROTEIN T28D9.2 IN CHROMOSOME II. | swissprot Q10021 | ND |
| 6428 | 157.7 | EXTENSIN-LIKE PROTEIN. | tremblnew CAB40769 | ND |
| 6429 | 157.7 | DIBASIC PROCESSING ENDOPROTEASE PRECURSOR (EC 3.4.21.-). | swissprot P42781 | ND |
| 6430 | 157.6 | PUTATIVE ZINC FINGER PROTEIN. | sptrembl Q9ZUM9 | ND |
| 6431 | 157.6 | MUCIN (FRAGMENT). | sptrembl Q14881 | ND |
| 6432 | 157.6 | WISKOTT-ALDRICH SYNDROME PROTEIN HOMOLOG 1. | sptrembl O36027 | ND |
| 6433 | 157.6 | ORF 1 AND ORF2 5' REGION PRECURSOR. | sptrembl Q54913 | ND |
| 6434 | 157.5 | CTG26 ALTERNATE OPEN READING FRAME (FRAGMENT). | sptrembl O15421 | ND |
| 6435 | 157.3 | PROTEOPHOSPHOGLYCAN (FRAGMENT). | sptrembl Q9Y075 | ND |
| 6436 | 157.3 | HYDROLASE 314 aa, chain A | pdb 7PCK | ND |
| 6437 | 157.2 | EMPTY SPIRACLES HOMEOTIC PROTEIN. | swissprot P18488 | ND |
| 6438 | 157.1 | POSITIONAL COUNTERPART OF HSV-1 GENE US5. | sptrembl O39307 | ND |
| 6439 | 1567.6 | 40S RIBOSOMAL PROTEIN S4-2. | tremblnew CAB57920 | Translation, ribosomal structure and biogenesis |
| 6440 | 1566.9 | PUTATIVE YEAST CELL DIVISION CYCLE CDC50 HOMOLOG. | sptrembl O94568 | ND |
| 6441 | 1566.3 | ACONITASE. | sptrembl O74699 | Energy production and conversion |
| 6442 | 1563.2 | VACUOLAR ATP SYNTHASE CATALYTIC SUBUNIT A (EC 3.6.1.34) (V-ATPASE 67 KD SUBUNIT). | swissprot P11592 | Energy production and conversion |
| 6443 | 1562.9 | ACETYL-COA ACETYLTRANSFERASE IB (EC 2.3.1.9) (PEROXISOMAL ACETOACETYL-COA THIOLASE) (THIOLASE IB). | swissprot Q04677 | Lipid metabolism |
| 6444 | 156.9 | GASTRIC MUCIN (FRAGMENT). | sptrembl Q29071 | ND |
| 6445 | 156.8 | G-BOX BINDING PROTEIN. | sptrembl O65887 | ND |
| 6446 | 156.8 | HISTIDINE-RICH PROTEIN. | sptrembl O33447 | ND |
| 6447 | 156.8 | PROBABLE E4 PROTEIN. | swissprot P17384 | ND |
| 6448 | 156.7 | EXTENSIN PRECURSOR (PROLINE-RICH GLYCOPROTEIN). | swissprot P24152 | ND |
| 6449 | 156.7 | Porphorymonas gingivalis protein PG87. | geneseqp Y34563 | ND |
| 6450 | 156.5 | NUCLEOLAR PHOSPHOPROTEIN P130. | sptrembl Q14978 | ND |
| 6451 | 156.4 | Residues 253–425 of human type A EBNA2 (strain B95-8). | geneseqp W45092 | ND |
| 6452 | 156.4 | PROLINE RICH PROTEIN. | sptrembl O22514 | ND |
| 6453 | 156.4 | NADH OXIDASE. | sptrembl Q9WYL1 | ND |
| 6454 | 156.4 | HANSENULA MRAKII KILLER TOXIN-RESISTANT PROTEIN 1 PRECURSOR. | swissprot P41809 | ND |
| 6455 | 156.4 | HYPOTHETICAL 28.9 KD PROTEIN. | sptrembl Q03931 | ND |
| 6456 | 156.3 | Sequence of Histidine-rich protein (HisRP). | geneseqp R24393 | ND |
| 6457 | 156.3 | SERINE-RICH PROTEIN. | sptrembl O94317 | ND |

TABLE 3-continued

_Aspergillus oryzae ESTs_

| Sequence Listing | zscore | Annotation | Database | Functional Category |
|---|---|---|---|---|
| 6458 | 156.0 | NEUROMODULIN (AXONAL MEMBRANE PROTEIN GAP-43) (PP46) (B-50) (PROTEIN F1) (CALMODULIN-BINDING PROTEIN P-57). | swissprot P55860 | ND |
| 6459 | 156.0 | GLYCOPROTEIN G-2 (FRAGMENT). | tremblnew CAB65666 | ND |
| 6460 | 156.0 | PRE-NECK APPENDAGE PROTEIN (LATE PROTEIN GP12). | swissprot P20345 | ND |
| 6461 | 156.0 | 167AA LONG HYPOTHETICAL PROTEIN. | sptrembl Q9YAM3 | ND |
| 6462 | 156.0 | CODED FOR BY C. ELEGANS CDNA CEMSE92F. | sptrembl Q19059 | ND |
| 6463 | 1557.7 | PUTATIVE CALCIUM P-TYPE ATPASE (FRAGMENT). | tremblnew CAB65295 | Inorganic ion transport and metabolism |
| 6464 | 1554.5 | PUTATIVE THIAZOLE SYNTHASE. | tremblnew AAF25444 | ND |
| 6465 | 155.9 | G2 GLYCOPROTEIN (FRAGMENT). | sptrembl O55365 | ND |
| 6466 | 155.9 | TR3BETA. | sptrembl Q15627 | ND |
| 6467 | 155.9 | R07E5.6 PROTEIN. | sptrembl Q21823 | ND |
| 6468 | 155.8 | HYDROXYPROLINE-RICH GLYCOPROTEIN. | sptrembl Q40692 | ND |
| 6469 | 155.8 | LORICRIN. | swissprot P23490 | ND |
| 6470 | 155.8 | HYPOTHETICAL 11.7 KD PROTEIN. | sptrembl Q9Y7P8 | ND |
| 6471 | 155.8 | HL60 cell line protein fragment. | geneseqp W73307 | ND |
| 6472 | 155.7 | SALIVARY GLUE PROTEIN SGS-3 PRECURSOR. | swissprot P13729 | ND |
| 6473 | 155.6 | HYPOTHETICAL PROTEIN (ORF2) (FRAGMENT). | swissprot O33369 | ND |
| 6474 | 155.6 | PROLINE RICH PROTEIN. | sptrembl O22514 | ND |
| 6475 | 155.6 | EARLY NODULIN 20 PRECURSOR (N-20). | swissprot P93329 | ND |
| 6476 | 155.5 | Cotton fibrous tissue specific protein KC03. | geneseqp W15761 | ND |
| 6477 | 155.4 | SIGNAL RECEPTOR PROTEIN (FRAGMENT). | tremblnew CAB65469 | ND |
| 6478 | 155.3 | HYPOTHETICAL 63.8 KD PROTEIN IN GUT1-RIM1 INTERGENIC REGION PRECURSOR. | swissprot P38739 | ND |
| 6479 | 155.2 | INTEGRAL MEMBRANE PROTEIN. | sptrembl Q9Y786 | ND |
| 6480 | 155.2 | EYELID. | sptrembl O61603 | ND |
| 6481 | 155.2 | KINESIN-LIKE PROTEIN. | sptrembl O94053 | ND |
| 6482 | 155.2 | 191AA LONG HYPOTHETICAL PROTEIN. | sptrembl Q9YDC9 | ND |
| 6483 | 155.2 | PROTO-ONCOGENE AF4. | sptrembl O88573 | ND |
| 6484 | 155.2 | Fructosyl amino acid oxidase. | geneseqp W24134 | ND |
| 6485 | 155.1 | PREPROACROSIN. | tremblnew CAA41441 | ND |
| 6486 | 155.1 | T04F8.8 PROTEIN. | sptrembl Q22168 | ND |
| 6487 | 155.0 | W07G1.3 PROTEIN. | sptrembl Q9XUK2 | ND |
| 6488 | 1545.4 | TUBULIN BETA CHAIN. | swissprot Q00264 | ND |
| 6489 | 1543.2 | HYPOTHETICAL 30.8 KD PROTEIN. | sptrembl O74710 | ND |
| 6490 | 154.9 | SP85 (FRAGMENT). | sptrembl O61134 | ND |
| 6491 | 154.9 | PACMAN PROTEIN. | sptrembl Q9XZU2 | ND |
| 6492 | 154.6 | NEURAL RETINA-SPECIFIC LEUCINE ZIPPER PROTEIN (NRL) (D14S46E). | swissprot P54845 | ND |
| 6493 | 154.5 | Delivery peptide used in peptide macromolecule complex. | geneseqp W38808 | ND |
| 6494 | 154.4 | EXTENSIN-LIKE PROTEIN, DIF54 PRECURSOR. | sptrembl Q43505 | ND |

TABLE 3-continued

_Aspergillus oryzae ESTs_

| Sequence Listing | zscore | Annotation | Database | Functional Category |
|---|---|---|---|---|
| 6495 | 154.4 | *Mycobacterium* species protein sequence 41T#2. | geneseqp Y04954 | ND |
| 6496 | 154.3 | MEROZOITE SURFACE PROTEIN 1 (FRAGMENT). | tremblnew CAB60129 | ND |
| 6497 | 154.3 | HYPOTHETICAL 73.6 KD PROTEIN RV2082. | swissnew Q10690 | ND |
| 6498 | 154.2 | *Trypanosoma cruzi* TCR27 polypeptide, Ag15. | geneseqp R84568 | ND |
| 6499 | 154.2 | HYPOTHETICAL 97.1 KD PROTEIN C32A11.02C IN CHROMOSOME I. | swissprot Q10327 | ND |
| 6500 | 154.2 | CYTOCHROME B (FRAGMENT). | sptrembl O03563 | ND |
| 6501 | 154.2 | KIAA0324 PROTEIN (FRAGMENT). | tremblnew BAA20782 | ND |
| 6502 | 154.2 | HIGH MOLECULAR WEIGHT BASIC NUCLEAR PROTEIN (FRAGMENT). | sptrembl Q91238 | ND |
| 6503 | 154.0 | PUTATIVE PHOSPHOTRANSFERASE. | sptrembl Q9X8F0 | ND |
| 6504 | 154.0 | Y24F12A.4 PROTEIN. | tremblnew CAB60327 | ND |
| 6505 | 1539.0 | PROBABLE ISOCITRATE DEHYDROGENASE. | tremblnew CAB62099 | Amino acid transport and metabolism |
| 6506 | 1537.1 | PUTATIVE PHOSPHATIDYLINOSITOL-KINASE (FRAGMENT). | sptrembl Q9Y7K2 | ND |
| 6507 | 153.9 | MAJOR FACILITATOR SUPERFAMILY PROTEIN. | sptrembl O59738 | ND |
| 6508 | 153.9 | SPORE COAT PROTEIN SP96. | swissprot P14328 | ND |
| 6509 | 153.9 | HERPES SIMPLEX VIRUS TYPE 2 (STRAIN HG52), COMPLETE GENOME. | sptrembl P90493 | ND |
| 6510 | 153.5 | F40H3.1 PROTEIN. | tremblnew AAC67429 | ND |
| 6511 | 153.5 | PROLINE RICH PROTEIN. | sptrembl Q91810 | ND |
| 6512 | 153.5 | EYELID. | sptrembl O61603 | ND |
| 6513 | 153.5 | 111AA LONG HYPOTHETICAL PROTEIN. | sptrembl O59222 | ND |
| 6514 | 153.4 | PENICILLIN-BINDING PROTEIN 1. | tremblnew AAF10059 | ND |
| 6515 | 153.4 | ENDOSTYLE-SPECIFIC. | sptrembl O44238 | ND |
| 6516 | 153.2 | PREDICTED PROTEIN. | sptrembl O49570 | ND |
| 6517 | 153.2 | SPLICING FACTOR U2AF 65 KD SUBUNIT (U2 AUXILIARY FACTOR 65 KD SUBUNIT) (U2 SNRNP AUXILIARY FACTOR LARGE SUBUNIT) (U2AF65). | swissprot P90727 | ND |
| 6518 | 153.2 | HRCQ HOMOLOG. | tremblnew AAD46901 | ND |
| 6519 | 153.2 | HYPOTHETICAL 46.5 KD PROTEIN. | sptrembl Q9X7U6 | ND |
| 6520 | 153.1 | PUTATIVE 3 BETA-HYDROXYSTEROID DEHYDROGENASE/DELTA 5--4-ISOMERASE (3BETA-HSD) [INCLUDES: 3-BETA-HYDROXY-DELTA(5)-STEROID DEHYDROGENASE (EC 1.1.1.145) (3-BETA-HYDROXY-5-ENE STEROID DEHYDROGENASE) (PROGESTERONE REDUCTASE); STEROID DELTA-ISOMERASE (EC 5.3.3.1) (DELTA-5-3-KETOSTEROID ISOMERASE)]. | swissprot P53199 | ND |
| 6521 | 153.1 | (TGGCA-BINDING PROTEIN). | sptrembl Q91797 | ND |

TABLE 3-continued

*Aspergillus oryzae* ESTs

| Sequence Listing | zscore | Annotation | Database | Functional Category |
|---|---|---|---|---|
| 6522 | 153.0 | CONSERVED HYPOTHETICAL PROTEIN. | tremblnew AAF12297 | ND |
| 6523 | 153.0 | SPORE COAT PROTEIN SP96. | swissprot P14328 | ND |
| 6524 | 153.0 | NUCLEAR PROTEIN. | sptrembl Q24898 | ND |
| 6525 | 153.0 | PUTATIVE PROLINE-RICH PROTEIN PRP2 PRECURSOR. | sptrembl Q9ZQ10 | ND |
| 6526 | 153.0 | ZINC FINGER PROTEIN 157. | swissprot P51786 | ND |
| 6527 | 153.0 | MYOSIN-IA. | sptrembl O77202 | ND |
| 6528 | 1527.6 | ACID PHOSPHATASE PRECURSOR (EC 3.1.3.2). | swissprot P34724 | ND |
| 6529 | 1526.1 | ALPHA-MANNOSIDASE (EC 3.2.1.113). | sptrembl Q12563 | ND |
| 6530 | 152.9 | SERINE-RICH PROTEIN. | sptrembl O94317 | ND |
| 6531 | 152.9 | ZHB0005.1. | tremblnew CAB55413 | ND |
| 6532 | 152.8 | CAVEOLIN-2. | swissprot Q18879 | ND |
| 6533 | 152.8 | SIALIDASE (EC 3.2.1.18) (EXO-ALPHA-SIALIDASE) (NEURAMINIDASE) (N-ACYLNEURAMINATE GLYCOHYDROLASE) (ALPHA-NEURAMINIDASE). | sptrembl Q59164 | ND |
| 6534 | 152.7 | MFS14 PROTEIN PRECURSOR. | swissprot Q01900 | ND |
| 6535 | 152.6 | SIMILAR TO PHOSPHATIDIC ACID PHOSPHATASE. | tremblnew CAB52620 | ND |
| 6536 | 152.6 | F32D8.7 PROTEIN. | sptrembl Q19961 | ND |
| 6537 | 152.6 | F24J5.4. | tremblnew AAD49970 | ND |
| 6538 | 152.6 | GENOME, PARTIAL SEQUENCE. | sptrembl Q98457 | ND |
| 6539 | 152.6 | OVERLAPPING PROTEIN. | tremblnew AAF09239 | ND |
| 6540 | 152.3 | PUTATIVE PROLINE-RICH CELL WALL PROTEIN. | sptrembl O82327 | ND |
| 6541 | 152.3 | CYTOCHROME P450-LIKE PROTEIN. | tremblnew CAB38283 | ND |
| 6542 | 152.1 | GENE 3 PROTEIN. | swissprot P28988 | ND |
| 6543 | 152.0 | P21 REX {ALTERNATIVELY SPLICED}. | tremblnew G263535 | ND |
| 6544 | 1517.8 | VACUOLAR ATP SYNTHASE SUBUNIT AC39 (EC 3.6.1.34) (V-ATPASE AC39 SUBUNIT) (V-ATPASE 41 KD SUBUNIT). | swissprot P53659 | Energy production and conversion |
| 6545 | 1515.2 | CYSTEINE SYNTHASE (EC 4.2.99.8) (O-ACETYLSERINE SULFHYDRYLASE) (O-ACETYLSERINE (THIOL)-LYASE) (CSASE). | swissprot P50867 | Amino acid transport and metabolism |
| 6547 | 1513.5 | ACETAMIDASE (EC 3.5.1.4). | swissprot P08158 | ND |
| 6548 | 1510.5 | CYTOCHROME C1, HEME PROTEIN PRECURSOR. | swissprot P07142 | ND |
| 6549 | 151.9 | HYPOTHETICAL ZINC-FINGER PROTEIN. | sptrembl O74823 | ND |
| 6550 | 151.8 | GIANT SECRETORY PROTEIN I-A PRECURSOR (GSP-IA) (BALBIANI RING-1 CHAIN) (FRAGMENT). | sptrembl Q00625 | ND |
| 6551 | 151.8 | PUTATIVE TRANSCRIPTIONAL ACTIVATOR. | sptrembl O59830 | ND |
| 6552 | 151.7 | F53B7.5 PROTEIN. | sptrembl Q19522 | ND |
| 6553 | 151.7 | PROBABLE GLUCONOKINASE (EC 2.7.1.12) (GLUCONATE KINASE). | swissprot Q10242 | ND |
| 6554 | 151.7 | 232AA LONG HYPOTHETICAL PROTEIN. | sptrembl Q9YA94 | ND |

TABLE 3-continued

_Aspergillus oryzae ESTs_

| Sequence Listing | zscore | Annotation | Database | Functional Category |
|---|---|---|---|---|
| 6555 | 151.6 | GLUTAMYL-TRNA REDUCTASE 3 PRECURSOR (EC 1.2.1.-)(GLUTR). | swissprot O65796 | ND |
| 6556 | 151.5 | PROTEASE 1. | sptrembl O13304 | ND |
| 6557 | 151.5 | RNA BINDING PROTEIN (FRAGMENT). | tremblnew BAA83717 | ND |
| 6558 | 151.5 | HYPOTHETICAL 34.8 KD PROTEIN. | tremblnew CAB41147 | ND |
| 6559 | 151.4 | 50 KD PROLINE RICH PROTEIN. | sptrembl Q9ZBP2 | ND |
| 6560 | 151.4 | ORF58. | sptrembl O36408 | ND |
| 6561 | 151.3 | HYPOTHETICAL 61.1 KD PROTEIN (FRAGMENT). | tremblnew CAB63715 | ND |
| 6562 | 151.3 | SPLICING FACTOR, ARGININE/SERINE-RICH 10 (PUTATIVE MYELIN REGULATORY FACTOR 1) (MRF-1) (FRAGMENT). | swissprot Q60701 | ND |
| 6563 | 151.2 | _Acetobacter xylinum_ CMCase ORF2 gene product. | geneseqp W69762 | ND |
| 6564 | 151.2 | JC8.8 PROTEIN. | sptrembl O62289 | ND |
| 6565 | 151.2 | CCAAT/ENHANCER CORE BINDING PROTEIN. | sptrembl Q91346 | ND |
| 6566 | 151.1 | 375AA LONG HYPOTHETICAL PROTEIN. | sptrembl Q9Y949 | ND |
| 6567 | 151.1 | HYDROXYPROLINE-RICH GLYCOPROTEIN PRECURSOR. | sptrembl Q41719 | ND |
| 6568 | 151.0 | HYPOTHETICAL 40.0 KD PROTEIN. | tremblnew AAF10516 | ND |
| 6569 | 1509.7 | HOMOACONITASE PRECURSOR (EC 4.2.1.36) (HOMOACONITATE HYDRATASE). | swissprot Q92412 | ND |
| 6570 | 1509.3 | NMT1 PROTEIN HOMOLOG. | swissprot P42882 | Inorganic ion transport and metabolism |
| 6571 | 1506.7 | PHOSPHATIDYLGLYCEROL /PHOSPHATIDYLINOSITOL TRANSFER PROTEIN. | sptrembl O94183 | ND |
| 6572 | 1505.6 | 6-PHOSPHOGLUCONATE DEHYDROGENASE, DECARBOXYLATING 1 (EC 1.1.1.44). | swissprot P38720 | Carbohydrate transport and metabolism |
| 6573 | 1503.8 | _A. niger_ 2,3-dihydroxybenzoic acid decarboxylase protein. | geneseqp W93483 | ND |
| 6574 | 1502.3 | CITRATE SYNTHASE, MITOCHONDRIAL PRECURSOR (EC 4.1.3.7). | swissprot O00098 | Energy production and conversion |
| 6575 | 1500.0 | GTP-BINDING PROTEIN YPT1. | swissprot P33723 | ND |
| 6576 | 150.9 | FLGA insert stabilising polypeptide. | geneseqp W79128 | ND |
| 6577 | 150.8 | EMR1 (FRAGMENT). | sptrembl O08743 | ND |
| 6578 | 150.8 | SALIVARY GLUE PROTEIN SGS-3 PRECURSOR. | swissprot P02840 | ND |
| 6579 | 150.7 | OXIDOREDUCTASE, SHORT-CHAIN DEHYDROGENASE/REDUC TASE FAMILY. | tremblnew AAF09705 | ND |
| 6580 | 150.7 | PROBABLE E4 PROTEIN. | swissprot P06425 | ND |
| 6581 | 150.6 | PUTATIVE ABC-TRANSPORTER, PERMEASE SUBUNIT. | sptrembl Q9Y8J6 | ND |
| 6582 | 150.6 | PUTATIVE GLYCOSYLTRANSFERASE. | tremblnew CAB60235 | ND |
| 6583 | 150.5 | REGULATORY PROTEIN E2. | sptrembl O40620 | ND |
| 6584 | 150.4 | NEM (NEM). | sptrembl Q94543 | ND |
| 6585 | 150.3 | HYPOTHETICAL 20.8 KD PROTEIN (FRAGMENT). | sptrembl Q69020 | ND |
| 6586 | 150.2 | MAJOR CENTROMERE AUTOANTIGEN B | swissnew P49451 | ND |

TABLE 3-continued

Aspergillus oryzae ESTs

| Sequence Listing | zscore | Annotation | Database | Functional Category |
|---|---|---|---|---|
| | | (CENTROMERE PROTEIN B) (CENP-B) (FRAGMENT). | | |
| 6587 | 150.2 | FISSION YEAST (FRAGMENT). | sptrembl P78755 | ND |
| 6588 | 150.2 | MULTIDRUG RESISTANCE PROTEIN. | tremblnew AAF15356 | ND |
| 6589 | 150.2 | HYPOTHETICAL 42.2 KD PROTEIN. | tremblnew CAB63772 | ND |
| 6590 | 150.2 | Human urogenital sinus-derived growth inhibitory factor ps20. | geneseqp W18066 | ND |
| 6591 | 150.2 | Immunodominant fragment of flagellar pocket antigen of *T. brucei*. | geneseqp R85174 | ND |
| 6592 | 150.2 | TRANSLATION RELEASE FACTOR SUBUNIT 1. | sptrembl O59948 | ND |
| 6593 | 150.1 | KIAA0339. | sptrembl O15047 | ND |
| 6594 | 150.1 | T16O11.4 PROTEIN. | tremblnew AAF07827 | ND |
| 6595 | 150.1 | SER/ARG-RELATED NUCLEAR MATRIX PROTEIN. | sptrembl O60585 | ND |
| 6596 | 150.0 | CYTOCHROME OXIDASE I (FRAGMENT). | sptrembl O21778 | ND |
| 6597 | 150.0 | RNA BINDING PROTEIN (FRAGMENT). | tremblnew BAA83714 | ND |
| 6598 | 1496.1 | *A. oryzae* DEBY 1058 locus protein sequence. | geneseqp Y39874 | Inorganic ion transport and metabolism |
| 6599 | 1495.3 | 3-KETOACYL-COA THIOLASE, PEROXISOMAL PRECURSOR (EC 2.3.1.16) (BETA-KETOTHIOLASE) (ACETYL-COA ACYLTRANSFERASE) (PEROXISOMAL 3-OXOACYL-COA THIOLASE). | swissprot Q05493 | Lipid metabolism |
| 6600 | 1495.1 | ORYZIN PRECURSOR (EC 3.4.21.63) (ALKALINE PROTEINASE) (ALP) (ASPERGILLUS PROTEINASE B) (ASPERGILLOPEPTIDASE B). | swissprot P12547 | Posttranslational modification, protein turnover, chaperones |
| 6601 | 1494.2 | PUTATIVE ARYL-ALCOHOL DEHYDROGENASE AAD14 (EC 1.1.1.-). | swissprot P42884 | Energy production and conversion |
| 6602 | 1494.1 | ARGININOSUCCINATE SYNTHASE (EC 6.3.4.5) (CITRULLINE--ASPARTATE LIGASE). | sptrembl O94354 | Amino acid transport and metabolism |
| 6603 | 1493.3 | BETA-N-ACETYLHEXOSAMINIDASE PRECURSOR (EC 3.2.1.52). | tremblnew AAF00010 | ND |
| 6604 | 1492.7 | AMIDOPHOSPHORIBOSYLT RANSFERASE (EC 2.4.2.14) (GLUTAMINE PHOSPHORIBOSYLPYROPH OSPHATE AMIDOTRANSFERASE) (ATASE). | swissnew Q12698 | Nucleotide transport |
| 6606 | 149.7 | 61 KD PROTEIN HOMOLOG. | swissprot O10270 | ND |
| 6607 | 149.7 | F57H12.6 PROTEIN. | sptrembl O45097 | ND |
| 6608 | 149.6 | MATING PROCESS PROTEIN MID2 (SERINE-RICH PROTEIN SMS1) (PROTEIN KINASE A INTERFERENCE PROTEIN). | swissprot P36027 | ND |
| 6609 | 149.6 | OMEGA SECALIN. | sptrembl O04365 | ND |
| 6610 | 149.6 | PUTATIVE EXTENSIN. | sptrembl Q9ZNU3 | ND |

TABLE 3-continued

Aspergillus oryzae ESTs

| Sequence Listing | zscore | Annotation | Database | Functional Category |
|---|---|---|---|---|
| 6611 | 149.6 | Rabphilin-3A. | geneseqp R57421 | ND |
| 6612 | 149.5 | HISTONE H1. | swissprot P23444 | ND |
| 6613 | 149.5 | Recombinant transcription enhancer factor 1 RTEF-1A. | geneseqp W58599 | ND |
| 6614 | 149.4 | AT2G22180 PROTEIN. | tremblnew AAD23622 | ND |
| 6615 | 149.4 | PROLINE RICH PROTEIN. | sptrembl O22514 | ND |
| 6616 | 149.3 | Human proteasome-inhibiting protein (PI31). | geneseqp Y31376 | ND |
| 6617 | 149.3 | GASTRIC MUCIN (FRAGMENT). | sptrembl Q29070 | ND |
| 6618 | 149.3 | PROLINE RICH PROTEIN. | sptrembl O22514 | ND |
| 6619 | 149.3 | Y18D10A.12 PROTEIN. | sptrembl Q9XW11 | ND |
| 6620 | 149.2 | PROTEIN KINASE DC2 (EC 2.7.1.-). | swissprot P16912 | ND |
| 6621 | 149.2 | SALIVARY PROLINE-RICH PROTEIN PRECURSOR (CLONE CP7) [CONTAINS: BASIC PEPTIDE P-F] (FRAGMENT). | swissprot P02812 | ND |
| 6622 | 149.2 | T7I23.17 PROTEIN. | sptrembl O81911 | ND |
| 6623 | 149.0 | RIBOSOMAL PROTEIN S4 (FRAGMENT). | tremblnew CAA58926 | ND |
| 6624 | 149.0 | Human Nkx2.2 protein fragment corresponding to exon 2. | geneseqp Y25175 | ND |
| 6625 | 1484.6 | ADP-RIBOSYLATION FACTOR. | swissprot P34727 | ND |
| 6626 | 1482.2 | GTP-BINDING NUCLEAR PROTEIN GSP2/CNR2. | swissprot P32836 | ND |
| 6627 | 148.9 | PROTEOPHOSPHOGLYCAN (FRAGMENT). | sptrembl Q9Y075 | ND |
| 6628 | 148.9 | Human neurofilament-M mutant protein fragment 10. | geneseqp Y20728 | ND |
| 6629 | 148.8 | TRANSCRIPTION FACTOR SOX-9. | swissprot P48436 | ND |
| 6630 | 148.8 | CHROMOBOX HOMOLOG 4 (DROSOPHILA PC CLASS) (TRANSCRIPTIONAL REPRESSOR MPC2). | sptrembl O55187 | ND |
| 6631 | 148.7 | Human apolipoprotein E mutant protein fragment 11. | geneseqp Y20298 | ND |
| 6632 | 148.7 | Human secreted protein encoded from gene 16. | geneseqp Y30826 | ND |
| 6633 | 148.5 | ZINC FINGER PROTEIN GLI3. | swissnew Q61602 | ND |
| 6634 | 148.5 | HYPOTHETICAL 35.1 KD PROTEIN. | tremblnew CAB38264 | ND |
| 6635 | 148.4 | F23H12.1 PROTEIN. | sptrembl Q19767 | ND |
| 6636 | 148.4 | 56 KD TYPE-SPECIFIC ANTIGEN PRECURSOR (TSA) (56 KD SCRUB TYPHUS ANTIGEN) (STA56) (TSR56). | swissprot P37916 | ND |
| 6637 | 148.3 | OPACITY OUTERMEMBRANE PROTEIN (FRAGMENT). | sptrembl Q51125 | ND |
| 6638 | 148.3 | M. grisea PTH12 gene product. | geneseqp Y06786 | ND |
| 6639 | 148.2 | CAMP RESPONSE ELEMENT-BINDING PROTEIN CRE-BPA (FRAGMENT). | tremblnew AAC79689 | ND |
| 6640 | 148.2 | ENVELOPE POLYPROTEIN GP160 PRECURSOR [CONTAINS: EXTERIOR MEMBRANE GLYCOPROTEIN (GP120); TRANSMEMBRANE GLYCOPROTEIN (GP41)]. | swissprot P15831 | ND |
| 6641 | 148.2 | Glucose repressor CRE1 of T. harzianum. | geneseqp W13845 | ND |
| 6642 | 148.2 | Trypanosoma cruzi antigen repeat sequence. | geneseqp W19102 | ND |

TABLE 3-continued

*Aspergillus oryzae* ESTs

| Sequence Listing | zscore | Annotation | Database | Functional Category |
|---|---|---|---|---|
| 6643 | 148.2 | *Mycobacterium* species protein sequence 50B. | geneseqp Y04998 | ND |
| 6644 | 148.1 | U2 SMALL NUCLEAR RIBONUCLEOPROTEIN AUXILIARY FACTOR 35 KD SUBUNIT RELATED-PROTEIN 1. | swissprot Q15695 | ND |
| 6645 | 148.1 | PUTATIVE ACETYL TRANSFERASE. | tremblnew AAF05992 | ND |
| 6646 | 148.1 | AMPHOTROPIC MURINE RETROVIRUS RECEPTOR. | sptrembl Q63488 | ND |
| 6647 | 148.1 | 40S RIBOSOMAL PROTEIN S4 (S7) (YS6) (RP5). | swissprot P05753 | ND |
| 6648 | 148.0 | HYPOTHETICAL 316.1 KD PROTEIN ZC84.1 IN CHROMOSOME III. | swissprot Q03610 | ND |
| 6649 | 1473.8 | ALPHA-GLUCOSIDASE (EC 3.2.1.20) (MALTASE). | swissprot Q02751 | Carbohydrate transport and metabolism |
| 6650 | 1472.1 | 60S RIBOSOMAL PROTEIN L1-B (L10A). | swissprot O74836 | Translation, ribosomal structure and biogenesis |
| 6651 | 1471.7 | OSMOTIC SENSITIVITY MAP KINASE. | tremblnew AAF09475 | Signal transduction mechanisms |
| 6652 | 1471.2 | BIFUNCTIONAL PURINE BIOSYNTHESIS PROTEIN ADE17 [INCLUDES: PHOSPHORIBOSYLAMINOI MIDAZOLECARBOXAMIDE FORMYLTRANSFERASE (EC 2.1.2.3) (AICAR TRANSFORMYLASE); IMP CYCLOHYDROLASE (EC 3.5.4.10) (INOSINICASE) (IMP SYNTHETASE) (ATIC)]. | swissprot P38009 | Nucleotide transport |
| 6653 | 147.9 | DLXIN-1. | tremblnew BAA87959 | ND |
| 6654 | 147.9 | HCR1. | sptrembl O22112 | ND |
| 6655 | 147.9 | PROLINE-RICH PROTEIN. | tremblnew CAB62487 | ND |
| 6656 | 147.8 | F22D6.5 PROTEIN. | sptrembl Q19727 | ND |
| 6657 | 147.8 | Y53H1A.1 PROTEIN. | tremblnew CAB63392 | ND |
| 6658 | 147.8 | PROTEASE. | sptrembl O40637 | ND |
| 6659 | 147.7 | MYOSIN LIGHT CHAIN KINASE ISOFORM-I. | sptrembl O01651 | ND |
| 6660 | 147.5 | HYDROXYPROLINE-RICH PROTEIN. | sptrembl Q39949 | ND |
| 6661 | 147.5 | HYPOTHETICAL 37.9 KD PROTEIN C17D1.05 IN CHROMOSOME II. | swissprot Q10203 | ND |
| 6662 | 147.4 | LOW TEMPERATURE ESSENTIAL PROTEIN. | swissprot P07866 | ND |
| 6663 | 147.3 | HYPOTHETICAL 79.7 KD PROTEIN (FRAGMENT). | sptrembl Q9Y4Q3 | ND |
| 6664 | 147.3 | Prod. of DNA of pMG07 used to isolate style-stigma specific gene STG07. | geneseqp R10531 | ND |
| 6665 | 147.3 | T23F1.5 PROTEIN. | sptrembl O18117 | ND |
| 6666 | 147.3 | HYDROXYPROLINE-RICH GLYCOPROTEIN. | sptrembl Q41814 | ND |
| 6667 | 147.3 | DNA-DIRECTED RNA POLYMERASE II LARGE (205 KD) SUBUNIT (EC 2.7.7.6) (FRAGMENT). | sptrembl Q99367 | ND |
| 6668 | 147.2 | 3-ISOPROPYLMALATE DEHYDROGENASE (LEUB). | sptrembl Q51345 | ND |
| 6669 | 147.2 | HYPOTHETICAL 34.9 KD PROTEIN. | sptrembl O65548 | ND |
| 6670 | 147.1 | HYDROPHOBIN COH2. | sptrembl P78602 | ND |

TABLE 3-continued

_Aspergillus oryzae ESTs_

| Sequence Listing | zscore | Annotation | Database | Functional Category |
|---|---|---|---|---|
| 6671 | 147.1 | CODED FOR BY _C. ELEGANS_ CDNA YK102F9.3. | sptrembl O01593 | ND |
| 6672 | 147.0 | PUTATIVE ARGININE/SERINE-RICH SPLICING FACTOR. | sptrembl O82021 | ND |
| 6673 | 147.0 | HYPOTHETICAL 50.7 KD PROTEIN. | tremblnew AAD49204 | ND |
| 6674 | 1467.3 | ATP CITRATE LYASE. | sptrembl O93988 | ND |
| 6675 | 1461.7 | Mutant _Aspergillus oryzae_ DEBY932 rescued locus. | geneseqp W37992 | Carbohydrate transport and metabolism |
| 6677 | 146.9 | HYPOTHETICAL 22.8 KD PROTEIN. | tremblnew AAF11733 | ND |
| 6678 | 146.9 | ZHB0005.1. | tremblnew CAB55413 | ND |
| 6679 | 146.8 | HYPOTHETICAL 96.1 KD PROTEIN IN RIM1-RPS14A INTERGENIC REGION. | swissprot P25623 | ND |
| 6680 | 146.8 | ARGININE/SERINE-RICH PROTEIN. | tremblnew AAF19004 | ND |
| 6681 | 146.7 | GASTRIC MUCIN (FRAGMENT). | sptrembl Q29071 | ND |
| 6682 | 146.7 | TRANSPOSABLE ELEMENT ACTIVATOR HYPOTHETICAL 12 KD PROTEIN (AC 12 KD PROTEIN). | swissprot P08771 | ND |
| 6683 | 146.6 | HYPOTHETICAL 102.5 KD PROTEIN B0001.5 IN CHROMOSOME IV. | sptrembl Q17414 | ND |
| 6684 | 146.5 | HYPOTHETICAL 72.1 KD PROTEIN. | sptrembl O23333 | ND |
| 6685 | 146.5 | SPLICEOSOME ASSOCIATED PROTEIN 62 (SAP 62) (SF3A66). | swissprot Q62203 | ND |
| 6686 | 146.5 | CTG26 ALTERNATE OPEN READING FRAME (FRAGMENT). | sptrembl O15421 | ND |
| 6687 | 146.3 | FUSION PROTEIN. | sptrembl Q9YTP6 | ND |
| 6688 | 146.3 | 32 KDA PROTEIN. | sptrembl O09501 | ND |
| 6689 | 146.3 | SEC24A PROTEIN (FRAGMENT). | sptrembl O95486 | ND |
| 6690 | 146.2 | COLLAGEN (FRAGMENT). | sptrembl Q17266 | ND |
| 6691 | 146.2 | _Mycobacterium_ species protein sequence 41T#3. | geneseqp Y04955 | ND |
| 6692 | 146.1 | DNA-BINDING PROTEIN. | sptrembl P87016 | ND |
| 6693 | 146.1 | EXTENSIN PRECURSOR (PROLINE-RICH GLYCOPROTEIN). | swissprot P14918 | ND |
| 6694 | 146.1 | COLLAGEN ALPHA 1(X) CHAIN PRECURSOR. | swissprot P23206 | ND |
| 6695 | 146.0 | ORF MSV234 HYPOTHETICAL PROTEIN. | sptrembl Q9YVK9 | ND |
| 6696 | 146.0 | PUTATIVE PROLINE-RICH PROTEIN. | sptrembl Q9ZW08 | ND |
| 6697 | 146.0 | PHYTOCHROME A. | swissprot P06592 | ND |
| 6698 | 146.0 | EXTENSIN. | sptrembl Q39600 | ND |
| 6699 | 1459.6 | BETA-MANNOSIDASE (EC 3.2.1.25). | tremblnew CAB63902 | ND |
| 6700 | 1458.3 | 1,3-BETA-D-GLUCAN SYNTHASE CATALYTIC SUBUNIT. | sptrembl Q92225 | ND |
| 6701 | 1457.4 | MALATE SYNTHASE, GLYOXYSOMAL (EC 4.1.3.2). | swissnew P28344 | Energy production and conversion |
| 6702 | 1455.0 | MODA. | tremblnew AAF24514 | ND |
| 6703 | 1450.9 | ADP-RIBOSYLATION FACTOR. | swissprot P34727 | ND |
| 6704 | 145.9 | LEUCYL AMINOPEPTIDASE, PUTATIVE. | tremblnew AAF10295 | ND |
| 6705 | 145.9 | ENDOSTYLE-SPECIFIC. | sptrembl O44238 | ND |

TABLE 3-continued

_Aspergillus oryzae ESTs_

| Sequence Listing | zscore | Annotation | Database | Functional Category |
|---|---|---|---|---|
| 6706 | 145.8 | CODED FOR BY C. ELEGANS CDNA YK24B4.5. | sptrembl Q23064 | ND |
| 6707 | 145.8 | HISTIDINE-RICH. | sptrembl Q18751 | ND |
| 6708 | 145.8 | PANCREATIC HORMONE PRECURSOR (PANCREATIC POLYPEPTIDE) (PP). | swissprot P13083 | ND |
| 6709 | 145.7 | INTRONIC ORF6 (FRAGMENT). | sptrembl O79867 | ND |
| 6710 | 145.7 | Fusaric acid resistance protein encoded by fadB. | geneseqp R13839 | ND |
| 6711 | 145.7 | Human oncoprotein hhc-M mutant protein #3. | geneseqp W40357 | ND |
| 6712 | 145.4 | HYPOTHETICAL 23.0 KD PROTEIN. | sptrembl O94539 | ND |
| 6713 | 145.4 | HYPOTHETICAL 14.4 KD PROTEIN. | tremblnew AAF11093 | ND |
| 6714 | 145.4 | HYPOTHETICAL 56.0 KD PROTEIN. | sptrembl O66965 | ND |
| 6715 | 145.4 | Secreted protein of clone B0114_1. | geneseqp W69339 | ND |
| 6716 | 145.4 | ARGININE-RICH 54 KD NUCLEAR PROTEIN. | sptrembl Q05519 | ND |
| 6717 | 145.3 | YUSZ PROTEIN. | sptrembl O34907 | ND |
| 6718 | 145.3 | CCA2 PROTEIN. | sptrembl O35048 | ND |
| 6719 | 145.2 | 144AA LONG HYPOTHETICAL PROTEIN. | sptrembl Q9YD73 | ND |
| 6720 | 145.2 | OLFACTORY RECEPTOR (FRAGMENT). | sptrembl Q9Z232 | ND |
| 6721 | 145.1 | SPERM HISTONE P2 PRECURSOR (PROTAMINE 2). | sptrembl Q02097 | ND |
| 6722 | 145.0 | FIN19.3. | tremblnew AAF19693 | ND |
| 6723 | 145.0 | COPROPORPHYRINOGEN III OXIDASE PRECURSOR (EC 1.3.3.3) (COPROPORPHYRINOGENASE) (COPROGEN OXIDASE) (COX). | swissprot P36551 | ND |
| 6724 | 1449.1 | PEROXISOME ASSEMBLY PROTEIN CAR1 (PEROXIN-2). | swissprot P51021 | ND |
| 6725 | 1449.0 | NAD-SPECIFIC GLUTAMATE DEHYDROGENASE (EC 1.4.1.2) (NAD-GDH) (FRAGMENTS). | swissprot P00365 | Amino acid transport and metabolism |
| 6726 | 1448.4 | 60S RIBOSOMAL PROTEIN L2. | sptrembl O94253 | Translation, ribosomal structure and biogenesis |
| 6727 | 1445.5 | 60S RIBOSOMAL PROTEIN L2 (YL6) (L5) (RP8). | swissprot P05736 | Translation, ribosomal structure and biogenesis |
| 6728 | 1444.9 | _Aspergillus fumigatus_ protein 3. | geneseqp W69392 | Amino acid transport and metabolism |
| 6729 | 1443.0 | 26S PROTEASE REGULATORY SUBUNIT 8 HOMOLOG (SUG1 PROTEIN) (CIM3 PROTEIN) (TAT-BINDING PROTEIN TBY1). | swissprot Q01939 | Posttranslational modification, protein turnover, chaperones |
| 6730 | 1442.1 | EPOXIDE HYDROLASE (EC 3.3.2.3). | tremblnew CAB59812 | ND |
| 6731 | 144.8 | LWS OPSIN. | sptrembl Q9W771 | ND |
| 6732 | 144.7 | Banana ripening fruit chitinase. | geneseqp Y05847 | ND |
| 6733 | 144.7 | (AG876 ISOLATE) U2-IR2 DOMAIN ENCODING NUCLEAR PROTEIN EBNA2, COMPLETE CDS. | sptrembl Q69022 | ND |

TABLE 3-continued

Aspergillus oryzae ESTs

| Sequence Listing | zscore | Annotation | Database | Functional Category |
|---|---|---|---|---|
| 6734 | 144.6 | CODED FOR BY C. ELEGANS CDNA YK91G9.5. | sptrembl Q21721 | ND |
| 6735 | 144.6 | PISTIL-SPECIFIC EXTENSIN-LIKE PROTEIN PRECURSOR (FRAGMENT). | sptrembl Q40548 | ND |
| 6736 | 144.6 | LSFR1 PROTEIN (FRAGMENT). | sptrembl Q9W6U3 | ND |
| 6737 | 144.5 | MYCB. | tremblnew AAF08796 | ND |
| 6738 | 144.5 | PROBABLE MANNOSYLTRANSFERASE KTR5 (EC 2.4.1.131). | swissprot P53966 | ND |
| 6739 | 144.5 | HYPOTHETICAL 50.6 KD PROTEIN IN THE 5'REGION OF GYRA AND GYRB (ORF 3). | swissprot P21561 | ND |
| 6740 | 144.5 | Thyroid peroxidase deletion mutant 10. | geneseqp W48791 | ND |
| 6741 | 144.4 | FILAGGRIN (PROFILAGGRIN) (FRAGMENT). | sptrembl Q03840 | ND |
| 6742 | 144.3 | Murine secreted protein K39_7. | geneseqp Y08631 | ND |
| 6743 | 144.3 | P2X2 RECEPTOR (FRAGMENT). | sptrembl O88481 | ND |
| 6744 | 144.1 | Human interferon alpha2/omega1(Glu) hybrid. | geneseqp R24030 | ND |
| 6745 | 144.0 | R12E2.5 PROTEIN. | sptrembl O61787 | ND |
| 6746 | 144.0 | BETA-GALACTOSIDASE ALPHA PEPTIDE (FRAGMENT). | sptrembl Q46478 | ND |
| 6747 | 144.0 | COMPLETE GENOME (FRAGMENT). | sptrembl O41250 | ND |
| 6748 | 1437.3 | PROBABLE CALCIUM-TRANSPORTING ATPASE 6 (EC 3.6.1.38). | swissprot P39986 | Inorganic ion transport and metabolism |
| 6749 | 1434.1 | PROLYL DIPEPTIDYL PEPTIDASE PRECURSOR (EC 3.4.14.5) (DIPEPTIDYL-PEPTIDASE IV) (DIPEPTIDYL AMINOPEPTIDASE IV) (XAA-PRO-DIPEPTIDYLAMINOPEPTIDASE) (GLY-PRO NAPHTHYLAMIDASE) (POST-PROLINE DIPEPTIDYL AMINOPEPTIDASE IV). | sptrembl O42812 | Amino acid transport and metabolism |
| 6750 | 143.9 | PUTATIVE PROLINE-RICH PROTEIN. | tremblnew CAB43973 | ND |
| 6751 | 143.9 | N-MYC PROTO-ONCOGENE PROTEIN. | swissprot P03966 | ND |
| 6752 | 143.9 | Bovine prion protein derived peptide III. | geneseqp Y07999 | ND |
| 6753 | 143.8 | Protein encoded by pLIV1 gene partial sequence. | geneseqp W34528 | ND |
| 6754 | 143.8 | HEPATITIS A VIRUS CELLULAR RECEPTOR 1 LONG FORM (HEPATITIS A VIRUS CELLULAR RECEPTOR 1 SHORT FORM). | sptrembl O46597 | ND |
| 6755 | 143.8 | HRSMAD1/5. | sptrembl O97044 | ND |
| 6756 | 143.8 | SERUM OPACITY FACTOR PRECURSOR (FRAGMENT). | sptrembl Q9XCK5 | ND |
| 6757 | 143.8 | F45B8.3 PROTEIN. | tremblnew CAB05726 | ND |
| 6758 | 143.8 | NADH DEHYDROGENASE SUBUNIT 4 (FRAGMENT). | tremblnew AAF17853 | ND |
| 6759 | 143.8 | EXTENSIN (PROLINE-RICH GLYCOPROTEIN) (CLONE UG) (FRAGMENT). | sptrembl Q01944 | ND |

TABLE 3-continued

_Aspergillus oryzae ESTs_

| Sequence Listing | zscore | Annotation | Database | Functional Category |
|---|---|---|---|---|
| 6760 | 143.7 | HTLV-I RELATED ENDOGENOUS RETROVIRAL SEQUENCE P25 (HRES-1/1). | sptrembl P13985 | ND |
| 6761 | 143.7 | NUCLEAR FACTOR I-B2 (NUCLEAR FACTOR 1 B-TYPE). | sptrembl O00712 | ND |
| 6762 | 143.7 | HOMEOBOX PROTEIN GOOSECOID. | swissnew P54366 | ND |
| 6763 | 143.7 | Y47H9B.1 PROTEIN. | sptrembl Q9XWZ7 | ND |
| 6764 | 143.6 | LW OPSIN (FRAGMENT). | sptrembl Q28879 | ND |
| 6765 | 143.5 | HYPOTHETICAL 45.9 KD PROTEIN AC3.3 IN CHROMOSOME V PRECURSOR. | sptrembl Q17400 | ND |
| 6766 | 143.5 | Rat rSK2 protein. | geneseqp W63702 | ND |
| 6767 | 143.5 | F07A5.2 PROTEIN. | sptrembl Q19138 | ND |
| 6768 | 143.4 | PROTAMINE. | swissprot P17502 | ND |
| 6769 | 143.4 | MITOCHONDRIAL TRANSFER RNA HIS, 16S RIBOSOMAL RNA (16S RRNA) GENES, ND3 (16S RRNA). | sptrembl Q35014 | ND |
| 6770 | 143.3 | HYPOTHETICAL 34.6 KD PROTEIN. | sptrembl Q9Y7R6 | ND |
| 6771 | 143.3 | GROUCHO 1 PROTEIN (FRAGMENT). | swissprot O13168 | ND |
| 6772 | 143.3 | SERICIN PRECURSOR. | swissprot P07856 | ND |
| 6774 | 143.3 | SERINE-RICH PROTEIN. | sptrembl O94317 | ND |
| 6775 | 143.2 | ARGININE/SERINE-RICH PROTEIN. | tremblnew AAF19004 | ND |
| 6776 | 143.2 | SALIVARY GLAND SECRETION PROTEIN (FRAGMENT). | sptrembl Q9Y0E8 | ND |
| 6777 | 143.2 | P28II antigen. | geneseqp P82966 | ND |
| 6778 | 143.1 | STRAIN Z29, COMPLETE GENOME. | tremblnew AAD49620 | ND |
| 6779 | 143.1 | Collagen like protein (CLP)-V1. | geneseqp R95144 | ND |
| 6780 | 143.0 | Z10F PROTEIN. | sptrembl O87025 | ND |
| 6781 | 1427.2 | SULFATE PERMEASE SUTB. | tremblnew AAF14539 | Inorganic ion transport and metabolism |
| 6782 | 1421.8 | MALATE SYNTHASE, GLYOXYSOMAL (EC 4.1.3.2). | swissnew P28345 | Energy production and conversion |
| 6783 | 1420.4 | PROTEIN TRANSPORT PROTEIN SEC23 HOMOLOG. | sptrembl O74873 | ND |
| 6784 | 1420.4 | 60S RIBOSOMAL PROTEIN L15. | swissprot O13418 | Translation, ribosomal structure and biogenesis |
| 6785 | 142.9 | C29F7.5 PROTEIN. | sptrembl O17617 | ND |
| 6786 | 142.9 | _Drosophila_ Acp36DE protein. | geneseqp Y22176 | ND |
| 6787 | 142.8 | GIBBERELLIN-REGULATED PROTEIN 1 PRECURSOR. | swissprot P46689 | ND |
| 6788 | 142.8 | NADH-UBIQUINONE OXIDOREDUCTASE SUBUNIT 1. | tremblnew CAB55576 | ND |
| 6789 | 142.7 | PISTIL EXTENSIN-LIKE PROTEIN. | sptrembl Q40385 | ND |
| 6790 | 142.7 | SANT DOMAIN PROTEIN SMRTER. | tremblnew AAD52614 | ND |
| 6791 | 142.7 | ALDEHYDE DEHYDROGENASE, CYTOCHROME C SUBUNIT PRECURSOR. | sptrembl O30327 | ND |
| 6792 | 142.7 | Y49E10.17 PROTEIN. | sptrembl Q9XTU4 | ND |
| 6793 | 142.7 | CODED FOR BY _C. ELEGANS_ CDNA YK65E4.5. | sptrembl P91497 | ND |

TABLE 3-continued

_Aspergillus oryzae ESTs_

| Sequence Listing | zscore | Annotation | Database | Functional Category |
|---|---|---|---|---|
| 6794 | 142.7 | DEFORMED (FRAGMENT). | sptrembl O44258 | ND |
| 6795 | 142.7 | MUCIN. | sptrembl Q63549 | ND |
| 6796 | 142.7 | HISTONE H1 PROTEIN. | sptrembl Q9XYY5 | ND |
| 6797 | 142.7 | PROTEIN UL53 (HFRF2 PROTEIN). | swissprot P16794 | ND |
| 6798 | 142.6 | F14M4.8 PROTEIN. | sptrembl O80716 | ND |
| 6799 | 142.6 | HPLC6 PROTEIN (FRAGMENT). | sptrembl Q03659 | ND |
| 6800 | 142.6 | LIMA (FRAGMENT). | sptrembl P90533 | ND |
| 6801 | 142.6 | PHOSPHOGLUCOMUTASE. | sptrembl O74374 | ND |
| 6802 | 142.6 | Papilloma virus major capsid protein. | geneseqp R88275 | ND |
| 6803 | 142.5 | VERY HYPOTHETICAL 14.3 KD PROTEIN IN AAC1-FET3 INTERGENIC REGION. | swissprot Q04674 | ND |
| 6804 | 142.5 | ORF 59. | sptrembl Q9YTK8 | ND |
| 6805 | 142.5 | PRPL-2 PROTEIN. | sptrembl Q15220 | ND |
| 6806 | 142.4 | SMALL S PROTEIN. | sptrembl O55496 | ND |
| 6807 | 142.4 | INSECT INTESTINAL MUCIN IIM14. | sptrembl O18510 | ND |
| 6808 | 142.4 | EG:140G11.3 PROTEIN. | sptrembl O97172 | ND |
| 6809 | 142.4 | ALLERGEN. | sptrembl O74682 | ND |
| 6810 | 142.4 | PYRROLIDONE-CARBOXYLATE PEPTIDASE (EC 3.4.19.3)(5-OXOPROLYL-PEPTIDASE) (PYROGLUTAMYL-PEPTIDASE I). | tremblnew CAB50353 | ND |
| 6811 | 142.3 | RNA-BINDING PROTEIN. | sptrembl Q15287 | ND |
| 6812 | 142.2 | LIN-15B PROTEIN. | sptrembl Q27395 | ND |
| 6813 | 142.2 | F23N19.12. | tremblnew AAF19547 | ND |
| 6814 | 142.2 | AXOTROPHIN. | sptrembl Q9WV66 | ND |
| 6815 | 142.2 | _Porphoryomonas gingivalis_ protein PG121. | geneseqp Y34466 | ND |
| 6816 | 142.2 | HYPOTHETICAL 32.1 KD PROTEIN. | sptrembl O74387 | ND |
| 6817 | 142.2 | Clone HNFGW06 of EGFR receptor family. | geneseqp W61630 | ND |
| 6818 | 142.2 | NUCLEOPORIN-LIKE PROTEIN. | sptrembl O23173 | ND |
| 6819 | 142.1 | AMELOGENIN (FRAGMENT). | swissprot O97647 | ND |
| 6820 | 142.0 | PAX6-LIKE PROTEIN. | sptrembl Q25411 | ND |
| 6821 | 142.0 | SER- AND THR-RICH PROTEIN (FRAGMENT). | sptrembl Q26596 | ND |
| 6822 | 142.0 | SCO-SPONDIN (FRAGMENT). | sptrembl Q9XSV8 | ND |
| 6823 | 1416.2 | 60S ACIDIC RIBOSOMAL PROTEIN P0 (L10E). | swissprot P05317 | Translation, ribosomal structure and biogenesis |
| 6824 | 1411.8 | THIOREDOXIN REDUCTASE (EC 1.6.4.5). | swissprot P43496 | Posttranslational modification, protein turnover, chaperones |
| 6825 | 141.9 | HYPOTHETICAL 39.0 KD PROTEIN. | sptrembl O74371 | ND |
| 6826 | 141.9 | F17L21.1. | sptrembl Q9ZW67 | ND |
| 6827 | 141.9 | 60S RIBOSOMAL PROTEIN L7, MITOCHONDRIAL PRECURSOR (YML7). | swissprot P36519 | ND |
| 6828 | 141.8 | ACTIVATING TRANSCRIPTION FACTOR 2. | sptrembl Q91576 | ND |
| 6829 | 141.8 | HYPOTHETICAL 27.8 KD PROTEIN. | sptrembl O54181 | ND |
| 6830 | 141.8 | Amino acid sequence of a virulence factor encoded by ORF30221. | geneseqp Y29214 | ND |

TABLE 3-continued

_Aspergillus oryzae ESTs_

| Sequence Listing | zscore | Annotation | Database | Functional Category |
|---|---|---|---|---|
| 6831 | 141.7 | CASEIN KINASE II BETA' CHAIN (CK II) (EC 2.7.1.37). | swissprot P38930 | ND |
| 6832 | 141.7 | EXTENSIN= NODULE-SPECIFIC PROLINE-RICH PROTEIN {CLONE VFNDS-E}. | tremblnew G425682 | ND |
| 6833 | 141.7 | Human 5' EST secreted protein SEQ ID NO:344. | geneseqp Y12313 | ND |
| 6834 | 141.6 | V1-Lab-Vh construction (5A), single chain antibody. | geneseqp R14698 | ND |
| 6835 | 141.6 | HYPOTHETICAL PROTEIN (FRAGMENT). | sptrembl Q17269 | ND |
| 6836 | 141.6 | PLENTY-OF-PROLINES-101. | sptrembl O70495 | ND |
| 6837 | 141.6 | PLENTY-OF-PROLINES-101. | sptrembl O70495 | ND |
| 6838 | 141.5 | T1J1.3 PROTEIN. | sptrembl Q9ZPH7 | ND |
| 6839 | 141.3 | F16B22.21 PROTEIN. | sptrembl O80511 | ND |
| 6840 | 141.3 | 130AA LONG HYPOTHETICAL PROTEIN. | sptrembl Q9YD79 | ND |
| 6841 | 141.2 | PUTATIVE SERINE/THREONINE PROTEIN KINASE. | sptrembl Q9ZNQ8 | ND |
| 6842 | 141.1 | AGR RELATED DNA SEQUENCE, TWO COMPLETE CODING REGIONS AND TWO INCOMPLETE CODING REGIONS. | sptrembl Q54337 | ND |
| 6843 | 141.1 | MICROTUBULE-ASSOCIATED PROTEIN 4. | swissprot P27546 | ND |
| 6844 | 141.1 | Keratan sulphate 6-sulphotransferase. | geneseqp W61100 | ND |
| 6845 | 141.1 | PUTATIVE. | sptrembl Q9ZLR2 | ND |
| 6846 | 141.1 | HYPOTHETICAL 40.9 KD PROTEIN C08B11.5 IN CHROMOSOME II. | swissprot Q09442 | ND |
| 6847 | 141.0 | A_IG002N01.14. | sptrembl O04621 | ND |
| 6848 | 141.0 | _R. eutropha_ Mgt partial ORF3 encoded protein. | geneseqp W92640 | ND |
| 6849 | 141.0 | F56D12.5 PROTEIN. | sptrembl O16646 | ND |
| 6850 | 141.0 | PEPTIDE FOLLOWING ISV-A1. | sptrembl Q48355 | ND |
| 6851 | 141.0 | Cardiac adenylyl cyclase. | geneseqp R78519 | ND |
| 6852 | 141.0 | PUTATIVE 60S RIBOSOMAL PROTEIN L24. | tremblnew AAD24643 | ND |
| 6853 | 1406.7 | PUTATIVE YEAST CELL DIVISION CONTROL PROTEIN 68 HOMOLOG, PUTATIVE TRANSCRIPTIONAL ACTIVATOR. | sptrembl O94267 | ND |
| 6854 | 1405.2 | PROTEASOME COMPONENT PUP1 PRECURSOR (EC 3.4.99.46) (MACROPAIN SUBUNIT PUP1) (PROTEINASE YSCE SUBUNIT PUP1) (MULTICATALYTIC ENDOPEPTIDASE COMPLEX SUBUNIT PUP1). | swissprot P25043 | Posttranslational modification, protein turnover, chaperones |
| 6855 | 1405.1 | BETA-GLUCOSIDASE I PRECURSOR (EC 3.2.1.21) (GENTIOBIASE) (CELLOBIASE) (BETA-D-GLUCOSIDE GLUCOHYDROLASE). | swissprot P48825 | ND |
| 6856 | 1401.2 | HYPOTHETICAL 126.6 KD PROTEIN IN RPL36A-VTI1 INTERGENIC REGION. | swissprot Q04336 | ND |
| 6857 | 140.9 | Human normal ovarian tissue derived protein 68. | geneseqp Y59791 | ND |
| 6858 | 140.9 | HYPOTHETICAL 61.1 KD PROTEIN (FRAGMENT). | tremblnew CAB63715 | ND |
| 6859 | 140.9 | F56D12.5 PROTEIN. | sptrembl O16646 | ND |
| 6860 | 140.8 | EG:63B12.11 PROTEIN. | sptrembl O97419 | ND |

TABLE 3-continued

_Aspergillus oryzae ESTs_

| Sequence Listing | zscore | Annotation | Database | Functional Category |
|---|---|---|---|---|
| 6861 | 140.8 | HYPOTHETICAL 6.0 KD PROTEIN IN THI12 5' REGION. | swissprot P53820 | ND |
| 6862 | 140.8 | 120 KDA STYLE GLYCOPROTEIN. | sptrembl O49986 | ND |
| 6863 | 140.8 | TRANSGLUTAMINASE PRECURSOR (EC 2.3.2.13). | tremblnew CAA70055 | ND |
| 6864 | 140.6 | SIMILARITY TO HUMAN SYNAPSIN IB. | sptrembl Q23352 | ND |
| 6865 | 140.6 | SRC2-LIKE PROTEIN. | sptrembl O81814 | ND |
| 6866 | 140.6 | ER interacting domain of AIB1 protein. | geneseqp W81028 | ND |
| 6867 | 140.6 | CZP-3. | geneseqp R48068 | ND |
| 6868 | 140.5 | Porcine retrovirus GAG protein. | geneseqp W39271 | ND |
| 6869 | 140.5 | HYPOTHETICAL 91.1 KD PROTEIN R144.2 IN CHROMOSOME III. | swissprot Q09345 | ND |
| 6870 | 140.5 | SERINE/THREONINE PROTEIN KINASE. | sptrembl O32382 | ND |
| 6871 | 140.4 | ORF115. | sptrembl Q37123 | ND |
| 6872 | 140.4 | Fragment of human secreted protein encoded by gene 76. | geneseqp W78321 | ND |
| 6873 | 140.4 | MEROZOITE SURFACE PROTEIN-1 (FRAGMENT). | tremblnew AAD49716 | ND |
| 6874 | 140.4 | ENVELOPE PROTEIN (FRAGMENT). | sptrembl O73231 | ND |
| 6875 | 140.4 | PROTODERMAL FACTOR 1. | tremblnew AAD33869 | ND |
| 6876 | 140.3 | ALXA AND HSDM. | sptrembl P95510 | ND |
| 6877 | 140.3 | COUNTERPART OF HSV-1 GENE RL2 AND VZV GENE 61. | sptrembl O39303 | ND |
| 6878 | 140.3 | ANTIGENIC POLYPEPTIDE (FRAGMENT). | sptrembl O96082 | ND |
| 6879 | 140.3 | HYPOTHETICAL 30.9 KD PROTEIN B1549_C2_213. | swissnew P52063 | ND |
| 6880 | 140.3 | CARROT HYPOCOTIL SPECIFIC. | sptrembl P93705 | ND |
| 6881 | 140.3 | SIGNAL RECOGNITION PARTICLE 19 KD PROTEIN (SRP19). | swissprot P49964 | ND |
| 6882 | 140.3 | HYPOTHETICAL 41.1 KD PROTEIN. | tremblnew CAB51986 | ND |
| 6883 | 140.3 | P2V PROTEIN. | sptrembl O89170 | ND |
| 6884 | 140.2 | HYPOTHETICAL 90.0 KD PROTEIN. | sptrembl Q9WQH0 | ND |
| 6885 | 140.2 | MG1 = HIGH MOLECULAR WEIGHT MUCIN {3' REGION (FRAGMENT). | sptrembl Q93043 | ND |
| 6886 | 140.2 | HLARK. | sptrembl O02916 | ND |
| 6887 | 140.2 | SPERM CHROMATIN HMRBNP/H1. | sptrembl Q98979 | ND |
| 6888 | 140.1 | SPLICING FACTOR, ARGININE/SERINE-RICH 6 (PRE-MRNA SPLICING FACTOR SRP55). | swissnew Q13247 | ND |
| 6889 | 140.1 | SODIUM- AND CHLORIDE-DEPENDENT CREATINE TRANSPORTER 1 (CT1). | swissprot P31661 | ND |
| 6890 | 140.1 | HYPOTHETICAL 47.8 KD PROTEIN YOR009W. | sptrembl Q12218 | ND |
| 6891 | 140.0 | DESB (EC 3.5.4.5). | tremblnew AAD30442 | ND |
| 6892 | 140.0 | HYPOTHETICAL PROTEIN E-115. | swissprot P03290 | ND |
| 6893 | 1393.7 | HYPOTHETICAL 38.3 KD PROTEIN IN RPL11B-PDC6 INTERGENIC REGION. | swissprot P53252 | ND |
| 6894 | 1393.0 | PUTATIVE MITOCHONDRIAL PROTEIN IMPORT PROTEIN - DNAJ PROTEIN. | sptrembl O74752 | Posttranslational modification, protein turnover, chaperones |

TABLE 3-continued

_Aspergillus oryzae ESTs_

| Sequence Listing | zscore | Annotation | Database | Functional Category |
|---|---|---|---|---|
| 6895 | 1392.9 | VACUOLAR ATP SYNTHASE SUBUNIT B (EC 3.6.1.34) (V-ATPASE 57 KD SUBUNIT). | swissprot P22550 | Energy production and conversion |
| 6896 | 1390.1 | ORNITHINE DECARBOXYLASE. | tremblnew CAB56523 | Amino acid transport and metabolism |
| 6897 | 139.8 | CYCLIC NUCLEOTIDE-GATED CHANNEL BETA SUBUNIT. | sptrembl O35788 | ND |
| 6898 | 139.8 | Toxic shock syndrome toxin-1. | geneseqp R95904 | ND |
| 6899 | 139.7 | HYPOTHETICAL 18.3 KD PROTEIN ZK1321.1 IN CHROMOSOME II. | swissprot Q09368 | ND |
| 6900 | 139.7 | OUTER CAPSID PROTEIN VP4 (HEMAGGLUTININ) (OUTER LAYER PROTEIN VP4) [CONTAINS: OUTER CAPSID PROTEINS VP5 AND VP8]. | swissprot P13842 | ND |
| 6901 | 139.7 | 464AA LONG HYPOTHETICAL PROTEIN. | sptrembl Q9YEB8 | ND |
| 6902 | 139.7 | HYPOTHETICAL 91.0 KD PROTEIN. | sptrembl Q9X4P5 | ND |
| 6903 | 139.6 | HYPOTHETICAL 96.9 KD PROTEIN. | tremblnew CAA22569 | ND |
| 6904 | 139.6 | IMMUNOGLOBULIN 216 aa, chain A + B | pdb 1MCJ | ND |
| 6905 | 139.5 | 202AA LONG HYPOTHETICAL PROTEIN. | sptrembl Q9Y9D4 | ND |
| 6906 | 139.5 | HYPOTHETICAL 13.9 KD PROTEIN. | tremblnew AAF19661 | ND |
| 6907 | 139.5 | PHLB PROTEIN PRECURSOR. | swissprot P18954 | ND |
| 6908 | 139.5 | HYPOTHETICAL 14.6 KD PROTEIN. | sptrembl O53621 | ND |
| 6909 | 139.4 | F18B13.26 PROTEIN. | tremblnew AAD55474 | ND |
| 6910 | 139.3 | CELL WALL PROTEIN. | sptrembl Q40336 | ND |
| 6911 | 139.3 | VIRAL PROTEIN 1 (FRAGMENT). | sptrembl Q85146 | ND |
| 6912 | 139.3 | T2N18.14 PROTEIN. | sptrembl Q9ZQC7 | ND |
| 6913 | 139.3 | SIMILARITY TO C2H2-TYPE ZINC FINGER DOMAIN. | sptrembl Q17548 | ND |
| 6914 | 139.3 | 22 KD GAMMA-COIXIN PRECURSOR. | sptrembl Q00318 | ND |
| 6915 | 139.3 | DIHYDROOROTASE (EC 3.5.2.3) (DHOASE). | swissprot P96081 | ND |
| 6916 | 139.3 | deg-3 gene product. | geneseqp R42747 | ND |
| 6917 | 139.2 | C09G9.2 PROTEIN. | sptrembl Q17872 | ND |
| 6918 | 139.1 | RECEPTOR-LIKE KINASE LRK10 (FRAGMENT). | sptrembl Q9XHQ3 | ND |
| 6919 | 139.1 | COSMID F56D3. | sptrembl Q20877 | ND |
| 6920 | 139.0 | GLUCOAMYLASE. | tremblnew AAC49609 | ND |
| 6921 | 139.0 | SUBMAXILLARY GLAND ANDROGEN REGULATED PROTEIN 3 PRECURSOR (MSG3 MRNA). | sptrembl Q61902 | ND |
| 6922 | 139.0 | XNP-1. | tremblnew AAD55361 | ND |
| 6923 | 139.0 | NAPF. | sptrembl O86474 | ND |
| 6924 | 139.0 | TRANSCRIPTION INITIATION FACTOR IIE BETA SUBUNIT (TFIIE-BETA) (_S. POMBE_ TFA2 HOMOLOG). | sptrembl P79011 | ND |
| 6925 | 139.0 | DJ789O11.1 (PUTATIVE GAMMA-HEREGULIN LIKE PROTEIN) (FRAGMENT). | sptrembl O75999 | ND |

TABLE 3-continued

*Aspergillus oryzae* ESTs

| Sequence Listing | zscore | Annotation | Database | Functional Category |
|---|---|---|---|---|
| 6926 | 1387.7 | ACTIN-LIKE PROTEIN ARP2. | swissprot P32381 | Cell division and chromosome partitioning |
| 6927 | 1386.5 | OROTIDINE 5'-PHOSPHATE DECARBOXYLASE (EC 4.1.1.23) (OMP DECARBOXYLASE). | swissprot O13416 | Nucleotide transport |
| 6928 | 1383.8 | ANTHRANILATE SYNTHASE COMPONENT I (EC 4.1.3.27). | swissprot P00899 | Coenzyme metabolism |
| 6929 | 138.9 | SERINE HYDROXYMETHYLTRANSFERASE (EC 2.1.2.1) (SERINE METHYLASE) (SHMT). | swissprot O29406 | ND |
| 6930 | 138.9 | EG:114E2.2 PROTEIN. | sptrembl O46042 | ND |
| 6931 | 138.9 | LONG-CHAIN-FATTY-ACID COA LIGASE. | sptrembl P73004 | ND |
| 6932 | 138.9 | GLUCOSE TRANSPORTER TYPE 4, INSULIN-RESPONSIVE. | swissprot Q27994 | ND |
| 6933 | 138.9 | HYPOTHETICAL PROTEIN (FRAGMENT). | sptrembl P72068 | ND |
| 6934 | 138.8 | SIMILARITY TO RHODOPSIN. | sptrembl Q19607 | ND |
| 6935 | 138.8 | HISTONE H1.2. | sptrembl Q94555 | ND |
| 6936 | 138.8 | ORF79 PROTEIN. | tremblnew BAA84914 | ND |
| 6937 | 138.8 | OVERLAPPING PROTEIN. | sptrembl O91259 | ND |
| 6938 | 138.7 | METALLOTHIONEIN ISOFORM (FRAGMENT). | sptrembl P79375 | ND |
| 6939 | 138.7 | PTS SYSTEM, CELLOBIOSE-SPECIFIC IIC COMPONENT (EIIC-CEL) (CELLOBIOSE-PERMEASE IIC COMPONENT) (PHOSPHOTRANSFERASE ENZYME II, C COMPONENT). | swissprot Q45400 | ND |
| 6940 | 138.6 | N-MYC 2 PROTO-ONCOGENE PROTEIN. | swissprot Q64210 | ND |
| 6941 | 138.6 | hCG/hFSH chimera, B12. | geneseqp R15072 | ND |
| 6942 | 138.6 | BETA-B-PROTEIN. | sptrembl Q85079 | ND |
| 6943 | 138.6 | Bovine neutrophil beta-defensin peptide BNBD-5. | geneseqp R63514 | ND |
| 6944 | 138.5 | Neuropeptide receptor. | geneseqp W06124 | ND |
| 6945 | 138.5 | MAD HOMOLOG SMAD5. | sptrembl P97454 | ND |
| 6946 | 138.5 | Autotaxin derived from human liver cells. | geneseqp R86580 | ND |
| 6947 | 138.4 | HYPOTHETICAL 65.2 KD PROTEIN. | sptrembl O61105 | ND |
| 6948 | 138.4 | GENTISATE 1,2-DIOXYGENASE (FRAGMENT). | sptrembl O73956 | ND |
| 6949 | 138.3 | HIV Tat protein. | geneseqp Y05097 | ND |
| 6950 | 138.2 | E2 GLYCOPROTEIN PRECURSOR (SPIKE GLYCOPROTEIN) (PEPLOMER PROTEIN) [CONTAINS: SPIKE PROTEIN S1; SPIKE PROTEIN S2]. | swissprot P11223 | ND |
| 6951 | 138.1 | ATP SYNTHASE PROTEIN 8 (EC 3.6.1.34) (A6L). | swissprot P03929 | ND |
| 6952 | 138.1 | HOMEOBOX PROTEIN HOX-A10 (HOX-1H) (HOX-1.8) (PL). | swissnew P31260 | ND |
| 6953 | 138.0 | SERINE-RICH PROTEIN. | sptrembl O94317 | ND |
| 6954 | 1376.9 | ACETYL-COENZYME A SYNTHETASE (EC 6.2.1.1) (ACETATE--COA LIGASE) (ACYL-ACTIVATING ENZYME). | swissprot P16928 | Lipid metabolism |

TABLE 3-continued

_Aspergillus oryzae ESTs_

| Sequence Listing | zscore | Annotation | Database | Functional Category |
|---|---|---|---|---|
| 6955 | 1373.9 | PHOSPHATE-REPRESSIBLE PHOSPHATE PERMEASE. | swissprot P15710 | Inorganic ion transport and metabolism |
| 6956 | 137.9 | KIAA1048 PROTEIN. | tremblnew BAA83000 | ND |
| 6957 | 137.9 | HYPOTHETICAL PROTEIN. | tremblnew BAA87840 | ND |
| 6958 | 137.8 | HOMEOTIC CAUDAL PROTEIN. | swissprot P09085 | ND |
| 6959 | 137.8 | POSTSYNAPTIC DENSITY PROTEIN. | tremblnew AAC25483 | ND |
| 6960 | 137.8 | HYPOTHETICAL 14.7 KD PROTEIN. | sptrembl O33136 | ND |
| 6961 | 137.8 | HYPOTHETICAL 14.2 KD PROTEIN. | tremblnew AAF10317 | ND |
| 6962 | 137.8 | SENSOR KINASE. | sptrembl O34757 | ND |
| 6963 | 137.7 | PISTIL-SPECIFIC EXTENSIN-LIKE PROTEIN PRECURSOR (FRAGMENT). | sptrembl Q40548 | ND |
| 6964 | 137.7 | ENDOSTYLE-SPECIFIC. | sptrembl O44238 | ND |
| 6965 | 137.6 | PUTATIVE CARBOXYPEPTIDASE S PRECURSOR (EC 3.4.17.4) (YSCS) (GLY-X CARBOXYPEPTIDASE). | sptrembl O13968 | ND |
| 6966 | 137.5 | SMALL NUCLEAR RIBONUCLEOPROTEIN B. | tremblnew AAD54488 | ND |
| 6967 | 137.5 | OMP of _Bordetella pertussis_. | geneseqp R21691 | ND |
| 6968 | 137.5 | LIPID TRANSFER PROTEIN. | sptrembl O22110 | ND |
| 6969 | 137.5 | HYPOTHETICAL 18.9 KD PROTEIN. | sptrembl Q55554 | ND |
| 6970 | 137.5 | HYPOTHETICAL 32.8 KD PROTEIN (FRAGMENT). | tremblnew CAB59245 | ND |
| 6971 | 137.4 | NUCLEAR TRANSITION PROTEIN 2 (TP-2). | sptrembl Q64561 | ND |
| 6972 | 137.3 | MAMMALIAN ACYL COA OXIDASE HOMOLOGOUS (FRAGMENT). | sptrembl Q43476 | ND |
| 6973 | 137.3 | TRANSCRIPTION FACTOR SOX-10. | swissprot O55170 | ND |
| 6974 | 137.3 | HYPOTHETICAL 28.1 KD PROTEIN. | sptrembl O23285 | ND |
| 6975 | 137.2 | PHOSPHOLIPASE D2. | sptrembl O43580 | ND |
| 6976 | 137.2 | GLUCOAMYLASE S1/S2 PRECURSOR (EC 3.2.1.3) (GLUCAN 1,4-ALPHA-GLUCOSIDASE) (1,4-ALPHA-D-GLUCAN GLUCOHYDROLASE). | swissprot P08640 | ND |
| 6977 | 137.2 | DIPEPTIDE ABC TRANSPORTER, ATP-BINDING PROTEIN (DPPF). | sptrembl O28503 | ND |
| 6978 | 137.1 | INSULIN RECEPTOR SUBSTRATE-2. | sptrembl Q9Y615 | ND |
| 6979 | 137.1 | DESSICATION-RELATED PROTEIN CLONE PCC6-19 (CDET6-19). | swissprot P22239 | ND |
| 6980 | 1366.0 | UBIQUITIN-CONJUGATING ENZYME E2-16 KD (EC 6.3.2.19) (UBIQUITIN-PROTEIN LIGASE) (UBIQUITIN CARRIER PROTEIN) (COLLETOTRICHUM HARD-SURFACE-INDUCED PROTEIN 1). | sptrembl O74196 | ND |
| 6981 | 1364.6 | TRANSALDOLASE (EC 2.2.1.2). | sptrembl O42700 | Carbohydrate transport and metabolism |
| 6982 | 1355.4 | METHYLCITRATE SYNTHASE PRECURSOR (EC 4.1.3.31). | tremblnew CAB53336 | Energy production and conversion |
| 6983 | 1354.5 | 100 KDA PROTEIN. | sptrembl O60040 | ND |

TABLE 3-continued

Aspergillus oryzae ESTs

| Sequence Listing | zscore | Annotation | Database | Functional Category |
|---|---|---|---|---|
| 6984 | 1352.3 | A. oryzae DEBY932 locus protein sequence. | geneseqp Y39873 | Carbohydrate transport and metabolism |
| 6985 | 1352.2 | MITOCHONDRIAL CARRIER PROTEIN. | sptrembl O74439 | ND |
| 6986 | 1352.2 | PYRUVATE KINASE (EC 2.7.1.40) (PK). | swissprot P22360 | Carbohydrate transport and metabolism |
| 6987 | 1348.0 | CYTOCHROME C OXIDASE SUBUNIT V. | sptrembl O93980 | ND |
| 6988 | 1346.7 | ALPHA-GALACTOSIDASE A PRECURSOR (EC 3.2.1.22) (MELIBIASE). | swissprot P28351 | ND |
| 6989 | 1344.2 | HYPOTHETICAL ALDEHYDE-DEHYDROGENASE LIKE PROTEIN IN COQ1-HHF1 INTERGENIC REGION. | swissprot P38067 | Energy production and conversion |
| 6990 | 1341.2 | POTASSIUM TRANSPORTER. | sptrembl O74724 | ND |
| 6991 | 1339.0 | CHORISMATE MUTASE (EC 5.4.99.5). | sptrembl Q9Y7B2 | ND |
| 6992 | 1337.5 | PUTATIVE DIPHTHINE SYNTHASE. | sptrembl O74898 | Translation, ribosomal structure and biogenesis |
| 6993 | 1334.4 | HOMOCITRATE SYNTHASE (EC 4.1.3.21). | sptrembl O94225 | Amino acid transport and metabolism |
| 6994 | 1334.2 | PEPTIDE TRANSPORTER PTR2. | swissprot P46030 | ND |
| 6995 | 1334.0 | PDI RELATED PROTEIN A. | sptrembl O93914 | Energy production and conversion |
| 6996 | 1333.3 | MITOTIC CONTROL PROTEIN DIS3. | swissprot P37202 | Transcription |
| 6997 | 1332.4 | GTP-BINDING PROTEIN SARA. | swissnew P52886 | ND |
| 6998 | 1332.2 | RIBOSOMAL PROTEIN L13A. | tremblnew AAD54383 | Translation, ribosomal structure and biogenesis |
| 6999 | 1328.3 | COENZYME A SYNTHETASE. | sptrembl O74976 | Lipid metabolism |
| 7000 | 1327.3 | ALPHA,ALPHA-TREHALOSE-PHOSPHATE SYNTHASE [UDP-FORMING] 2 (EC 2.4.1.15) (TREHALOSE-6-PHOSPHATE SYNTHASE) (UDP-GLUCOSE-GLUCOSEPHOSPHATE GLUCOSYLTRANSFERASE). | swissprot Q00217 | Carbohydrate transport and metabolism |
| 7001 | 1325.1 | TUBULIN BETA CHAIN. | swissprot P22012 | ND |
| 7002 | 1324.3 | RHO1 PROTEIN. | swissprot Q09914 | ND |
| 7003 | 1322.4 | 60 KD CHAPERONIN (PROTEIN CPN60) (GROEL PROTEIN) (HEAT SHOCK PROTEIN 60). | sptrembl O94110 | Posttranslational modification, protein turnover, chaperones |
| 7004 | 1319.7 | PROBABLE UTP--GLUCOSE-1-PHOSPHATE URIDYLYLTRANSFERASE. | tremblnew CAA22857 | ND |
| 7005 | 1317.8 | MALATE DEHYDROGENASE, MITOCHONDRIAL PRECURSOR (EC 1.1.1.37). | swissprot P17505 | Energy production and conversion |
| 7006 | 1317.1 | E1-LIKE PROTEIN. | sptrembl O93922 | Coenzyme metabolism |
| 7007 | 1315.8 | Human transport-associated protein-6 (TRANP-6). | geneseqp Y31644 | ND |
| 7008 | 1314.0 | OUTER MITOCHONDRIAL MEMBRANE PROTEIN PORIN. | swissprot P07144 | ND |

TABLE 3-continued

*Aspergillus oryzae* ESTs

| Sequence Listing | zscore | Annotation | Database | Functional Category |
|---|---|---|---|---|
| 7009 | 1313.7 | RIBONUCLEOTIDE REDUCTASE LARGE SUBUNIT. | tremblnew AAD49743 | Nucleotide transport |
| 7010 | 1307.1 | 60S RIBOSOMAL PROTEIN L5. | swissprot O59953 | Translation, ribosomal structure and biogenesis |
| 7011 | 1304.2 | GLUCOSE-6-PHOSPHATE 1-DEHYDROGENASE (EC 1.1.1.49) (G6PD). | swissprot P48826 | Carbohydrate transport and metabolism |
| 7012 | 1299.2 | C-5 STEROL DESATURASE (EC 1.3.-.-) (STEROL-C5-DESATURASE). | swissprot P50860 | ND |
| 7013 | 1298.5 | CYCLOPHILIN B (EC 5.2.1.8). | sptrembl O94190 | Posttranslational modification, protein turnover, chaperones |
| 7014 | 1294.8 | PROBABLE GLUCOSE TRANSPORTER RCO-3. | swissprot Q92253 | ND |
| 7015 | 1294.7 | ORNITHINE AMINOTRANSFERASE (EC 2.6.1.13) (ORNITHINE--OXO-ACID AMINOTRANSFERASE). | swissprot Q92413 | Amino acid transport and metabolism |
| 7016 | 1292.9 | PROTEASOME COMPONENT PUP2 (EC 3.4.99.46) (MACROPAIN SUBUNIT PUP2) (PROTEINASE YSCE SUBUNIT PUP2) (MULTICATALYTIC ENDOPEPTIDASE COMPLEX SUBUNIT PUP2). | swissprot P32379 | Posttranslational modification, protein turnover, chaperones |
| 7017 | 1291.3 | UDP-N-ACETYLGLUCOSAMINE PYROPHOSPHORYLASE (EC 2.7.7.23). | swissprot O74933 | ND |
| 7018 | 1290.3 | GAP-DH. | geneseqp R12995 | Carbohydrate transport and metabolism |
| 7019 | 1289.5 | ACONITASE. | sptrembl O74699 | Energy production and conversion |
| 7020 | 1289.4 | *A. niger* PacC zinc finger DNA binding domain. | geneseqp Y08483 | ND |
| 7021 | 1289.1 | Murine RENT1 protein. | geneseqp W36509 | DNA replication, recombination and repair |
| 7022 | 1287.5 | 40S RIBOSOMAL PROTEIN S0 (RIBOSOME-ASSOCIATED PROTEIN 1). | swissprot Q01291 | Translation, ribosomal structure and biogenesis |
| 7023 | 1287.3 | CHAPERONIN HSP78P. | sptrembl O74402 | Posttranslational modification, protein turnover, chaperones |
| 7024 | 1279.0 | MALATE DEHYDROGENASE (EC 1.1.1.37). | sptrembl O94137 | Energy production and conversion |
| 7025 | 1278.5 | QUINATE PERMEASE (QUINATE TRANSPORTER). | swissprot P15325 | ND |
| 7026 | 1277.5 | ER CHAPERONE BIP. | tremblnew BAA82597 | Posttranslational modification, protein turnover, chaperones |
| 7027 | 1274.9 | NADH-UBIQUINONE OXIDOREDUCTASE 24 KD SUBUNIT PRECURSOR (EC 1.6.5.3) (EC 1.6.99.3). | swissprot P40915 | Energy production and conversion |
| 7028 | 1274.1 | HEAT SHOCK PROTEIN 70 (FRAGMENT). | sptrembl Q92260 | Posttranslational modification, protein turnover, chaperones |

TABLE 3-continued

_Aspergillus oryzae ESTs_

| Sequence Listing | zscore | Annotation | Database | Functional Category |
|---|---|---|---|---|
| 7029 | 1273.4 | FATTY ACID SYNTHASE, ALPHA SUBUNIT. | sptrembl P78615 | Lipid metabolism |
| 7030 | 1273.1 | CADMIUM RESISTANCE PROTEIN. | sptrembl O94284 | ND |
| 7031 | 1272.6 | ACETYL-COA CARBOXYLASE (EC 6.4.1.2). | sptrembl O60033 | Lipid metabolism |
| 7032 | 1271.4 | HYPOTHETICAL 80.7 KD PROTEIN IN ERG7-NMD2 INTERGENIC REGION. | swissprot P38795 | Coenzyme metabolism |
| 7033 | 1270.6 | NUCLEOSOME ASSEMBLY PROTEIN. | sptrembl O59797 | ND |
| 7034 | 1268.6 | T-COMPLEX PROTEIN 1, BETA SUBUNIT (TCP-1-BETA) (CCT-BETA). | swissprot P39076 | Posttranslational modification, protein turnover, chaperones |
| 7035 | 1263.8 | SPERMIDINE SYNTHASE. | sptrembl Q9Y8H7 | Amino acid transport and metabolism |
| 7036 | 1263.7 | ACETYL-COA-ACETYLTRANSFERASE (EC 2.3.1.9). | sptrembl Q9Y838 | Lipid metabolism |
| 7037 | 1262.2 | SAGA. | sptrembl Q12076 | ND |
| 7038 | 1261.6 | HYPOTHETICAL 63.8 KD PROTEIN. | tremblnew CAB61159 | ND |
| 7039 | 1260.2 | PUTATIVE PROTEASOME COMPONENT C9/Y13 (EC 3.4.99.46) (MACROPAIN SUBUNIT) (MULTICATALYTIC ENDOPEPTIDASE COMPLEX SUBUNIT). | swissprot Q09682 | Posttranslational modification, protein turnover, chaperones |
| 7040 | 1259.3 | UBIQUITIN-CONJUGATING ENZYME E2-17 KD (EC 6.3.2.19) (UBIQUITIN-PROTEIN LIGASE 2) (UBIQUITIN CARRIER PROTEIN). | swissprot P52493 | ND |
| 7041 | 1254.9 | KETOL-ACID REDUCTOISOMERASE PRECURSOR (EC 1.1.1.86) (ACETOHYDROXY-ACID REDUCTOISOMERASE) (ALPHA-KETO-BETA-HYDROXYLACIL REDUCTOISOMERASE). | swissnew P38674 | Amino acid transport and metabolism |
| 7042 | 1252.6 | EUKARYOTIC INITIATION FACTOR 4A-LIKE PROTEIN C1F5.10. | swissprot Q10055 | DNA replication, recombination and repair |
| 7043 | 1251.6 | ADENOSINE-5'PHOSPHOSULFATE KINASE (EC 2.7.1.25) (ADENYLYLSULFATE KINASE) (APS KINASE). | sptrembl Q12657 | Inorganic ion transport and metabolism |
| 7044 | 1250.7 | 40S RIBOSOMAL PROTEIN S9 (S7). | swissprot P52810 | Translation, ribosomal structure and biogenesis |
| 7045 | 1248.6 | VALYL-TRNA SYNTHETASE, MITOCHONDRIAL PRECURSOR (EC 6.1.1.9) (VALINE--TRNA LIGASE) (VALRS). | swissprot P28350 | Translation, ribosomal structure and biogenesis |
| 7046 | 1247.2 | SCONCP. | tremblnew AAB18274 | ND |
| 7047 | 1244.9 | ACID TREHALASE PRECURSOR (EC 3.2.1.28) (ALPHA,ALPHA-TREHALASE) (ALPHA,ALPHA-TREHALOSE GLUCOHYDROLASE). | swissprot P78617 | ND |
| 7048 | 1243.0 | SCONCP. | tremblnew AAB18274 | ND |

TABLE 3-continued

_Aspergillus oryzae ESTs_

| Sequence Listing | zscore | Annotation | Database | Functional Category |
|---|---|---|---|---|
| 7049 | 1242.8 | NADH-UBIQUINONE OXIDOREDUCTASE 23 KD SUBUNIT PRECURSOR (EC 1.6.5.3) (EC 1.6.99.3) (COMPLEX I-23 KD) (CI-23 KD). | swissprot Q12644 | Energy production and conversion |
| 7050 | 1242.8 | TRANSLATION RELEASE FACTOR ERF3. | sptrembl O42787 | Amino acid transport and metabolism |
| 7051 | 1242.2 | 3-ISOPROPYLMALATE DEHYDRATASE (EC 4.2.1.33) (ISOPROPYLMALATE ISOMERASE) (ALPHA-IPM ISOMERASE) (IPMI). | swissprot P17279 | Amino acid transport and metabolism |
| 7052 | 1240.0 | IMPORTIN ALPHA SUBUNIT (KARYOPHERIN ALPHA SUBUNIT) (SERINE-RICH RNA POLYMERASE I SUPPRESSOR PROTEIN). | swissnew O14063 | ND |
| 7053 | 1235.2 | PUTATIVE C-4 METHYL STEROL OXIDASE. | tremblnew CAB52730 | ND |
| 7054 | 1228.8 | CHITIN SYNTHASE 6 (EC 2.4.1.16) (CHITIN-UDP ACETYL-GLUCOSAMINYL TRANSFERASE 6) (CLASS-V CHITIN SYNTHASE 6). | swissprot O13395 | ND |
| 7055 | 1228.8 | CARBOXYPEPTIDASE S3, PENICILLOPEPTIDASE S3, CPD-S3. | tremblnew G1168044 | ND |
| 7056 | 1228.8 | ARG-6 PROTEIN PRECURSOR [CONTAINS: N-ACETYL-GAMMA-GLUTAMYL-PHOSPHATE REDUCTASE (EC 1.2.1.38) (N-ACETYL-GLUTAMATE SEMIALDEHYDE DEHYDROGENASE) (NAGSA DEHYDROGENASE); ACETYLGLUTAMATE KINASE (EC 2.7.2.8) (NAG KINASE) (AGK) (N-ACETYL-L-GLUTAMATE 5-PHOSPHOTRANSFERASE)]. | swissnew P54898 | Amino acid transport and metabolism |
| 7057 | 1226.4 | PROBABLE GLUTAMINYL-TRNA SYNTHETASE. | sptrembl Q9Y7Y8 | Translation, ribosomal structure and biogenesis |
| 7058 | 1225.8 | _Aspergillus niger_ tpiA gene. | geneseqp P70498 | Carbohydrate transport and metabolism |
| 7059 | 1225.3 | 60S RIBOSOMAL PROTEIN L10. | tremblnew CAA22664 | Translation, ribosomal structure and biogenesis |
| 7060 | 1223.0 | 60S RIBOSOMAL PROTEIN L8 (L7A) (L4). | swissprot O13672 | Translation, ribosomal structure and biogenesis |
| 7061 | 1219.3 | RAS-RELATED PROTEIN RAB-11B. | swissprot P46638 | ND |
| 7062 | 1218.6 | FISSION YEAST (FRAGMENT). | sptrembl P78903 | Amino acid transport and metabolism |
| 7063 | 1214.9 | UBIQUITIN. | tremblnew BAA88168 | ND |
| 7064 | 1214.6 | CATALASE A (EC 1.11.1.6). | swissprot P78574 | ND |
| 7065 | 1212.8 | TUBULIN ALPHA-1 CHAIN. | swissprot P24633 | ND |
| 7066 | 1212.5 | METHYLCITRATE SYNTHASE PRECURSOR (EC 4.1.3.31). | tremblnew CAB53336 | Energy production and conversion |

TABLE 3-continued

Aspergillus oryzae ESTs

| Sequence Listing | zscore | Annotation | Database | Functional Category |
|---|---|---|---|---|
| 7067 | 1210.5 | NAD(+)-SPECIFIC GLUTAMATE DEHYDROGENASE. | sptrembl Q02222 | Amino acid transport and metabolism |
| 7068 | 1209.0 | *Aspergillus oryzae* aminopeptidase II. | geneseqp W89586 | ND |
| 7069 | 1208.4 | HAPE. | sptrembl O59849 | ND |
| 7070 | 1206.4 | PUTATIVE HOMOSERINE O-ACETYLTRANSFERASE. | sptrembl O13389 | Amino acid transport and metabolism |
| 7071 | 1203.9 | HYPOTHETICAL 33.9 KD PROTEIN C16C9.02C IN CHROMOSOME I. | swissprot Q09816 | Nucleotide transport |
| 7072 | 1202.8 | PYRUVATE KINASE (EC 2.7.1.40) (PK). | swissprot P22360 | Carbohydrate transport and metabolism |
| 7073 | 1200.3 | *Microscilla furvescens* catalase-53CA1. | geneseqp W33810 | Inorganic ion transport and metabolism |
| 7074 | 1199.9 | PROTEASOME COMPONENT PUP3 (EC 3.4.99.46) (MACROPAIN SUBUNIT PUP3) (MULTICATALYTIC ENDOPEPTIDASE COMPLEX SUBUNIT PUP3). | swissprot P25451 | Posttranslational modification, protein turnover, chaperones |
| 7075 | 1199.4 | MYO-INOSITOL-1-PHOSPHATE SYNTHASE. | tremblnew BAA84084 | Lipid metabolism |
| 7076 | 1194.0 | 26S PROTEASOME REGULATORY SUBUNIT S3 (PROTEASOME SUBUNIT P58) (TRANSPLANTATION ANTIGEN P91A) (TUM-P91A ANTIGEN). | swissprot P14685 | ND |
| 7077 | 1193.1 | KINASE. | sptrembl Q00611 | Signal transduction mechanisms |
| 7078 | 1190.6 | PMR1. | sptrembl O74637 | ND |
| 7079 | 1190.3 | DIHYDROLIPOAMIDE ACETYLTRANSFERASE COMPONENT OF PYRUVATE DEHYDROGENASE COMPLEX, MITOCHONDRIAL PRECURSOR (EC 2.3.1.12) (E2) (PDC-E2) (MRP3). | swissprot P20285 | Energy production and conversion |
| 7080 | 1188.1 | CARBOXYPEPTIDASE S3, PENICILLOPEPTIDASE S3, CPD-S3. | tremblnew G1168044 | ND |
| 7081 | 1183.0 | SUAPRGA1. | tremblnew CAB62571 | ND |
| 7082 | 1182.6 | PUTATIVE SEPTIN. | tremblnew CAB61437 | ND |
| 7083 | 1179.6 | PROTEASOME COMPONENT C7-ALPHA (EC 3.4.99.46) (MACROPAIN SUBUNIT C7-ALPHA) (PROTEINASE YSCE SUBUNIT 7) (MULTICATALYTIC ENDOPEPTIDASE COMPLEX C7) (COMPONENT Y8) (SCL1 SUPPRESSOR PROTEIN). | swissprot P21243 | Posttranslational modification, protein turnover, chaperones |
| 7084 | 1178.9 | UBI1. | tremblnew AAF24230 | ND |
| 7085 | 1177.7 | ASPERGILLOPEPSIN O. | sptrembl Q00249 | ND |
| 7086 | 1176.0 | ELONGATION FACTOR 1-GAMMA 2 (EF-1-GAMMA 2). | swissprot P36008 | ND |
| 7087 | 1174.2 | P68-LIKE PROTEIN. | tremblnew CAA21801 | DNA replication, recombination and repair |

TABLE 3-continued

Aspergillus oryzae ESTs

| Sequence Listing | zscore | Annotation | Database | Functional Category |
|---|---|---|---|---|
| 7088 | 1173.8 | 60S RIBOSOMAL PROTEIN L18. | swissnew Q10192 | Translation, ribosomal structure and biogenesis |
| 7089 | 1170.3 | TUBULIN BETA CHAIN. | swissprot P22012 | ND |
| 7090 | 1165.8 | CALCIUM/CALMODULIN DEPENDENT PROTEIN KINASE B. | sptrembl Q9Y899 | Signal transduction mechanisms |
| 7091 | 1164.6 | CALMODULIN. | swissnew P19533 | ND |
| 7092 | 1164.1 | HYPOTHETICAL 31.6 KD PROTEIN. | sptrembl O13844 | ND |
| 7093 | 1164.0 | Aspergillus oryzae hemA deletion allele-encoded protein. | geneseqp W30559 | Coenzyme metabolism |
| 7094 | 1163.5 | PHOSPHOGLUCOMUTASE 2 (EC 5.4.2.2) (GLUCOSE PHOSPHOMUTASE 2) (PGM 2). | swissprot P37012 | Carbohydrate transport and metabolism |
| 7095 | 1162.5 | CALCIUM/CALMODULIN-DEPENDENT PROTEIN KINASE (EC 2.7.1.123) (CMPK). | swissprot Q00771 | Signal transduction mechanisms |
| 7096 | 1161.9 | ENOLASE (EC 4.2.1.11) (2-PHOSPHOGLYCERATE DEHYDRATASE) (2-PHOSPHO-D-GLYCERATE HYDRO-LYASE). | swissprot Q12560 | Carbohydrate transport and metabolism |
| 7097 | 1158.5 | RIBOSOMAL PROTEIN S28. | tremblnew CAB56815 | Translation, ribosomal structure and biogenesis |
| 7098 | 1157.0 | An enzyme with sugar transferase activity. | geneseqp W88044 | Carbohydrate transport and metabolism |
| 7099 | 1156.7 | SERINE/THREONINE-PROTEIN KINASE STE20 (EC 2.7.1.-). | swissnew Q03497 | Signal transduction mechanisms |
| 7100 | 1152.3 | THREONYL-TRNA SYNTHETASE, CYTOPLASMIC (EC 6.1.1.3) (THREONINE--TRNA LIGASE) (THRRS). | swissprot P87144 | Translation, ribosomal structure and biogenesis |
| 7101 | 1152.2 | PUTATIVE GLYCYL-TRNA SYNTHETASE (EC 6.1.1.14) (GLYCINE--TRNA LIGASE) (GLYRS). | swissprot Q10179 | Translation, ribosomal structure and biogenesis |
| 7102 | 1151.5 | PROBABLE MEMBRANE PROTEIN YOL130W. | sptrembl O13657 | Inorganic ion transport and metabolism |
| 7103 | 1151.0 | NAD(+)-SPECIFIC GLUTAMATE DEHYDROGENASE. | sptrembl Q02222 | ND |
| 7104 | 1147.9 | PHENYLALANYL-TRNA SYNTHETASE ALPHA CHAIN. | sptrembl O42849 | Translation, ribosomal structure and biogenesis |
| 7105 | 1143.7 | SP62_HUMAN. | sptrembl O75245 | ND |
| 7106 | 1143.4 | 40S RIBOSOMAL PROTEIN S6. | swissprot P05752 | Translation, ribosomal structure and biogenesis |
| 7107 | 1141.0 | ADENOSYLHOMOCYSTEINASE (EC 3.3.1.1) (S-ADENOSYL-L-HOMOCYSTEINE HYDROLASE) (ADOHCYASE). | swissprot P39954 | Coenzyme metabolism |
| 7108 | 1140.7 | CYCLOPHILIN-LIKE PEPTIDYL PROLYL CIS-TRANS ISOMERASE (EC 5.2.1.8). | sptrembl O94184 | Posttranslational modification, protein turnover, chaperones |
| 7109 | 1138.6 | UBIQUINOL-CYTOCHROME C REDUCTASE IRON-SULFUR SUBUNIT, | swissprot P07056 | Energy production and conversion |

TABLE 3-continued

_Aspergillus oryzae ESTs_

| Sequence Listing | zscore | Annotation | Database | Functional Category |
|---|---|---|---|---|
| | | MITOCHONDRIAL PRECURSOR (EC 1.10.2.2) (RIESKE IRON-SULFUR PROTEIN) (RISP). | | |
| 7110 | 1138.1 | GLYCEROL KINASE (EC 2.7.1.30) (ATP:GLYCEROL 3-PHOSPHOTRANSFERASE) (GLYCEROKINASE) (GK). | swissprot Q64516 | Energy production and conversion |
| 7111 | 1135.1 | Cephalosporin C #2. | geneseqp R49827 | Energy production and conversion |
| 7112 | 1132.7 | REDUCTASE (FRAGMENT). | sptrembl O74646 | ND |
| 7113 | 1131.8 | 40S RIBOSOMAL PROTEIN S5 (S2) (YS8) (RP14). | swissprot P26783 | Translation, ribosomal structure and biogenesis |
| 7114 | 1130.9 | 60S RIBOSOMAL PROTEIN L7-C. | swissprot O60143 | Translation, ribosomal structure and biogenesis |
| 7115 | 1127.4 | 5-METHYLTETRAHYDROPTE ROYLTRIGLUTAMATE--HOMOCYSTEI METHYLTRANSFERASE(EC 2.1.1.14). | tremblnew CAB57427 | Amino acid transport and metabolism |
| 7116 | 1126.5 | REGULATORY PROTEIN. | sptrembl Q00170 | ND |
| 7117 | 1125.8 | RASP F 9 (FRAGMENT). | sptrembl O42800 | Carbohydrate transport and metabolism |
| 7118 | 1119.7 | FIBRILLARIN (NUCLEOLAR PROTEIN 1). | swissprot P15646 | Translation, ribosomal structure and biogenesis |
| 7119 | 1115.8 | PHOSPHO-2-DEHYDRO-3-DEOXYHEPTONATE ALDOLASE, TYROSINE-INHIBITED (EC 4.1.2.15) (PHOSPHO-2-KETO-3-DEOXYHEPTONATE ALDOLASE) (DAHP SYNTHETASE) (3-DEOXY-D-ARABINO-HEPTULOSONATE 7-PHOSPHATE SYNTHASE). | swissprot P32449 | Amino acid transport and metabolism |
| 7120 | 1115.8 | PROBABLE PEROXISOMAL MEMBRANE PROTEIN PMP20 (ALLERGEN ASP F 3). | swissprot O43099 | ND |
| 7121 | 1113.7 | Yeast Pad1 protein. | geneseqp Y08454 | ND |
| 7122 | 1111.9 | GLUCOSAMINE-6-PHOSPHATE DEAMINASE. | tremblnew AAD42233 | Carbohydrate transport and metabolism |
| 7123 | 1111.6 | BETA GLUCOSIDASE HOMOLOG. | sptrembl O13385 | ND |
| 7124 | 1110.3 | SERINE/THREONINE PROTEIN KINASE. | sptrembl Q99012 | Signal transduction mechanisms |
| 7125 | 1108.9 | ATP SYNTHASE ALPHA CHAIN, MITOCHONDRIAL PRECURSOR (EC 3.6.1.34). | swissnew P37211 | Energy production and conversion |
| 7126 | 1108.4 | SULFATE ADENYLYLTRANSFERASE (EC 2.7.7.4) (SULFATE ADENYLATE TRANSFERASE) (ATP-SULFURYLASE) (SULFURYLASE). | sptrembl Q12555 | Inorganic ion transport and metabolism |
| 7127 | 1106.0 | PUTATIVE CTP SYNTHASE C10F6.03C (EC 6.3.4.2) (UTP--AMMONIA LIGASE C10F6.03C) (CTP SYNTHETASE C10F6.03C). | sptrembl O42644 | Nucleotide transport |

TABLE 3-continued

_Aspergillus oryzae ESTs_

| Sequence Listing | zscore | Annotation | Database | Functional Category |
|---|---|---|---|---|
| 7128 | 1105.5 | CYCLOPHILIN-LIKE PEPTIDYL PROLYL CIS-TRANS ISOMERASE (EC 5.2.1.8). | sptrembl O94184 | Posttranslational modification, protein turnover, chaperones |
| 7129 | 1105.2 | HYDROXYMETHYLGLUTA RYL-COA SYNTHASE (EC 4.1.3.5) (HMG-COA SYNTHASE) (3-HYDROXY-3-METHYLGLUTARYL COENZYME A SYNTHASE). | swissprot P54839 | Lipid metabolism |
| 7130 | 1104.2 | NEGATIVE REGULATOR OF MITOSIS. | swissprot P24686 | ND |
| 7131 | 1103.9 | SACCHAROPINE DEHYDROGENASE [NAD+, L-LYSINE FORMING] (EC 1.5.1.7) (LYSINE--2-OXOGLUTARATE REDUCTASE) (SDH). | swissprot P38997 | Energy production and conversion |
| 7132 | 1102.6 | REPLICATION FACTOR-A PROTEIN 1. | tremblnew CAA22533 | ND |
| 7133 | 1100.7 | QUEUINE TRNA-RIBOSYLTRANSFERASE. | sptrembl O94460 | Translation, ribosomal structure and biogenesis |
| 7134 | 1099.7 | 60S RIBOSOMAL PROTEIN L12. | swissprot P23358 | Translation, ribosomal structure and biogenesis |
| 7135 | 1099.6 | PRP12P/SAP130. | tremblnew BAA86918 | ND |
| 7136 | 1099.4 | ACYL-COA DESATURASE 1 (EC 1.14.99.5) (STEAROYL-COA DESATURASE 1) (FATTY ACID DESATURASE 1). | sptrembl Q12619 | Lipid metabolism |
| 7137 | 1098.0 | YPT1-RELATED PROTEIN 5. | swissprot P36586 | ND |
| 7138 | 1094.5 | Mouse cyclophilin 40 protein sequence. | geneseqp Y34196 | Posttranslational modification, protein turnover, chaperones |
| 7139 | 1093.9 | PUTATIVE FAMILY-31 GLUCOSIDASE. | tremblnew CAB65603 | Carbohydrate transport and metabolism |
| 7140 | 1093.9 | LEUCINE ZIPPER. | sptrembl Q00096 | ND |
| 7141 | 1093.6 | SPLICING FACTOR U2AF 23 KD SUBUNIT (U2 AUXILIARY FACTOR 23 KD SUBUNIT) (U2 SNRNP AUXILIARY FACTOR SMALL SUBUNIT) (U2AF23). | swissprot Q09176 | ND |
| 7142 | 1093.0 | COMPONENT OF CHAPERONIN-CONTAINING T-COMPLEX (ZETA SUBUNIT). | sptrembl O94515 | Posttranslational modification, protein turnover, chaperones |
| 7143 | 1092.4 | HYPOTHETICAL 41.8 KD PROTEIN. | sptrembl O59715 | ND |
| 7144 | 1091.5 | 1,4-BENZOQUINONE REDUCTASE. | sptrembl Q9Y763 | ND |
| 7145 | 1091.1 | PROBABLE VACUOLAR SORTING PROTEIN, DYNAMIN FAMILY (FRAGMENT). | tremblnew CAB62830 | ND |
| 7146 | 1090.3 | UBIQUITIN-CONJUGATING ENZYME E2-18 KD (EC 6.3.2.19) (UBIQUITIN-PROTEIN LIGASE HUS5) (UBIQUITIN CARRIER PROTEIN HUS5). | swissprot P40984 | ND |
| 7147 | 1086.9 | MITOGEN-ACTIVATED PROTEIN KINASE (EC 2.7.1.-) (MAPK). | sptrembl Q00859 | Signal transduction mechanisms |
| 7148 | 1085.5 | HOMOGENTISATE 1,2-DIOXYGENASE (EC | swissprot Q00667 | ND |

TABLE 3-continued

*Aspergillus oryzae* ESTs

| Sequence Listing | zscore | Annotation | Database | Functional Category |
|---|---|---|---|---|
| | | 1.13.11.5) (HOMOGENTISICASE) (HOMOGENTISATE OXYGENASE) (HOMOGENTISIC ACID OXIDASE). | | |
| 7149 | 1084.0 | ION TRANSPORTER. | sptrembl O59768 | Inorganic ion transport and metabolism |
| 7150 | 1078.8 | PEPTIDE TRANSPORT PROTEIN. | tremblnew CAA22021 | ND |
| 7151 | 1078.4 | PYRUVATE DECARBOXYLASE (EC 4.1.1.1). | swissprot P51844 | Coenzyme metabolism |
| 7152 | 1068.6 | ALDEHYDE DEHYDROGENASE (EC 1.2.1.3) (ALDDH) (ALLERGEN CLA H 3) (CLA H III). | swissprot P40108 | Energy production and conversion |
| 7153 | 1068.5 | VALYL-TRNA SYNTHETASE, MITOCHONDRIAL PRECURSOR (EC 6.1.1.9) (VALINE--TRNA LIGASE) (VALRS). | swissprot P28350 | Translation, ribosomal structure and biogenesis |
| 7154 | 1065.8 | 40S RIBOSOMAL PROTEIN S15 (S12). | swissprot P34737 | Translation, ribosomal structure and biogenesis |
| 7155 | 1065.4 | U3 SMALL NUCLEOLAR RIBONUCLEOPROTEIN PROTEIN IMP4. | swissnew P53941 | ND |
| 7156 | 1064.0 | POTASSIUM TRANSPORTER. | sptrembl Q9Y7B9 | Inorganic ion transport and metabolism |
| 7157 | 1063.6 | PUTATIVE SEPTIN. | tremblnew CAB52419 | ND |
| 7158 | 1063.2 | GLUTATHIONE-DEPENDENT FORMALDEHYDE DEHYDROGENASE (EC 1.2.1.1) (FDH) (FALDH) (FLD1). | sptrembl O74685 | ND |
| 7159 | 1061.9 | 60S RIBOSOMAL PROTEIN L11. | swissprot Q10157 | Translation, ribosomal structure and biogenesis |
| 7160 | 1060.4 | PUTATIVE GLUCOSE SENSOR. | sptrembl O13477 | ND |
| 7161 | 1059.8 | ADENYLATE KINASE CYTOSOLIC (EC 2.7.4.3) (ATP-AMP TRANSPHOSPHORYLASE). | swissprot P07170 | Nucleotide transport |
| 7162 | 1059.7 | NADH-UBIQUINONE OXIDOREDUCTASE 21 KD SUBUNIT (EC 1.6.5.3) (EC 1.6.99.3) (COMPLEX I-21 KD) (CI-21 KD). | swissprot Q02854 | ND |
| 7163 | 1059.1 | 40S RIBOSOMAL PROTEIN S3. | swissprot O60128 | Translation, ribosomal structure and biogenesis |
| 7164 | 1058.1 | HEAT SHOCK PROTEIN 70. | sptrembl O42808 | Posttranslational modification, protein turnover, chaperones |
| 7165 | 1057.4 | Beta-1 integrin modulator B171. | geneseqp W19771 | ND |
| 7166 | 1056.9 | PROLIFERATING CELL NUCLEAR ANTIGEN (PCNA). | swissprot Q03392 | DNA replication, recombination and repair |
| 7167 | 1055.9 | O-METHYLTRANSFERASE. | tremblnew BAA86103 | ND |

TABLE 3-continued

_Aspergillus oryzae ESTs_

| Sequence Listing | zscore | Annotation | Database | Functional Category |
|---|---|---|---|---|
| 7168 | 1054.2 | HYPOTHETICAL 49.1 KD PROTEIN IN SSB2-SPX18 INTERGENIC REGION. | swissprot P40160 | Signal transduction mechanisms |
| 7169 | 1054.1 | _M. grisea_ PTH2 gene product. | geneseqp Y06783 | ND |
| 7170 | 1051.1 | 40S RIBOSOMAL PROTEIN S7. | swissprot O43105 | ND |
| 7171 | 1049.8 | ATP SYNTHASE BETA CHAIN, MITOCHONDRIAL PRECURSOR (EC 3.6.1.34). | swissnew P23704 | Energy production and conversion |
| 7172 | 1049.2 | PRE-MRNA SPLICING FACTOR. | sptrembl Q12381 | ND |
| 7173 | 1046.5 | GLYCOGEN PHOSPHORYLASE (EC 2.4.1.1). | swissprot P06738 | Carbohydrate transport and metabolism |
| 7174 | 1046.1 | HISTONE H2A. | sptrembl O13413 | ND |
| 7175 | 1044.6 | DIMETHYL-ALLYL-TRYPTPHAN-SYNTHASE. | sptrembl O94204 | ND |
| 7176 | 1044.3 | SIMILAR TO GLYCOGEN DEBRANCHING ENZYME. | sptrembl Q06625 | Carbohydrate transport and metabolism |
| 7177 | 1041.1 | CHITIN SYNTHASE D (EC 2.4.1.16) (CHITIN-UDP ACETYL-GLUCOSAMINYL TRANSFERASE D) (CLASS-V CHITIN SYNTHASE D). | swissprot P78611 | ND |
| 7178 | 1040.4 | PUTATIVE HYDROXYACYLGLUTATHIONE HYDROLASE. | tremblnew CAB57337 | ND |
| 7179 | 1039.8 | _A. crysogenum_ cystathionine beta-synthase. | geneseqp R72589 | Amino acid transport and metabolism |
| 7180 | 1036.9 | PUTATIVE DIHYDROXY-ACID DEHYDRATASE, MITOCHONDRIAL PRECURSOR (EC 4.2.1.9) (DAD) (2,3-DIHYDROXY ACID HYDROLYASE). | swissprot Q10318 | Amino acid transport and metabolism |
| 7181 | 1036.6 | _Malassezia fungus_ MF-5 antigenic protein. | geneseqp W29772 | Energy production and conversion |
| 7182 | 1035.6 | LEUCYL-TRNA SYNTHETASE, MITOCHONDRIAL PRECURSOR (EC 6.1.1.4) (LEUCINE--TRNA LIGASE) (LEURS). | swissprot P15181 | Translation, ribosomal structure and biogenesis |
| 7183 | 1033.6 | HYPOTHETICAL 69.2 KD PROTEIN. | sptrembl O60164 | ND |
| 7184 | 1032.1 | PROBABLE SUCCINATE DEHYDROGENASE FLAVOPROTEIN SUBUNIT PRECURSOR(EC 1.3.5.1). | tremblnew CAB61213 | Energy production and conversion |
| 7185 | 1032.0 | PUTATIVE ELONGATION FACTOR 3. | sptrembl O94489 | ND |
| 7186 | 1028.5 | ISOPENTENYL-DIPHOSPHATE DELTA-ISOMERASE. | tremblnew CAB53731 | Lipid metabolism |
| 7187 | 1028.1 | PUTATIVE PROTEASE SUBUNIT, CHAPERONIN. | sptrembl O94641 | Posttranslational modification, protein turnover, chaperones |
| 7188 | 1027.1 | T-COMPLEX PROTEIN 1 GAMMA SUBUNIT HOMOLOG. | sptrembl O74341 | ND |
| 7189 | 1024.3 | SUPEROXIDE DISMUTASE (CU—ZN) (EC 1.15.1.1). | sptrembl Q9Y8D9 | Inorganic ion transport and metabolism |
| 7190 | 1022.5 | BCDNA.LD14392. | sptrembl Q9XZ58 | ND |
| 7191 | 1022.1 | ALCOHOL OXIDASE 1. | tremblnew AAF02494 | ND |
| 7192 | 1020.8 | T-COMPLEX PROTEIN 1, DELTA SUBUNIT (TCP-1-DELTA) (CCT-DELTA) | swissprot P50991 | Posttranslational modification, protein turnover, |

TABLE 3-continued

Aspergillus oryzae ESTs

| Sequence Listing | zscore | Annotation | Database | Functional Category |
|---|---|---|---|---|
| | | (STIMULATOR OF TAR RNA BINDING). | | chaperones |
| 7193 | 1020.0 | An enzyme with sugar transferase activity. | geneseqp W88044 | ND |
| 7194 | 1019.3 | GAP-DH. | geneseqp R12995 | Carbohydrate transport and metabolism |
| 7195 | 1018.7 | HYPOTHETICAL 49.3 KD PROTEIN C30D11.06C IN CHROMOSOME I. | swissprot Q09906 | ND |
| 7196 | 1018.2 | UBIQUITIN-ACTIVATING ENZYME E1 1 (FRAGMENT). | swissprot P52495 | Coenzyme metabolism |
| 7197 | 1018.0 | NUCLEAR MOVEMENT PROTEIN NUDC. | swissprot P17624 | ND |
| 7198 | 1018.0 | GAP-DH. | geneseqp R12995 | Carbohydrate transport and metabolism |
| 7199 | 1017.4 | CARNITINE/ACYL CARNITINE CARRIER. | sptrembl Q9Y7G4 | ND |
| 7200 | 1016.8 | REHYDRIN-LIKE PROTEIN. | sptrembl O94014 | Posttranslational modification, protein turnover, chaperones |
| 7201 | 1016.4 | HYPOTHETICAL 37.2 KD PROTEIN IN CHA1-PRD1 INTERGENIC REGION. | swissprot P25586 | Translation, ribosomal structure and biogenesis |
| 7202 | 1014.5 | HYPOTHETICAL 69.0 KD PROTEIN. | sptrembl O94022 | ND |
| 7203 | 1009.3 | RHO2 PROTEIN. | swissprot Q10133 | ND |
| 7204 | 1006.6 | PUTATIVE LYSYL-TRNA SYNTHETASE. | tremblnew CAB52801 | Translation, ribosomal structure and biogenesis |
| 7205 | 1004.7 | GLYCYL-TRNA SYNTHETASE (EC 6.1.1.14) (GLYCINE--TRNA LIGASE) (GLYRS). | swissprot P38088 | Translation, ribosomal structure and biogenesis |
| 7206 | 1004.2 | UBIQUITIN-CONJUGATING ENZYME E2-18 KD (EC 6.3.2.19) (UBIQUITIN-PROTEIN LIGASE) (UBIQUITIN CARRIER PROTEIN). | swissprot O00102 | ND |
| 7207 | 1003.8 | ISOLEUCYL-TRNA SYNTHETASE, CYTOPLASMIC (EC 6.1.1.5) (ISOLEUCINE--TRNA LIGASE) (ILERS). | swissprot P09436 | Translation, ribosomal structure and biogenesis |
| 7208 | 1001.0 | CHITIN SYNTHASE A (EC 2.4.1.16) (CHITIN-UDP ACETYL-GLUCOSAMINYL TRANSFERASE A) (CLASS-II CHITIN SYNTHASE A). | swissprot P30584 | ND |
| 7209 | 1000.9 | VACUOLAR ATP SYNTHASE 98 KD SUBUNIT (EC 3.6.1.34) (VACUOLAR ATPASE 98 KD SUBUNIT). | swissprot Q01290 | Energy production and conversion |

TABLE 4

Trichoderma reesei ESTs

| Sequence Listing | zscore | Annotation | Database | Functional Category |
|---|---|---|---|---|
| 7401 | 3514.6 | EXOGLUCANASE I PRECURSOR (EC 3.2.1.91) (EXOCELLOBIOHYDROLASE I) (CBHI) (1,4-BETA-CELLOBIOHYDROLASE). | swissprot P00725 | ND |

TABLE 4-continued

*Trichoderma reesei* ESTs

| Sequence Listing | zscore | Annotation | Database | Functional Category |
|---|---|---|---|---|
| 7402 | 3143.2 | Cellobiohydrolase CBH II protein. | geneseqp P50308 | ND |
| 7403 | 2899.7 | HEAT SHOCK 70 KD PROTEIN (HSP70). | swissprot Q01233 | Posttranslational modification, protein turnover, chaperones |
| 7404 | 2335.7 | BETE-GLUCOSIDASE. | sptrembl O93785 | ND |
| 7405 | 2276.9 | BETA-XYLOSIDASE PRECURSOR (EC 3.2.1.37). | sptrembl Q92458 | ND |
| 7406 | 2270.7 | PROTEIN DISULPHIDE ISOMERASE PRECURSOR. | sptrembl O74568 | ND |
| 7407 | 1899.1 | ENDOGLUCANASE IV. | sptrembl O14405 | ND |
| 7408 | 1808.4 | ENDOGLUCANASE EG-II PRECURSOR (EC 3.2.1.4) (ENDO-1,4-BETA-GLUCANASE) (CELLULASE). | swissprot P07982 | ND |
| 7409 | 1731.4 | Enzyme with endoglucanase activity. | geneseqp R66548 | ND |
| 7410 | 1719.7 | Endoglucanase-I protein sequence. | geneseqp R79539 | ND |
| 7411 | 1691.7 | ACETYLXYLAN ESTERASE PRECURSOR (EC 3.1.1.72). | sptrembl Q99034 | ND |
| 7412 | 1640.1 | PUTATIVE PROTEASE SUBUNIT, CHAPERONIN. | sptrembl O94641 | Posttranslational modification, protein turnover, chaperones |
| 7413 | 1526.2 | ELONGATION FACTOR 1-ALPHA (EF-1-ALPHA). | swissprot P34825 | Amino acid transport and metabolism |
| 7414 | 1453.5 | 78 KD GLUCOSE-REGULATED PROTEIN HOMOLOG PRECURSOR (GRP 78) (IMMUNOGLOBULIN HEAVY CHAIN BINDING PROTEIN HOMOLOG) (BIP). | swissnew P78695 | Posttranslational modification, protein turnover, chaperones |
| 7415 | 1408.0 | GLYCERALDEHYDE 3-PHOSPHATE DEHYDROGENASE 2 (EC 1.2.1.12) (GAPDH2). | swissprot P17730 | Carbohydrate transport and metabolism |
| 7416 | 1405.7 | AMINO-ACID PERMEASE INDA1. | swissprot P34054 | Amino acid transport and metabolism |
| 7417 | 1395.0 | NADH DEHYDROGENASE SUBUNIT. | sptrembl Q01388 | Energy production and conversion |
| 7418 | 1393.9 | POLYUBIQUITIN. | sptrembl O74274 | ND |
| 7419 | 1346.1 | ADP,ATP CARRIER PROTEIN (ADP/ATP TRANSLOCASE) (ADENINE NUCLEOTIDE TRANSLOCATOR) (ANT). | swissprot P02723 | ND |
| 7420 | 1323.7 | PYRUVATE CARBOXYLASE. | sptrembl O93918 | Amino acid transport and metabolism |
| 7421 | 1309.3 | GLUCAN SYNTHASE. | sptrembl Q9Y8B3 | ND |
| 7422 | 1262.0 | BETA-XYLOSIDASE PRECURSOR (EC 3.2.1.37). | sptrembl Q92458 | ND |
| 7423 | 1257.6 | HEAT SHOCK PROTEIN 90 HOMOLOG (SUPPRESSOR OF VEGETATIVE INCOMPATIBILITY MOD-E). | swissprot O43109 | Posttranslational modification, protein turnover, chaperones |
| 7424 | 1236.9 | ALPHA-L-ARABINOFURANOSIDASE PRECURSOR (EC 3.2.1.55) (ARABINOSIDASE). | swissprot O54161 | ND |
| 7425 | 1236.1 | STRESS-RESPONSIVE GENE PRODUCT. | tremblnew BAA85305 | ND |
| 7426 | 1233.4 | *T. longibrachiatum* endoglucanase EGII. | geneseqp R77264 | ND |
| 7427 | 1209.2 | EXOGLUCANASE I PRECURSOR (EC 3.2.1.91) (EXOCELLOBIOHYDROLASE | swissprot P00725 | ND |

TABLE 4-continued

Trichoderma reesei ESTs

| Sequence Listing | zscore | Annotation | Database | Functional Category |
|---|---|---|---|---|
| | | I) (CBHI) (1,4-BETA-CELLOBIOHYDROLASE). | | |
| 7428 | 1202.4 | ACID TREHALASE PRECURSOR (EC 3.2.1.28) (ALPHA,ALPHA-TREHALASE) (ALPHA,ALPHA-TREHALOSE GLUCOHYDROLASE). | swissprot P78617 | ND |
| 7429 | 1180.9 | *A. chrysogenum* gamma-actin. | geneseqp W77101 | Cell division and chromosome partitioning |
| 7430 | 1175.1 | SERINE HYDROXYMETHYLTRANS-FERASE, CYTOSOLIC (EC 2.1.2.1) (SERINE METHYLASE) (GLYCINE HYDROXYMETHYLTRANS-FERASE) (SHMT). | swissprot P34898 | Amino acid transport and metabolism |
| 7431 | 1158.1 | ELONGATION FACTOR 1-ALPHA (EF-1-ALPHA). | swissprot P34825 | Amino acid transport and metabolism |
| 7432 | 1155.9 | RIBOSE-PHOSPHATE PYROPHOSPHOKINASE. | sptrembl O94413 | Nucleotide transport |
| 7433 | 1140.3 | NAD(+)-ISOCITRATE DEHYDROGENASE SUBUNIT I PRECURSOR. | sptrembl O13302 | Amino acid transport and metabolism |
| 7434 | 1132.8 | PLASMA MEMBRANE ATPASE (EC 3.6.1.35) (PROTON PUMP). | swissprot P07038 | Inorganic ion transport and metabolism |
| 7435 | 1127.0 | HISTIDINE KINASE (FRAGMENT). | tremblnew AAD40816 | ND |
| 7436 | 1122.6 | HYPOTHETICAL 44.2 KD GTP-BINDING PROTEIN IN SCO2-MRF1 INTERGENIC REGION. | swissprot P38219 | ND |
| 7437 | 1073.9 | GUANINE NUCLEOTIDE-BINDING PROTEIN BETA SUBUNIT-LIKE PROTEIN (CROSS-PATHWAY CONTROL WD-REPEAT PROTEIN CPC-2). | swissprot Q01369 | ND |
| 7438 | 1063.3 | GTP-BINDING PROTEIN YPT1. | swissprot P33723 | ND |
| 7440 | 993.7 | FUMARATE HYDRATASE PRECURSOR (EC 4.2.1.2) (FUMARASE). | swissprot P55250 | Energy production and conversion |
| 7441 | 985.3 | PH RESPONSIVE PROTEIN 1 PRECURSOR (PH-REGULATED PROTEIN 1). | swissprot P43076 | ND |
| 7442 | 985.0 | 60S RIBOSOMAL PROTEIN L5. | swissprot O59953 | Translation, ribosomal structure and biogenesis |
| 7443 | 980.7 | INORGANIC PYROPHOSPHATASE (EC 3.6.1.1) (PYROPHOSPHATE PHOSPHO-HYDROLASE) (PPASE). | swissprot P19117 | Energy production and conversion |
| 7444 | 977.7 | 40S RIBOSOMAL PROTEIN S3AE (S1). | swissprot P40910 | Translation, ribosomal structure and biogenesis |
| 7445 | 971.3 | MONOUBIQUITIN/CARBOXY EXTENSION PROTEIN FUSION. | sptrembl O74216 | ND |
| 7446 | 968.6 | PROBABLE ATP-DEPENDENT PERMEASE C3F10.11C. | swissprot Q10185 | ND |
| 7447 | 959.7 | HEAT SHOCK PROTEIN 90 HOMOLOG (SUPPRESSOR OF VEGETATIVE INCOMPATIBILITY MOD-E). | swissprot O43109 | Posttranslational modification, protein turnover, chaperones |

TABLE 4-continued

*Trichoderma reesei* ESTs

| Sequence Listing | zscore | Annotation | Database | Functional Category |
|---|---|---|---|---|
| 7448 | 957.2 | CYCLOPHILIN B (EC 5.2.1.8). | sptrembl O94190 | Posttranslational modification, protein turnover, chaperones |
| 7450 | 944.8 | AMINO-ACID PERMEASE INDA1. | swissprot P34054 | Amino acid transport and metabolism |
| 7451 | 936.4 | PLASMA MEMBRANE H(+)ATPASE. | sptrembl O93862 | Inorganic ion transport and metabolism |
| 7452 | 925.1 | 78 KD GLUCOSE-REGULATED PROTEIN HOMOLOG PRECURSOR (GRP 78) (IMMUNOGLOBULIN HEAVY CHAIN BINDING PROTEIN HOMOLOG) (BIP). | swissnew P78695 | Posttranslational modification, protein turnover, chaperones |
| 7453 | 907.3 | PUTATIVE BETA-SUBUNIT OF K+ CHANNELS. | sptrembl O82064 | Energy production and conversion |
| 7454 | 902.5 | CHROMOSOME XV READING FRAME ORF YOR262W. | sptrembl Q08726 | ND |
| 7455 | 900.3 | ACYL-COA DESATURASE 1 (EC 1.14.99.5) (STEAROYL-COA DESATURASE 1) (FATTY ACID DESATURASE 1). | sptrembl Q12618 | Lipid metabolism |
| 7456 | 899.4 | PROTEIN TRANSPORT PROTEIN SEC61 ALPHA SUBUNIT. | swissprot P78979 | Cell motility and secretion |
| 7457 | 876.0 | 60S RIBOSOMAL PROTEIN L23 (L17). | swissprot P04451 | Translation, ribosomal structure and biogenesis |
| 7458 | 867.5 | BETA-GLUCOSIDASE. | sptrembl O93784 | ND |
| 7459 | 861.2 | 78 KD GLUCOSE-REGULATED PROTEIN HOMOLOG PRECURSOR (GRP 78) (IMMUNOGLOBULIN HEAVY CHAIN BINDING PROTEIN HOMOLOG) (BIP). | swissnew P78695 | Posttranslational modification, protein turnover, chaperones |
| 7460 | 856.5 | PUTATIVE GTP CYCLOHYDROLASE. | tremblnew CAB65619 | ND |
| 7461 | 849.6 | PROTEASOME COMPONENT PUP2 (EC 3.4.99.46) (MACROPAIN SUBUNIT PUP2) (PROTEINASE YSCE SUBUNIT PUP2) (MULTICATALYTIC ENDOPEPTIDASE COMPLEX SUBUNIT PUP2). | swissprot P32379 | Posttranslational modification, protein turnover, chaperones |
| 7462 | 839.0 | 40S RIBOSOMAL PROTEIN S4. | swissprot P87158 | Translation, ribosomal structure and biogenesis |
| 7463 | 837.8 | PCZA361.14. | sptrembl O52801 | ND |
| 7464 | 835.2 | CALCINEURIN B SUBUNIT (PROTEIN PHOSPHATASE 2B REGULATORY SUBUNIT) (CALCINEURIN REGULATORY SUBUNIT). | swissprot P87072 | ND |
| 7465 | 834.2 | 3-ISOPROPYLMALATE DEHYDROGENASE (EC 1.1.1.85) (BETA-IPM DEHYDROGENASE) (IMDH) (3-IPM-DH). | swissprot P34738 | Amino acid transport and metabolism |
| 7466 | 832.8 | HEAT SHOCK PROTEIN 60 PRECURSOR (ANTIGEN HIS-62). | swissprot P50142 | Posttranslational modification, protein turnover, chaperones |

TABLE 4-continued

_Trichoderma reesei ESTs_

| Sequence Listing | zscore | Annotation | Database | Functional Category |
|---|---|---|---|---|
| 7467 | 829.9 | 40S RIBOSOMAL PROTEIN S17 (CRP3). | swissprot P27770 | Translation, ribosomal structure and biogenesis |
| 7468 | 823.2 | 4-DIHYDROMETHYL-TRISPORATE DEHYDROGENASE. | sptrembl Q01213 | ND |
| 7469 | 801.8 | CYCLOPHILIN, MITOCHONDRIAL FORM PRECURSOR (EC 5.2.1.8). | sptrembl Q99009 | Posttranslational modification, protein turnover, chaperones |
| 7470 | 800.4 | ATP SYNTHASE BETA CHAIN, MITOCHONDRIAL PRECURSOR (EC 3.6.1.34). | swissnew P23704 | Energy production and conversion |
| 7471 | 797.6 | _A. niger_ xylanase regulator xylR. | geneseqp W08586 | ND |
| 7472 | 796.4 | 40S RIBOSOMAL PROTEIN S8 (S14) (YS9) (RP19). | swissprot P05754 | Translation, ribosomal structure and biogenesis |
| 7473 | 787.3 | 60S RIBOSOMAL PROTEIN L2. | sptrembl O94253 | Translation, ribosomal structure and biogenesis |
| 7474 | 780.1 | ELONGATION FACTOR 2 (FRAGMENT). | tremblnew CAB52147 | Translation, ribosomal structure and biogenesis |
| 7475 | 778.8 | VACUOLAR ATP SYNTHASE SUBUNIT B (EC 3.6.1.34) (V-ATPASE 57 KD SUBUNIT). | swissprot P11593 | Energy production and conversion |
| 7476 | 778.0 | 40S RIBOSOMAL PROTEIN S14 (CRP2). | swissprot P19115 | Translation, ribosomal structure and biogenesis |
| 7477 | 757.6 | PROBABLE UTP--GLUCOSE-1-PHOSPHATE URIDYLYLTRANSFERASE. | tremblnew CAA22857 | ND |
| 7478 | 746.3 | _Candida albicans_ CaCLA4 protein. | geneseqp W48896 | Signal transduction mechanisms |
| 7479 | 736.5 | CTR1 SUPPRESSOR PROTEIN. | swissprot P32784 | ND |
| 7480 | 728.0 | ACETYL-COENZYME A SYNTHETASE (EC 6.2.1.1) (ACETATE--COA LIGASE) (ACYL-ACTIVATING ENZYME). | swissprot P16928 | Lipid metabolism |
| 7481 | 725.0 | TRANSALDOLASE (EC 2.2.1.2). | swissprot P15019 | Carbohydrate transport and metabolism |
| 7482 | 724.0 | PROTEIN KINASE. | sptrembl O59790 | Signal transduction mechanisms |
| 7483 | 720.8 | PDI RELATED PROTEIN A. | sptrembl O93914 | Energy production and conversion |
| 7484 | 711.9 | 40S RIBOSOMAL PROTEIN S22 (S15A) (YS24). | swissprot P33953 | Translation, ribosomal structure and biogenesis |
| 7485 | 709.2 | Yeast RNA-binding protein ZPR1. | geneseqp W38455 | ND |
| 7486 | 700.7 | pI 5.5 endoxylanase. | geneseqp R47123 | ND |
| 7487 | 700.5 | PUTATIVE ALPHA,ALPHA-TREHALOSE-PHOSPHATE SYNTHASE. | tremblnew CAB52715 | Carbohydrate transport and metabolism |
| 7488 | 693.1 | POTENTIAL PROTEASOME COMPONENT C5 (EC 3.4.99.46) (MULTICATALYTIC ENDOPEPTIDASE COMPLEX SUBUNIT C5). | swissprot P23724 | Posttranslational modification, protein turnover, chaperones |

TABLE 4-continued

*Trichoderma reesei* ESTs

| Sequence Listing | zscore | Annotation | Database | Functional Category |
|---|---|---|---|---|
| 7489 | 684.0 | VACUOLAR ASPARTIC PROTEASE PRECURSOR. | sptrembl O42630 | ND |
| 7490 | 682.5 | PHOSPHOGLUCOMUTASE. | sptrembl O74374 | Carbohydrate transport and metabolism |
| 7491 | 681.8 | 40S RIBOSOMAL PROTEIN S6. | swissprot P05752 | Translation, ribosomal structure and biogenesis |
| 7492 | 678.4 | PROTEIN TRANSPORT PROTEIN SEC13. | swissprot P53024 | ND |
| 7493 | 667.9 | EBURICOL 14 ALPHA-DEMETHYLASE. | tremblnew AAF18468 | ND |
| 7494 | 663.8 | NADP-SPECIFIC GLUTAMATE DEHYDROGENASE (EC 1.4.1.4) (NADP-GDH). | swissprot P00369 | Amino acid transport and metabolism |
| 7495 | 653.0 | HYPOTHETICAL 17.4 KD PROTEIN. | sptrembl O59727 | ND |
| 7496 | 643.2 | DIHYDROLIPOAMIDE ACETYLTRANSFERASE COMPONENT OF PYRUVATE DEHYDROGENASE COMPLEX, MITOCHONDRIAL PRECURSOR (EC 2.3.1.12) (E2) (PDC-E2) (MRP3). | swissprot P20285 | Energy production and conversion |
| 7497 | 641.3 | CAMP-DEPENDENT PROTEIN KINASE CATALYTIC SUBUNIT. | sptrembl Q9Y777 | Signal transduction mechanisms |
| 7498 | 639.5 | CELL DIVISION-ASSOCIATED PROTEIN BIMB. | swissprot P33144 | ND |
| 7499 | 632.0 | HIGH-AFFINITY GLUCOSE TRANSPORTER. | swissprot P49374 | ND |
| 7500 | 631.2 | HYPOTHETICAL 58.8 KD PROTEIN C16A3.10 IN CHROMOSOME II. | sptrembl O42916 | ND |
| 7501 | 628.2 | PROTEIN KINASE DSK1 (EC 2.7.1.-) (DIS1-SUPPRESSING PROTEIN KINASE). | swissprot P36616 | Signal transduction mechanisms |
| 7502 | 627.2 | 14-3-3. | tremblnew BAA89421 | ND |
| 7503 | 623.1 | 78 KD GLUCOSE-REGULATED PROTEIN HOMOLOG PRECURSOR (GRP 78) (IMMUNOGLOBULIN HEAVY CHAIN BINDING PROTEIN HOMOLOG) (BIP). | swissprot P36604 | Posttranslational modification, protein turnover, chaperones |
| 7504 | 618.5 | CYTOCHROME C549. | tremblnew BAA85768 | ND |
| 7505 | 617.0 | 3-HYDROXYBUTYRYL-COA DEHYDROGENASE (EC 1.1.1.157) (BETA-HYDROXYBUTYRYL-COA DEHYDROGENASE) (BHBD). | swissprot Q45223 | Lipid metabolism |
| 7506 | 616.9 | HEAT SHOCK 70 KD PROTEIN COGNATE 5. | swissprot P29845 | Posttranslational modification, protein turnover, chaperones |
| 7507 | 607.2 | 01232. | sptrembl Q05663 | ND |
| 7508 | 605.9 | SERINE THREONINE-PROTEIN KINASE. | sptrembl O94537 | Signal transduction mechanisms |
| 7509 | 597.9 | FRUCTOSE-1,6-BISPHOSPHATASE (EC 3.1.3.11) (D-FRUCTOSE-1,6-BISPHOSPHATE 1-PHOSPHOHYDROLASE) (FBPASE). | swissprot P09202 | Carbohydrate transport and metabolism |

TABLE 4-continued

*Trichoderma reesei* ESTs

| Sequence Listing | zscore | Annotation | Database | Functional Category |
|---|---|---|---|---|
| 7510 | 593.3 | NADH-DEPENDENT GLUTAMATE SYNTHASE. | sptrembl Q40360 | Amino acid transport and metabolism |
| 7511 | 585.6 | AVICELASE III. | sptrembl O74170 | ND |
| 7512 | 577.5 | HISTONE H4.1. | swissprot P23750 | DNA replication, recombination and repair |
| 7513 | 572.1 | GLYCEROL-3-PHOSPHATE DEHYDROGENASE (FRAGMENT). | tremblnew AAB50200 | Energy production and conversion |
| 7514 | 568.8 | HEAT SHOCK PROTEIN HSP88. | sptrembl O74225 | ND |
| 7515 | 564.0 | DOLICHOL-PHOSPHATE MANNOSYLTRANSFERASE (EC 2.4.1.83) (DOLICHOL-PHOSPHATE MANNOSE SYNTHASE) (DOLICHYL-PHOSPHATE BETA-D-MANNOSYLTRANSFERASE) | sptrembl O14466 | ND |
| 7516 | 552.8 | PROBABLE SYNAPTOBREVIN HOMOLOG C6G9.11. | swissprot Q92356 | ND |
| 7517 | 552.8 | 60S RIBOSOMAL PROTEIN L1-B (L10A). | swissprot O74836 | Translation, ribosomal structure and biogenesis |
| 7518 | 551.9 | VANILLIN: NAD+ OXIDOREDUCTASE. | sptrembl O69763 | ND |
| 7519 | 545.5 | PEROXISOMAL HYDRATASE-DEHYDROGENASE-EPIMERASE (HDE) (MULTIFUNCTIONAL BETA-OXIDATION PROTEIN) (MFP) [INCLUDES: 2-ENOYL-COA HYDRATASE (EC 4.2.1.-); D-3-HYDROXYACYL COA DEHYDROGENASE (EC 1.1.1.-)]. | swissnew Q01373 | ND |
| 7520 | 543.1 | UREASE (EC 3.5.1.5) (UREA AMIDOHYDROLASE). | sptrembl O14420 | Amino acid transport and metabolism |
| 7521 | 541.4 | PUTATIVE SECRETED HYDROLASE. | sptrembl O69962 | ND |
| 7522 | 540.4 | 60S RIBOSOMAL PROTEIN L13. | swissprot O59931 | ND |
| 7523 | 535.2 | BETA-GLUCOSIDASE PRECURSOR (EC 3.2.1.21) (GENTIOBIASE) (CELLOBIASE) (BETA-D-GLUCOSIDE GLUCOHYDROLASE). | swissprot P07337 | ND |
| 7524 | 532.0 | PUTATIVE TRANSCRIPTIONAL REPRESSOR C30D10.02. | sptrembl O14348 | ND |
| 7525 | 523.6 | MYOSIN I HEAVY CHAIN. | sptrembl Q00647 | ND |
| 7526 | 521.8 | PUTATIVE MITOCHONDRIAL CARRIER C8C9.12C. | sptrembl O14281 | ND |
| 7527 | 520.3 | MALATE DEHYDROGENASE, MITOCHONDRIAL PRECURSOR (EC 1.1.1.37). | swissprot P17505 | Energy production and conversion |
| 7528 | 518.6 | U6 SNRNA-ASSOCIATED SM-LIKE PROTEIN LSM5. | tremblnew AAD56229 | ND |
| 7529 | 511.2 | PHOSPHOGLUCOMUTASE 1 (EC 5.4.2.2) (GLUCOSE PHOSPHOMUTASE 1) (PGM 1). | swissprot P33401 | Carbohydrate transport and metabolism |

TABLE 4-continued

*Trichoderma reesei* ESTs

| Sequence Listing | zscore | Annotation | Database | Functional Category |
|---|---|---|---|---|
| 7530 | 510.1 | Yeast CAAX processing enzyme Afc1p. | geneseqp W48301 | Posttranslational modification, protein turnover, chaperones |
| 7531 | 507.9 | c424 gene product. | geneseqp R43654 | ND |
| 7532 | 505.8 | PURINE NUCLEOSIDE PERMEASE. | sptrembl O93844 | ND |
| 7533 | 504.5 | CHAPERONIN HSP78P. | sptrembl O74402 | Posttranslational modification, protein turnover, chaperones |
| 7534 | 500.8 | 60S RIBOSOMAL PROTEIN L26. | swissnew P78946 | Translation, ribosomal structure and biogenesis |
| 7535 | 499.0 | STIL+. | sptrembl O13458 | ND |
| 7536 | 494.4 | UBIQUITIN CARBOXYL-TERMINAL HYDROLASE (HOMOLOGY TO UBIQUITIN CARBOXYL-TERMINAL HYDROLASE). | sptrembl Q11119 | ND |
| 7537 | 491.7 | HYPOTHETICAL 30.8 KD PROTEIN. | sptrembl O74710 | ND |
| 7538 | 487.5 | TRANSLATIONALLY CONTROLLED TUMOR PROTEIN HOMOLOG (TCTP). | swissprot P35691 | ND |
| 7539 | 476.3 | DNA BINDING PROTEIN NSDD. | sptrembl Q92226 | ND |
| 7540 | 475.9 | 60S RIBOSOMAL PROTEIN L34-A. | swissprot P87262 | Translation, ribosomal structure and biogenesis |
| 7541 | 469.2 | HYPOTHETICAL 36.7 KD PROTEIN C2E11.10 IN CHROMOSOME I. | sptrembl O14075 | ND |
| 7542 | 460.3 | SIMILAR TO ASPARTATE AMINOTRANSFERASE. | sptrembl Q17994 | ND |
| 7543 | 458.0 | HYPOTHETICAL 36.7 KD PROTEIN C2F7.14C IN CHROMOSOME I. | swissprot Q09704 | Translation, ribosomal structure and biogenesis |
| 7544 | 455.2 | 60S RIBOSOMAL PROTEIN L35. | swissprot P17078 | Translation, ribosomal structure and biogenesis |
| 7545 | 439.7 | HYPOTHETICAL 53.4 KD PROTEIN (FRAGMENT). | sptrembl Q9Y7E2 | ND |
| 7546 | 438.1 | HYPOTHETICAL 59.0 KD PROTEIN C30D11.14 IN CHROMOSOME I. | swissprot Q09911 | ND |
| 7547 | 435.2 | NADPH-DEPENDENT ALDEHYDE REDUCTASE (EC 1.1.1.2) (ALCOHOL DEHYDROGENASE (NADP+)) (ALDEHYDE REDUCTASE (NADPH)). | sptrembl Q12707 | ND |
| 7548 | 428.2 | 60S RIBOSOMAL PROTEIN L27A (L29). | swissprot P78987 | Translation, ribosomal structure and biogenesis |
| 7549 | 427.9 | THIOREDOXIN. | swissprot P42115 | ND |
| 7550 | 420.0 | 30 KD HEAT SHOCK PROTEIN. | swissprot P19752 | ND |
| 7551 | 418.0 | HYPOTHETICAL 25.2 KD PROTEIN. | sptrembl Q9Y7K7 | ND |
| 7552 | 411.8 | CALCIUM/PROTON EXCHANGER. | sptrembl O59940 | ND |
| 7553 | 410.0 | ASPARTIC PROTEINASE. | sptrembl Q9Y740 | ND |
| 7554 | 409.7 | ALPHA,ALPHA-TREHALASE {EC 3.2.1.28}. | tremblnew G1911650 | ND |
| 7555 | 409.4 | HYPOTHETICAL 34.2 KD PROTEIN IN CUS1-RPL20A INTERGENIC REGION. | swissprot Q04013 | ND |

TABLE 4-continued

_Trichoderma reesei ESTs_

| Sequence Listing | zscore | Annotation | Database | Functional Category |
|---|---|---|---|---|
| 7556 | 407.7 | CARBOXYLIC ACID TRANSPORTER PROTEIN HOMOLOG. | swissprot P36035 | ND |
| 7557 | 402.5 | UBIQUITIN-CONJUGATING ENZYME E2-34 KD (EC 6.3.2.19) (UBIQUITIN-PROTEIN LIGASE) (UBIQUITIN CARRIER PROTEIN) (CELL DIVISION CONTROL PROTEIN 34). | swissprot P14682 | ND |
| 7558 | 400.5 | DIHYDROLIPOAMIDE SUCCINYLTRANSFERASE. | tremblnew AAD47296 | ND |
| 7559 | 398.0 | NPL1 PROTEIN (SEC63 PROTEIN). | swissprot P14906 | Posttranslational modification, protein turnover, chaperones |
| 7560 | 395.3 | HYPOTHETICAL OXIDOREDUCTASE C23D3.11 IN CHROMOSOME I (EC 1.-.-.-). | swissnew Q09851 | ND |
| 7561 | 386.2 | HYPOTHETICAL 121.8 KD PROTEIN. | sptrembl O43001 | ND |
| 7562 | 383.9 | MDJ1 PROTEIN PRECURSOR. | swissprot P35191 | Posttranslational modification, protein turnover, chaperones |
| 7563 | 383.6 | CONSERVED HYPOTHETICAL PROTEIN. | sptrembl O74739 | ND |
| 7564 | 378.5 | CELL DIVISION CONTROL PROTEIN 4. | swissprot P53699 | ND |
| 7565 | 366.5 | VACUOLAR ATP SYNTHASE SUBUNIT G (EC 3.6.1.34) (V-ATPASE 13 KD SUBUNIT) (VACUOLAR H(+)-ATPASE SUBUNIT G). | swissprot P78713 | ND |
| 7566 | 364.8 | VIP1 PROTEIN (P53 ANTIGEN HOMOLOG). | sptrembl P87216 | ND |
| 7567 | 359.1 | F45H11.2 PROTEIN. | sptrembl Q93725 | ND |
| 7568 | 357.4 | CARBONIC ANHYDRASE (EC 4.2.1.1). | sptrembl Q43060 | ND |
| 7569 | 355.5 | HYPOTHETICAL 61.3 KD PROTEIN CY369.29. | sptrembl P71838 | ND |
| 7570 | 353.3 | ASCOSPORE MATURATION 1 PROTEIN. | sptrembl Q92251 | ND |
| 7571 | 351.2 | OUTER MITOCHONDRIAL MEMBRANE PROTEIN PORIN. | swissprot P07144 | ND |
| 7572 | 350.2 | HYPOTHETICAL 30.7 KD PROTEIN IN RVS161-ADP1 INTERGENIC REGION. | swissprot P25613 | ND |
| 7573 | 349.8 | HEAT SHOCK FACTOR PROTEIN (HSF) (HEAT SHOCK TRANSCRIPTION FACTOR) (HSTF). | swissprot Q02953 | ND |
| 7574 | 346.1 | HYDROXYPROLINE-RICH GLYCOPROTEIN DZ-HRGP PRECURSOR. | tremblnew CAB62280 | ND |
| 7575 | 340.5 | W02A2.5 PROTEIN. | sptrembl Q9XUB4 | ND |
| 7576 | 338.3 | HYPOTHETICAL 32.6 KD PROTEIN IN VPS15-YMC2 INTERGENIC REGION. | swissprot P38260 | ND |
| 7577 | 337.0 | BRANCHED-CHAIN AMINO ACID AMINOTRANSFERASE, CYTOSOLIC (EC 2.6.1.42) (BCAT) (TWT2 PROTEIN). | swissprot P47176 | ND |
| 7578 | 336.9 | HYPOTHETICAL 34.0 KD PROTEIN IN CTF13-YPK2 INTERGENIC REGION. | swissprot Q03161 | ND |
| 7579 | 330.8 | REHYDRIN-LIKE PROTEIN. | sptrembl O94014 | ND |
| 7580 | 329.1 | PUTATIVE 20 KDA SUBUNIT OF THE V-ATPASE. | sptrembl P87252 | ND |

TABLE 4-continued

*Trichoderma reesei* ESTs

| Sequence Listing | zscore | Annotation | Database | Functional Category |
|---|---|---|---|---|
| 7581 | 328.5 | PXP-18. | tremblnew BAA85152 | ND |
| 7582 | 328.0 | HYPOTHETICAL 49.6 KD PROTEIN IN ELM1-PRI2 INTERGENIC REGION. | swissprot P36091 | ND |
| 7583 | 326.7 | HYDROXYPROLINE-RICH GLYCOPROTEIN DZ-HRGP PRECURSOR. | tremblnew CAB62280 | ND |
| 7584 | 325.9 | THIOREDOXIN-LIKE PROTEIN. | tremblnew CAB54816 | ND |
| 7585 | 322.7 | PROBABLE EUKARYOTIC TRANSLATION INITIATION FACTOR 3 RNA-BINDING SUBUNIT (EIF-3 RNA-BINDING SUBUNIT) (EIF3 P33) (TRANSLATION INITIATION FACTOR EIF3, P33 SUBUNIT). | swissprot P78795 | ND |
| 7586 | 320.8 | MALTOSE PERMEASE. | sptrembl Q9Y845 | ND |
| 7587 | 318.7 | HYPOTHETICAL 57.2 KD PROTEIN C12B10.16C IN CHROMOSOME I. | swissprot Q10449 | ND |
| 7588 | 317.3 | SOL FAMILY PROTEIN HOMOLOG. | sptrembl O74455 | ND |
| 7589 | 317.2 | CLOCK-CONTROLLED GENE-6 PROTEIN. | sptrembl O74694 | ND |
| 7590 | 313.4 | PUTATIVE STERIGMATOCYSTIN BIOSYNTHESIS PROTEIN STCT. | swissprot Q00717 | ND |
| 7591 | 311.9 | HYPOTHETICAL 92.4 KD PROTEIN. | sptrembl P74690 | ND |
| 7592 | 292.9 | PUTATIVE GLUCOSYLTRANSFERASE C17C9.07 (EC 2.4.1.-). | swissprot Q10479 | ND |
| 7593 | 292.5 | HYPOTHETICAL 22.0 KD PROTEIN IN FOX3-UBP7 INTERGENIC REGION. | swissprot P40452 | ND |
| 7594 | 288.6 | Mutant 2,5-diketo-D-gluconic acid reductase A. | geneseqp R49932 | ND |
| 7595 | 282.6 | PUTATIVE BRANCHED-CHAIN AMINO ACID AMINOTRANSFERASE. | sptrembl Q9Y885 | ND |
| 7596 | 280.5 | MUCIN 2 PRECURSOR (INTESTINAL MUCIN 2). | swissprot Q02817 | ND |
| 7597 | 273.8 | CHROMOSOME XV READING FRAME ORF YOL092W. | sptrembl Q12010 | ND |
| 7598 | 273.7 | GLUCOSAMINE--FRUCTOSE-6-PHOSPHATE AMINOTRANSFERASE [ISOMERIZING] (EC 2.6.1.16) (HEXOSEPHOSPHATE AMINOTRANSFERASE) (D-FRUCTOSE-6-PHOSPHATE AMIDOTRANSFERASE) (GFAT). | swissprot P53704 | ND |
| 7599 | 272.0 | H(+)/MONOSACCHARIDE COTRANSPORTER. | sptrembl O13411 | ND |
| 7600 | 270.1 | HYPOTHETICAL 36.8 KD PROTEIN. | sptrembl P71847 | ND |
| 7601 | 269.9 | PHOSPHATIDYLETHANOLAMINE N-METHYLTRANSFERASE (EC 2.1.1.17). | swissprot P05374 | ND |
| 7602 | 269.8 | EXTENSIN PRECURSOR (CELL WALL HYDROXYPROLINE-RICH GLYCOPROTEIN). | swissprot P13983 | ND |
| 7603 | 269.2 | HYPOTHETICAL 69.0 KD PROTEIN IN PPX1-RPS4B INTERGENIC REGION. | swissprot P38887 | ND |

TABLE 4-continued

*Trichoderma reesei* ESTs

| Sequence Listing | zscore | Annotation | Database | Functional Category |
|---|---|---|---|---|
| 7604 | 263.9 | 30 KD HEAT SHOCK PROTEIN. | swissprot P19752 | ND |
| 7605 | 261.4 | HYDROXYPROLINE-RICH GLYCOPROTEIN DZ-HRGP PRECURSOR. | tremblnew CAB62280 | ND |
| 7606 | 259.9 | Polypeptide fragment encoded by gene 29. | geneseqp Y01464 | ND |
| 7607 | 255.7 | Klebsiella pneumoniae glycerol-3-phosphate dehydrogenase. | geneseqp W60255 | ND |
| 7608 | 254.9 | HYDROXYPROLINE-RICH GLYCOPROTEIN. | sptrembl Q42366 | ND |
| 7609 | 253.2 | Sugar beet chitinase 1. | geneseqp R28150 | ND |
| 7610 | 250.2 | THIOREDOXIN-LIKE PROTEIN. | tremblnew CAB54816 | ND |
| 7611 | 247.7 | P7 PREINSERTION DNA. | sptrembl Q60501 | ND |
| 7612 | 240.7 | PROLINE-RICH CELL WALL PROTEIN. | sptrembl Q39789 | ND |
| 7613 | 240.5 | COFILIN. | swissprot P78929 | ND |
| 7614 | 238.5 | IUCB. | sptrembl Q9XCH3 | ND |
| 7615 | 238.0 | Human actVA-ORF4-like protein sequence. | geneseqp Y14147 | ND |
| 7616 | 233.1 | HYDROXYPROLINE-RICH GLYCOPROTEIN DZ-HRGP PRECURSOR. | tremblnew CAB62280 | ND |
| 7617 | 232.3 | HYPOTHETICAL 38.8 KD PROTEIN IN MIC1-SRB5 INTERGENIC REGION. | swissprot P53259 | ND |
| 7618 | 232.0 | HYPOTHETICAL 41.8 KD PROTEIN (FRAGMENT). | tremblnew CAB55926 | ND |
| 7619 | 231.3 | HYPOTHETICAL 22.2 KD PROTEIN IN ERP6-TFG2 INTERGENIC REGION. | swissprot P53200 | ND |
| 7620 | 230.2 | WP6 PRECURSOR. | sptrembl Q39492 | ND |
| 7621 | 228.1 | D-3-PHOSPHOGLYCERATE DEHYDROGENASE (EC 1.1.1.95) (PGDH). | swissprot P73821 | ND |
| 7622 | 225.7 | EXTENSIN (FRAGMENT). | sptrembl Q41645 | ND |
| 7623 | 225.5 | HYPOTHETICAL PROTEIN MJ1527 PRECURSOR. | sptrembl Q58922 | ND |
| 7624 | 225.3 | EXTENSIN (FRAGMENT). | sptrembl Q41645 | ND |
| 7625 | 225.3 | CELL DIVISION-ASSOCIATED PROTEIN BIMB. | swissprot P33144 | ND |
| 7626 | 225.0 | CYSTEINE-RICH PROTEIN (FRAGMENT). | sptrembl Q16861 | ND |
| 7627 | 223.6 | PUTATIVE UBIQUITIN CARBOXYL-TERMINAL HYDROLASE C6G9.08 (EC 3.1.2.15) (UBIQUITIN THIOLESTERASE) (UBIQUITIN-SPECIFIC PROCESSING PROTEASE) (DEUBIQUITINATING ENZYME). | swissprot Q92353 | ND |
| 7628 | 223.0 | EPD2 PROTEIN. | sptrembl O74137 | ND |
| 7629 | 221.4 | PROLINE-RICH CELL WALL PROTEIN. | sptrembl Q39789 | ND |
| 7630 | 220.5 | CHROMOSOME XII COSMID 8167. | sptrembl Q05790 | ND |
| 7631 | 220.4 | HYPOTHETICAL PROTEIN C30B4.01C IN CHROMOSOME II (FRAGMENT). | sptrembl P87179 | ND |
| 7632 | 219.3 | 26S PROTEASOME REGULATORY SUBUNIT. | sptrembl O74762 | ND |
| 7633 | 218.6 | NEUROFIBROMATOSIS TYPE 1. | sptrembl Q9YGV2 | ND |
| 7634 | 217.6 | 30 KD HEAT SHOCK PROTEIN. | swissprot P19752 | ND |
| 7635 | 217.6 | DNA-DIRECTED RNA POLYMERASE III 36 KD | swissprot P32910 | ND |

TABLE 4-continued

*Trichoderma reesei* ESTs

| Sequence Listing | zscore | Annotation | Database | Functional Category |
|---|---|---|---|---|
| | | POLYPEPTIDE (EC 2.7.7.6) (C34). | | |
| 7636 | 217.3 | EXTENSIN PRECURSOR (PROLINE-RICH GLYCOPROTEIN). | swissprot P24152 | ND |
| 7637 | 216.9 | PROTEOPHOSPHOGLYCAN (FRAGMENT). | sptrembl Q9Y075 | ND |
| 7638 | 214.5 | MUCIN (FRAGMENT). | sptrembl Q14888 | ND |
| 7639 | 213.6 | HYPOTHETICAL 141.6 KD PROTEIN. | sptrembl O59704 | ND |
| 7640 | 212.3 | ATPASE INHIBITOR, MITOCHONDRIAL PRECURSOR. | swissprot P01097 | ND |
| 7641 | 209.6 | AVICELASE III. | sptrembl O74170 | ND |
| 7642 | 207.1 | CYSTEINE SYNTHASE (EC 4.2.99.8) (O-ACETYLSERINE SULFHYDRYLASE) (O-ACETYLSERINE (THIOL)-LYASE) (CSASE). | swissprot P50867 | ND |
| 7643 | 205.8 | CHROMOSOME XVI COSMID 9659. | sptrembl Q06505 | ND |
| 7644 | 205.4 | EXTENSIN PRECURSOR (PROLINE-RICH GLYCOPROTEIN). | swissprot P14918 | ND |
| 7645 | 204.9 | DIMERIC DIHYDRODIOL DEHYDROGENASE (EC 1.3.1.20). | tremblnew BAA83488 | ND |
| 7646 | 204.1 | HYPOTHETICAL 29.3 KD PROTEIN (ORF92). | swissprot O10341 | ND |
| 7647 | 203.6 | Intestinal mucin deduced from clone SMUC 40. | geneseqp R07670 | ND |
| 7648 | 202.8 | PUTATIVE GLUCANASE PRECURSOR. | tremblnew CAB57923 | ND |
| 7649 | 202.7 | PDI RELATED PROTEIN A. | sptrembl O93914 | ND |
| 7650 | 202.6 | UTR4 PROTEIN (UNKNOWN TRANSCRIPT 4 PROTEIN). | swissprot P32626 | ND |
| 7651 | 201.8 | HYPOTHETICAL 32.8 KD PROTEIN. | sptrembl O60110 | ND |
| 7652 | 199.7 | EXTENSIN-LIKE PROTEIN. | tremblnew CAA22152 | ND |
| 7653 | 199.1 | MUCIN (FRAGMENT). | sptrembl Q14887 | ND |
| 7654 | 198.3 | HYPOTHETICAL PROTEIN KIAA0107. | swissprot Q15008 | ND |
| 7655 | 197.6 | HYDROXYPROLINE-RICH GLYCOPROTEIN DZ-HRGP PRECURSOR. | tremblnew CAB62280 | ND |
| 7656 | 197.3 | PIPSQUEAK PROTEIN (ORF-A SHORT). | sptrembl Q24455 | ND |
| 7657 | 196.8 | CHA4 ACTIVATORY PROTEIN. | swissprot P43634 | ND |
| 7658 | 195.7 | PUTATIVE ALPHA,ALPHA-TREHALOSE-PHOSPHATE SYNTHASE. | tremblnew CAB52715 | ND |
| 7659 | 193.6 | NEURON-DERIVED ORPHAN RECEPTOR-1 BETA. | sptrembl O97727 | ND |
| 7660 | 193.5 | HYDROXYPROLINE-RICH GLYCOPROTEIN PRECURSOR. | sptrembl Q41719 | ND |
| 7661 | 193.4 | SPLICING FACTOR, ARGININE/SERINE-RICH 2 (SPLICING FACTOR SC35) (SC-35) (SPLICING COMPONENT, 35 KD) (PR264 PROTEIN). | swissprot Q01130 | ND |
| 7662 | 193.0 | ALPHA/BETA-GLIADIN CLONE PW1215 PRECURSOR (PROLAMIN). | swissprot P04726 | ND |
| 7663 | 193.0 | ORF-3. | sptrembl Q01823 | ND |
| 7664 | 192.1 | SULFATED SURFACE GLYCOPROTEIN 185 (SSG 185). | swissprot P21997 | ND |

TABLE 4-continued

*Trichoderma reesei* ESTs

| Sequence Listing | zscore | Annotation | Database | Functional Category |
|---|---|---|---|---|
| 7665 | 191.8 | RNA BINDING PROTEIN (FRAGMENT). | tremblnew BAA83714 | ND |
| 7666 | 191.1 | PUTATIVE PROLINE-RICH PROTEIN. | sptrembl Q9ZW08 | ND |
| 7667 | 190.8 | NAPG OXIDOREDUCTASE. | sptrembl Q9X653 | ND |
| 7668 | 190.0 | EXTENSIN (FRAGMENT). | sptrembl Q41645 | ND |
| 7669 | 189.5 | NADH-UBIQUINONE OXIDOREDUCTASE 21 KD SUBUNIT (EC 1.6.5.3) (EC 1.6.99.3) (COMPLEX I-21 KD) (CI-21 KD). | swissprot Q02854 | ND |
| 7670 | 188.9 | SALIVARY GLUE PROTEIN SGS-3 PRECURSOR. | swissprot P02840 | ND |
| 7671 | 188.3 | DOLICHYL-DIPHOSPHOOLIGOSACCHA-RIDE--PROTEIN GLYCOSYLTRANSFERASE ALPHA SUBUNIT PRECURSOR (EC 2.4.1.119) (OLIGOSACCHARYL TRANSFERASE ALPHA SUBUNIT) (OLIGOSACCHARYL TRANSFERASE 64 KD SUBUNIT). | swissprot P41543 | ND |
| 7672 | 188.2 | CDC-LIKE PROTEIN (FRAGMENT). | sptrembl O08837 | ND |
| 7673 | 186.3 | PUTATIVE PROLINE-RICH PROTEIN. | sptrembl Q9ZW08 | ND |
| 7674 | 186.3 | HYDROLASE 434 aa, chain A + B | pdb 4CEL | ND |
| 7675 | 185.9 | SPLICING COACTIVATOR SUBUNIT SRM300. | tremblnew AAF21439 | ND |
| 7676 | 184.3 | HEAT SHOCK PROTEIN-LIKE PROTEIN. | sptrembl O23323 | ND |
| 7677 | 183.9 | PLENTY-OF-PROLINES-101. | sptrembl O70495 | ND |
| 7678 | 183.3 | PROLINE-RICH SALIVARY PROTEIN (FRAGMENT). | sptrembl Q62107 | ND |
| 7679 | 181.6 | SUGAR TRANSPORTER, PUTATIVE. | tremblnew AAF12486 | ND |
| 7680 | 180.8 | KIAA0775 PROTEIN. | sptrembl O94873 | ND |
| 7681 | 179.8 | GAMMA GLIADIN (FRAGMENT). | sptrembl Q41602 | ND |
| 7682 | 179.6 | HYPOTHETICAL 61.1 KD PROTEIN (FRAGMENT). | tremblnew CAB63715 | ND |
| 7683 | 179.4 | NADH-UBIQUINONE OXIDOREDUCTASE 21 KD SUBUNIT (EC 1.6.5.3) (EC 1.6.99.3) (COMPLEX I-21 KD) (CI-21 KD). | swissprot Q02854 | ND |
| 7684 | 179.2 | PROLINE-RICH CELL WALL PROTEIN. | sptrembl Q39763 | ND |
| 7685 | 178.1 | Amino acid sequence of a virulence factor encoded by ORF25510. | geneseqp Y29194 | ND |
| 7686 | 176.8 | HYPOTHETICAL 47.5 KD PROTEIN IN APE3-APM3 INTERGENIC REGION. | swissprot P38355 | ND |
| 7687 | 176.8 | LOW MOLECULAR WEIGHT GLUTENIN (FRAGMENT). | sptrembl Q41550 | ND |
| 7688 | 176.2 | HYPOTHETICAL 57.2 KD PROTEIN. | sptrembl O68872 | ND |
| 7689 | 175.9 | T1G11.14 PROTEIN. | sptrembl O23024 | ND |
| 7690 | 175.4 | GLYCOLIPID ANCHORED SURFACE PROTEIN PRECURSOR (GLYCOPROTEIN GP115). | swissprot P22146 | ND |
| 7691 | 175.1 | Bioadhesive precursor protein from cDNA 52. | geneseqp P82971 | ND |
| 7692 | 175.0 | PISTIL EXTENSIN-LIKE PROTEIN. | sptrembl Q40385 | ND |

TABLE 4-continued

_Trichoderma reesei ESTs_

| Sequence Listing | zscore | Annotation | Database | Functional Category |
|---|---|---|---|---|
| 7693 | 174.7 | PROLINE-RICH PROTEOGLYCAN PRPG2. | sptrembl Q07611 | ND |
| 7694 | 174.7 | Antibiotic potentiating peptide #3. | geneseqp W21591 | ND |
| 7695 | 174.7 | HOMEOBOX PROTEIN MOX-2 (GROWTH ARREST-SPECIFIC HOMEOBOX). | swissprot P39020 | ND |
| 7696 | 173.6 | REPETIN. | swissprot P97347 | ND |
| 7697 | 172.9 | PROTEOPHOSPHOGLYCAN (FRAGMENT). | sptrembl Q9Y075 | ND |
| 7698 | 172.6 | Sugar beet chitinase 1. | geneseqp R28150 | ND |
| 7699 | 172.1 | FORMYLTETRAHYDROFOLATE DEFORMYLASE (EC 3.5.1.10) (FORMYL-FH(4) HYDROLASE). | swissprot Q46339 | ND |
| 7700 | 171.9 | HYPOTHETICAL 23.2 KD PROTEIN. | sptrembl O41979 | ND |
| 7701 | 170.6 | CORTICOTROPIN RELEASING HORMONE RECEPTOR TYPE I (FRAGMENT). | sptrembl O77677 | ND |
| 7702 | 170.3 | 31-KDA PROLINE-RICH SALIVARY PROTEIN, COMPLETE CDS OF CLONE PUMP125. | sptrembl Q62105 | ND |
| 7703 | 169.6 | BLUE-COPPER BINGING PROTEIN III. | sptrembl Q96316 | ND |
| 7704 | 169.0 | D9461.20P. | sptrembl Q04080 | ND |
| 7705 | 168.8 | 50 KD PROLINE RICH PROTEIN. | sptrembl Q9ZBP2 | ND |
| 7706 | 168.3 | FLGA insert stabilising polypeptide. | geneseqp W79128 | ND |
| 7707 | 168.1 | VRG53 PROTEIN (FRAGMENT). | sptrembl Q05844 | ND |
| 7708 | 168.0 | _Mycobacterium_ species protein sequence 5C. | geneseqp Y04773 | ND |
| 7709 | 167.8 | CHAPERONIN HSP78P. | sptrembl O74402 | ND |
| 7710 | 167.0 | Microtubule-associated tau protein epitope corresp. to pos. 146–251. | geneseqp R92516 | ND |
| 7711 | 166.2 | SPLICING FACTOR SRP54. | sptrembl O61646 | ND |
| 7712 | 166.1 | Fragmented human NF-H gene +2 frameshift mutant product. | geneseqp W18663 | ND |
| 7713 | 166.0 | Amino acid sequence of Huntington's gene exon 1 in GST-HD fusion protein. | geneseqp W95071 | ND |
| 7714 | 165.8 | BIFID PROTEIN (OPTOMOTOR-BLIND PROTEIN). | sptrembl Q26303 | ND |
| 7715 | 165.6 | 212AA LONG HYPOTHETICAL PROTEIN. | sptrembl Q9YEG1 | ND |
| 7716 | 164.5 | Amino acid sequence of a virulence factor encoded by ORF31784. | geneseqp Y29225 | ND |
| 7717 | 164.4 | SIMILAR TO CUTICULAR COLLAGEN. | sptrembl Q19813 | ND |
| 7718 | 164.4 | Amino acid sequence of a virulence factor encoded by ORF32832. | geneseqp Y29230 | ND |
| 7719 | 164.2 | ZINC-FINGER PROTEIN. | sptrembl O74308 | ND |
| 7720 | 163.9 | BAT2. | sptrembl Q9Z1R1 | ND |
| 7721 | 163.7 | PAD-1. | sptrembl Q9Y7A8 | ND |
| 7722 | 163.3 | TRANSCRIPTION FACTOR BF-2 (BRAIN FACTOR 2) (BF2) (HFK2). | swissprot P55316 | ND |
| 7723 | 163.2 | HYPOTHETICAL 27.0 KD PROTEIN. | sptrembl P95286 | ND |
| 7724 | 163.0 | A-AGGLUTININ ATTACHMENT SUBUNIT PRECURSOR. | swissprot P32323 | ND |
| 7725 | 162.4 | _Trichoderma reesei_ endoglucanase. | geneseqp R83401 | ND |
| 7726 | 162.1 | T12F5.5 PROTEIN. | sptrembl O44760 | ND |

TABLE 4-continued

*Trichoderma reesei* ESTs

| Sequence Listing | zscore | Annotation | Database | Functional Category |
|---|---|---|---|---|
| 7727 | 162.0 | RNA BINDING PROTEIN (FRAGMENT). | tremblnew BAA83717 | ND |
| 7728 | 161.9 | TRANSDUCIN-LIKE ENHANCER PROTEIN 4 (GROUCHO-RELATED PROTEIN 4) (FRAGMENT). | swissnew Q62441 | ND |
| 7729 | 161.5 | *Mycobacterium* species protein sequence 14Q#2. | geneseqp Y07202 | ND |
| 7730 | 161.3 | SWI/SNF COMPLEX 170 KDA SUBUNIT. | sptrembl Q92923 | ND |
| 7731 | 161.1 | HIV Tat protein. | geneseqp Y05097 | ND |
| 7732 | 160.7 | HYPOTHETICAL 118.4 KD PROTEIN IN BAT2-DAL5 INTERGENIC REGION PRECURSOR. | swissprot P47179 | ND |
| 7733 | 160.6 | COMES FROM THIS GENE. | sptrembl O23054 | ND |
| 7734 | 160.6 | PYRUVATE DEHYDROGENASE E1 COMPONENT ALPHA SUBUNIT (EC 1.2.4.1) (PYRUVATE DEHYDROGENASE (LIPOAMIDE)) (PYRUVATE DECARBOXYLASE) (PYRUVIC DEHYDROGENASE). | sptrembl O13392 | ND |
| 7735 | 160.6 | GLYCINE-RICH PROTEIN. | sptrembl Q43308 | ND |
| 7736 | 160.5 | METHYLTRANSFERASE. | sptrembl Q51774 | ND |
| 7737 | 160.4 | RHBA. | tremblnew AAF24249 | ND |
| 7738 | 160.3 | ULTRA-HIGH SULPHUR KERATIN. | sptrembl Q64526 | ND |
| 7739 | 160.2 | PROLYL AMINOPEPTIDASE. | sptrembl P94800 | ND |
| 7740 | 159.9 | HOMEOBOX PROTEIN GBX-2 (GASTRULATION AND BRAIN-SPECIFIC HOMEOBOX PROTEIN 2). | swissprot P52951 | ND |
| 7741 | 159.6 | PUTATIVE MEMBRANE PROTEIN. | sptrembl Q9X780 | ND |
| 7742 | 159.4 | Human secreted protein encoded by gene 41c lone HSZAF47. | geneseqp Y02690 | ND |
| 7743 | 159.0 | Human apolipoprotein E gene +2 frameshift mutant product. | geneseqp W18652 | ND |
| 7744 | 158.6 | HYPOTHETICAL 9.0 KD PROTEIN (FRAGMENT). | sptrembl Q9XSS3 | ND |
| 7745 | 158.4 | ORF993. | sptrembl P72344 | ND |
| 7746 | 158.2 | ORF1B. | sptrembl Q47393 | ND |
| 7747 | 157.7 | SMR2 PROTEIN PRECURSOR. | swissprot P18897 | ND |
| 7748 | 157.5 | RECOMBINATION PROTEIN RECR. | swissprot P24277 | ND |
| 7749 | 157.3 | Human alpha 5 (IV) of type IV collagen. | geneseqp R23873 | ND |
| 7750 | 157.1 | PROLINE-RICH PROTEIN. | tremblnew CAB62486 | ND |
| 7751 | 156.5 | GAMMA PROTEIN CONSTANT REGION (FRAGMENT). | sptrembl Q23723 | ND |
| 7752 | 156.1 | NK-TUMOR RECOGNITION MOLECULE-RELATED PROTEIN. | sptrembl O43273 | ND |
| 7753 | 155.6 | SPLICING FACTOR, ARGININE/SERINE-RICH 7 (SPLICING FACTOR 9G8). | swissnew Q16629 | ND |
| 7754 | 154.3 | ACETYLCHOLINESTERASE-ASSOCIATED COLLAGEN (FRAGMENT). | sptrembl O35348 | ND |
| 7755 | 153.8 | PROBABLE PROTEIN KINASE. | tremblnew CAB55520 | ND |
| 7756 | 153.6 | Human high mobility group protein HMGI-C wild type fragment 2. | geneseqp Y21432 | ND |

TABLE 4-continued

Trichoderma reesei ESTs

| Sequence Listing | zscore | Annotation | Database | Functional Category |
|---|---|---|---|---|
| 7757 | 153.6 | NANBH virus antigenic fragment #12. | geneseqp R50080 | ND |
| 7758 | 153.6 | Del-1 epidermal growth factor like domain #2. | geneseqp W94687 | ND |
| 7759 | 153.5 | SH3 DOMAIN BINDING PROTEIN. | sptrembl Q62775 | ND |
| 7760 | 153.3 | COLLAGEN ALPHA 5(IV) CHAIN (FRAGMENT). | swissprot Q28247 | ND |
| 7761 | 153.0 | SALIVARY GLUE PROTEIN SGS-3 PRECURSOR. | swissprot P13729 | ND |
| 7762 | 152.5 | MRNA EXPRESSED IN CUCUMBER HYPOCOTYLS, COMPLETE CDS. | sptrembl Q9XIV1 | ND |
| 7763 | 152.4 | PROTEOPHOSPHOGLYCAN PRECURSOR (FRAGMENT). | sptrembl Q9Y076 | ND |
| 7764 | 152.3 | ARL-6 INTERACTING PROTEIN-5 (FRAGMENT). | sptrembl Q9WUG9 | ND |
| 7765 | 150.4 | HYPOTHETICAL 70.4 KD PROTEIN IN SNZ1-YPK2 INTERGENIC REGION. | swissprot Q03153 | ND |
| 7766 | 150.3 | L779.3 PROTEIN. | sptrembl Q9XTP1 | ND |
| 7767 | 150.3 | Fragment of human secreted protein encoded by gene 15. | geneseqp Y36459 | ND |
| 7768 | 150.3 | HOX1B PROTEIN. | sptrembl O24569 | ND |
| 7769 | 149.8 | HYPOTHETICAL 13.9 KD PROTEIN. | tremblnew AAF19661 | ND |
| 7770 | 149.7 | Mycobacterium species protein sequence 50B. | geneseqp Y04998 | ND |
| 7771 | 149.6 | T06E4.11 PROTEIN. | sptrembl Q22265 | ND |
| 7772 | 148.8 | Avian reovirus strain 138 sigma 3 protein. | geneseqp Y06109 | ND |
| 7773 | 148.3 | GSC-2. | sptrembl O15499 | ND |
| 7774 | 148.2 | CODED FOR BY C. ELEGANS CDNA YK127B8.5. | sptrembl Q20648 | ND |
| 7775 | 147.8 | ORF225. | sptrembl Q44479 | ND |
| 7776 | 146.8 | WD-40 domain-contg. TUP1 homolog protein. | geneseqp R85879 | ND |
| 7777 | 146.8 | EN/SPM-LIKE TRANSPOSON PROTEIN. | tremblnew AAD20682 | ND |
| 7778 | 146.5 | PROLINE RICH PROTEIN. | sptrembl O22514 | ND |
| 7779 | 146.4 | Secreted protein encoded by gene 6 clone HTSEW17. | geneseqp Y01388 | ND |
| 7780 | 146.3 | HOMEOBOX PROTEIN GBX-2 (GASTRULATION AND BRAIN-SPECIFIC HOMEOBOX PROTEIN 2). | swissprot P52951 | ND |
| 7781 | 145.6 | NUCLEOPLASMIN. | swissnew P05221 | ND |
| 7782 | 145.3 | TYROSINE-PROTEIN KINASE ACK (EC 2.7.1.112). | sptrembl Q07912 | ND |
| 7783 | 144.9 | INTEGRIN BETA-SUBUNIT. | sptrembl Q27874 | ND |
| 7784 | 144.2 | SIMILARITY WITH WILMS' TUMOR PROTEIN. | sptrembl Q18233 | ND |
| 7785 | 143.5 | F25965_3. | sptrembl O14560 | ND |
| 7786 | 142.5 | HYPOTHETICAL 38.0 KD PROTEIN. | sptrembl O06232 | ND |
| 7787 | 142.5 | DAN26 PROTEIN, PARTIAL (FRAGMENT). | sptrembl Q99492 | ND |
| 7788 | 142.2 | ATTACHMENT REGION BINDING PROTEIN (FRAGMENT). | sptrembl O42403 | ND |
| 7789 | 142.1 | S-LAYER RELATED PROTEIN PRECURSOR. | swissprot P35824 | ND |
| 7790 | 141.9 | NONSTRUCTURAL POLYPROTEIN (FRAGMENT). | sptrembl Q9W181 | ND |
| 7791 | 141.9 | ATTI. | sptrembl Q9WWD7 | ND |
| 7792 | 141.3 | ENDOGLUCANASE IV. | sptrembl O14405 | ND |
| 7793 | 141.1 | GAMMA-GLIADIN PRECURSOR (FRAGMENT). | swissprot P08079 | ND |
| 7794 | 140.9 | Mycobacterium species protein sequence 36B. | geneseqp Y04923 | ND |
| 7795 | 140.9 | VPR. | sptrembl O90320 | ND |

TABLE 4-continued

*Trichoderma reesei* ESTs

| Sequence Listing | zscore | Annotation | Database | Functional Category |
|---|---|---|---|---|
| 7796 | 140.8 | NUCLEAR ANTIGEN EBNA-3B. | sptrembl Q69139 | ND |
| 7797 | 140.4 | TRANSCRIPTIONAL ACTIVATOR PROTEIN METR. | swissprot P19797 | ND |
| 7798 | 140.4 | CALCIUM-DEPENDENT PROTEIN KINASE. | sptrembl O82107 | ND |
| 7799 | 139.1 | (HHV-6). | sptrembl Q89893 | ND |
| 7800 | 139.1 | HYPOTHETICAL 12.0 KD PROTEIN (FRAGMENT). | sptrembl O43409 | ND |
| 7801 | 138.9 | SMAD6 PROTEIN. | tremblnew AAF14343 | ND |
| 7802 | 138.9 | ARGININE/SERINE-RICH PROTEIN. | tremblnew AAF19004 | ND |
| 7803 | 138.8 | 107AA LONG HYPOTHETICAL PROTEIN. | sptrembl Q9YCW7 | ND |
| 7804 | 137.9 | Human fibrosarcoma cell line HT-1080 clone HP10034 protein. | geneseqp W64540 | ND |
| 7805 | 137.9 | Extracellular domain of mouse syndecan-3 protein. | geneseqp R66810 | ND |
| 7806 | 137.8 | SIMILAR TO FURIN-LIKE PROTEASES. | sptrembl Q93015 | ND |
| 7807 | 137.7 | PROTEASOME COMPONENT SUN4. | swissprot P53616 | ND |
| 7808 | 137.6 | HYPOTHETICAL 26.9 KD PROTEIN. | tremblnew AAF10289 | ND |
| 7809 | 137.2 | HYPOTHETICAL 22.1 KD PROTEIN. | sptrembl P94570 | ND |
| 7810 | 137.1 | WINGLESS (FRAGMENT). | tremblnew AAD50945 | ND |

Example 15

DNA Microarrays

Details of the construction of a typical microarrayer can be found on the world wide web site of Professor Patrick Brown of Stanford University at the following URL: http://cmgm.stanford.edu/pbrown/mguide/index.html. Scanners and computer software for analysis of DNA microarrays are available from several commercial sources such as General Scanning Inc. (Watertown, Mass.; see http://www.genscan.com/sales/loc lifesci.html), or Axon Instruments (Foster City, Calif.; see http://www.axon.com).

Individual fungal EST clones were purified as plasmid minipreps using Qiagen Biorobot 9600 (QIAGEN, Inc., Valencia, Calif.). The plasmid minipreps were precipitated with isopropanol, aliquoted and stored as described on the web site of Professor Patrick Brown of Stanford University at the following URL: http://cmgm.stanford.edu/pbrown/mguide/index.html.

The amplified EST targets prepared in this manner were spotted individually onto polylysine-coated glass slides using a microarrayer device as described by DeRisi et al. (1997, *Science* 278: 680–686). For additional details, see http://cmgm.stanford.edu/pbrown/protocols/index.html).

The microarrays were probed with flurescently labeled cDNA prepared by reverse transcription of polyadenylated mRNA (DeRisi et al., 1997, supra) extracted from fungal mycelia (Example 2). Conditions for pretreatment of the microarrays, hybridization and washing conditions have been described previously (DeRisi et al., 1997, supra; see also http://cmgm.stanford.edu/pbrown/protocols/index.html).

To increase the reliability with which changes in expression levels could be discerned, probes prepared from induced or treated cells were labeled with the red fluorescent dye, Cy5 (Amersham Corporation, Arlington Heights, Ill.), and mixed with probes from uninduced, untreated, or "reference" cells were labeled with a green fluorescent dye, Cy3 (Amersham Corporation, Arlington Heights, Ill.) using the procedure described by http://cmgm.stanford.edu/pbrown/protocols/index.html. The relative ratio of fluorescence intensity measured for the Cy3 and Cy5 fluorophors corresponding to each EST target in the arrays was determined using ScanAlyze software, available free of charge at http://rama.stanford.edu/software/. This provides a reliable measure of the relative abundance of the corresponding mRNA in the two cell populations (e.g., treated cells versus reference cells).

Example 16

Monitoring Multiple Changes in Expression of *Fusarium venenatum* Genes

DNA microarrays were prepared as described in the preceding example by spotting 1152 selected EST clones from *Fusarium venenatum* as targets. In one experiment we compared the relative expression of each of these genes (as measured by transcript abundance) among cells grown in medium with glucose as the sole carbon source to the same strain grown with maltose as the sole carbon source. Identical shake flasks were inoculated with *Fusarium venenatum* strain CC1-3 growing in Vogel's minimal medium with either 2% glucose or 2% maltose as the sole carbon source. After 2 days growth at 28° C., total RNA and mRNA pools were purified from each culture using methods described in the previous examples. One microgram of polyA-selected mRNA was used as a template to prepare fluorescently labeled probes for hybridization (the protocol for fluorescent probe labeling is available at http://cmgm.stanford.edu/protocols/index.html). In this experiment, the probe from glucose-grown cells was labeled with Cy3 and the probe from maltose-grown cells was labeled with Cy5. The probes were combined and hybridized with the 1152 EST targets on the microarray. Methods for hybridization and washing of microarrays are also available at http://cmgm.stanford.edu/protocols/index.html. After hybridization and washing, the microarrays were scanned (see Example 15), and the images analyzed using ScanAlyze software (see Example 15) to determine the relative ratios of red and green fluorescence in each spot on the arrays. The tab-delimited text file generated by ScanAlyze can be imported into other software programs that are capable of sorting large amounts of data in spreadsheet formats (e.g., Microsoft Excel). In such a format, it is straightforward to sort the data on the basis of relative fluorescence ratios (red intensity/green intensity=RAT2 value) or perform other statistical analyses. For example, in this experiment it was desirable to specifically identify those genes whose expression (a) increased by a factor of approximately two, (b) remainde the same, or (c) decreased by a factor of approximately two in response to the presence of maltose as a sole carbon source. A number of genes satisfying these criteria were readily identified as shown in Table 5. The quality of the data is ensured by choosing only spots in which the correlation coefficients are at least 0.75 or greater.

TABLE 5

| Seq ID No. | RAT2.exp1 | RAT2.exp2 | AVG RAT2 | Std Error |
|---|---|---|---|---|
| 1902 | 3.84631093 | 1.90100237 | 2.87365665 | 0.97265428 |
| 170 | 1.43757588 | 3.08897138 | 2.26327363 | 0.82569775 |
| 1590 | 1.34067691 | 2.90504405 | 2.12286048 | 0.78218357 |
| 2342 | 2.48104772 | 1.74101079 | 2.11102925 | 0.37001846 |
| 2887 | 2.15781008 | 2.04587664 | 2.10184336 | 0.05596672 |
| 1290 | 2.18673515 | 2.00682358 | 2.09677936 | 0.08995579 |
| 1849 | 1.60461815 | 2.58254133 | 2.09357974 | 0.48896159 |

TABLE 5-continued

| Seq ID No. | RAT2.exp1 | RAT2.exp2 | AVG RAT2 | Std Error |
|---|---|---|---|---|
| 2718 | 1.07601253 | 1.13379863 | 1.10490558 | 0.02889305 |
| 2875 | 1.04636434 | 1.13480645 | 1.0905854 | 0.04422106 |
| 115 | 1.08685943 | 1.07748663 | 1.08217303 | 0.0046864 |
| 115 | 1.08252067 | 1.06766038 | 1.07509053 | 0.00743015 |
| 1453 | 1.09264445 | 1.0495196 | 1.07108202 | 0.02156242 |
| 1677 | 1.07456628 | 1.05581848 | 1.06519238 | 0.0093739 |
| 608 | 1.00586924 | 1.10205227 | 1.05396076 | 0.04809151 |
| 33 | 1.1157845 | 0.98879838 | 1.05229144 | 0.06349306 |
| 2768 | 1.08902881 | 0.9954752 | 1.04225201 | 0.04677681 |
| 336 | 1.08107442 | 0.97569671 | 1.02838557 | 0.05268885 |
| 1855 | 1.06155 | 0.99446738 | 1.02800869 | 0.03354131 |
| 1469 | 1.04708747 | 1.00026235 | 1.02367491 | 0.02341256 |
| 2951 | 0.46005321 | 0.6007873 | 0.55655 | 0.0084234 |
| 71 | 0.44219198 | 0.53023983 | 0.4862159 | 0.04402392 |
| 521 | 0.23356992 | 0.76644788 | 0.4657 | 0.18741504 |

SEQUENCE LISTINGS

This application contains 2 copies of the Sequence Listing on compact disk, which are incorporated herein by reference. Copy 1 is done on an Intel x86 machine format, in Windows XP operating system compatibility, there is one file saved as 5849.200 Sequence Listing, and is 7,167 kb bytes, and created on May 6, 2004. Copy 2 is identical to Copy 1.

The invention described and claimed herein is not to be limited in scope by the specific embodiments herein disclosed, since these embodiments are intended as illustrations of several of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07186513B2). An electronic copy of the "Sequence Listing" will also be available from the USPTO upon request and payment of the fee set forth in 37 CFR 1.19(b)(3).

What is claimed is:

1. A method for monitoring differential expression of a plurality of genes in a first filamentous fungal cell relative to expression of the same genes in one or more second filamentous fungal cells, comprising:
   (a) adding a mixture of fluorescence-labeled nucleic acids isolated from the filamentous fungal cells to a substrate containing an array of *Fusarium venenatum* ESTs comprising SEQ ID NOs. 1–3770, under conditions where the nucleic acids hybridize to complementary sequences of the ESTs in the array, wherein the nucleic acids from the first filamentous fungal cell are labeled with a first fluorescent reporter and the one or more second filamentous fungal cells are labeled with one or more different second fluorescent reporters; and
   (b) examining the array by fluorescence under fluorescence excitation conditions wherein the relative expression of the genes in the filamentous fungal cells is determined by the observed fluorescence emission color of each spot in the array in which (i) the fluorescence-labeled nucleic acids obtained from the first filamentous fungal cell that are hybridized to the ESTs in the array produce a distinct first fluorescence emission color and the fluorescence-labeled nucleic acids obtained from the one or more second filamentous fungal cells that are hybridized to the ESTs in the array produce a distinct second fluorescence emission color, and (ii) the fluorescence-labeled nucleic acids obtained from both the first and the one or more second filamentous fungal cells that are hybridized to the ESTs in the array produce a distinct combined fluorescence emission color.

2. The method of claim 1, wherein one or more of the filamentous fungal cells are selected from the group consisting of an *Acremonium, Aspergillus, Fusarium, Humicola, Mucor, Myceliophthora, Neurospora, Penicillium, Thielavia, Tolypocladium,* and *Trichoderma* cell.

3. The method of claim 1, wherein the two or more filamentous fungal cells are the same cell.

4. The method of claim 1, wherein the two or more filamentous fungal cells are *Fusarium venenatum* cells.

5. The method of claim 1, wherein the two or more filamentous fungal cells are *Aspergillus niger* cells.

6. The method of claim 1, wherein the two or more filamentous fungal cells are *Aspergillus oryzae* cells.

7. The method of claim 1, wherein the two or more filamentous fungal cells are different cells.

8. The method of claim 1, wherein the hybridization conditions are selected from the group consisting of very low, low, low-medium, medium, medium-high, high, and very high stringency conditions.

9. The method of claim 1, wherein the array comprises the EST of SEQ ID NO: 6 and one or more ESTs selected from the group consisting of SEQ ID Nos: 1–5 and 7–3770.

* * * * *